US012473298B2

(12) United States Patent
Xu et al.

(10) Patent No.: US 12,473,298 B2
(45) Date of Patent: Nov. 18, 2025

(54) AMIDE COMPOUNDS, PREPARATION METHOD THEREFOR, AND USE THEREOF IN THE MEDICAL FIELD

(71) Applicants: Shanghai Synergy Pharmaceutical Sciences Co., Ltd., Shanghai (CN); Zhejiang Huahai Pharmaceutical Co., Ltd., Zhejiang (CN)

(72) Inventors: Xin Xu, Shanghai (CN); Jia Chen, Shanghai (CN); Zhen Zhang, Shanghai (CN); Liming Zhang, Shanghai (CN); Qimei Wu, Shanghai (CN); Qingyun Jiang, Shanghai (CN); Fengying Guo, Shanghai (CN); Yuyun Zhang, Shanghai (CN); Hao Yu, Shanghai (CN); Xiaojuan Zhang, Shanghai (CN); Kang Sun, Shanghai (CN); Xiaobo Zhou, Shanghai (CN); Chengxu Zang, Shanghai (CN); Yijin Wang, Shanghai (CN); Xiaoer Xia, Shanghai (CN); Yunfei Li, Shanghai (CN); Jian Ge, Shanghai (CN)

(73) Assignees: SHANGHAI SYNERGY PHARMACEUTICAL SCIENCES CO., LTD., Shanghai (CN); ZHEJIANG HUAHAI PHARMACEUTICAL CO., LTD., Zhejiang (CN)

( * ) Notice: Subject to any disclaimer, the term of this patent is extended or adjusted under 35 U.S.C. 154(b) by 1018 days.

(21) Appl. No.: 17/442,331

(22) PCT Filed: Mar. 24, 2020

(86) PCT No.: PCT/CN2020/080874
§ 371 (c)(1),
(2) Date: Sep. 23, 2021

(87) PCT Pub. No.: WO2020/192652
PCT Pub. Date: Oct. 1, 2020

(65) Prior Publication Data

US 2022/0024941 A1 Jan. 27, 2022

(30) Foreign Application Priority Data

Mar. 25, 2019 (CN) ........................ 201910228244.8
Jul. 29, 2019 (CN) ........................ 201910687575.8

(51) Int. Cl.

| | |
|---|---|
| ***C07D 491/107*** | (2006.01) |
| ***A61P 35/00*** | (2006.01) |
| ***C07D 405/12*** | (2006.01) |
| ***C07D 405/14*** | (2006.01) |
| ***C07D 471/10*** | (2006.01) |
| ***C07D 487/04*** | (2006.01) |
| ***C07D 495/10*** | (2006.01) |

(52) U.S. Cl.
CPC .......... *C07D 491/107* (2013.01); *A61P 35/00* (2018.01); *C07D 405/12* (2013.01); *C07D 405/14* (2013.01); *C07D 471/10* (2013.01); *C07D 487/04* (2013.01); *C07D 495/10* (2013.01)

(58) Field of Classification Search
CPC ................................................ C07D 491/107
See application file for complete search history.

(56) References Cited

U.S. PATENT DOCUMENTS

2017/0217941 A1 8/2017 Campbell

FOREIGN PATENT DOCUMENTS

| | | | | |
|---|---|---|---|---|
| CN | 104080769 A1 | 10/2014 | | |
| CN | 105307683 A | 2/2016 | | |
| CN | 108314677 A | 7/2018 | | |
| JP | 2014513084 A | 5/2014 | | |
| JP | 2014516931 A | 7/2014 | | |
| JP | 2015531366 A | 11/2015 | | |
| JP | 2022528042 A | 6/2022 | | |
| JP | 2022528337 A | 6/2022 | | |
| WO | 2012142504 A1 | 10/2012 | | |
| WO | 2013155464 A1 | 10/2013 | | |
| WO | 2013173441 A1 | 11/2013 | | |
| WO | 2014172044 | 10/2014 | | |
| WO | 2015010049 A1 | 1/2015 | | |
| WO | 2015110999 A1 | 7/2015 | | |
| WO | WO-2017139404 A1 * | 8/2017 | ......... | A61K 31/4412 |
| WO | 2018137639 A1 | 8/2018 | | |
| WO | 2020192652 A1 | 10/2020 | | |

OTHER PUBLICATIONS

Christofides (Oncotarget, 2016, vol. 7, (No. 51), pp. 85624-85640) (Year: 2016).*
Klein (Can a person prevent multiple sclerosis? Medical News Today. Apr. 29, 2020. p. 1-9) (Year: 2020).*
Extended European Search Report for European Patent Application No. 20779835.6; Date of Mailing Mar. 31, 2022, 13 pages.
U.S. Appl. No. 17/442,899 issued on Dec. 19, 2024.

* cited by examiner

*Primary Examiner* — Kortney L. Klinkel
*Assistant Examiner* — Richard Grant Peckham
(74) *Attorney, Agent, or Firm* — CANTOR COLBURN LLP

(57) ABSTRACT

Provided are amide compounds, a preparation method therefor, and use thereof in the medical field. Specifically, provided are small molecule amide compounds. Such compounds are inhibitors of enhancer of Zeste homolog 2 (EZH2), and can be used for preventing and/or treating related diseases mediated by EZH2, including tumors, myeloproliferative diseases or autoimmune diseases.

4 Claims, No Drawings

AMIDE COMPOUNDS, PREPARATION METHOD THEREFOR, AND USE THEREOF IN THE MEDICAL FIELD

The present application claims the priorities of the Chinese Patent Application No. 201910228244.8, filed on Mar. 25, 2019 before the China National Intellectual Property Administration, with the title of "PREPARATION METHOD FOR AMIDE COMPOUND AND APPLICATION THEREOF IN THE FIELD OF MEDICINE" and of the Chinese Patent Application No. 201910687575.8, filed on Jul. 29, 2019 before the China National Intellectual Property Administration, with the title of "PREPARATION METHOD FOR AMIDE COMPOUND AND APPLICATION THEREOF IN THE FIELD OF MEDICINE"; which are hereby incorporated by reference in their entireties.

FIELD OF THE INVENTION

The present invention relates to the field of medical technology, particularly to an amide small molecule compound, a pharmaceutical composition comprising the same, a preparation method therefor, and an application thereof in the field of medicine. The present application discloses the use of the amide small molecule compound as an inhibitor of Enhancer of Zeste homolog 2 (EZH2) for preventing and/or treating EZH2-mediated diseases, such as malignant tumors.

BACKGROUND OF THE INVENTION

Malignant tumor is a serious threat to human health. In recent years, its morbidity and mortality have been on the rise, and it has become a serious health problem worldwide. The occurrence and development of tumor is a multi-factor and multi-stage evolutionary process, involving a variety of gene mutations and epigenetic variations. Epigenetics refers to a kind of genetic phenomenon that the expression level and function of a gene changes and produces a heritable phenotype under the condition that the DNA sequence of the gene does not change. Polycomb group protein (PcG) is an important protein factor involved in the negative epigenetic regulation of chromatin genes. The PcG family includes two kinds of polycomplexes: polycomb repressive complex 1 (PRC1) and polycomb repressive complex 2 (PRC2). Enhancer of Zeste homolog 2 (EZH2) is a core member of the Polycomb group protein (PcG) family. EZH2 is a catalytic subunit of PRC2 protein complex, which plays a central role in the function of the PRC2 protein complex. EZH2 contains a highly conserved SET domain and has a histone methyl transferase (HMT) activity. It catalyzes the histone H3 trimethylation at lysine 27 (H3K27me3) and then triggers the aggregation of PRC1 complex components at specific gene sites, resulting in the silencing of downstream target genes, which is involved in the regulation of a variety of basic biological processes, such as apoptosis, cell cycle regulation, cell aging, and cell differentiation. Recent studies have shown that EZH2 is highly expressed in a variety of tumor tissues, and is closely related to the malignant progression, invasion, and metastasis of tumors.

The high expression of EZH2 is often associated with the progression and adverse prognosis of human terminal cancers, such as prostate cancer, breast cancer, bladder cancer, lung cancer, rectal cancer, lymphoma, and the like. Mutation or deletion of EZH2 is associated with tumors, such as diffuse large B cell lymphoma, follicular lymphoma, myelodysplastic syndrome, myeloproliferative disease, and the like. Currently, the Y641 and A677 mutations of EZH2 enhance the activity of the encoded protein, leading to an increase of H3K27me3 level, resulting in a promotion of lymphoma cell proliferation.

In conclusion, since EZH2 is involved in the occurrence and development of tumors as an epigenetic enzyme, EZH2 inhibitors, as a medicament, have good application prospects in the pharmaceutical industry.

Selective EZH2 inhibitors that have been disclosed include those disclosed in WO2012005805, WO2012050532, WO2012118812, WO2015143424A2, WO2016102493A1, WO2017084494A1, WO2018045971A1, etc. At present, a series of EZH2 inhibitor patents have been published, but there is still a need to develop new EZH2 inhibitors to meet the demand of the market.

The present invention redesigns and synthesizes a class of EZH2 inhibitors, which, through experimental research, have high selectivity for EZH2 targets and excellent pharmacodynamic effects in animal experiments in vivo.

SUMMARY OF THE INVENTION

A purpose of the present invention is to provide a compound represented by formula (I), and a tautomer, a mesomer, a racemate, an enantiomer, a diastereomer or a mixture thereof, a pharmaceutically acceptable salt, a polymorph, a solvate, a prodrug, a metabolite or an isotope derivative thereof, (I)

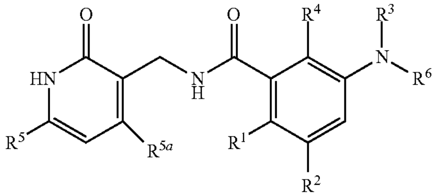

wherein, $R^1$ is H or halogen, preferably H, F or Cl;

$R^2$ is a 11- to 16-membered tricyclic group; wherein rings in the tricyclic group are fused connected, or are connected by a carbon atom into a spiro compound; wherein at least one ring in the tricyclic group is an aromatic ring, and in case that one ring in the tricyclic group is a heterocyclic ring containing a nitrogen atom, the nitrogen atom is not substituted or substituted by $R^e$; a methylene of the ring in the tricyclic group is not substituted, substituted by 0 to form a ketone group, substituted by one $R^f$, or substituted by both $R^f$ and $R^g$, the aromatic ring in the tricyclic group is not substituted or is substituted by one $R^e$; preferably $R^2$ is

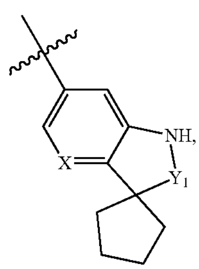

,

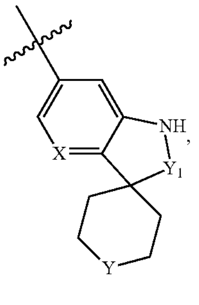

,

-continued

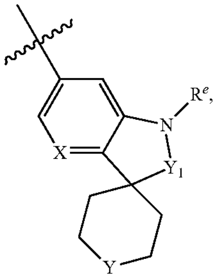

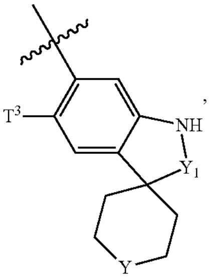

,

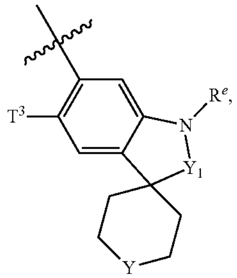

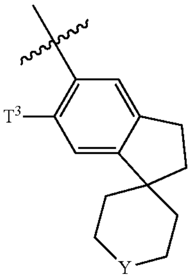

,

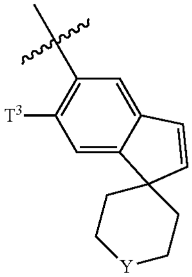

,

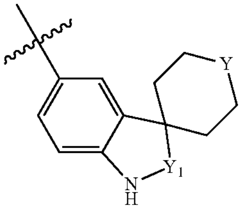

,

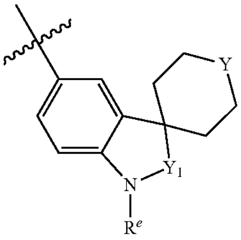

,

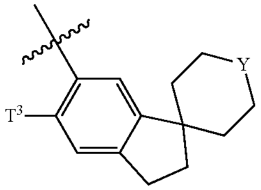

,

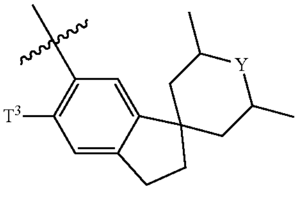

,

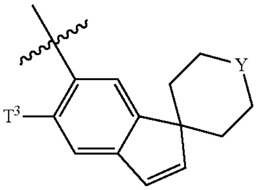

,

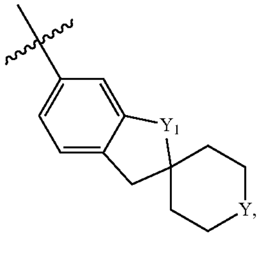

-continued

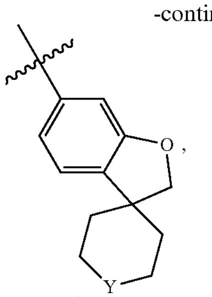

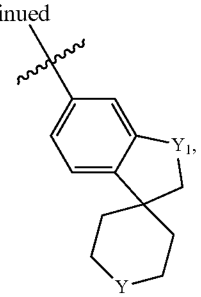

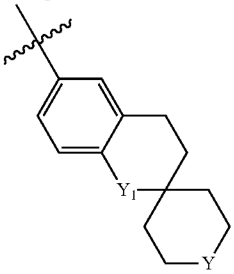

or

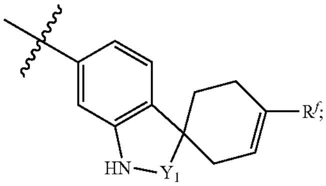

X is N or C;

Y is $—CH_2—$, $—CHR^f—$, $—CR^fR^g—$, —C(O)—, NH—, $—NR^{e1}—$, —O—, —S— or $—S(O)_2—$;

$Y_1$ is $—CH_2—$ or —C(O)—;

$T^3$ is —H, halogen, $—C_{1-3}$ alkyl, —CN, —OH or $—C_{1-3}$ alkoxy;

$R^e$ is $—C_{1-4}$ alkyl, $—C_{2-4}$ alkyl substituted by $—C_{1-3}$ alkyl, $—C_{2-4}$ alkyl substituted by —OH, $—C_{1-4}$ alkylene-OH, $—T^0$, $—C_{1-3}$ alkylene-$T^0$, $—(CH_2)_n—CF_3$, $—(CH_2)_n—CF_2—CF_3$, $—(CH_2)_n—CHF_2$, $—(CH_2)_n—CH_2F$, $—(CH_2)_n—O—C_{1-3}$ alkyl, $—C(O)—C_{1-3}$ alkyl, $—(CH_2)_n—C(O)—C_{1-3}$ alkyl, $—C(O)—C_{2-4}$ alkenyl, $—C(O)—CF_3$, $—C(O)—(CH_2)_n—CF_3$, $—C(O)—(CH_2)_n—CF_2—CF_3$, $—C(O)—(CH_2)_n—CHF_2$, $—C(O)—(CH_2)_n—CH_2F$, $—C(O)—T^0$, $—C(O)—C_{1-3}$ alkylene-$T^0$, tert-butoxy-carbonyl, $—C(O)—O—C_{1-3}$ alkyl, $—C(O)—O—(CH_2)_n—CF_3$, $—C(O)—O—(CH_2)_n—CHF_2$, $—C(O)—O—(CH_2)_n—CH_2F$, $—C(O)—O-T^0$, $—C(O)—O—C_{1-3}$ alkylene-$T^0$, $—S(O)_2—C_{1-3}$ alkyl, $—S(O)_2—(CH_2)_n—CF_3$, $—S(O)_2—(CH_2)_n—CHF_2$, $—S(O)_2—(CH_2)_n—CH_2F$, $—S(O)_2—T^0$ or $—S(O)_2—C_{1-3}$ alkylene-$T^0$;

$R^{e1}$ is $—C_{1-4}$ alkyl, $—C_{2-4}$ alkyl substituted by $—C_{1-3}$ alkyl, $—C_{2-4}$ alkyl substituted by —OH, $—C_{1-4}$ alkylene-OH, $—T^0$, $—C_{1-3}$ alkylene-$T^0$, $—(CH_2)_n—CF_3$, $—(CH_2)_n—CF_2—CF_3$, $—(CH_2)_n—CHF_2$, $—(CH_2)_n—CH_2F$, $—(CH_2)_n—O—C_{1-3}$ alkyl, $—(CH_2)_n—C(O)—C_{1-3}$ alkyl, $—C(O)—C_{1-3}$ alkyl, $—C(O)—C_{2-4}$ alkenyl, $—C(O)—CF_3$, $—C(O)—(CH_2)_n—CF_3$, $—C(O)—(CH_2)_n—CF_2—CF_3$, $—C(O)—(CH_2)_n—CHF_2$, $—C(O)—(CH_2)_n—CH_2F$, $—C(O)—T^0$, $—C(O)—C_{1-3}$ alkylene-$T^0$, tert-butoxy-carbonyl, $—C(O)—O—C_{1-3}$ alkyl, $—C(O)—O—(CH_2)_n—CF_3$, $—S(O)_2—C_{1-3}$ alkyl or $—S(O)_2—T^0$.

preferably $R^e$ and $R^{e1}$ are each independently methyl, ethyl, propyl, $—CH(CH_3)—CH_3$, $—CH(CH_3)—$ $(CH_2)_n$ $CH_3$, —$CH(CH_3)$—$CH(CH_3)_2$, —$CH_2$—$C(CH_3)_3$, —$(CH_2)_n$—$C_{3-6}$ cycloalkyl, —$(CH_2)_n$-morpholinyl, $T^0$, —$(CH_2)_n$-$T^0$, —$(CH_2)_n$—$CF_3$, —$(CH_2)_n$—CH(OH)—$CH_3$, —$(CH_2)_n$—$CF_2$—$CF_3$, —$(CH_2)_2$—O—$C_{1-3}$ alkyl, —C(O)—$C_{1-3}$ alkyl, —$(CH_2)_n$—C(O)—$C_{1-3}$ alkyl, —C(O)—$C_{2-4}$ alkenyl, —C(O)—$CF_3$, —C(O)—$(CH_2)_n$—$CF_3$, —C(O)-morpholinyl, —C(O)—$C_{3-6}$ cycloalkyl, tert-butoxycarbonyl, —C(O)—O—$C_{1-3}$ alkyl or —$S(O)_2$—$C_{1-3}$ alkyl;

$R^f$ and $R^g$ are each independently halogen, —OH, —$C_{1-4}$ alkylene-OH, —$CF_3$, —$CHF_2$, —$CH_2F$, —$C_{1-4}$ alkyl, —$C_{2-4}$ alkyl substituted by —$C_{1-3}$ alkyl, —$(CH_2)_n$—$CF_3$, —$(CH_2)_n$—$CHF_2$, —$(CH_2)_n$—$CH_2F$, —$T^0$, —$C_{1-3}$ alkylene-$T^0$, —$NR^aR^b$, —$C_{1-3}$ alkylene-$NR^aR^b$, —O—$C_{1-4}$ alkyl, —O—$C_{2-4}$ alkenyl, —O—$C_{1-4}$ alkylene-OH, —O—$(CH_2)_n$—$CF_3$, —O—$(CH_2)_n$—$CHF_2$, —O—$(CH_2)_n$—$CH_2F$, —O-$T^0$, —O—$C_{1-3}$ alkylene-$T^0$, —NH—C(O)—$C_{2-4}$ alkenyl, —C(O)—$C_{1-3}$ alkyl, —$(CH_2)_n$—C(O)—$C_{1-3}$ alkyl, —C(O)—$C_{2-4}$ alkenyl, —C(O)—$(CH_2)_n$—$CF_3$, —C(O)—$(CH_2)_n$—$CHF_2$, —C(O)—$(CH_2)_n$—$CH_2F$, —C(O)—$T^0$, —C(O)—$C_{1-3}$ alkylene-$T^0$, tert-butoxycarbonyl, —C(O)—O—$C_{1-3}$ alkyl, —C(O)—O—$(CH_2)_n$—$CF_3$, —C(O)—O—$(CH_2)_n$—$CHF_2$, —C(O)—O—$(CH_2)_n$—$CH_2F$, —C(O)—O-$T^0$, —C(O)—O—$C_{1-3}$ alkylene-$T^0$, —$S(O)_2$—$C_{1-3}$ alkyl, —$S(O)_2$—$(CH_2)_n$—$CF_3$, —$S(O)_2$—$(CH_2)_n$—$CHF_2$, —$S(O)_2$—$(CH_2)_n$—$CH_2F$, —$S(O)_2$—$T^0$ or —$S(O)_2$—$C_{1-3}$ alkylene- $T^0$;

Preferably, $R^f$ and $R^g$ are each independently —F, —OH, —$CF_3$, methyl, ethyl, propyl, —$C_{2-3}$ alkyl substituted by —$C_{1-2}$ alkyl, —$(CH_2)_n$—$CF_3$, —$T^0$, —$C_{1-3}$ alkylene-$T^0$, —$NR^aR^b$, —$C_{1-3}$ alkylene-$NR^aR^b$, —O—$C_{1-4}$ alkyl, —O—$C_{2-4}$ alkenyl, —O-$T^0$, —NH—C(O)—$C_{2-4}$ alkenyl, —C(O)—$C_{1-3}$ alkyl, —C(O)—$C_{2-4}$ alkenyl, —C(O)—$(CH_2)_n$—$CF_3$, —C(O)—$T^0$, tert-butoxycarbonyl, —C(O)—O—$C_{1-3}$ alkyl or —C(O)—O-$T^0$;

$R^f$ is more preferably methyl, ethyl, propyl, —F, —Cl, —OH, $T^0$ or —$C_{1-3}$ alkylene-$T^0$;

$R^g$ is more preferably —$T^0$, —$C_{1-3}$ alkylene-$T^0$, —NH—C(O)—$C_{2-3}$ alkenyl, —$NR^aR^b$ or —F; in case that the methylene in the ring of the tricyclic group is substituted by both $R^f$ and $R^g$, $R^f$ and $R^g$ are each independently halogen, —OH or —$C_{1-3}$ alkyl;

$R^j$ is

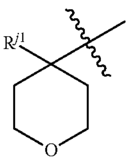 or 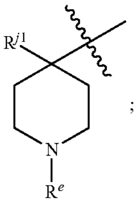 ;

$R^{j1}$ is —CN, —COOH, C(O)O—$C_{1-3}$ alkyl, —$(CH_2)_n$—OH or —$(CH_2)_n$—O—$C_{1-3}$ alkyl;

$R^a$ and $R^b$ and are each independently —H, —$C_{1-3}$ alkyl, —$C_{1-4}$ alkylene-OH, —$T^0$, —$C_{1-3}$ alkylene-$T^0$, —$(CH_2)_n$—$CF_3$, —$(CH_2)_n$—$CHF_2$, —$(CH_2)_n$—$CH_2F$, —C(O)—$C_{1-3}$ alkyl, —C(O)—$C_{2-4}$ alkenyl, —C(O)—$(CH_2)_n$—$CF_3$, —C(O)—$(CH_2)_n$—$CHF_2$, —C(O)—$(CH_2)_n$—$CH_2F$, —C(O)—$T^0$, —C(O)—$C_{1-3}$ alkylene-$T^0$, —$C_{2-4}$ alkylene-$OCH_3$ or —$C_{2-6}$ alkylene-$CH_3$, wherein the $C_{2-6}$ alkylene is optionally inserted by 0 and/or optionally substituted by one or more —$C_{1-3}$ alkyl;

alternatively, $R^a$ and $R^b$, together with the nitrogen atoms they are attached to, form an unsubstituted or substituted 4- to 6-membered heterocycloalkyl, wherein the 4- to 6-membered heterocycloalkyl is a heterocycloalkyl in which the heteroatom(s) is/are one N, two N, or one N and one O;

more preferably, $R^a$ and $R^b$ are each independently methyl, ethyl, propyl, —$C_{1-4}$ alkylene-OH, —$C_{2-4}$alkylene-$OCH_3$ or

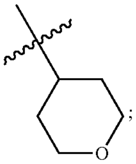 [SMILES: *C1CCOCC1];

most preferably, $R^a$ and $R^b$ are each independently methyl, ethyl, propyl or

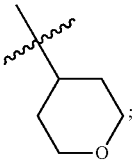;

$T^0$ is unsubstituted or $T^1$-substituted —$C_{3-8}$ cycloalkyl, 4- to 6-membered heterocycloalkyl, phenyl or 5- to 6-membered heteroaryl, in case that $T^0$ is 4- to 6-membered heterocycloalkyl or 5- to 6-membered heteroaryl, if the heteroatom is N, then the N is unsubstituted or $T^2$-substituted; preferably, $T^0$ is

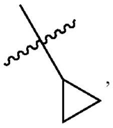, 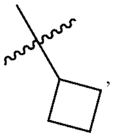, 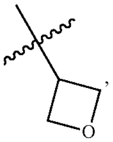, 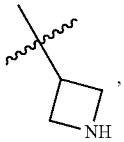, 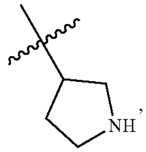, 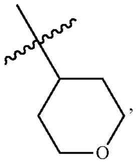 [SMILES: *C1CCOCC1], 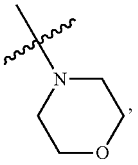, 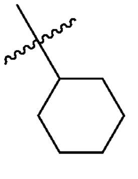 or 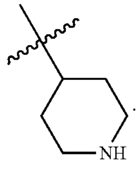.

$T^1$ is halogen, —$C_{1-6}$ alkyl, —$C_{1-3}$ alkoxy, —$C_{1-6}$ alkyl substituted by —$C_{1-3}$ alkyl, or —$NR^0$Rd; $T^1$ is preferably —F, methyl, ethyl, propyl, —$C_{1-3}$ alkoxy, —$C_{2-3}$ alkyl substituted by —$C_{1-2}$ alkyl, or —$NR^0R^d$;

$T^2$ is —$C_{1-4}$ alkyl, —$C_{2-4}$ alkyl substituted by —$C_{1-3}$ alkyl, —$C_{1-4}$ alkylene-OH, —$C_{3-6}$ cycloalkyl, 4- to 6-membered heterocycloalkyl, —$(CH_2)_n$—$CF_3$, —$(CH_2)_n$—$CHF_2$, —$(CH_2)_n$—$CH_2F$, —C(O)—$C_{1-3}$ alkyl, —C(O)—$C_{2-4}$ alkenyl, —C(O)—$(CH_2)_n$—$CF_3$, —C(O)—$(CH_2)_n$—$CHF_2$, —C(O)—$(CH_2)_n$—$CH_2F$, tert-butoxycarbonyl, —S(O)$_2$—$C_{1-3}$ alkyl, —S(O)$_2$—(CH$_2$)$_n$—CF$_3$ or —S(O)$_2$—(CH$_2$)$_n$—CHF$_2$;

n is 1, 2, 3 or 4;

$R^3$ is —H, —$C_{1-4}$ alkyl or substituted —$C_{1-4}$ alkyl, wherein the substituted —$C_{1-4}$ alkyl is optionally substituted by one or more of hydroxyl, carboxyl and —C(O)O—R', preferably $R^3$ is —H or —$C_{1-4}$ alkyl, more preferably $R^3$ is —H, methyl or ethyl;

$R^e$ is —$C_{1-6}$ alkyl, —$C_{2-6}$ alkenyl, —$C_{2-6}$ alkynyl, —$C_{3-8}$ cycloalkyl or —$C_{4-10}$ heterocycloalkyl;

$R^4$ and $R^5$ are each independently —$C_{1-6}$ alkyl;

$R^{5a}$ is —$C_{1-6}$ alkyl or —$C_{1-6}$ alkoxy, preferably $R^{5a}$ is —$C_{1-2}$ alkyl or —$C_{1-2}$ alkoxy;

$R^6$ is —$C_{1-6}$ alkyl, 5- to 6-membered cycloalkyl, 5- to 6-membered heterocycloalkyl or bicyclic group with 8 to 10 carbon atoms, wherein the heteroatom of the 5- to 6-membered heterocycloalkyl is selected from the group consisting of N, S and O, the rings of the bicyclic group are fused connected, each ring of the bicyclic group is saturated, unsaturated or aromatic, the cycloalkyl, heterocycloalkyl or bicyclic group with 8 to 10 carbon atoms are unsubstituted or substituted by one or more $R^{6a}$, in which $R^{6a}$ is halogen, hydroxy, —$C_{1-3}$ alkyl, —$C_{1-3}$ alkoxy, 3- to 6-membered cycloalkyl, 4- to 6-membered heterocycloalkyl, —$NR^hR^k$, —C(O)—$C_{1-3}$ alkyl, —C(O)—$C_{3-6}$ cycloalkyl, —S(O)$_2$—$C_{1-3}$ alkyl, —(CH$_2$)$_n$—CF$_3$ or —S(O)$_2$—$C_{3-6}$ cycloalkyl;

in case that $R^6$ is a sulphureous heterocyclic group containing one sulfur atom, the sulfur heteroatom is not oxidized, or is oxidized by two oxygen-containing groups to form a sulphone group;

in case that $R^6$ is a nitrogenous heterocyclic group containing one nitrogen atom, the nitrogen atom is unsubstituted or substituted by $R^{6b}$, in which $R^{6b}$ is —$C_{1-4}$ alkyl, —$C_{2-4}$ alkyl substituted by —$C_{1-3}$ alkyl, —$C_{1-4}$ alkyl-OH, —$C_{3-8}$ cycloalkyl, 4- to 6-membered heterocycloalkyl, —C(O)—$C_{1-3}$ alkyl, —C(O)—$C_{3-6}$ cycloalkyl, —(CH$_2$)$_n$—CF$_3$, —S(O)$_2$—$C_{1-3}$ alkyl or —S(O)$_2$—$C_{3-6}$ cycloalkyl;

more preferably, $R^{6b}$ is —$C_{1-3}$ alkyl, —$C_{2-3}$ alkyl substituted by —$C_{1-2}$ alkyl, —$C_{3-6}$ cycloalkyl, 4- to 6-membered heterocycloalkyl, —C(O)—$C_{1-3}$ alkyl, —C(O)—$C_{3-6}$ cycloalkyl, —(CH$_2$)$_n$—CF$_3$, —S(O)$_2$—$C_{1-3}$ alkyl or —S(O)$_2$—$C_{3-6}$ cycloalkyl, wherein the heteroatom of the 4- to 6-membered heterocycloalkyl is selected from more preferably, $R^6$ is methyl, ethyl, propyl,

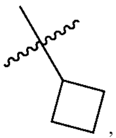
,
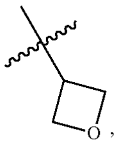
,
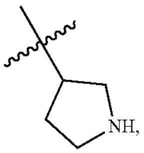
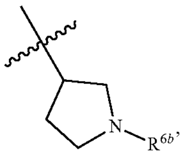
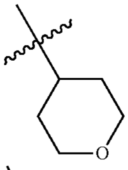
,
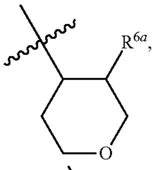
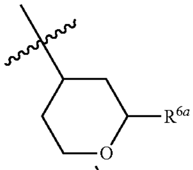
,
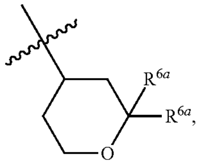
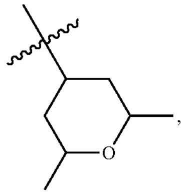
,
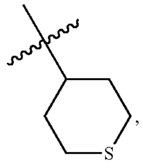
, -continued

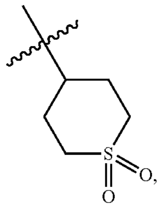
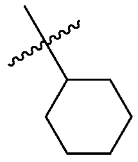
,
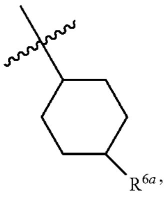
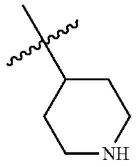
,
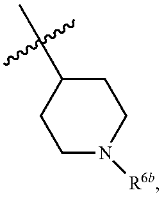
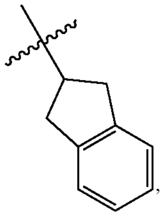
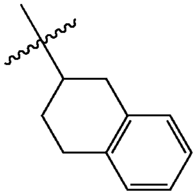
,
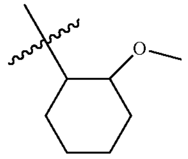
or
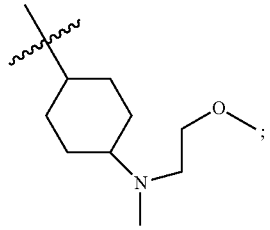

most preferably, $R^6$ is methyl, ethyl, propyl,

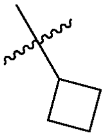
,
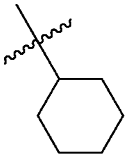
,
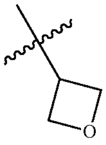
,
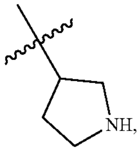
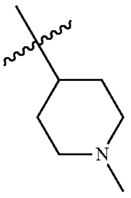
,
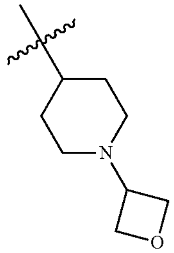
,
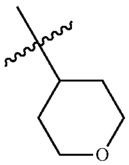
,
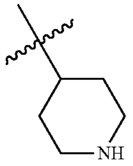
,
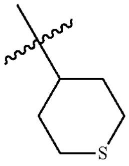
,
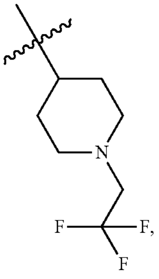

-continued

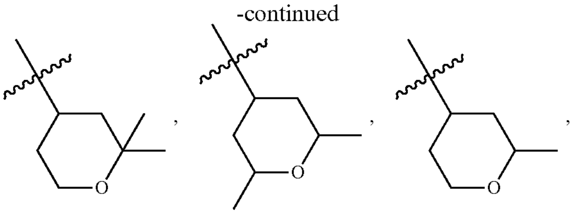

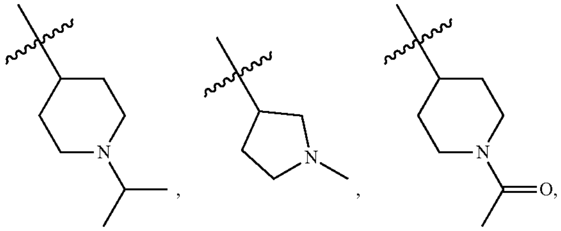

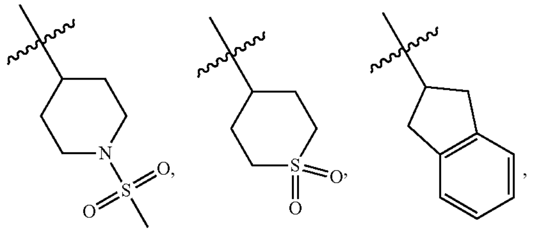

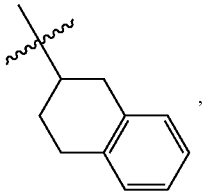

or

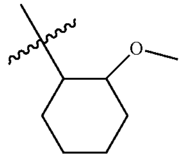

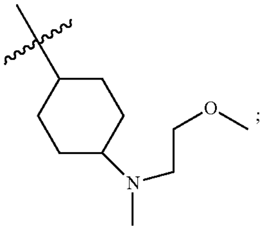

$R^h$ and $R^k$ and are each independently —H, —$C_{1-3}$ alkyl, —$C_{1-4}$ alkylene-OH, —$T^0$, —$C_{1-3}$ alkylene-$T^0$, —$(CH_2)_n$—$CF_3$, —$(CH_2)_n$—$CHF_2$, —$(CH_2)_n$—$CH_2F$, —C(O)—$C_{1-3}$ alkyl, —C(O)—$C_{2-4}$ alkenyl, —C(O)—$(CH_2)_n$—$CF_3$, —C(O)—$(CH_2)_n$—$CHF_2$, —C(O)—$(CH_2)_n$—$CH_2F$, —C(O)—$T^0$, —C(O)—$C_{1-3}$ alkylene-$T^0$, —$C_{2-4}$ alkylene-$OCH_3$ or —$C_{2-6}$ alkylene-$CH_3$, wherein the —$C_{2-6}$ alkylene is optionally inserted by O and/or optionally substituted by one or more —$C_{1-3}$ alkyl;

$R^h$ and $R^k$, optionally together with the nitrogen atoms they are attached to, form a unsubstituted 4- to 6-membered heterocycloalkyl, or a 4- to 6-membered heterocycloalkyl substituted by one or two T groups, wherein T is halogen, —$C_{1-4}$ alkyl, —$C_{2-4}$ alkyl substituted by —$C_{1-3}$ alkyl, or —$NR^0R^d$, wherein the $R^0$ and $R^d$ are each independently —H, —$C_{1-3}$ alkyl, —$C_{1-4}$ alkylene-OH, —$C_{2-4}$ alkylene-$OCH_3$ or —$C_{2-6}$ alkylene-$CH_3$, and wherein —$C_{2-6}$ alkylene is optionally inserted by O and/or optionally substituted by one or more —$C_{1-3}$ alkyl;

$R^1$ and $R^k$ are preferably each independently —H, —$C_{1-3}$ alkyl, —$C_{2-3}$ alkylene-OH or —$C_{2-6}$ alkylene-$CH_3$, wherein the —$C_{2-6}$ alkylene is optionally inserted by O and/or optionally substituted by one or more —$C_{1-3}$ alkyl.

The Synthesis Process of the Compounds Provided by the Present Invention

The compounds represented by the general formula of the present invention can be synthesized according to a variety of reaction schemes, and those skilled in the art can easily design reaction schemes for other compounds through some of the preparation methods provided in the Examples herein.

The present invention relates to a preparation method of the compound represented by formula (I) or pharmaceutically acceptable salts thereof.

Scheme I

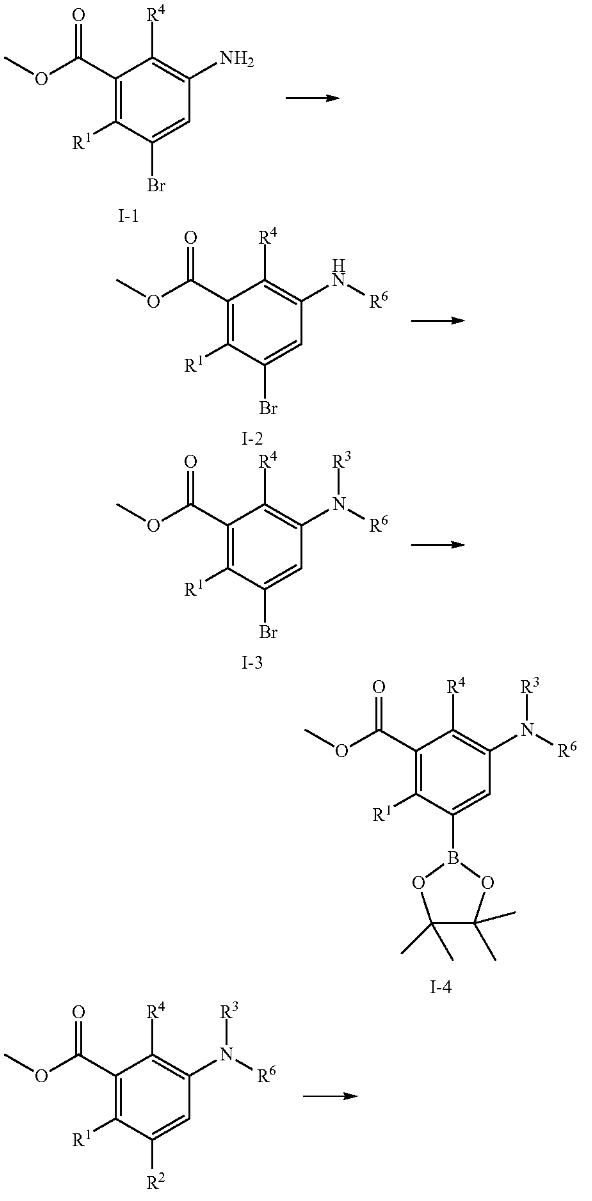

I-1 I-2 I-3 I-4 I-5

-continued

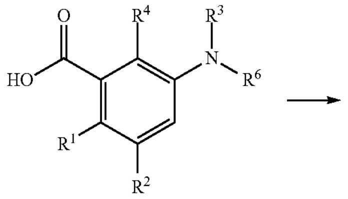

I-6

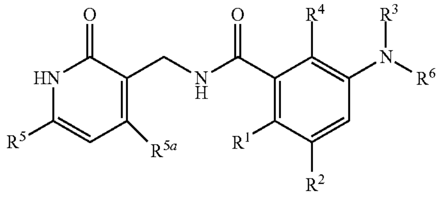

I-7

Reacting a compound represented by general formula (I-1) with ketone compound K1 through a reductive amination reaction to obtain a compound represented by general formula (I-2), wherein, K1 is $C_{1-3}$ alkyl-C(O)—$C_{1-3}$ alkyl, 4- to 6-membered oxocycloalkyl, 4- to 6-membered oxo-heterocycloalkyl, or oxobicyclic group with 8 to 10 carbon atoms, in which the heteroatom of the 4- to 6-membered heterocycloalkyl is selected from the group consisting of N, S and O, the rings of the bicyclic group are fused connected, each ring of the bicyclic group is saturated, unsaturated or aromatic, the oxo-cycloalkyl, oxo-heterocycloalkyl or oxo-bicyclic group with 8 to 10 carbon atoms are unsubstituted or are substituted by one or more $R^{6a}$ groups, in which $R^{6a}$ is halogen, hydroxy, —$C_{1-3}$ alkyl, —$C_{1-3}$ alkoxy, 3- to 6-membered cycloalkyl, 4- to 6-membered heterocycloalkyl, —$NR^hR^k$, —C(O)—$C_{1-3}$ alkyl, —C(O)—$C_{3-6}$ cycloalkyl, —$S(O)_2$—$C_{1-3}$ alkyl, —$(CH_2)_n$—$CF_3$ or —$S(O)_2$—$C_{3-6}$ cycloalkyl; K1 is preferably $C_{1-3}$ alkyl-C(O)—$C_{1-3}$ alkyl,

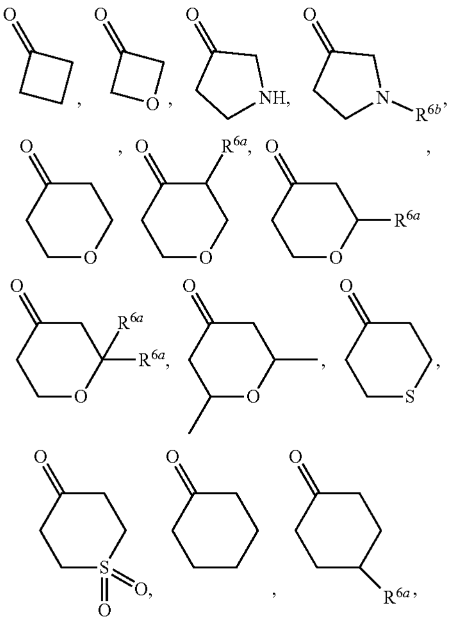

-continued

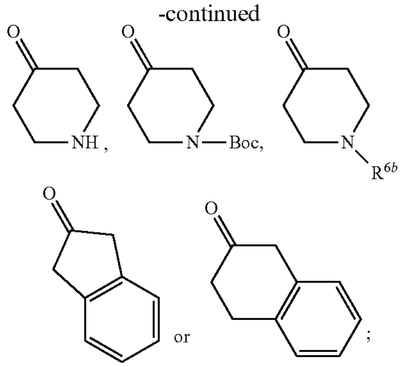

reacting the compound represented by general formula (I-2) with an aldehyde $R^7$—CHO through a reductive amination reaction in the present of a reductant, which can be sodium borohydride acetate, to obtain a compound represented by general formula (I-3), wherein $R^7$ is —H, —$C_{1-4}$ alkyl or substituted —$C_{1-4}$ alkyl, wherein the substituted —$C_{1-4}$ alkyl is optionally substituted by one or more of hydroxyl, preferably R is —H or —$C_{1-3}$ alkyl; reacting the compound represented by general formula (I-3) with a bis(pinacolato) diboron compound under a condition of heating, alkalinity, and the presence of a catalyst, to obtain a compound represented by general formula (I-4), wherein the alkaline condition can be provided by a reagent of potassium acetate, and the catalyst can be [1,1'-bis(diphenylphosphino)ferrocene]dichloropalladium; reacting the compound represented by general formula (I-4) with a corresponding halogenated aryl group ($R^2$—Z) under a condition of heating, alkalinity, and the presence of a catalyst, to obtain a compound represented by general formula (I-5), wherein the alkaline condition can be provided by a reagent of potassium carbonate, cesium carbonate, potassium hydroxide, sodium hydroxide or cesium fluoride, and the catalyst can be [1,1'-bis(diphenylphosphino)ferrocene] dichloropalladium, palladium acetate, tetrakis(triphenylphosphine)palladium or tris(dibenzylideneacetone) dipalladium, and wherein Z is halogen;

hydrolyzing the compound represented by general formula (I-5) under an alkaline condition to obtain a compound represented by general formula (I-6), wherein the alkaline condition can be provided by a reagent of sodium hydroxide; reacting the compound represented by general formula (1-6) with a corresponding amine

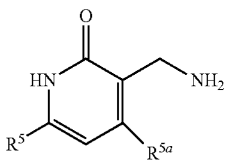

through a condensation reaction to obtain a compound represented by general formula (I-7).

Scheme II

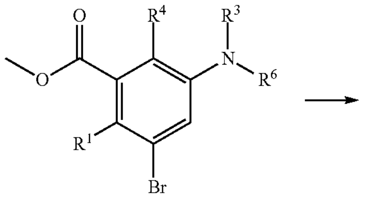

I-3

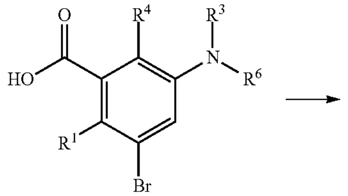

II-1

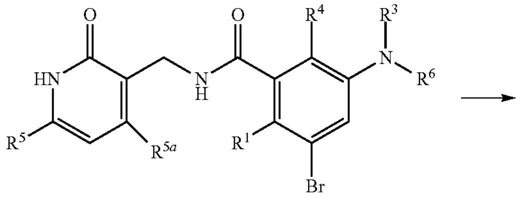

II-2

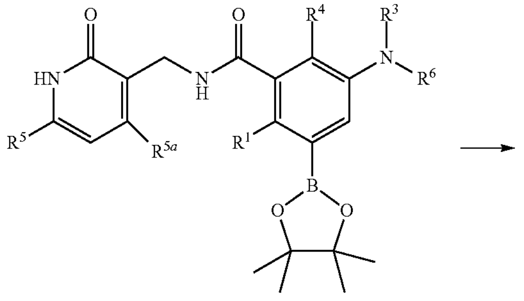

II-3

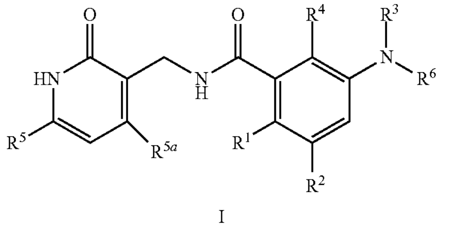

I

Hydrolyzing the compound represented by general formula (I-3) under a condition of heating and alkaline to obtain a compound represented by general formula (II-1), wherein the alkaline condition can be provided by a reagent selected from sodium hydroxide, potassium hydroxide, potassium carbonate, sodium carbonate and cesium carbonate; reacting the compound represented by general formula (II-1) with a corresponding amine

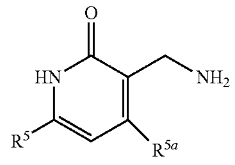

through a condensation reaction to obtain a compound represented by general formula (II-2); reacting the compound represented by general formula (II-2) with a bis (pinacolato)diboron compound under a condition of heating, alkalinity, and the presence of a catalyst, to obtain a compound represented by general formula (II-3), wherein the alkaline condition can be provided by a reagent of potassium acetate, and the catalyst can be [1,1'-bis(diphenylphosphino) ferrocene]dichloropalladium; reacting the compound represented by general formula (II-3) with a corresponding halogenated aryl group ($R^2$—Z) under a condition of heating, alkalinity, and the presence of a catalyst, to obtain a compound represented by general formula (I), wherein the alkaline condition can be provided by a reagent selected from potassium carbonate, cesium carbonate, potassium hydroxide, sodium hydroxide and cesium fluoride, and the catalyst can be preferably [1,1'-bis(diphenylphosphino)ferrocene]dichloropalladium, palladium acetate, tetrakis(triphenylphosphine)palladium or tris(dibenzylideneacetone)dipalladium.

Scheme III

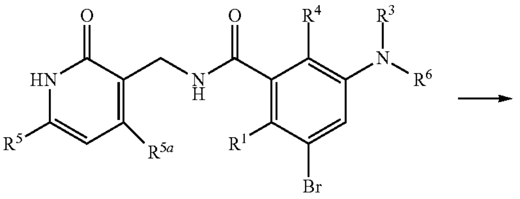

II-2

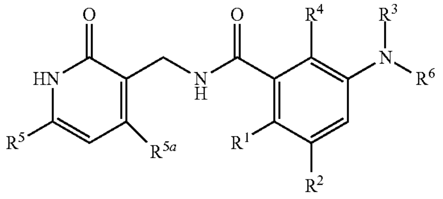

I

Reacting the compound represented by general formula (II-2) with a corresponding arylboronate

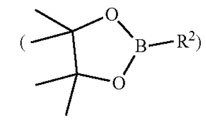

under a condition of heating, alkalinity, and the presence of a catalyst, to obtain a compound represented by general formula (I), wherein the alkaline condition can be provided by a reagent selected from potassium carbonate, cesium carbonate, potassium hydroxide, sodium hydroxide and cesium fluoride, the catalyst can be [1,1'-bis(diphenylphosphino)ferrocene]dichloropalladium, palladium acetate, tetrakis(triphenylphosphine)palladium or tris(dibenzylideneacetone)dipalladium; the reagent that provide the alkaline condition includes organic bases and inorganic bases, wherein the organic bases comprise, but not limited to, triethylamine, 4-dimethylaminopyridine, N,N-diisopropylethylamine, pyridine, potassium acetate, sodium tert-butoxide and potassium tert-butoxide, and the inorganic bases comprise sodium hydride, potassium phosphate, sodium carbonate, potassium carbonate, cesium carbonate, calcium carbonate and cesium fluoride. The catalysts involved comprise, but not limited to, tris(dibenzylideneacetone)dipalladium, 4,5-bis(diphenylphosphino)-9,9-dimethylxanthene, palladium acetate, tetrakis(triphenylphosphine)palladium, [1,1'-bis(diphenylphosphino)ferrocene]dichloropalladium, 2-dicyclohexylphosphino-2,4,6-triisopropylbiphenyl, 1,10-phenanthroline and cuprous iodide.

According to the compounds represented by formula (I) or pharmaceutically acceptable salts thereof, the specific compounds are as follows:

N-((4,6-dimethyl-2-oxo-1,2-dihydropyridin-3-yl)methyl)-3-(ethyl(1-methylpiperidin-4-yl)amino)-2-methyl-5-(2-oxo-2',3',5',6'-tetrahydrospiro[dihydroindole-3,4'-pyran]-6-yl)benzamide 5-(1-acetyl-2',3',5',6'-tetrahydrospiro[dihydroindole-3,4'-pyran]-6-yl)-3-(ethyl(tetrahydro-2H-pyran-4-yl)amino)-N-((4-methoxy-6-methyl-2-carbonyl-1,2-dihydropyridin-3-yl)methyl)-2-methylbenzamide N-((4,6-dimethyl-2-oxo-1,2-dihydropyridin-3-yl)methyl)-3-(ethyl(tetrahydro-2H-pyran-4-yl)amino)-2-methyl-5-(2-oxo-2',3',5',6'-tetrahydrospiro[dihydroindole-3,4'-pyran]-6-yl)benzamide 3-(ethyl(tetrahydro-2H-pyran-4-yl)amino)-N-((4-methoxy-6-methyl-2-oxo-1,2-dihydropyridin-3-yl)methyl)-2-methyl-5-(1'-methyl-2-oxospiro[dihydroindole-3,4'-piperidine]-6-yl)benzamide 3-(ethyl(piperidin-4-yl)amino)-N-((4-methoxy-6-methyl-2-oxo-1,2-dihydropyridin-3-yl)methyl)-2-methyl-5-(2',3',5',6'-tetrahydrospiro[indoline-3,4'-pyran]-6-yl)benzamide N-((4,6-dimethyl-2-oxo-1,2-dihydropyridin-3-yl)methyl)-3-(ethyl(piperidin-4-yl)amino)-2-methyl-5-(2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1'-methylspiro[dihydroindole-3,4'-piperidine]-6-yl)benzamide 3-(ethyl(tetrahydro-2H-pyran-4-yl)amino)-5-(6-fluoro-2',3',5',6'-tetrahydrospiro[indene-1,4'-pyran]-5-yl)-N-((4-methoxy-6-methyl-2-oxo-1,2-dihydropyridin-3-yl)methyl)-2-methylbenzamide 3-(ethyl(tetrahydro-2H-pyran-4-yl)amino)-5-(5-fluoro-2',3',5',6'-tetrahydrospiro[indene-1,4'-pyran]-6-yl)-N-((4-methoxy-6-methyl-2-oxo-1,2-dihydropyridin-3-yl)methyl)-2-methylbenzamide 3-(ethyl(tetrahydro-2H-pyran-4-yl)amino)-5-(6-fluoro-2,2',3,3',5',6'-hexahydrospiro[indene-1,4'-pyran]-5-yl)-N-((4-methoxy-6-methyl-2-oxo-1,2-dihydropyridin-3-yl)methyl)-2-methylbenzamide 3-(ethyl(tetrahydro-2H-pyran-4-yl)amino)-5-(5-fluoro-2,2',3,3',5',6'-hexahydrospiro[indene-1,4'-pyran]-6-yl)-N-((4-methoxy-6-methyl-2-oxo-1,2-dihydropyridin-3-yl)methyl)-2-methylbenzamide 2-chloro-N-((4,6-dimethyl-2-oxo-1,2-dihydropyridin-3-yl)methyl)-5-(ethyl(tetrahydro-2H-pyran-4-yl)amino)-6-methyl-3-(1-methyl-2-oxo-2',3',5',6'-tetrahydrospiro[dihydroindole-3,4'-pyran]-6-yl)benzamide 2-chloro-N-((4,6-dimethyl-2-carbonyl-1,2-dihydropyridin-3-yl)methyl)-5-(ethyl(tetrahydro-2H-pyran-4-yl)amino)-3-(1-isopropyl-2',3',5',6'-tetrahydrospiro[dihydroindole-3,4'-pyran]-6-yl)-6-methylbenzamide N-((4,6-dimethyl-2-carbonyl-1,2-dihydropyridin-3-yl)methyl)-3-(ethyl(tetrahydro-2H-pyran-4-yl)amino)-5-(5-fluoro-1-methyl-2-carbonyl-2',3',5',6'-tetrahydrospiro[dihydroindole-3,4'-pyran]-6-yl)-2-methylbenzamide N-((4,6-dimethyl-2-carbonyl-1,2-dihydropyridin-3-yl)methyl)-3-(ethyl(tetrahydro-2H-pyran-4-yl)amino)-2-methyl-5-(2-carbonyl-1-(2,2,2-trifluoroethyl)-2',3',5',6'-tetrahydrospiro[dihydroindole-3,4'-pyran]-6-yl)benzamide N-((4,6-dimethyl-2-carbonyl-1,2-dihydropyridin-3-yl)methyl)-3-(ethyl(tetrahydro-2H-pyran-4-yl)amino)-2-methyl-5-(2-carbonyl-1-(3,3,3-trifluoropropyl)-2',3',5',6'-tetrahydrospiro[dihydroindole-3,4'-pyran]-6-yl)benzamide N-((4,6-dimethyl-2-carbonyl-1,2-dihydropyridin-3-yl)methyl)-3-(ethyl(tetrahydro-2H-pyran-4-yl)amino)-5-(1'-isopropyl-1-methyl-2-carbonylspiro[dihydroindole-3,4'-piperidine]-6-yl)-2-methylbenzamide 3-(ethyl(tetrahydro-2H-pyran-4-yl)amino)-5-(5-fluoro-2,2',3,3',5',6'-hexahydrospiro[indene-1,4'-pyran]-6-yl)-N-((4-methoxy-6-methyl-2-carbonyl-1,2-dihydropyridin-3-yl)methyl)-2-methylbenzamide 3-(ethyl(tetrahydro-2H-pyran-4-yl)amino)-5-(6-fluoro-2,2',3,3',5',6'-hexahydrospiro[indene-1,4'-pyran]-5-yl)-N-((4-methoxy-6-methyl-2-carbonyl-1,2-dihydropyridin-3-yl)methyl)-2-methylbenzamide N-((4,6-dimethyl-2-carbonyl-1,2-dihydropyridin-3-yl)methyl)-3-(ethyl(tetrahydro-2H-pyran-4-yl)amino)-5-(1-ethyl-2-carbonyl-2',3',5',6'-tetrahydrospiro[dihydroindole-3,4'-pyran]-6-yl)-2-methylbenzamide N-((4,6-dimethyl-2-carbonyl-1,2-dihydropyridin-3-yl)methyl)-3-(ethyl(tetrahydro-2H-pyran-4-yl)amino)-2-methyl-5-(2-carbonyl-1-propyl-2',3',5',6'-tetrahydrospiro[dihydroindole-3,4'-pyran]-6-yl)benzamide N-((4,6-dimethyl-2-carbonyl-1,2-dihydropyridin-3-yl)methyl)-3-(ethyl(tetrahydro-2H-pyran-4-yl)amino)-2-methyl-5-(1-(2,2,2-trifluoroethyl)-2',3',5',6'-tetrahydrospiro[dihydroindole-3,4'-pyran]-6-yl)benzamide N-((4,6-dimethyl-2-carbonyl-1,2-dihydropyridin-3-yl)methyl)-3-(ethyl(tetrahydro-2H-pyran-4-yl)amino)-5-(1'-ethyl-1-methyl-2-carbonylspiro[dihydroindole-3,4'-piperidine]-6-yl)-2-methylbenzamide N-((4,6-dimethyl-2-carbonyl-1,2-dihydropyridin-3-yl)methyl)-3-(ethyl(tetrahydro-2H-pyran-4-yl)amino)-2-methyl-5-(1-methyl-1'-(2,2,2-trifluoroethyl)spiro[dihydroindole-3,4'-piperidine]-6-yl)benzamide N-((4,6-dimethyl-2-carbonyl-1,2-dihydropyridin-3-yl)methyl)-3-(ethyl(tetrahydro-2H-pyran-4-yl)amino)-5-(6-fluoro-2,2',3,3',5',6'-hexahydrospiro[indene-1,4'-pyran]-5-yl)-2-methylbenzamide N-((4,6-dimethyl-2-carbonyl-1,2-dihydropyridin-3-yl)methyl)-3-(ethyl(tetrahydro-2H-pyran-4-yl)amino)-5-(5-fluoro-2,2',3,3',5',6'-hexahydrospiro[indene-1,4'-pyran]-6-yl)-2-methylbenzamide N-((4,6-dimethyl-2-carbonyl-1,2-dihydropyridin-3-yl)methyl)-3-(ethyl(tetrahydro-2H-pyran-4-yl)amino)-5-(1-isopropyl-2',3',5',6'-tetrahydrospiro[dihydroindole-3,4'-pyran]-6-yl)-2-methylbenzamide N-((4,6-dimethyl-2-oxo-1,2-dihydropyridin-3-yl)methyl)-3-(ethyl(tetrahydro-2H-pyran-4-yl)amino)-2-methyl-5-(1-(3,3,3-trifluoropropyl)-2',3',5',6'-tetrahydrospiro[indoline-3,4'-pyran]-6-yl)benzamide N-((4,6-dimethyl-2-carbonyl-1,2-dihydropyridin-3-yl)methyl)-3-(ethyl(tetrahydro-2H-pyran-4-yl)amino)-2-methyl-5-(1-methyl-2-carbonyl-1'-(2,2,2-trifluoroethyl)spiro[dihydroindole-3,4'-piperidine]-6-yl)benzamide N-((4,6-dimethyl-2-carbonyl-1,2-dihydropyridin-3-yl)methyl)-5-(1,1'-dimethyl-2-carbonylspiro[dihydroindole-3,4'-piperidine]-6-yl)-3-(ethyl(tetrahydro-2H-pyran-4-yl)amino)-2-methylbenzamide N-((4,6-dimethyl-2-carbonyl-1,2-dihydropyridin-3-yl)methyl)-3-(ethyl(tetrahydro-2H-pyran-4-yl)amino)-2-methyl-5-(1-neopentyl-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-5-(1'-ethyl-1-methylspiro[dihydroindole-3,4'-piperidine]-6-yl)-2-methylbenzamide N-((4,6-dimethyl-2-oxo-1,2-dihydropyridin-3-yl)methyl)-3-(ethyl(tetrahydro-2H-pyran-4-yl)amino)-2-methyl-5-(1-propyl-2-oxo-2',3',5',6'-tetrahydrospiro[dihydroindole-3,4'-pyran]-6-yl)benzamide methyl 6-(3-(((4,6-dimethyl-2-carbonyl-1,2-dihydropyridin-3-yl)methyl)carbamoyl)-5-(ethyl(tetrahydro-2H-pyran-4-yl)amino)-4-methylphenyl)-1-methyl-2-carbonylspiro[dihydroindole-3,4'-piperidine]-1'-carboxylate methyl 6-(3-(((4,6-dimethyl-2-carbonyl-1,2-dihydropyridin-3-yl)methyl)carbamoyl)-5-(ethyl(tetrahydro-2H-pyran-4-yl)amino)-4-methylphenyl)-1-methylspiro[dihydroindole-3,4'-piperidine]-1'-carboxylate 3-(ethyl(tetrahydro-2H-pyran-4-yl)amino)-N-((4-methoxy-6-methyl-2-carbonyl-1,2-dihydropyridin-3-yl)methyl)-2-methyl-5-(1-methyl-2-carbonylspiro[dihydroindole-3,4'-piperidine]-6-yl)benzamide 3-(ethyl(tetrahydro-2H-pyran-4-yl)amino)-N-((4-methoxy-6-methyl-2-oxo-1,2-dihydropyridin-3-yl)methyl)-2-methyl-5-(1'-(2,2,2-trifluoroethyl)spiro[indene-1,4'-piperidine]-5-yl)benzamide 3-(ethyl(tetrahydro-2H-pyran-4-yl)amino)-N-((4-methoxy-6-methyl-2-oxo-1,2-dihydropyridin-3-yl)methyl)-2-methyl-5-(1'-(2,2,2-trifluoroethyl)-2,3-dihydrospiro[indene-1,4'-piperidine]-5-yl)benzamide 3-(ethyl(tetrahydro-2H-pyran-4-yl)amino)-N-((4-methoxy-6-methyl-2-carbonyl-1,2-dihydropyridin-3-yl)methyl)-2-methyl-5-(1'-(2,2,2-trifluoroethyl)-2,3-dihydrospiro[indene-1,4'-piperidine]-6-yl)benzamide 3-(ethyl(tetrahydro-2H-pyran-4-yl)amino)-5-(1'-isopropylspiro[indene-1,4'-piperidine]-5-yl)-N-((4-methoxy-6-methyl-2-carbonyl-1,2-dihydropyridin-3-yl)methyl)-2-methylbenzamide N-((4,6-dimethyl-2-oxo-1,2-dihydropyridin-3-yl)methyl)-3-(ethyl(tetrahydro-2H-pyran-4-yl)amino)-5-(1-ethyl-2',3',5',6'-tetrahydrospiro[dihydroindole-3,4'-pyran]-6-yl)-2-methylbenzamide N-((4,6-dimethyl-2-oxo-1,2-dihydropyridin-3-yl)methyl)-3-(ethyl(tetrahydro-2H-pyran-4-yl)amino)-2-methyl-5-(2-oxo-1-(2,2,3,3,3-pentafluoropropyl)-2',3',5',6'-tetrahydrospiro[dihydroindole-3,4'-pyran]-6-yl)benzamide 3-(ethyl(1-(2,2,2-trifluoroethyl)piperidin-4-yl)amino)-N-((4-methoxy-6-methyl-2-carbonyl-1,2-dihydropyridin-3-yl)methyl)-2-methyl-5-(1-methyl-2',3',5',6'-tetrahydrospiro[dihydroindole-3,4'-pyran]-6-yl)benzamide 3-(ethyl(tetrahydro-2H-pyran-4-yl)amino)-N-((4-methoxy-6-methyl-2-oxo-1,2-dihydropyridin-3-yl)methyl)-2-methyl-5-(2-oxo-1-(2,2,2-trifluoroethyl)spiro[dihydroindole-3,4'-piperidine]-6-yl)benzamide 3-(ethyl(tetrahydro-2H-pyran-4-yl)amino)-N-((4-methoxy-6-methyl-2-carbonyl-1,2-dihydropyridin-3-yl)methyl)-2-methyl-5-(1'-(2,2,3,3,3-pentafluoropropyl)-2,3-dihydrospiro[indene-1,4'-piperidine]-5-yl)benzamide 3-(ethyl(tetrahydro-2H-pyran-4-yl)amino)-N-((4-methoxy-6-methyl-2-carbonyl-1,2-dihydropyridin-3-yl)methyl)-2-methyl-5-(1'-(2,2,3,3,3-pentafluoropropyl)-2,3-dihydrospiro[indene-1,4'-piperidine]-6-yl)benzamide 3-((2,2-dimethyltetrahydro-2H-pyran-4-yl)(ethyl)amino)-5-(2,2',3,3',5',6'-hexahydrospiro[indene-1,4-pyran]-5-yl)-N-((4-methoxy-6-methyl-2-oxo-1,2-dihydropyridin-3-yl)methyl)-2-methylbenzamide N-((4,6-dimethyl-2-oxo-1,2-dihydropyridin-3-yl)methyl)-3-(ethyl(tetrahydro-2H-pyran-4-yl)amino)-2-methyl-5-(1-methyl-2-oxo-1'-(2,2,3,3,3-pentafluoroethyl)spiro[dihydroindole-3,4'-piperidine]-6-yl)benzamide N-((4,6-dimethyl-2-oxo-1,2-dihydropyridin-3-yl)methyl)-3-(ethyl(tetrahydro-2H-pyran-4-yl)amino)-5-(1-(2-methoxyethyl)-2-oxo-2',3',5',6'-tetrahydrospiro[dihydroindole-3,4'-pyran]-6-yl)-2-methylbenzamide 2-chloro-N-((4,6-dimethyl-2-carbonyl-1,2-dihydropyridin-3-yl)methyl)-5-(ethyl(tetrahydro-2H-pyran-4-yl)amino)-6-methyl-3-(2-carbonyl-1-propyl-2',3',5',6'-tetrahydrospiro[dihydroindole-3,4'-pyran]-6-yl)benzamide 2-chloro-N-((4,6-dimethyl-2-oxo-1,2-dihydropyridin-3-yl)methyl)-5-(ethyl(tetrahydro-2H-pyran-4-yl)amino)-3-(1-ethyl-2-oxo-2',3',5',6'-tetrahydrospiro[dihydroindole-3,4'-pyran]-6-yl)-6-methylbenzamide 2-chloro-5-(ethyl(tetrahydro-2H-pyran-4-yl)amino)-3-(1-isopropyl-2,3,5,6-tetrahydrospiro[dihydroindole-3,4-pyran]-6-yl)-N-((4-methoxy-6-methyl-2-oxo-1,2-dihydropyridin-3-yl)methyl)-6-methylbenzamide 3-(ethyl(tetrahydro-2H-pyran-4-yl)amino)-5-(1'-ethyl-2',6'-dimethyl-2,3-dihydrospiro[indene-1,4'-piperidine]-6-yl)-N-((4-methoxy-6-methyl-2-oxo-1,2-dihydropyridin-3-yl)methyl)-2-methylbenzamide formate N-((4,6-dimethyl-2-oxo-1,2-dihydropyridin-3-yl)methyl)-3-(ethyl(tetrahydro-2H-pyran-4-yl)amino)-2-methyl-5-(1-(2,2,3,3,3-pentafluoropropyl)-2',3',5',6'-tetrahydrospiro[dihydroindole-3,4'-pyran]-6-yl)benzamide 2-chloro-5-(ethyl(tetrahydro-2H-pyran-4-yl)amino)-3-(1-isopropyl-2-oxo-2',3',5',6'-tetrahydrospiro[dihydroindole-3-1,4'-pyran]-6-yl)-N-((4-methoxy-6-methyl-2-oxo-1,2-dihydropyridin-3-yl)methyl)-6-methylbenzamide 2-chloro-N-((4,6-dimethyl-2-oxo-1,2-dihydropyridin-3-yl)methyl)-5-(ethyl(tetrahydro-2H-pyran-4-yl)amino)-6-methyl-3-(2-oxo-1-(3,3,3-trifluoropropyl)-2',3',5',6'-tetrahydrospiro[dihydroindole-3,4'-pyran]-6-yl)benzamide 2-chloro-N-((4,6-dimethyl-2-carbonyl-1,2-dihydropyridin-3-yl)methyl)-5-(ethyl(tetrahydro-2H-pyran-4-yl)amino)-3-(1-ethyl-2',3',5',6'-tetrahydrospiro[dihydroindole-3,4'-pyran]-6-yl)-6-methylbenzamide 2-chloro-N-((4,6-dimethyl-2-oxo-1,2-dihydropyridin-3-yl)methyl)-5-(ethyl(tetrahydro-2H-pyran-4-yl)amino)-6-methyl-3-(1-(3-methylbutyl-2-yl)-2',3',5',6'-tetrahydrospiro[dihydroindole-3,4'-pyran]-6-yl)benzamide N-((4,6-dimethyl-2-oxo-1,2-dihydropyridin-3-yl)methyl)-5-(ethyl(tetrahydro-2H-pyran-4-yl)amino)-3-(1'-isopropyl-1-methyl-2-oxospiro[dihydroindole-3,4'-piperidine]-6-yl)-6-methylbenzamide 2-chloro-N-((4,6-dimethyl-2-carbonyl-1,2-dihydropyridin-3-yl)methyl)-5-(ethyl(tetrahydro-2H-pyran-4-yl)amino)-6-methyl-3-(1-propyl-2',3',5',6'-tetrahydrospiro[dihydroindole-3,4'-pyran]-6-yl)benzamide N-((4,6-dimethyl-2-carbonyl-1,2-dihydropyridin-3-yl)methyl)-3-(ethyl(tetrahydro-2H-pyran-4-yl)amino)-6-fluoro-2-methyl-5-(2-carbonyl-1-propyl-2',3',5',6'-tetrahydrospiro[dihydroindole-3,4'-pyran]-6-yl)benzamide N-((4,6-dimethyl-2-carbonyl-1,2-dihydropyridin-3-yl)methyl)-3-(ethyl(tetrahydro-2H-pyran-4-yl)amino)-6-fluoro-2-methyl-5-(1-propyl-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-6-fluoro-5-(1-isopropyl-2-oxo-2',3',5',6'-tetrahydrospiro[dihydroindole-3,4'-pyran]-6-yl)-2-methylbenzamide 2-chloro-N-((4,6-dimethyl-2-oxo-1,2-dihydropyridin-3-yl)methyl)-5-(ethyl(tetrahydro-2H-pyran-4-yl)amino)-3-(1-ethyl-2-oxo-2',3',5',6'-tetrahydrospiro[dihydroindole-3,4'-pyran]-6-yl)-6-methylbenzamide N-((4,6-dimethyl-2-oxo-1,2-dihydropyridin-3-yl)methyl)-3-(ethyl(tetrahydro-2H-pyran-4-yl)amino)-5-(1-ethyl-2-oxo-2',3',5',6'-tetrahydrospiro[dihydroindole-3,4'-pyran]-6-yl)-6-fluoro-2-methylbenzamide N-((4,6-dimethyl-2-oxo-1,2-dihydropyridin-3-yl)methyl)-3-(ethyl(tetrahydro-2H-pyran-4-yl)amino)-6-fluoro-5-(1-isopropyl-2',3',5',6'-tetrahydrospiro[dihydroindole-3,4'-pyran]-6-yl)-2-methylbenzamide 3-((2,2-dimethyltetrahydro-2H-pyran-4-yl)(ethyl)amino)-5-(1-isopropyl-2-carbonyl-2',3',5',6'-tetrahydrospiro[dihydroindole-3,4'-pyran]-6-yl)-N-((4-methoxy-6-methyl-2-carbonyl-1,2-dihydropyridin-3-yl)methyl)-2-methylbenzamide N-((4,6-dimethyl-2-oxo-1,2-dihydropyridin-3-yl)methyl)-3-(ethyl(tetrahydro-2H-pyran-4-yl)amino)-5-(1-isopropyl-2',3',5',6'-tetrahydrospiro[dihydroindole-3,4'-pyran]-6-yl)-2-methylbenzamide N-((4,6-dimethyl-2-oxo-1,2-dihydropyridin-3-yl)methyl)-3-(ethyl(tetrahydro-2H-pyran-4-yl)amino)-2-methyl-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1'-methyl-2-oxospiro[dihydroindole-3,4'-piperidine]-6-yl)benzamide 5-(1'-(cyclopropylmethyl)-2-oxospiro[dihydroindole-3,4'-piperidine]-6-yl)-N-((4,6-dimethyl-2-oxo-1,2-dihydropyridin-3-yl)methyl)-3-(ethyl(tetrahydro-2H-pyran-4-yl)amino)-2-methylbenzamide N-((4,6-dimethyl-2-oxo-1,2-dihydropyridin-3-yl)methyl)-3-(ethyl(tetrahydro-2H-pyran-4-yl)amino)-2-methyl-5-(2'-oxospiro[cyclohexane-1,3'-dihydroindole]-6'-yl)benzamide N-((4,6-dimethyl-2-oxo-1,2-dihydropyridin-3-yl)methyl)-3-(ethyl(tetrahydro-2H-pyran-4-yl)amino)-2-methyl-5-(spiro[cyclohexane-1,3'-dihydroindole]-6'-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1-methyl-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1-methyl-2-oxo-2',3',5',6'-tetrahydrospiro[dihydroindole-3,4'-pyran]-6-yl)benzamide 5-(1'-acetyl-2',3',5',6'-tetrahydrospiro[dihydroindole-3,4'-pyran]-6-yl)-N-((4,6-dimethyl-2-oxo-1,2-dihydropyridin-3-yl)methyl)-3-(ethyl(tetrahydro-2H-pyran-4-yl)amino)-2-methylbenzamide 5-(1-trifluoroacetyl-2',3',5',6'-tetrahydrospiro[dihydroindole-3,4'-pyran]-6-yl)-N-((4,6-dimethyl-2-carbonyl-1,2-dihydropyridin-3-yl)methyl)-3-(ethyl(tetrahydro-2H-pyran-4-yl)amino)-2-methylbenzamide N-((4,6-dimethyl-2-oxo-1,2-dihydropyridin-3-yl)methyl)-3-(ethyl(piperidin-4-yl)amino)-2-methyl-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(2-oxo-2',3',5',6'-tetrahydrospiro[dihydroindole-3,4'-pyran]-5-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1-oxo-1,2',3,3',5',6'-hexahydrospiro[indene-2,4'-pyran]-6-yl)benzamide tert-butyl 6-(3-(((4,6-dimethyl-2-oxo-1,2-dihydropyridin-3-yl)methyl)carbamoyl)-5-(ethyl(tetrahydro-2H-pyran-4-yl)amino)-4-methylphenyl)-2-oxospiro[dihydroindole-3,4'-piperidine]-1'-carboxylate N-((4,6-dimethyl-2-oxo-1,2-dihydropyridin-3-yl)methyl)-3-(ethyl(1-methylpiperidin-4-yl)amino)-2-methyl-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-2-methyl-3-(ethyl(1-(oxetan-3-yl)piperidin-4-yl)amino)-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1-methyl-2-oxo-2',3',5',6'-tetrahydrospiro[dihydroindole-3,4'-pyran]-5-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1'-(oxetan-3-yl)-2-oxospiro[dihydroindole-3,4'-piperidine]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1'-ethyl-2-oxospiro[dihydroindole-3,4'-piperidine]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(2'-oxospiro[cyclopentane-1,3'-dihydroindole]-6'-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1'-methylsulfonyl-2-oxospiro[dihydroindole-3,4'-piperidine]-6-yl)benzamide 5-(1'-acetyl-2-oxospiro[dihydroindole-3,4'-piperidine]-6-yl)-N-((4,6-dimethyl-2-oxo-1,2-dihydropyridin-3-yl)methyl)-3-(ethyl(tetrahydro-2H-pyran-4-yl)amino)-5-(1'-acetyl-2-oxospiro[dihydroindole-3,4'-piperidine]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(2-oxo-2',3',5',6'-tetrahydrospiro[dihydroindole-3,4'-thiapyran]-6-yl)benzamide N-((4,6-dimethyl-2-oxo-1,2-dihydropyridin-3-yl)methyl)-5-(1',1'-dioxo-2-oxo-2',3',5',6'-tetrahydrospiro[dihydroindole-3,4'-thiapyran]-6-yl)-3-(ethyl(tetrahydro-2H-pyran-4-yl)amino)-2-methylbenzamide 5-(4,4-difluoro-2'-oxospiro[cyclohexane-1,3'-dihydroindole]-6'-yl)-N-((4,6-dimethyl-2-oxo-1,2-dihydropyridin-3-yl)methyl)-3-(ethyl(tetrahydro-2H-pyran-4-yl)amino)-2-methylbenzamide N-((4,6-dimethyl-2-oxo-1,2-dihydropyridin-3-yl)methyl)-5-(2',4-dioxospiro[cyclohexane-1,3'-dihydroindole]-6'-yl)-3-(ethyl(tetrahydro-2H-pyran-4-yl)amino)-2-methylbenzamide N-((4,6-dimethyl-2-oxo-1,2-dihydropyridin-3-yl)methyl)-3-(ethyl(tetrahydro-2H-pyran-4-yl)amino)-5-(4-hydroxy-4-methyl-2'-oxospiro[cyclohexane-1,3'-dihydroindole]-6'-yl)-2-methylbenzamide N-((4,6-dimethyl-2-oxo-1,2-dihydropyridin-3-yl)methyl)-3-(ethyl(tetrahydro-2H-pyran-4-yl)amino)-5-(4-hydroxy-2'-oxospiro[cyclohexane-1,3'-dihydroindole]-6'-yl)-2-methylbenzamide N-((4,6-dimethyl-2-oxo-1,2-dihydropyridin-3-yl)methyl)-3-(ethyl(tetrahydro-2H-thiapyran-4-yl)amino)-2-methyl-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-3-((ethyl)(1,1-dioxotetrahydro-2H-thiapyran-4-yl)amino)-2-methyl-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(tetrahydro-2H-thiapyran-4-yl)amino)-2-methyl-5-(2-oxospiro[dihydroindole-3,4'-piperidine]-6-yl)benzamide N-((4,6-dimethyl-2-oxo-1,2-dihydropyridin-3-yl)methyl)-3-((ethyl)(4-dimethylamino-cyclohexyl)amino)-2-methyl-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(4-((2-methoxyethyl)(methyl)amino)cyclohexyl)amino)-2-methyl-5-(2-oxo-2',3',5',6'-tetrahydrospiro[dihydroindole-3,4'-pyran]-6-yl)benzamide N-((ethyl)(4-dimethylamino-cyclohexyl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(2'-oxo-1',2,2',3,5,6-hexahydrospiro[pyran-4,3'-pyrrolo[3,2-b]pyridine]-6'-yl)benzamide N-((4,6-dimethyl-2-oxo-1,2-dihydropyridin-3-yl)methyl)-3-(ethyl(3-methoxytetrahydro-2H-pyran-4-yl)amino)-2-methyl-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(3-fluorotetrahydro-2H-pyran-4-yl)amino)-2-methyl-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(2,6-dimethyltetrahydro-2H-pyran-4-yl)amino)-2-methyl-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(2',3',5',6'-tetrahydro-2H-spiro[benzofuran-3,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1-oxo-2',3,3',4,5',6'-hexahydro-1H-spiro[naphthalene-2,4'-pyran]-6-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1'-methyl-1-oxo-1,3-dihydrospiro[indene-2,4'-piperidine]-6-yl)benzamide N-((4,6-dimethyl-2-oxo-1,2-dihydropyridin-3-yl)methyl)-3-(ethyl(tetrahydro-2H-pyran-4-yl)amino)-5-(2,2',3,3',5',6'-hexahydrospiro[indene-1,4'-pyran]-5-yl)-2-methylbenzamide 3-(ethyl(1-(2,2,2-trifluoroethyl)piperidin-4-yl)amino)-N-((4-methoxy-6-methyl-2-oxo-1,2-dihydropyridin-3-yl)methyl)-2-methyl-5-(1-methyl-2-oxo-2',3',5',6'-tetrahydrospiro[dihydroindole-3,4'-pyran]-5-yl)benzamide 5-(1'-(cyclopropylmethyl)-2-oxospiro[dihydroindole-3,4'-piperidine]-6-yl)-3-(ethyl(tetrahydro-2H-pyran-4-yl)amino)-N-((4-methyl-6-methyl-2-oxo-1,2-dihydropyridin-3-yl)methyl)-2-methylbenzamide 3-(ethyl(tetrahydro-2H-pyran-4-yl)amino)-N-((4-methoxy-6-methyl-2-oxo-1,2-dihydropyridin-3-yl)methyl)-2-methyl-5-(2-oxospiro[dihydroindole-3,4'-piperidine]-6-yl)benzamide 3-(ethyl(3-methoxytetrahydro-2H-pyran-4-yl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 3-(ethyl(tetrahydro-2H-pyran-4-yl)amino)-5-(2,2',3,3',5',6'-hexahydrospiro[indene-1,4'-pyran]-5-yl)-N-((4-methoxy-6-methyl-2-oxo-1,2-dihydropyridin-3-yl)methyl)-2-methylbenzamide 3-(ethyl(tetrahydro-2H-pyran-4-yl)amino)-N-((4-methoxy-6-methyl-2-oxo-1,2-dihydropyridin-3-yl)methyl)-2-methyl-5-(1'-methyl-2-oxospiro[dihydroindole-3,4'-piperidine]-6-yl)benzamide 3-(ethyl(tetrahydro-2H-pyran-4-yl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 3-(ethyl(piperidin-4-yl)amino)-N-((4-methoxy-6-methyl-2-oxo-1,2-dihydropyridin-3-yl)methyl)-2-methyl-5-(2-oxospiro[indole-3,4'-piperidine]-6-yl)benzamide N-((4,6-dimethyl-2-carbonyl-1,2-dihydropyridin-3-yl)methyl)-3-(ethyl(tetrahydro-2H-pyran-4-yl)amino)-5-(4-fluoro-2'-carbonylspiro[cyclohexano-1,3'-dihydroindole]-3-ene-5'-yl)-2-methylbenzamide 5-(4-fluoro-2'-carbonylspiro[cyclohexano-1,3'-dihydroindole]-5'-yl)-N-((4,6-dimethyl-2-carbonyl-1,2-dihydropyridin-3-yl)methyl)-3-(ethyl(tetrahydro-2H-pyran-4-yl)amino)-2-methylbenzamide 3-(ethyl(4-((2-methoxyethyl)(methyl)amino)cyclohexyl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide N-((4,6-dimethyl-2-oxo-1,2-dihydropyridin-3-yl)methyl)-3-(ethyl(4-(methyl(oxetan-3-yl)amino)cyclohexyl)amino)-2-methyl-5-(2-oxo-2',3',5',6'-tetrahydrospiro[dihydroindole-3,4'-pyran]-6-yl)benzamide 3-(ethyl(4-(methyl(oxetan-3-yl)amino)cyclohexyl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 3-(ethyl(1-(2,2,2-trifluoroethyl)piperidin-4-yl)amino)-N-((4-methoxy-6-methyl-2-oxo-1,2-dihydropyridin-3-yl)methyl)-2-methyl-5-(1-methyl-2-oxo-2',3',5',6'-tetrahydrospiro[dihydroindole-3,4'-pyran]-5-yl)benzamide As used herein, the term "alkyl" refers to a saturated aliphatic group, including linear alkyl (e.g., methyl, ethyl, propyl, butyl, amyl, hexyl, heptyl, octyl, nonyl, decyl, etc.), branched alkyl (e.g., isopropyl, tert-butyl, isobutyl, etc.), cycloalkyl (e.g., cyclopropyl, cyclobutyl, cyclopentyl, cyclohexyl, cycloheptyl, cyclooctyl, cyclopentenyl, cyclohexenyl, cycloheptenyl and adamantyl, etc.), alkyl-substituted cycloalkyl, and cycloalkyl-substituted alkyl.

In some embodiments, preferably, a cycloalkyl group has 3-8 carbon atoms on its ring structure, and more preferably, a cycloalkyl group has 5 or 6 carbon atoms on its ring structure.

The term "$C_{1-6}$ alkyl" refers to alkyl groups having 1 to 6 carbon atoms, such as methyl, ethyl, n-propyl, isopropyl, n-butyl, sec-butyl, tert-butyl, n-pentyl, sec-pentyl and n-hexyl. The term "$C_{1-3}$ alkyl" refers to alkyl groups having 1 to 3 carbon atoms, specifically methyl, ethyl, n-propyl, and isopropyl.

In addition, the term "alkyl" refers to "unsubstituted alkyl" and "substituted alkyl", wherein "substituted alkyl" refers to an alkyl group that one or more hydrogen atoms attached to carbon atoms are substituted by substituents. The said substituents may comprise: alkenyl, alkynyl, halogen, hydroxyl, alkylcarbonyloxy, arylcarbonyloxo, alkoxycarbonyloxy, aryloxycarbonyloxy, hydroxycarbonyl, alkylcarbonyl, arylcarbonyl, alkoxycarbonyl, aminocarbonyl, alkylaminocarbonyl, dialkylaminocarbonyl, alkylsulphanylcarbonyl, alkoxy, phosphate group, phosphonate group, cyano group, amino (including alkylamino, dialkylamino, arylamino, diarylamino and alkylarylamino), acylamino (including alkylcarbonylamino, arylcarbonylamino, carbamoyl and uramido), amidine group, imino group, sulfhydryl, alkylthio, arylthio, hydroxythiocarbonyl, sulphate group, alkylsulfinyl, sulfonic acid group, aminosulfonyl, sulfonamido, nitryl, trifluoromethyl, cyano group, azide group, heterocyclyl, alkylaryl, aromatic group and heteroaromatic group.

As used herein, "heterocyclic group" or "heterocyclyl" refers to any ring structure (saturated, unsaturated, or aromatic) that having at least one heterocyclic atom (e.g., N, O or S). Heterocyclyl comprises heterocycloalkyl and heteroaryl, and examples of heterocyclyl include, but not limited to, furanyl, pyridazinyl, imidazolidinyl, imidazolinyl, imidazolyl, isoquinolyl, thiazolyl, isothiazolyl, isoxazolyl, methylenedioxyphenyl, morpholinyl, oxazolidinyl, oxazolyl, oxadiazolyl, 1,2,3-oxadiazolyl, 1,2,4-oxadiazolyl, 1,2,5-oxadiazolyl, 1,3,4-oxadiazolyl, 1,2,4-oxadiazolyl-5 (4H)-one group, piperazinyl, piperidinyl, piperidinonyl, 4-piperidinonyl, pyranyl, tetrahydropyranyl, pyrazinyl, pyrazolidinyl, pyrazolinyl, pyrazolyl, pyridazinyl, pyridinyl, pyrimidinyl, pyrrolidinyl, pyrrolinyl, 2H-pyrrolyl, pyrrolyl, tetrahydrofurfuryl, tetrazolyl, thiazolyl, thiophenyl, tetrahydrothiophenyl, 1,2,3-triazolyl, 1,2,4-triazolyl, 1,2,5-triazolyl, 1,3,4-triazolyl, oxetanyl and azetidinyl.

The term "aryl" or "aromatic ring" refers to 5- to 6-membered monocyclic aromatic groups that may have 0 to 4 heteroatoms, such as phenyl, pyrrolyl, furyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl and the like. Furthermore, the term "aryl" also refers to polycyclic aromatic groups, for example, tricyclic aromatic groups or dicyclic aromatic groups, such as naphthyl, benzoazolyl, benzodiazolyl, benzothiazolyl, benzimidazolyl, benzothiophenyl, methylenedioxyphenyl, quinolyl, isoquinolyl, naphthyridinyl, indolyl, benzofuryl, purinyl, deazapurinyl and indoHzinyl.

Aryl groups with heteroatoms are also referred to as "heterocyclic aryl", "aromatic heterocyclic group", "heteroaryl" or "heteroaromatic group", wherein the heteroatoms are independently selected from N, O and S, the N atoms are substituted or unsubstituted, and the N and S heteroatoms are optionally oxidized (i.e., N→O and $S(O)_p$, wherein p=1 or 2), and the total number of S and O atoms in the aromatic heterocyclic group is not more than 1.

Typical heteroaryl groups comprise: 2-thiophenyl, 3-thiophenyl; 2-furyl, 3-furyl; 2-pyrrolyl, 3-pyrrolyl; 2-imidazolyl, 4-imidazolyl, 5-imidazolyl; 3-pyrazolyl, 4-pyrazolyl, 5-pyrazolyl; 2-thiazolyl, 4-thiazolyl, 5-thiazolyl; 3-isothiazolyl, 4-isothiazolyl, 5-isothiazolyl; 2-azolyl, 4-azolyl, 5-azolyl; 3-isoazolyl, 4-isoazolyl, 5-isoazolyl; 3-1,2,4-triazolyl, 5-1,2,4-triazolyl; 4-1,2,3-triazolyl, 5-1,2,3-triazolyl; tetrazolyl; 2-pyridinyl, 3-pyridinyl, 4-pyridy; 3-pyridazinyl, 4-pyridazinyl; 3-pyrazinyl, 4-pyrazinyl, 5-pyrazinyl; 2-pyrazinyl; 2-pyrimidinyl, 4-pyrimidinyl, 5-pyrimidinyl.

The aromatic rings of "aryl" or "heteroaryl" may be replaced by the substituent described above in one or more ring positions, wherein the substituent is, for example, halogen, hydroxyl, alkoxy, alkylcarbonyloxy, arylcarbonyloxo, alkoxycarbonyloxy, aryloxycarbonyloxy, hydroxycarbonyl, alkylcarbonyl, alkylaminocarbonyl, arylalkylaminocarbonyl, alkenylaminocarbonyl, alkylcarbonyl, arylcarbonyl, arylalkylcarbonyl, alkenylcarbonyl, alkoxycarbonyl, aminocarbonyl, alkylthioxocarbonyl, phosphate group, phosphonate group, cyano group, amino (including alkylamino, dialkylamino, arylamino, diarylamino and alkylarylamino), acylamino (including alkylcarbonylamino, arylcarbonylamino, carbamoyl and uramido), amidine group, imino group, sulfhydryl, alkylthio, arylthio, hydroxythiocarbonyl, sulphate group, alkylsulfinyl, sulphonate group, aminosulfonyl, sulfonamido, nitryl, trifluoromethyl, cyano group, azide group, heterocyclyl, alkylaryl, aromatic group or heteroaromatic group, wherein the aryl group can also be fused or bridged with nonaromatic alicyclic or heterocyclic groups to form a polycyclic group (such as tetralyl).

As used herein, the term "bicyclic" or "tricyclic" refers to any stable bicyclic or tricyclic groups having a specific number of carbon atoms, wherein each of the groups may be saturated, unsaturated, or aromatic, and each of the rings can be a cycloalkyl, heteroalkyl, heteroaryl or aryl, and bridge rings, fused rings or spiro rings can be formed among the rings.

The term "alkenyl" refers to unsaturated aliphatic groups similar in length and possible substitution to the aforementioned alkyl groups, but containing at least one double bond.

For example, the term "alkenyl" comprises linear alkenyl (e.g., vinyl, propenyl, butenyl, pentenyl, hexenyl, heptenyl, octenyl, nonenyl, decenyl, and the like), branched alkenyl, cycloalkenyl (e.g., cyclopropenyl, cyclopentenyl, cyclohexenyl, cycloheptenyl, cyclooctenyl), alkyl- or alkenyl-substituted cycloalkenyl, and cycloalkenyl-substituted alkenyl. The term "alkenyl" also refers to alkenyl groups containing O, N, S, or P atoms that substitute one or more carbons of the hydrocarbon backbone. In some embodiments, linear or branched alkenyl groups have 6 or less carbon atoms in their backbone (e.g., linear $C_{2-6}$ alkenyl, branched $C_{3-6}$ alkenyl). The term "$C_{2-6}$ alkenyl" refers to alkenyl groups having 2 to 6 carbon atoms.

In addition, the term "alkenyl" also refers to "unsubstituted alkenyl" and "substituted alkenyl", wherein "substituted alkenyl" refers to an alkenyl group in which one or more hydrogen atoms attached to carbon atoms are substituted by substituents. Said substituents may comprise, for example, alkyl, alkynyl, halogen, hydroxyl, alkylcarbonyloxy, arylcarbonyloxo, alkoxycarbonyloxy, aryloxycarbonyloxy, hydroxycarbonyl, alkylcarbonyl, arylcarbonyl, alkoxycarbonyl, aminocarbonyl, alkylaminocarbonyl, dialkylaminocarbonyl, alkylsulphanylcarbonyl, alkoxy, phosphate group, phosphonate group, cyano group, amino (including alkylamino, dialkylamino, arylamino, diarylamino and alkylarylamino), acylamino (including alkylcarbonylamino, arylcarbonylamino, carbamoyl and uramido), amidine group, imino group, sulfhydryl, alkylthio, arylthio, hydroxythiocarbonyl, sulphate group, alkylsulfinyl, sulfonic acid group, aminosulfonyl, sulfonamido, nitryl, trifluoromethyl, cyano group, azide group, heterocyclyl, alkylaryl and aromatic group.

The term "alkoxy" refers to substituted or unsubstituted alkyl groups covalently attached to an oxygen atom. Examples of alkoxy comprise methoxy, ethoxy, isopropyloxy, propoxy, butoxy, and pentoxy. Example of substituted alkoxy comprise haloalkoxy. Alkoxy-containing groups may be substituted by the following substituents: alkenyl, alkynyl, halogen, hydroxyl, alkylcarbonyloxy, arylcarbonyloxo, alkoxycarbonyloxy, aryloxycarbonyloxy, hydroxycarbonyl, alkylcarbonyl, arylcarbonyl, alkoxycarbonyl, aminocarbonyl, alkylaminocarbonyl, dialkylaminocarbonyl, alkylsulphanylcarbonyl, phosphate group, cyano group, amino (including alkylamino, dialkylamino, arylamino, diarylamino and alkylarylamino), acylamino (including alkylcarbonylamino, arylcarbonylamino, carbamoyl and uramido), amidine group, imino group, sulfhydryl, alkylthio, arylthio, hydroxythiocarbonyl, alkylsulfinyl, sulfonic acid group, aminosulfonyl, sulfonamido, nitryl, trifluoromethyl, cyano group, azide group, heterocyclyl, alkylaryl or aromatic group.

As used herein, the term "substituted" refers to any one or more hydrogen atoms on a specified atom being substituted by substituents selected from a specified group resulting in a stable compound, wherein two hydrogen atoms on the specified atom are substituted when the substituent is an oxo group or a ketone group (i.e., =O), and the ketone substituent does not exist on an aromatic ring.

As used herein, the term "pharmaceutically acceptable salt" refers to an inorganic alkali salt, such as a sodium salt, a potassium salt, a calcium salt, a magnesium salt, a zinc salt, an ammonium salt, a quaternary ammonium salt or an aluminum salt; an organic alkali salt, such as a lysine salt, an arginine salt, a diethylamine salt, a triethylamine salt, an ethanolamine salt, a trimethylamine salt, a dicyclohexylamine salt, a choline salt, a dibenzylamine salt, a piperidine salt or other pharmaceutically acceptable organic amine salts.

When the compound of the invention contains at least one salt forming nitrogen atom in its molecule, it can be converted into the corresponding salt by reaction with the corresponding organic acid or inorganic acid in an organic solvent such as acetonitrile or tetrahydrofuran. Typical organic acids include oxalic acid, tartaric acid, maleic acid, succinic acid, methanesulfonic acid, benzoic acid, benzenesulfonic acid, toluenesulfonic acid, aminosulfonic acid, citric acid, glutamic acid, pyroglutamic acid, aspartic acid, glucuronic acid, naphthalenesulfonic acid, glutaric acid, acetic acid, trifluoroacetic acid, malic acid, fumaric acid, salicylic acid, 4-aminosalicylic acid, lactic acid, palmitic acid, stearic acid, lauric acid, cinnamic acid, alginic acid, and ascorbate. Typical inorganic acids include nitric acid, hydrochloric acid, sulfuric acid, and phosphoric acid.

When the compound of the invention has one or more asymmetric carbon atoms, they can exist in the following forms: optically pure enantiomer, optically pure diastereomer, enantiomeric mixture, diastereomeric mixture, enantiomeric racemic mixture, racemate or racemic mixture. All possible isomers, stereoisomers, and mixtures thereof of the compound represented by formula (II) are also within the scope of the present invention.

The present invention also provides a pharmaceutical composition, which comprises at least one of the above-mentioned compounds and optionally one or more of pharmaceutically acceptable carriers and/or diluents.

The pharmaceutical composition provided by the present invention can be formulated into any forms, such as granules, powders, tablets, coated tablets, capsules, pills, syrups, drops, solutions, suspensions and emulsions, or sustained-release preparations of active ingredients, wherein examples of capsules include hard or soft gelatin capsules, and granules and powders can be in non-effervescent or effervescent forms.

The pharmaceutical composition of the present invention can further comprise one or more of pharmaceutically or physiologically acceptable carriers, which will be properly formulated for administration. For example, a pharmaceutically or physiologically acceptable carrier can be saline, hot pressurized water, Ringer's solution, buffer saline, glucose, maltodextrin, glycerol, ethanol, and mixtures thereof. The pharmaceutical composition provided by the present invention can further comprise one or more of pharmaceutically or physiologically acceptable additives, such as diluents, lubricants, adhesives, glidants, disintegrating agents, sweeteners, corrigents, moistening agents, dispersants, surfactants, solvents, coating agents, foaming agents, and aromatics.

Examples of diluents include, but are not limited to, lactose, sucrose, starch, kaolin, salt, mannitol and dicalcium phosphate; examples of lubricants include, but are not limited to, talc, starch, magnesium or calcium stearate, lycopodium spores and stearic acid; examples of adhesives include, but are not limited to, microcrystalline cellulose, tragacanth gum, glucose solution, acacia mucilage, gelatin solution, sucrose and starch paste; examples of glidants include, but are not limited to, colloidal silica; examples of glidants include, but are not limited to, croscarmellose sodium, sodium carboxymethyl starch, alginic acid, corn starch, potato starch, bentonite, methylcellulose, agar and carboxymethyl cellulose; examples of sweeteners include, but are not limited to, sucrose, lactose, mannitol and artificial sweeteners such as sodium cyclamate and saccharin, and any amount of spray drying corrigents; examples of corrigents include, but are not limited to, natural corrigents derived from plants, e.g., fruits, and better tasting compounds, such as, but are not limited to, menthol and methyl salicylate; examples of moistening agents include, but not limited to, propylene glycol monostearate, sorbitan monooleate, diethylene glycol monolaurate and polyethylene glycol monooleyl ether.

The pharmaceutical composition of the present invention can be administered by various routes according to traditional methods, comprising oral, intravenous, intraarterial, intraperitoneal, intrathoracic, transdermal, nasal, inhalation, rectal, ophthalmic and subcutaneous delivery.

The pharmaceutically acceptable carriers optionally added to the pharmaceutical composition of the present invention can be: one or more of water, alcohol, honey, mannitol, sorbitol, dextrin, lactose, caramel, gelatin, calcium sulfate, magnesium stearate, talc, kaolin, glycerin, tween, agar, calcium carbonate, calcium bicarbonate, surfactants, cyclodextrin and its derivatives, phospholipids, phosphates, starch and its derivatives, silicon derivatives, cellulose and its derivatives, pyrrolidones, polyethylene glycols, acrylic resins, phthalates, acrylic copolymers and trimesic acid esters.

Through pharmacological experiments, the compound or pharmaceutical composition provided by the present invention can treat tumors, myeloproliferative diseases or autoimmune diseases through EZH2, wherein the tumor can be lymphoma, melanoma, glioma, gastrointestinal stromal tumor, prostate cancer, breast cancer, ovarian cancer, bladder cancer, lung cancer, rectal cancer, skin cancer, epithelial cell cancer, nasopharyngeal cancer, bone cancer, esophageal cancer or leukemia, and the autoimmune disease can be inflammatory enteritis, autoimmune encephalomyelitis or multiple sclerosis.

The general dosage of the compound provided by the present invention is in the range of about 0.001 mg/kg to 1000 mg/kg per day, preferably of about 0.01 mg/kg to 100 mg/kg per day, more preferably of about 0.1 mg/kg to 20 mg/kg per day, and the dosage of the pharmaceutical composition is calculated according to the amount of the above compound contained therein.

DETAILED DESCRIPTION OF THE INVENTION

Example 1 N-((4,6-dimethyl-2-oxo-1,2-dihydropyridin-3-yl)methyl)-3-(ethyl(1-methylpiperidin-4-yl)amino)-2-methyl-5-(2-oxo-2',3',5',6'-tetrahydrospiro[dihydroindole-3,4'-pyran]-6-yl)benzamide

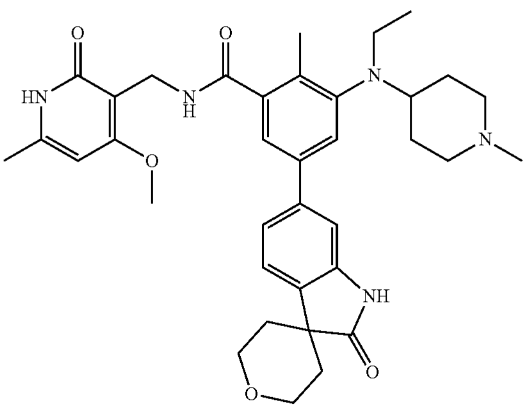
1

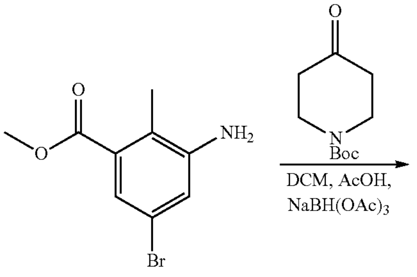

1a

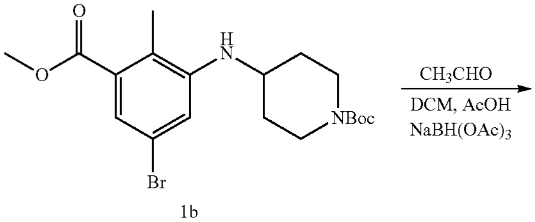

1b

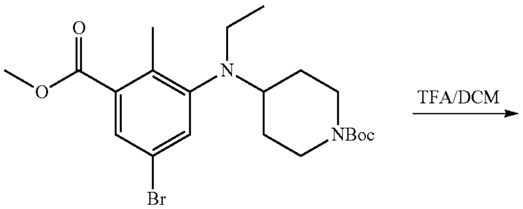

1c

-continued

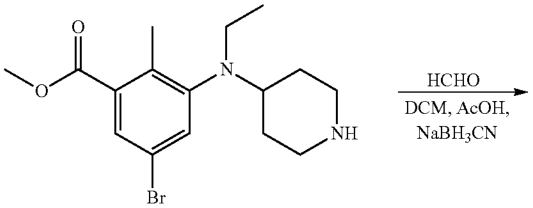

1d

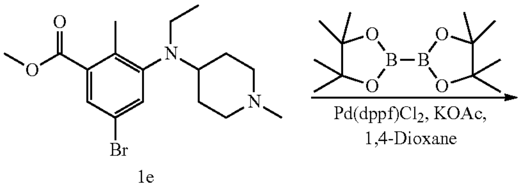

1e

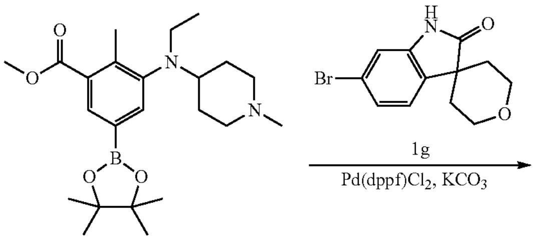

1f

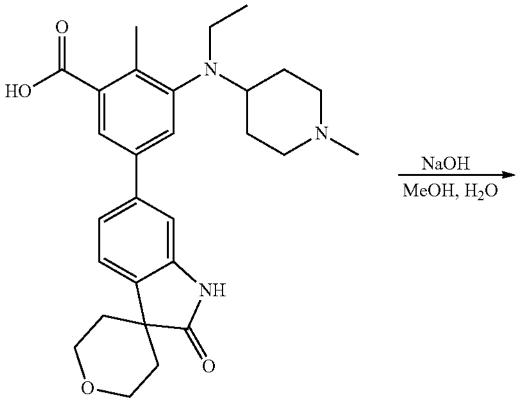

1h

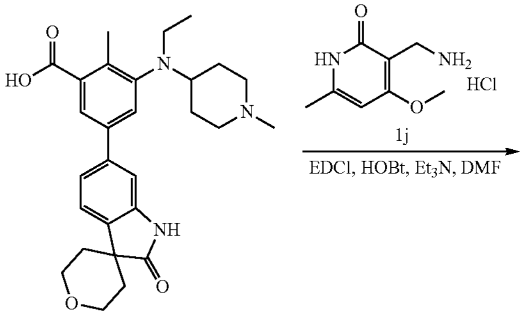

1h

-continued

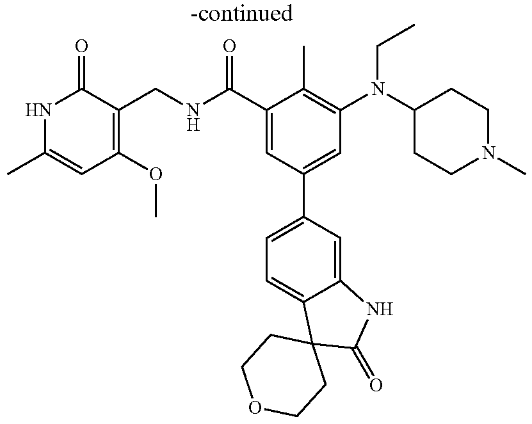

1

Step I Tert-butyl 4-((5-bromo-3-(methoxycarbonyl)-2-methylphenyl)amino)piperidin-1-carboxylate 1b The compound 1a (16 g, 65.6 mmol) was dissolved in DCM (400 mL), and tert-butyl 4-oxopiperidin-1-carboxylate (39.1 g, 196.7 mmol) and acetic acid (11.8 g, 196.7 mmol) were successively added. The mixture was stirred at room temperature for 1 hour, followed by adding sodium triacetoxyborohydride (41.7 g, 196.7 mmol) and stirring at room temperature overnight. 200 mL of water was then added to the mixture. The reaction solution was stirred for 10 minutes, separated, and the organic phase was extracted with DCM (100 mL×2). The organic phases were combined, washed with saturated NaCl solution twice, dried with anhydrous sodium sulfate, mixed and concentrated, and purified by column chromatography (petroleum ether: ethyl acetate=0%-30%) to obtain the title compound 1b (25 g, 58.7 mmol) with a yield of 83%.

MS m/z (ESI): 441 $[M-55]^+$.

Step II Tert-butyl 4-((5-bromo-3-(methoxycarbonyl)-2-methylphenyl)(ethyl)amino)piperidin-1-carboxylate 1c The compound 1b (25 g, 58.5 mmol) was dissolved in 400 mL of DCM, acetaldehyde (25.7 g, 585 mmol) and acetic acid (10.5 g, 175.5 mmol) were added. The mixture was stirred at room temperature for 1 hour, followed by adding sodium triacetoxyborohydride (37.2 g, 175.5 mmol) under ice bath, naturally raising to room temperature and reacting overnight. A saturated sodium bicarbonate aqueous solution was then added to the mixture to adjust pH to 7, and 200 mL of water was added. The reaction solution was stirred for 5 minutes, separated, and the aqueous phase was extracted with EA (100 mL×2). The organic phases were combined, dried with anhydrous sodium sulfate, mixed, concentrated, and purified by column chromatography (petroleum ether: ethyl acetate=0%-20%) to obtain the title compound 1c (20 g, 44.05 mmol) with a yield of 75.3%.

MS m/z (ESI): 457.1 $[M+H]^+$.

Step III Methyl 5-bromo-3-(ethyl(piperidin-4-yl)amino)-2-methylbenzoate 1d

The compound 1c (3.0 g, 6.61 mmol) was dissolved in 30 mL of DCM, TFA (10 mL) was added under an ice bath, and the mixture was naturally raised to room temperature and reacted overnight. The solvent was evaporated, and the residue was dried under vacuum to obtain a crude product of the title compound 1d (3.0 g, 6.61 mmol) with a yield of 100%.

MS m/z (ESI): 357.1 $[M+H]^+$.

Step IV Methyl 5-bromo-3-(ethyl(1-methylpiperidin-4-yl)amino)-2-methylbenzoate 1e The compound 1d (1.6 g, 3.55 mmol) was dissolved in 30 mL of DCM, and paraformaldehyde (1.06 g, 35.5 mmol), $NaBH_3CN$ (671 mg, 10.65 mmol) and methanol (1 mL) were successively added under an ice bath, and the mixture was naturally raised to room temperature and reacted overnight. 50 mL of water was added to the mixture. The reaction solution was stirred for 10 minutes, separated, and the aqueous phase was extracted with DCM (30 mL×3). The organic phases were combined, washed with saturated NaCl solution twice, dried with anhydrous sodium sulfate, mixed, concentrated, and purified by column chromatography (DCM/MeOH=0%-5%) to obtain the title compound 1e (1.05 g, 2.845 mmol) with a yield of 80%.

MS m/z (ESI): 369 $[M+H]^+$.

Step V Methyl 3-(ethyl(1-methylpiperidin-4-yl)amino)-2-methyl-5-(4,4,5,5-tetramethyl-1,3,2-dioxaborolan-2-yl)benzoate if The compound 1e (1.05 g, 2.84 mmol) was dissolved in 30 mL of 1,4-dioxane, and bis(pinacolato)diboron (1.08 g, 4.26 mmol), $Pd(dppf)Cl_2$ (208 mg, 0.284 mmol) and KOAc (556 mg, 5.68 mmol) were added and mixed well, the mixture was heated to 100° C. under the protection of $N_2$ and refluxed for 3 hours. After cooling to room temperature, 30 mL of water was added to dilute the mixture. The reaction solution was extracted with EA (50 mL×3), and the organic phases were combined, washed with 30 mL of saturated NaCl solution, dried, mixed, and purified by column chromatography (methanol/dichloromethane=0%-10%) to obtain the title compound 1f (1.06 g, 2.56 mmol) with a yield of 90%.

MS m/z (ESI): 417 $[M+H]^+$.

Step VI Methyl 3-(ethyl(1-methylpiperidin-4-yl)amino)-2-methyl-5-(2-oxo-2',3',5',6'-tetrahydrospiro[dihydroindole-3,4'-pyran]-6-yl)benzoate 1h The compound 1f (1.06 g, 2.56 mmol) was dissolved in 30 mL of 1,4-dioxane, the compound 1g (718 mg, 2.56 mmol), $Pd(dppf)Cl_2$ (187 mg, 0.256 mmol), potassium carbonate (1.06 g, 7.68 mmol) and 6 mL of water were successively added, and the mixture was heated to 100° C. under the protection of $N_2$ and reacted for 3 hours. After cooling to room temperature, 20 mL of water was added to dilute the mixture. The reaction solution was extracted with EA (20 mL×3), and the organic phases were combined, washed with saturated NaCl solution, dried, mixed, and purified by column chromatography (methanol/dichloromethane=0%-10%) to obtain the title compound 1h (1.07 g, 2.17 mmol) with a yield of 85%.

MS m/z (ESI): 492 $[M+H]^+$.

Step VII 3-(ethyl(1-methylpiperidin-4-yl)amino)-2-methyl-5-(2-oxo-2',3',5',6'-tetrahydrospiro[dihydroindole-3,4'-pyran]-6-yl)benzoic acid 1i The compound 1h (1.07 g, 2.17 mmol) was dissolved in a mixed solvent of 10 mL of methanol and 10 mL of water, sodium hydroxide (872 mg, 21.8 mmol) was added and well mixed, and the mixture was heated to 60° C. and stirred for 3 hours. After cooling to room temperature, an acetic acid solution was added dropwise to adjust pH to 6. The solvent was evaporated, after that 5 mL of methanol was added. A white insoluble substance was filtered out and the residue was re-evaporated to obtain 1 g of a crude product of the title compound 1i, which was used directly in the next step.

MS m/z (ESI): 478 $[M+H]^+$.

Step VIII 3-(ethyl(1-methylpiperidin-4-yl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 1

The compound 1i (72 mg, 0.151 mmol) was dissolved in 4 mL of DMF, the compound 1j (46 mg, 0.226 mmol), EDCI (57 mg, 0.302 mmol), HOBt (20 mg, 0.151 mmol) and triethylamine (46 mg, 0.453 mmol) were successively added under stirring, and the mixture was stirred at room temperature overnight. The mixture was then added with a mixed solvent of EA/water (10 mL/10 mL), stirred for 5 minutes, and separated. The aqueous phase was extracted with EA (10 mL×3), and the organic phases were combined, washed with saturated NaCl solution (10 mL×3), dried, mixed, and purified by column chromatography (methanol/dichloromethane=0%-20%) to obtain the title compound 1 (40 mg, 0.0638 mmol) with a yield of 42.2%.

$^1H$ NMR (400 MHz, Methanol-$d_4$) δ 7.52 (d, J=7.8 Hz, 1H), 7.46 (d, J=1.8 Hz, 1H), 7.33 (d, J=1.8 Hz 1H), 7.25 (dd, J=7.9, 1.7 Hz, 1H), 7.11 (d, J=1.6 Hz, 1H), 6.27 (s, 1H), 4.45 (s, 2H), 4.17 (ddd, J=114, 7.5, 3.7 Hz, 2H), 3.98-3.83 (m, 5H), 3.39 (d, J=5.7 Hz, 2H), 3.25-3.18 (m, 2H), 3.12-3.10 (m, 1H), 3.03 (s, 2H), 2.80 (s, 3H), 2.32 (d, J=11.3 Hz, 6H), 2.05 (d, J=13.0 Hz, 2H), 1.92-1.77 (m, 6H), 0.90 (t, J=6.9 Hz, 3H).

MS m/z (ESI): 628.7$[M+H]^+$.

Example 2 5-(1-acetyl-2',3',5',6'-tetrahydrospiro[dihydroindole-3,4'-pyran]-6-yl)-3-(ethyl(tetrahydro-2H-pyran-4-yl)amino)-N-((4-methoxy-6-methyl-2-carbonyl-1,2-dihydropyridin-3-yl)methyl)-2-methylbenzamide

2

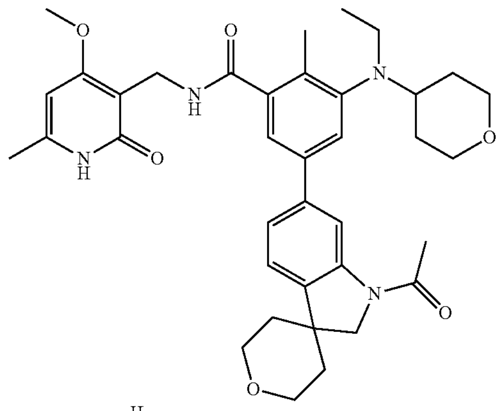

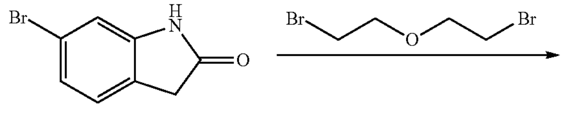

2a

-continued

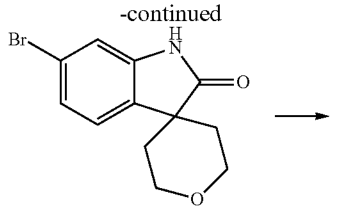

1g

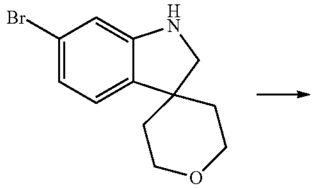

2c

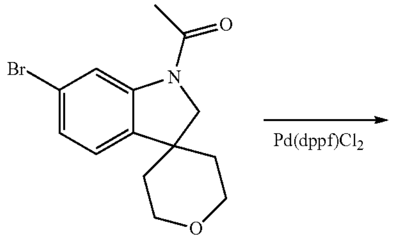

2d

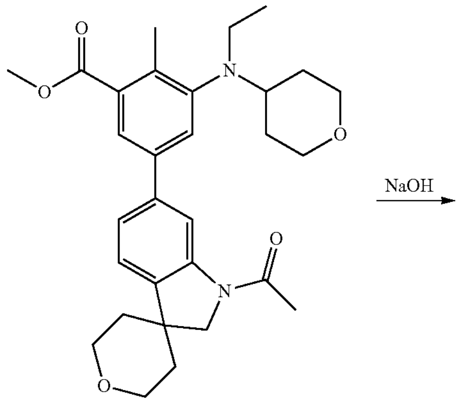

2e

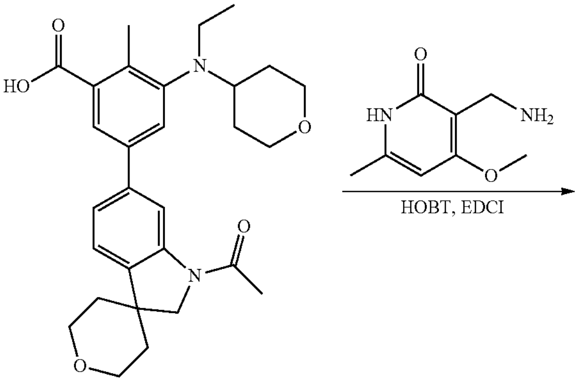

2f

-continued

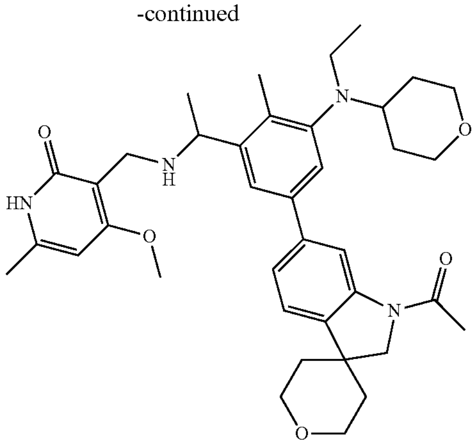

2

Step I 6-bromo-2',3',5',6'-tetrahydrospiro[indoline-3, 4'-pyran]-2-one 1g

A compound 2a (6-bromo-1,3-dihydro-2H-indol-2-one) (1.0 g, 4.74 mmol) was dissolved in tetrahydrofuran (20 mL), and lithium bis(trimethylsilyl)amide (23.7 mL, 23.7 mmol) was slowly added dropwise at −78° C. The mixture was stirred at this temperature for 30 minutes, followed by adding 2,2'-dibromodiethyl ether (1.3 g, 5.69 mmol) and slowly heating to 70° C. and stirring for 6 hours. After the reaction was completed, it was quenched with water under ice water bath, and the reaction solution was extracted by adding water and ethyl acetate. The organic phase was washed with saturated NaCl solution, dried with anhydrous sodium sulfate, filtered, concentrated, and purified by column chromatography to obtain the title compound 1g (40 mg, 1.42 mmol) with a yield of 30%.

Step II 6-bromo-2',3',5',6'-tetrahydrospiro[dihydroindole-3,4'-pyran]2c

The compound 1g (6-bromo-2',3',5',6'-tetrahydrospiro[indoline-3,4'-pyran]-2-one) (500 mg, 1.78 mmol) was dissolved in tetrahydrofuran (6 mL), $BF_3$-THF (5.34 mL, 5.34 mmol) was slowly added dropwise under an ice bath, and the mixture was stirred at room temperature overnight. The reaction was quenched with methanol under ice bath and water was added. The reaction solution was extracted with ethyl acetate, washed with saturated NaCl solution, dried with anhydrous sodium sulfate, filtered, concentrated, and purified by column chromatography to obtain the title compound 2c (370 mg, 1.38 mmol) with a yield of 77.8%.

Step III 1-(6-bromo-2',3',5',6'-tetrahydrospiro[dihydroindole-3,4'-pyran]-1-yl)ethan-1-one 2d The compound 2c (6-bromo-2',3',5',6'-tetrahydrospiro[dihydroindole-3,4'-pyran]) (200 mg, 0.75 mmol) was dissolved in acetic anhydride (2 mL), an aqueous solution (1 mL) of sodium hydroxide (33 mL, 0.825 mmol) was slowly added dropwise at room temperature, and the mixture was stirred at room temperature for 3 hours. The reaction was quenched with water, and the reaction solution was extracted with ethyl acetate, washed with saturated NaCl solution, dried with anhydrous sodium sulfate, filtered, concentrated, and purified by column chromatography to obtain the title compound 2d (90 mg, 0.291 mmol) with a yield of 38.8%.

Step IV 5-(1-acetyl-2',3',5',6'-tetrahydrospiro[dihydroindole-3,4'-pyran]-6-yl)-3-(ethyl(tetrahydro-2H-pyran-4-yl)amino)-2-methylbenzoate 2e The compound 2d (90 mg, 0.29 mmol) and methyl 3-(ethyl(tetrahydro-2H-pyran-4-yl)amino-2-methyl-5-(4,4,5,5-tetramethyl-1,3,2-dioxaborolan-2-yl)benzoate (synthesis process see Example 81) (105 mg, 0.26 mmol) were dissolved in 1,4-dioxane (2.0 mL), [1,1'-bis(diphenylphosphino)ferrocene]dichloropalladium (26 mg, 0.0355 mmol) and potassium carbonate (122 mg, 0.887 mmol) were added, and the mixture was heated to 100° C. under the protection of nitrogen and stirred for 2 hours. After cooling down, the reaction solution was spin-dried, extracted with dichloromethane three times, washed with saturated NaCl solution, dried with anhydrous sodium sulfate, filtered, concentrated, and purified by plate chromatography to obtain the title compound 2e (100 mg, 0.19 mmol) with a yield of 65.5%.

Step V 5-(1-acetyl-2',3',5',6'-tetrahydrospiro[dihydroindole-3,4'-pyran]-6-yl)-3-(ethyl(tetrahydro-2H-pyran-4-yl)amino)-2-methylbenzoic acid 2f The compound 2e (100 mg, 0.19 mmol) was dissolved in methanol (2 mL), and sodium hydroxide (61 mg, 1.5 mmol) and water (1.0 mL) were added, and the reaction was completed after stirring at room temperature for 4 hours. The reaction solution was neutralized with hydrochloric acid to pH=6-7, extracted with dichloromethane for three times, washed with saturated NaCl solution, dried with anhydrous sodium sulfate, filtered, concentrated, and purified by plate chromatography to obtain a title compound 2f (70 mg, 0.14 mmol) with a yield of 73.6%.

Step VI5-(1-acetyl-2',3',5',6'-tetrahydrospiro[dihydroindole-3,4'-pyran]-6-yl)-3-(ethyl(tetrahydro-2H-pyran-4-yl)amino)-N-((4-methoxy-6-methyl-2-carbonyl-1,2-dihydropyridin-3-yl)methyl)-2-methylbenzamide 2

The compound 2f (200 mg, 0.14 mmol) and 3-(aminomethyl)-4-methoxy-6-methylpyridin-2(1H)-one hydrochloride (prepared according to the method disclosed in "J. Med. Chem. 2016, 59, 9928-9941") (108 mg, 0.533 mmol) were dissolved in N,N-dimethylformamide (2.0 mL), 1-(3-dimethylaminopropyl)-3-ethylcarbodiimide hydrochloride (157 mg, 0.82 mmol), 1-hydroxybenzotriazole (55 mg, 0.41 mmol) and triethylamine (124 mg, 1.23 mmol) were added. The mixture was stirred at room temperature overnight until the reaction was completed. The reaction solution was washed with water, extracted with dichloromethane for three times, washed with saturated NaCl solution, dried with anhydrous sodium sulfate, filtered, concentrated, and purified by plate chromatography to obtain the title compound 2 (118.0 mg, 0.184 mmol) with a yield of 44.8%.

1H NMR (400 MHz, DMSO-d6) δ 11.38 (s, 1H), 8.27 (d, J=1.7 Hz, 1H), 7.96 (t, J 4.6 Hz, 1H), 7.32 (d, J=7.8 Hz, 1H), 7.26 (d, J=1.8 Hz, 1H), 7.21 (dd, J=7, 17 Hz, 1H), 7.08 (d, J=1.8 Hz, 1H), 6.05 (s, 1H), 4.20 (d, J=4.6 Hz, 2H), 4.08 (s, 2H), 3.88-3.78 (m, 4H), 3.78 (s, 1H), 3.50 (t, J=12.0 Hz, 2H), 3.21 (t, J=11.3 Hz, 2H), 3.04 (q, J=7.1 Hz, 2H), 2.97 (d, J=11.4 Hz, 1H), 2.20 (d, J=3.5 Hz, 5H), 2.13 (s, 3H), 1.87 (td, J=12.9, 4.7 Hz, 2H), 1.62 (d, J=12.4 Hz, 2H), 1.51 (t, J=13.3 Hz, 4H), 0.80 (t, J=6.9 Hz, 3H),

MS m/z (ESI): 643.5 $[M+H]^+$.

Example 3 N-((4,6-dimethyl-2-oxo-1,2-dihydropyridin-3-yl)methyl)-3-(ethyl(tetrahydro-2H-pyran-4-yl)amino)-2-methyl-5-(2-oxo-2',3',5',6'-tetrahydrospiro[dihydroindole-3,4'-pyran]-6-yl)benzamide

3

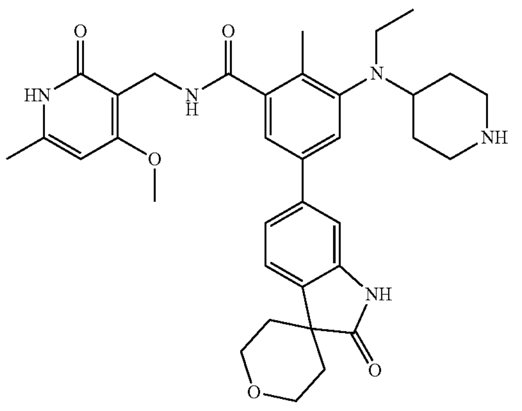

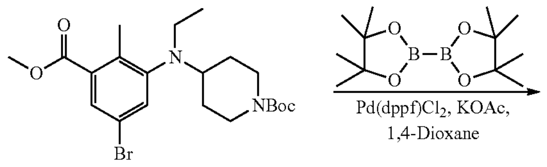

1e

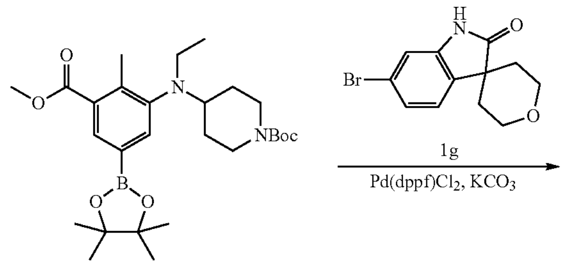

3a-1

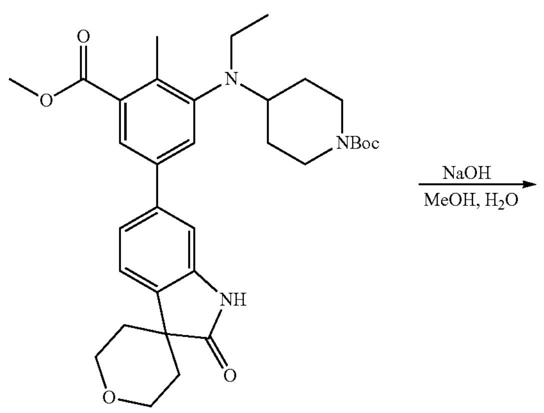

3a-2

-continued

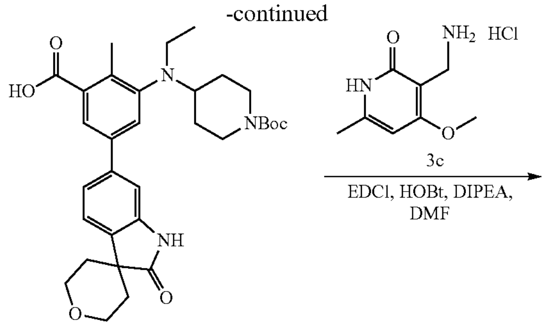

3a

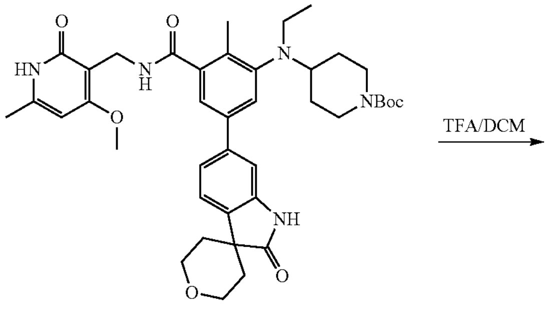

3b

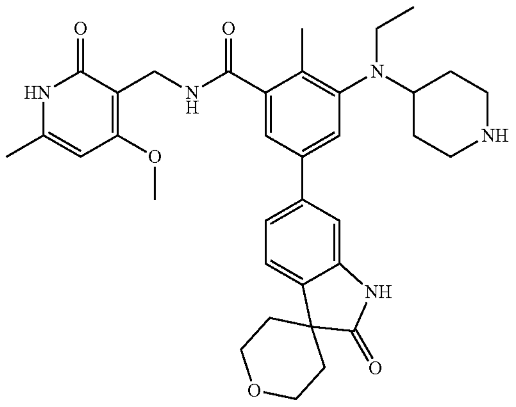

3

Step I Tert-butyl 4-(ethyl(3-(methoxycarbonyl)-2-methyl-5-(4,4,5,5-tetramethyl-1,3,2-dioxaborolan-2-yl)phenyl)amino)piperidin-1-formate 3a-1

The compound 1c (1.29 g, 2.84 mmol) was dissolved in 30 mL of 1,4-dioxane, and bis(pinacolato)diboron (1.08 g, 4.26 mmol), Pd(dppf)$Cl_2$ (208 mg, 0.284 mmol) and KOAc (556 mg, 5.68 mmol) were added and well mixed, and the mixture was heated to 100° C. under the protection of $N_2$ and refluxed for 3 hours. After cooling to room temperature, 30 mL of water was added to dilute the mixture. The reaction solution was extracted with EA (50 mL×3), and the organic phases were combined, washed with 30 mL of saturated NaCl solution, dried, mixed, and purified by column chromatography (methanol/dichloromethane=0%-10%) to obtain the title compound 3a-1 (1.285 g, 2.56 mmol) with a yield of 90%.

MS m/z (ESI): 503.1 $[M+H]^+$.

Step II Tert-butyl 4-(ethyl(3-(methoxycarbonyl)-2-methyl-5-(2-oxo-2',3',5',6'-tetrahydrospiro[dihydroindole-3,4'-pyran]-6-yl)phenyl)amino)piperidin-1-formate 3a-2

The compound 3a-1 (1.285 g, 2.56 mmol) was dissolved in 30 mL of 1,4-dioxane, the compound 1g (718 mg, 2.56 mmol), Pd(dppf)$Cl_2$ (187 mg, 0.256 mmol), potassium carbonate (1.06 g, 7.68 mmol) and 6 mL of water were successively added, the mixture was heated to 100° C. under the protection of $N_2$ and reacted for 3 hours. After cooling to room temperature, 20 mL of water was added to dilute the mixture. The reaction solution was extracted with EA (20 mL×3), the organic phases were combined, washed with saturated of NaCl solution, dried, mixed, and purified by column chromatography (methanol/dichloromethane=0%-10%) to obtain the title compound 3a-2 (1.25 g, 2.17 mmol) with a yield of 85%.

MS m/z (ESI): 578.1 $[M+H]^+$.

Step III 3-((1-(tert-butoxycarbonyl)piperidin-4-yl)(ethyl)amino)-2-methyl-5-(2-oxo-2',3',5',6'-tetrahydrospiro[dihydroindole-3,4'-pyran]-6-yl)benzoic acid 3a The compound 3a-2 (1.25 g, 2.17 mmol) was dissolved in a mixed solvent of 10 mL of methanol and 10 mL of water, sodium hydroxide (872 mg, 21.8 mmol) was added and well mixed, and the mixture was heated to 60° C. and stirred for 3 hours. After cooling to room temperature, an acetic acid solution was added dropwise to adjust pH=6. The solvent was evaporated, after that 5 mL of methanol was added. A white insoluble substance was filtered out and the residue was re-evaporated to obtain 1 g of a crude product of the title compound 3a, which was used directly in the next step.

MS m/z (ESI): 564.1 $[M+H]^+$.

Step IV Tert-butyl 4-(ethyl(3-(((4-methoxy-6-methyl-2-oxo-1,2-dihydropyridin-3-yl)methyl)carbamoyl)-2-methyl-5-(2-oxo-2',3',5',6'-tetrahydrospiro[dihydroindole-3,4'-pyran]-6-yl)phenyl)amino)piperidin-1-formate 3b The compound 3a (400 mg, 0.71 mmol) and 3-(aminomethyl)-4-methoxy-6-methyl-1H-pyridin-2-one hydrochloride (217 mg, 1.065 mmol) were dissolved in N,N-dimethylformamide (10.0 mL), 1-(3-dimethylaminopropyl)-3-ethylcarbodiimide hydrochloride (203 mg, 1.065 mmol), 1-hydroxybenzotriazole (144 mg, 1.065 mmol) and diisopropylethylamine (458 mg, 3.55 mmol) were added. The reaction was completed after stirring at 60° C. for 4 hours. The reaction solution was washed with water, extracted with dichloromethane for three times, washed with saturated NaCl solution, dried with anhydrous sodium sulfate, filtered, concentrated, and purified by plate chromatography to obtain the title compound 3b (300 mg, 0.42 mmol) with a yield of 59%.

MS m/z (ESI): 714.6 $[M+H]^+$.

Step V 3-(ethyl(piperidin-4-yl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 3

The compound 3b (300 mg, 0.42 mmol) was dissolved in dichloromethane (4.0 mL), trifluoroacetic acid (4 mL) was added, and the reaction was completed after stirring at room temperature for 2 hours. The reaction solution was spin-dried, added with methanol, neutralized with saturated potassium carbonate solution, filtered, concentrated, and purified by plate chromatography to obtain the title compound 3 (140 mg, 0.28 mmol) with a yield of 65%.

$^1H$ NMR (400 MHz, Methanol-d4) δ 7.51 (d, J=7.8 Hz, 1H), 7.44 (d, J=1.9 Hz, 1H), 7.33 (d, J=1.9 Hz, H), 7.24 (dd, J=7.8, 1.7 Hz, 1H), 7.10 (d, J=1.6 Hz, 1H), 6.24 (d, J=0.9 Hz, 1H), 4.45 (s, 2H), 4.16 (td, J=7.8, 3.8 Hz, 2H), 3.92 (s, 5H), 3.34 (d, J=12.8 Hz, 2H), 3.24 (d, J=10.0 Hz, 1H), 3.14 (d, J=7.1 Hz, 2H), 2.95 (t, J=10.7 Hz, 2H), 2.34 (s, 3H), 2.29 (d, J=0.7 Hz, 3H), 2.03 (d, J=14.2 Hz, 2H), 1.92-0.70 (m, 6H), 0.91 (t, J=7.0 Hz, 3H), MS m/z (ESI): 614.5$[M+1]^+$.

Example 4 3-(ethyl(tetrahydro-2H-pyran-4-yl)amino)-N-((4-methoxy-6-methyl-2-oxo-1,2-dihydropyridin-3-yl)methyl)-2-methyl-5-(1'-methyl-2-oxospiro[dihydroindole-3,4'-piperidine]-6-yl)benzamide

4

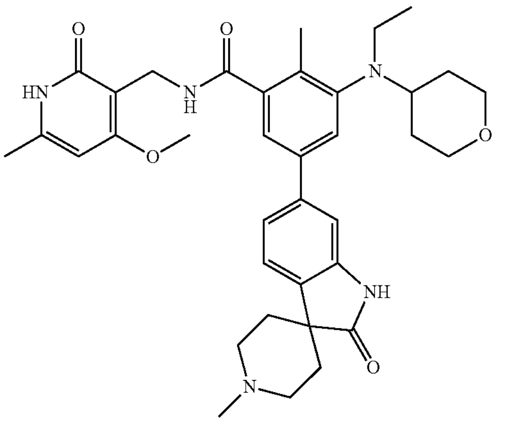

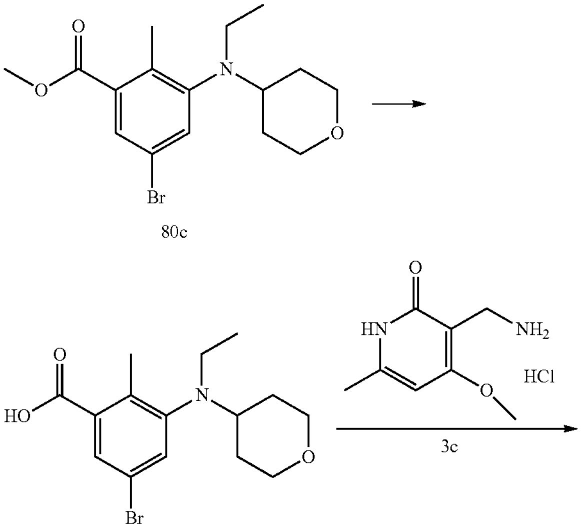

80c 4a-1

-continued

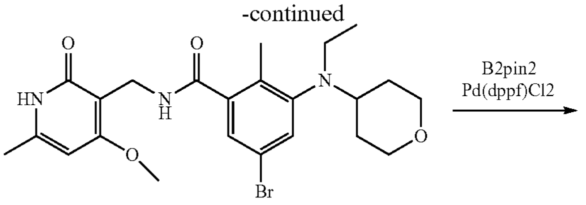

4a-2

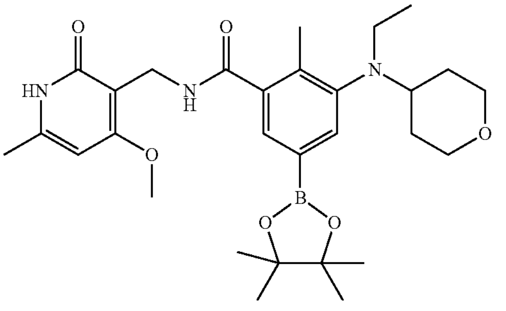

4a

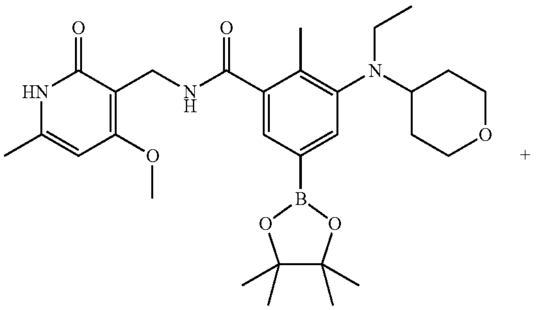

4a

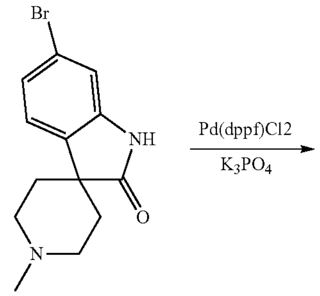

4b

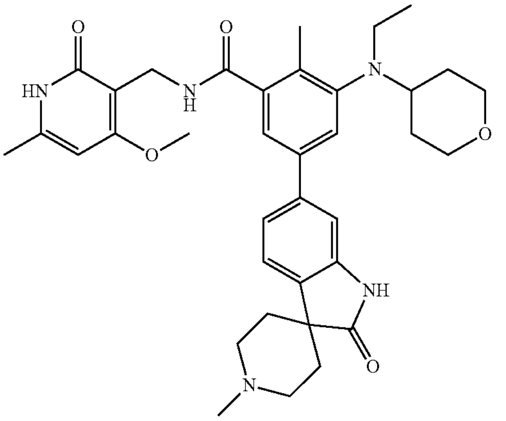

4

Step 1 5-bromo-3-(ethyl(tetrahydro-2H-pyran-4-yl)amino)-2-methylbenzoic acid 4a-1

The compound 80c (synthesis process see Example 80) (1 g, 2.8 mmol) was dissolved in methanol (12 mL), added with 6 mL of NaOH (2 M), and reacted at 50° C. for 5 hours. The reaction solution was neutralized to pH=6-7 by adding 2 N HCl, concentrated to obtain the title compound 4a-1 (950 mg, 2.7 mmol) with a yield of 99%.

LCMS(ESI):356.3-$(M+1)^+$.

Step II 5-bromo-N-((4-methoxy-6-methyl-2-oxo-1,2-dihydropyridin-3-yl)methyl)-3-(ethyl(tetrahydro-2H-pyran-4-yl)amino)-2-methylbenzamide 4a-2

The compound 4a-1 (0.95 g, 2.7 mmol), compound 3c (790 mg, 4.0 mmol), EDCI (1075 mg, 5.6 mmol), HOBT (378 mg, 2.8 mmol) and TEA (848 mg, 8.4 mmol) were dissolved in DMF (10 mL) and stirred at room temperature overnight. The reaction solution was concentrated, and purified by flash column chromatography to obtain the compound 4a-2 (300 mg, 0.63 mmol) with a yield of 23%.

LCMS(ESI): 493.2 $(M+1)^+$.

Step III N-((4-methoxy-6-methyl-2-oxo-1,2-dihydropyridin-3-yl)methyl)-3-(ethyl(tetrahydro-2H-pyran-4-yl)amino)-2-methyl-5-(4,4,5,5-tetramethyl-1,3,2-dioxaborane-2-yl)benzamide The compound 4a-2 (600 mg, 1.20 mmol), bis(pinacolato) diboron (480 mg, 1.89 mmol), $Pd(dppf)Cl_2$ (278 mg, 0.38 mmol) and KOAc (370 mg, 3.78 mmol) were added to 1,4-dioxane (10 mL) and refluxed at 100° C. for 4 hours. The reaction solution was concentrated, and purified by flash column chromatography to obtain the compound 4a (600 mg, 1.10 mmol) with a yield of 90%.

LCMS(ESI): 540.4 $(M+1)^+$.

Step 4 3-(ethyl(tetrahydro-2H-pyran-4-yl)amino)-N-((4-methoxy-6-methyl-2-oxo-1,2-dihydropyridin-3-yl)methyl)-2-methyl-5-(1'-methyl-2-oxospiro[dihydroindole-3,4'-piperidine]-6-yl)benzamide The compound 4a (400 mg, 0.74 mmol), compound 4b (synthesis process see Example 7) (219 mg, 0.74 mmol), $Pd(dppf)Cl_2$ (54 mg, 0.07 mmol) and potassium phosphate (313 mg, 1.48 mmol) were added to 1,4-dioxane (10 mL) and refluxed at 100° C. for 4 hours. The reaction solution was concentrated, and purified by flash column chromatography to obtain the compound 4 (190 mg, 0.30 mmol) with a yield of 40%.

$^1$H NMR (400 MHz, DMSO-d6) δ 10.58 (s, 1H), 8.27 (t, J=5.0 Hz, 1H) 7.56 (s, 1H), 7.40 (d, J=1.8 Hz, 1H), 7.25 (dd, J=22.7, 4.6 Hz, 2H), 7.11 (d, J=1.7 Hz, 1H), 5.92 (s, 1H), 4.35 (d, J=5.0 Hz, 2H), 3.89 (d, J=11.4 Hz, 2H), 3.31 (t, J=11.4 Hz, 41H), 3.19-3.06 (m, 4H), 2.70 (s, 2H), 2.28 (d, J=17.3 Hz, 6H), 2.17 (s, 3H), 1.98 (d, J=10.3 Hz, 51H), 1.78-1.49 (m, 5H), 0.89 (1, J=6.9 Hz, 3H),

MS m/z (ES): 628-$(M+1)^+$.

Example 5 3-(ethyl(piperidin-4-yl)amino)-N-((4-methoxy-6-methyl-2-oxo-1,2-dihydropyridin-3-yl)methyl)-2-methyl-5-(2',3',5',6'-tetrahydrospiro[indoline-3,4'-pyran]-6-yl)benzamide
5
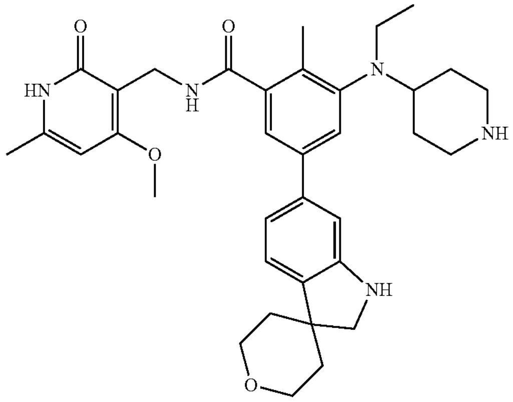
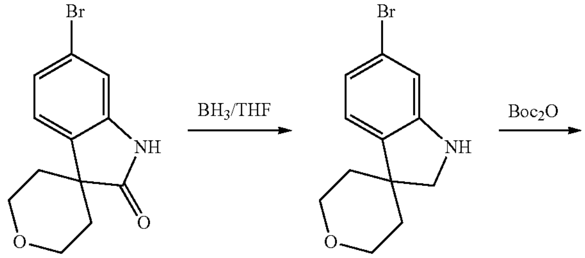
1g
5b
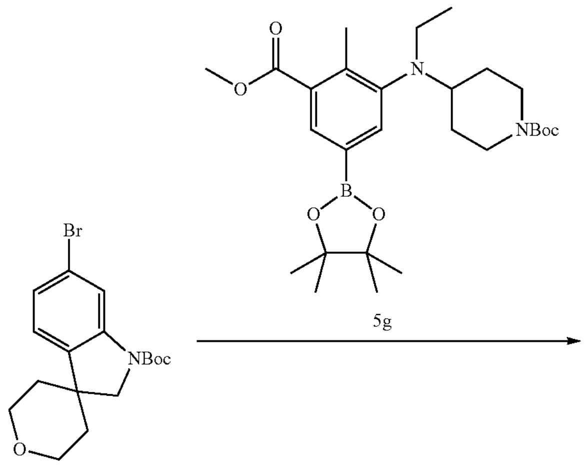
5c
-continued
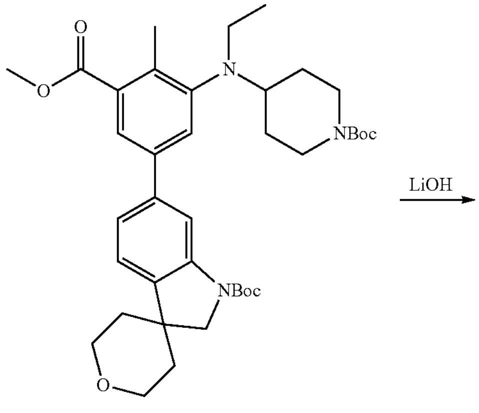
5d
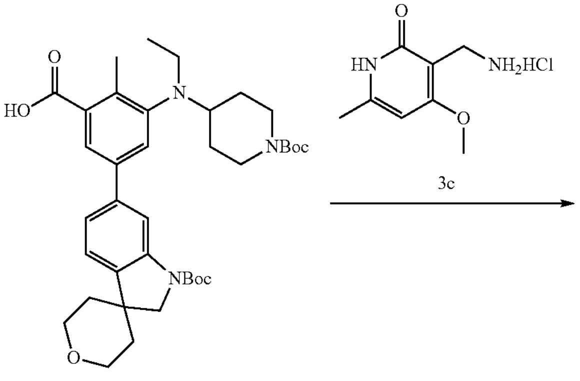
5e
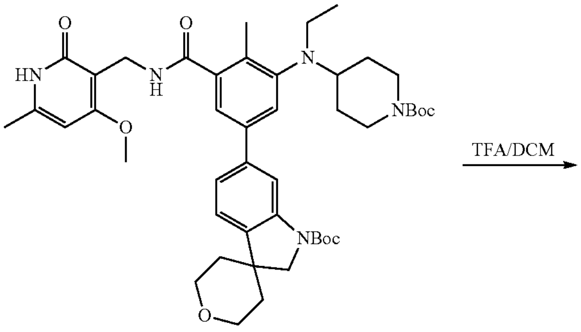
5f
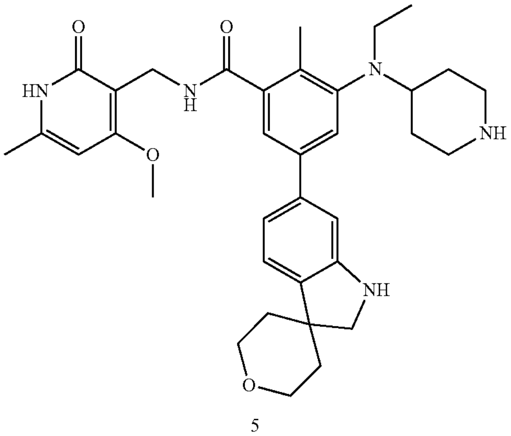
5

Step I 6-bromo-2',3',5',6'-tetrahydrospiro[indoline-3,4'-pyran]5b

The compound 1g (2 g, 7.092 mmol) was dissolved in THF (20 mL) at 0° C., slowly added with $BH_3$/THF (28.5 mL, 28.5 mmol), and the mixture was stirred at room temperature overnight. The reaction was quenched by adding methanol, the reaction solution was concentrated, added with water, extracted with dichloromethane for three times, washed with saturated NaCl solution, dried with anhydrous sodium sulfate, filtered, concentrated, and purified by column chromatography to obtain the title compound 5b (0.9 g, 3.35 mmol) with a yield of 47%.

MS m/z (ESI): 268 $[M+1]^+$.

Step II Tert-butyl 6-bromo-2',3',5',6'-tetrahydrospiro[indoline-3,4'-pyran]-1-carboxylate 5c The compound 5c (0.9 g, 3.358 mmol) was dissolved in THF (20 mL), NaOH (0.269 g, 6.716 mmol) and water (10 mL) were slowly added, then $(Boc)_2O$ (1090 mg, 5 mmol) was slowly added to the mixture and stirred at room temperature overnight. The reaction solution was added with water, extracted with dichloromethane for three times, washed with saturated NaCl solution, dried with anhydrous sodium sulfate, filtered, concentrated, and purified by plate chromatography to obtain the title compound 5c (1.1 g, 2.98 mmol) with a yield of 89%.

MS m/z (ESI): 368 $[M+1]^+$.

Step III Tert-butyl 6-(3-((1-(tert-butoxycarbonyl)piperidin-4-yl)(ethyl)amino)-5-(methoxycarbonyl)-4-methylphenyl)-2',3',5',6'-tetrahydrospiro[indoline-3,4'-pyran]-1-carboxylate 5d The compound 5c (1.1 g, 2.98 mmol), $K_2CO_3$ (0.824 g, 5.978 mmol), compound 5g (1.636 g, 3.26 mmol) and $Pd(dppf)Cl_2$ (218 mg, 0.298 mmol) were dissolved in dioxane (20 mL) and $H_2O$ (5 mL), the mixture was heated to 100° C. under the protection of argon and stirred for 6 hours until the reaction was completed. The reaction solution was added with water and extracted with ethyl acetate. The organic phase was washed with saturated NaCl solution, dried with anhydrous sodium sulfate, filtered, concentrated, and purified by column chromatography to obtain the title compound 5d (1.6 g, 2.413 mmol) with a yield of 80%.

MS m/z (ESI): 664 $[M+1]^+$.

Step IV 5-(1-(tert-butoxycarbonyl)-2',3',5',6'-tetrahydrospiro[indoline-3,4'-pyran]-6-yl)-3-((1-(tert-butoxycarbonyl)piperidin-4-yl)(ethyl)amino)-2-methylbenzoic acid 5e The compound 5d (1.6 g, 2.413 mmol) was added to a mixture of MeOH (30 mL), $H_2O$ (2.0 mL) and $LiOH \cdot H_2O$ (0.506 g, 12 mmol), and the reaction solution was heated to 45° C. and stirred for 2 hours.

The raw materials were completely reacted as determined by TLC monitoring. The reaction solution was neutralized with dilute hydrochloric acid, concentrated to remove MeOH, extracted with EA, dried with anhydrous sodium sulfate, filtered, and concentrated to obtain the title compound 5e (1.2 g, 1.848 mmol) with a yield of 76%.

MS m/z (ESI): 650 $[M+1]^+$.

Step V Tert-butyl 6-(3-((1-(tert-butoxycarbonyl)piperidin-4-yl)(ethyl)amino)-5-((4-methoxy-6-methyl-2-oxo-1,2-dihydropyridin-3-yl)methyl)carbamoyl)-4-methylphenyl)-2',3',5',6'-tetrahydrospiro[indoline-3,4'-pyran]-1-carboxylate 5f The compound 5e (450 mg, 0.693 mmol) and compound 3c (212 mg, 1.04 mmol) were dissolved in N,N-dimethylformamide (10 mL), 1-(3-dimethylaminopropyl)-3-ethylcarbodiimide hydrochloride (198 mg, 1.04 mmol), 1-hydroxybenzotriazole (140 mg, 1.04 mmol) and triethylamine (350 mg, 3.465 mmol) were added. The reaction was completed after stirring at room temperature for 24 hours. The reaction solution was washed with water, extracted with dichloromethane for three times, washed with saturated NaCl solution, dried with anhydrous sodium sulfate, filtered, concentrated, and purified by plate chromatography to obtain the title compound 5f (350 mg, 0.4375 mmol) with a yield of 63%.

MS m/z (ESI): 800 $[M+1]^+$.

Step VI 3-(ethyl(piperidin-4-yl)amino)-N-((4-methoxy-6-methyl-2-oxo-1,2-dihydropyridin-3-yl)methyl)-2-methyl-5-(2',3',5',6'-tetrahydrospiro[indoline-3,4'-pyran]-6-yl)benzamide 5

The compound 5f (350 mg, 0.4375 mmol) was dissolved in DCM (5.0 mL), TFA (5 mL) was added, and the reaction was completed after stirring at room temperature for 2 hours. The reaction solution was spin-dried, added with methanol, neutralized with saturated potassium carbonate solution, filtered, concentrated, and purified by plate chromatography to obtain the title compound 5 (180 mg, 0.3 mmol) with a yield of 68%.

1H NMR (400 MHz, Methanol-d4) δ 7.39 (d, J=1.9 Hz, 1H), 7.28 (d, J=1.8 Hz, 1H), 7.11 (d, J=7.7 Hz, 1H), 6.90 (dd, J=7.7, 1.7 Hz, 1H), 6.82 (d, J=1.5 Hz, 1H), 6.24 (d, J=0.9 Hz, 1H), 4.45 (s, 2H), 3.99-3.86 (m, 5H), 3.60 (td, J=11.9, 2.2 Hz, 2H), 3.52 (s, 2H), 3.38-3.31 (m, 2H), 3.25 (s, 3H), 3.12 (d, J=7.1 Hz, 2H), 3.00-2.90 (m, 2H), 2.33 (s, 3H), 2.29 (d, J=0.7 Hz, 3H), 1.07-1.89 (m, 4H), 1.77 (d, J=12.1 Hz, 2H), 168-1.58 (m, 2H), 0.90 (t, J=7.0 Hz, 3H), MS n/z (ESI): 600 $[M+H]^+$.

Example 6 N-((4,6-dimethyl-2-oxo-1,2-dihydropyridin-3-yl)methyl)-3-(ethyl(piperidin-4-yl)amino)-2-methyl-5-(2',3',5',6'-tetrahydrospiro[dihydroindole-3,4'-pyran]-6-yl)benzamide

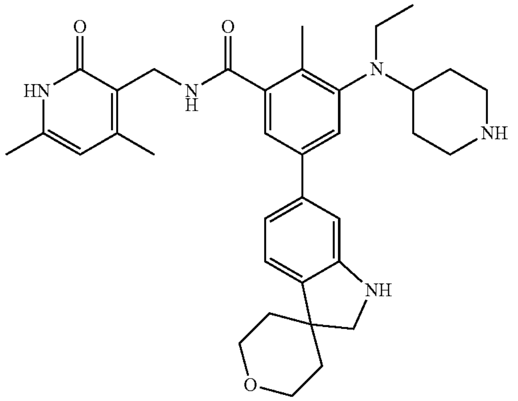

6

-continued

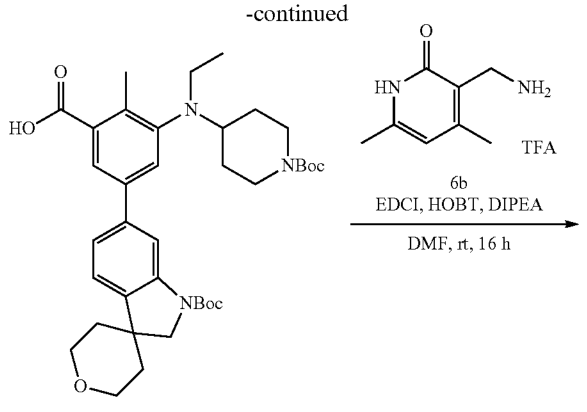

5e

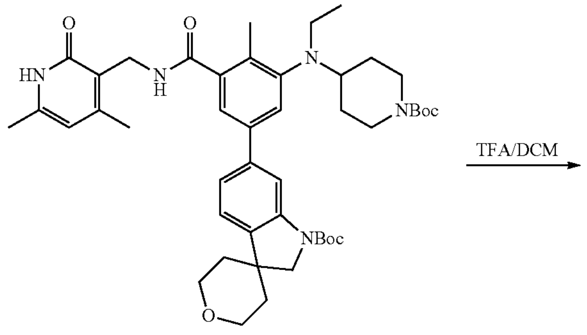

6c

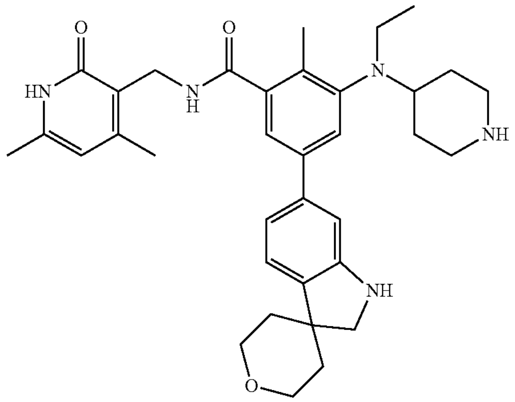

6

Step I Tert-butyl 6-(3-((1-(tert-butoxycarbonyl)piperidin-4-yl)(ethyl)amino)-5-(((4,6-dimethyl-2-oxo-1,2-dihydropyridin)-pyridin-3-yl)methyl)carbamoyl)-4-methylphenyl)-2',3',5',6'-tetrahydrospiro[indoline-3,4'-pyran]-1-carboxylate 6c The compound 5e (synthesis process see Example 5) (400 mg, 0.616 mmol) was dissolved in 10 mL of DMF, the compound 6b (245 mg, 0.924 mmol), EDCI (176 mg, 0.924 mmol), HOBT (166 mg, 1.232 mmol) and DIPEA (238 mg, 1.848 mmol) were successively added under stirring, and the mixture was stirred at room temperature overnight. The mixture was added with a mixed solvent of EA/water (30 mL/30 mL), stirred for 5 minutes, and separated. The aqueous phase was extracted with EA (20 mL×3), the organic phases were combined, washed with saturated NaCl solution (20 mL×3), dried, mixed, and purified by column chromatography (methanol/EA=0%-5%) to obtain the title compound 6c (310 mg, 0.395 mmol) with a yield of 60.6%.

MS m/z (ESI): 785 $[M+H]^+$.

Step II N-((4,6-dimethyl-2-oxo-1,2-dihydropyridin-3-yl)methyl)-3-(ethyl(piperidin-4-yl)amino)-2-methyl-5-(2',3',5',6'-tetrahydrospiro[dihydroindole-3,4'-pyran]-6-yl)benzamide 6

The compound 6c (310 mg, 0.395 mmol) was dissolved in 20 mL of DCM, added with TFA (5 mL) under an ice water bath, the mixture was naturally raised to room temperature and reacted overnight. The mixture was evaporated to remove solvent, added with a mixed solvent of methanol/water (5 mL/5 mL), stirred until dissolved. The reaction solution was adjusted to pH=7-8 by potassium carbonate aqueous solution, extracted with DCM (10 mL×3). The organic phases were combined, washed with saturated NaCl solution, dried with anhydrous sodium sulfate, concentrated, mixed, and purified by column chromatography (methanol/dichloromethane=0%-10%) to obtain a white solid of the title compound 6 (207 mg, 0.355 mmol) with a yield of 89.8%.

1H NMR (400 MHz, Methanol-d4) δ 7.40 (d, J=1.9 Hz, 1H), 7.27 (d, J=18 Hz, 1H), 7.10 (d, J=7.7 Hz, 1H), 6.90 (dd, J=7.7, 1.6Hz, 1H), 6.82 (d, J=1.6 Hz, 1H), 6.09 (d, J=1.0 Hz, 1H), 4.47 (s, 2H), 3.91 (ddd, J=1.8, 4.5, 2.3 Hz, 2H), 3.59 (td, J=11.9, 2.2 Hz, 2H), 3.51 (s, 2H), 3.38-3.30 (m, 2H), 3.27-3.20 (n. 1H), 3.12 (q, J=7.0 Hz, 2H), 299-289 (m), 2H), 2.37 (s, 3H), 2.31 (s, 3H), 222 (d, J=0.8 Hz, 3H), 2.06-1.89 (m, 4H), 1.84-1.72 (m, 2H), 1.66-1.59 (n, 2H), 0.90 (1, J=7.0 Hz, 3H), MS m/z (ESI): 584.6$[M+H]^+$.

Example 7 N-((4,6-dimethyl-2-oxo-1,2-dihydropyridin-3-yl)methyl)-3-(ethyl(tetrahydro-2H-pyran-4-yl)amino)-2-methyl-5-(1'-methylspiro[dihydroindole-3,4'-piperidine]-6-yl)benzamide

7

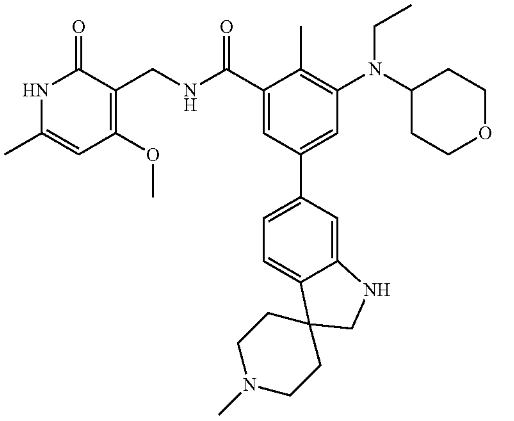

-continued

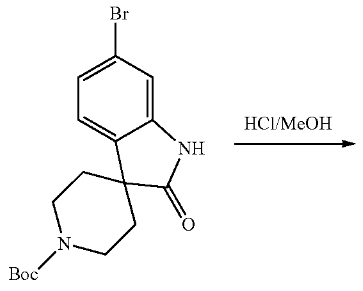

7a

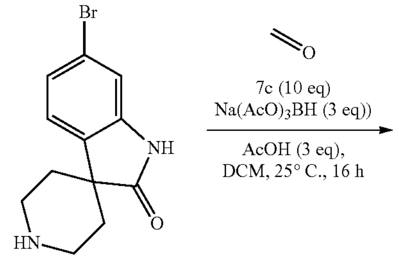

7b

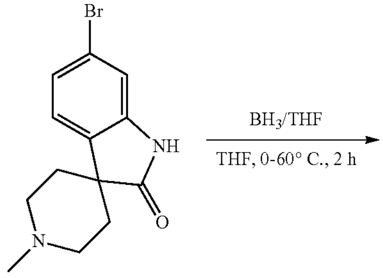

7d

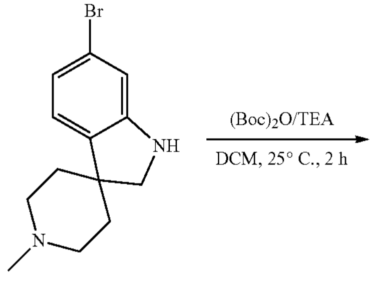

7e

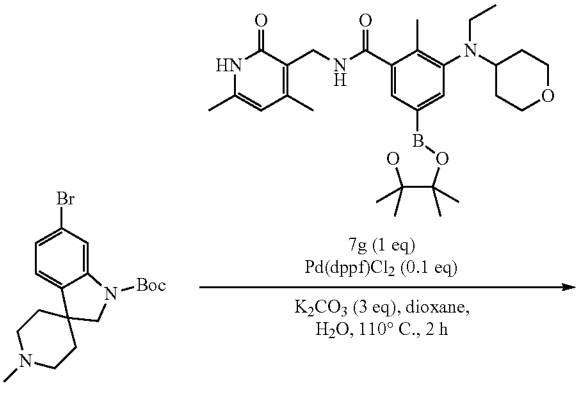

7f

-continued

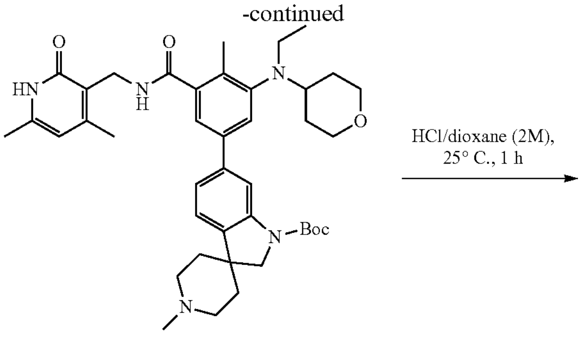

7h

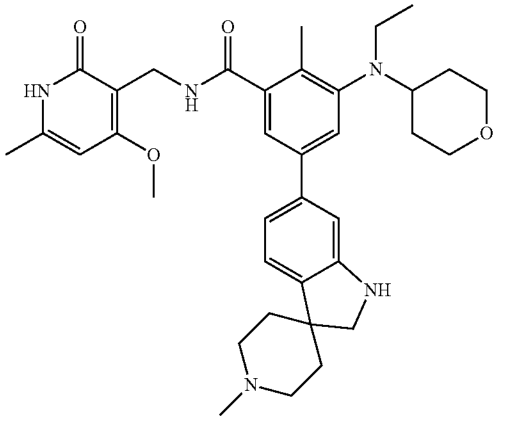

7

Step I 6-bromospiro[dihydroindole-3,4'-piperidine]-2-one 7b

The compound 7a (synthesized according to the method disclosed in EP2108641) (4.7 g, 12.33 mmol) was added in a 250 mL single-necked flask, HCl/MeOH (46 mL, 184 mmol) was added and reacted at 25° C. for 1.5 hours. The raw materials were completely reacted as determined by TLC monitoring and there were new spots formed. The reaction solution was concentrated, added with water, neutralized with NaOH (1 M), extracted with DCM/MeOH (10/1), and concentrated. A light pink solid compound 7b (3 g, 10.67 mmol) was obtained with a yield of 86%, detected by 1H NMR.

1H NMR (400 MHz. DMSO-d6) δ 10.44 (s, 1H), 7.42 (d, J=8.0 Hz, 1H), 7.13 (dd, J=1 Hz, 9 Hz, 1H), 6.98 (d, J=1.9 Hz, 1H), 3.06 (ddd, J=12.7, 6.8, 3.9 Hz, 2H), 2.86 (ddd, J=12.4, 8.2, 3.6 Hz, 2H), 2.13 (s, 1H), 1.67 (ddd, J=12.5, 8.1, 3.8 Hz, 2H), 1.48 (ddd, J=13.1, 6.9, 3.6 Hz, 2H), Step II 6-bromo-1'-methylspiro[dihydroindole-3,4'-piperidine]-2-one 7d The compound 7b (2.9 g, 10.31 mmol), DCM (50 mL), compound 7c (3.1 g, 103 mmol) and AcOH (1.86 g, 30.9 mmol) were added in a 250 mL single-necked flask followed by adding Na(AcO)$_3$BH (6.56 g, 30.9 mmol), reacted for 16 hours. The raw materials were completely reacted as determined by LCMS, and there was MS value of the product in the main peak. The reaction was quenched by adding water to the reaction solution, which was extracted with DCM, washed with saturated NaCl solution, dried, concentrated, mixed with silica gel, and purified by flash column chromatography to obtain a white solid of compound 7d (2 g, 6.78 μmol) with a yield of 40%.

Step III 6-bromo-1'-methylspiro[dihydroindole-3,4'-piperidine]7e

The compound 7d (1.4 g, 4.74 mmol) and THF (10 mL) were added in a 100 mL three-necked flask at 0° C. followed by slowly adding $BH_3$/THF (38 mL, 38 mmol) in the flask, the reaction system was heated to 60° C. and reacted for 2 hours. A residue of raw materials was detected by LCMS monitoring and several new spots were detected by TLC. The reaction was quenched by adding methanol to the reaction solution under ice bath, which was concentrated and purified by flash column chromatography. A white solid of compound 7e (230 mg, 818 μmol) was obtained with a yield of 17%, detected by 1H NMR. 1H NMR (400 MHz, DMSO-d6) δ 7.14 (d, J=7.8 Hz, 1H), 6.67 (dd, J=7, 1.8 Hz, 1H), 6.59 (d, J=1.8 Hz. 1H), 5.88 (s, 1H), 3.36 (d, J=1.8 Hz, 2H), 2.97-2.81 (m, 4H), 2.62 (s, 3H), 1.99 (s, 2H), 1.53 (d, J=14.4 Hz. 2H), Step IV Tert-butyl 6-bromo-1'-methylspiro[dihydroindole-3,4'-piperidine]-1-carboxylate 7f The compound 7e (230 mg, 818 mol), DCM (10 mL) and $(Boc)_2O$ (358 mg, 1.64 mmol) were added in a 100 mL three-necked flask. Then NaOH (82 mg, 2.04 mmol) was dissolved in $H_2O$ (1 mL) and added to the reaction solution dropwise at 25° C., reacted for 16 hours. The raw materials were completely reacted as determined by TLC monitoring. The reaction solution was added with water, extracted with DCM, concentrated, and purified by flash column chromatography. A white solid of compound 7f (230 mg, 603 μmol) was obtained with a yield of 74%.

$^1$H NMR (400 MHz, DMSO-$d_6$) δ 7.84 (s, 1H), 7.46 (d, J=8.1 Hz, 1H), 7.17 (dd, J=8.0, 1.9 Hz, 1H), 3.84 (s, 2H), 2.90 (d, J=12.6 Hz, 4H), 2.65 (s, 3H), 2.08-2.00 (m, 2H), 1.52 (s, 1H),

Step V Tert-butyl 6-(3-(((4,6-dimethyl-2-oxo-1,2-dihydropyridin-3-yl)methyl)carbamoyl)-5-(ethyl (tetrahydro-2H-pyran-4-yl)amino)-4-methylphenyl)-1'-methylspiro[dihydroindole-3,4'-piperidine]-1-carboxylate 7h The compound 7f (100 mg, 262 μmol), compound 7g (synthesized according to the method disclosed in US20120264734) (153 mg, 262 μmol), $K_2CO_3$ (108 mg, 787 μmol), Pd(dppf)$Cl_2$ (23 mg, 31 mol) and dioxane (4 mL) were added in a 50 mL single-necked flask, followed by adding $H_2O$ (1 mL). The reaction solution was heated to 110° C. under the protection of Ar and reacted for 2 hours. The raw materials were completely reacted as determined by LCMS monitoring, and there was MS value of the product in the main peak. The reaction solution was concentrated, mixed with silica gel, and purified by flash column chromatography. A dark brown solid of compound 7h (120 mg, 172 μmol) was obtained with a yield of 44%.

Step VI N-((4,6-dimethyl-2-oxo-1,2-dihydropyridin-3-yl)methyl)-3-(ethyl(tetrahydro-2H-pyran-4-yl) amino)-2-methyl-5-(1'-methylspiro[dihydroindole-3,4'-piperidine]-6-yl)benzamide 7

The compound 7h (120 mg, 192 μmol) and dioxane (2 mL) were added in a 50 mL single-necked flask and dissolved until classified. Then the mixture was added with HCl/dioxane (1.7 mL, 6.88 mmol) and reacted at 25° C. for 2 hours. The raw materials were completely reacted as determined by TLC monitoring. The reaction solution was concentrated, added with water, extracted with EA, and the aqueous phase was neutralized with NaOH (1 M), extracted with DCM, dried with anhydrous sodium sulfate, filtrated, concentrated, and purified by preparative TLC. A light-yellow solid of compound 7f (27.5 mg, 46 μmol) was obtained with a yield of 26.7%.

$^3$H NMR (400 MHz, DMSO-$d_6$) δ 11.45 (s, 1H), 8-17 (t, J=4.9 Hz, 1H), 7.27 (d, 1=1.8 Hz, 1H), 7.10 (d, J=1.7 Hz, 1H), 7.03 (d, J=7.6 Hz, 1H), 6.75 (dd, J=7.5, 1.6 Hz, 1H), 6.66 (d, J=1.5 Hz, 1H), 5.85 (s, 1H), 5.60 (s, 1H), 4.28 (d, J=5.0 Hz, 2H), 3.83 (d, J=11.6 Hz, 2H), 3.32 (s 2H), 3.24 (t, J=11.3 Hz, 1H), 3.11-2.94 (m, 3H), 2.72 (s, 2H), 2.50 (s, 3H), 2.23-2, 19 (m, 6H), 2.10 (s, 5H), 1.80 (t, J=12.3 Hz, 2H), 1-58 (td, J=25.4, 21.7, 12.1 Hz, 6H), 0.82 (t, J=6.9 Hz, 3H),

MS m/z (ES1): 598.5 $[M+H]^+$.

Example 8 3-(ethyl(tetrahydro-2H-pyran-4-yl) amino)-5-(6-fluoro-2',3',5',6'-tetrahydrospiro[indene-1,4'-pyran]-5-yl)-N-((4-methoxy-6-methyl-2-oxo-1,2-dihydropyridin-3-yl)methyl)-2-methylbenzamide 8-1 and 3-(ethyl(tetrahydro-2H-pyran-4-yl)amino)-5-(5-fluoro-2',3',5',6'-tetrahydrospiro[indene-1,4'-pyran]-6-yl)-N-((4-methoxy-6-methyl-2-oxo-1,2-dihydropyridin-3-yl)methyl)-2-methylbenzamide 8-2

8-1

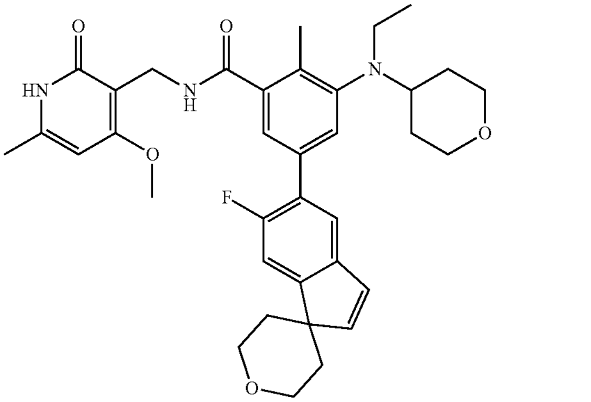

8-2

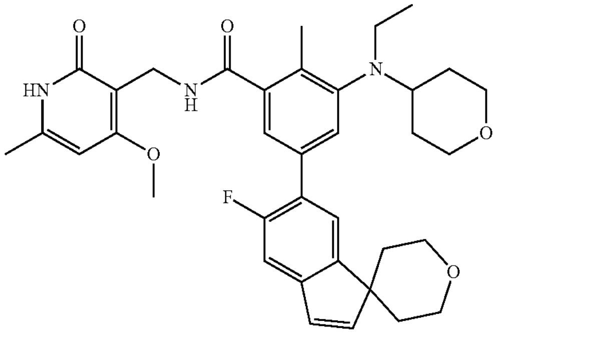

-continued

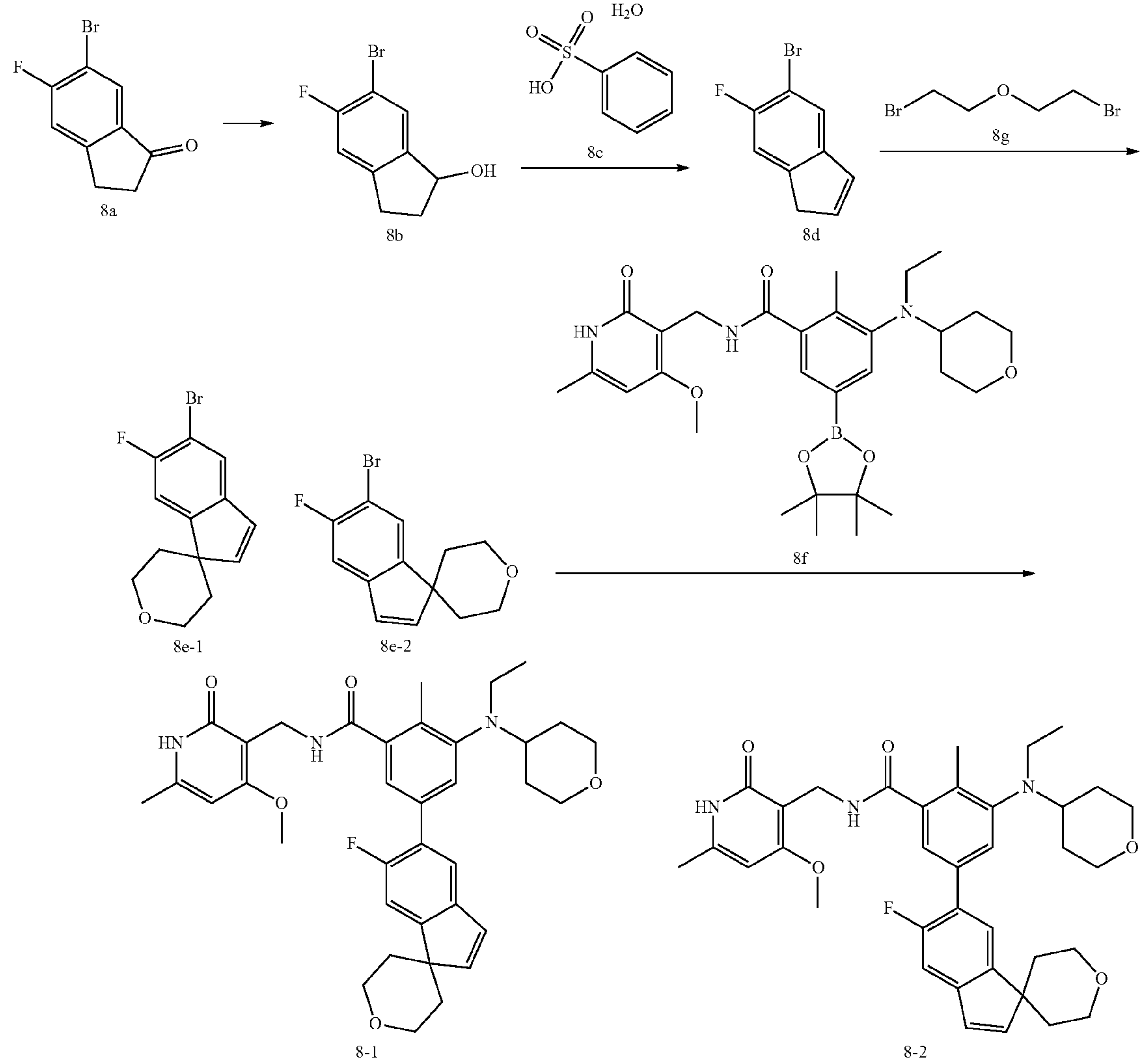

Step I 6-bromo-5-fluoro-2,3-dihydro-1H-inden-1-ol 8b

The compound 8a (4.66 g, 20.35 mmol) and MeOH (70 mL) were added in a 250 mL single-necked flask at 0° C. followed by slowly adding $NaBH_4$ (1.15 g, 30.52 mmol) in the flask, the reaction system was heated to 25° C. and reacted for 2 hours. The raw materials were completely reacted as determined by TLC monitoring and there were new spots formed. The reaction solution was quenched by adding $H_2O$, concentrated to remove methanol, extracted with EA, dried, and concentrated. A light-yellow solid of compound 8b (4.65 g, 20.12 mmol) was obtained with a yield of 99%.

Step II 5-bromo-6-fluoro-1H-indene 8d

The compound 8b (4.65 g, 20.12 mmol), compound 8c (383 mg, 2.01 mmol) and methylbenzene (50 mL) were added in a 250 mL single-necked flask, heated to 110° C. and reacted for 1.5 hours. The raw materials were completely reacted as determined by TLC monitoring. The reaction solution was added with sodium carbonate solution, stirred for 5 minutes, extracted with EA, concentrated, and purified by flash column chromatography to obtain a light-yellow solid of compound 8d (3.45 g, 16.19 mmol) with a yield of 80%.

1H NMR (400 MHz, DMSO-d6) δ 7.72 (d, J=6.6 Hz, 1H), 7.51 (dt, J=8.9, 0.9 Hz, 1H), 6.91-6.85 (m, 1H), 6.68 (dt, J=5.6, 2.0 Hz, 1H), 3.43 (td, J=1.9, 0.9 Hz, 2H),

Step III Mixture of 5-bromo-6-fluoro-2',3',5',6'-tetrahydrospiro[indene-1,4'-pyran]8e-1 and 6-bromo-5-fluoro-2',3',5',6'-tetrahydrospiro[indene-1,4'-pyran]8e-2

The compound 8d (2.3 g, 10.8 mmol), THF (40 mL) and compound 8g (3 g, 12.95 mmol) were added in a 250 mL three-necked flask under the protection of Ar under dry ice bath, followed by adding LiHMDS (34 mL, 43 mmol, 24%) dropwise. The mixture was slowly heated to 70° C. and reacted for 3 hours. The raw materials were completely reacted as determined by TLC monitoring. The reaction solution was quenched by adding $H_2O$, extracted with EA, dried, concentrated, and purified by flash column chromatography to obtain a light-yellow solid of a mixture of compound 8e-1 and compound 8e-2 (1.95 g, 6.89 mmol) with a yield of 63.8%.

$^1$H NMR (400 MHz, DMSO-$d_6$) δ 7.81 (dd, J=6.5, 0.7 Hz, 0.4H), 7.65 (d, J=6.6 Hz, 0.6H), 7.60 (dd, J=9.0, 0.6 Hz, 0.6H), 7.35 (d, J=9.0 Hz, 0.4H), 7.31-7.27 (m, 0.4H), 7.21 (d, J=5.7 Hz, 0.6H), 6.79 (dd, J=6.9, 5.7 Hz, 1H), 3.99-3.87 (m, 2H), 3.71 (td, J=12.1, 2.2 Hz, 2H), 2.21-2.06 (m, 2H), 1.11 (dd, J=13.1, 4.7, 2.2 Hz, 2H),

Step IV Mixture of 3-(ethyl(tetrahydro-2H-pyran-4-yl)amino)-5-(6-fluoro-2',3',5',6'-tetrahydrospiro[indene-1,4'-pyran]-5-yl)-N-((4-methoxy-6-methyl-2-oxo-1,2-dihydropyridin-3-yl)methyl)-2-methylbenzamide 8-1 and 3-(ethyl(tetrahydro-2H-pyran-4-yl)amino)-5-(5-fluoro-2',3',5',6'-tetrahydrospiro[indene-1,4'-pyran]-6-yl)-N-((4-methoxy-6-methyl-2-oxo-1,2-dihydropyridin-3-yl)methyl)-2-methylbenzamide 8-2

The mixture of 8e-1 and 8e-2 (250 mg, 883 μmol), $K_2CO_3$ (366 mg, 2.65 mmol) and Pd(dppf)$Cl_2$ (78 mg, 106 μmol) were added in a 100 mL single-necked flask. The compound 8f (524 mg, 971 μmol) was dissolved in dioxane (5 mL) and added to the flask, which was then added with $H_2O$ (1.2 mL), heated to 110° C. under the protection of Ar and reacted for 3 hours. The raw materials were completely reacted as determined by LCMS monitoring, and there was MS value of the product in the main peak. The reaction solution was concentrated, mixed with silica gel, and purified by flash column chromatography. A light-yellow crude solid was obtained, and 110 mg of the crude was then purified by preparative TLC to obtain a white solid of a mixture of compound 8-1 and 8-2 (22.4 mg, 36 μmol).

$^1$H NMR (400 MHz. Chloroform-d) δ 12.21 (s, 1H), 7.48-7.27 (m, 4-H), 7.12-6.93 (m, 2H), 6.78-6.72 (m, 1H), 5.90 (d, J=3.3 Hz, 1H), 4.60 (t, J=5.1 Hz, 2H), 4.15-4.06 (m, 2H), 3.96 (d, J=11.7 Hz, 2H), 3.89 (d, J=2.3 Hz, 3H), 3.79 (m, J=11.9, 9.5 Hz, 2H), 3.34 (t, J=1.1.4 Hz, 2H), 3.11 (s, 3H), 2.40 (d, J=11.5 Hz, 3H), 2.17 (d, J=4.2 Hz, 4H), 1.73 (s, 4H), 1.34-1.27 (m, 3H), 0.92 (d, J=7.3 Hz, 3H), MS m/z (ES1): 616.7 $[M+H]^+$.

Example 9 3-(ethyl(tetrahydro-2H-pyran-4-yl)amino)-5-(6-fluoro-2,2',3,3',5',6'-hexahydrospiro[indene-1,4'-pyran]-5-yl)-N-((4-methoxy-6-methyl-2-oxo-1,2-dihydropyridin-3-yl)methyl)-2-methylbenzamide 9-1 and 3-(ethyl(tetrahydro-2H-pyran-4-yl)amino)-5-(5-fluoro-2,2',3,3',5',6'-hexahydrospiro[indene-1,4'-pyran]-6-yl)-N-((4-methoxy-6-methyl-2-oxo-1,2-dihydropyridin-3-yl)methyl)-2-methylbenzamide 9-2

9-1

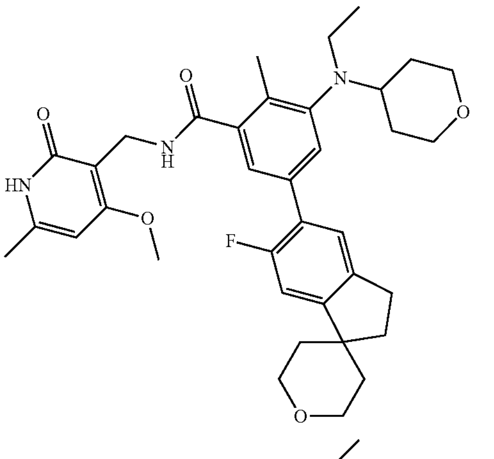

9-2

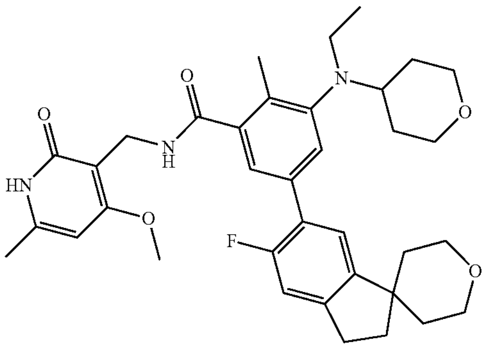

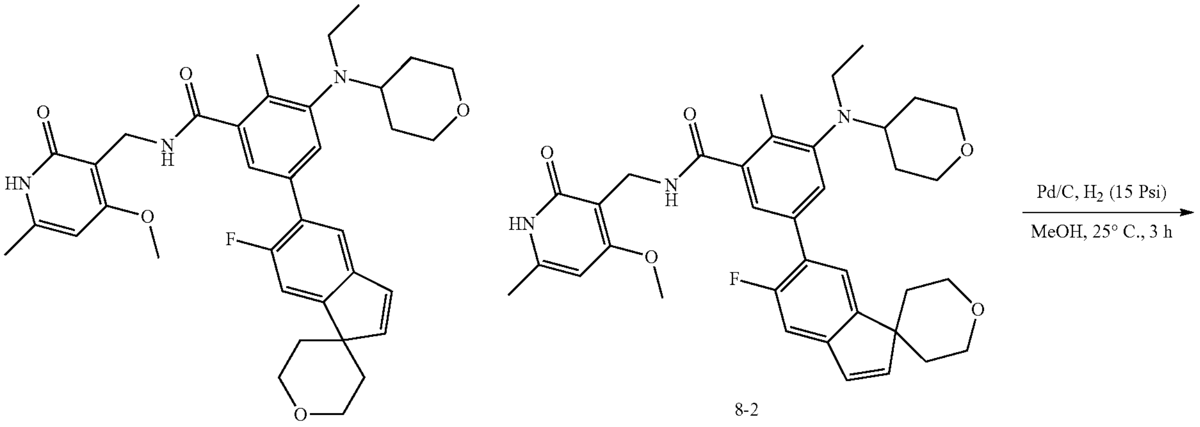

8-2

8-1

-continued

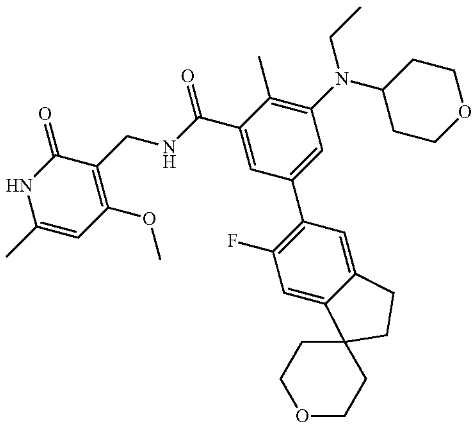

9-1

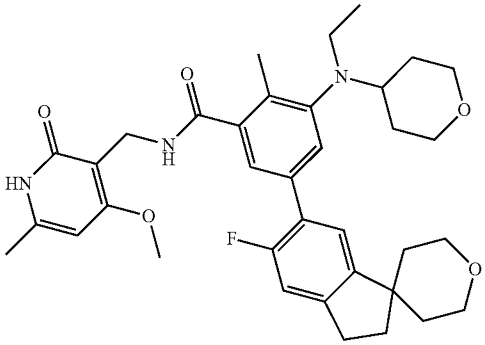

9-2

Step I 3-(ethyl(tetrahydro-2H-pyran-4-yl)amino)-5-(6-fluoro-2,2',3,3',5',6'-hexahydrospiro[indene-1,4'-pyran]-5-yl)-N-((4-methoxy-6-methyl-2-oxo-1,2-dihydropyridin-3-yl)methyl)-2-methylbenzamide 9-1 and 3-(ethyl(tetrahydro-2H-pyran-4-yl)amino)-5-(5-fluoro-2,2',3,3',5',6'-hexahydrospiro[indene-1,4'-pyran]-6-yl)-N-((4-methoxy-6-methyl-2-oxo-1,2-dihydropyridin-3-yl)methyl)-2-methylbenzamide 9-2

The mixture of compound 8-1 and 8-2 (130 mg, 211 μmol), MeOH (15 mL) and Pd/C (130 mg) were added in a 50 mL single-necked flask. The reaction system was replaced with $H_2$ for 3 times and stirred at room temperature for 2 hours. The raw materials were completely reacted as determined by LCMS monitoring, and there was MS value of the product in the main peak. The reaction solution was filtered, concentrated, and purified by flash column chromatography (DCM: MeOH<10:1) to obtain a white solid, which was confirmed to be a mixture of compound 9-1 and 9-2 (26.8 mg, 43 μmol) by 1H NMR, LCMS and HPLC with a yield of 21%.

1H NMR (400 MHz, Chloroform-d) δ 12.53 (s, 1H), 7.27 (s, 3H), 7.17 (dd, J=14.5, 7.3 Hz, 1H), 6.94 (dd, J=15.9, 10.7 Hz, 1H), 5.90 (d, J=2.9 Hz, I1H), 4.59 (t, J=4.9 Hz, 2H), 3.97 (dt, J=11.9, 5.1 Hz, 41), 3.89 (d, J=2.1 Hz, 3H), 3.63 (dt, J=12.6, 10.0 Hz, 2H), 3.33 (t, J=11.4 Hz, 2H), 3.13 (s, 3H), 2.91 (q, J=7.9 Hz, 2H), 2.43 (s, 3H), 217 (dd, J=7.4, 4.6 Hz, 4H), 199-1.90 (m, 2H), 1.74 (s, 4H), 1.50-143 (m, 2H), 0.91 (d, J=16.7 Hz, 3H), MS n/z (ESI): 618.7[M+H]$^+$.

Example 10 2-chloro-N-((4,6-dimethyl-2-oxo-1,2-dihydropyridin-3-yl)methyl)-5-(ethyl(tetrahydro-2H-pyran-4-yl)amino)-6-methyl-3-(1-methyl-2-oxo-2',3',5',6'-tetrahydrospiro[dihydroindole-3,4'-pyran]-6-yl) benzamide

10

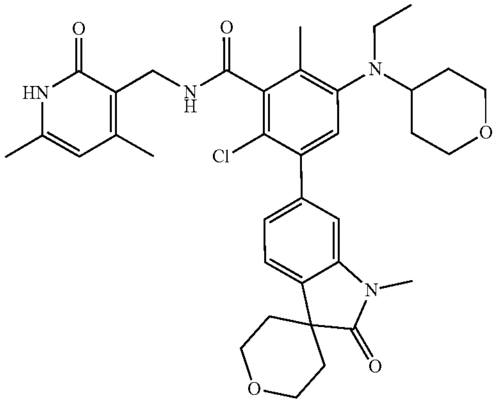

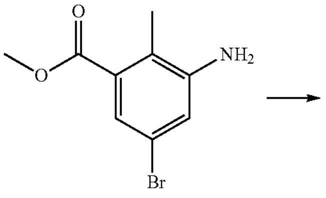

10a

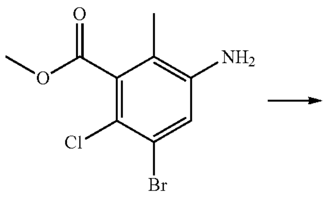

10b

-continued

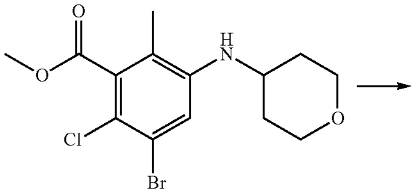

10c

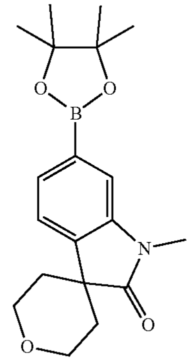

10e

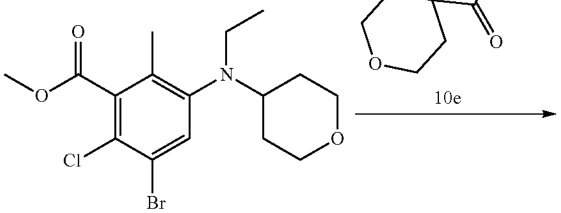

10d

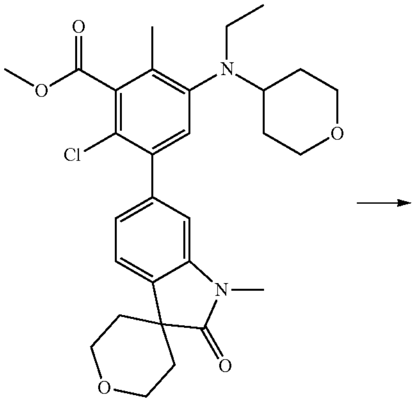

10f

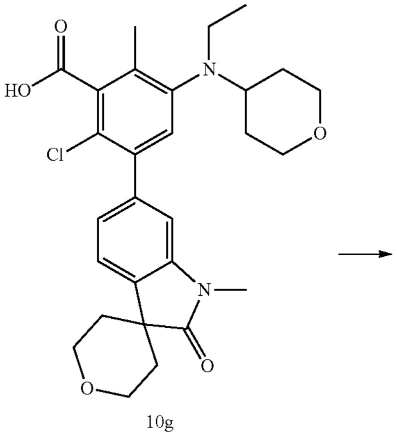

10g

-continued

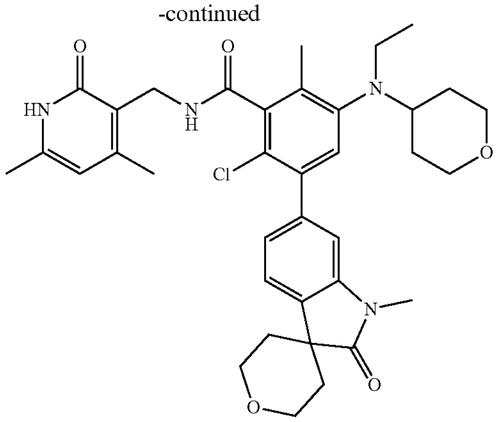

10

Step I Methyl 3-amino-5-bromo-6-chloro-2-methylbenzoate 10b

The compound 10a (6.0 g, 24.7 mmol) was dissolved in dichloromethane (60 mL), added with NCS (3.3 g, 24.7 mmol) slowly dropwise under ice bath, stirred at this temperature for 1 hour, raised to room temperature and reacted overnight. The reaction solution was extracted with DCM, washed with water, dried with anhydrous sodium sulfate, spin-dried, and purified by flash column chromatography (PE:EA=5:1) to obtain a light-yellow oily product, i.e., the title compound 10b (3.6 g, 12.95 mmol) with a yield of 53.6%.

Step II Methyl 3-bromo-2-chloro-5-((tetrahydro-2H-pyran-4-yl)amino)-6-methylbenzoate 10c The compound 10b (3.6 g, 12.95 mmol) and tetrahydro-4H-pyran-4-one (2.6 g, 26.0 mmol) were dissolved in DCM (40 mL), followed by adding acetic acid (2.0 mL) and stirring at room temperature for 0.5 hour. Then sodium triacetoxyborohydride (8.3 g, 39.0 mmol) was added to the mixture and stirred at room temperature overnight. The reaction solution was added with 100 mL of $H_2O$, stirred at room temperature for 0.5 hour, extracted with EA (150 mL×3), dried with anhydrous sodium sulfate, mixed, concentrated, and purified by column chromatography (petroleum ether: ethyl acetate=3:1) to obtain the title compound 10c (3.4 g, 9.4 mmol) with a yield of 80%.

Step III Methyl 3-bromo-2-chloro-5-(ethyl(tetrahydro-2H-pyran-4-yl)amino)-6-methylbenzoate 10d The compound 10c (3.4 g, 9.4 mmol) was dissolved in 30 mL of DCM, acetaldehyde (2.1 g, 47.1 mmol) and acetic acid (2.0 mL) were added. The mixture was stirred at room temperature for 0.5 hour, followed by adding sodium triacetoxyborohydride (6.0 g, 28.3 mmol) under ice bath, naturally raising to room temperature and reacting overnight. A saturated sodium bicarbonate aqueous solution was added to the mixture to adjust the pH to 7, and 200 mL of water was added for extraction. The aqueous phase was extracted with EA (100 mL×2). The organic phases were combined, dried with anhydrous sodium sulfate, concentrated and mixed, and purified by column chromatography (petroleum ether: ethyl acetate=3:1) to obtain the title compound 10d (3.0 g, 7.7 mmol) with a yield of 81.9%.

Step IV 6-Bromo-1-methyl-2',3',5',6'-tetrahydrospiro [dihydroindole-3,4'-pyran]-2-one 10e-1

The compound 1g (6-bromo-2',3',4',5'-tetrahydrospiro[dihydroindole-3,4'-pyran]-2-one) (150 mg, 0.56 mmol) was dissolved DMF (2 mL). Then iodomethane (158.9 mL, 1.12 mmol) and sodium hydride (67.2 mg, 1.68 mmol) were added slowly dropwise under ice bath, and the mixture was stirred under ice bath for 3 hours. The reaction was quenched by water under ice bath, and the reaction solution was extracted with ethyl acetate. The organic phase was washed with saturated NaCl solution, dried with anhydrous sodium sulfate, filtered, concentrated, and purified by column chromatography to obtain the title compound 10e-1 (100 mg, 0.355 mmol) with a yield of 63.5%.

Step V 1-Methyl-6-(4,4,5,5-tetramethyl-1,3,2-dioxaborolan-2-yl)-2',3',5',6'-tetrahydrospiro[dihydroindole-3,4'-pyran]-2-one 10e The compound 10e-1 (6-bromo-1-methyl-2',3',5',6'-tetrahydrospiro[dihydroindole-3,4'-pyran]-2-one) (1.66 g, 5.63 mmol) and bis(pinacolato)diboron (2.2 g, 8.45 mmol) were dissolved in 1,4-dioxane (20 mL), [1,1'-bis(diphenylphosphino)ferrocene]dichloropalladium (0.82 g, 1.13 mmol) and potassium acetate (1.7 g, 16.9 mmol) were added. The mixture was heated to 100° C. under the protection of nitrogen and stirred for 2 hours until the reaction was completed. The reaction solution was extracted with water and ethyl acetate, the organic phase was washed with saturated NaCl solution, dried with anhydrous sodium sulfate, filtered, concentrated, and purified by column chromatography to obtain the title compound 10e (1.6 g, 7.6 mmol) with a yield of 70%.

Step VI Methyl 2-chloro-5-(ethyl(tetrahydro-2H-pyran-4-yl)amino)-6-methyl-3-(1-methyl-2-oxo-2',3',5',6'-tetrahydrospiro[dihydroindole-3,4'-pyran]-6-yl) benzoate 10f The compound 10e (88 mg, 0.256 mmol) was dissolved in 1,4-dioxane (5 mL) and transferred to a microwave tube. The compound 10d (100 mg, 0.256 mmol), Pd(dppf)$_2$Cl$_2$ (38 mg, 0.0512 mmol), potassium carbonate (106 mg, 0.768 mmol) and 1 mL of water were added to the microwave tube, which was then replaced with nitrogen, heated to 100° C. and reacted for 3 hours. The reaction solution was diluted with 20 mL of water and extracted with DCM (20 mL×3). The organic phases were combined, washed with saturated NaCl solution, dried, mixed, and purified by column chromatography (methanol: dichloromethane=1:20) to obtain the title compound 10f (120 mg, 0.228 mmol) with a yield of 88%.

Step VII 2-chloro-5-(ethyl(tetrahydro-2H-pyran-4-yl)amino)-6-methyl-3-(1-methyl-2-oxo-2',3',5',6'-tetrahydrospiro[dihydroindole-3,4'-pyran]-6-yl)benzoic acid 10g The compound 10f (120 mg, 0.228 mmol) was dissolved in tetrahydrofuran (2.0 mL), sodium hydroxide (91 mg, 2.28 mmol) and water (2.0 mL) were added. The mixture was heated to 80° C. and stirred for 16 hours until the reaction was completed. The reaction solution was neutralized to pH=5-6 with hydrochloric acid, extracted with dichloromethane for three times, washed with saturated NaCl solution, dried with anhydrous sodium sulfate, filtered, concentrated, and purified by plate chromatography to obtain a target compound 10g (90 mg, 0.175 mmol) with a yield of 92%.

Step VIII 2-chloro-N-((4,6-dimethyl-2-oxo-1,2-dihydropyridin-3-yl)methyl)-5-(ethyl(tetrahydro-2H-pyran-4-yl)amino)-6-methyl-3-(1-methyl-2-oxo-2',3',5',6'-tetrahydrospiro[dihydroindole-3,4'-pyran]-6-yl) benzamide 10

The compound 10g (90 mg, 0.175 mmol) and 3-(aminomethyl)-4,6-dimethyl-1H-pyridin-2-one hydrochloride (49 mg, 0.263 mmol) was dissolved in N,N-dimethylformamide (4.0 mL), and 1-(3-dimethylaminopropyl)-3-ethylcarbodiimide hydrochloride (50 mg, 0.263 mmol), 1-hydroxybenzotriazole (36 mg, 0.263 mmol) and triethylamine (88 mg, 0.88 mmol) were added. The mixture was reacted at room temperature overnight until the reaction was completed. The reaction solution was washed with water, extracted with dichloromethane for three times, washed with saturated NaCl solution, dried with anhydrous sodium sulfate, filtered, concentrated, and purified by plate chromatography to obtain the title compound 10 (8.0 mg, 0.0124 mmol) with a yield of 7.0%.

$^1$H NMR (400 MHz, DMSO-d6) δ 11.42 (s, 1H), 8.31 (s, 1H), 759 (d, J=7.7 Hz, 1H), 7.06 (s, 1H), 7.01-6.85 (m, 2H), 5.81 (s, 1H), 4.20 (d, J=30.5 Hz, 2H), 4.03 (s, 2H), 3.79 (s, 4H), 319 (t, J=11.3 Hz, 2H), 3.10 (s, 3H), 2.97 (d, J=9.9 Hz, 3H), 2.27-1.97 (m, 9H), 1.72 (s, 4H), 1.60 (d, J=12.0 Hz, 2H), 1.46 (s, 2H), 0.79 (s, 3H),

MS m/z (ESI): 647.7 [M+H]$^+$.

Example 11 2-chloro-N-((4,6-dimethyl-2-carbonyl-1,2-dihydropyridin-3-yl)methyl)-5-(ethyl(tetrahydro-2H-pyran-4-yl)amino)-3-(1-isopropyl-2',3',5',6'-tetrahydrospiro[dihydroindole-3,4'-pyran]-6-yl)-6-methylbenzamide

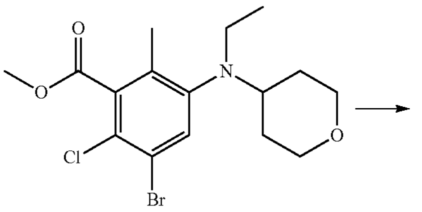

10d

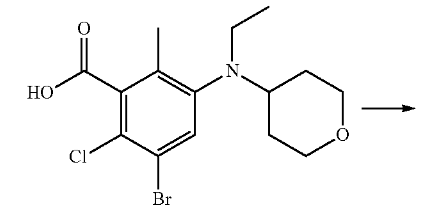

11a

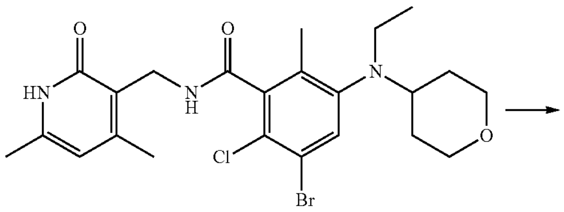

11b

-continued

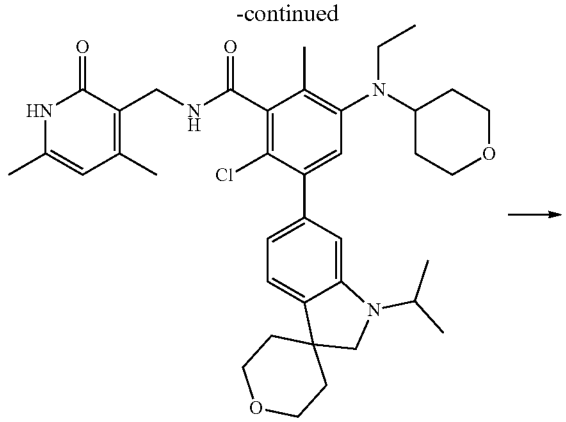

11

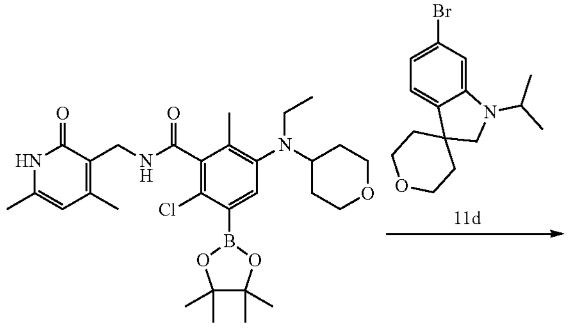

11c

11d

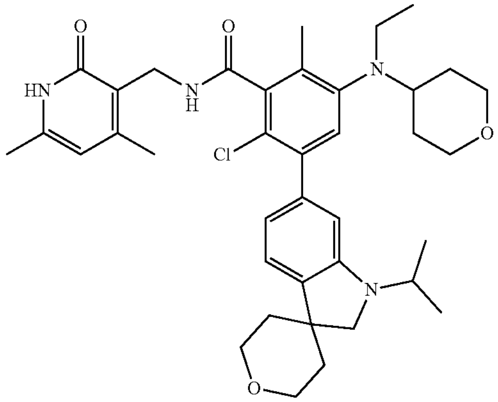

11

Step I 3-bromo-2-chloro-5-(ethyl(tetrahydro-2H-pyran-4-yl)amino)-6-methylbenzoic acid 11a The compound 10d (1000 mg, 2.57 mmol) was dissolved in tetrahydrofuran (2.0 mL), sodium hydroxide (1030 mg, 25.7 mmol) and water (4.0 mL) were added. The mixture was heated to 80° C. and stirred for 16 hours until the reaction was completed. The reaction solution was neutralized to pH=5-6 with hydrochloric acid, extracted with dichloromethane for three times, washed with saturated NaCl solution, dried with anhydrous sodium sulfate, filtered, concentrated, and purified by plate chromatography to obtain a target compound 11a (600 mg, 1.6 mmol) with a yield of 62.2%.

Step II 3-bromo-2-chloro-N-((4,6-dimethyl-2-carbonyl-1,2-dihydropyridin-3-yl)methyl)-5-(ethyl(tetrahydro-2H-pyran-4-yl)amino)-6-methylbenzamide 11b The compound 11a (600 mg, 1.6 mmol) and 3-(aminomethyl)-4,6-dimethyl-1H-pyridin-2-one hydrochloride (450 mg, 2.4 mmol) were dissolved in N,N-dimethylformamide (10.0 mL), 1-(3-dimethylaminopropyl)-3-ethylcarbodiimide hydrochloride (460 mg, 2.4 mmol), 1-hydroxybenzotriazole (324 mg, 2.4 mmol) and triethylamine (810 mg, 8.0 mmol) were added. The mixture was reacted at room temperature overnight until the reaction was completed. The reaction solution was washed with water, extracted with dichloromethane for three times, washed with saturated NaCl solution, dried with anhydrous sodium sulfate, filtered, concentrated, and purified by plate chromatography to obtain the title compound 11b (300 mg, 0.59 mmol) with a yield of 36.8%.

Step III 2-chloro-N-((4,6-dimethyl-2-carbonyl-1,2-dihydropyridin-3-yl)methyl)-5-(ethyl(tetrahydro-2H-pyran-4-yl)amino)-6-methyl-3-(4,4,5,5-tetramethyl-1,3,2-dioxaborolan-2-yl)-benzamide 11c The compound 11b (300 mg, 0.59 mmol) was dissolved in 1,4-dioxane (10 mL) and transferred to a microwave tube. Bis(pinacolato)diboron (299 mg, 1.18 mmol), $Pd(dppf)_2Cl_2$ (96 mg, 0.118 mmol) and potassium acetate (173 mg, 1.77 mmol) were added to the microwave tube, which was replaced with nitrogen, heated to 100° C. and reacted for 3 hours. The reaction solution was diluted with 50 mL of water and extracted with DCM (50 mL×3). The organic phases were combined, washed with 100 mL of saturated NaCl solution, dried, mixed, and purified by column chromatography (methanol: dichloromethane=1:15) to obtain the title compound 11c (200 mg, 0.36 mmol) with a yield of 60.9%.

Step IV 2-chloro-N-((4,6-dimethyl-2-carbonyl-1,2-dihydropyridin-3-yl)methyl)-5-(ethyl(tetrahydro-2H-pyran-4-yl)amino)-3-(1-isopropyl-2',3',5',6'-tetrahydrospiro[dihydroindole-3,4'-pyran]-6-yl)-6-methylbenzamide 11

The compound 11c (100 mg, 0.18 mmol) was dissolved in 1,4-dioxane (10 mL) and transferred to a microwave tube. The compound 1id (synthesis process see Example 30) (56 mg, 0.18 mmol), $Pd(dppf)_2Cl_2$ (30 mg, 0.036 mmol), potassium carbonate (50 mg, 0.36 mmol) and 1 mL of water were added to the microwave tube, which was replaced with nitrogen, heated to 100° C. and reacted for 4 hours. The reaction solution was diluted with 30 mL of water and extracted with DCM (20 mL×3). The organic phases were combined, washed with 50 mL of saturated NaCl solution, dried, mixed, and purified by column chromatography (methanol: dichloromethane=1:20) to obtain the title compound 11 (30.0 mg, 0.0454 mmol) with a yield of 25.3%.

$^1$H NMR (400 MHz, DMSO-d6) δ 11.41 (s 1H), 9.40 (s, 1H), 8.29 (t, J=5.1 Hz, 1H), 7.08-6.95 (m, 2H), 6.45 (d, J=7.5 Hz, 1H), 6.33 (s, 1H), 5.81 (s, 1H), 4.24 (m, 2H), 4.17 (d, J=4.9 Hz, 1H), 3.78 (d, J=8.6 Hz, 4H), 3.47 (t, J=11.7 Hz, 2H), 3.31 (s, 2H), 3.19 (t, J=11.5 Hz, 2H), 2.95 (dd, J=15.8, 9.0 Hz, 3H), 2.16 (s, 2H), 2.11 (s, 2H), 2.08 (d, J=3.1 Hz, 2H), 2.06 (s, 2H), 1.87-1.73 (m, 2H), 1.59 (d, J=12.4 Hz, 2H), 1.47 dd, J=22.9, 12.3 Hz, 4H), 1.07 (d, J 6.5 Hz, 6H), 0.78 (t, J=6.9 Hz, 3H),

MS m/z (ESI): 661.8 $[M+H]^+$.

Example 12 N-((4,6-dimethyl-2-carbonyl-1,2-dihydropyridin-3-yl)methyl)-3-(ethyl(tetrahydro-2H-pyran-4-yl)amino)-5-(5-fluoro-1-methyl-2-carbonyl-2',3',5',6'-tetrahydrospiro[dihydroindole-3,4'-pyran]-6-yl)-2-methylbenzamide

12

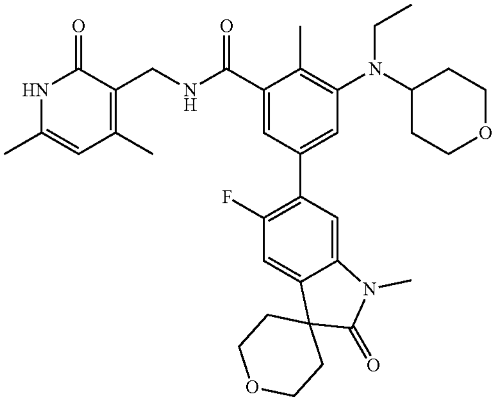

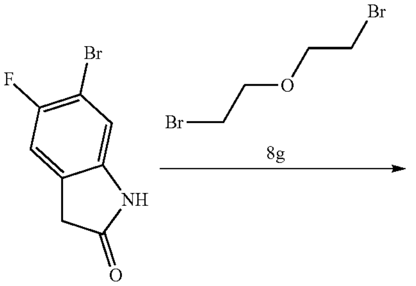

12a

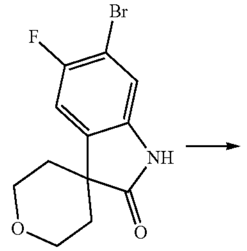

12b

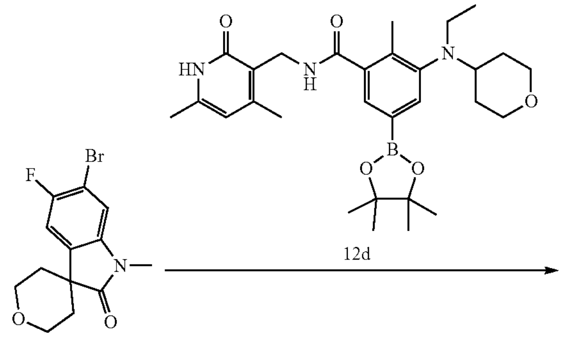

12c

-continued

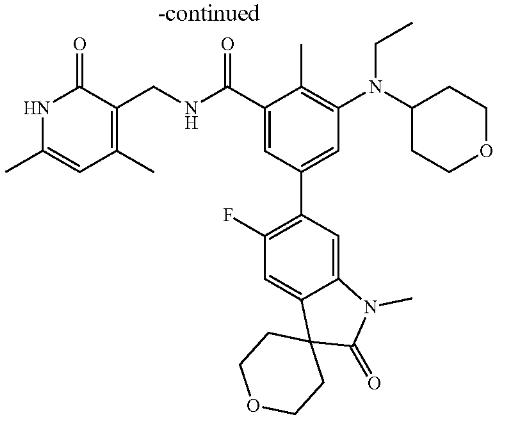

12

Step I 6-bromo-5-fluoro-2',3',5',6'-tetrahydrospiro [dihydroindole-3,4'-pyran]-2-one 12b A compound 12a (2.0 g, 8.7 mmol) was dissolved in tetrahydrofuran (100 mL), and lithium bis(trimethylsilyl) amide (21.8 mL, 43.5 mmol) was slowly added dropwise at −78° C. The mixture was stirred at this temperature for 30 minutes, followed by adding 2,2'-dibromodiethyl ether (2.0 g, 8.7 mmol) slowly heating to 70° C. and stirring for 1 hours. After the reaction was completed, it was quenched with water under ice water bath, and the reaction solution was extracted by water and ethyl acetate. The organic phase was washed with saturated NaCl solution, dried with anhydrous sodium sulfate, filtered, concentrated, and purified by column chromatography to obtain the title compound 12b (200 mg, 0.67 mmol) with a yield of 77%.

Step II 6-bromo-5-fluoro-1-methyl-2',3',5',6'-tetrahydrospiro[dihydroindole-3,4'-pyran]-2-one 12c The compound 12b (200 mg, 0.67 mmol) was dissolved in DMF (10 mL), and sodium iodide (189 mg, 1.33 mmol) was added under ice bath and stirred at room temperature overnight. The reaction solution was added with 100 mL of $H_2O$, stirred at room temperature for 0.5 hour, extracted with EA (100 mL×3), dried with anhydrous sodium sulfate, mixed, concentrated, and purified by column chromatography (petroleum ether: ethyl acetate=3:1) to obtain the title compound 12c (120 mg, 0.382 mmol) with a yield of 57%.

Step III N-((4,6-dimethyl-2-carbonyl-1,2-dihydropyridin-3-yl)methyl)-3-(ethyl(tetrahydro-2H-pyran-4-yl)amino)-5-(5-fluoro-1-methyl-2-carbonyl-2',3',5',6'-tetrahydrospiro[dihydroindole-3,4'-pyran]-6-yl)-2-methylbenzamide 12

The compound 12d (200 mg, 0.38 mmol) was dissolved in 1,4-dioxane (20.0 mL) and transferred to a microwave tube. The compound 12c (120 mg, 0.38 mmol), Pd(dppf)$_2$ $Cl_2$ (62 mg, 0.077 mmol), potassium carbonate (106 mg, 0.76 mmol) and 2.0 mL of water were added to the microwave tube, which was replaced with nitrogen, heated to 100° C. and reacted for 4 hours. The reaction solution was diluted with 30 mL of water and extracted with DCM (20 mL×3). The organic phases were combined, washed with 50 mL of saturated NaCl solution, dried, mixed, and purified by column chromatography (methanol: dichloromethane=1:20) to obtain the title compound 12 (13.0 mg, 0.021 mmol) with a yield of 5.4%.

$^1$H NMR (400 MHz, DMSO-d6) δ 11.41 (s, 1H), 813 (t, J=4.9 Hz, 1H), 7.57 (d, J=10.3 Hz, 1H), 7.29 (S, 1H), 7.12 (s, 1H), 7.05 (d, J=6.3 Hz, 1H), 5.82 (s, 1H), 4:24 (d, J=4.9 Hz, 2H), 4.02 (ddd, J=11.1, 7.4, 3.6 Hz, 2H), 3.79 (d, J=11.7 Hz, 4H), 3.31 (s, 2H), 3.21 (t, J=11.3 Hz, 2H), 3.13 (s, 2H), 3.00 (dd, J=15.2, 8.4 Hz, 3H), 2.28-2.07 (m, 6H), 2.06 (s, 3H) 1.80-1.66 (m, 3H), 1.62 (d, J=12.1 Hz, 2H), 1.55-1.41 (m, 2H), 0.80 (t, J=6.9 Hz, 3H), MS m/z (ESI): 631.6 $[M+H]^+$.

Example 13 N-((4,6-dimethyl-2-carbonyl-1,2-dihydropyridin-3-yl)methyl)-3-(ethyl(tetrahydro-2H-pyran-4-yl)amino)-2-methyl-5-(2-carbonyl-1-(2,2,2-trifluoroethyl)-2',3',5',6'-tetrahydrospiro [dihydroindole-3,4'-pyran]-6-yl)benzamide

13

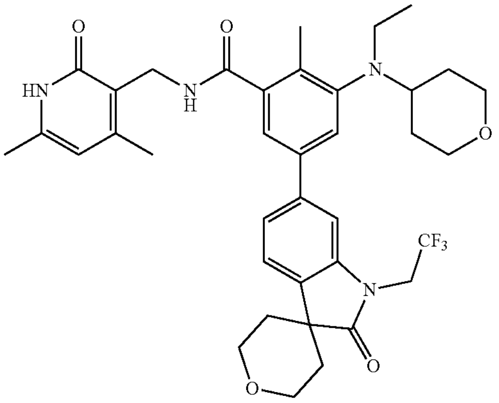

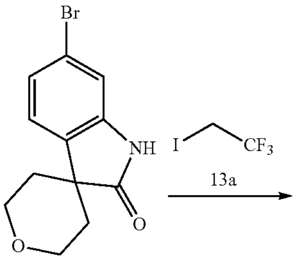

5a

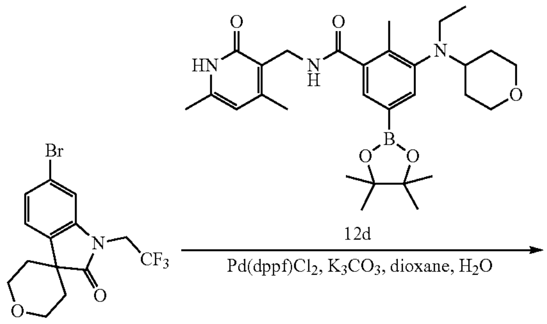

13b

-continued

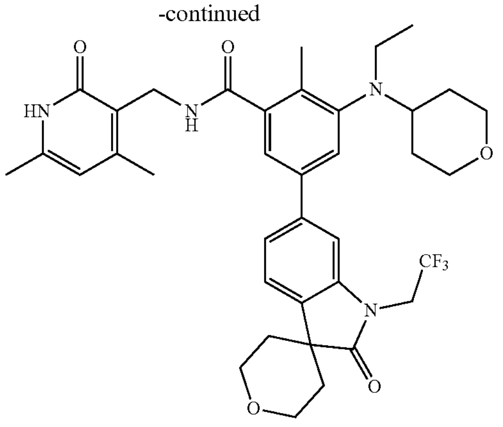

13

Step I 6-bromo-1-(2,2,2-trifluoroethyl)-2',3',5',6'-tetrahydrospiro[dihydroindole-3,4'-pyran]-2-one 13b The compound 5a (600 mg, 2.127 mmol) was dissolved in DMF (10 mL), the compound 13a (1787 mg, 8.51 mmol) and $K_2CO_3$ (587 mg, 4.25 mmol) were added. The mixture was heated to 100° C. and reacted for 48 hours, followed by quenching with water. The reaction solution was extracted with dichloromethane for three times, washed with saturated NaCl solution, dried with anhydrous sodium sulfate, filtered, concentrated, and purified by column chromatography to obtain the title compound 13b (0.45 g, 1.23 mmol) with a yield of 58%.

MS m/z (ESI): 366 $[M+1]^+$.

Step II N-((4,6-dimethyl-2-carbonyl-1,2-dihydropyridin-3-yl)methyl)-3-(ethyl(tetrahydro-2H-pyran-4-yl)amino)-2-methyl-5-(2-carbonyl-1-(2,2,2-trifluoroethyl)-2',3',5',6'-tetrahydrospiro[dihydroindole-3, 4'-pyran]-6-yl)benzamide 13

The compound 13b (120 mg, 0.3296 mmol), $K_2CO_3$ (136 mg, 0.98 mmol), $Pd(dppf)Cl_2$ (24 mg, 0.03296 mmol), compound 12d (206 mg, 0.3956 mmol) were dissolved in dioxane (15 mL) and $H_2O$ (5 mL). The mixture was heated to 100° C. under the protection of Ar and stirred for 6 hours until the reaction was completed. The reaction solution was extracted with water and ethyl acetate, and the organic phase was washed with saturated NaCl solution, dried with anhydrous sodium sulfate, filtered, concentrated, and purified by column chromatography to obtain the title compound 13 (80 mg, 0.117 mmol) with a yield of 35.7%.

1H NMR (400 MHz, Methanol-d4) δ 7.54 (d, J=7.8 Hz, 1H), 7.45 (d, J=1.9 Hz, 1H), 7.37-727 (m, 3H), 6.09 (s, 1H), 4.57 (t, J=9.1 Hz, 2H), 448 (s, 2H), 4.19 (ddd, J=1L9, 8.6, 3.3 Hz, 2H), 3.98-3.83 (m, 4H), 3.34 (dd, J=12.2, 10.1 Hz, 2H), 3.18-3.04 (m, 3H), 2.38 (s, 3H), 2.31 (s, 3H), 2.26-2.18 (m, 3H), 1.89 (dd, J=8.8, 4.3 Hz, 2H), 1.86-1.70 (m, 4H), 1.63 (dd, J=12.1, 4.1 Hz, 2H), 0.89 (t, J=7.0 Hz, 3H), MS m/z (ESI):681.8 $[M+1]^+$.

Example 14 N-((4,6-dimethyl-2-carbonyl-1,2-dihydropyridin-3-yl)methyl)-3-(ethyl(tetrahydro-2H-pyran-4-yl)amino)-2-methyl-5-(2-carbonyl-1-(3,3,3-trifluoropropyl)-2',3',5',6'-tetrahydrospiro[dihydroindole-3,4'-pyran]-6-yl)benzamide

14

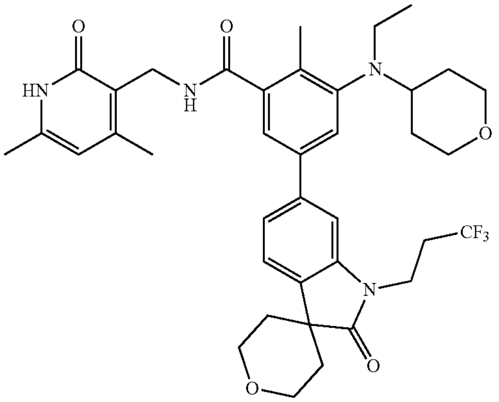

A similar method of Example 13 was used to obtain the title compound 14 with a yield of 54%, wherein the 1,1,1-trifluoro-2-iodoethane was replaced with 1,1,1-trifluoro-3-iodopropane.

$^1$H NMR (400 MHz, Methanol-d4) δ 7.54 (d, J=7.8 Hz, 1H), 7.46 (d, J=1.9 Hz, 1H), 7.36-7.27 (ml, 2H) 7.19 (d, J=1.5 Hz, 1H), 6.09 (s, 1H), 4.48 (s, 2H), 4.23-4.13 (m, 2H), 4.07 (t, J=6.6 Hz, 2H), 3.92 (dt, J=2, 1, 5.1 Hz, 4H), 3.34 (dd, J=12.1, 1 Hz, 2H), 3.18-3.04 (m, 3H), 2.68-2.53 (m, 2H), 2.38 (s, 3H) 2.31 (s, 3H), 2.22 (s, 3H), 1.82 (t, J=3.9 Hz, 4H), 1.75 (d, J=12.7 Hz, 2H), 1.63 (dd, J=12.0, 4.1 Hz, 2H), 0.89 (t, J=7.0 Hz, 3H), MS m/z (ESI):695.8 [M+H]+

Example 15 N-((4,6-dimethyl-2-carbonyl-1,2-dihydropyridin-3-yl)methyl)-3-(ethyl(tetrahydro-2H-pyran-4-yl)amino)-5-(1'-isopropyl-1-methyl-2-carbonylspiro[dihydroindole-3,4'-piperidine]-6-yl)-2-methylbenzamide

15

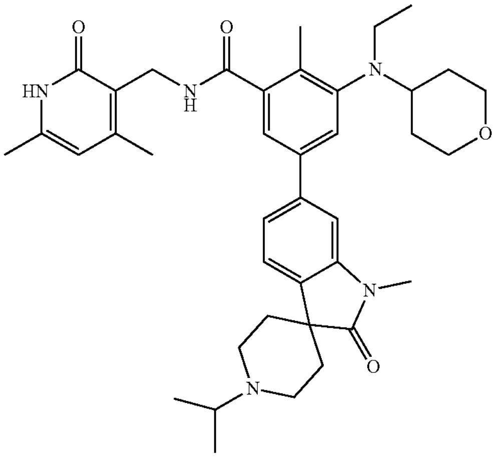

-continued

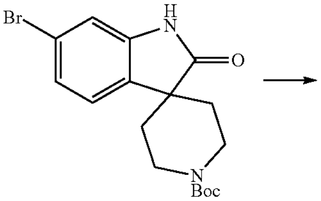

7a

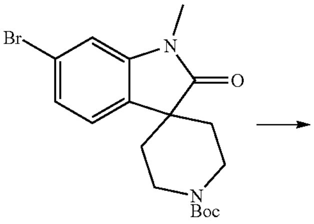

15a-1

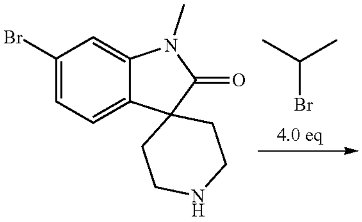

15a

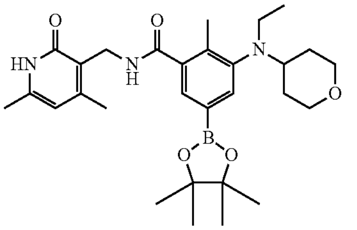

12d

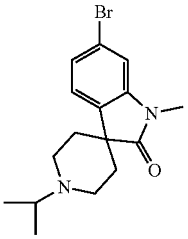

15b

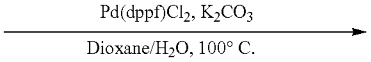

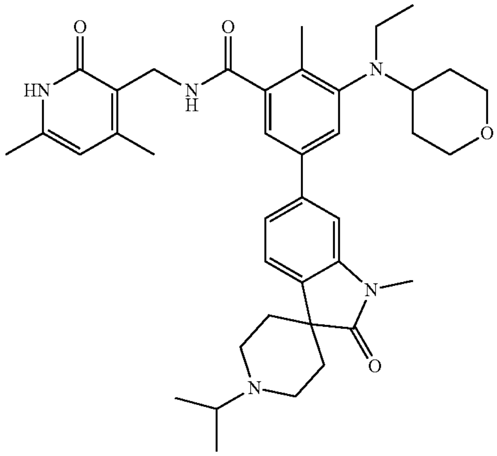

15

Step I Tert-butyl 6-bromo-1-methyl-2-oxospiro[dihydroindole-3,4'-piperidine]-1'-carboxylate The compound 7a (0.87 g, 2.2 mmol) was dissolved in DMF (10 mL), followed by adding iodomethane (0.62 g, 4.4 mmol) and potassium carbonate (0.67 g, 4.4 mmol) and stirring at 70° C. for 4 hours. The reaction solution was washed with water, concentrated to obtain the title compound 15a-1 (0.60 g, 2.1 mmol) with a yield of 80%.

Step II 6-bromo-1-methylspiro[dihydroindole-3,4'-piperidine]-2-one

The compound 15a-1 (0.60 g, 2.1 mmol) was dissolved in DCM (10 mL), followed by adding trifluoroacetic acid (4 mL) and stirred at room temperature overnight. The reaction solution was concentrated to obtain the title compound 15a (0.50 g, 2.1 mmol) with a yield of 95%.

Step III 6-bromo-1'-isopropyl-1-methylspiro[dihydroindole-3,4'-piperidine]-2-one 15b The compound 15a (200 mg, 0.678 mmol) was dissolved in DCM (3 mL), bromoisopropane (334 mg, 2.71 mmol) and potassium carbonate (561 mg, 4.074 mmol) were successively added, followed by stirring at room temperature for 24 hours. The mixture was added with EA/$H_2O$ (20 mL/20 mL), stirred for 5 minutes and separated. The aqueous phase was extracted with EA (10 mL×3), and the organic phases were combined, washed with saturated NaCl solution, dried, mixed, and purified by column chromatography (EA/PE=0%-100%) to obtain a white solid of the title compound 15b (90 mg, 0.267 mmol) with a yield of 39.4%.

MS m/z (ESI): 337.3 $[M+H]^+$.

Step IV N-((4,6-dimethyl-2-carbonyl-1,2-dihydropyridin-3-yl)methyl)-3-(ethyl(tetrahydro-2H-pyran-4-yl)amino)-5-(1'-isopropyl-1-methyl-2-carbonyl-spiro[dihydroindole-3,4'-piperidine]-6-yl)-2-methylbenzamide 15

The compound 15b (90 mg, 0.267 mmol) was dissolved in 3 mL of 1,4-dioxane, the compound 12d (140 mg, 0.267 mmol), Pd(dppf)$Cl_2$ (20 mg, 0.03267 mmol), potassium carbonate (74 mg, 0.534 mmol) and 1 mL of water were added. The mixture was heated to 100° C. under the protection of nitrogen and reacted for 3 hours. After cooling to room temperature, the reaction solution was diluted with 3 mL of water and extracted with EA (5 mL×3). The organic phases were combined, washed with saturated NaCl solution, dried, mixed, and purified by column chromatography (methanol: dichloromethane=0%-10%) to obtain a white solid of the title compound 15 (35 mg, 0.0536 mmol) with a yield of 20%. MS m/z (ESI): 654 $[M+H]^+$.

Example 16 3-(ethyl(tetrahydro-2H-pyran-4-yl)amino)-5-(5-fluoro-2,2',3,3',5',6'-hexahydrospiro[indene-1,4'-pyran]-6-yl)-N-((4-methoxy-6-methyl-2-carbonyl-1,2-dihydropyridin-3-yl)methyl)-2-methylbenzamide

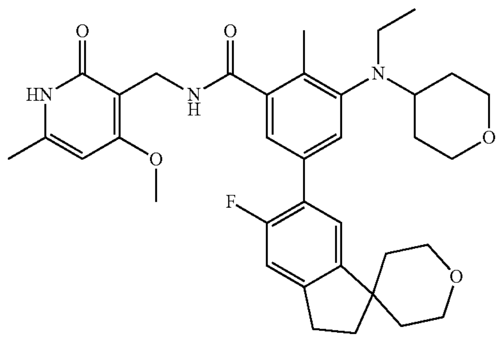

16

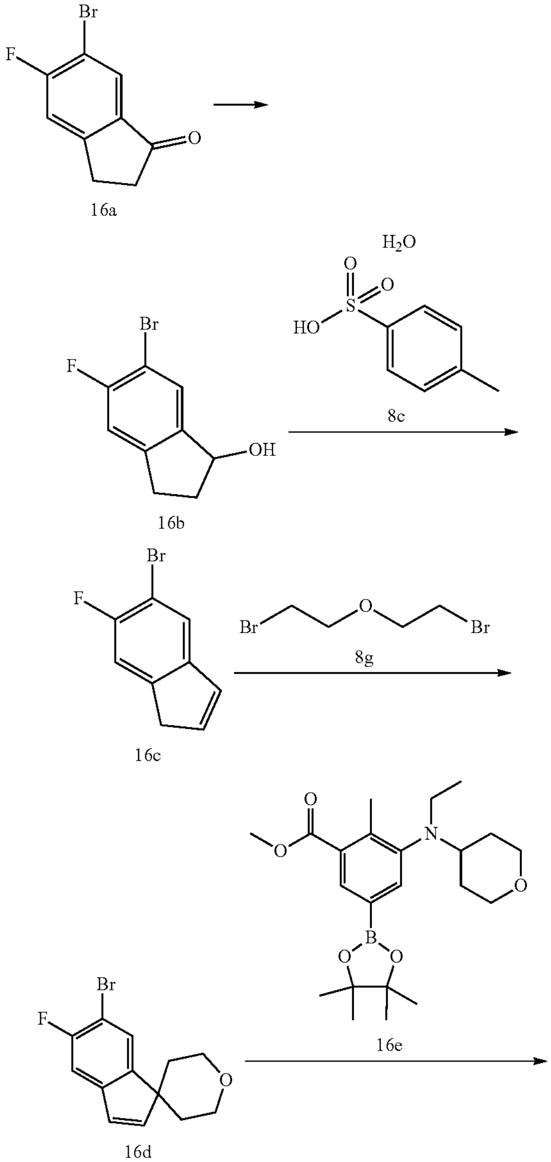

16a

16b

16c

16d

-continued

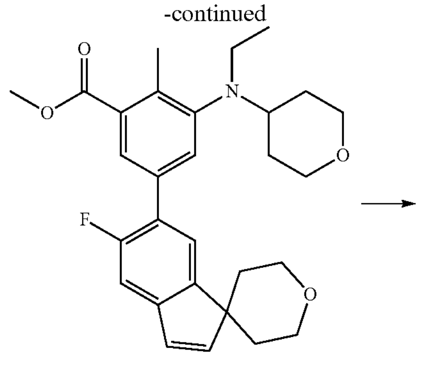

16f

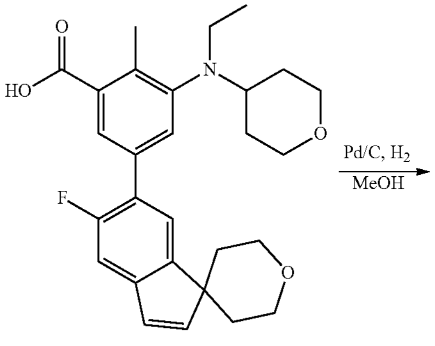

16g

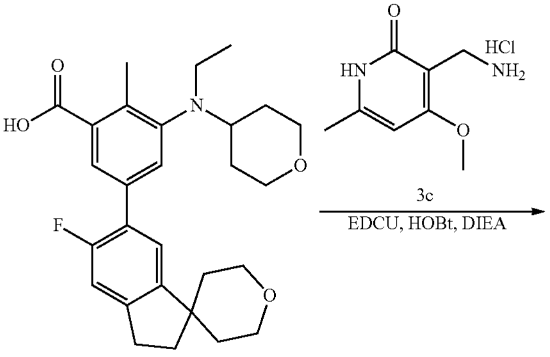

16h

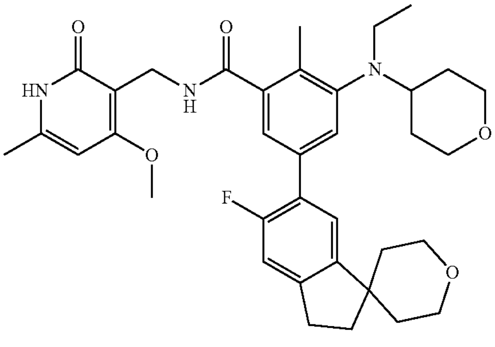

16

Step I 6-bromo-5-fluoro-2,3-dihydro-1H-inden-1-ol 16b

The compound 16a (4.66 g, 20.35 mmol) and MeOH (70 mL) were added in a 250 mL single-necked flask, and $NaBH_4$ (1.15 g, 30.52 mmol) was added under ice bath. The mixture was heated to 15° C. and reacted for 2 hours. The raw materials were completely reacted as determined by TLC monitoring and there were new spots formed. The reaction solution was quenched by adding $H_2O$, concentrated, extracted with EA, and dried. A light-yellow solid of compound 17b (4.65 g, 20.12 mmol) was obtained with a yield of 99%.

Step II 5-bromo-6-fluoro-1H-indene 16c

The compound 16b (4.65 g, 20.12 mmol), compound 8c (383 mg, 2.01 mmol) and toluene (50 mL) were added in a 250 mL single-necked flask, the mixture was heated to 110° C. and reacted for 1.5 hours. The raw materials were completely reacted as determined by TLC monitoring and there were new spots formed. The reaction solution was added with $H_2O$ and sodium carbonate solution, stirred for 5 minutes, extracted with EA, dried, and purified by flash column chromatography to obtain a light-yellow solid of compound 16c (3.45 g, 16.19 mmol) with a yield of 80%.

1H NMR (400 MHz, DMSO-d6) δ 7.72 (d, J=6.6 Hz, 1H), 7.51 (dt, J=8.9, 0.9 Hz, 1H), 6.91-6.85 (m, 1H), 6.68 (dt, J=56, 2.0 Hz, 1H), 3.43 (td, J=1.9, 0.9 Hz, 2H),

Step III 6-bromo-5-fluoro-2',3',5',6'-tetrahydrospiro [indene-1,4'-pyran]16d

The compound 16c (2.3 g, 10.8 mmol), THF (40 mL) and compound 8g (3 g, 12.95 mmol) were added in a 250 mL three-necked flask under the protection of Ar and under dry ice bath, followed by adding LiHMDS (34 mL, 43.18 mmol, 24%) dropwise. The mixture was slowly heated to 70° C. and reacted for 3 hours. The raw materials were completely reacted as determined by TLC monitoring and there were new spots formed. The reaction solution was quenched by adding $H_2O$, extracted with EA, dried with anhydrous sodium sulfate, filtrated, concentrated, and purified by flash column chromatography to obtain a light-yellow solid of compound 16d (1.95 g, 6.89 mmol) with a yield of 63.8%.

1H NMR (400 MHz, DMSO-d6) δ 7.81 (dd, J=6.5, 0.7 Hz, OH), 7.65 (d, J 6.6 Hz, 1H), 7.60 (dd, J=9.0, 0.6 Hz, 1H), 7.35 (d, J=9.0 Hz, OH), 731-7.27 (m, 0H), 7.21 (d, J=5.7 Hz, 1H), 6.79 (dd, J=6.9, 57 Hz, 1H), 3.99-3.87 (m, 2H), 3.71 (td. J=12.1, 2.2 Hz, 2H), 2.21, 2.06 (m, 2H), 1.11 (ddd, J=13.1, 4.7, 2.2 Hz, 2H), Step IV Methyl 3-(ethyl(tetrahydro-2H-pyran-4-yl) amino)-5-(5-fluoro-2',3',5',6'-tetrahydrospiro[indene-1,4'-pyran]-6-yl)-2-methylbenzoate 16f The compound 17d (500 mg, 1.77 mmol), compound 16e (854.7 mg, 2.12 mmol), $Pd(dppf)Cl_2$ (129 mg, 177 mol), $K_2CO_3$ (976 mg, 7.06 mmol), dioxane (10 mL) and $H_2O$ (2.5 mL) were added in a 100 mL single-necked flask. The mixture was heated to 100° C. under the protection of Ar and reacted for 3 hours, detected by LCMS monitoring. There was MS value of the product in the main peak. The raw materials were completely reacted as determined by TLC monitoring. The reaction solution was then added with $H_2O$ and sodium carbonate solution, stirred for 5 minutes, extracted with EA, dried, purified by flash column chromatography, and purified by preparative TLC to obtain a white solid of compound 16f (200 mg, 417 μmol).

$^1$H NMR (400 MHz, Chloroform-d) δ 7.76 (s, 1H), 7.50 (s, H), 738 (d, J=7.4 Hz, 1H), 7.15-7.06 (m, 2H), 6.79 (d, J=5.6 Hz, 1H), 4.13-4.08 (m, 2H), 3.94 (s, 5H), 3.80 (d, J=12.1, 2.1 Hz, 2H), 336 (t, J=11.3 Hz, 2H), 108 (d, J=36.7

Hz, 3H), 2.58 (s, 3H): 2.32-2.20 (m, 2H), 1.74 (d, J=21.1 Hz, 4H), 139-1.31 (m, 2H), 0.94 (s, 3H),

Step V 3-(ethyl(tetrahydro-2H-pyran-4-yl)amino)-5-(5-fluoro-2',3',5',6'-tetrahydrospiro[indene-1,4'-pyran]-6-yl)-methyl-benzoic acid 16g The compound 8 (200 mg, 417 μmol), MeOH (6 mL), $H_2O$ (2 mL) and NaOH (50 mg, 1.25 mmol) were added in a 50 mL single-necked flask, which were reacted at room temperature for 16 hours. The raw materials were completely reacted as determined by LCMS monitoring. The reaction solution was concentrated, added with $H_2O$, extracted with EA, and the aqueous phase was neutralized with HCl, extracted with DCM, and concentrated to obtain a white solid of compound 16g (150 mg, 322 μmol) with a yield of 77%.

Step VI 3-(ethyl(tetrahydro-2H-pyran-4-yl)amino)-5-(5-fluoro-2,2',3,3',5',6'-hexahydrospiro[indene-1,4'-pyran]-6-yl)-2-methylbenzoic acid 16h The compound 16g (150 mg, 322 μmol), MeOH (10 mL) and Pd/C (150 mg, 10%, wet) were added in a 100 mL single-necked flask. The reaction system was replaced with $H_2$ (15 Psi) for 3 times, and reacted at 25° C. for 3 hours. The raw materials were completely reacted as determined by LCMS monitoring, and there was MS value of the product in the main peak. The reaction solution was filtered and concentrated to obtain a white solid of compound 16h (130 mg, 278 μmol) with a yield of 86%.

Example 16 3-(ethyl(tetrahydro-2H-pyran-4-yl)amino)-5-(5-fluoro-2,2',3,3',5',6'-hexahydrospiro[indene-1,4'-pyran]-6-yl)-N-((4-methoxy-6-methyl-2-carbonyl-1,2-dihydropyridin-3-yl)methyl)-2-methylbenzamide 16

The compound 16h (70 mg, 150 μmol), EDCI(57 mg, 299 μmol), HOBt (57 mg, 299 μmol), DMF(3 mL), DIPEA (0.18 mL, 1.2 mmol, 0.75 g/mL) and compound 3c (61 mg, 299 μmol) were added in a 50 mL single-necked flask. The mixture was reacted at 25° C. for 16 hours. The raw materials were completely reacted as determined by LCMS monitoring, and there was MS value of the product in the main peak. The reaction solution was added with water, extracted with DCM, dried with anhydrous sodium sulfate, concentrated, and purified by flash column chromatography to obtain a light-yellow solid, which was confirmed to be compound 16 (37.2 mg, 60 μmol) by $^1$H NMR and LCMS with a yield of 40%.

$^1$H NMR (400 MHz, DNSO-d6) δ 11.41 (s, 1H), 7.96 (s, 1H), 7.32-7.25 (m, 2H), 7.14-7.07 (m, 2H), 6.08 (s, 1H), 4.23 (d, J=4.6 Hz, 2H), 3.82 (d, J=17.2 Hz, 7H), 3.53 (s, 2H), 3.25 (s, 2H), 3.04 (dd, J=16.9, 9.8 Hz, 3H), 2.90 (t, J=7.3 Hz, 2H), 2.26 (s, 3H), 2.19-2.15 (m, 3H), 2.12 (t, J=7.3 Hz, 2H), 1.90 (d, J=4.7 Hz, 2H), 1.65 (s, 2H), 1.58-1.49 (m, 2H), 1.40 (d, J=13.1 Hz, 2H), 0.84 (t, J=6.9 Hz, 3H),

MS m/z (ESI): 618.7 $[M+H]^+$.

Example 17 3-(ethyl(tetrahydro-2H-pyran-4-yl)amino)-5-(6-fluoro-2,2',3,3',5',6'-hexahydrospiro[indene-1,4'-pyran]-5-yl)-N-((4-methoxy-6-methyl-2-carbonyl-1,2-dihydropyridin-3-yl)methyl)-2-methylbenzamide

17

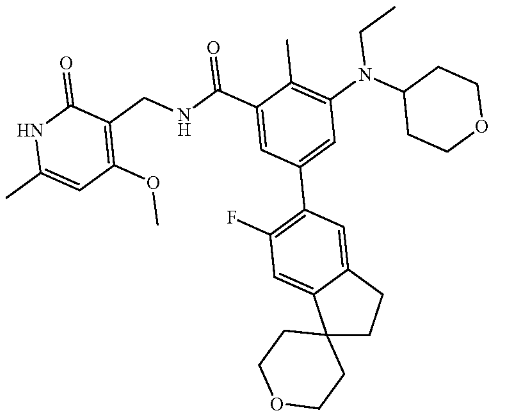

A similar method of Example 16 was used to obtain the title compound 17 with a yield of 64%, wherein the 6-bromo-5-fluoro-2',3',5',6'-tetrahydrospiro[indene-1,4'-pyran]was replaced with 5-bromo-6-fluoro-2',3',5',6'-tetrahydrospiro[indene-1,4'-pyran].

$^1$H NMR (400 MHz, DMSO-d6) δ 11.41 (s, 1H), 7.96 (t, J=4.1 Hz, 1H), 7.32-7.23 (m, 2H), 7.17 (d, J=11.1 Hz, 1H), 7.07 (s, 1H), 6.08 (s, 1H), 4.22 (d, J=4.5 Hz, 2H), 3.82 (d, J=14.0 Hz, 711), 3.53 (t, J=1.1.7 Hz, 2H), 3.24 (t, J=11.4 Hz, 2H), 3.07-2.96 (m, 3H), 2.89 (1, J=7.0 Hz, 2H), 2:25 (s, 3H), 2.14 (d, J=16.5 Hz, 5H), 1.91-1.82 (m, 2H), 1.65 (d, J=12.4 Hz, 2H), 1.52 (d, J=11.4 Hz, 2H), 1.41 (d, J=13.0 Hz, 2H), 0.83 (t, J=6.9 Hz, 3H),

MS m/z (ESI): 618.7 $[M+H]^+$.

Example 18 N-((4,6-dimethyl-2-carbonyl-1,2-dihydropyridin-3-yl)methyl)-3-(ethyl(tetrahydro-2H-pyran-4-yl)amino)-5-(1-ethyl-2-carbonyl-2',3',5',6'-tetrahydrospiro[dihydroindole-3,4'-pyran]-6-yl)-2-methylbenzamide

18

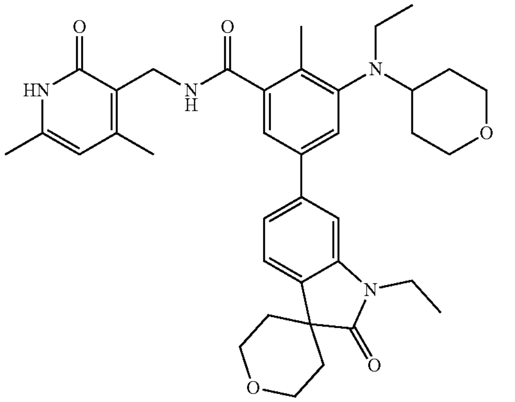

A similar method of Example 13 was used to obtain the title compound 18 with a yield of 12%, wherein the 1,1,1-trifluoro-2-iodoethane was replaced with iodoethane.

$^1$H NMR (400 MHz, Methanol-$d_4$) δ 7.55 (d, J=8.7 Hz, 1H), 7.44 (s, 1H), 7.33 (s, 1H), 7.27 (d, J=9.1 Hz, 1H), 7, 19 (s, 1H), 6.09 (s, 1H), 4.48 (s, 2H), 4.22-4.14 (m, 2H), 3.97-3.86 (m, 4H), 3.82 (q, J=7.7, 7.2 Hz, 21), 3.38-3.31 (m, 2H), 3.14 (q, J=7.0 Hz, 2H), 3.10-3.04 (m, 1H), 2.38 (s, 3H), 2.31 (s, 3H), 2.22 (s, 3H), 1.85-1.79 (m, 3H), 1.79-1.68 (m, 3H), 1.69-1.56 (m, 3H), 1.29-1.20 (n, 4H), 0.89 (t, J=7.1 Hz, 3H), MS m/z (ESI): 627.7 [M+H]$^+$.

Example 19 N-((4,6-dimethyl-2-carbonyl-1,2-dihydropyridin-3-yl)methyl)-3-(ethyl(tetrahydro-2H-pyran-4-yl)amino)-2-methyl-5-(2-carbonyl-1-propyl-2',3',5',6'-tetrahydrospiro[dihydroindole-3,4'-pyran]-6-yl)benzamide

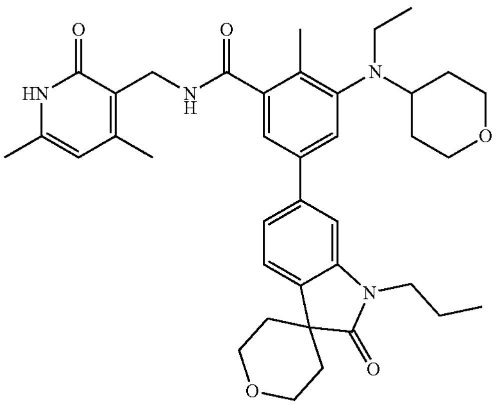

19

A similar method of Example 13 was used to obtain the title compound 19 with a yield of 24%, wherein the 1,1,1-trifluoro-2-iodoethane was replaced with iodopropane.

$^1$H NMR (400 MHz, Methanol-d$_4$) δ 7.55 (s, 1H), 7.44 (s, 1H), 7.32 (s, 1H), 7.27 (d, J=7.7 Hz, 1H), 7.17 (s, 1H), 6.09 (s, 1H), 4.48 (s, 2H), 4.17 (d, J=7.4 Hz, 2H), 3.98-3.85 (m, 4H), 3.76 (t, J=7.3 Hz, 2H), 3.21-3.02 (m, 2H), 2.38 (s, 3H), 2.31 (s, 3H), 2.22 (s, 3H), 1.86-1.79 (m, 3H), 1.79-1.69 (m, 4H), 1.68-1.60 (m, 2H), 1.29 (d, J=18.9 Hz, 4H), 0.91 (dt, J=15.7, 7.1 Hz, 6H), MS m/z (ESI): 641.7 [M+H]$^+$.

Example 20 N-((4,6-dimethyl-2-carbonyl-1,2-dihydropyridin-3-yl)methyl)-3-(ethyl(tetrahydro-2H-pyran-4-yl)amino)-2-methyl-5-(1-(2,2,2-trifluoroethyl)-2',3',5',6'-tetrahydrospiro[dihydroindole-3,4'-pyran]-6-yl)benzamide

20

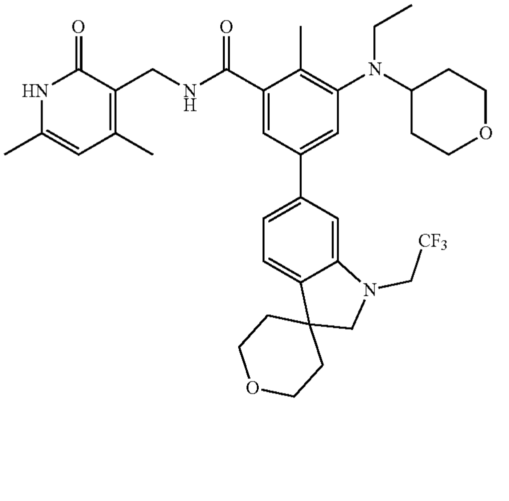

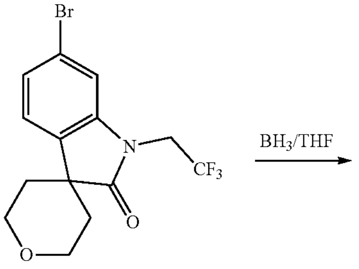

20a

-continued

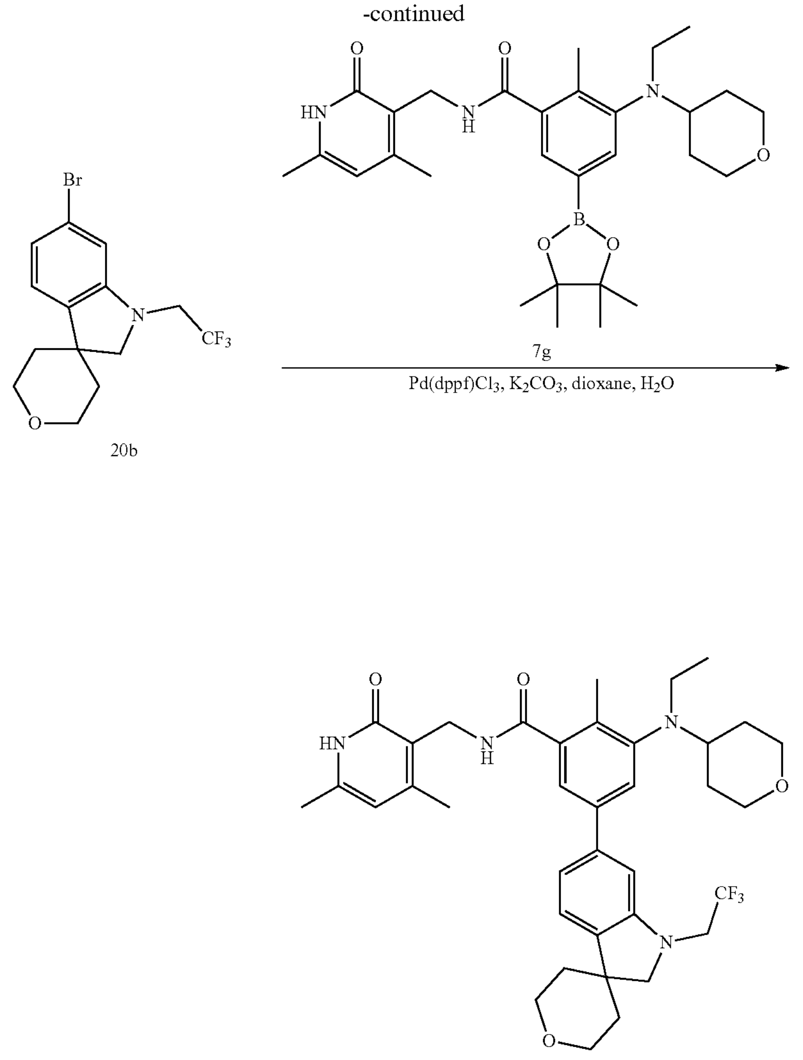

20b

7g

20

Step I 6-bromo-1-(2,2,2-trifluoroethyl)-2',3',5',6'-tetrahydrospiro[dihydroindole-3,4'-pyran]20b The compound 20a (0.2 g, 0.55 mmol) was dissolved in THF (15 mL) at 0° C., and $BH_3$/THF (2.2 mL, 2.2 mmol) was added slowly. The mixture was stirred at room temperature overnight, followed by quenching with methanol. The reaction solution was concentrated, added with water, extracted with dichloromethane for 3 times, washed with saturated NaCl solution, dried with anhydrous sodium sulfate, filtered, concentrated, and purified by column chromatography to obtain the title compound 20b (100 mg, 0.285 mmol) with a yield of 52%.

MS m/z (ESI): 350.3 $[M+1]^+$.

Step II N-((4,6-dimethyl-2-carbonyl-1,2-dihydropyridin-3-yl)methyl)-3-(ethyl(tetrahydro-2H-pyran-4-yl)amino)-2-methyl-5-(1-(2,2,2-trifluoroethyl)-2',3',5',6'-tetrahydrospiro[dihydroindole-3,4'-pyran]-6-yl)benzamide 20

The compound 20b (100 mg, 0.285 mmol), $K_2CO_3$ (118 mg, 0.858 mmol), Pd(dppf)$Cl_2$ (21 mg, 0.0286 mmol), compound 7g (180 mg, 0.343 mmol) were dissolved in dioxane (15 mL) and $H_2O$ (5 mL). The mixture was heated to 100° C. under the protection of Ar and stirred for 6 hours until the reaction was completed. The reaction solution was extracted with water and ethyl acetate, and the organic phase was washed with saturated NaCl solution, dried with anhydrous sodium sulfate, filtered, concentrated, and purified by column chromatography to obtain the title compound 20 (105 mg, 0.117 mmol) with a yield of 55%.

$^1$H NMR (400 MHz, Methanol-d4) δ 7.41-7.32 (m, 1H), 7.25 (s, 1H), 7.12 (d, J=7.7 Hz, 1H), 6.90 (d, J=7.6 Hz, 1H), 6.72 (s, 1H), 6.09 (s, 1H), 4.47 (s, 2H), 3.91 (t, J=10.5 Hz, 5H), 3.60 (d, J=10.7 Hz, 3H), 3.33 (t, J=11.4 Hz, 2H), 3.10 (dd, J=16.5, 9.4 Hz, 3H), 2.37 (s, 3H), 2.29 (s, 3H), 2.22 (s, 3H), 1.96 (td, J=12.7, 4.4 Hz, 2H), 1.73 (d, J=12.9 Hz, 2H), 1.61 (d, J=13.3 Hz, 3H), 1.17 (s, 3H), 0.87 (t, J=7.0 Hz, 3H), MS m/z (ESI): 667 $[M+H]^+$.

Example 21 N-((4,6-dimethyl-2-carbonyl-1,2-dihydropyridin-3-yl)methyl)-3-(ethyl(tetrahydro-2H-pyran-4-yl)amino)-5-(1'-ethyl-1-methyl-2-carbonyl-spiro[dihydroindole-3,4'-piperidine]-6-yl)-2-methylbenzamide

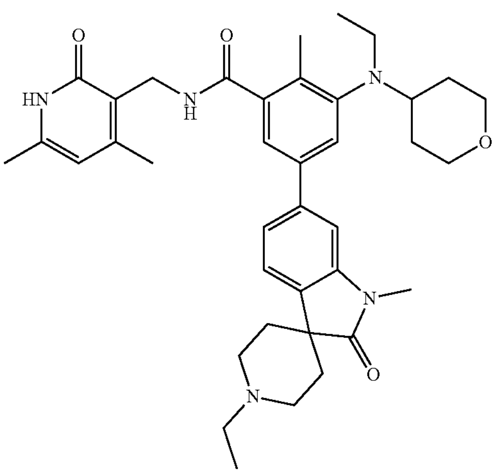

21

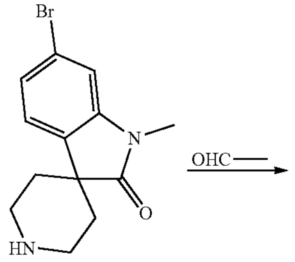

21a

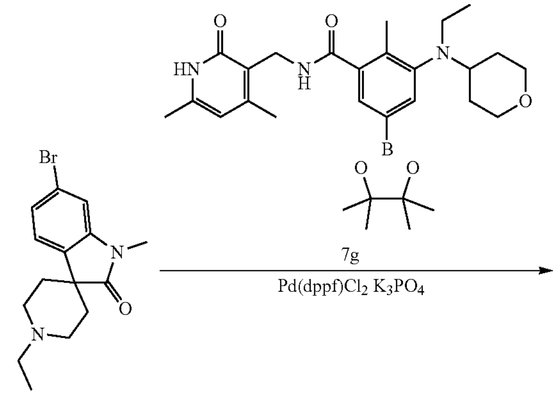

21b

-continued

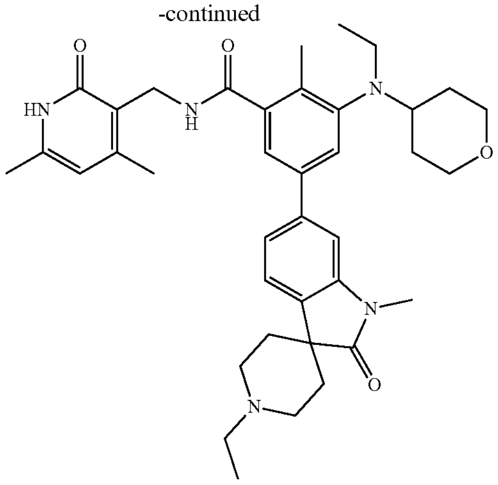

21

Step I 6-bromo-1'-ethyl-1-methylspiro[dihydroindole-3,4'-piperidine]-2-one 21b

The compound 21a (100 mg, 0.33 mmol), acetaldehyde (72 mg, 1.65 mmol) and acetic acid (100 mg, 1.65 mmol) were dissolved in DCM and stirred at room temperature for 0.5 hour. The mixture was added with sodium triacetoxyborohydride (350 mg, 1.65 mmol) and stirred at room temperature overnight. The reaction solution was added with water and DCM, and was stirred until the solution was separated. The organic phase was washed with sodium bicarbonate solution twice, dried, and concentrated to obtain a compound 21b (415 mg, 1.24 mmol) with a yield of 40%. MS m/z (ESI): 325 $[M+H+2]^+$.

Step II N-((4,6-dimethyl-2-carbonyl-1,2-dihydropyridin-3-yl)methyl)-3-(ethyl(tetrahydro-2H-pyran-4-yl)amino)-5-(1'-ethyl-1-methyl-2-carbonylspiro[dihydroindole-3,4'-piperidine]-6-yl)-2-methylbenzamide 21

The compound 7g (400 mg, 0.76 mmol), compound 21b (256 mg, 0.76 mmol), $Pd(dppf)Cl_2$ (51 mg, 0.07 mmol) and potassium phosphate (483 mg, 2.28 mmol) were added to 1,4-dioxane (10 mL) and refluxed at 110° C. for 4 hours. The reaction solution was concentrated, and purified by flash column chromatography to obtain a compound 21 (260 mg, 0.39 mmol) with a yield of 53%.

$^1H$ NMR (400 MHz, DMSO-$d_6$) δ 11.42 (s, 1H), 8.15 (t, J=4.9 Hz, 1H), 7.38 (s, 1H), 7.24 (t, J=10.3 Hz, 3H), 5.82 (s, 1H), 4.25 (d, J=4.9 Hz, 2H), 3.25 (d, J=31.8 Hz, 8H), 3.18 (s, 3H) 3111-2.93 (n, 5H), 2.19 (d, J=13.2 Hz, 61), 2.06 (s, 3H), 1.87 (s, 4H), 1.63 (d, J=12.4 Hz, 2H), 1.50 (dt, J=12.8, 5.7 Hz, 2H), 1.18 (s, 3H), 0.80 (t, J=6.9 Hz, 3H),

MS m/z (ESI): 640 $[M+H]^+$.

Example 22 N-((4,6-dimethyl-2-carbonyl-1,2-dihydropyridin-3-yl)methyl)-3-(ethyl(tetrahydro-2H-pyran-4-yl)amino)-2-methyl-5-(1-methyl-1'-(2,2,2-trifluoroethyl)spiro[dihydroindole-3,4'-piperidine]-6-yl)benzamide

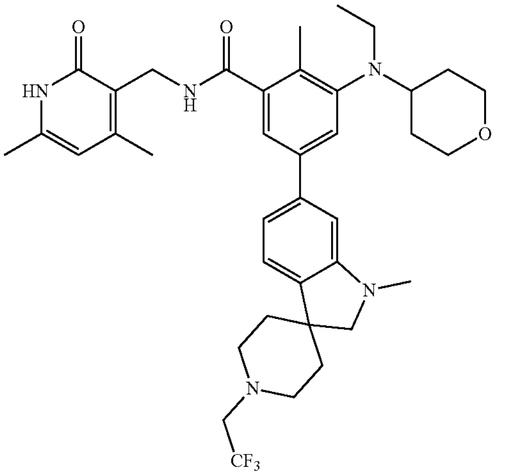

22

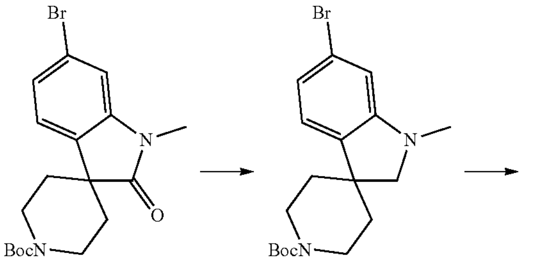

22a 22b

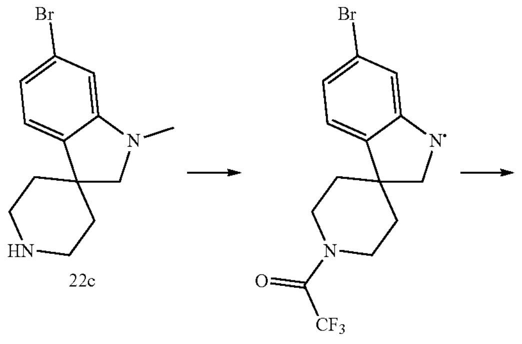

22c 22d

-continued

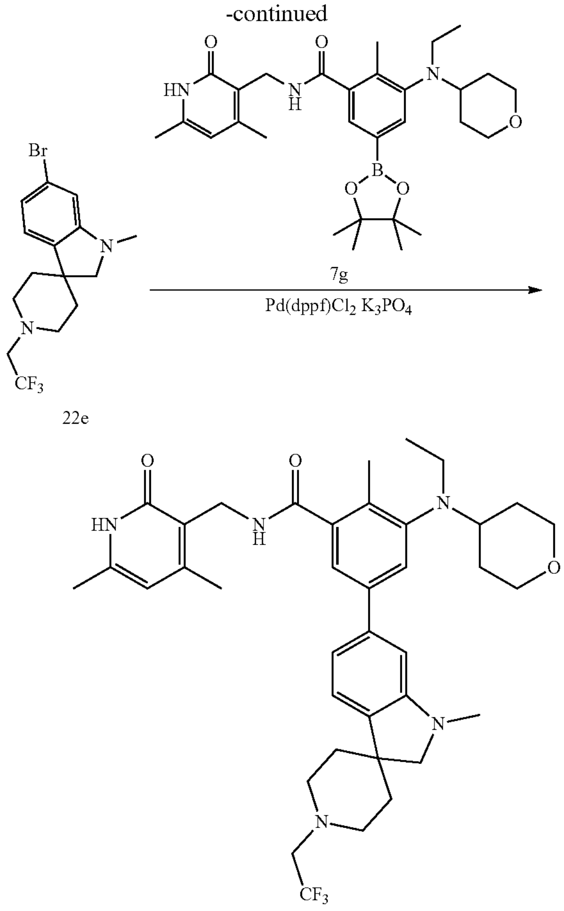

22e

22

Step I Tert-butyl 6-bromo-1-methylspiro[dihydroindole-3,4'-piperidine]-1'-carboxylate 22b The compound 22a (synthesis process see Example 16) (1 g, 2.6 mmol) was dissolved in THF (12 mL), followed by adding $BH_3$/THF (13 mL) and reacting at 50° C. for 5 hours. The reaction was quenched by adding methanol dropwise, and the reaction solution was concentrated and purified by column chromatography to obtain a compound 23b (800 mg, 2.1 mmol) with a yield of 80%.

MS m/z (ESI): 383 $[M+H]^+$.

Step II 6-bromo-1-methylspiro[dihydroindole-3,4'-piperidine]22c

The compound 22b (0.80 g, 2.1 mmol) was dissolved in DCM (10 mL), followed by adding trifluoroacetic acid (4 mL) and stirred at room temperature overnight. The reaction solution was concentrated to obtain a compound 22c (0.53 g, 1.9 mmol) with a yield of 95%.

Step III 1-(6-bromo-1-methylspiro[dihydroindole-3,4'-piperidine]-1'-yl)-2,2,2-trifluoroethane-1-one 22d The compound 22c (300 mg, 0.76 mmol), trifluoroacetic anhydride (239 mg, 1.14 mmol) and DIPEA (196 mg, 1.52 mmol) were added to DCM (10 mL) and refluxed at 110° C. for 4 hours. The reaction solution was concentrated, and purified by flash column chromatography to obtain a compound 22d (250 mg, 1.14 mmol) with a yield of 90%.

MS m/z (ESI): 377 $[M+H]^+$.

Step IV 6-bromo-1-methyl-1'-(2,2,2-trifluoroethyl) spiro[dihydroindole-3,4'-piperidine]22e The compound 22d (286 mg, 0.76 mmol) was dissolved in THF (12 mL), followed by adding $BH_3$/THF (5 mL) and reacting at 50° C. for 5 hours. The reaction was quenched by adding methanol dropwise, the reaction solution was concentrated and purified by column chromatography to obtain a compound 22e (120 mg, 0.33 mmol) with a yield of 43%.

MS m/z (ESI): 363 $[M+H]^+$.

Step V N-((4,6-dimethyl-2-carbonyl-1,2-dihydropyridin-3-yl)methyl)-3-(ethyl(tetrahydro-2H-pyran-4-yl)amino)-2-methyl-5-(1-methyl-1'-(2,2,2-trifluoroethyl)spiro[dihydroindole-3,4'-piperidine]-6-yl) benzamide 22

The compound 7g (151 mg, 0.29 mmol), compound 22e (110 mg, 0.29 mmol), Pd(dppf)$Cl_2$ (30 mg, 0.029 mmol) and potassium phosphate (184 mg, 0.87 mmol) were added to 1,4-dioxane (10 mL) and $H_2O$ (1 mL) and refluxed at 110° C. for 4 hours. The reaction solution was concentrated, and purified by flash column chromatography to obtain a compound 22 (40 mg, 0.06 mmol) with a yield of 20%.

$^1$H NMR (400 MHz, Methanol-$d_4$) δ 7.37 (d, J=1H, 1H), 7.25 (d, J=10.8 Hz, 1H), 7.06 (d, J=7.6 Hz, 1H), 6.83 (dd, J=7.6, 1.6 Hz, 1H), 6.63 (d, J=1.5 Hz, 1H), 6.09 (d, J=0.9 Hz, 1H), 4.46 (s, 2H), 3.93-3.85 (m, 2H), 3.35 (dd, J=11.7, 2.1 Hz, 2H), 3.24 (s, 2H), 3.17-2.99 (m, 5H), 2.99-2.90 (m, 2H), 2.78 (s, 3H), 2.58-2.47 (m, 2H), 2.37 (s, 3H), 2.29 (s, 3H), 2.22 (d, J=0.8 Hz, 3H), 0.95 (td, J=12.9, 4.1 Hz, 2H), 1.77-1.53 (m, 6H), 0.87 (t, J=7.0 Hz, 3H), MS n/z (ESI): 680 $[M+H]^+$.

Example 23 N-((4,6-dimethyl-2-carbonyl-1,2-dihydropyridin-3-yl)methyl)-3-(ethyl(tetrahydro-2H-pyran-4-yl)amino)-5-(6-fluoro-2,2',3,3',5',6'-hexahydrospiro[indene-1,4'-pyran]-5-yl)-2-methylbenzamide

23

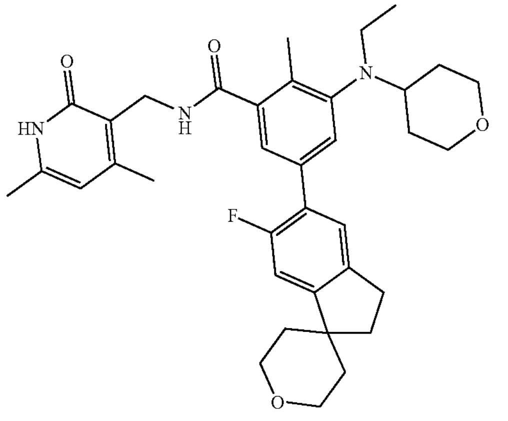

A similar method of Example 16 was used to obtain the title compound 23 with a yield of 50%, wherein the 3-(aminomethyl)-4-methoxy-6-methylpyridin-2(1H)-one hydrochloride was replaced with 3-(aminomethyl)-4,6-dimethylpyridin-2(1H)-one trifluoroacetate.

$^1$H NMR (400 MHz, DMSO-d6) δ 11.45 (s, 1H), 8.16 (t, J=5.0 Hz, 1H), 7.33-724 (n. 2H), 7.17 (d, J=11.1 Hz, 1H), 7.07 (d, J=1.7 Hz, 1H, 5.85 (s, 1H), 4.27 (d, J=4.9 Hz, 2H), 3.89-3.78 (m, 41H), 3.54 (t, J=11.7 Hz, 2H), 3.24 (t, J=11.3 Hz, 2H), 3.03 (dd, J=15.3, 8.7 Hz, 3H), 2.89 (t, J=7.2 Hz, 2H), 2.25 (s, 3H), 2.19 (s, 3H), 2.15-2.07 (m, 5H), 1.91-1.82 (m, 2H), 1.65 (d, J=12.0 Hz, 2H), 1.51 (dd, J=12.0, 4.1 Hz, 2H), 1.44-1.37 (m, 2H), 0.83 (t, J=6.9 Hz, 3H),

MS m/z (ESI): 602.8 $[M+H]^+$.

Example 24 N-((4,6-dimethyl-2-carbonyl-1,2-dihydropyridin-3-yl)methyl)-3-(ethyl(tetrahydro-2H-pyran-4-yl)amino)-5-(5-fluoro-2,2',3,3',5',6'-hexahydrospiro[indene-1,4'-pyran]-6-yl)-2-methylbenzamide

24

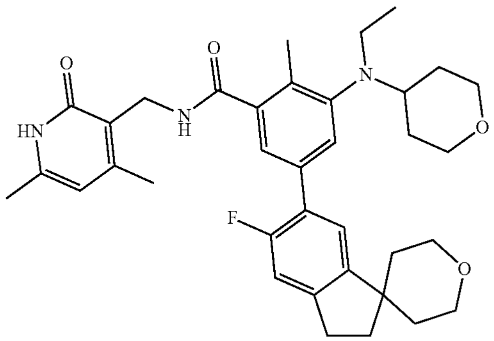

A similar method of Example 16 was used to obtain the title compound 24 with a yield of 40%, wherein the 3-(aminomethyl)-4-methoxy-6-methylpyridin-2(1H)-one hydrochloride was replaced with 3-(aminomethyl)-4,6-dimethylpyridin-2(1H)-one trifluoroacetate.

$^1$H NMR (400 MHz. DMSO-d6) δ 11.48-11.42 (m, 1H), 8.17 (t, J=4.9 Hz, 1H), 7.34-7.26 (m, 2H), 7.15-7.08 (m, 2H), 5.85 (s, 1H), 4.29 (d, J=4.9 Hz, 2H), 3.83 (d, J=11.1 Hz, 4H), 3.53 (t, J=11.8 Hz, 2H), 3.24 (t, J=11.2 Hz, 2H), 3.05 (q, J=7.0 Hz, 3H), 2.90 (t, J=7.3 Hz, 2H), 2.24 (s, 3H), 2.20 (s, 3H), 2.11 (d, J=7.9 Hz, 5H), 1.91 (td, J=12.9, 4.6 Hz, 2H), 1.65 (d, J=12.2 Hz, 2H), 1.57-1.46 (m, 2H), 1.40 (d, J=13.0 Hz, 2H), 0.84 (t, J=6.9 Hz, 3H),

MS n/z (ES): 602.8 $[M+H]^+$.

Example 25 N-((4,6-dimethyl-2-carbonyl-1,2-dihydropyridin-3-yl)methyl)-3-(ethyl(tetrahydro-2H-pyran-4-yl)amino)-5-(1-isopropyl-2',3',5',6'-tetrahydrospiro[dihydroindole-3,4'-pyran]-6-yl)-2-methylbenzamide

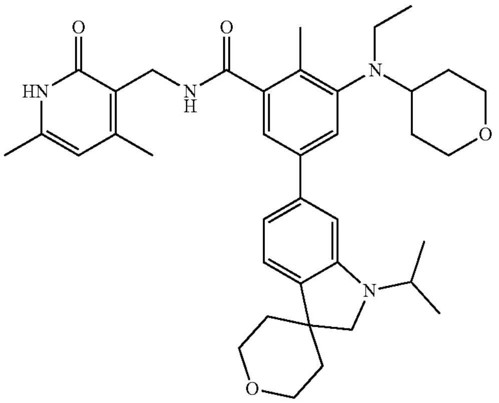

25

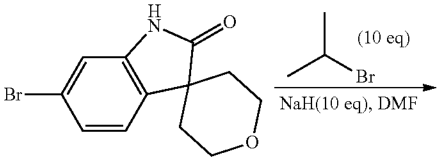

1g

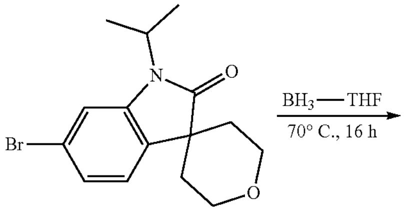

25a

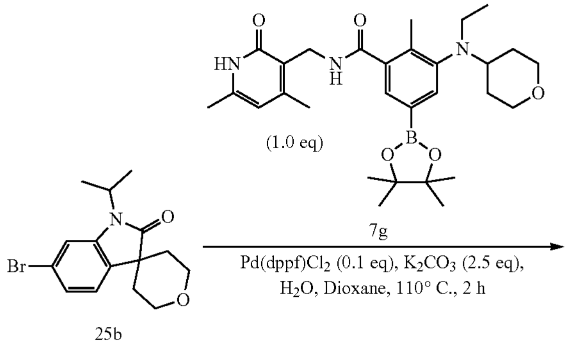

25b

-continued

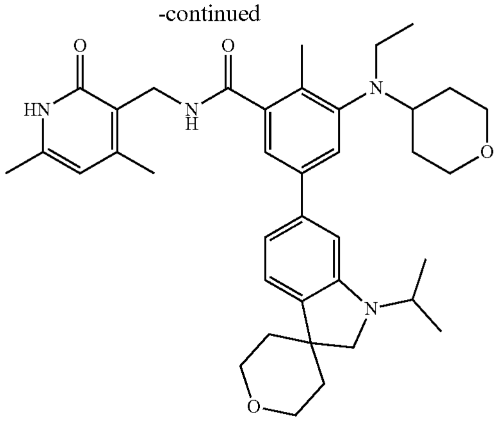

25

Step I 6-bromo-1-isopropyl-2',3',5',6'-tetrahydrospiro[dihydroindole-3,4'-pyran]-2-one 25a The compound 1g (100 mg, 0.373 mmol), 2-bromopropane (458 mg, 3.73 mmol), sodium hydride (150 mg, 3.73 mmol) and 5 mL of DMF were added in a 100 mL single-necked flask. The reaction solution was stirred at room temperature overnight, added with water, extracted with EA, dried with anhydrous sodium sulfate, mixed, concentrated, and purified by column chromatography (petroleum ether: ethyl acetate=6:1) to obtain the title compound 25a (90 mg, 0.255 mmol) with a yield of 72.2%.

MS m/z (ESI): 324 $[M+H]^+$.

Step II 6-bromo-1-isopropyl-2',3',5',6'-tetrahydrospiro[dihydroindole-3,4'-pyran]25b The compound 25a (400 mg, 1.233 mmol) and 20 mL of borane tetrahydrofuran solution were heated to 80° C. and stirred for 8 hours. The reaction was quenched by adding methanol dropwise under ice bath. The reaction solution was dried by evaporation, dissolved with EA, washed with saturated sodium bicarbonate solution, and re-dried by evaporation to obtain a crude product of the title compound 25b (380 mg, 1.17 mmol) with a yield of 95%.

MS m/z (ESI): 310 $[M+H]^+$.

Step III N-((4,6-dimethyl-2-carbonyl-1,2-dihydropyridin-3-yl)methyl)-3-(ethyl(tetrahydro-2H-pyran-4-yl)amino)-5-(1-isopropyl-2',3',5',6'-tetrahydrospiro[dihydroindole-3,4'-pyran]-6-yl)-2-methylbenzamide The compound 25b (160 mg, 0.516 mmol), compound 7g (270 mg, 0.516 mmol), $Pd(dppf)Cl_2$ (37 mg, 0.0516 mmol) and potassium carbonate (178 mg, 1.29 mmol) were dissolved in 1 mL of water and 4 mL of 1,4-dioxane. The reaction system was replaced with nitrogen, heated to 110° C. and reacted for 2 hours. The reaction solution was added with 30 mL of water and extracted with EA (30 mL×3). The organic phases were combined, washed with saturated NaCl solution (30 mL×3), dried, mixed, and purified by column chromatography (methanol: dichloromethane=1:6) to obtain the title compound 25 (30 mg, 0.048 mmol) with a yield of 9.2%.

$^1H$ NMR (400 MHz, DMSO-$d_6$) δ 11.42 (s, 1H), 8.12 (t, J=4.9 Hz, 1H), 7.27 (d, J=1.8 Hz, 1H), 711 (d, J=1.8 Hz, 1H), 7.04 (d, J=7.6 Hz, 1H), 6.70 (dd, J=7.6, 1.5 Hz, 0.1H), 6.56 (d, J=5 Hz, 1H), 5.82 (s, 1H), 4.25 (d, J=5.0 Hz, 2H), 3.96-3.75 (m, 5H), 3.48 (t, J=5 Hz, 2H), 3.31 (s, 2H), 3.21 (t, J=11.3 Hz, 2H), 3.08-2.94 (m, 3H), 2.18 (d, J=8.8 Hz, 6H), 2.07 (s, 3H), 1.79 (d, J=12.9, 4.6 Hz, 2H), 1.62 (d, J=12.6 Hz, 2H), 1.48 (d, J=12.9 Hz, 4H), 1.09 (d, J=6.6 Hz, 6H), 0.80 (t, J=7.0 Hz, 3H),

MS m/z (ESI): 627 $[M+H]^+$.

Example 26 N-((4,6-dimethyl-2-oxo-1,2-dihydropyridin-3-yl)methyl)-3-(ethyl(tetrahydro-2H-pyran-4-yl)amino)-2-methyl-5-(1-(3,3,3-trifluoropropyl)-2',3',5',6'-tetrahydrospiro[indoline-3,4'-pyran]-6-yl)benzamide

26

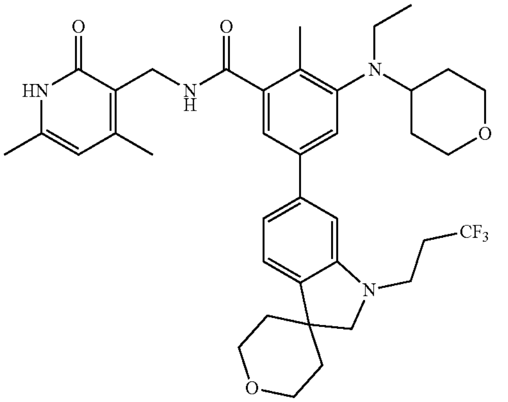

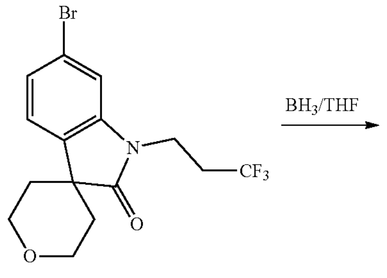

26a

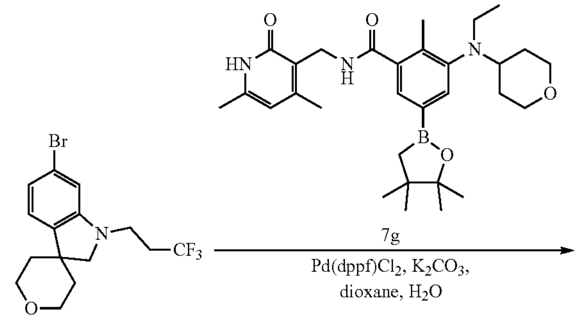

26b

-continued

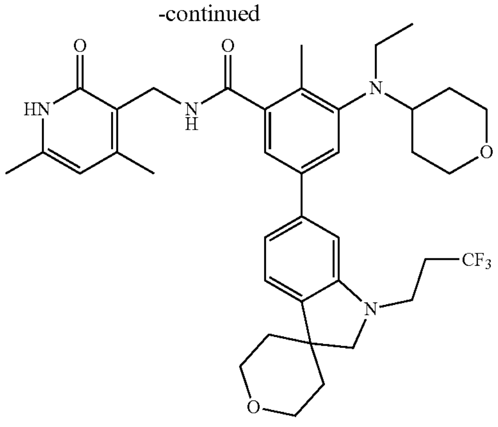

26

Step I 6-bromo-1-(3,3,3-trifluoropropyl)-2',3',5',6'-tetrahydrospiro[indoline-3,4'-pyran]26b The compound 26a (160 mg, 0.424 mmol) was dissolved in THF (15 mL) at 0° C., and $BH_3$/THF (2.2 mL, 2.2 mmol) was added slowly. The mixture was stirred at room temperature overnight, followed by quenching with water. The reaction solution was concentrated, added with water, extracted with dichloromethane for 3 times, washed with saturated NaCl solution, dried with anhydrous sodium sulfate, filtered, concentrated, and purified by column chromatography to obtain the title compound 26b (80 mg, 0.219 mmol) with a yield of 51.8%.

MS m/z (ESI): 364.3 $[M+1]^+$.

Step II N-((4,6-dimethyl-2-oxo-1,2-dihydropyridin-3-yl)methyl)-3-(ethyl(tetrahydro-2H-pyran-4-yl)amino)-2-methyl-5-(1-(3,3,3-trifluoropropyl)-2',3',5',6'-tetrahydrospiro[indoline-3,4'-pyran]-6-yl)benzamide 26

The compound 26b (80 mg, 0.219 mmol), $K_2CO_3$ (91 mg, 0.657 mmol), Pd(dppf)$Cl_2$ (16 mg, 0.0219 mmol) and compound 1 (126 mg, 0.241 mmol) were dissolved in dioxane (15 mL) and $H_2O$ (5 mL). The mixture was heated to 100° C. under the protection of Ar and stirred for 6 hours until the reaction was completed. The reaction solution was extracted with water and ethyl acetate, and the organic phase was washed with saturated NaCl solution, dried with anhydrous sodium sulfate, filtered, concentrated, and purified by column chromatography to obtain the title compound 26 (24 mg, 0.035 mmol) with a yield of 16%.

$^1$H NMR (400 MHz, Methanol-d4) δ 7.38 (d, J=1.8 Hz, 1H), 7.25 (d, J=1.8 Hz, 1H), 7.09 (d, J=7.6 Hz, 1H), 6.85 (dd, J=7.5, 1.5 Hz, 1H), 6.62 (d, J=1.5 Hz, 1H), 6.09 (s, 1H), 447 (s, 2H), 3.91 (t, J=6.6 Hz, 411), 367-3.54 (m, 2H), 3.49-3.40 (m, 3H), 3.34 (t, J=1.4 Hz, 2H), 3.20-3.02 (m, 3H), 2.57-2.45 (m, 2H), 2.37 (s, 3H), 2.28 (d, J=9.3 Hz, 3H), 2.22 (s, 3H), 2.00-1.86 (n, 2H), L74 (d, J=12.9 Hz, 2H), 1.61 (d, J=12.9 Hz, 4H), 1.28 (d, J=7.2 Hz, 1H), 0.88 (t, J=7.0 Hz, 3H), MS m/z (ESI):68 $[M+1]^+$.

Example 27 N-((4,6-dimethyl-2-carbonyl-1,2-dihydropyridin-3-yl)methyl)-3-(ethyl(tetrahydro-2H-pyran-4-yl)amino)-2-methyl-5-(1-methyl-2-carbonyl-1'-(2,2,2-trifluoroethyl)spiro[dihydroindole-3,4'-piperidine]-6-yl)benzamide

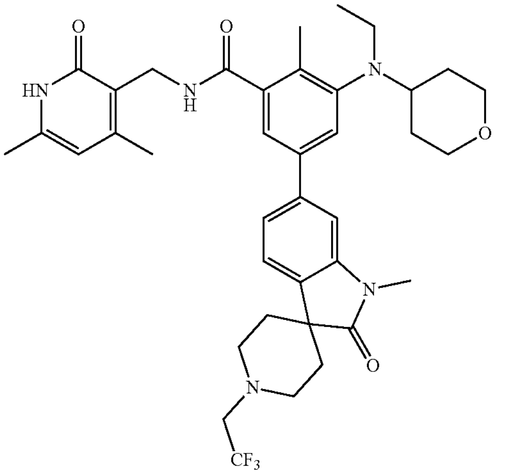

27

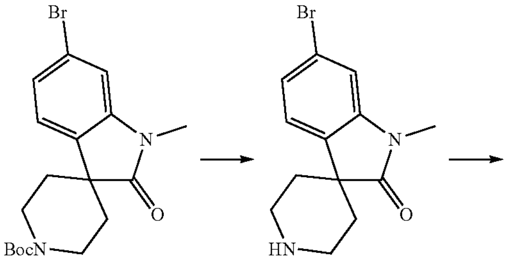

22a

27a

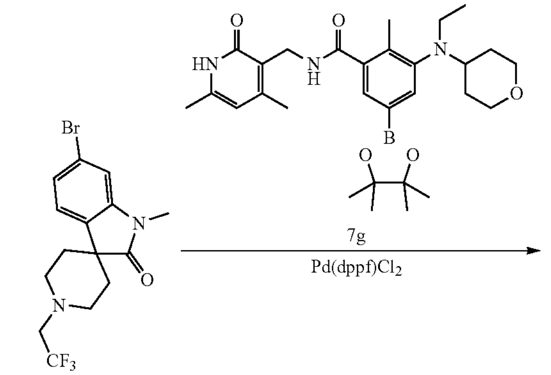

27b

-continued

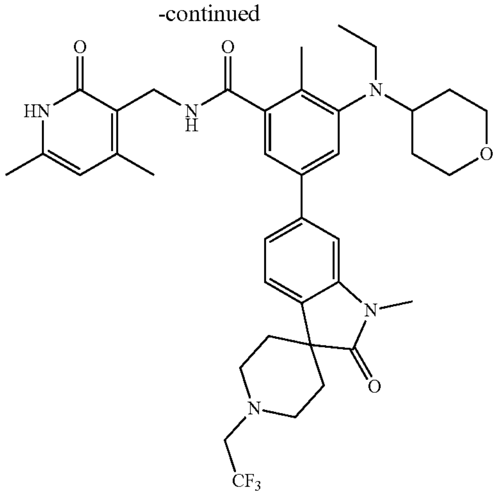

27

Step I 6-bromo-1-methylspiro[dihydroindole-3,4'-piperidine]-2-one 27a

The compound 22a (10.80 g, 2.1 mmol) was dissolved in DCM (10 mL), followed by adding trifluoroacetic acid (4 mL) and stirred at room temperature overnight. The reaction solution was concentrated to obtain a compound 27a (0.53 g, 1.9 mmol) with a yield of 95%.

Step II 6-bromo-1-methyl-1'-(2,2,2-trifluoroacetyl) spiro[dihydroindole-3,4'-piperidine]-2-one 27b The compound 27a (100 mg, 0.33 mmol) was dissolved in DMF (10 mL), 1,1,1-trifluoro-2-iodoethane (141 mg, 0.66 mmol) and $K_2CO_3$ (91 mg, 0.66 mmol) were added. The mixture was heated to 70° C., and stirred at room temperature for 4 hours. The reaction solution was concentrated, and purified by flash column chromatography to obtain a compound 27b (80 mg, 0.20 mmol) with a yield of 60%.

MS m/z (ESI): 377 $[M+H]^+$.

Step III N-((4,6-dimethyl-2-carbonyl-1,2-dihydropyridin-3-yl)methyl)-3-(ethyl(tetrahydro-2H-pyran-4-yl)amino)-2-methyl-5-(1-methyl-2-carbonyl-1'-(2,2,2-trifluoroethyl)spiro[dihydroindole-3,4'-piperidine]-6-yl)benzamide 27

The compound 32b (80 mg, 0.20 mmol), compound 7g (110 mg, 0.21 mmol), $Pd(dppf)Cl_2$ (30 mg, 0.029 mmol) and potassium phosphate (113 mg, 0.63 mmol) were added to 1,4-dioxane (10 mL) and $H_2O$ (1 mL) and refluxed at 110° C. for 4 hours. The reaction solution was concentrated, and purified by flash column chromatography to obtain a compound 27 (40 mg, 0.05 mmol) with a yield of 20%.

$^1H$ NMR (400 MHz, Methanol-$d_4$) δ 7.51 (s, 1H), 7.46 (d, J=2.0 Hz, 1H), 737-773 (m, 3H), 6.09 (d, J=3J Hz, 1H), 4.51-4.41 (m, 2H), 3.89 (s, 2H), 3.40-3.28 (m, 6H), 3.26-3.04 (m, 6H), 3.03-2.89 (m, 2H), 2.43-2.17 (m, 9H), 1.98-L52 (r, 71), 1.34-1.24 (n, 1H), 0.85 (dt, J=27.1, 6.8 Hz, 3H), MS m/z (ESI): 694 $[M+H]^+$.

Example 28 N-((4,6-dimethyl-2-carbonyl-1,2-dihydropyridin-3-yl)methyl)-5-(1,1'-dimethyl-2-carbonylspiro[dihydroindole-3,4'-piperidine]-6-yl)-3-(ethyl(tetrahydro-2H-pyran-4-yl)amino)-2-methylbenzamide

28

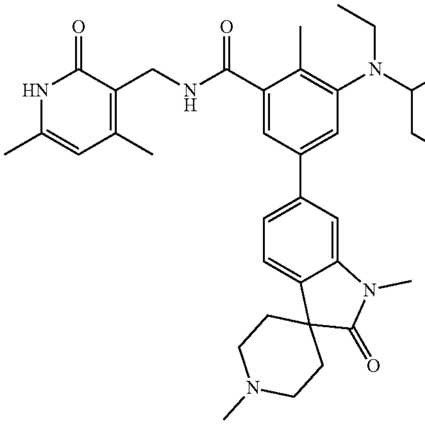

A similar method of Example 27 was used to obtain the title compound 28 with a yield of 20%, wherein the 1,1,1-trifluoro-2-iodoethane was replaced with paraformaldehyde.

$^1$H NMR (400 MHz, Methanol-$d_4$) δ 7.48-7.42 (m, 2H), 7.37-7.26 (m, 2H), 7.19 (d, J=1.5 Hz, 1H), 6.10 (s, 1H), 4.47 (s, 2H), 3.90 (d, J=11.5 Hz, 2H), 3.41-3.29 (m, 5H), 3.25 (s, 3H), 3.15 (dd, J=8.5, 5.5 Hz, 3H), 3.08 (s, 2H), 2.69 (s, 3H), 2.38 (s, 3H), 2.31 (s, 3H), 2.22 (s, 3H), 2.00 (s, 3H), 1.74 (d, J=12.7 Hz, 2H), 1.70-1.59 (m, 2H), 0.88 (t, J=7.0 Hz, 3H), MS m/z (ESI): 626 $(M+1)^+$.

Example 29 N-((4,6-dimethyl-2-carbonyl-1,2-dihydropyridin-3-yl)methyl)-3-(ethyl(tetrahydro-2H-pyran-4-yl)amino)-2-methyl-5-(1-neopentyl-2',3',5',6'-tetrahydrospiro[dihydroindole-3,4'-pyran]-6-yl)benzamide

29

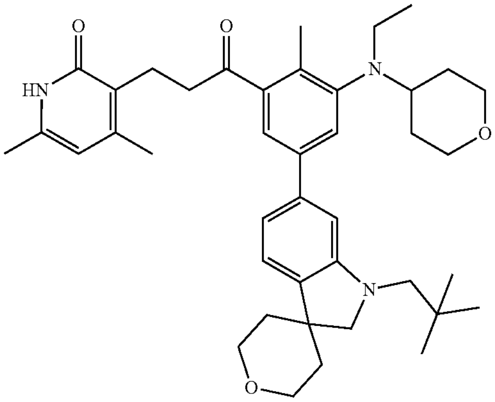

-continued

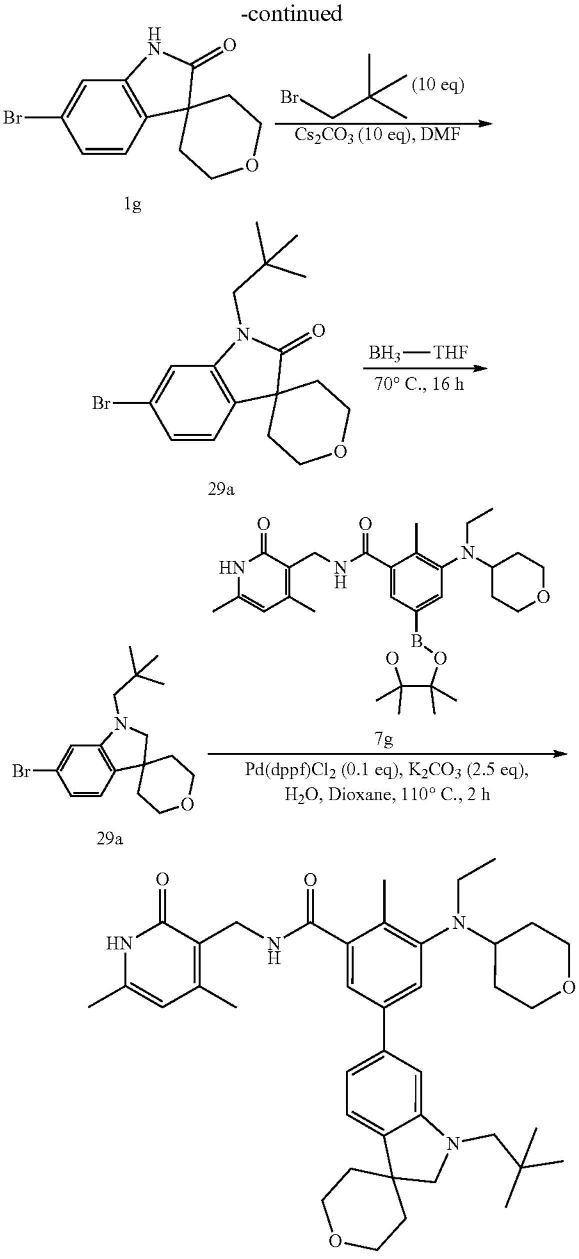

29

Step I 6-bromo-1-neopentyl-2',3',5',6'-tetrahydrospiro[dihydroindole-3,4'-pyran]2-one 29a The compound 1g (100 mg, 0.354 mmol), 1-bromo-2,2-dimethylpropane (535 mg, 3.54 mmol), cesium carbonate (1.15 g, 3.54 mmol) and 5 mL of DMF were added in a 20 mL microwave tube. The mixture was heated to 70° C. and refluxed for 14 hours. The reaction solution was added with water, extracted with EA, dried with anhydrous sodium sulfate, mixed, concentrated, and purified by column chromatography (petroleum ether: ethyl acetate=6:1) to obtain the title compound 29a (90 mg, 0.255 mmol) with a yield of 72.2%.

MS m/z (ESI): 352 $[M+H]^+$.

Step II 6-bromo-1-neopentyl-2',3',5',6'-tetrahydrospiro[dihydroindole-3,4'-pyran]29b The compound 29a (350 mg, 1 mmol) and 10 mL of borane tetrahydrofuran solution were heated to 70° C. and stirred for 8 hours. The reaction was quenched by adding methanol dropwise under ice bath. The reaction solution was dried by evaporation, dissolved with EA, washed with saturated sodium bicarbonate solution, and re-dried by evaporation to obtain a crude product of the title compound 29b (300 mg, 0.887 mmol) with a yield of 88%.

MS m/z (ESI): 338 $[M+H]^+$.

Step III N-((4,6-dimethyl-2-oxo-1,2-dihydropyridin-3-yl)methyl)-3-(ethyl(tetrahydro-2H-pyran-4-yl)amino)-2-methyl-5-(1-neopentyl-2',3',5',6'-tetrahydrospiro[dihydroindole-3,4'-pyran]-6-yl)benzamide 29

The compound 29b (97 mg, 0.286 mmol), compound 7g (150 mg, 0.286 mmol), $Pd(dppf)Cl_2$ (21 mg, 0.0286 mmol) and potassium carbonate (99 mg, 0.429 mmol) were dissolved in 1 mL of water and 8 mL of 1,4-dioxane. The reaction system was replaced with nitrogen, heated to 110° C. and reacted for 2 hours. The reaction solution was added with 30 mL of water and extracted with EA (30 mL×3). The organic phases were combined, washed with saturated NaCl solution (30 mL×3), dried, mixed, and purified by column chromatography (methanol: dichloromethane=1:6) to obtain the title compound 34 (30 mg, 0.0458 mmol) with a yield of 16%.

$^1$H NMR (400 MHz, DMSO-dc) δ 11.41 (s, 11), 8.14 (t, J=4.9 Hz, 1H), 7.24 (d, J=1.8 Hz, 1H), 7.09-7.02 (m, 2H), 6.72 (dd, J=7.5, 1.4 Hz, 1H), 6.50 (d, J=1.5 Hz, 1H), 5.81 (s, 1H), 4.25 (d, J=4.9 Hz, 2H), 3.92-3.68 (m, 4H), 3.46 (d, J=4.5 Hz, 3H), 3.22 (t, J=11.3 Hz, 2H), 3.01 (dd, J=15.6, 8.9 Hz, 4H), 2.85 (s, 2H), 2.18 (d, J=14.6 Hz, 6H), 2.07 (s, 3H), 1.82 (td, J=12.9, 4.5 Hz, 2H), 1.63 (d, J=12.6 Hz, 2H), 1.50 (t, J 15.2 Hz, 4H), 0.93 (s, 91H), 0.80 (t, J=7.0 Hz, 3H),

MS m/z (ESI): 655 $[M+H]^+$.

Example 30 N-((4,6-dimethyl-2-oxo-1,2-dihydropyridin-3-yl)methyl)-3-(ethyl(tetrahydro-2H-pyran-4-yl)amino)-5-(1'-ethyl-1-methylspiro[dihydroindole-3,4'-piperidine]-6-yl)-2-methylbenzamide

30

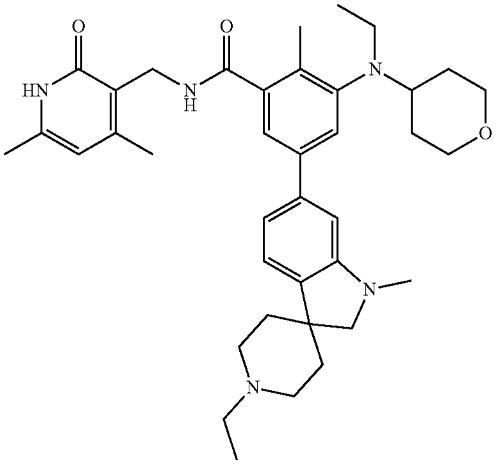

A similar method of Example 22 was used to obtain the title compound 30 with a yield of 18%, wherein the trifluoroacetic acid was replaced with acetic acid.

$^1$H NMR (400 MHz, Methanol-$d_4$) δ 7.38 (d, J=1.9 Hz, 1H), 7.25 (d, J=1.8 Hz, 1H), 7.17 (d, J=7.6 Hz. 1H), 6.85 (dd, J=7.7, 1.6 Hz, 1H), 6.65 (d, J=1.5 Hz, 1H), 6.09 (s, 1H), 4.47 (s, 2H), 3.90 (d, J=11.0 Hz, 2H), 3.35 (d, J=11.7 Hz, 2H), 3.19-3.01 (a. 6H), 2.80 (s, 3H), 2.74 (d, J=7.2 Hz, 2H), 2.50 (s, 1H), 2.38 (s, 3H), 2.29 (s, 3H), 2.22 (s, 3H), 1.99 (td, J=13.4, 12.8, 4.0 Hz, 2H), 1.82 (d, J=13.9 Hz, 2H), 1.73 (d, J=12.5 Hz, 2H), 1.69-1.55 (m, 3H), 1:28-1:21 (m, 4H), 0.87 (t, 1=7.0 Hz, 3H), MS m/z (ESI): 626 (M+1)}.

Example 31 N-((4,6-dimethyl-2-oxo-1,2-dihydropyridin-3-yl)methyl)-3-(ethyl(tetrahydro-2H-pyran-4-yl)amino)-2-methyl-5-(1-propyl-2-oxo-2',3',5',6'-tetrahydrospiro[dihydroindole-3,4'-pyran]-6-yl)benzamide

31

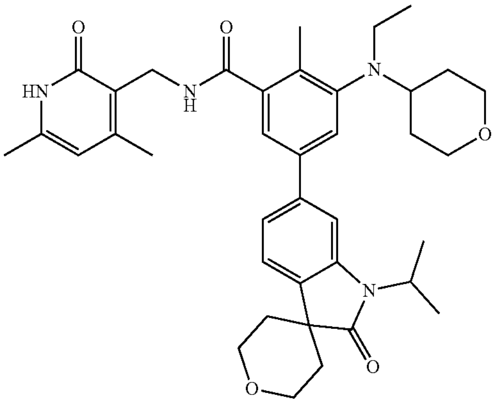

A similar method of Example 13 was used to obtain the title compound 31 with a yield of 54%, wherein the 1,1,1-trifluoro-2-iodoethane was replaced with 2-iodopropane.

$^1$H NMR (400 MHz, Methanol-$d_4$) δ 7.54 (d, J=81 Hz, 1H), 7.42 (d, J=1.7 Hz, 1H), 7.30 (d, J=1.8 Hz, 11), 7.25 (dd, J=4.0, 2.5 Hz, 2H), 6.10 (s, 1H), 4.64-4.56 (m, 1H), 4.48 (s, 2H), 4.22-4.14 (m, 2H), 3.96-3.88 (m, 4H), 3.36 (d J=11.7 Hz, 2H), 3.18-3.12 (m, 2H), 2.38 (s, 3H), 2.32 (s, 3H), 2122 (s, 3H), 1.83-1.70 (m, 6H), 1.64 (d, J=2.2 Hz, 2H), 1.49 (d, J=7.0 Hz, 6H), 1.27 (d, J=3.6 Hz, 1H), 0.89 (t, J=7.0 Hz. 31H), MS m/z (ESI): 641.8 $[M+H]^+$.

Example 32 Methyl 6-(3-(((4,6-dimethyl-2-carbonyl-1,2-dihydropyridin-3-yl)methyl)carbamoyl)-5-(ethyl(tetrahydro-2H-pyran-4-yl)amino)-4-methylphenyl)-1-methyl-2-carbonylspiro[dihydroindole-3,4'-piperidine]-1'-carboxylate

32

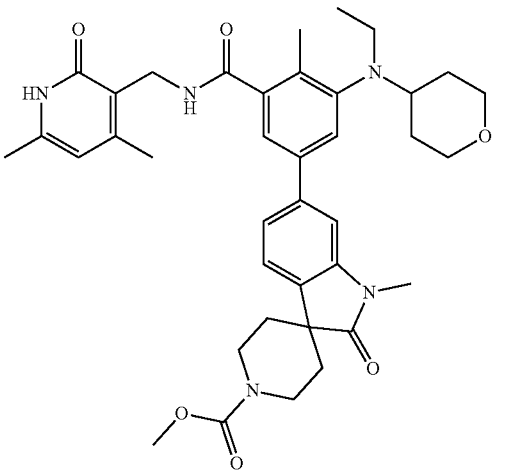

A similar method of Example 27 was used to obtain the title compound 32 with a yield of 20%, wherein the 1,1,1-trifluoro-2-iodoethane was replaced with triphosgene. H NMR (400 MHz, Methanol-$d_4$) δ 7.46 (dd, J=4.9, 3-0 Hz, 2H), 7.34 (d, J=L. Hz, 1H), 7.27 (dd, J=7.8, 1.6 Hz, 1H), 7.18 (d, J=1.5 Hz, 1H), 6.09 (s, 1H), 4.47 (s, 2H), 3.90 (d, J=1 1.8 Hz, 3H), 3.87-3.75 (m, 2H), 3.72 (s, 3H), 3.34 (dd, J=12.3, 10.1 Hz, 3H), 3:25 (3.3.14 (q, J=7.3 Hz, 3H), 2.38 (s, 3H), 2.31 (s, 3H), 2.22 (s, 3H), 1.79 (t, J=5.6 z, 4H), 1.73 (s, 2H), 1.63 (d, J=11.8, 4.4 Hz, 2H), 0.88 (t, J=7.0 Hz, 3H), MS m/z (ESI): 670 [M+H]$^+$.

Example 33 Methyl 6-(3-(((4,6-dimethyl-2-carbonyl-1,2-dihydropyridin-3-yl)methyl)carbamoyl)-5-(ethyl(tetrahydro-2H-pyran-4-yl)amino)-4-methylphenyl)-1-methylspiro[dihydroindole-3,4'-piperidine]-1'-carboxylate

33

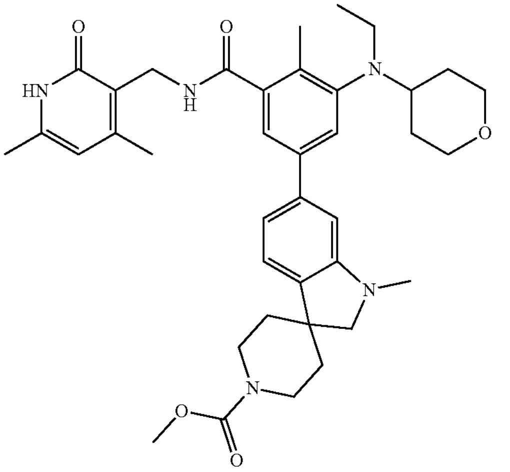

A similar method of Example 22 was used to obtain the title compound 33 with a yield of 20%, wherein the 1,1,1-trifluoro-2-iodoethane was replaced with triphosgene.

$^1$H NMR (400 MHz, Methanol-$d_4$) δ 7.37 (d, J=1.9 Hz, 1H), 7.25 (d, J=1.9 Hz, 1H), 7.04 (d, J=7.6 Hz, 1H), 6.83 (dd, J=7.6, 1.6 Hz, 1H), 6.64 (d, J=1.5 Hz, 1H), 6.09 (s, 1H), 4.45 (d, J=9.7 Hz, 2H), 4.05 (d, J=13.7 Hz, 2H), 3.89 (d, J=10.5 Hz, 2H), 3.69 (d, J=5.7 Hz, 3H), 3.38-3.29 (m, 5H), 3.19-2.93 (m, 5H), 2.80 (s, 2H), 2.36 (d, J=5.9 Hz, 3H), 2.33-2.19 (m, 6H), 1.85-1.52 (m, 8H), 0.84 (d, J=22.4, 7.0 Hz, 3H), MS m/z (ESI): 656 [M+H]$^+$.

Example 34 3-(ethyl(tetrahydro-2H-pyran-4-yl)amino)-N-((4-methoxy-6-methyl-2-carbonyl-1,2-dihydropyridin-3-yl)methyl)-2-methyl-5-(1-methyl-2-carbonylspiro[dihydroindole-3,4'-piperidine]-6-yl)benzamide

34

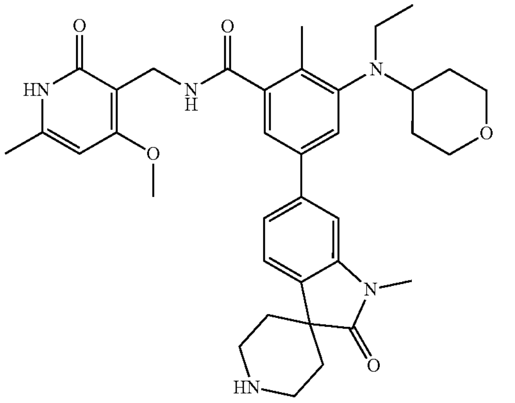

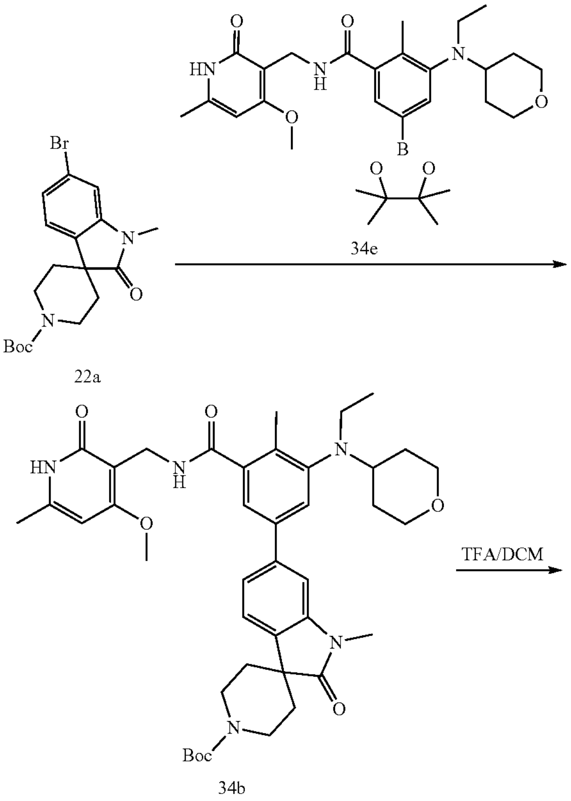

-continued

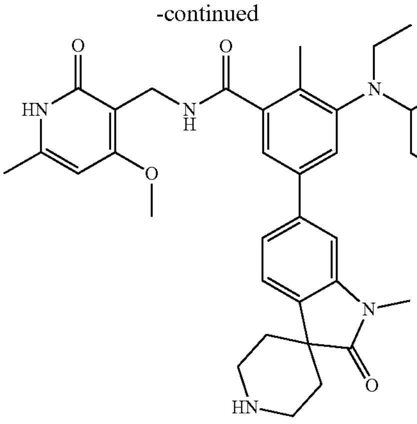

34

Step I Tert-butyl 6-(3-(ethyl(tetrahydro-2H-pyran-4-yl)amino)-5-(((4-methoxy-6-methyl-2-carbonyl-1,2-dihydropyridin-3-yl)methyl)carbamoyl)-4-methylphenyl)-1-methyl-2-carbonylspiro[dihydroindole-3,4'-piperidine]-1'-carboxylate 34b The compound 22a (240 mg, 0.6 mmol), compound 34a (539 mg, 0.72 mmol), $K_2CO_3$ (248 mg, 1.8 mmol) and Pd(dppf)$Cl_2$ (44 mg, 0.06 mmol) were dissolved in dioxane (20 mL) and $H_2O$ (5 mL). The mixture was heated to 100° C. under the protection of Ar and stirred for 6 hours until the reaction was completed. The reaction solution was extracted with water and ethyl acetate, and the organic phase was washed with saturated NaCl solution, dried with anhydrous sodium sulfate, filtered, concentrated, and purified by column chromatography to obtain the title compound 34b (130 mg, 0.1788 mmol) with a yield of 30%.

MS m/z (ESI): 728.5 $[M+H]^+$.

Step II 3-(ethyl(tetrahydro-2H-pyran-4-yl)amino)-N-((4-methoxy-6-methyl-2-carbonyl-1,2-dihydropyridin-3-yl)methyl)-2-methyl-5-(1-methyl-2-carbonylspiro[dihydroindole-3,4'-piperidine]-6-yl) benzamide 34

The compound 34b (130 mg, 0.1788 mmol) was dissolved in dichloromethane (4.0 mL), and trifluoroacetic acid (4 mL) was added. The mixture was stirred at room temperature for 2 hours until the reaction was completed. The reaction solution was spin-dried, added with methanol, neutralized with saturated potassium carbonate solution, filtered, concentrated, and purified by plate chromatography to obtain the title compound 34 (60 mg, 0.0956 mmol) with a yield of 53%.

1H NMR (400 MHz. Methanol-d4) δ 7.50 (d, J=7.8 Hz. 1H), 7.45 (d, J=1.9 Hz, 1H) 7.35 (d, J=1.8 Hz, 1H), 7.28 (dd, J=7.8, 1.6 Hz, 1H), 7.17 (d, J=t, 5 Hz, 1H), 6.24 (d, J=0.9 Hz, 1H), 4.46 (s, 2H), 3.92 (s, 5W)t 3.35 (ddd, J=12.5, 9.9, 2.6 Hz, 4H), 3.24 (s, 3H), 3.19-3.01 (m, 5H), 2.33 (s, 3H), 2.29 (d, J=0.8 Hz, 3H), 1.87-1.57 (m, 8H), 0.89 (t, J=7.0 Hz, 3H), MS m/z (ESI): 628.6$[M+1]^+$.

Example 35 3-(ethyl(tetrahydro-2H-pyran-4-yl)amino)-N-((4-methoxy-6-methyl-2-oxo-1,2-dihydropyridin-3-yl)methyl)-2-methyl-5-(1'-(2,2,2-trifluoroethyl)spiro[indene-1,4'-piperidine]-5-yl)benzamide 35-1

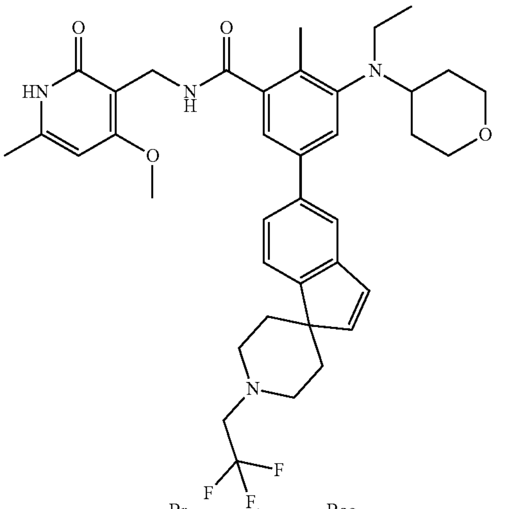

35-2

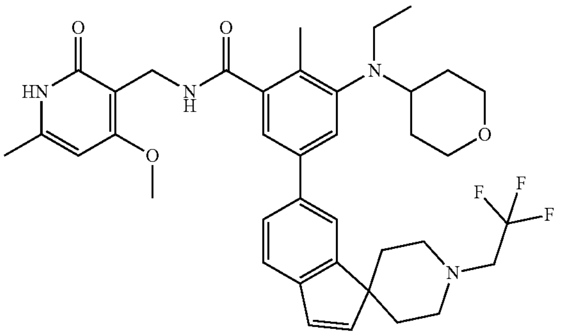

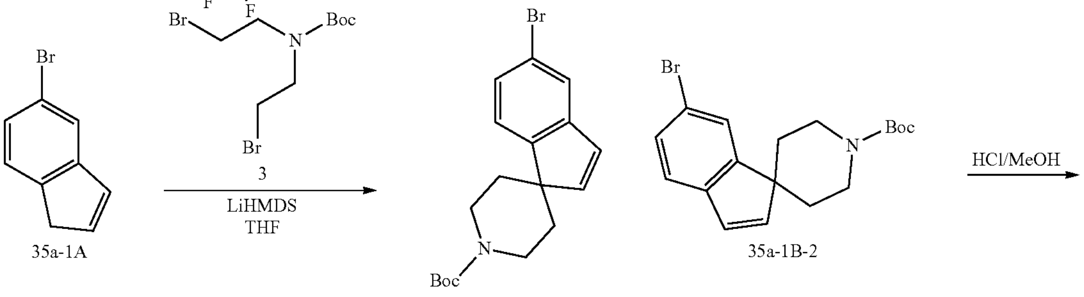

35a-1A 35a-1B-1

35a-1B-2

-continued

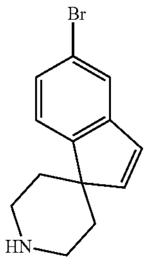

35a-1

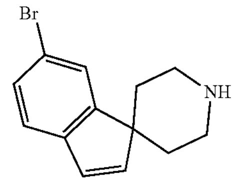

35a-2

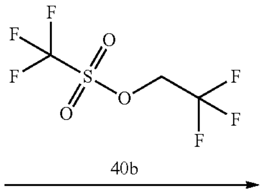

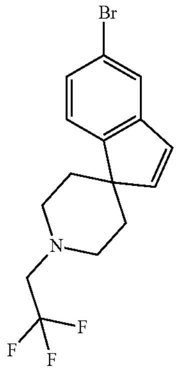

35c-1

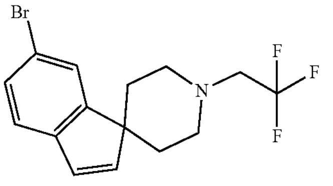

35c-2

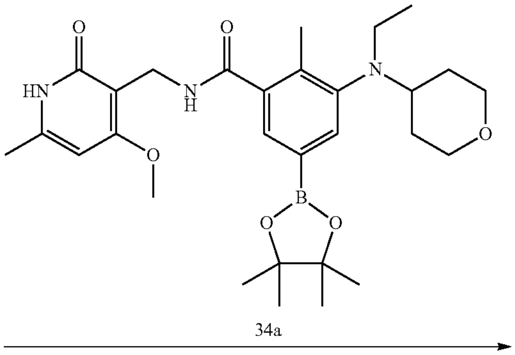

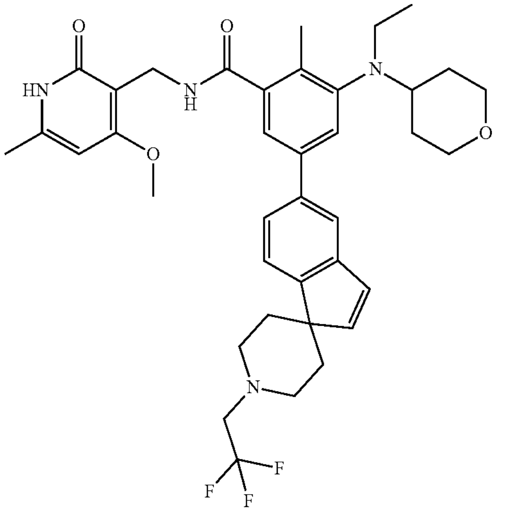

35-1

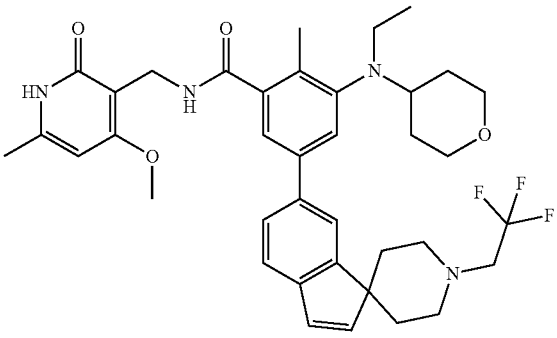

35-2

Step I Tert-butyl 5-bromospiro[indene-1,4'-piperidine]-1'-carboxylate and tert-butyl 6-bromospiro [indene-1,4'-piperidine]-1'-carboxylate 35a-1B-1 and 35a-1B-2

The compound 35a-1A (5 g, 25.64 mmol), THF (80 mL) and compound 3 (10.18 g, 30.76 mmol) were added in a 250 mL three-necked flask under the protection of Ar and under dry ice bath, followed by adding LiHMDS (103 mL, 103 mmol, 1 M) dropwise. The mixture was slowly heated to 70° C. and reacted for 8 hours. The raw materials were completely reacted as determined by TLC monitoring and there were new spots formed. The reaction solution was quenched with $H_2O$, extracted with EA, dried with anhydrous sodium sulfate, filtrated, concentrated, and purified by flash column chromatography to obtain a light-yellow solid of compound 35a-1B-1 and 35a-1B-2 (4.4 g, 12.08 mmol) with a yield of 47%.

Step II 5-bromospiro[indene-1,4'-piperidine]40a-1 and 6-bromospiro[indene-1,4'-piperidine]35a-2

The compound 35a-1B-1 and 35a-1B-2 (4.4 g, 12.08 mmol) and HCl/MeOH (46 mL, 184 mmol) were added in a 250 mL single-necked flask. The mixture was reacted at 25° C. for 1.5 hours. The raw materials were completely reacted as determined by TLC monitoring and there were new spots formed. The reaction solution was concentrated, added with water, neutralized with NaOH (1 M), extracted with DCM/MeOH (10/1), and concentrated to obtain a light-pink solid of compound 35a-1 and 35a-2 (2.8 g, 10.06 mmol) with a yield of 88%.

Step III 5-bromo-1'-(2,2,2-trifluoroethyl)spiro[indene-1,4'-piperidine]35c-1 and 6-bromo-1'-(2,2,2-trifluoroethyl)spiro[indene-1,4'-piperidine]35c-2

The mixture of compound 35a-1 and 35a-2 (150 mg, 568 μmol), DMF (6 mL), $K_2CO_3$ (196 mg, 1.42 mmol), and compound 35b (264 mg, 1.14 mmol) were added in a 50 mL single-necked flask. The mixture was reacted at 50° C. for 3 hours. The raw materials were completely reacted as determined by TLC monitoring and there were new spots formed. The reaction solution was added with water, extracted with DCM, dried with anhydrous sodium sulfate, concentrated, and purified by flash column chromatography to obtain a white solid of a compound 35c-1 and 35c-2 (160 mg, 462 μmol) with a yield of 81%.

Step IV 3-(ethyl(tetrahydro-2H-pyran-4-yl)amino)-N-((4-methoxy-6-methyl-2-oxo-1,2-dihydropyridin-3-yl)methyl)-2-methyl-5-(1'-(2,2,2-trifluoroethyl)spiro[indene-1,4'-piperidine]-5-yl)benzamide 40-1 and 3-(ethyl(tetrahydro-2H-pyran-4-yl)amino)-N-((4-methoxy-6-methyl-2-carbonyl-1,2-dihydropyridin-3-yl)methyl)-2-methyl-5-(1'-(2,2,2-trifluoroethyl)spiro[indene-1,4'-piperidine]-6-yl)benzamide 35-2

The compound 35c (160 mg, 462 μmol), compound 34a (299 mg, 555 μmol), $K_2CO_3$ (256 mg, 1.85 mmol), Pd(dppf)$Cl_2$ (34 mg, 46 μmol), dioxane (6 mL) and $H_2O$ (2 mL) were added in a 50 mL single-necked flask. The mixture was heated to 100° C. under the protection of Ar and reacted for 3 hours. The raw materials were completely reacted as determined by LCMS monitoring and there was MS value of the product in the main peak. The reaction solution was concentrated, extracted with DCM, dried with anhydrous sodium sulfate, concentrated, and purified by flash column chromatography to obtain 120 mg of a light-yellow solid, and 20 mg thereof was then purified by preparative TLC. $^1H$ NMR, LCMS and HPLC were used to confirm that the product was compound 35-1 and 35-2 (5.8 mg, 8.5 μmol).

$^1H$ NMR (400 MHz, DMSO-d6) δ 11.42 (s, 1H), 7.99 (t, J=4.5 Hz, H), 7.59-7.54 (m, 1H), 7.49-7.37 (n. 3H), 7.21 (d, J=1.8 Hz, 1H), 7.01 (d, J=5.9 Hz, 1H), 6.85 (dd, J=13.0, 5.6 Hz, 1H), 6.09 (s, 1H), 4.23 (d, J=4.6 Hz, 2H), 3.81 (s, 5H), 3.32-3.21 (m, 4H), 3.14-2.97 (m, 5H), 2.75 (t, J=11.8 Hz, 2H), 2.26 (s, 3H), 2.17 (s, 5H), 1.67 (d, J=12.6 Hz, 2H), 1.53 (d, J=11.8 Hz, 2H), 1.22 (s, 2H), 0.87-0.82 (n, 3H),

MS m/z (ESI): 679.5 $[M+H]^+$.

Example 36 3-(ethyl(tetrahydro-2H-pyran-4-yl)amino)-N-((4-methoxy-6-methyl-2-oxo-1,2-dihydropyridin-3-yl)methyl)-2-methyl-5-(1'-(2,2,2-trifluoroethyl)-2,3-dihydrospiro[indene-1,4'-piperidine]-5-yl)benzamide 36-1 and 3-(ethyl(tetrahydro-2H-pyran-4-yl)amino)-N-((4-methoxy-6-methyl-2-carbonyl-1,2-dihydropyridin-3-yl)methyl)-2-methyl-5-(1'-(2,2,2-trifluoroethyl)-2,3-dihydrospiro[indene-1,4'-piperidine]-6-yl)benzamide 36-2

36-1

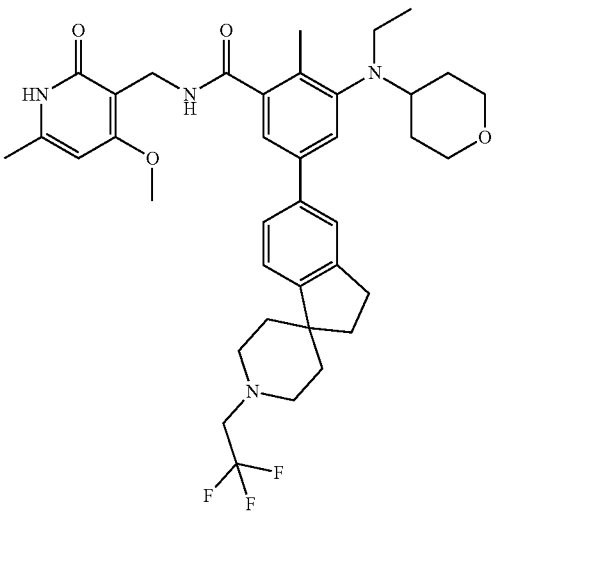

36-2

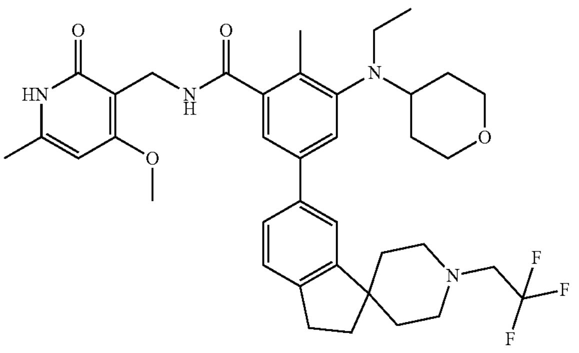

-continued

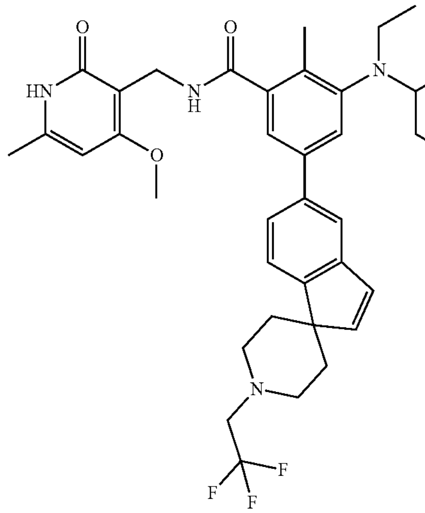

35-1

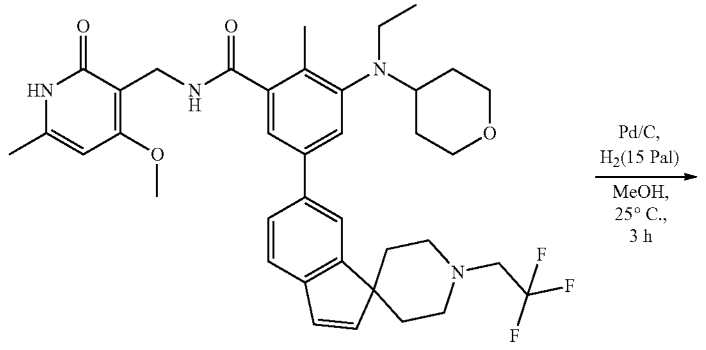

35-2

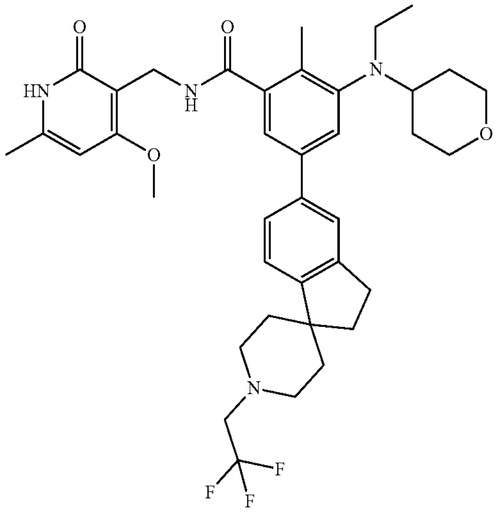

36-1

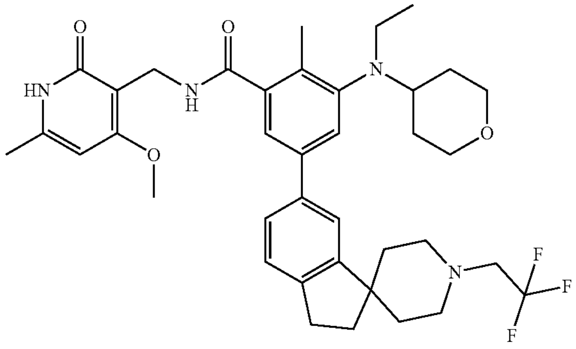

36-2

Step I 3-(ethyl(tetrahydro-2H-pyran-4-yl)amino)-N-((4-methoxy-6-methyl-2-oxo-1,2-dihydropyridin-3-yl)methyl)-2-methyl-5-(1'-(2,2,2-trifluoroethyl)-2,3-dihydrospiro[indene-1,4'-piperidine]-5-yl)benzamide 36-1 and 3-(ethyl(tetrahydro-2H-pyran-4-yl)amino)-N-((4-methoxy-6-methyl-2-carbonyl-1,2-dihydro-pyridin-3-yl)methyl)-2-methyl-5-(1'-(2,2,2-trifluoro-ethyl)-2,3-dihydrospiro[indene-1,4'-piperidine]-6-yl) benzamide 36-2

The mixture of compound 35-1 and 35-2 (100 mg, 147 μmol), MeOH (10 mL) and Pd/C (100 mg, wet, 10%) were added in a 50 mL single-necked flask. The reaction system was replaced with $H_2$ (15 psi) for 3 times and reacted at 25° C. for 3 hours. The raw materials were completely reacted as determined by LCMS monitoring and there was MS value of the product in the main peak. The reaction solution was filtrated, concentrated, and purified by preparative TLC to obtain a white solid, which was confirmed to be a mixture of 36-1 and 36-2 (55.2 mg, 81 mol) by $^1$H NMR, LCMS and HPLC, with a yield of 55%.

1H NMR (400 MHz, DMSO-d6) δ 11.42 (s, 1H), 7.98 (1, J 4.7 Hz, 1H), 7.45-7.17 (m, 5H), 6.09 (d, J=4.0 Hz 1H), 4.24 (t, J=4.6 Hz, 2H), 3.81 (d, J=1.2 Hz, 51-), 3.27 (d, J=11.6 Hz, 2H), 3.17 (s, 2H), 3.13-3.00 (m, 3H), 2.98-2.82 (m, 4H), 2.25 (s, 3H), 2.17 (s, 3H), 2.03-1.84 (m, 4H), 1.67 (d, J=12.9 Hz, 2H), 0.49 (dd, J=24.8, 12.5 Hz, 4H), 0.84 (td, J=7.0, 3.7 Hz, 3H),

MS m/z (ESI): 681.4 [M+H]$^+$.

Example 37 3-(ethyl(tetrahydro-2H-pyran-4-yl)amino)-5-(1'-isopropylspiro[indene-1,4'-piperidine]-5-yl)-N-((4-methoxy-6-methyl-2-carbonyl-1,2-dihydropyridin-3-yl)methyl)-2-methylbenzamide

37

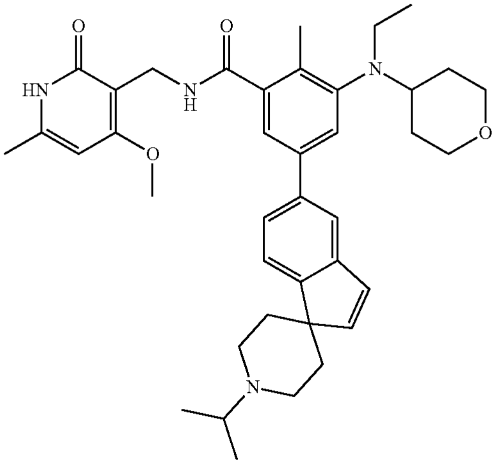

A similar method of Example 16 was used to obtain the title compound 37 with a yield of 5%, wherein the 6-bromo-5-fluoro-2,3-dihydro-1H-inden-1-one was replaced with 6-bromo-2,3-dihydro-1H-inden-1-one.

$^1$H NMR (400 MHz, Chloroform-d) δ 764-7.55 (mi, 1H), 7.44-7.30 (m, 4H), 6.80 (d, J=3.8 Hz, 2H), 5.91 (d, J=2.7 Hz, 1H), 4.64-4.55 (m, 2H), 4.02-3.84 (m, 5H), 3.49-3.26 (m, 5H), 3.16-2.80 (m, 7H), 2.40 (d, J=10.8 Hz, 3H), 2.22 (s, 1H), 2.15 (s, 2H), 1.70 (d, J=16.9 Hz, 6H), 1.49-1.38 (m, 6H), 0.91 (t, J=7.0 Hz, 3H), MS m/z (ESI): 638.9 [M+H]$^+$.

Example 38 N-((4,6-dimethyl-2-oxo-1,2-dihydropyridin-3-yl)methyl)-3-(ethyl(tetrahydro-2H-pyran-4-yl)amino)-5-(1-ethyl-2',3',5',6'-tetrahydrospiro[dihydroindole-3,4'-pyran]-6-yl)-2-methylbenzamide

38

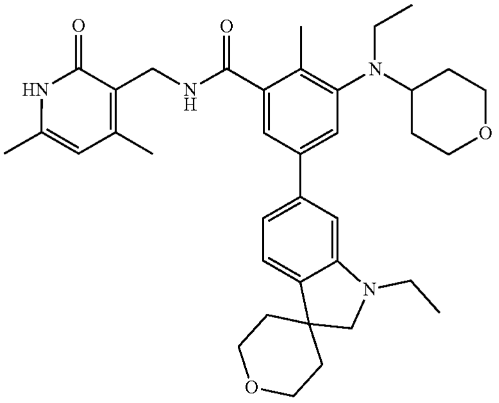

-continued

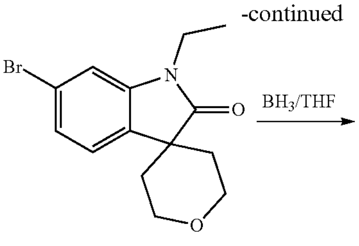

38a

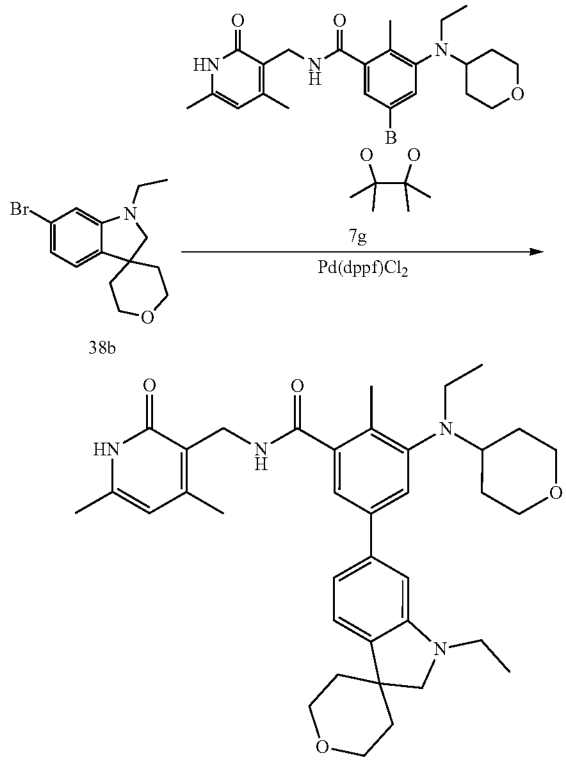

38b

38

Step I 6-bromo-1-ethyl-2',3',5',6'-tetrahydrospiro[dihydroindole-3,4'-pyran]38b

The compound 38a (6-bromo-1-ethyl-2',3',5',6'-tetrahydrospiro[dihydroindole-3,4'-pyran]-2-one) (250 mg, 0.80 mmol) was dissolved in tetrahydrofuran (5 mL), followed by adding 50 mL of $BH_3$/THF solution and reacting at room temperature for 16 hours. The reaction was quenched with water. The reaction solution was extracted with ethyl acetate for three times, dried with anhydrous sodium sulfate, concentrated, and dried to obtain the title compound 38b (210 mg, 0.71 mmol) with a yield of 92%.

Example 38 N-((4,6-dimethyl-2-oxo-1,2-dihydropyridin-3-yl)methyl)-3-(ethyl(tetrahydro-2H-pyran-4-yl)amino)-5-(1-ethyl-2',3',5',6'-tetrahydrospiro[dihydroindole-3,4'-pyran]-6-yl)-2-methylbenzamide 38

The compound 38b (6-bromo-1-ethyl-2',3',5',6'-tetrahydrospiro[dihydroindole-3,4'-pyran]) (100 mg, 0.33 mmol) and compound 7g (120 mg, 0.33 mmol) were dissolved in a mixture of 1,4-dioxane and $H_2O$ (1,4-dioxane:$H_2O$=3:1, v/v, 20 mL), and [1,1'-bis(diphenylphosphino)ferrocene]dichloropalladium (23 mg, 0.032 mmol) and potassium carbonate (88 mg, 0.66 mmol) were added. The mixture was heated to 100° C. under the protection of Ar and stirred for 5 hours. The reaction solution was cooled down, spin-dried, and the residue was extracted with ethyl acetate for 3 times, dried with anhydrous sodium sulfate, concentrated, and purified by thin-layer chromatography to obtain the title compound 38 (11.0 mg, yield 5.2%).

$^1$H NMR (400 MHz, Methanol-d4) δ 7.37 (d, J=1.8 Hz, 1H), 7.24 (d, J=1.8H, 1H), 7.07 (d, J=7.6 Hz, 1H), 6.82 (d, J=1.5 Hz, 1H), 6.63 (d, J=1.5 Hz, 1H), 6.09 (s, 1H), 4.57 (s, 1H), 4.47 (s, 2H), 3.91 (q, J=7.5, 4.3 Hz, 3H), 3.70-3.52 (m, 2H), 3.38 (d, J=4.8 Hz, 1H), 3.34 (d, J=2.0 Hz, 1H), 3.22 (q, J=72 Hz, 1H), 3.17-2.98 (m, 3H), 2.37 (s, 2H), 2.29 (s, 2H), 2.22 (s, 3H), 2.05-1.85 (m, 3H), 1.72 (s, 2H), 1.62 (d, J=13.7 Hz, 3H), 1.40-1.22 (m, 6H), 1.19 (t, J=7.2 Hz, 2H), 0.93-0.80 (n, 3H), MS m/z (ESI): 614.4 [M+H]$^+$.

Example 39 N-((4,6-dimethyl-2-oxo-1,2-dihydropyridin-3-yl)methyl)-3-(ethyl(tetrahydro-2H-pyran-4-yl)amino)-2-methyl-5-(2-oxo-1-(2,2,3,3,3-pentafluoropropyl)-2',3',5',6'-tetrahydrospiro[dihydroindole-3,4'-pyran]-6-yl)benzamide

39

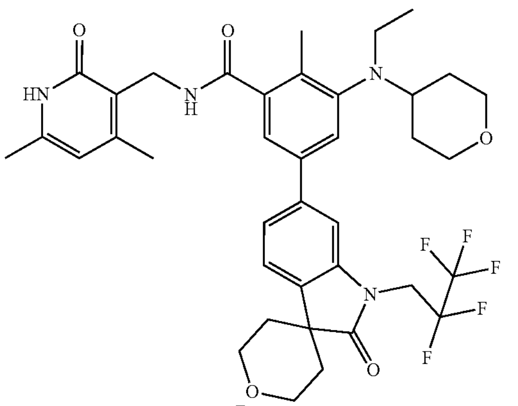

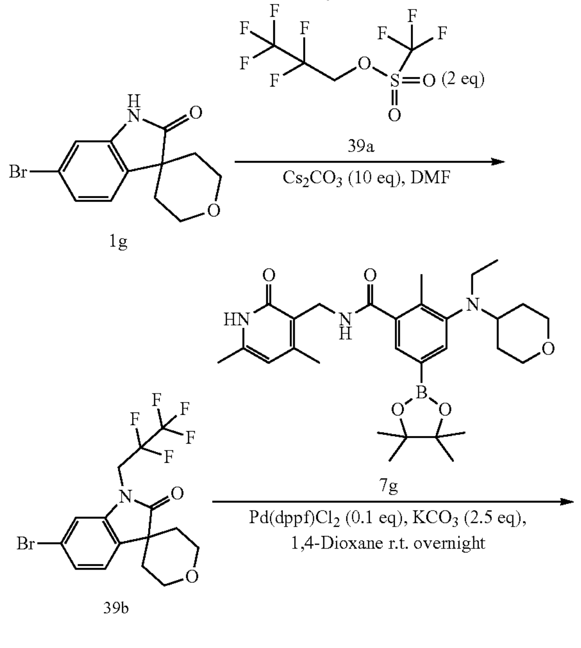

-continued

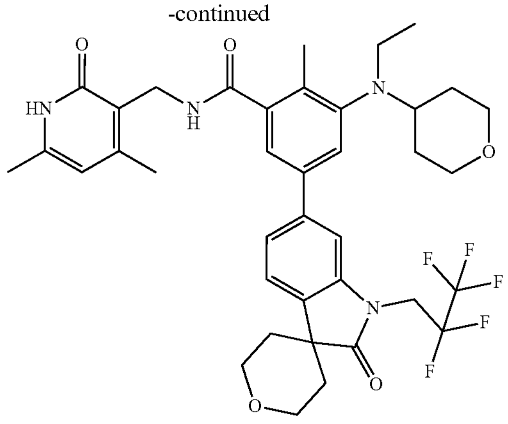

39

Step I 6-bromo-1-(2,2,3,3,3-pentafluoropropyl)-2',3',5',6'-tetrahydrospiro[dihydroindole-3,4'-pyran]-2-one 39a The compound 1g (250 mg, 0.886 mmol), compound 39a (500 mg, 1.773 mmol), cesium carbonate (2.9 g, 8.86 mmol) and 4 mL of DMF were added to a 10 mL microwave tube, which was then replaced with nitrogen. The mixture was stirred at 20° C. for 2 hours. The reaction solution was added with water, extracted with EA, dried with anhydrous sodium sulfate, mixed, concentrated, and purified by column chromatography (petroleum ether: ethyl acetate=3:1) to obtain the title compound 39b (167 mg, 0.404 mmol) with a yield of 45.6%.

MS m/z (ESI): 414 [M+H]$^+$.

Step II N-((4,6-dimethyl-2-oxo-1,2-dihydropyridin-3-yl)methyl)-3-(ethyl(tetrahydro-2H-pyran-4-yl)amino)-2-methyl-5-(2-oxo-1-(2,2,3,3,3-pentafluoropropyl)-2',3',5',6'-tetrahydrospiro[dihydroindole-3,4'-pyran]-6-yl)benzamide 39

The compound 39b (120 mg, 0.29 mmol), compound 7g (150 mg, 0.29 mmol), Pd(dppf)$Cl_2$ (21 mg, 0.029 mmol), potassium carbonate (120 mg, 0.87 mmol), 1 mL of water and 5 mL of 1,4-dioxane were added to a microwave tube. The reaction system was replaced with nitrogen, heated to 100° C. and reacted for 1 hour. The reaction solution was added with 30 mL of water and extracted with EA (30 mL×3). The organic phases were combined, washed with saturated NaCl solution (30 mL×3), dried, mixed, and purified by column chromatography (methanol: dichloromethane=1:15) to obtain the title compound 39 (25 mg, 0.034 mmol) with a yield of 11.8%.

$^1$H NMR (400 MHz, Methanol-d4) δ 7.86 (s, 1H), 7.69 (s, 1H), 7.58 (d, J=7.8 Hz, 1H), 7.45 (dd, J=7.8, 1.5 Hz, 1H), 7.36 (d, J=1.6 Hz, 1H), 6.14 (s, 1H), 4.65 (t, J=14.8 Hz, 2H), 4.56-4.46 (m, 3H), 41.9 (ddd, J=12.0, 9.1, 3.1 Hz, 2H), 4.03-3.87 (m, 4H), 3.73 (d, J=7.6 Hz, 2H), 3.36 (dd, J=12.6, 10.4 Hz, 2H), 2.40 (d, J=22.6 Hz, 6H) 2.24 (s, 3H), 1.0.97-1.88 (m, 3H), I 0.79 (dt, J=13.9, 4.2 Hz, 3H), 1.64 (d, J=7.0 Hz, 2H), 103 (t, J=70 Hz, 3H), MS m/z (ESI): 731 [M+H]$^+$.

Example 40 3-(ethyl(1-(2,2,2-trifluoroethyl)piperidin-4-yl)amino)-N-((4-methoxy-6-methyl-2-carbonyl-1,2-dihydropyridin-3-yl)methyl)-2-methyl-5-(1-methyl-2',3',5',6'-tetrahydrospiro[dihydroindole-3,4'-pyran]-6-yl)benzamide

40

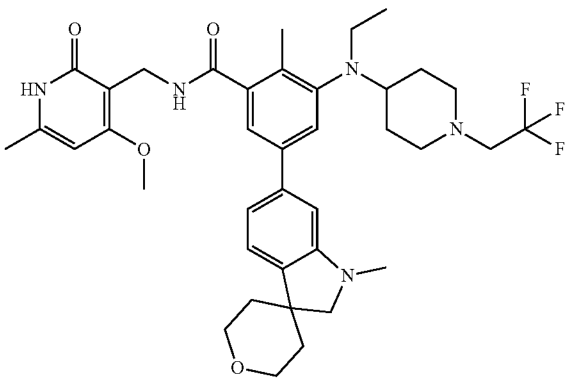

A similar method of Example 5 was used to obtain the title compound 40 with a yield of 15%, wherein Boc was replaced with 1,1,1-trifluoro-2-iodoethane, the 3-(aminomethyl)-4,6-dimethyl-1H-pyridin-2-one hydrochloride was replaced with 3-(aminomethyl)-4-methoxy-6-methyl-1H-pyridin-2-one hydrochloride.

$^1$H NMR (400 MHz, DMSO-d6) δ 11.41 (s, 1H), 7.97 (s, 11), 7.72 (d, J=1.7 Hz, 1H), 7.55-7.51 (m, 1H), 7.36 (d, J=1.7 Hz, 1H), 7.22 (d, J=1.8 Hz, 1H), 7.08 (d, J=8.1 Hz, 1H), 6.09 (s, 1H), 4.24 (d, J=4.6 Hz, 2H), 4.10 (d, J=10.0 Hz, 2H), 3.81 (s, 5H), 3.12 (d, J=25.4 Hz, 71), 2.89 (d, J=11.3 Hz, 2H), 2.79 (s, 1H), 2.311 (d, J=11.4 Hz, 2H), 2.23 (s, 3H), 2.17 (s, 3H), 1.96 (d, J=10.2 Hz, 2H), 1.69 (d, J=1 L4 Hz, 4H), 1.56 (d, J=11.5 Hz, 2H), 0.84 (t, J=6.9 Hz, 3H),

MS m/z (ESI): 696.4 [M+H]$^+$.

Example 41 3-(ethyl(tetrahydro-2H-pyran-4-yl)amino)-N-((4-methoxy-6-methyl-2-oxo-1,2-dihydropyridin-3-yl)methyl)-2-methyl-5-(2-oxo-1-(2,2,2-trifluoroethyl)spiro[dihydroindole-3,4'-piperidine]-6-yl)benzamide

41

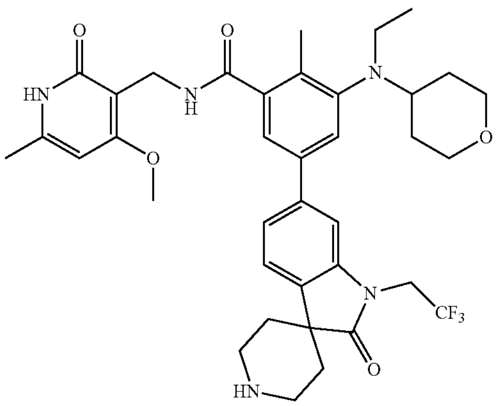

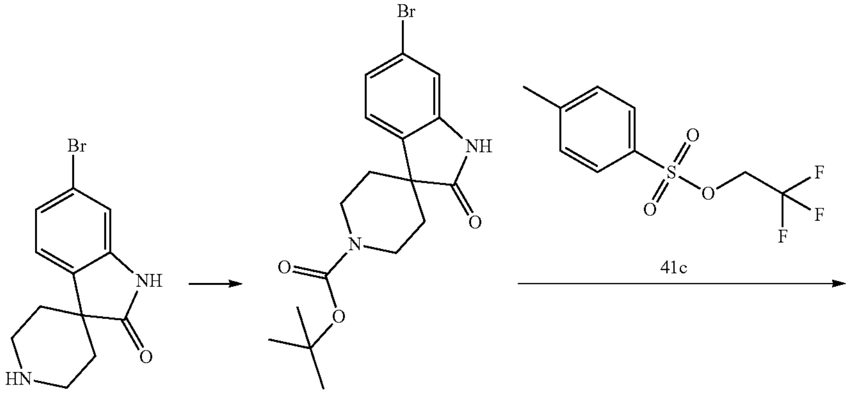

41a

41b

-continued

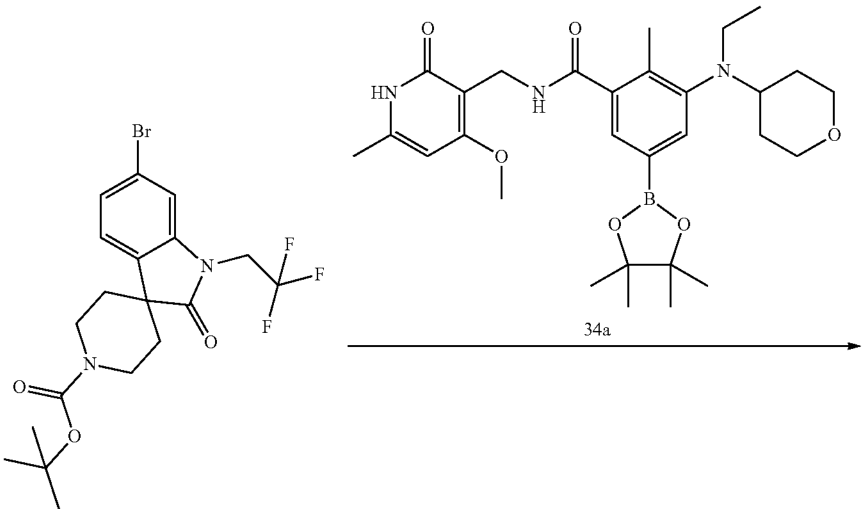

41d

34a

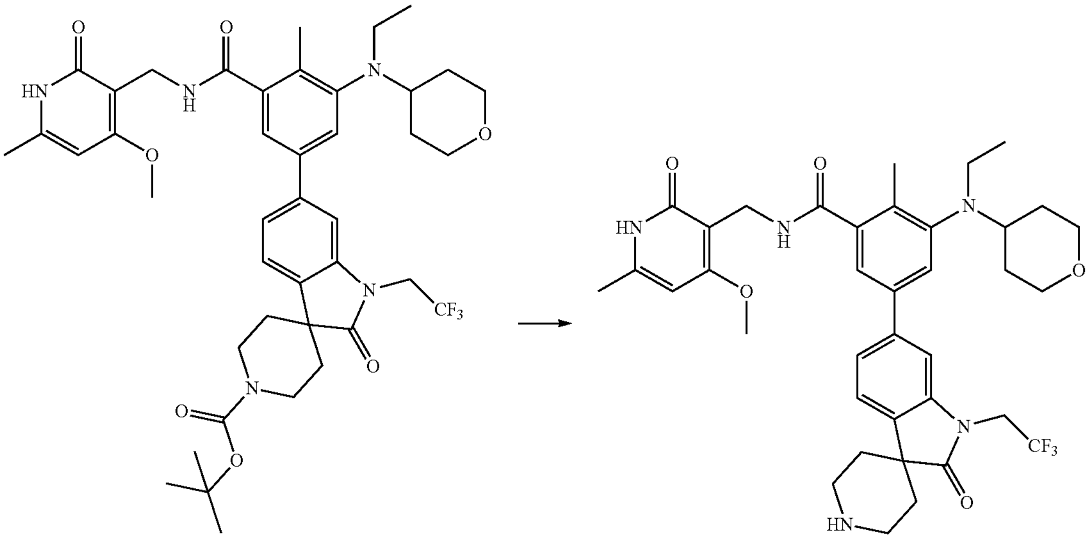

41e

41

Step I Tert-butyl 6-bromo-2-oxospiro[dihydroindole-3,4'-piperidine]-1'-carboxylate 41b The compound 41a (100 mg, 222 μmol), DCM (10 mL), $(Boc)_2O$ (388 mg, 1.78 mmol) and DIPEA (460 mg, 3.56 mmol) were added in a 50 mL single-necked flask and stirred at room temperature for 40 minutes. The raw materials were completely reacted as determined by TLC monitoring and there were new spots formed. The reaction solution was concentrated, dissolved with EA, washed with water and concentrated to obtain a light-yellow solid of compound 41b (650 mg, 1.7 mmol) with a yield of 96%.

$^1$H NMR (400 MHz, DMSO-d6) δ 10.57 (s, 1H), 7.43 (d, J=8.0 Hz, 1H), 7.12 (dd, J=8.0, 1.9 Hz, 1H), 6.99 (d, J=18 Hz, 1H), 3.74-3.54 (m, 4H), 1.66 (dt, J=7.6, 4.7 Hz, 4H), 1.43 (s, 9H),

Step II Tert-butyl 6-bromo-2-oxo-1-(2,2,2-trifluoroethyl)spiro[dihydroindole-3,4'-piperidine]-1'-carboxylate 41d The compound 41b (460 mg, 1.21 μmol), DMF (10 mL), $Cs_2CO_3$ (128 mg, 3.93 mmol) and compound 41c (680 mg, 2.67 μmol) were added in a 50 mL single-necked flask. The mixture was reacted at 50° C. for 3 hours under the protection of Ar. The raw materials were completely reacted as determined by LCMS monitoring and there was MS value of the product in the main peak. The reaction solution was added with water, extracted with EA, dried with anhydrous sodium sulfate, concentrated, and purified by flash column chromatography to obtain a white solid of the title compound 41d (450 mg, 971 μmol) with a yield of 81%.

$^1$H NMR (400 MHz, DMSO-d6) δ 7.55-7.48 (n, 2H), 7.27 (dd, J=8.0, 1.8 Hz, 1I1), 4.65 (q, J=9.3 Hz, 2H), 3.75-3.55 (m, 4H), 1.79-1.63 (m, 411), 1.43 (s, 9H),

Step III Tert-butyl 6-(3-(ethyl(tetrahydro-2H-pyran-4-yl)amino)-5-(((4-methoxy-6-methyl-2-oxo-1,2-dihydropyridin-3-yl)tert-butyl)methyl)carbamoyl)-4-methylphenyl)-2-oxo-1-(2,2,2-trifluoroethyl)spiro[dihydroindole-3,4'-piperidine]-1'-carboxylate 41e The compound 48d (200 mg, 432 μmol), compound 34a (233 mg, 432 μmol), $K_2CO_3$ (179 mg, 1.3 mmol), Pd(dppf)$Cl_2$ (32 mg, 43 μmol), dioxane (4 mL) and $H_2O$ (1 mL) were added in a 50 mL single-necked flask. The mixture was heated to 110° C. under the protection of Ar and reacted for 3 hours. The raw materials were completely reacted as determined by LCMS monitoring and there was MS value of the product in the main peak. The reaction solution was added with water, extracted with DCM, dried, concentrated, mixed with silica gel, and purified by flash column chromatography to obtain a white solid of compound 41e (150 mg, 189 μmol) with a yield of 43%.

$^1$H NMR (4(0) MHz, DMSO-d6) δ 11.41 (s, 11), 7.97 (d, J=4.5 Hz, 1H), 7.60 (d, J=7.8 Hz, 1H), 7.46 (s, 1H), 7.39 (d, J=1.8 Hz, 1H), 7.34-7.25 (m, 2H), 6.09 (s, 1H), 4.77 (d, J=9.3 Hz, 2H), 4.24 (d, J=4.5 Hz, 2H), 3.93 (s, 1H), 3.80 (s, 5H), 3.70 (s, 41), 3.25 (t, J=11.4 Hz, 2H), 3.10 (d, J=7.1 Hz, 3H), 2.25 (s, 3H), 2.17 (s, 3H), 1.80-1.64 (n, 6H), 1.55 (s, 2H), 1.45 (s, 9H), 0.85 (t, J=6.9 Hz, 3H),

Step IV 3-(ethyl(tetrahydro-2H-pyran-4-yl)amino)-N-((4-methoxy-6-methyl-2-oxo-1,2-dihydropyridin-3-yl)methyl)-2-methyl-5-(2-oxo-1-(2,2,2-trifluoroethyl)spiro[dihydroindole-3,4'-piperidine]-6-yl)benzamide 41

The compound 41e (125 mg, 157 μmol) and MeOH (5 mL) were added in a 100 mL single-necked flask, followed by adding HCl/MeOH (1.18 mL). The mixture was reacted at 22° C. for 2 hours. The raw materials were completely reacted as determined by LCMS monitoring and there was MS value of the product in the main peak. The raw materials were completely reacted as determined by TLC monitoring and there were new spots formed. The reaction solution was concentrated, added with water, neutralized with NaOH (1 M), extracted with DCM/MeOH (10/1), concentrated, and purified by preparative TLC to obtain a light-yellow solid of compound 41 (10.4 mg, 14.2 μmol) with a yield of 9%.

$^1$H NMR (400 MHz, Methanol-d4) δ 7 52 (d, J=7.7 Hz, 1H), 7.46 (d, J=1.9 Hz, 1H), 7.38-7.30 (m, 3H), 6.26 (s, 1H), 4.60 (d, J=9.0 Hz, 2H), 4.48 (s, 2H), 3.94 (s, 5H), 3.44-334 (m, 4H), 3.20-3.06 (m, 51H), 2.36 (s, 3H), 2.31 (s, 3H), 1.86 (d, J=5.2 Hz, 4H), 1.77 (d, J=12.3 Hz, 2H), 1.67 (d, J=4.2 Hz, 2H), 0.92 (d, J=6.9 Hz, 3H), MS m/z (ESI): 696.3 [M+H]$^+$ Example 42 3-(ethyl(tetrahydro-2H-pyran-4-yl)amino)-N-((4-methoxy-6-methyl-2-carbonyl-1,2-dihydropyridin-3-yl)methyl)-2-methyl-5-(1'-(2,2,3,3,3-pentafluoropropyl)-2,3-dihydrospiro[indene-1,4'-piperidine]-5-yl)benzamide 42-1 and 3-(ethyl(tetrahydro-2H-pyran-4-yl)amino)-N-((4-methoxy-6-methyl-2-carbonyl-1,2-dihydropyridin-3-yl)methyl)-2-methyl-5-(1'-(2,2,3,3,3-pentafluoropropyl)-2,3-dihydrospiro[indene-1,4'-piperidine]-6-yl)benzamide 42-2

42-1

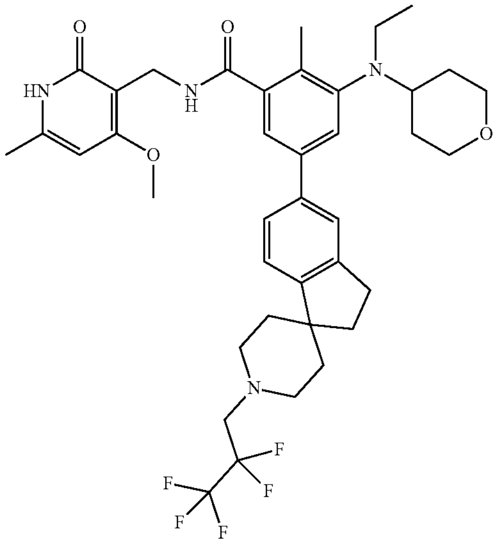

42-2

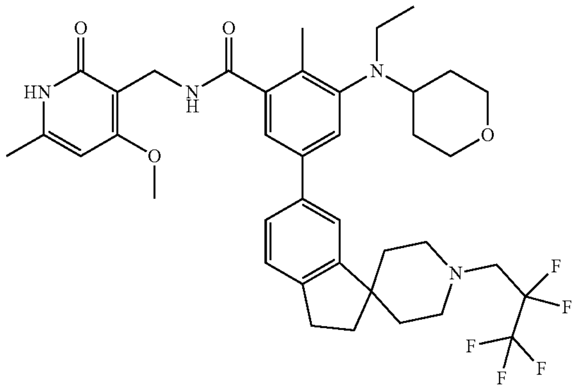

A similar method of Example 35 and 36 was used to obtain the title compound 42-1 and 42-2 with a yield of 55%, wherein 2,2,2-trifluoroethyl trifluoromethanesulfonate was replaced with 2,2,3,3,3-pentafluoropropyl trifluoromethanesulfonate.

$^1$H NMR (400 MHz, DMSO-d6) δ 11.43 (s, 1H), 7.98 (d, J=3.9 Hz, 1H), 7.44-7.33 (m, 3H), 7.26 (dd, J=7.8, 5.1 Hz, 1H), 7.19 (dd, J=14.5, 1.7 Hz, 1H), 6.09 (d, J=5.7 Hz, 1H), 4.23 (t, J=4.5 Hz, 2H), 3.81 (d, J=1L7 Hz, 5H), 3.25 (t, J=11.3 Hz, 4H), 3.14-3.00 (m, 3H), 2.88 (dt, J=14.6, 7.3 Hz, 4H), 2.25 (5, 3H), 2.17 (d, J=1.6 Hz, 3H), 2.01 (d, J=4.0 Hz, 4H), 1.66 (d, J=12.8 Hz, 2H), 1.49 (dd, J=23.2, 12.9 Hz, 4H), 1.23 (s, 2H), 0.83 (td, J=7.0, 3.3 Hz, 3H),

MS m/z (ESI): 731.4 [M+H]$^+$.

Example 43 3-((2,2-dimethyltetrahydro-2H-pyran-4-yl)(ethyl)amino)-5-(2,2',3,3',5',6'-hexahydrospiro[indene-1,4-pyran]-5-yl)-N-((4-methoxy-6-methyl-2-oxo-1,2-dihydropyridin-3-yl)methyl)-2-methylbenzamide
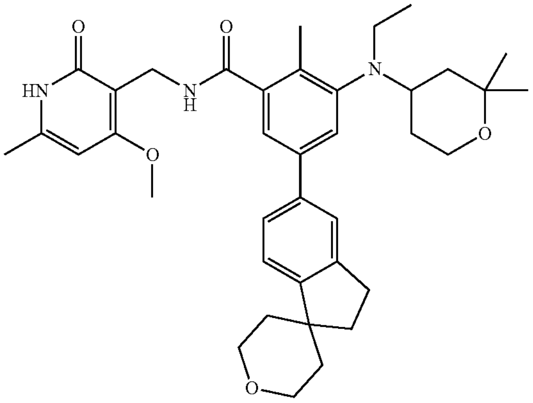
43
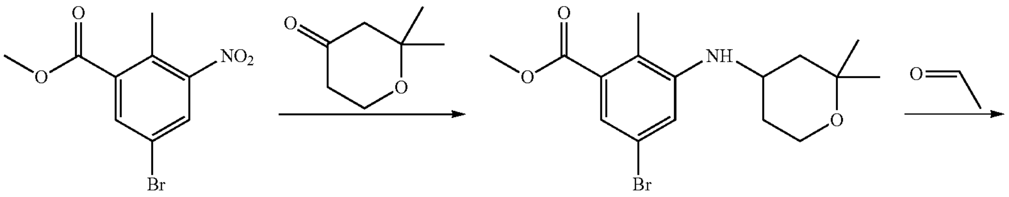
43a-1
43b-1
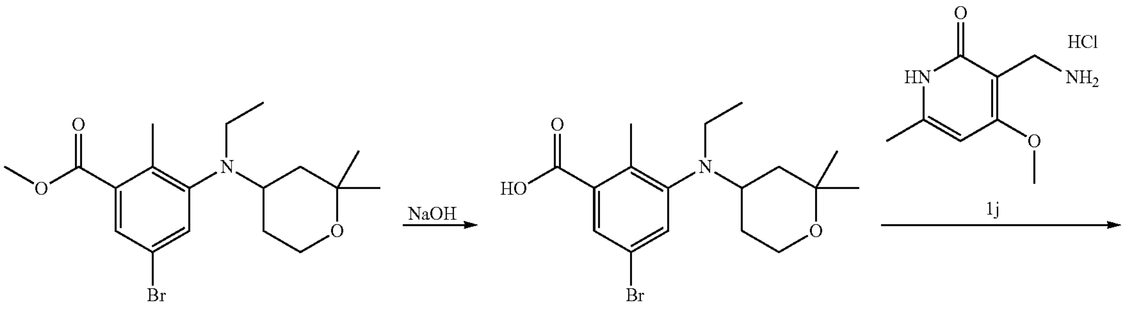
43b-2
43b-3
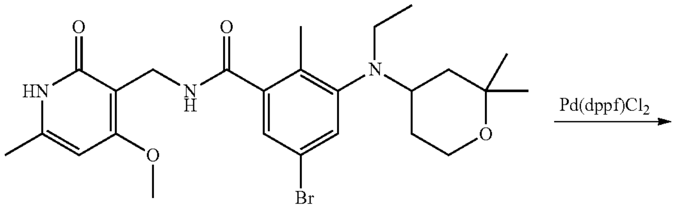
43b-4

-continued

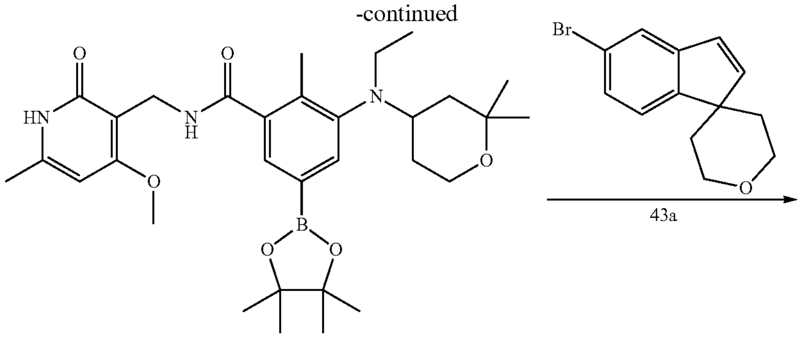

43b

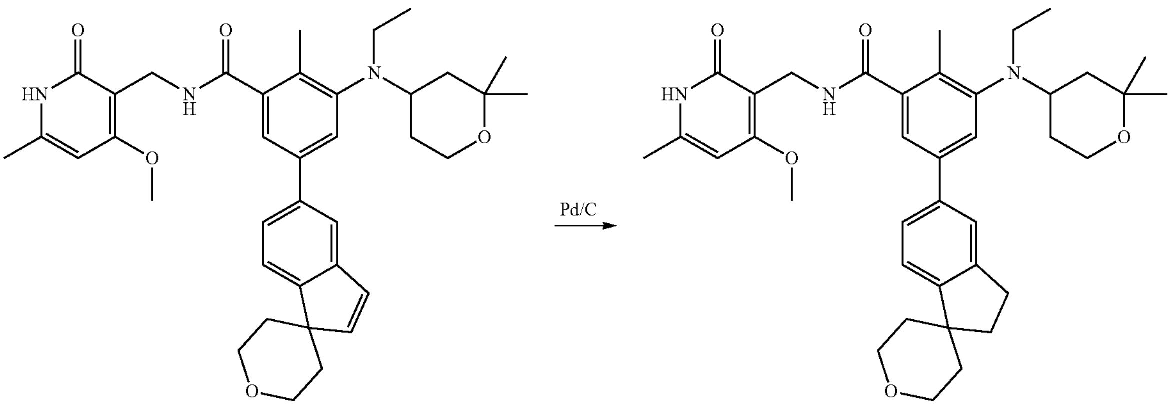

43c

43

Step I Methyl 5-bromo-3-((2,2-dimethyltetrahydro-2H-pyran-4-yl)amino)-2-methylbenzoate 50b-1

The compound methyl 3-amino-5-bromo-2-methylbenzoate (5 g, 20.5 mmol) and compound 2,2-dimethyl-4H-pyran-4-one (5.24 g, 41.0 mmol) were dissolved in 50 mL of dichloromethane and stirred at room temperature for 30 minutes. Sodium triacetoxyborohydride (13 g, 61.4 mmol) was added to the mixture, followed by adding acetic acid (2.45 g, 40.9 mmol) dropwise. The mixture was reacted at room temperature overnight. The reaction solution was added with $NaHCO_3$ solution for neutralizing acetic acid and was extracted with dichloromethane for 3 times, dried with sodium sulphate anhydrous, concentrated, and purified by column chromatography to obtain the title compound 43b-1 (6 g, yield 82%).

Step II Methyl 5-bromo-3-((2,2-dimethyltetrahydro-2H-pyran-4-yl)(ethyl)amino)-2-methylbenzoate 43b-2

The compound methyl 5-bromo-3-((2,2-dimethyltetrahydro-2H-pyran-4-yl)amino)-2-methylbenzoate (6 g, 16.8 mmol) and acetaldehyde (2.24 g, 50.5 mmol) were dissolved in 50 mL of dichloromethane and stirred at room temperature for 30 minutes. The mixture was added with sodium triacetoxyborohydride (10.7 g, 50.5 mmol), and acetic acid (2.45 g, 40.9 mmol) dropwise. The mixture was reacted at room temperature overnight. The reaction solution was added with $NaHCO_3$ solution for neutralizing acetic acid and extracted with dichloromethane for 3 times, dried with sodium sulphate anhydrous, concentrated, and purified by column chromatography to obtain the title compound 43b-2 (5.8 g, yield 89.8%).

Step III 5-bromo-3-((2,2-dimethyltetrahydro-2H-pyran-4-yl)(ethyl)amino)-2-methylbenzoic acid 43b-3

The compound methyl 5-bromo-3-((2,2-dimethyltetrahydro-2H-pyran-4-yl)(ethyl)amino)-2-methylbenzoate (5.8 g, 15.1 mmol) was dissolved in 30 mL of methanol, added with 30 mL of water and NaOH (2.4 g, 60.4 mmol). The mixture was reacted at 100° C. for 12 hours. The reaction solution was cooled down, adjusted to be weakly acidic with dilute hydrochloric acid, and extracted with EA for 3 times to obtain the title compound 43b-3 (4.5 g, yield 80%).

Step IV 5-bromo-3-((2,2-dimethyltetrahydro-2H-pyran-4-yl)(ethyl)amino)-N-((4-methoxy-6-methyl-2-oxo-1,2-dihydropyridin-3-yl)methyl)-2-methylbenzamide 43b-4

The compound 5-bromo-3-((2,2-dimethyltetrahydro-2H-pyran-4-yl)(ethyl)amino)-2-methylbenzoic acid (4.5 g, 12.1 mmol), compound 3-(aminomethyl)-4-methoxy-6-methylpyridin-2(1H)-one (2.04 g, 12.1 mmol), HATU (9.2 g, 24.2 mmol) and HOBT (1.97 g, 14.5 mmol) were dissolved in 50 mL of DMF. The mixture was added with triethylamine (2.45 g, 24.2 mmol) and stirred at room temperature overnight. The reaction solution was added with water, extracted with EA for 3 times, the organic phase was washed with saturated NaCl solution twice, concentrated, and purified by column chromatography to obtain the title compound 43b-4 (3.8 g, yield 60.3%).

Step V 3-((2,2-dimethyltetrahydro-2H-pyran-4-yl)(ethyl)amino)-N-((4-methoxy-6-methyl-2-oxo-1,2-dihydropyridin-3-yl)methyl)-2-methyl-5-(4,4,5,5-tetramethyl-1,3,2-dioxaborane-2-yl)benzamide 43b The compound 5-bromo-3-((2,2-dimethyltetrahydro-2H-pyran-4-yl)(ethyl)amino)-N-((4-methoxy-6-methyl-2-oxo-1,2-dihydropyridin-3-yl)methyl)-2-methylbenzamide (3.8 g, 7.3 mmol) and bis(pinacolato)diboron (3.7 g, 14.6 mmol) were dissolved in 1,4-dioxane (80 mL). The mixture was added with [1,1'-bis(diphenylphosphino)ferrocene]dichloropalladium (534 mg, 1.46 mmol) and potassium acetate (2.14 g, 21.9 mmol), heated to 100° C. under the protection of Ar and stirred for 2 hours. The reaction solution was cooled down, spin-dried, and the residue was extracted with ethyl acetate for 3 times, dried with anhydrous sodium sulfate, concentrated, and purified by thin-layer chromatography to obtain the title compound 43b (3.9 g, 6.87 mmol) with a yield of 94%.

MS m/z (ESI): 568.3 $[M+H]^+$.

Step VI 3-((2,2-dimethyltetrahydro-2H-pyran-4-yl)(ethyl)amino)-N-((4-methoxy-6-methyl-2-oxo-1,2-dihydropyridin-3-yl)methyl)-2-methyl-5-(2',3',5',6'-dihydrospiro[indene-1,4'-pyran]-5-yl)benzamide 43c The compound 43a (5-bromo-2',3',5',6'-tetrahydrospiro[indene-1,4'-pyran]) (200 mg, 0.75 mmol) and compound 43b (260 mg, 0.75 mmol) were dissolved in a mixture of 1,4-dioxane and $H_2O$ (1,4-dioxane:$H_2O$=3:1, v/v, 20 mL), [1,1'-bis(diphenylphosphino)ferrocene]dichloropalladium (55 mg, 0.075 mmol) and potassium carbonate (208 mg, 1.5 mmol) were added. The mixture was heated to 100° C. under the protection of Ar and stirred for 3 hours. The reaction solution was cooled down, spin-dried, and the residue was extracted with ethyl acetate for 3 times, dried with anhydrous sodium sulfate, concentrated, and purified by column chromatography to obtain the title compound 50c (300 mg, yield 63%).

Step VII 3-((2,2-dimethyltetrahydro-2H-pyran-4-yl)(ethyl)amino)-5-(2,2',3,3',5',6'-hexahydrospiro[indene-1,4-pyran]-5-yl)-N-((4-methoxy-6-methyl-2-oxo-1,2-dihydropyridin-3-yl)methyl)-2-methylbenzamide 43

The compound 43c (300 mg) was dissolved in methanol (20 mL), followed by adding Pd/C (5 mg). The reaction system was replaced with $H_2$ and reacted at room temperature for 20 hours. After the reaction was completed, the reaction solution was spin-dried and purified by thin-layer chromatography to obtain the title compound 43 (5.8 mg, 1.7%).

$^1H$ NMR (400 MHz, Methanol-$d_4$) δ 7.37 (d, J=7.0 Hz, 2H), 7.34-7.31 (m, 1H), 7.27 (s, 1H), 7.23 (d, J=8.6 Hz, 1H), 6.24 (s, 1H), 4.45 (d, J=3.5 Hz, 2H), 3.92 (s, 2H), 3.67 (t, J=11.1 Hz, 4H), 2.98-2.90 (m, 2H), 2.32-2.27 (m, 6H), 2.18 (td, J=7.4, 3.7 Hz, 3H), 1.98 (dd, J=13.1, 4.6 Hz, 2H), 1.73 (d, J=11.7 Hz, 2H), 1.44 (d, J=10.2 Hz, 4H), 1.27 (d, J=2.6 Hz, 5H), 1.17 (s, 6H), 0.88 (dt, J=7.0, 3.5 Hz, 3H), MS m/z (ESI): 628.3 $[M+H]^+$.

Example 44 N-((4,6-dimethyl-2-oxo-1,2-dihydropyridin-3-yl)methyl)-3-(ethyl(tetrahydro-2H-pyran-4-yl)amino)-2-methyl-5-(1-methyl-2-oxo-1'-(2,2,3,3,3-pentafluoroethyl)spiro[dihydroindole-3,4'-piperidine]-6-yl)benzamide

44

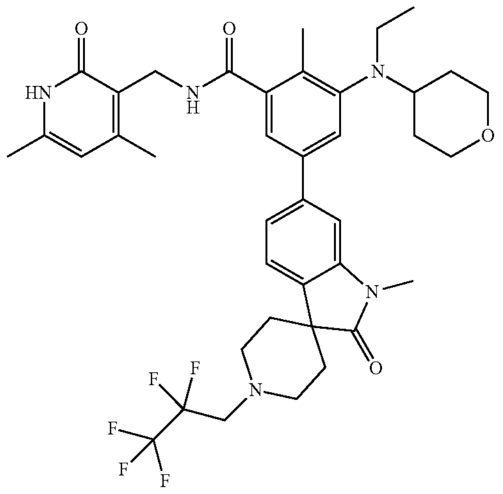 [SMILES: CCN(c1cc(-c2ccc3c(c2)N(C)C(=O)C32CCN(C(C)C)CC2)cc(C(=O)NCc2c(C)cc(C)[nH]c2=O)c1C)C1CCOCC1]

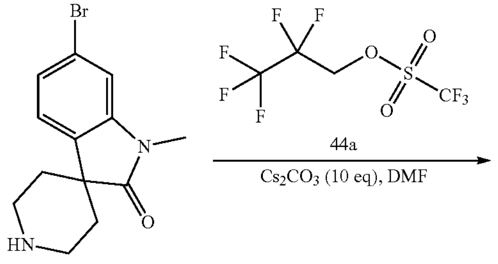

21a

-continued

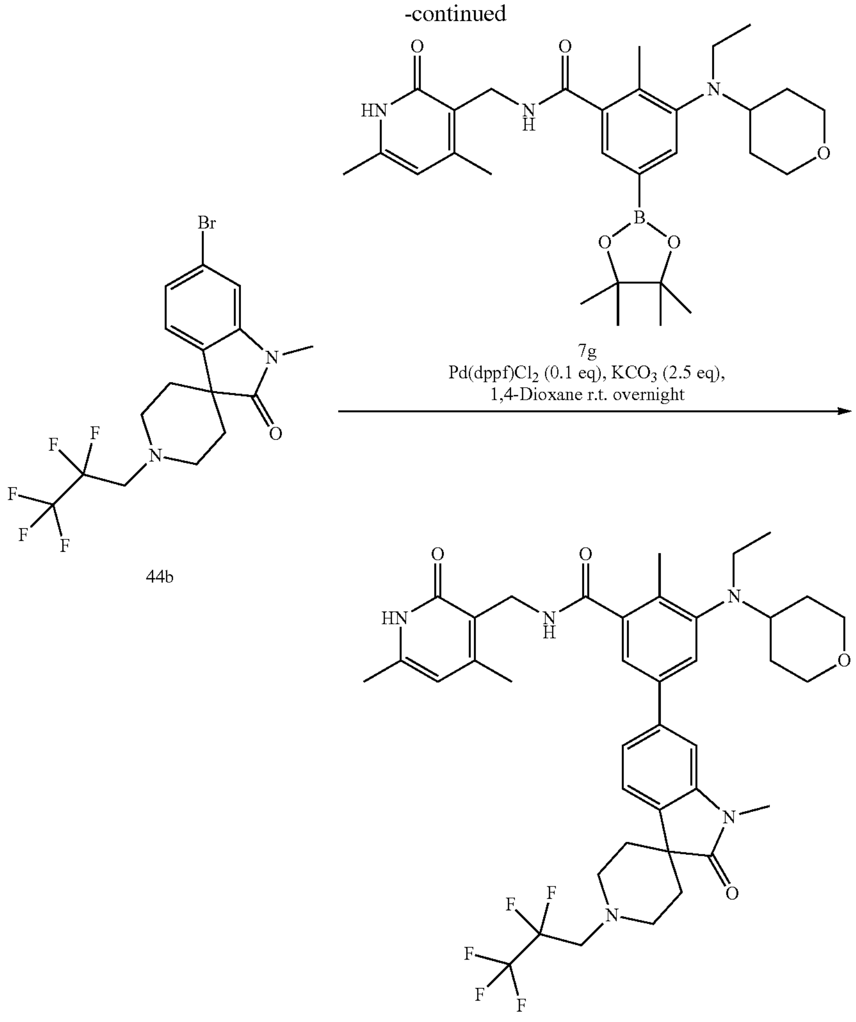

44

Step I 6-bromo-1-methyl-1'-(2,2,3,3,3-pentafluoroethyl)spiro[dihydroindole-3,4'-piperidine]-2-one 44b The compound 21a (250 mg, 0.850 mmol), compound 44a (726 mg, 1.701 mmol), cesium carbonate (3.23 g, 8.5 mmol) and 10 mL of DMF were added to a 25 mL reaction flask, which was then replaced with nitrogen. The mixture was stirred at 20° C. for 2 hours. The reaction solution was added with water/EA (20 mL/20 mL), stirred for 5 minutes, separated, and the aqueous phase was extracted with EA. The organic phases were then combined, washed with saturated NaCl solution (20 mL×4), dried with anhydrous sodium sulfate, mixed, concentrated, and purified by column chromatography (petroleum ether: ethyl acetate=3:1) to obtain the title compound 44b (75 mg, 0.1756 mmol) with a yield of 20.7%.

MS m/z (ESI): 427.1 $[M+H]^+$.

Step II N-((4,6-dimethyl-2-oxo-1,2-dihydropyridin-3-yl)methyl)-3-(ethyl(tetrahydro-2H-pyran-4-yl)amino)-2-methyl-5-(1-methyl-2-oxo-1'-(2,2,3,3,3-pentafluoroethyl)spiro[dihydroindole-3,4'-piperidine]-6-yl)benzamide 44

The compound 44b (75 mg, 0.1756 mmol), compound 7g (92 mg, 0.1756 mmol), Pd(dppf)$Cl_2$ (13 mg, 0.01756 mmol), potassium carbonate (73 mg, 0.5268 mmol), 1 mL of water and 5 mL of 1,4-dioxane were added to a microwave tube. The reaction system was replaced with nitrogen, heated to 100° C. and reacted for 1 hour. The reaction solution was added with 30 mL of water and extracted with EA (30 mL×3). The organic phases were combined, washed with saturated NaCl solution (30 mL×3), dried, mixed, and purified by column chromatography (methanol: dichloromethane=1:15) to obtain the title compound 44 (37 mg, 0.0497 mmol) with a yield of 28.3%.

$^1H$ NMR (400 MHz, Methanol-$d_4$) δ 7.54 (d, J=7.7 Hz, 1H), 7.46 (d, J=1.9 Hz, 1H), 7.34 (d, J=1.8 Hz, 1H), 7.27 (dd, J=7.9, 1.6 Hz, 1H), 7.17 (d, J=1.6 Hz, 1H), 6.09 (s, 1H), 4.47 (s, 2H), 3.90 (d, J=11.6 Hz, 2H), 340-3.31 (m, 2H), 3.24 (s, 5H), 3.21-3.05 (m, 5H), 2.99-2.87 (m, 2H), 2.38 (s, 3H), 2.31 (s, 3H), 2.22 (s, 3H), 1.98-1.55 (n. 8H), 0.88 (t, J=7.0 Hz, 3H), MS n/z (ESI): 744.2 $[M+H]^+$.

Example 45 N-((4,6-dimethyl-2-oxo-1,2-dihydropyridin-3-yl)methyl)-3-(ethyl(tetrahydro-2H-pyran-4-yl)amino)-5-(1-(2-methoxyethyl)-2-oxo-2',3',5',6'-tetrahydrospiro[dihydroindole-3,4'-pyran]-6-yl)-2-methylbenzamide

45

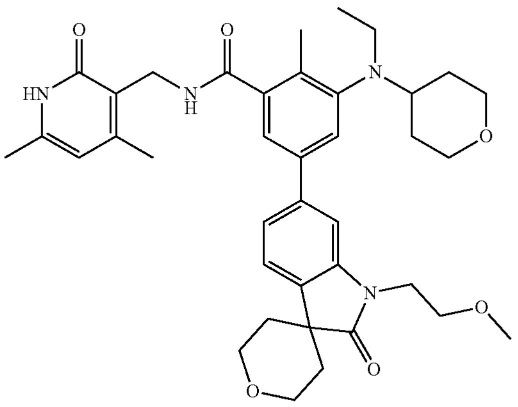

A similar method of Example 25 was used to obtain the title compound 45 with a yield of 18%, wherein the 2-bromopropane was replaced with 1-bromo-2-methoxyethane.

$^1$H NMR (400 MHz, Methanol-$d_4$) δ 7 53 (d, J=8.1 Hz, 1H), 7.44 (s, 1H), 7.35-7.24 (m, 3H), 6.09 (s, 1H), 4.48 (s, 2H), 4.19 (dt, J=11.7, 5.7 Hz, 2R), 4.00-3.87 (m, 61), 3.64 (t, J=5.3 Hz, 2H), 3.40-3.30 (m, 4H), 3.13 (dd, J=17.5, 9.8 Hz, 3H), 2.38 (s, 3H), 2.31 (s, 3H), 2.22 (s, 3H), 1.84 (d, J=5.7 Hz, 4H), 1.78-1.58 (nm 5H), 0.89 (t, J=7.0 Hz, 3H), MS m/z (ESI): 657-$(M+1)^+$.

Example 46 2-chloro-N-((4,6-dimethyl-2-oxo-1,2-dihydropyridin-3-yl)methyl)-5-(ethyl(tetrahydro-2H-pyran-4-yl)amino)-3-(1-isopropyl-2-oxo-2',3',5',6'-tetrahydrospiro[dihydroindole-3,4'-pyran]-6-yl)-6-methylbenzamide

46

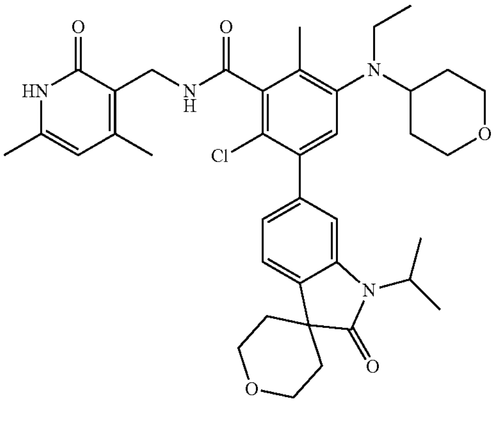

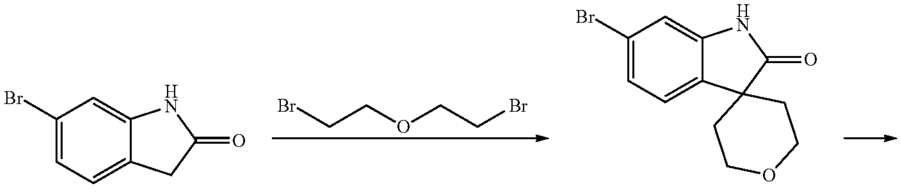

2a

1g

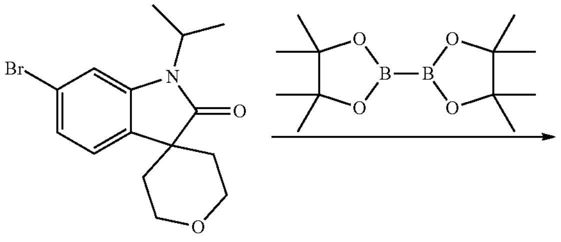

46a

-continued

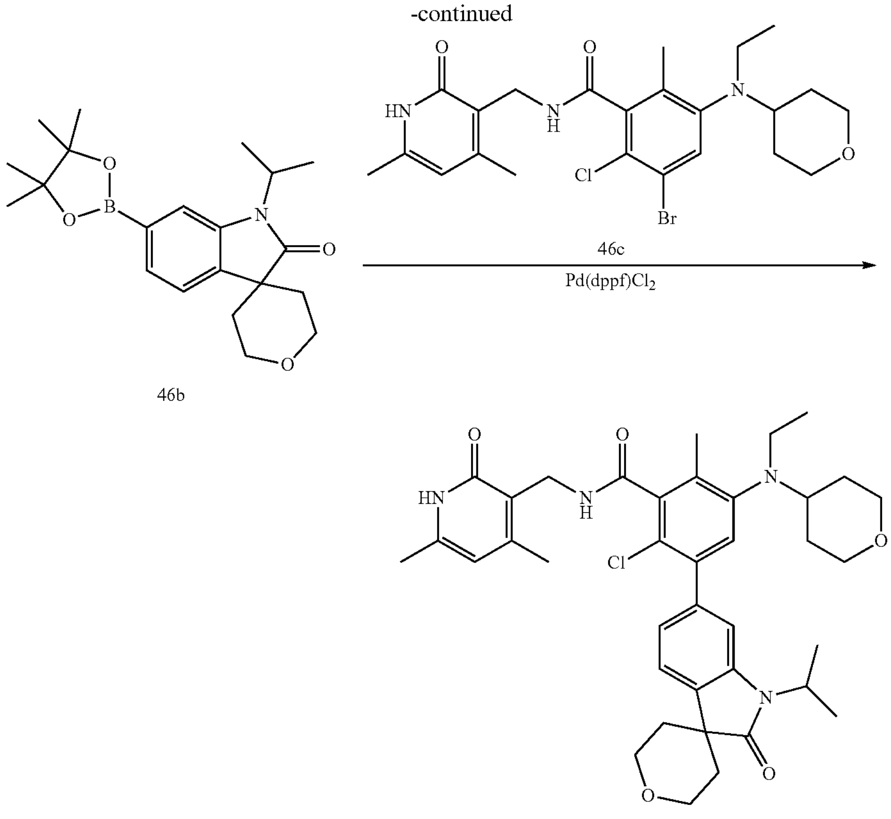

46b

46

Step I 6-bromo-2',3',5',6'-tetrahydrospiro[dihydroindole-3,4'-pyran]-2-one 1g

The compound 2a (6-bromo-1,3-dihydro-2H-indol-2-one) (15 g, 70.7 mmol) was dissolved in tetrahydrofuran (120 mL), and lithium bis(trimethylsilyl)amide (285 mL, 285 mmol) was slowly added dropwise at −78° C. The mixture was stirred at this temperature for 2 hours, followed by adding 2,2'-dibromodiethyl ether (19.5 g, 84.4 mmol) and slowly heating to 70° C. and stirring for 4 hours. After the reaction was completed, it was quenched with saturated $NH_4Cl$ solution under ice water bath. The reaction solution was added with water, and solid was precipitated, which was filtered to obtain the title compound 1g (11.2 g, 39.7 mmol) with a yield of 55%.

Step II 6-bromo-1-isopropyl-2',3',5',6'-tetrahydrospiro[dihydroindole-3,4'-pyran]-2-one 46a The compound 1g (6-bromo-2',3',5',6'-tetrahydrospiro[dihydroindole-3,4'-pyran]-2-one) (1 g, 3.5 mmol) was dissolved in DMF (30 mL), followed by adding NaH (0.17 g, 7.0 mmol) dropwise under ice bath and stirring at room temperature for 30 minutes. Subsequently 2-iodopropane (1.2 g, 7.0 mmol) was added dropwise, and the mixture was stirred at room temperature overnight. The reaction solution was added with water after the reaction was completed, and was extracted with ethyl acetate. The organic phase was washed with saturated NaCl solution, dried with anhydrous sodium sulfate, filtered, concentrated, and purified by column chromatography to obtain the title compound 46a (750 mg, 2.3 mmol) with a yield of 65.3%.

Step III 1-isopropyl-6-(4,4,5,5-tetramethyl-1,3,2-dioxaborolan-2-yl)-2',3',5',6'-tetrahydrospiro[dihydroindole-3,4'-pyran]-2-one 46b The compound 46a (6-bromo-1-isopropyl-2',3',5',6'-tetrahydrospiro[dihydroindole-3,4'-pyran]-2-one) (430 mg, 1.32 mmol) and bis(pinacolato)diboron (671 mg, 2.64 mmol) were dissolved in 1,4-dioxane (20 mL). The mixture was added with [1,1'-bis(diphenylphosphino)ferrocene]dichloropalladium (97 mg, 0.132 mmol) and potassium acetate (390 mg, 3.96 mmol), heated to 100° C. under the protection of Ar and stirred for 4 hours. The reaction solution was cooled down, spin-dried, and the residue was extracted with ethyl acetate for 3 times, dried with anhydrous sodium sulfate, concentrated, and purified by thin-layer chromatography to obtain the title compound 46b (430 mg, 1.15 mmol) with a yield of 86%.

Step IV 2-chloro-N-((4,6-dimethyl-2-oxo-1,2-dihydropyridin-3-yl)methyl)-5-(ethyl(tetrahydro-2H-pyran-4-yl)amino)-3-(1-isopropyl-2-oxo-2',3',5',6'-tetrahydrospiro[dihydroindole-3,4'-pyran]-6-yl)-6-methylbenzamide 46

The compound 46b (1-isopropyl-6-(4,4,5,5-tetramethyl-1,3,2-dioxaborolan-2-yl)-2',3',5',6'-tetrahydrospiro[dihydroindole-3,4'-pyran]-2-one) (100 mg, 0.27 mmol) and compound 3-bromo-2-chloro-N-((4,6-dimethyl-2-oxo-1,2-dihydropyridin-3-yl)methyl)-5-(ethyl(tetrahydro-2H-pyran-4-yl)amino)-6-methylbenzamide (137 mg, 0.27 mmol) were dissolved in a mixture of 1,4-dioxane and $H_2O$ (1,4-dioxane: $H_2O$=3:1, v/v, 20 mL), [1,1'-bis(diphenylphosphino)ferrocene]dichloropalladium (19.7 mg, 0.027 mmol) and potassium carbonate (75 mg, 0.54 mmol) were added. The mixture was heated to 100° C. under the protection of Ar and stirred for 2 hours. The reaction solution was cooled down, spin-dried, and the residue was extracted with ethyl acetate for 3 times, dried with anhydrous sodium sulfate, concentrated, and purified by thin-layer chromatography to obtain the title compound 46 (16.0 mg, 0.023 mmol) with a yield of 8.8%.

$^1$H NMR (400 MHz, Methanol-d4) δ 7.54 (d, J=7.7 Hz, 1H), 7.17-7.11 (m, 2H), 7.01 (dd, J=7.7, 1.5 Hz, 1H), 6.08 (s, 1H), 4.58 (s, 1H), 4.48 (s, 2H), 4.19 (dt, J=11.7, 5.8 Hz, 2H), 3.92 (dt, J=12.0, 5.9 Hz, 4H), 334 (dd, J=11.8, 2.1 Hz, 2H), 3.12-3.00 (n, 3H), 2.38 (s, 3H), 2.27 (s, 3H), 2.22 (s, 3H), 1.82 (t, J=5.5 Hz, 4H), 0.72 (d, J=12.5 Hz, 2H), 1.61 (t, J=11.9, 6.0 Hz, 2H), 1.44 (d, J=7.0 Hz, 6H), 127 (q, J=9.1 Hz, 5H), 0.88 (t, J=6.9 Hz, 3H), MS m/z (ES1): 675.2 [M+H]$^+$.

Example 47 2-chloro-N-((4,6-dimethyl-2-carbonyl-1,2-dihydropyridin-3-yl)methyl)-5-(ethyl(tetrahydro-2H-pyran-4-yl)amino)-6-methyl-3-(2-carbonyl-1-propyl-2',3'.5',6'-tetrahydrospiro[dihydroindole-3,4'-pyran]-6-yl)benzamide

47

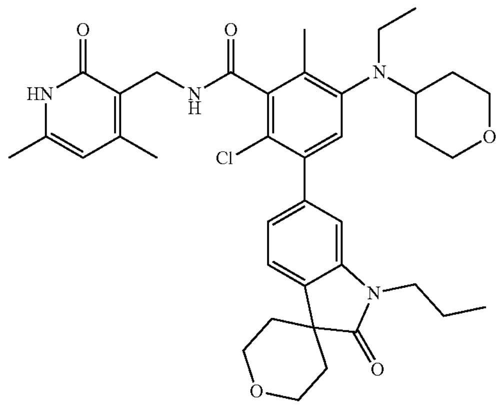

A similar method of Example 46 was used to obtain the title compound 47 with a yield of 23%, wherein the 2-iodopropane was replaced with 1-iodopropane.

$^1$H NMR (400 MHz, Methanol-d4) δ 7.56 (d, J=7.6 Hz, 1H), 7.15 (s, 1H), 705-6.94 (n, 2H), 6.08 (s, 1H), 4.48 (s, 2H), 4.25-4.13 (m, 2H), 4.01-3.83 (m, 4H), 3.70 (t, J=7.1 Hz, 2H), 3.34 (d, J=11.3 Hz, 2H), 3.06 (t, J=6.9 Hz, 3H), 2.38 (s, 3H), 2.27 (s, 3H), 2.22 (s, 3H), 1.85 (d, J=6.1 Hz, 4H), 1.76-1.52 (m, 6H), 0.89 (dt, J=13.5, 7.1 Hz, 6H), MS n/z (ESI):675.2[M+1]$^+$.

Example 48 2-chloro-N-((4,6-dimethyl-2-oxo-1,2-dihydropyridin-3-yl)methyl)-5-(ethyl(tetrahydro-2H-pyran-4-yl)amino)-3-(1-ethyl-2-oxo-2',3',5',6'-tetrahydrospiro[dihydroindole-3,4'-pyran]-6-yl)-6-methylbenzamide

48

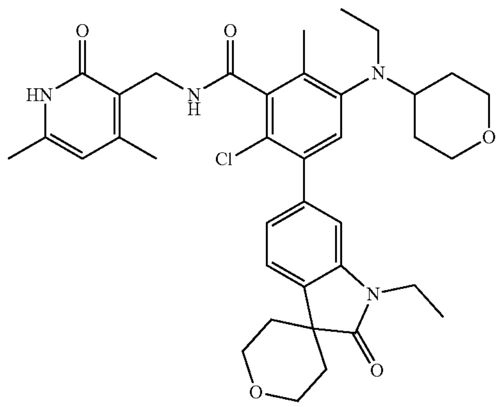

A similar method of Example 46 was used to obtain the title compound 48 with a yield of 11%, wherein the 2-iodopropane was replaced with iodoethane.

$^1$H NMR (400 MHz, Methanol-d4) δ 7.59-7.52 (m, 1H), 7.15 (s, 1H), 7.01 (s, 2H), 6.08 (s, 1H), 4.48 (s, 2H), 4.24-4.14 (m, 2H), 3.99-3.86 (m, 4H), 3.76 (q, J=7.2 Hz, 2H), 34 (dd, J=11.8, 2.1 Hz, 2H), 3.12-2.95 (m, 3H), 2.38 (s, 3H), 2.27 (s, 3H), 2.22 (s, 3H), 1.88-1.77 (m, 4H), 1.72 (d, J=11.9 Hz, 2H), 1.0.60 (qd, J=11.8, 4.3 Hz, 2H), 1.21 (t, J=7.2 Hz, 3H), 0.87 (t, J=7.0 Hz, 3H), MS m/z (ESI): 662 [M+H]$^+$.

Example 49 2-chloro-5-(ethyl(tetrahydro-2H-pyran-4-yl)amino)-3-(1-isopropyl-2,3,5,6-tetrahydrospiro[dihydroindole-3,4-pyran]-6-yl)-N-((4-methoxy-6-methyl-2-oxo-1,2-dihydropyridin-3-yl)methyl)-6-methylbenzamide

49

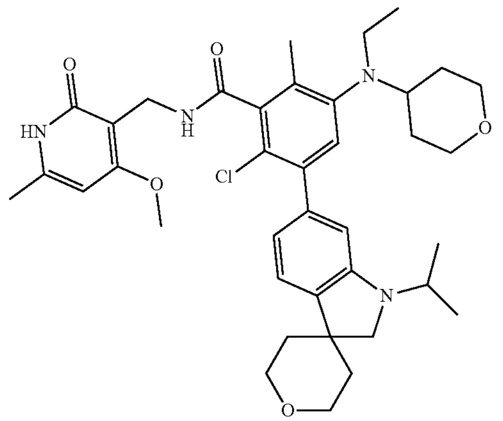

-continued

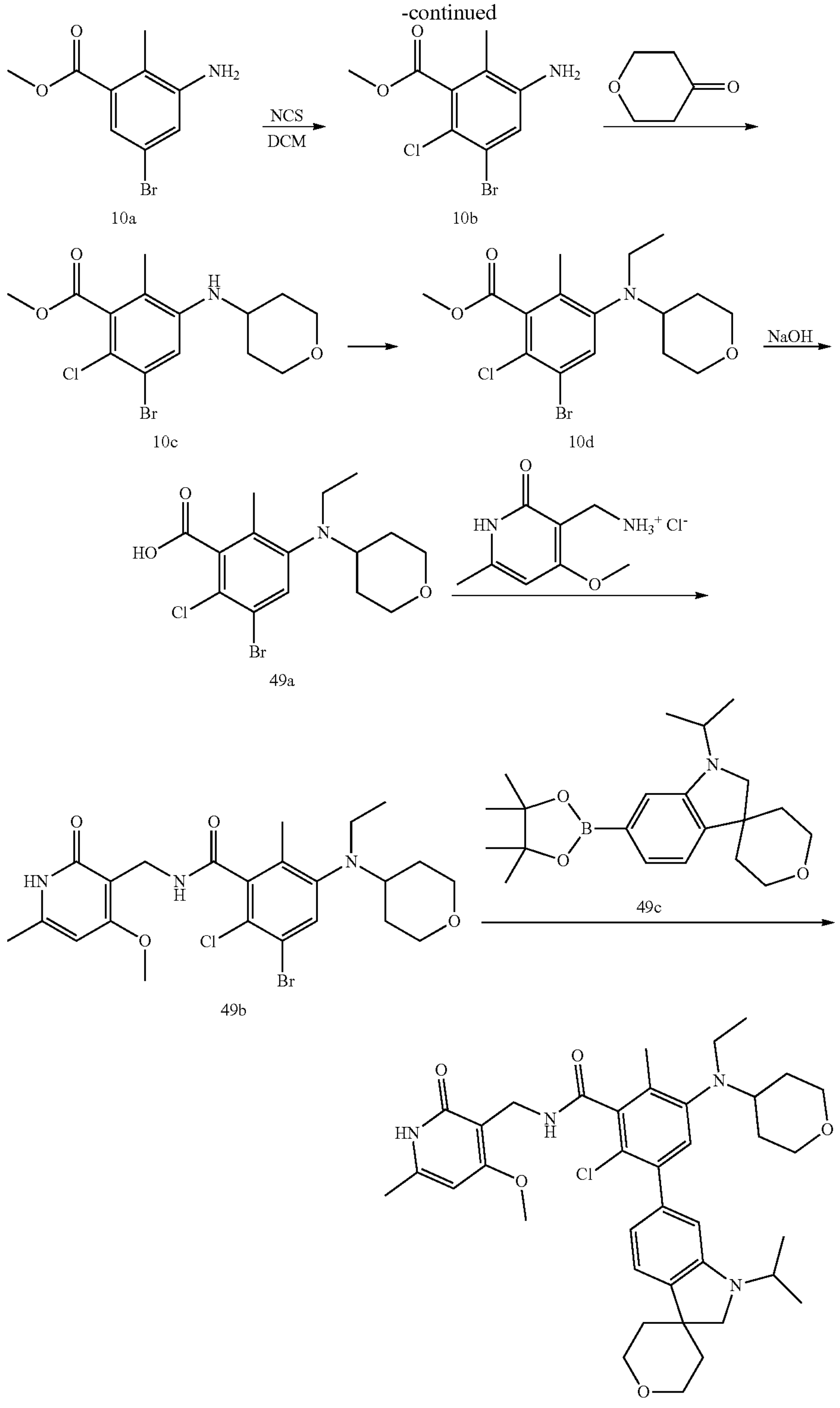

10a 10b 10c 10d 49a 49b

49

Step I Methyl 3-amino-5-bromo-6-chloro-2-methylbenzoate 10b

The compound 10a (6 g, 24.69 mmol) was added in a 250 mL single-necked flask, and was dissolved by DCM (100 mL). Subsequently, NCS (3.3 g, 24.7 mmol) was added in batches. The mixture was stirred at 25° C. for 2 hours. The raw materials were completely reacted as determined by TLC monitoring and there were new spots formed. The reaction solution was washed with water, extracted with DCM, and purified by flash column chromatography to obtain a yellow oily product of target compound 10b (3.6 g) with a yield of 52.6%.

Step II Methyl 3-bromo-2-chloro-6-methyl-5-((tetrahydro-2H-pyran-4-yl)amino)benzoate 10c The compound 10b (3.6 g, 13.0 mmol) was added in a 250 mL single-necked flask, and was dissolved by DCM (50 mL). The mixture was added with compound tetrahydro-2H-pyran-4-one (2.6 g, 0.26.0 mmol) and acetic acid (2 mL), stirred for 30 minutes, and added with $NaBH(AcO)_3$ (8.3 g, 39.0 mmol), followed by stirring at 25° C. for 2 hours. The raw materials were completely reacted and there were new spots formed. The reaction solution was washed with water and saturated $NaHCO_3$ solution, extracted with DCM, dried with anhydrous sodium sulfate, and dried by evaporation to obtain a light-yellow oily product of a target compound 10c (3.4 g) with a yield of 80%.

Step III Methyl 3-bromo-2-chloro-5-(ethyl(tetrahydro-2H-pyran-4-yl)amino)-6-methylbenzoate 10d The compound 10c (3.4 g, 9.4 mmol) was added in a 250 mL single-necked flask, and was dissolved by DCM (50 mL). The mixture was added with compound acetaldehyde (4.2 g, 94 mmol) and acetic acid (2 mL), stirred for 30 minutes, and added with $NaBH(AcO)_3$ (6.0 g, 28.3 mmol), followed by stirring at 25° C. for 2 hours. The raw materials were completely reacted and there were new spots formed. The reaction solution was washed with water and saturated $NaHCO_3$ solution, extracted with DCM, dried with anhydrous sodium sulfate, purified by flash column chromatography, and dried by evaporation to obtain a light-yellow oily product of a target compound 10c (3.0g) with a yield of 81.9%.

Step IV 3-bromo-2-chloro-5-(ethyl(tetrahydro-2H-pyran-4-yl)amino)-6-methylbenzoic acid 49a The compound 10d (3.0 mg, 7.69 mmol), isopropanol (100 mL), water (5 mL) and NaOH (3 g, 76.9 mmol) were added in a 50 mL single-necked flask successively, the mixture was heated to 90° C. and refluxed for 8 hours. The raw materials were completely reacted, dried by evaporation, and the residue was added with water, adjusted to be neutral with dilute hydrochloric acid, extracted with DCM to obtain the aqueous phase. Such kind of operation to the reaction solution was repeated for three times. The organic phase was then washed with water once, extracted with DCM, dried with anhydrous sodium sulfate, and concentrated to obtain a light-yellow solid, i.e., the target compound 49a (2 g) with a yield of 70%.

Step V 3-bromo-2-chloro-5-(ethyl(tetrahydro-2H-pyran-4-yl)amino)-N-((4-methoxy-6-methyl-2-oxo-1,2-dihydropyridin-3-yl)methyl)-6-methylbenzamide 49b The compound 49a (600 mg, 1.6 mmol), 3-(aminomethyl)-4-methoxy-6-methylpyridin-2(1H)-one hydrochloride (450 mg, 2.4 mmol), EDCI (460 mg, 2.4 mmol), HOBT (324 mg, 2.4 mmol), DMF (15 mL) and DIPEA (800 mg, 8.0 mmol) were added in a 50 mL single-necked flask, the mixture was heated to 50° C. and refluxed for 3 hours. The raw materials were completely reacted, concentrated, washed with water, extracted with DCM, dried with anhydrous sodium sulfate, and purified by flash column chromatography to obtain a yellow solid of target compound 49b (300 mg) with a yield of 36.8%.

Step VI 2-chloro-5-(ethyl(tetrahydro-2H-pyran-4-yl)amino)-3-(1-isopropyl-2,3,5,6-tetrahydrospiro[dihydroindole-3,4-pyran]-6-yl)-N-((4-methoxy-6-methyl-2-oxo-1,2-dihydropyridin-3-yl)methyl)-6-methylbenzamide 49

The compound 49b (100 mg, 0.19 mmol), compound 49c (7 mg, 0.18 mmol), $K_2CO_3$ (50 mg, 0.07 mmol) and $Pd(dppf)Cl_2$ (25 mg, 0.03 mmol) were added in a 50 mL single-necked flask, dissolved by 1.4-dioxane. The mixture was added with 2 mL of water, heated to 100° C. and refluxed for 2 hours under the protection of $N_2$. The raw materials were completely reacted as determined by LCMS monitoring. The reaction solution was purified by flash column chromatography to obtain a white solid of compound 49 (54 mg).

$^1H$ NMR (400 MHz, DMSO-d6) δ 11.37 (s, 1H), 8.06 (t, J=4.7 Hz, 1H), 7.08-6.96 (m, 2H), 6.46 (dd, J=7.5, 1.5 Hz. 1H), 6.34 (d, J=1.4 Hz, 1H), 6.04 (s, 1H), 4.19 (s, 2H), 3.77 (d, J=17.0 Hz, 8H), 3.54-3.42 (m, 2H), 3.18 (d, J=10.9 Hz, 2H), 2.97 (q, J=8.7, 7.7 Hz, 3H), 2.13 (d, J=6.2 Hz, 6H), 1.80 (td. J=13.0.4.6 Hz, 2H), 1.64-1.39 (m, 6H), 1.08 (d, J=6.5 Hz, 6H), 0.78 (t, J=6.9 Hz, 3H),

MS m/z (ESI): 677.3 $[M+H]^+$.

Example 50 3-(ethyl(tetrahydro-2H-pyran-4-yl)amino)-5-(1'-ethyl-2',6'-dimethyl-2,3-dihydrospiro[indene-1,4'-piperidine]-6-yl)-N-((4-methoxy-6-methyl-2-oxo-1,2-dihydropyridin-3-yl)methyl)-2-methylbenzamide formate

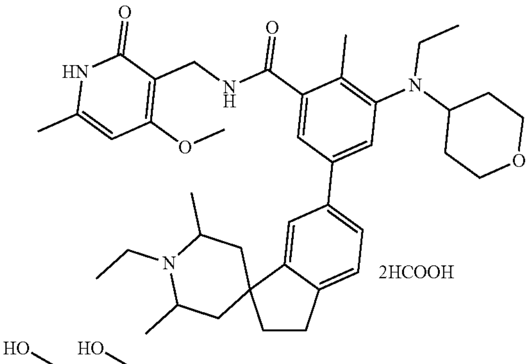

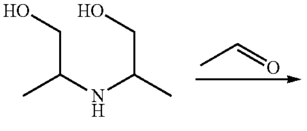

50a

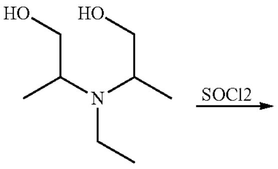

50b

-continued

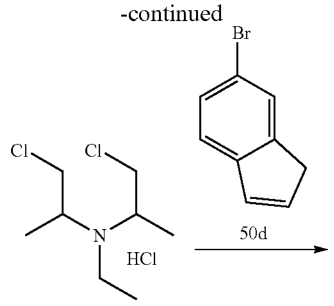

50c

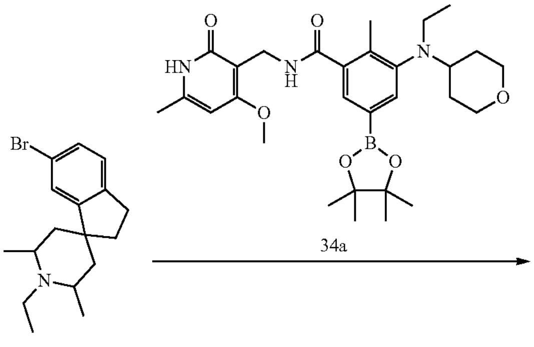

50e

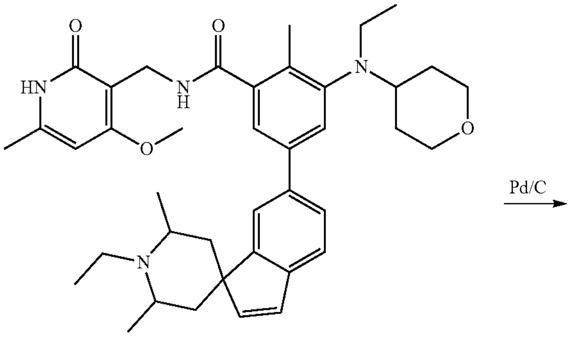

50f

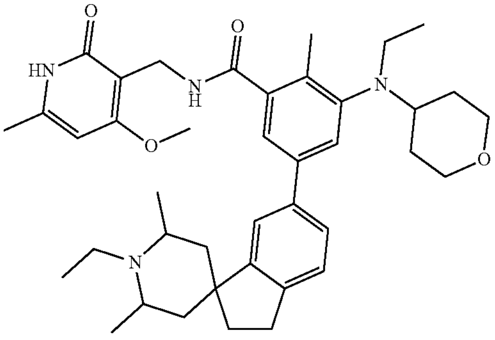

50

Step I 2,2'-(ethylazanediyl)bis(propan-1-ol) 50b

The compound 50a (3 g, 22.556 mmol) was dissolved in dichloromethane (80 mL), acetic acid (1.353 g, 22.556 mmol) and acetaldehyde (9.9 g, 225.56 mmol) were added. The mixture was stirred at room temperature for 30 minutes, added with sodium borohydride acetate (14.348 g, 67.68 mmol) followed by stirring at room temperature for 15 hours until the reaction was completed. The reaction solution was quenched with water, extracted with dichloromethane for three times, washed with saturated NaCl solution, dried with anhydrous sodium sulfate, filtered, concentrated, and purified by column chromatography to obtain the title compound 50b (1.8 g, 11.18 mmol) with a yield of 49%.

MS m/z (ESI): 162 $[M+1]^+$.

Step II 1-chloro-N-(1-chloropropyl-2-yl)-N-ethylpropyl-2-amine 50c

The compound 50b (0.35 g, 2.173 mmol) was dissolved in dichloromethane (10 mL), and thionyl chloride (4 mL) was added. The mixture was stirred at room temperature for 3 hours, spin-dried to remove the solvent. A compound 50c (350 mg, 1.5 mmol) was obtained with a yield of 69%, which was used directly in the next step.

MS m/z (ESI): 198 $[M+1]^+$.

Step III 6-bromo-1'-ethyl-2',6'-dimethylspiro[indene-1,4'-piperidine]50e

The compound 50c (350 mg, 1.5 mmol) and compound 50d (195 mg, 1 mmol) were added to THF (15 mL), and LiHMDS (6 mL, 6 mmol) was added dropwise under the protection of Ar and under ice bath. The mixture was heated to 70° C. slowly and reacted for 3 hours. The raw materials were completely reacted as determined by TLC monitoring. The reaction solution was quenched with water, extracted with ethyl acetate. The organic phase was washed with saturated NaCl solution, dried with anhydrous sodium sulfate, filtered, concentrated, and purified by column chromatography to obtain the title compound 50e (40 mg, 0.125 mmol) with a yield of 12.5%.

MS m/z (ESI): 320 $[M+1]^+$.

Step IV 3-(ethyl(tetrahydro-2H-pyran-4-yl)amino)-5-(1'-ethyl-2',6'-dimethylspiro[indene-1,4'-piperidine]-6-yl)-N-((4-methoxy-6-methyl-2-carbonyl-1,2-dihydropyridin-3-yl)methyl)-2-methylbenzamide 60f The compound 50e (40 mg, 0.125 mmol) and compound 34a (101 mg, 0.1875 mmol) were dissolved in 1,4-dioxane (10 mL) and water (3 mL), Pd(dppf)$Cl_2$-(10 mg, 0.0125 mmol) and potassium carbonate (52 mg, 0.375 mmol) were added. The mixture was heated to 100° C. and stirred for 4 hours under the protection of Ar. The reaction solution was cooled down, spin-dried, extracted with dichloromethane for three times, washed with saturated NaCl solution, dried with anhydrous sodium sulfate, filtered, concentrated, and purified by plate chromatography to obtain the title compound 50f (30 mg, 0.046 mmol) with a yield of 36.8%.

MS m/z (ESI): 653 $[M+1]^+$.

Step V 3-(ethyl(tetrahydro-2H-pyran-4-yl)amino)-5-(1'-ethyl-2',6'-dimethyl-2,3-dihydrospiro[indene-1,4'-piperidine]-6-yl)-N-((4-methoxy-6-methyl-2-oxo-1,2-dihydropyridin-3-yl)methyl)-2-methylbenzamide formate 50

The compound 50f (30 mg, 0.046 mmol) was dissolved in methanol (8.0 mL), and Pd/C (10 mg) was added. The mixture was stirred at room temperature for 24 hours under the condition of flowing hydrogen. The reaction solution was filtered, washed with methanol, concentrated, and purified by Prep-HPLC to obtain the compound 50 (1.4 mg, 0.00214 mmol) with a yield of 5%.

$^1$H NMR (400 MHz, Methanol-d4) 8.50 (s, 2H), 7.41 (d, J=9.9 Hz, 2H), 7.35-7.22 (m, 3H), 6.26 (s, 1H), 4.60 (s, 1H), 4.45 (s, 2H), 3.92 (s, 4H), 3.36 (d, J=11.6 Hz, 3H), 322-2.88 (m, 7H), 2.48 (d, J=67.6 Hz, 3H), 2.31 (d, J=8.2 Hz, 5H), 2.17-1.81 (m, 5H), 1.74 (d, J=12.8 Hz, 2H), 1.70-1.57 (m, 2H), 1.46-1.22 (m, 6H), 0.88 (t, J=6.9 Hz, 3H), 0.67 (dd, J=16.4, 6.7 Hz, 3H),
MS m/z (ESI): 655.3[M+H]$^+$.
Example 51 N-((4,6-dimethyl-2-oxo-1,2-dihydropyridin-3-yl)methyl)-3-(ethyl(tetrahydro-2H-pyran-4-yl)amino)-2-methyl-5-(1-(2,2,3,3,3-pentafluoropropyl)-2',3',5',6'-tetrahydrospiro[dihydroindole-3,4'-pyran]-6-yl)benzamide
51
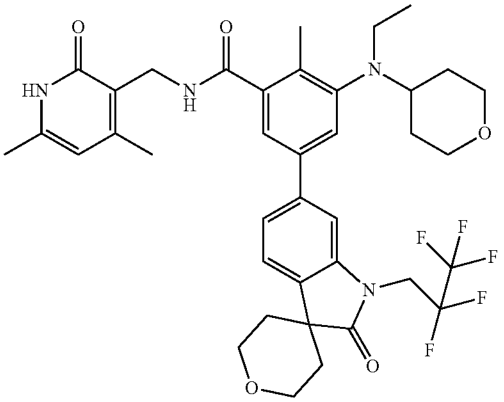
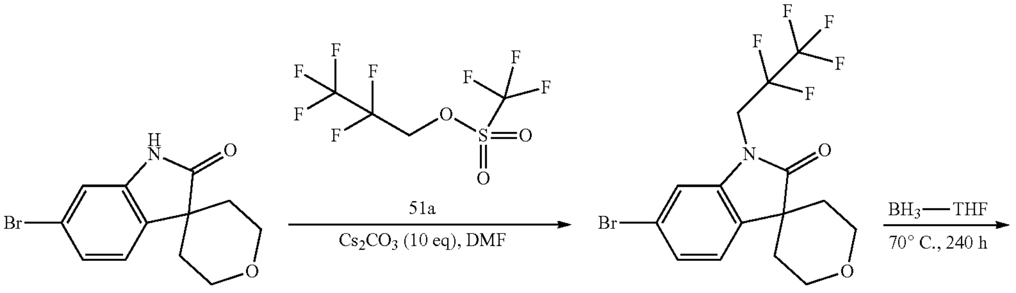
1g
51b
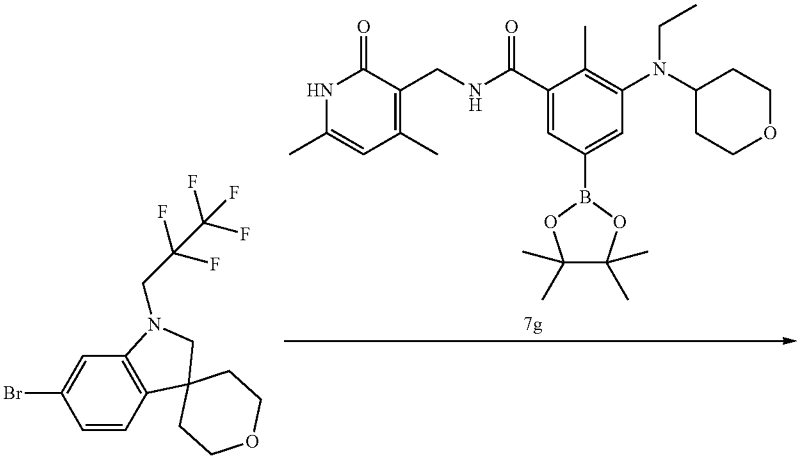
51c -continued

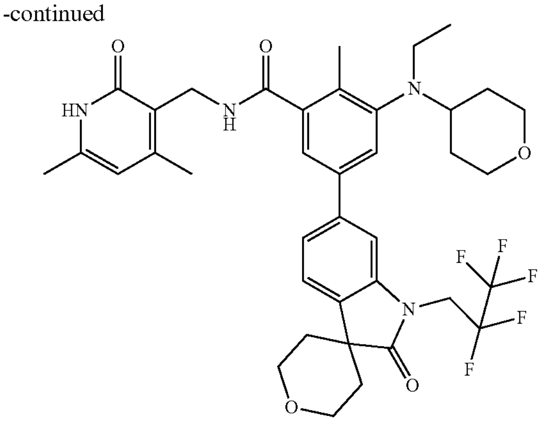

51

Step I 6-bromo-1-(2,2,3,3,3-pentafluoropropyl)-2',3',5',6'-tetrahydrospiro[dihydroindole-3,4'-pyran]-2-one 51b The compound 1g (250 mg, 0.886 mmol), compound 51a (500 mg, 1.773 mmol), cesium carbonate (2.9 g, 8.86 mmol) and 4 mL of DMF were added to a 10 mL microwave tube, which was then replaced with nitrogen. The mixture was stirred at 20° C. for 2 hours. The reaction solution was added with water, extracted with EA, dried with anhydrous sodium sulfate, mixed, concentrated, and purified by column chromatography (petroleum ether: ethyl acetate=3:1) to obtain the title compound 51b (167 mg, 0.404 mmol) with a yield of 45.6%.

MS m/z (ESI): 414 $[M+H]^+$.

Step II 6-bromo-1-(2,2,3,3,3-pentafluoropropyl)-2',3',5',6'-tetrahydrospiro[dihydroindole-3,4'-pyran]51c The compound 51b (120 mg, 0.289 mmol) and 15 mL of 2.5 M borane tetrahydrofuran solution were added in a 50 mL single-necked flask. The mixture was heated to 50° C. and stirred for 8 days followed by quenching with methanol. The solvent was evaporated, and the residue was extracted with water and EA twice. The organic phase was dried and concentrated to obtain the title compound 51c (100 mg, 0.25 mmol) with a yield of 86.5%.

MS m/z (ESI): 400 $[M+H]^+$.

Step III N-((4,6-dimethyl-2-oxo-1,2-dihydropyridin-3-yl)methyl)-3-(ethyl(tetrahydro-2H-pyran-4-yl)amino)-2-methyl-5-(1-(2,2,3,3,3-pentafluoropropyl)-2',3',5',6'-tetrahydrospiro[dihydroindole-3,4'-pyran]-6-yl)benzamide 51

The compound 51c (110 mg, 0.275 mmol), compound 7g (144 mg, 0.275 mmol), $Pd(dppf)Cl_2$ (20 mg, 0.0275 mmol), potassium carbonate (114 mg, 0.825 mmol), 1 mL of water and 5 mL of 1,4-dioxane were added to a microwave tube. The reaction system was replaced with nitrogen, heated to 100° C. and reacted for 1 hour. The reaction solution was added with 30 mL of water and extracted with EA (30 mL×3). The organic phases were combined, washed with saturated NaCl solution (30 mL×3), dried, mixed, and purified by column chromatography (methanol: dichloromethane=1:15) to obtain the title compound 51 (142 mg, 0.198 mmol) with a yield of 72%.

$^1H$ NMR (400 MHz, Methanol-d4) δ 7.57 (d, J=54.7 Hz, 2H), 7.16 (d, J=7.7 Hz, 1H), 6.99 (d, J=7.5 Hz, 1H), 6.75 (s, 1H), 6.11 (s, 1H), 4.48 (s, 3H), 4.10-3.83 (ma, 6H), 3.60 (d, J=11.8 Hz, 5H), 3.35 (t, J=12.0 Hz, 2H), 2.30 (d, J=56.5 Hz, 9H), 1.96 (td, J=13.0, 4.6 Hz, 3H), 1.81-1.57 (m, 6H), 0.98 (t, J=7.0 Hz, 3H), MS m/z (ESI): 717 $[M+H]^+$.

Example 52 2-chloro-5-(ethyl(tetrahydro-2H-pyran-4-yl)amino)-3-(1-isopropyl-2-oxo-2',3',5',6'-tetrahydrospiro[dihydroindole-3-1,4'-pyran]-6-yl)-N-((4-methoxy-6-methyl-2-oxo-1,2-dihydropyridin-3-yl)methyl)-6-methylbenzamide

52

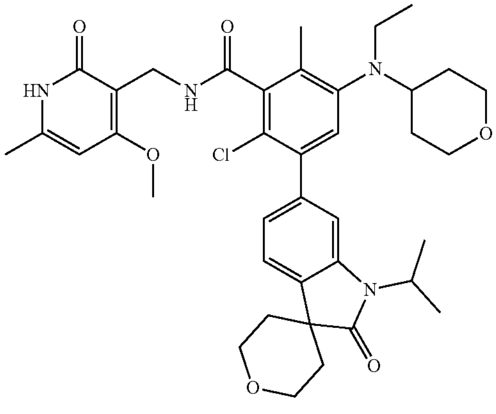

A similar method of Example 46 was used to obtain the title compound 52 with a yield of 23%, wherein the 3-(aminomethyl)-4,6-dimethyl-1H-pyridin-2-one hydrochloride was replaced with 3-(aminomethyl)-4-methoxy-6-methyl-1H-pyridin-2-one hydrochloride.

$^1H$ NMR (400 MHz, Methanol-d4) δ 7.55 (d, J=7.7 Hz, 1.1), 7.29-7.19 (m, 2H), 7.14 (d, J=7.7 Hz, 1H), 6.08 (s, 11H), 4.58 (p. J=7.0 Hz, 1H), 4.49 (s, 2H), 4.17 (dt, J=11.7, 5:7 Hz, 2H), 3.90 (dq, J=12.0, 3.9, 3.0 Hz, 4H), 3.34 (dd, J=11.7, 2.1 Hz, 2H), 3.05 (dd, J=17.0, 9.7 Hz, 3H), 2.36 (s, 3H), 2.24 (d, J=19.5 Hz, 6H), 1.80 (t, J=5.4 Hz, 4H), 1.73 (d, J=12.9 Hz, 2H), 1.57 (tt, J=11.7, 5.9 Hz, 2H), 1.46 (d, J=7.0 Hz, 6H), 0.87 (t, J=7.0 Hz, 3H), MS n/z (ESI): 691.2 $[M+H]^+$.

Example 53 2-chloro-N-((4,6-dimethyl-2-oxo-1,2-dihydropyridin-3-yl)methyl)-5-(ethyl(tetrahydro-2H-pyran-4-yl)amino)-6-methyl-3-(2-oxo-1-(3,3,3-trifluoropropyl)-2',3',5',6'-tetrahydrospiro[dihydroindole-3,4'-pyran]-6-yl)benzamide

53

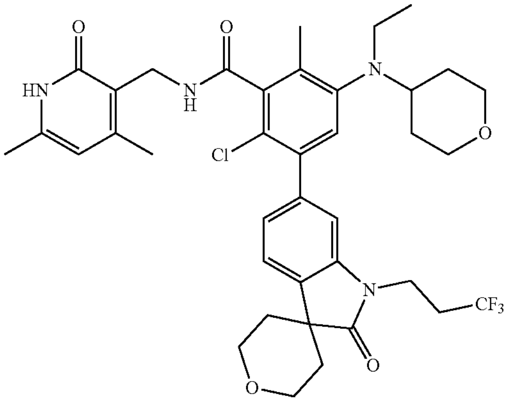

A similar method of Example 46 was used to obtain the title compound 53 with a yield of 17%, wherein the 2-iodopropane was replaced with 1-iodo-3,3,3-trifluoropropane.

$^1$H NMR (400 MHz, DMSO-$d_6$) δ 11.43 (s, 1H), 8.32 (t, J=5.0 Hz, 1H), 7.61 (d, J=7.9 Hz, 1H), 7.10 (s, 1H), 7.01 (d, J=6.5 Hz, 2H), 5.82 (s, 11), 4.26 (s, 2H), 4.10-3.74 (m 1.8), 3:21 (t, J=11.4 Hz, 2H), 2.97 (dd, J=16.7, 9.5 Hz, 3H), 2.62 (dq, J=11.3, 5.4 Hz, 2H, 2.30-1.95 (m, 9H, 1.87-1.28 (m, 8H), 0.80 (t, J=6.9 Hz. 3H),

MS m/z (ESI): 729 [M+H]$^+$.

Example 54 2-chloro-N-((4,6-dimethyl-2-carbonyl-1,2-dihydropyridin-3-yl)methyl)-5-(ethyl(tetrahydro-2H-pyran-4-yl)amino)-3-(1-ethyl-2',3',5',6'-tetrahydrospiro[dihydroindole-3,4'-pyran]-6-yl)-6-methylbenzamide

54

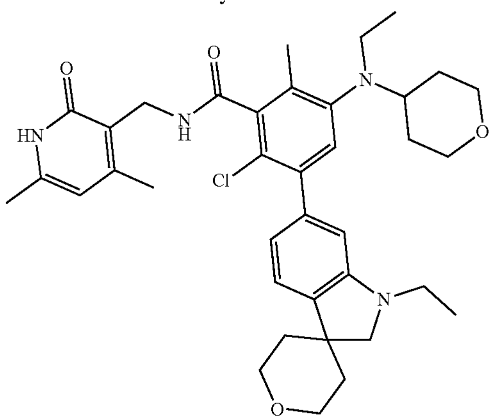

A similar method of Example 51 was used to obtain the title compound 54 with a yield of 26%, wherein the 2-iodopropane was replaced with iodoethane, and the 3-(aminomethyl)-4,6-dimethyl-1H-pyridin-2-one hydrochloride was replaced with 3-(aminomethyl)-4-methoxy-6-methyl-1H-pyridin-2-one hydrochloride.

$^1$H NMR (400 MHz, DMSO-d6) δ 11.41 (s, 1H), 8.29 (t, J=5.0 Hz, 1H), 7.07 (d, J=7.5 Hz, 1H), 7.00 (s, 1H), 6.49 (dd, J=7.6, 1.5 Hz, 1H), 6.38 (d, J=1.5 Hz, 1H), 5.81 (s, 1H), 4.24 (s, 2H), 3.78 (d, J=11.6 Hz, 4H, 3.47 (t, J=11.6 Hz, 2H), 3.24-3.08 (m, 4H), 3.03-2.83 (m, 4H), 2.17 (s, 3H), 2.08 (dd, J=17.1, 8.3 Hz, 7H), 1.81 (td, J=13.0, 12.5, 4.7 Hz, 2H), J=0.52 (td, J=29.6, 12.2 Hz, 6H), 1.07 (t, J=7.2 Hz, 3H), 0.82-0.72 (m, 3H),

MS m/z (ESI): 647.3 [M+H]$^+$

Example 55 2-chloro-N-((4,6-dimethyl-2-oxo-1,2-dihydropyridin-3-yl)methyl)-5-(ethyl(tetrahydro-2H-pyran-4-yl)amino)-6-methyl-3-(1-(3-methylbutyl-2-yl)-2',3',5',6'-tetrahydrospiro[dihydroindole-3,4'-pyran]-6-yl)benzamide

55

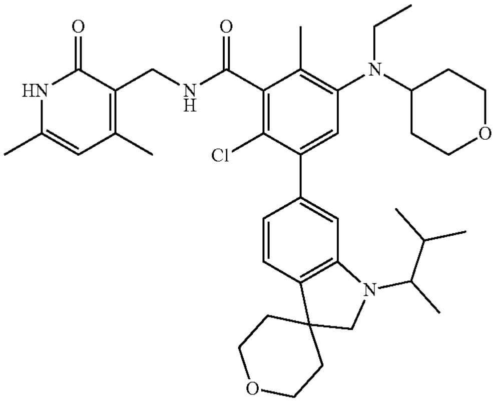

-continued

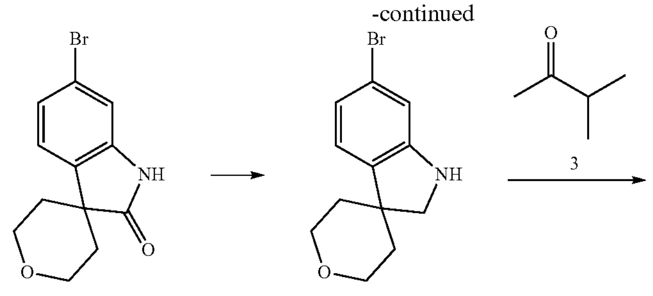

1g 2g

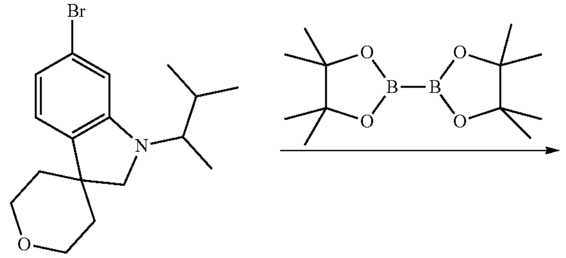

55a

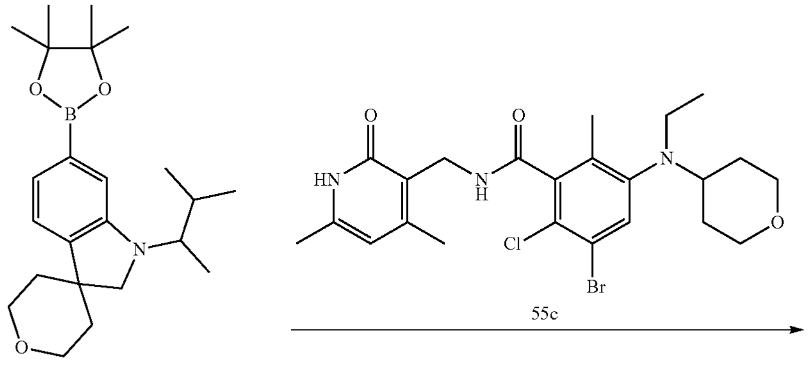

55c

55b

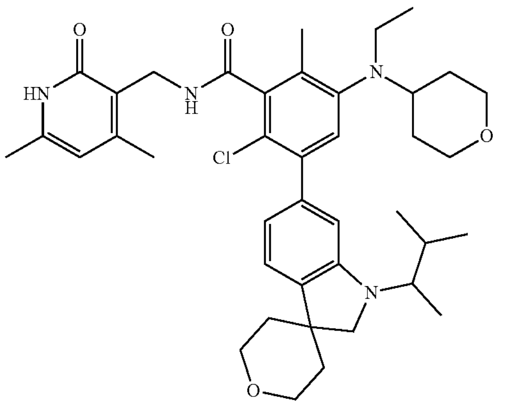

55

Step I 6-bromo-2',3',5',6'-tetrahydrospiro[dihydroindole-3,4'-pyran]2c

The compound 1g (4.5 g, 15.95 mmol) and THF (80 mL) were added in a 500 mL three-necked flask at room temperature, and $BH_3$/THF (80 mL, 80 mmol) was added slowly. The mixture was heated to 60° C. and reacted for 10 hours. The raw materials were completely reacted as determined by LCMS monitoring, and there was MS value of the product in the main peak. TLC monitoring was used and determined that there were new spots formed. The reaction solution was quenched with methanol under ice bath, concentrated, dissolved with DCM, washed with water, dried, concentrated, mixed with silica gel, and purified by flash column chromatography to obtain a white solid of compound 2c (4 g, 14.9 mmol) with a yield of 94%.

MS m/z (ESI): 268.0 $[M+H]^+$.

Step II 6-bromo-1-(3-methylbutyl-2-yl)-2',3',5',6'-tetrahydrospiro[dihydroindole-3,4'-pyran]55a The compound 2c (800 mg, 2.98 mmol), DCM (20 mL), compound 3 (771 mg, 8.95 mmol) and AcOH (537 mg, 8.95 mmol) were added in a 100 mL single-necked flask and reacted at room temperature for 5 minutes. Then the mixture was added with $Na(AcO)_3BH$ (1.9 g, 8.95 mmol) at 18° C. and reacted for 16 hours. The raw materials were completely reacted as determined by LCMS monitoring, and there was MS value of the product in a small peak. TLC monitoring was used and determined that there were new spots formed. The reaction solution was quenched with water, extracted with DCM, dried, concentrated, mixed with silica gel, and purified by flash column chromatography to obtain a white solid of compound 66a (150 mg, 443 μmol) with a yield of 15%.

MS m/z (ESI): 338.1 $[M+H]^+$.

Step III 1-(3-methylbutyl-2-yl)-6-(4,4,5,5-tetramethyl-1,3,2-dioxaborolan-2-yl)-2',3',5',6'-tetrahydrospiro[dihydroindole-3,4'-pyran]55b The compound 55a (150 mg, 443 μmol), bis(pinacolato) diboron (225 mg, 887 μmol), KAcO (174 mg, 1.77 mmol) and $Pd(dppf)Cl_2$ (32 mg, 44 μmol) were added in a 100 mL single-necked flask, followed by adding dioxane (10 mL). The mixture was heated to 110° C. under the protection of Ar and reacted for 2 hours. The raw materials were completely reacted as determined by LCMS monitoring, and there was MS value of the product in the main peak. The reaction solution was added with water, extracted with DCM, dried, concentrated, mixed with silica gel, and purified by flash column chromatography to obtain a light red solid of compound 55b (190 mg, 493 μmol), which is impure but not affecting the reaction of next step.

MS m/z (ESI): 386.2 $[M+H]^+$.

Step IV 2-chloro-N-((4,6-dimethyl-2-oxo-1,2-dihydropyridin-3-yl)methyl)-5-(ethyl(tetrahydro-2H-pyran-4-yl)amino)-6-methyl-3-(1-(3-methylbutyl-2-yl)-2',3',5',6'-tetrahydrospiro[dihydroindole-3,4'-pyran]-6-yl)benzamide 55

The compound 55b (90 mg, 273 μmol), compound 55c (264 mg, 273 μmol), $K_2CO_3$ (113 mg, 820 mmol), Pd(dppf) $Cl_2$ (20 mg, 27 μmol), dioxane (4 mL) and $H_2O$ (1 mL) were added in a 100 mL single-necked flask. The mixture was heated to 110° C. under the protection of Ar and reacted for 3 hours. The raw materials were completely reacted as determined by LCMS monitoring, and there was MS value of the product in the main peak. The reaction solution was added with water, extracted with DCM, dried, concentrated, mixed with silica gel, and purified by flash column chromatography to obtain a white solid of compound 55 (57 mg, 83 μmol) with a yield of 35%.

$^1H$ NMR (400 MHz, DMSO-d6) δ 11.45 (s, 1H), 831 (d, J=5.2 Hz, 1H), 7.08-7.01 (m, 2H), 6.43 (dd, J=7.5, 1.4 Hz, 1H), 6.32 (d, J=1.3 Hz, 1H), 5.85 (s, 1H), 4.27 (s, 2H), 3.82 (d, J=12.1 Hz, 4H), 3.57 (d, J=11.5 Hz, 1H), 3.46 (s, 1H), 3.24 (d, J=10.1 Hz, 2H), 3.17 (d, J=5.2 Hz, 2H), 3.02-2.95 (m, 3H), 2.20 (s, 3H), 2.15-2.08 (m, 8H), 1.63 (d, J=12.4 Hz, 2H), 1.54-1.44 (m, 4H), 1.06 (d, J=6.9 Hz, 5H), 0.92 (dd, J=14.1, 6.5 Hz, 6H), 0.82 (t, J=6.9 Hz, 3H),

MS m/z (ESI): 689.3 $[M+H]^+$.

Example 56 2-chloro-N-((4,6-dimethyl-2-oxo-1,2-dihydropyridin-3-yl)methyl)-5-(ethyl(tetrahydro-2H-pyran-4-yl)amino)-3-(1'-isopropyl-1-methyl-2-oxospiro[dihydroindole-3,4'-piperidine]-6-yl)-6-methylbenzamide

56

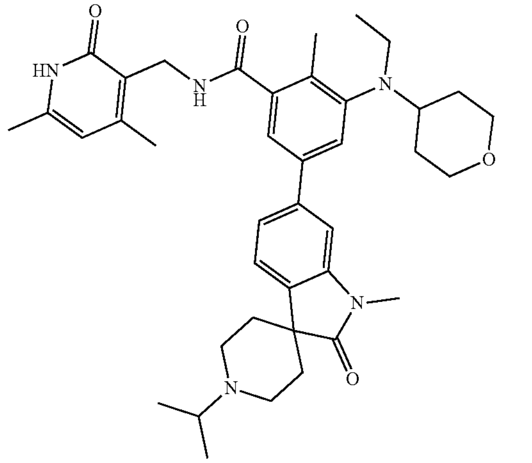

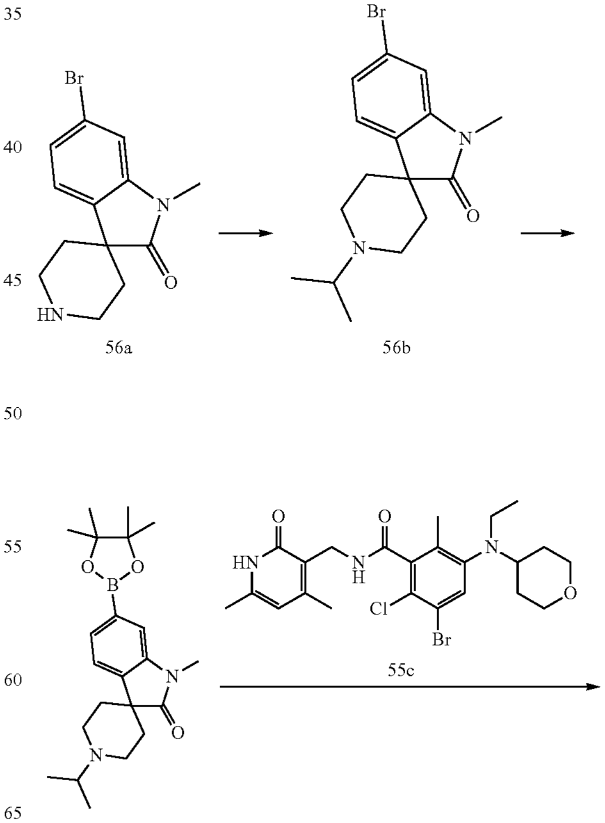

56a 56b 56c 55c

-continued

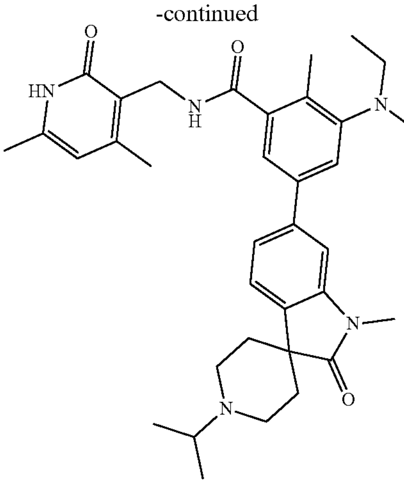

56

Step I 6-bromo-1'-isopropyl-1-methylspiro[dihydroindole-3,4'-piperidine]-2-one 56b The compound 56a (0.8 g, 1.96 mmol) and 2-iodopropane (0.66 g, 3.91 mmol) were dissolved in DMF (10 mL), followed by adding potassium carbonate (0.54 g, 3.91 mmol) and stirred at 70° C. for 4 hours.

The reaction solution was concentrated and purified by flash column chromatography to obtain a compound 56b (0.5 g, 1.5 mmol) with a yield of 76%.

MS m/z (ESI): 337 $[M+H]^+$.

Step II 1'-isopropyl-1-methyl-6-(4,4,5,5-tetramethyl-1,3,2-dioxaborolan-2-yl)spiro[dihydroindole-3,4'-piperidine]-2-one 56c The compound 56b (0.5 g, 1.54 mmol), bis(pinacolato) diboron (0.59 g, 2.3 mmol), $Pd(dppf)Cl_2$ (100 mg, 0.15 mmol) and potassium acetate (0.45 g, 4.6 mmol) were added to 1,4-dioxane (10 mL), and the mixture was refluxed at 110° C. for 4 hours. The reaction solution was concentrated and purified by flash column chromatography to obtain a compound 56c (0.5 g, 1.3 mmol) with a yield of 89%.

MS m/z (ESI): 385 $[M+H]^+$.

Step III 2-chloro-N-((4,6-dimethyl-2-oxo-1,2-dihydropyridin-3-yl)methyl)-5-(ethyl(tetrahydro-2H-pyran-4-yl)amino)-3-(1'-isopropyl-1-methyl-2-oxospiro[dihydroindole-3,4'-piperidine]-6-yl)-6-methylbenzamide 56

The compound 56c (110 mg, 0.29 mmol), compound 55c (150 mg, 0.29 mmol), $Pd(dppf)Cl_2$ (22 mg, 0.03 mmol) and potassium phosphate (190 mg, 0.9 mmol) were added to 1,4-dioxane (10 mL) and $H_2O$ (1 mL), and the mixture was refluxed at 110° C. for 4 hours. The reaction solution was concentrated and purified by flash column chromatography to obtain a compound 56 (60 mg, 0.08 mmol) with a yield of 24%.

$^1H$ NMR (400 MHz, Methanol-$d_4$) δ 7.41 (d, J=7.7 Hz, 1H), 7.14 (s, 1H), 7.08-6.96 (m, 2H, 6.08 (s, 1H), 4.48 (s, 2H), 3.90 (d, J=11.2 Hz, 2H), 352 (s, 1H), 3.38-3.30 (m, 3H), 3.20 (s, 3H), 3.18-2.98 (m, 6H), 2.38 (s, 3H), 2.24 (d, J=19.2 Hz, 6H), 2.12 (s, 1H), 2.01 (d, J=14.0H7, 2H), 1.71 (d, J=12.7 Hz, 2H), 1.61 (dd, J=14.2, 10.1 Hz, 2H), 140-1.22 (m, 7H), 0.87 (t, J=6.9 Hz, 3H), MS m/z (ESI): 689$[M+H]^+$.

Example 57 2-chloro-N-((4,6-dimethyl-2-carbonyl-1,2-dihydropyridin-3-yl)methyl)-5-(ethyl(tetrahydro-2H-pyran-4-yl)amino)-6-methyl-3-(1-propyl-2',3',5',6'-tetrahydrospiro[dihydroindole-3,4'-pyran]-6-yl) benzamide

57

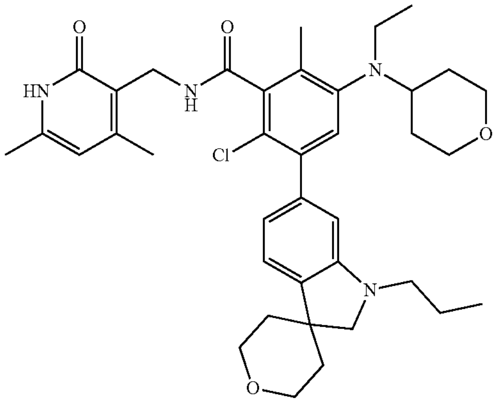

A similar method of Example 55 was used to obtain the title compound 57 with a yield of 16%, wherein the 3-methyl-butan-2-one was replaced with iodopropane.

$^1H$ NMR (400 MHz. Methanol-d4) δ 7.09 (s, 1H), 7.04 (d, J=7.5 Hz, 1H), 6.53 (dd, J=7.5, 1.5 Hz, 1H), 6.39 (d, J=1.5 Hz, 1H), 6.08 (s, 1H), 4.47 (s, 2H), 3.99-3.80 (m, 4H), 3.66-3.56 (m, 2H), 3.40 (s, 2H), 3.37-3.30 (m, 2H), 3.15-2.92 (m, 5H), 238 (d, J=1.8 Hz, 3H), 232-$2^1$0.17 (m, 6H), L95 (d, J=4.4 Hz, 2H), 1.78-1.49 (mi, 8H), 0.95 (t, J=7.4 Hz, 3H), 0.86 (t, J=6.9 Hz, 3H), MS m/z (ESI):661 0.3$[M+1]^+$.

Example 58 N-((4,6-dimethyl-2-carbonyl-1,2-dihydropyridin-3-yl)methyl)-3-(ethyl(tetrahydro-2H-pyran-4-yl)amino)-6-fluoro-2-methyl-5-(2-carbonyl-1-propyl-2',3',5',6'-tetrahydrospiro[dihydroindole-3,4'-pyran]-6-yl)benzamide

58

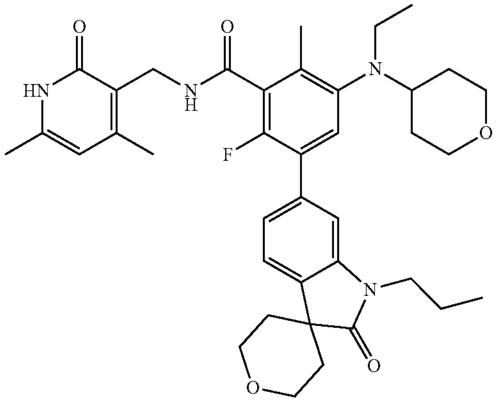

-continued
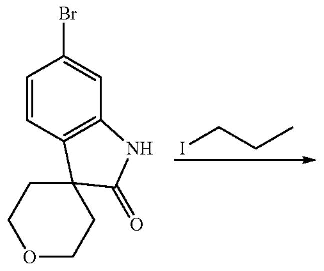
1g
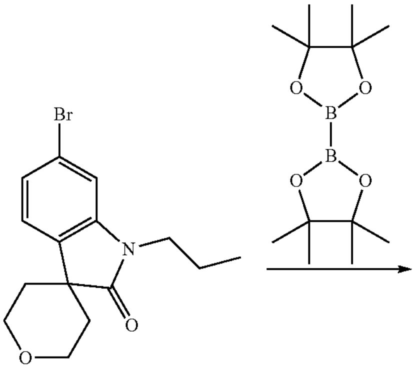
58a
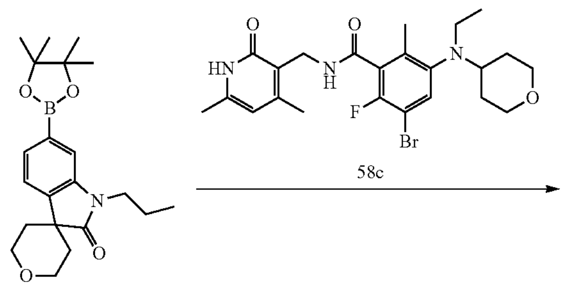
58b
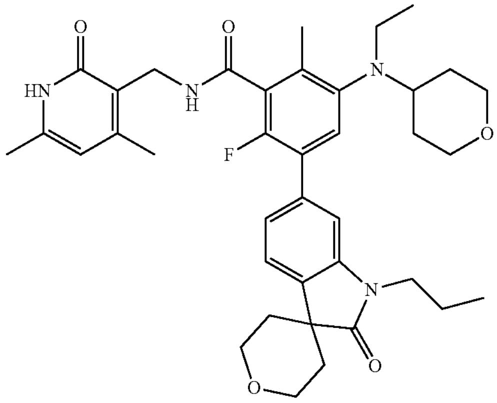
58
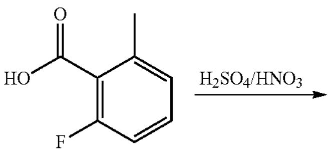
58c-1
-continued
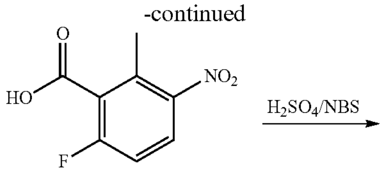
58c-2
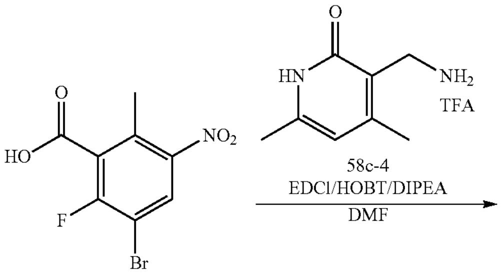
58c-3
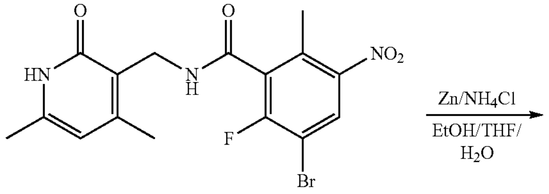
58c-5
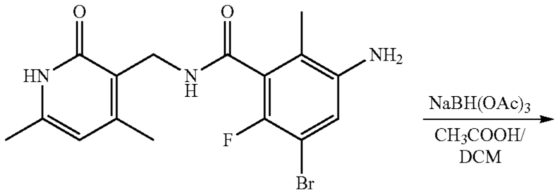
58c-6
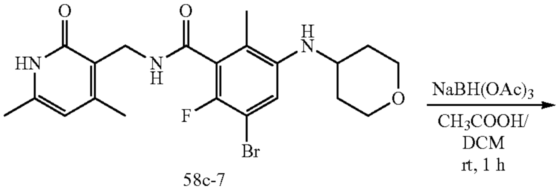
58c-7
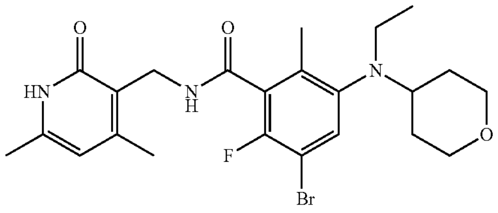
58c
Step I 6-bromo-1-ipropyl-2',3',5',6'-tetrahydrospiro [dihydroindole-3,4'-pyran]-2-one 58a
The compound 1g (1.5 g, 5.319 mmol) was dissolved in DMF (20 mL), and the compound NaH (60%) (638 mg, 15.957 mmol) were added. The mixture was stirred for 1 hour, added with iodopropane (2712 mg, 15.957 mmol), and reacted for 16 hours, followed by quenching with water. The reaction solution was extracted with dichloromethane for three times, washed with saturated NaCl solution, dried with anhydrous sodium sulfate, filtered, concentrated, and purified by column chromatography to obtain the title compound 58a (800 mg, 2.469 mmol) with a yield of 46%.

MS m/z (ESI): 324 $[M+1]^+$.

Step II 1-propyl-6-(4,4,5,5-tetramethyl-1,3,2-dioxaborolan-2-yl)-2',3',5',6'-tetrahydrospiro[dihydroindole-3,4'-pyran]-2-one 58b The compound 58a (800 mg, 2.469 mmol) and bis(pinacolato)diboron (1.254 g, 4.938 mmol) were dissolved in 1,4-dioxane (20 mL), [1,1'-bis(diphenylphosphino)ferrocene]dichloropalladium (180 mg, 0.2469 mmol) and potassium acetate (426 mg, 7.407 mmol) were added. The mixture was heated to 100° C. under the protection of nitrogen and stirred for 2 hours until the reaction was completed. The reaction solution was extracted with water and ethyl acetate, the organic phase was washed with saturated NaCl solution, dried with anhydrous sodium sulfate, filtered, concentrated, and purified by column chromatography to obtain the title compound 58b (600 mg, 1.617 mmol) with a yield of 65.5%.

MS m/z (ESI): 372 $[M+1]^+$.

Step III 6-fluoro-2-methyl-3-nitrobenzoic acid 58c-2

Concentrated sulfuric acid (40 mL) was added into a 100 mL single-mouth flask, cooled to −15° C. under dry ice bath, and added with the compound 58c-1 (5 g, 32.47 mmol) under stirring. Then a mixed acid (fuming nitric acid/concentrated sulfuric acid: 1.75 mL/7.5 mL) was added to the reaction solution slowly dropwise, followed by stirring the solution at 0° C. for 1 hour. The reaction solution was poured into a large quantity of ice water and a large amount of solid was precipitated. The solid was filtered out, dissolved with EA, washed with water, dried with anhydrous sodium sulfate, and concentrated to obtain a light-yellow solid of title compound 58c-2 (5.1 g, 25.6 mmol) with a yield of 78.9%.

Step IV 3-bromo-2-fluoro-6-methyl-5-nitrobenzoic acid 58c-3

The compound 58c-2 (4.1 g, 20.6 mmol) was dissolved in concentrated sulfuric acid (100 mL). The mixture was added with NBS (3.85 g, 21.63 mmol), stirred at room temperature for 6 hours, and poured into a large quantity of ice water. A large amount of solid was precipitated, which was then filtered out, washed with water, and dried under vacuum to obtain a light-yellow solid of target compound 58c-3 (4.4 g, 15.8 mmol) with a yield of 76.8%.

MS m/z (ESI): 277.8 $[M+H]^+$.

Step V 3-bromo-N-((4,6-dimethyl-2-oxo-1,2-dihydropyridin-3-yl)methyl)-2-fluoro-6-methyl-5-nitrobenzamide 58c-5

The compound 64c (4.4 g, 15.8 mmol) was dissolved in DMF (20 mL), and the compound 58c-4 (157 mg, 23.7 mmol), EDCI (6.04 g, 31.6 mmol), HOBt (2.13 g, 15.8 mmol) and triethylamine (8 g, 79 mmol) were added successively under stirring. The mixture was stirred at room temperature overnight. The mixture was added with EA/$H_2O$ (50 mL/50 mL), stirred for 5 minutes and separated. The aqueous phase was extracted with EA (50 mL×3), the organic phases were combined, washed with saturated NaCl solution (30 mL×3), dried, mixed, and purified by column chromatography (EA/PE=0%-100%) to obtain a colorless oily product of target compound 120d (6.2 g, 15.05 mmol) with a yield of 95%.

MS m/z (ESI): 412.0 $[M+H]^+$.

Step VI 3-amino-5-bromo-N-((4,6-dimethyl-2-oxo-1,2-dihydropyridin-3-yl)methyl)-6-fluoro-2-methylbenzamide 58c-6

The compound 58c-4 (5.7 g, 13.83 mmol) and $NH_4Cl$ (5.92 g, 110 mmol) were dissolved in a mixed solvent of ethanol/THF/$H_2O$ (100 mL/25 mL/2 mL). Iron powder (6.16 g, 110 mmol) was added in the reaction solution in batches under ice bath, then the ice bath was removed. The reaction solution was heated to 60° C. and stirred for 3 hours. The solution was cooled to room temperature, filtered to remove the solid, concentrated to remove the solvent, added with water, and extracted with EA (50 mL×3). The organic phases were combined, washed with NaCl solution (50 mL×3), dried, concentrated, mixed, and purified by column chromatography (EA/PE=0%-100%) to obtain a light-yellow oily product of target compound 58c-6 (4.2 g, 11.05 mmol) with a yield of 80%.

MS m/z (ESI): 382 $[M+H]^+$.

Step VII 3-bromo-N-((4,6-dimethyl-2-oxo-1,2-dihydropyridin-3-yl)methyl)-2-fluoro-6-methyl-5-((tetrahydro-2H-pyran-4-yl)amino)benzamide 58c-7

The compound 58c-6 (2.4 g, 6.28 mmol) was dissolved in DCM (50 mL), and tetrahydro-4H-pyran-4-one (1.25 g, 12.56 mmol) and acetic acid (377 mg, 6.28 mmol) were successively added. The mixture was stirred at room temperature for 1 hour, followed by adding sodium triacetoxyborohydride (5.3 g, 25.12 mmol) and stirring at room temperature overnight. 50 mL of water was then added to the mixture. The reaction solution was stirred for 10 minutes, separated, and the organic phase was extracted with DCM (50 mL×2). The organic phases were combined, washed with saturated NaCl solution twice, dried with anhydrous sodium sulfate, mixed, concentrated, and purified by column chromatography (petroleum ether: ethyl acetate=0%-30%) to obtain a colorless oily product of title compound 58c-7 (2.4 g, 5.21 mmol) with a yield of 83%.

MS m/z (ESI): 466 $[M+H]^+$.

Step VIII 3-bromo-N-((4,6-dimethyl-2-oxo-1,2-dihydropyridin-3-yl)methyl)-5-(ethyl(tetrahydro-2H-pyran-4-yl)amino)-2-fluoro-6-methylbenzamide 58c The compound 58c-7 (2.4 g, 5.21 mmol) was dissolved in 30 mL of DCM, acetaldehyde (0.917 g, 20.84 mmol) and acetic acid (312 mg, 5.21 mmol) were successively added under ice water bath. The mixture was stirred at room temperature for 1 hour, followed by adding sodium triacetoxyborohydride (4.42 g, 20.84 mmol) and stirring at room temperature overnight. 30 mL of water was then added to the mixture. The reaction solution was stirred for 10 minutes, separated, and the organic phase was extracted with DCM (50 mL×2). The organic phases were then combined, washed with saturated NaCl solution twice, dried with anhydrous sodium sulfate, mixed, concentrated, and purified by column chromatography (petroleum ether: ethyl acetate=0%-30%) to obtain a white solid of title compound 58c (2.1 g, 4.25 mmol) with a yield of 81.5%.

MS m/z (ESI): 494.1 $[M+H]^+$.

Step IX N-((4,6-dimethyl-2-carbonyl-1,2-dihydropyridin-3-yl)methyl)-3-(ethyl(tetrahydro-2H-pyran-4-yl)amino)-6-fluoro-2-methyl-5-(2-carbonyl-1-propyl-2',3',5',6'-tetrahydrospiro[dihydroindole-3,4'-pyran]-6-yl)benzamide 58

The compound 58b (200 mg, 0.539 mmol), $K_2CO_3$ (149 mg, 1.078 mmol), Pd(dppf)$Cl_2$ (39 mg, 0.0539 mmol) and compound 58c (266 mg, 0.539 mmol) were dissolved in dioxane (15 mL) and $H_2O$ (5 mL). The mixture was heated to 100° C. under the protection of Ar and stirred for 6 hours until the reaction was completed. The reaction solution was extracted with water and ethyl acetate, and the organic phase was washed with saturated NaCl solution, dried with anhydrous sodium sulfate, filtered, concentrated, and purified by column chromatography to obtain the title compound 58 (116 mg, 0.176 mmol) with a yield of 32%.

$^1$H NMR (400 MHz, Methanol-d4) δ 7.57 (d, J=7.8 Hz, 1H), 7.26 (d, J=7.5 Hz, 1H), 7.16 (d, J=7.8 Hz, 1H), 7.09 (t, J=1.8 Hz, 1H), 6.08 (s, 1H), 4.49 (s, 2H), 4.18 (td, J=6.9, 3.3 Hz, 2H), 3.91 (ddd, J=17.2, 11 6, 4.31 Hz, 4H), 3.72 (t, J=7.1 Hz, 2H), 3.39-3.30 (m, 2H), 3.14-2.93 (n, 3H), 2.36 (s, 3H), 2:26 (s, 3H), 2.22 (s, 3H), 1.83 (q, J=4.0 Hz, 4H), 1.79-1.63 (m, 4H), 1.57 (dd, J=12.3, 4.3 Hz, 2H), 0.89 (dt, J=16.9, 7.2 Hz, 6H), MS m/z (EST):659.2$[M+1]^+$.

Example 59 N-((4,6-dimethyl-2-carbonyl-1,2-dihydropyridin-3-yl)methyl)-3-(ethyl(tetrahydro-2H-pyran-4-yl)amino)-6-fluoro-2-methyl-5-(1-propyl-2',3',5',6'-tetrahydrospiro[dihydroindole-3,4'-pyran]-6-yl)benzamide

59

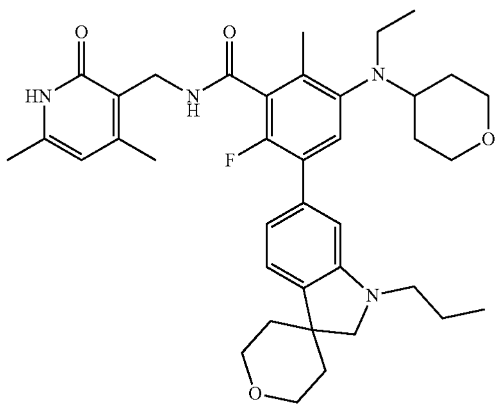

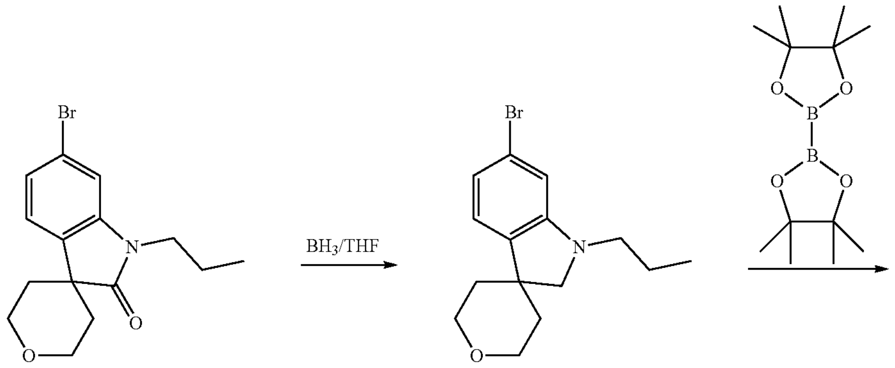

58a

59a

-continued

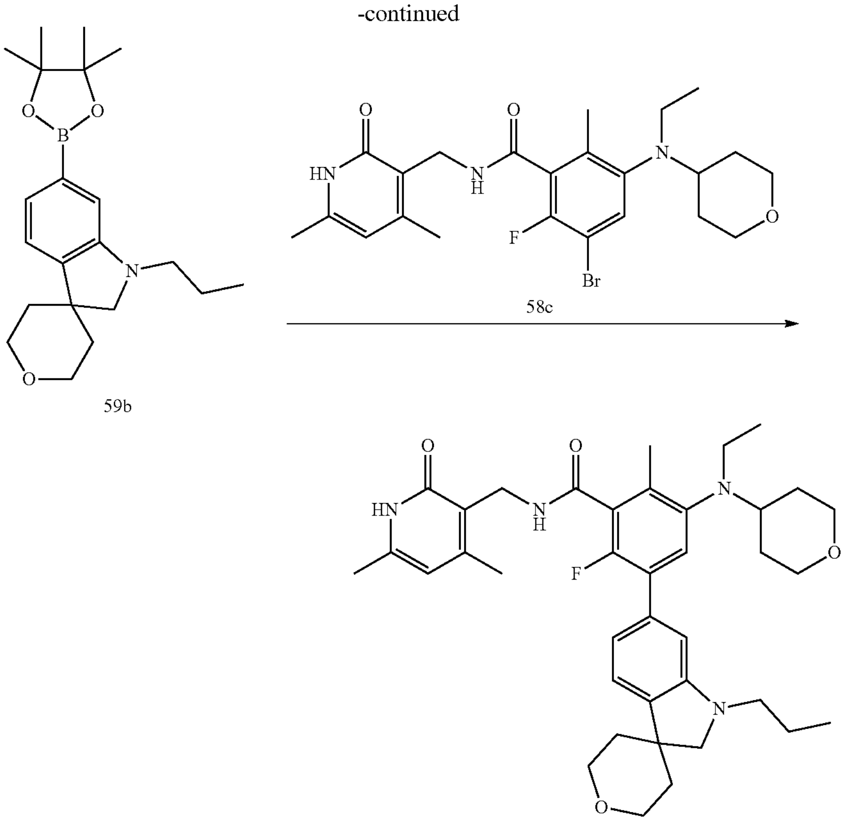

59b

59

Step I 6-bromo-1-propyl-2',3',5',6'-tetrahydrospiro [dihydroindole-3,4'-pyran]59a The compound 58a (1 g, 3.086 mmol) was dissolved in THF (15 mL) at 0° C., and $BH_3$/THF (9.5 mL, 9.5 mmol) was added slowly. The mixture was stirred at room temperature overnight, followed by quenching with methanol. The reaction solution was concentrated, added with water, extracted with dichloromethane for 3 times, washed with saturated NaCl solution, dried with anhydrous sodium sulfate, filtered, concentrated, and purified by column chromatography to obtain the title compound 59a (600 mg, 1.935 mmol) with a yield of 62.7%.

MS m/z (ESI): 310 $[M+1]^+$.

Step II 1-propyl-6-(4,4,5,5-tetramethyl-1,3,2-dioxaborolan-2-yl)-2',3',5',6'-tetrahydrospiro[dihydroindole-3,4'-pyran]59b The compound 59a (600 mg, 1.935 mmol) and bis(pinacolato)diboron (982 mg, 3.87 mmol) were dissolved in 1,4-dioxane (20 mL), [1,1'-bis(diphenylphosphino)ferrocene]dichloropalladium (141 mg, 0.01935 mmol) and potassium acetate (569 mg, 5.805 mmol) were added. The mixture was heated to 100° C. under the protection of nitrogen and stirred for 3 hours until the reaction was completed. The reaction solution was extracted with water and ethyl acetate, and the organic phase was washed with saturated NaCl solution, dried with anhydrous sodium sulfate, filtered, concentrated, and purified by column chromatography to obtain the title compound 59b (480 mg, 1.344 mmol) with a yield of 69.4%.

MS m/z (ESI): 358 $[M+1]^+$.

Step III N-((4,6-dimethyl-2-carbonyl-1,2-dihydropyridin-3-yl)methyl)-3-(ethyl(tetrahydro-2H-pyran-4-yl)amino)-6-fluoro-2-methyl-5-(1-propyl-2',3',5',6'-tetrahydrospiro[dihydroindole-3,4'-pyran]-6-yl) benzamide 59

The compound 59b (200 mg, 0.56 mol), $K_2CO_3$ (155 mg, 1.12 mmol), Pd(dppf)$Cl_2$ (41 mg, 0.056 mmol) and compound 58c (277 mg, 0.56 mmol) were dissolved in dioxane (15 mL) and $H_2O$ (5 mL). The mixture was heated to 100° C. under the protection of Ar and stirred for 6 hours until the reaction was completed. The reaction solution was extracted with water and ethyl acetate, and the organic phase was washed with saturated NaCl solution, dried with anhydrous sodium sulfate, filtered, concentrated, and purified by column chromatography to obtain the title compound 59 (106 mg, 0.164 mmol) with a yield of 29%.

$^1$H NMR (400 MHz, Methanol-d4) δ 7.19 (d, J=7.4 Hz, 1H), 7.06 (d, J=7.5 Hz, 1H), 6.67 (d, J=7.6 Hz. 1H), 6.51 (s, 1H), 6.08 (s, 1H), 4.48 (s, 2H), 3.91 (dt, J=13.4, 6.8 Hz, 4H), 3.69-3.54 (m, 2H), 3.36 (d, J=27.1 Hz, 4H), 3.05 (q, J=7.0 Hz, 5H), 2.36 (s, 3H), 2.23 (d, J=9.7 Hz, 6H), 1.94 (td, J=12.7, 12.2, 4.5 Hz, 21), 1.80-1.43 (m, 8H), 0.96 (t, J=7.4 Hz, 3H), 0.86 (t, J=7.0 Hz, 3H), MS m/z (ESI):645[M+1].

Example 60

N-((4,6-dimethyl-2-oxo-1,2-dihydropyridin-3-yl)methyl)-3-(ethyl(tetrahydro-2H-pyran-4-yl)amino)-6-fluoro-5-(1-isopropyl-2-oxo-2',3',5',6'-tetrahydrospiro[dihydroindole-3,4'-pyran]-6-yl)-2-methylbenzamide

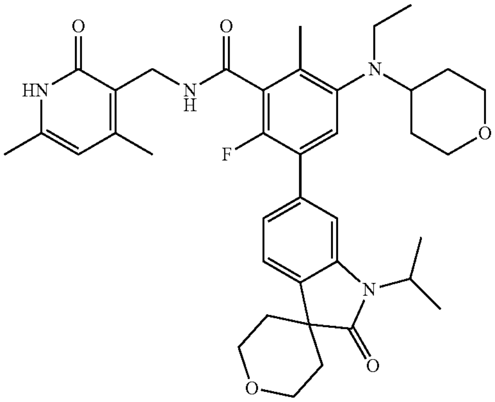

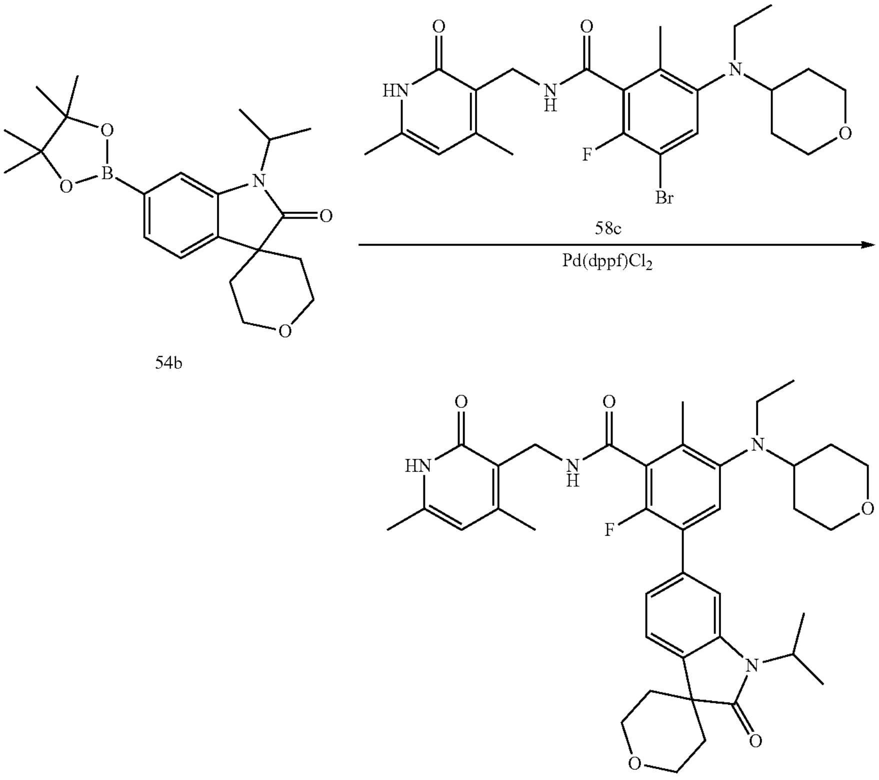

54b

60

Step I N-((4,6-dimethyl-2-oxo-1,2-dihydropyridin-3-yl)methyl)-3-(ethyl(tetrahydro-2H-pyran-4-yl)amino)-6-fluoro-5-(1-isopropyl-2-oxo-2',3',5',6'-tetrahydrospiro[dihydroindole-3,4'-pyran]-6-yl)-2-methylbenzamide 60

The compound 54b (1-isopropyl-6-(4,4,5,5-tetramethyl-1,3,2-dioxaborolan-2-yl)-2',3',5',6'-tetrahydrospiro[dihydroindole-3,4'-pyran]-2-one) (150 mg, 0.41 mmol) and compound 3-bromo-N-((4,6-dimethyl-2-oxo-1,2-dihydropyridin-3-yl)methyl)-5-(ethyl(tetrahydro-2H-pyran-4-yl)amino)-2-fluoro-6-methylbenzamide (200 mg, 0.41 mmol) were dissolved in a mixture of 1,4-dioxane and $H_2O$ (1,4-dioxane:$H_2O$=3:1, v/v, 20 mL), [1,1'-bis(diphenylphosphino)ferrocene]dichloropalladium (29 mg, 0.041 mmol) and potassium carbonate (111 mg, 0.80 mmol) were added. The mixture was heated to 100° C. under the protection of Ar and stirred for 2 hours. The reaction solution was cooled down, spin-dried, and the residue was extracted with ethyl acetate for 3 times, dried with anhydrous sodium sulfate, concentrated, and purified by thin-layer chromatography to obtain the title compound 60 (67 mg, yield 25%).

The synthesis process of compound 54b is similar to that of compound 58b in Example 58.

$^1$H NMR (400 MHz, Methanol-d4) δ 7.55 (d, J 7.7 Hz, 1H), 7.29-7.19 (m, 2H), 7.14 (d, J=7.7 Hz, 1H), 6.08 (s, 1H), 4.58 (p, J=7.0 Hz. 1H), 4.49 (s, 2H), 4.17 (dt J=11.7, 5.7 Hz, 2H), 3.90 (dq, J=12.0, 3.9, 3.0 Hz, 4H), 3.34 (dd, J=11.7; 2.1 Hz, 2H), 3.05 (dd, J=0.17.0, 9.7 Hz, 3H), 2.36 (s, 3H), 2.24 (d, J=19.5 Hz, 6H), 1.80 (t, J=54 Hz, 4H), 1.73 (d, J=12.9 Hz, 2H), 1.57 (tt, J=11.7, 5.9 Hz, 2H), 1.46 (d, J=7.0 Hz, 6H), 0.87 (t, J=7.0 Hz, 3H), MS m/z (ESI): 659.2 [M+H]$^+$.

Example 61 2-chloro-N-((4,6-dimethyl-2-oxo-1,2-dihydropyridin-3-yl)methyl)-5-(ethyl(tetrahydro-2H-pyran-4-yl)amino)-3-(1-ethyl-2-oxo-2',3',5',6'-tetrahydrospiro[dihydroindole-3,4'-pyran]-6-yl)-6-methylbenzamide

61

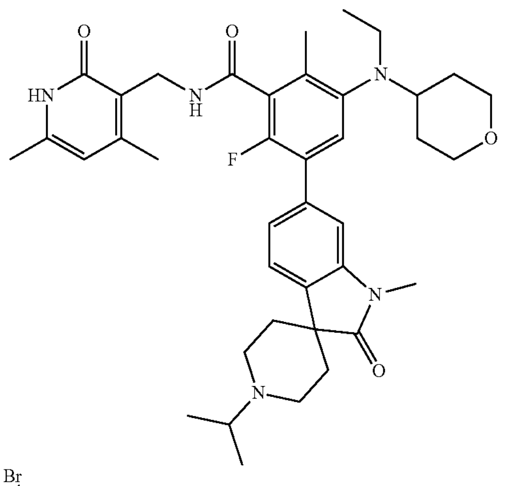

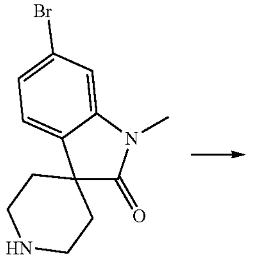

21a

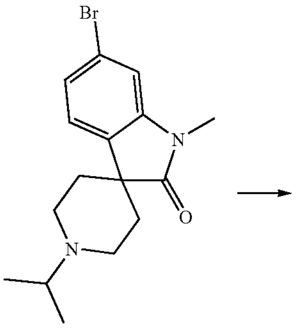

61a

-continued

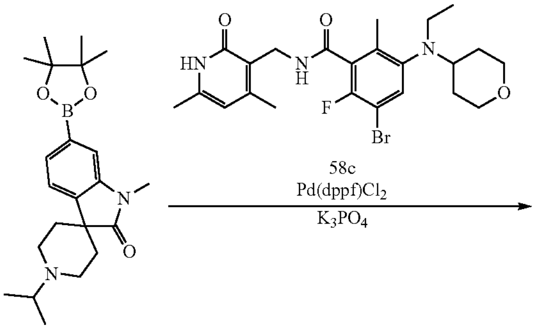

61b

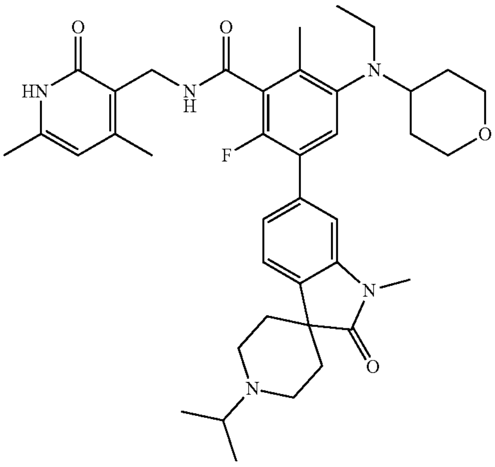

61

Step I 6-bromo-1'-isopropyl-1-methylspiro[dihydroindole-3,4'-piperidine]-2-one 61a The compound 21a (0.8 g, 1.96 mmol) and 2-iodopropane (0.66 g, 3.91 mmol) were dissolved in DMF (10 mL), followed by adding potassium carbonate (0.54 g, 3.91 mmol) and stirred at 70° C. for 4 hours. The reaction solution was concentrated and purified by flash column chromatography to obtain a compound 2 (0.5 g, 1.5 mmol) with a yield of 76%.

MS m/z (ESI): 337 [M+H]$^+$.

Step II 1'-isopropyl-1-methyl-6-(4,4,5,5-tetramethyl-1,3,2-dioxaborolan-2-yl)spiro[dihydroindole-3,4'-piperidine]-2-one 61b The compound 61a (0.5 g, 1.54 mmol), bis(pinacolato) diboron (0.59 g, 2.3 mmol), Pd(dppf)$Cl_2$ (100 mg, 0.15 mmol) and potassium acetate (0.45 g, 4.6 mmol) were added to 1,4-dioxane (10 mL), and the mixture was refluxed at 110° C. for 4 hours. The reaction solution was concentrated and purified by flash column chromatography to obtain a compound 61b (0.5 g, 1.3 mmol) with a yield of 89%.

MS m/z (ESI): 385 $[M+H]^+$.

Step III N-((4,6-dimethyl-2-oxo-1,2-dihydropyridin-3-yl)methyl)-3-(ethyl(tetrahydro-2H-pyran-4-yl)amino)-6-fluoro-5-(1'-isopropyl-1-methyl-2-oxospiro[dihydroindole-3,4'-piperidine]-6-yl)-2-methylbenzamide 61

The compound 61b (110 mg, 0.29 mmol), compound 58c (150 mg, 0.29 mmol), $Pd(dppf)Cl_2$ (22 mg, 0.03 mmol) and potassium phosphate (190 mg, 0.9 mmol) were added to 1,4-dioxane (10 mL) and $H_2O$ (1 mL), and the mixture was refluxed at 110° C. for 4 hours. The reaction solution was concentrated and purified by flash column chromatography to obtain a compound 61 (28 mg, 0.04 mmol) with a yield of 12%.

$^1$H NMR (400 MHz, Methanol-d4) δ 7.41 (d, J=7.7 Hz, 1H), 7.24 (dd, J=27.2, 7.6 Hz, 2H), 7.11 (s, 1H), 6.09 (s, 1H), 449 (s, 2H), 3.90 (d, J=11.6 Hz, 2H), 3.68 (s, 1H), 3.39-3.30 (m, 2H), 3.22 (s, 3H), 3.06 (dd, J=18.0, 10.8 Hz, 5H), 2.36 (s, 3H), 2.24 (d, 1=17.9 Hz, 7H), 2.04 (d, J=14.2 Hz, 2H), 1.73 (d, J=12.6 Hz, 2H), 1.57 (d, J=12.3 Hz, 2H), 1.40-1.22 (m, 9H), 0.87 (t, J=7.0 Hz, 3H), MS m/z (ESI): 672 $[M+H]^+$.

Example 62 N-((4,6-dimethyl-2-oxo-1,2-dihydropyridin-3-yl)methyl)-3-(ethyl(tetrahydro-2H-pyran-4-yl)amino)-5-(1-ethyl-2-oxo-2',3',5',6'-tetrahydrospiro[dihydroindole-3,4'-pyran]-6-yl)-6-fluoro-2-methylbenzamide

62

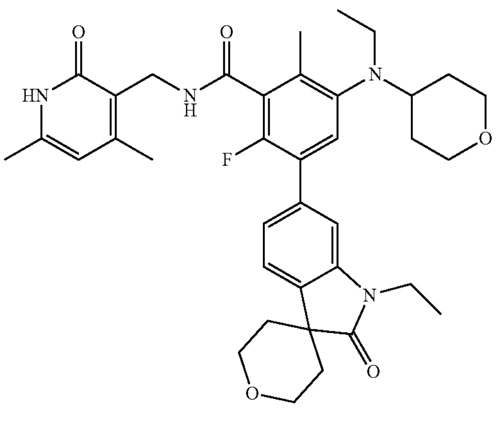

-continued

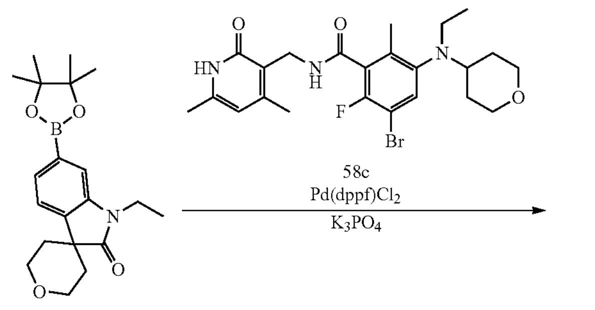

62a

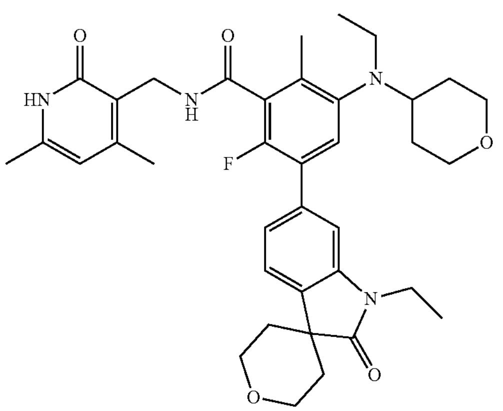

62

Step I N-((4,6-dimethyl-2-oxo-1,2-dihydropyridin-3-yl)methyl)-3-(ethyl(tetrahydro-2H-pyran-4-yl)amino)-5-(1-ethyl-2-oxo-2',3',5',6'-tetrahydrospiro[dihydroindole-3,4'-pyran]-6-yl)-6-fluoro-2-methylbenzamide 62

The compound 62a (107 mg, 0.29 mmol), compound 58c (150 mg, 0.29 mmol), $Pd(dppf)Cl_2$ (22 mg, 0.03 mmol) and potassium phosphate (190 mg, 0.9 mmol) were added to 1,4-dioxane (10 mL) and $H_2O$ (1 mL), and the mixture was refluxed at 110° C. for 4 hours. The reaction solution was concentrated and purified by flash column chromatography to obtain a compound 62 (100 mg, 0.15 mmol) with a yield of 51%.

$^1$H NMR (400 MHz, Methanol-$d_4$) δ 7.57 (d, J=7.8 Hz, 1H), 7.27 (d, J=7.4 Hz, 11H), 719-7.08 (m, 2H), 6.09 (s, 1H), 4.49 (s, 2H), 4.18 (ddd, J=11.6, 6.9, 4.6 Hz, 2H), 3.92 (td. J=12.7, 11.7, 6.6 Hz, 4H), 3.78 (q. J=7.2 Hz 2H), 3.33 (t, J=11.4 Hz, 3H): 3.13-2.97 (mi, 3H), 2.36 (s, 3H), 2.24 (d, J=19.5 Hz, 6H), 183 (s, 3H), 1.73 (d, J=12.7 Hz, 2H), 1.57 (qd, J=11.6, 4.1 Hz, 2H), 1.29-1.17 (m, 3H), 0.87 (t, J=7.0 Hz, 3H), MS m/z (ESI): 645$[M+H]^+$.

Example 63 N-((4,6-dimethyl-2-oxo-1,2-dihydropyridin-3-yl)methyl)-3-(ethyl(tetrahydro-2H-pyran-4-yl)amino)-6-fluoro-5-(1-isopropyl-2',3',5',6'-tetrahydrospiro[dihydroindole-3,4'-pyran]-6-yl)-2-methylbenzamide

63

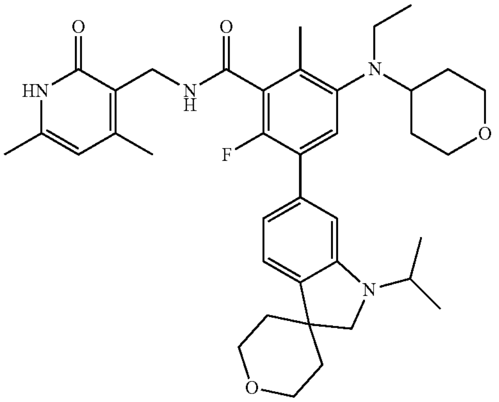

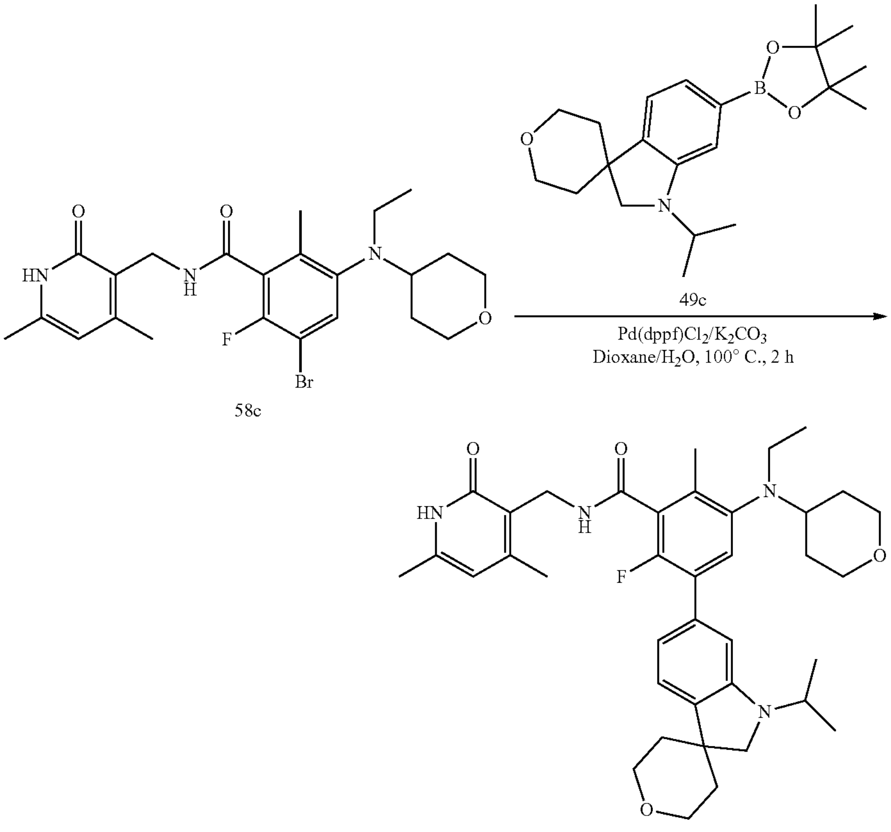

49c

58c

63

Step I N-((4,6-dimethyl-2-oxo-1,2-dihydropyridin-3-yl)methyl)-3-(ethyl(tetrahydro-2H-pyran-4-yl)amino)-6-fluoro-5-(1-isopropyl-2',3',5',6'-tetrahydrospiro[dihydroindole-3,4'-pyran]-6-yl)-2-methylbenzamide 63

The compound 58c (100 mg, 0.202 mmol) was dissolved in 3 mL of 1,4-dioxane, the compound 49c (72 mg, 0.202 mmol), Pd(dppf)$Cl_2$ (14.7 mg, 0.0202 mmol), potassium carbonate (56 mg, 0.404 mmol) and 1 mL of water were successively added. The mixture was then heated to 100° C. under the protection of nitrogen and reacted for 2 hours. After cooling to room temperature, the reaction solution was diluted with 3 mL of water and extracted with EA (5 mL×3). The organic phases were combined, washed with saturated NaCl solution, dried, mixed, and purified by column chromatography (methanol: dichloromethane=0%-10%) to obtain a white solid of the title compound 63 (41 mg, 0.0636 mmol) with a yield of 31.5%.

$^1$H NMR (400 MHz, Methanol-d4) δ 7.19 (d, J=7.5H, 1H), 705 (d, J=7.6 Hz, 1), 6.66 (dt, J=7.5, 1.3 Hz, 1H), 6.52 (d, J=1.9 Hz, 1H), 6.08 (s, 1H), 4.48 (s, 2H), 3.97-3.81 (m, 5H), 3.61 (td, J=11.9.2.1 Hz, 2H), 3.41-3.30 (m, 4H), 3.08-2.94 (m, 3H), 2.36 (s, 3H), 2.23 (d, J=9.6 Hz, 6H), 1.93 (td, J=12.9, 4.6 Hz, 2H), 1.72 (d, J=12.9 Hz, 2H), 1.65-1.49 (m, 4H), 1.6 (d, J=6.6 Hz, 6H), 0.86 (t, J=7.1 Hz, 3H), MS m/z (ESI): 645.3 $[M+H]^+$.
Example 64 3-((2,2-dimethyltetrahydro-2H-pyran-4-yl)(ethyl)amino)-5-(1-isopropyl-2-carbonyl-2',3',5',6'-tetrahydrospiro[dihydroindole-3,4'-pyran]-6-yl)-N-((4-methoxy-6-methyl-2-carbonyl-1,2-dihydropyridin-3-yl)methyl)-2-methylbenzamide
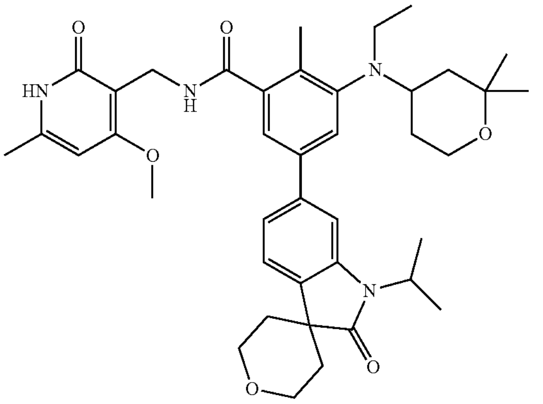
64
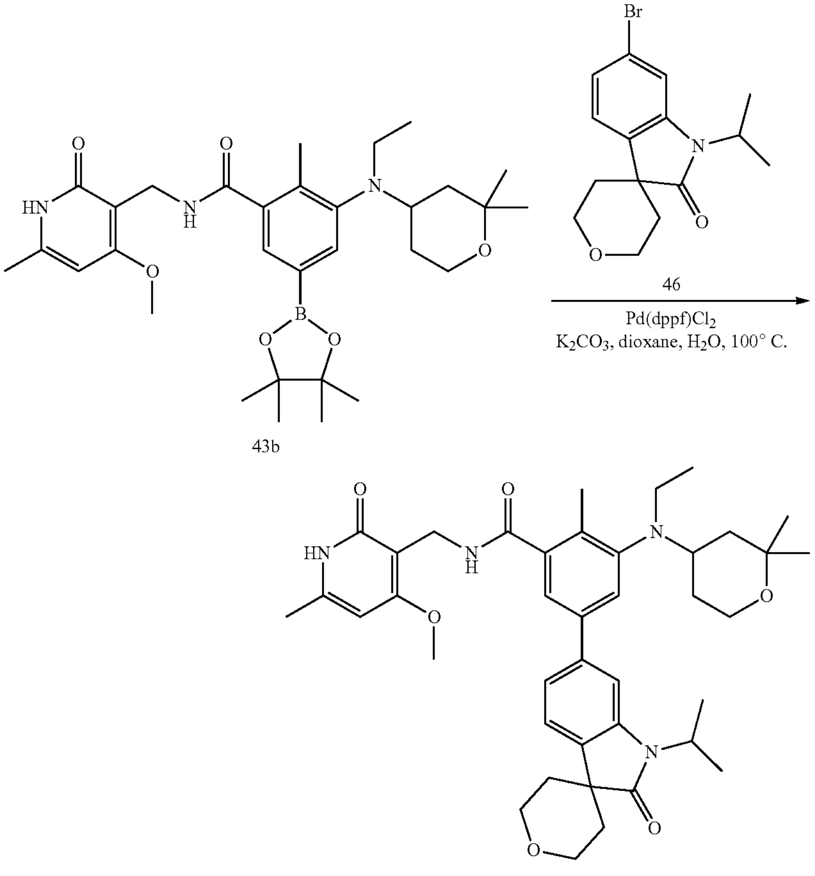

Step I 3-((2,2-dimethyltetrahydro-2H-pyran-4-yl)(ethyl)amino)-5-(1-isopropyl-2-carbonyl-2',3',5',6'-tetrahydrospiro[dihydroindole-3,4'-pyran]-6-yl)-N-((4-methoxy-6-methyl-2-carbonyl-1,2-dihydropyridin-3-yl)methyl)-2-methylbenzamide 64

The compound 43b (100 mg, 0.176 mol), $K_2CO_3$ (48 mg, 0.352 mmol), $Pd(dppf)Cl_2$ (13 mg, 0.0176 mmol), compound 46a (57 mg, 0.176 mmol) were dissolved in dioxane (15 mL) and $H_2O$ (5 mL). The mixture was heated to 100° C. under the protection of Ar and stirred for 6 hours until the reaction was completed. The reaction solution was extracted with water and ethyl acetate, and the organic phase was washed with saturated NaCl solution, dried with anhydrous sodium sulfate, filtered, concentrated, and purified by column chromatography to obtain the title compound 64 (58 mg, 0.084 mmol) with a yield of 48%.

$^1H$ NMR (400 MHz, Methanol-$d_4$) δ 7.54 (d, J=7.9 Hz, 1H), 7.41 (s, 1H), 7.30 (d, J=1.9 Hz, 1H), 7.25 (d, J=4.0 Hz, 2H), 6.25 (s, 1H), 4.59 (dd, J=14.1, 7.3 Hz, 1H), 4.46 (s, 2H), 4.24-4.13 (m, 2H), 3.91 (s, 5H), 3.65 (dt, J=24.4, 11.3 Hz, 2H), 3.13 (d, J=13.4 Hz, 4H), 2.31 (d, J=14.9 Hz, 6H), 1.93-1.61 (m, 6H), 1.49 (d, J=7.0 Hz, 7H), 1.17 (s, 61H), 0.88 (t, J=6.9 Hz, 3H), MS m/z (ESI):685.3[M+1]$^+$.

Example 65 N-((4,6-dimethyl-2-oxo-1,2-dihydropyridin-3-yl)methyl)-3-(ethyl(tetrahydro-2H-pyran-4-yl)amino)-5-(1-isopropyl-2',3',5',6'-tetrahydrospiro[dihydroindole-3,4'-pyran]-6-yl)-2-methylbenzamide

65

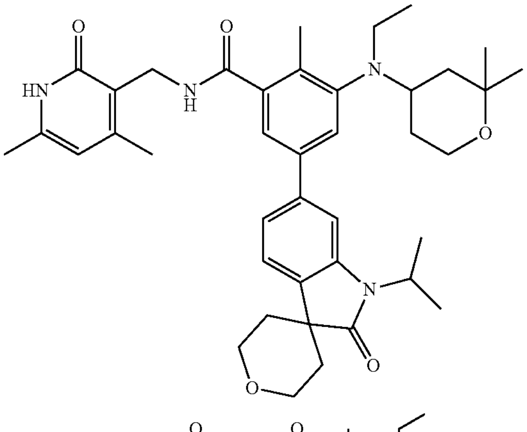

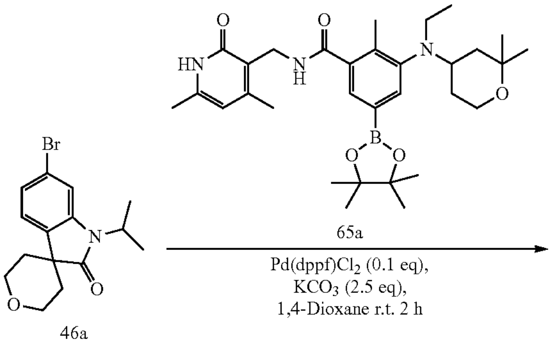

65a

46a

-continued

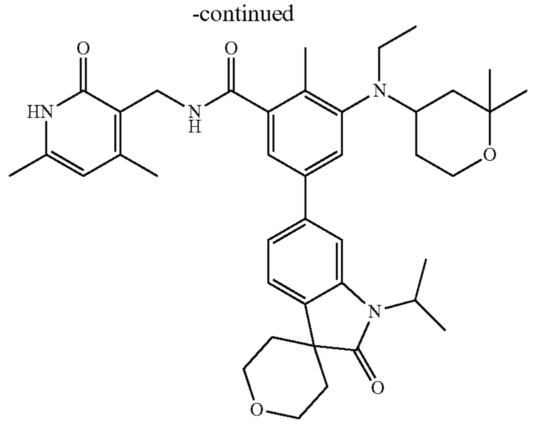

65

Step I N-((4,6-dimethyl-2-oxo-1,2-dihydropyridin-3-yl)methyl)-3-(ethyl(tetrahydro-2H-pyran-4-yl)amino)-5-(1-isopropyl-2',3',5',6'-tetrahydrospiro[dihydroindole-3,4'-pyran]-6-yl)-2-methylbenzamide 65

The compound 46a (150 mg, 0.462 mmol), compound 65a (233 mg, 0.462 mmol), $Pd(dppf)Cl_2$ (34 mg, 0.0462 mmol) and potassium carbonate (191 mg, 1.386 mmol) were dissolved in 1 mL of water and 4 mL of 1,4-dioxane. The reaction system was replaced with nitrogen, heated to 110° C. and reacted for 2 hours. The reaction solution was added with 30 mL of water and extracted with EA (30 mL×3). The organic phases were combined, washed with saturated NaCl solution (30 mL×3), dried, mixed, and purified by column chromatography (methanol: dichloromethane=1: 15) to obtain the title compound 65 (35 mg, 0.050 mmol) with a yield of 10.8%.

$^1H$ NMR (400 MHz. DMSO-$d_4$) δ 11.42 (s, H), 8.18 (s, 1H), 7.57 (d, J=7.7 Hz, 1H), 7.33 (d, J=1.9 Hz, 1H), 7.25-7.08 (m, 3H), 5.82 (s, 1H), 4.55 (p, J=6.9 Hz, 1H), 426 (s, 2H, 4.04 (dd, J=11.2, 4.9 Hz, 2H), 3.88-3.73 (m, 2H), 3.64-3.41 (m, 2H), 3.29 (s, 3H), 3.25-2.88 (m, 4H), 2.35-1.95 (m, 9H), 1.64 (d, J=44.0 Hz, 51), 1.44-1.25 (m, 6H), 1.09 (s, 5H), 0.76 dt, J=26.4, 6.9 Hz, 3H),

MS m/z (ESI): 689 [M+H]$^+$.

Example 66 N-((4,6-dimethyl-2-oxo-1,2-dihydropyridin-3-yl)methyl)-3-(ethyl(tetrahydro-2H-pyran-4-yl)amino)-2-methyl-5-(2-oxo-2',3',5',6'-tetrahydrospiro[dihydroindole-3,4'-pyran]-6-yl)benzamide

66

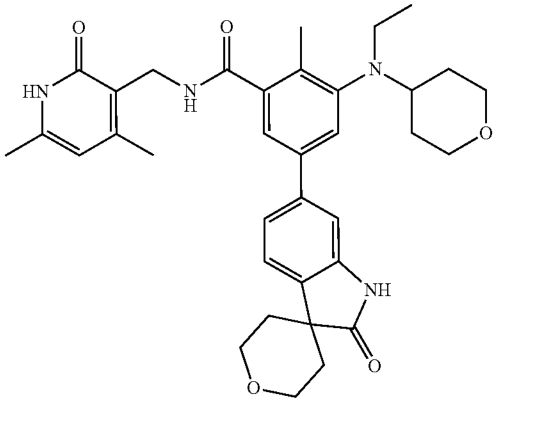

-continued

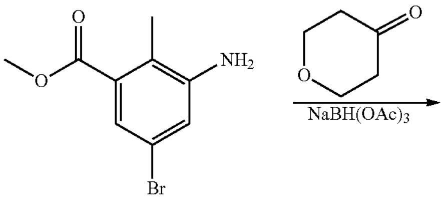

66a-1

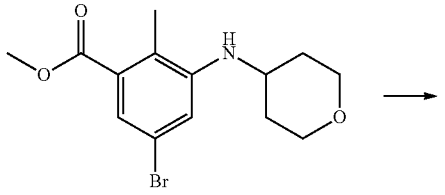

66a-2

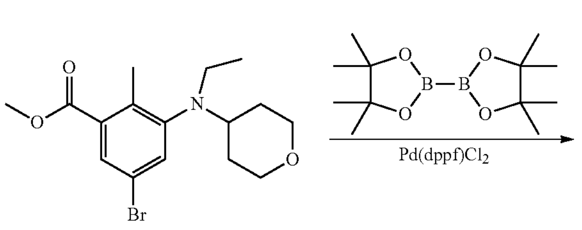

66a-3

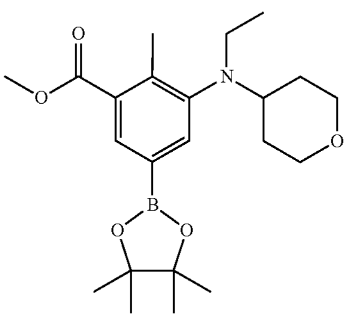

66a

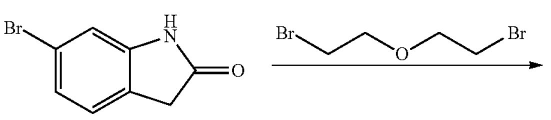

66b

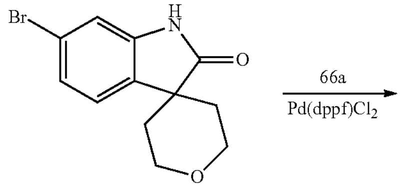

66c

-continued

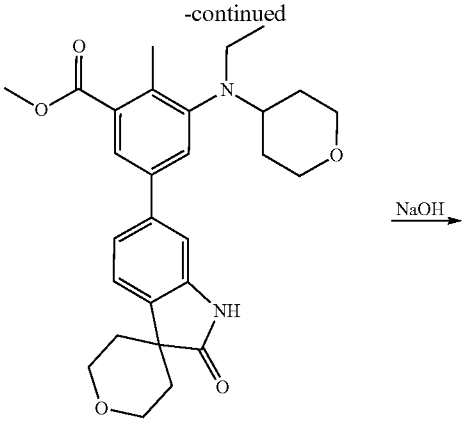

66d

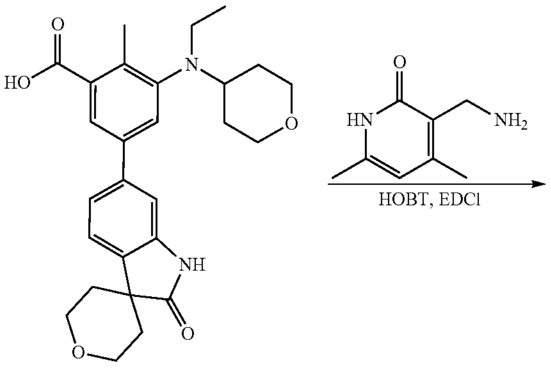

66e

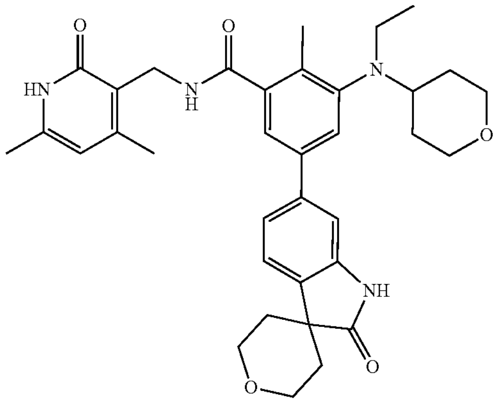

66

Step I Methyl 5-bromo-2-methyl-3-((tetrahydro-2H-pyran-4-yl)amino)benzoate 66a-2

The compound 66a-1 (2.3 g, 9.4 mmol) was dissolved in 1,2-dichloroethane (5.0 mL), acetic acid (2.83 g, 47.2 mmol) and tetrahydro-4H-pyran-4-one (1.4 g, 14.2 mmol) were added. The mixture was stirred at room temperature for 30 minutes, added with sodium borohydride acetate (3.0 g, 14.2 mmol) followed by stirring at room temperature for 3.5 hours until the reaction was completed. The reaction solution was quenched with water, extracted with dichloromethane for three times, washed with saturated NaCl solution, dried with anhydrous sodium sulfate, filtered, concentrated, and purified by plate chromatography to obtain the title compound 66a-2 (2.6 g, 7.9 mmol) with a yield of 84%.

Step II Methyl 5-bromo-3-(ethyl(tetrahydro-2H-pyran-4-yl)amino)-2-methylbenzoate 66a-3

The compound 66a-2 (2.0 g, 6.1 mmol) was dissolved in 1,2-dichloroethane (5.0 mL), acetic acid (2.2 g, 36.7 mmol) and acetaldehyde (0.7 mL, 12.2 mmol) were added. The mixture was stirred at room temperature for 30 minutes, added with sodium borohydride acetate (3.9 g, 18.4 mmol) followed by stirring at room temperature for 3 hours until the reaction was completed. The reaction solution was quenched with water, extracted with dichloromethane for three times, washed with saturated NaCl solution, dried with anhydrous sodium sulfate, filtered, concentrated, and purified by plate chromatography to obtain the title compound 66a-3 (2.0 g, 5.62 mmol) with a yield of 92%.

Step III Methyl 3-(ethyl(tetrahydro-2H-pyran-4-yl)amino)-2-methyl-5-(4,4,5,5-tetramethyl-1,3,2-dioxaborolan-2-yl)benzoate 66a The compound 66a-3 (methyl 5-bromo-3-(ethyl(tetrahydro-2H-pyran-4-yl)amino)-2-methylbenzoate) (2.0 g, 5.63 mmol) and bis(pinacolato)diboron (2.2 g, 8.45 mmol) were dissolved in 1,4-dioxane (20 mL), [1,1'-bis(diphenylphosphino)ferrocene]dichloropalladium (0.82 g, 1.13 mmol) and potassium acetate (1.7 g, 16.9 mmol) were added. The mixture was heated to 100° C. under the protection of nitrogen and stirred for 2 hours until the reaction was completed. The reaction solution was extracted with water and ethyl acetate, the organic phase was washed with saturated NaCl solution, dried with anhydrous sodium sulfate, filtered, concentrated, and purified by column chromatography to obtain the title compound 66a (1.6 g, 7.6 mmol) with a yield of 70%.

Step IV 6-bromo-2',3',5',6'-tetrahydrospiro[dihydroindole-3,4'-pyran]-2-one 66c

The compound 66b (6-bromo-dihydroindole-2-one) (1.0 g, 4.74 mmol) was dissolved in tetrahydrofuran (20 mL), and lithium bis(trimethylsilyl)amide (23.7 mL, 23.7 mmol) was slowly added dropwise at −78° C. The mixture was stirred at this temperature for 30 minutes, followed by adding 2,2'-dibromodiethyl ether (1.3 g, 5.69 mmol) and slowly heating to 70° C. and stirring for 6 hours. After the reaction was completed, it was quenched with water under ice water bath, and the reaction solution was extracted by water and ethyl acetate. The organic phase was washed with saturated NaCl solution, dried with anhydrous sodium sulfate, filtered, concentrated, and purified by column chromatography to obtain the title compound 66c (400 mg, 0.84 mmol) with a yield of 30%.

Step V Methyl 3-(ethyl(tetrahydro-2H-pyran-4-yl)amino)-2-methyl-5-(2-oxo-2',3',5',6'-tetrahydrospiro[dihydroindole-3,4'-pyran]-6-yl)benzoate 66d The compound 66c (84 mg, 0.30 mmol) and methyl 3-(ethyl(tetrahydro-2H-pyran-4-yl)amino-2-methyl-5-(4,4,5,5-tetramethyl-1,3,2-dioxaborolan-2-yl)benzoate (120 mg, 0.3 mmol) were dissolved in 1,4-dioxane (2.0 mL), and [1,1'-bis(diphenylphosphino)ferrocene]dichloropalladium (44 mg, 0.06 mmol) and potassium carbonate (124 mg, 0.9 mmol) were added, the mixture was heated to 100° C. under the protection of nitrogen and stirred for 2 hours. The reaction solution was cooled down, spin-dried, extracted with dichloromethane for three times, washed with saturated NaCl solution, dried with anhydrous sodium sulfate, filtered, concentrated, and purified by plate chromatography to obtain the title compound 66d (110 mg, 0.23 mmol) with a yield of 77%.

Step VI 3-(ethyl(tetrahydro-2H-pyran-4-yl)amino)-2-methyl-5-(2-oxo-2',3'.5',6'-tetrahydrospiro[dihydroindole-3,4'-pyran]-6-yl)benzoic acid 66e The compound 66d (110 mg, 0.15 mmol) was dissolved in methanol (4.0 mL), sodium hydroxide (61 mg, 1.5 mmol) and water (1.0 mL) were added. The mixture was stirred at room temperature for 4 hours until the reaction was completed. The reaction solution was neutralized to pH=6-7 with hydrochloric acid, extracted with dichloromethane for three times, washed with saturated NaCl solution, dried with anhydrous sodium sulfate, filtered, concentrated, and purified by plate chromatography to obtain the title compound 66e (60 mg, 0.11 mmol) with a yield of 56%.

MS m/z (ESI): 465 $[M+H]^+$.

Step VII N-((4,6-dimethyl-2-oxo-1,2-dihydropyridin-3-yl)methyl)-3-(ethyl(tetrahydro-2H-pyran-4-yl)amino)-2-methyl-5-(2-oxo-2',3',5',6'-tetrahydrospiro[dihydroindole-3,4'-pyran]-6-yl)benzamide 66

The compound 66e (60 mg, 0.13 mmol) and 3-(aminomethyl)-4,6-dimethyl-1H-pyridin-2-one hydrochloride (29 mg, 0.16 mmol) was dissolved in N,N-dimethylformamide (2.0 mL), and 1-(3-dimethylaminopropyl)-3-ethylcarbodiimide hydrochloride (50 mg, 0.26 mmol), 1-hydroxybenzotriazole (18 mg, 0.13 mmol) and triethylamine (40 mg, 0.39 mmol) were added. The mixture was heated to 60° C. and stirred for 4 hours until the reaction was completed. The reaction solution was washed with water, extracted with dichloromethane for three times, washed with saturated NaCl solution, dried with anhydrous sodium sulfate, filtered, concentrated, and purified by plate chromatography to obtain the title compound 66 (16.0 mg, 0.027 mmol) with a yield of 21%.

$^1$H NMR (400 MHz, DMSO) δ 11.43 (s, 1H), 10.40 (s, 1H), 8.19 (s, 1H), 7.55-7.54 (d, J=7.6 Hz, 1H), 7.31 (s, 1H), 7.17-7.15 (d, J=8.8 Hz, 1H), 7, 2 (s, 1H), 7.0 (s, 1H), 5.82 (s, 1H), 4.26-4.25 (d, J=4.8 Hz, 2H), 4.00 (m, 2H), 3.81 (m, 4H), 3.24-3.18 (t, J=11.6 Hz, 2H), 3.05-(n, 3H), 2.21 (s, 3H), 2.16 (s, 3H), 2.07 (s, 3H), 1.71 (m, 6H), 1.63 (m, 2H), 0.81-0.78 (t, J=6.8 Hz, 3H),

MS n/z (ESI): 599 $[M+H]^+$,

Example 67 N-((4,6-dimethyl-2-oxo-1,2-dihydropyridin-3-yl)methyl)-3-(ethyl(tetrahydro-2H-pyran-4-yl)amino)-2-methyl-5-(2',3',5',6'-tetrahydrospiro[dihydroindole-3,4'-pyran]-6-yl)benzamide

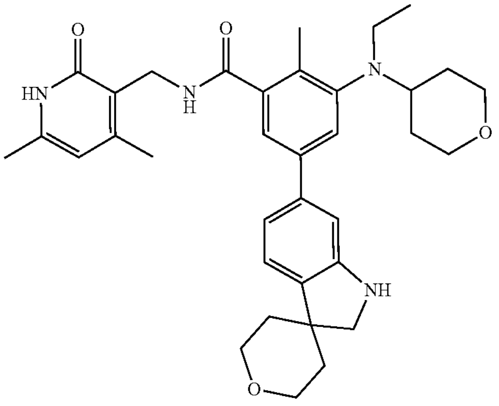

67

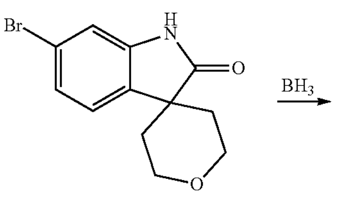

66c

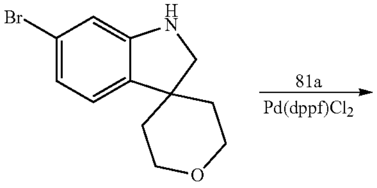

67a

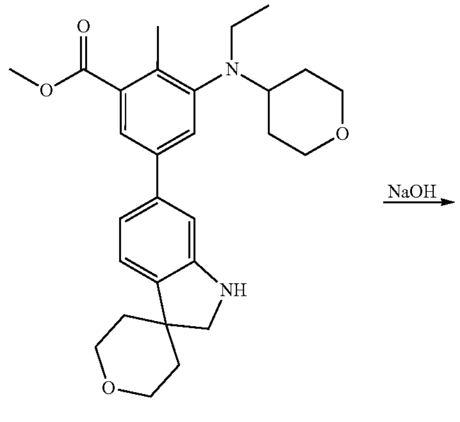

67b

-continued

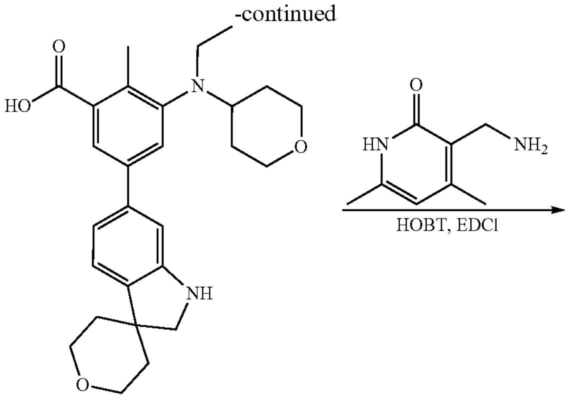

67c

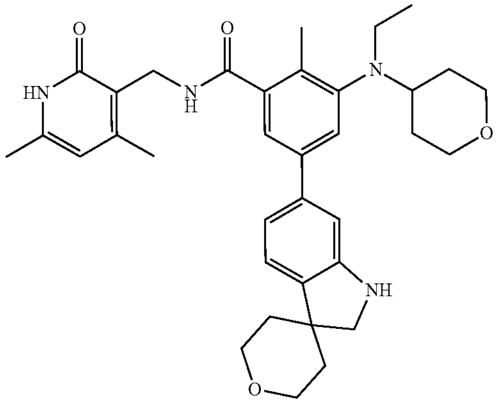

67

Step I 6-bromo-2',3',5',6'-tetrahydrospiro[dihydroindole-3,4'-pyran]67a

The compound 66c (6-bromo-2',3',5',6'-tetrahydrospiro[dihydroindole-3,4'-pyran]-2-one) (200 mg, 0.71 mmol) was dissolved in anhydrous tetrahydrofuran (20 mL), and borane tetrahydrofuran solution was added slowly dropwise under ice bath. The mixture was stirred at room temperature for 2 hours until the reaction was completed. The reaction solution was added with methanol slowly dropwise under ice bath for quenching the reaction, extracted with water and ethyl acetate, and the organic phase was washed with saturated NaCl solution, dried with anhydrous sodium sulfate, filtered, concentrated, and purified by column chromatography to obtain the title compound 67a (160 mg, 0.6 mmol) with a yield of 81%.

A similar method of Example 66 was used to obtain the title compound 67 (16.0 mg, 0.027 mmol) with a yield of 21%, wherein the compound 66c was replaced with compound 67a.

$^1$H NMR (400 MHz, DMSO) δ 11.43 (s, 1H), 8.15 (s, 1H), 7.24 (s, 1H), 707 (s, 1H), 7.04 (s, 1H), 6.74-6.72 (d, J=11.2 Hz, 1H), 6.64 (s, Ili), 5.82 (s, 1H), 5.62 (s, 1H), 4.25-4.24 (d, J=3.2 Hz, 2H), 3.80-3.77 (d, J=11.2 Hz, 4H), 3.47-3.40 (t, J=1.6 Hz, 4H), 3.23-3.18 (t, J=7.6 Hz, 2H), 31.04-(n, 3H), 2.19 (s, 3H), 2.16-(s, 3H), 2.07 (s, 3H), 1.71 (m, 2H), 1.63 (m, 2H), 1.50 (m, 2H), 0.80-0.77 (t, J=6.8 Hz, 3H),

MS m/z (ESI): 585 [M+H]$^+$.

Example 68 N-((4,6-dimethyl-2-oxo-1,2-dihydropyridin-3-yl)methyl)-3-(ethyl(tetrahydro-2H-pyran-4-yl)amino)-2-methyl-5-(1'-methyl-2-oxospiro[dihydroindole-3,4'-piperidine]-6-yl)benzamide
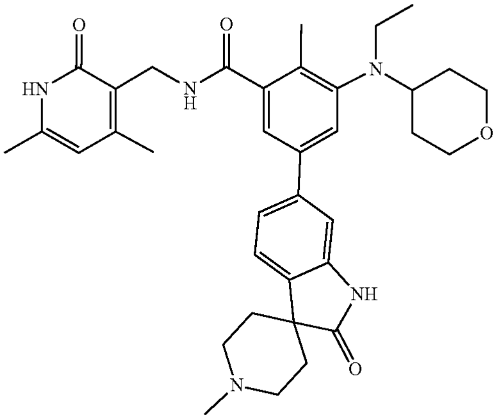
68
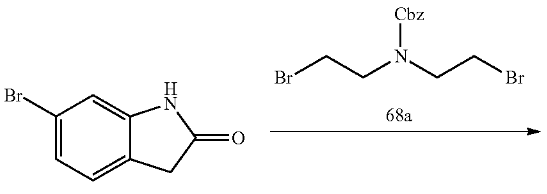
66b
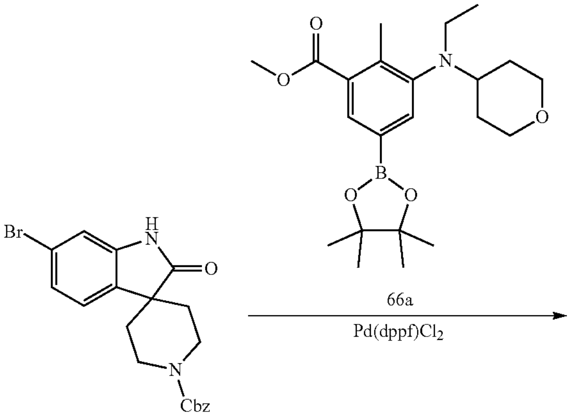
68b
-continued
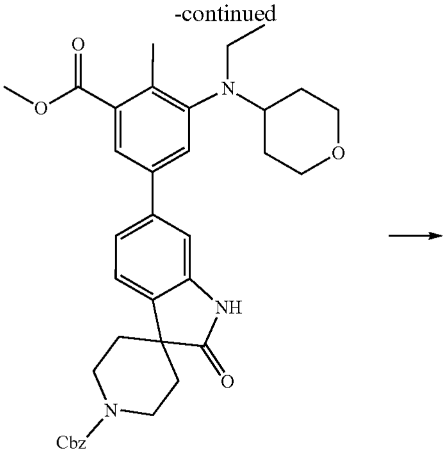
68c
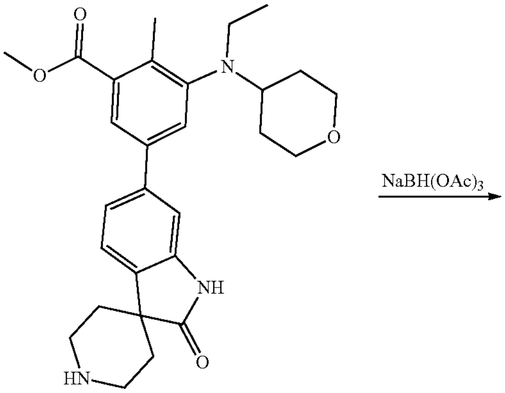
68d
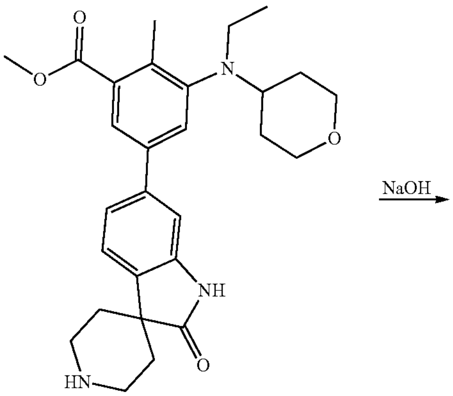
68a -continued

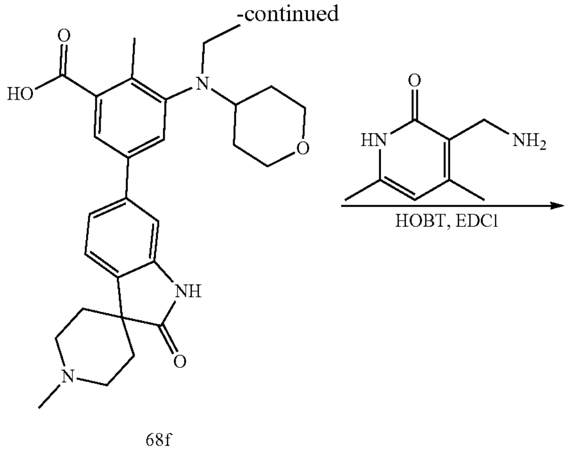

68f

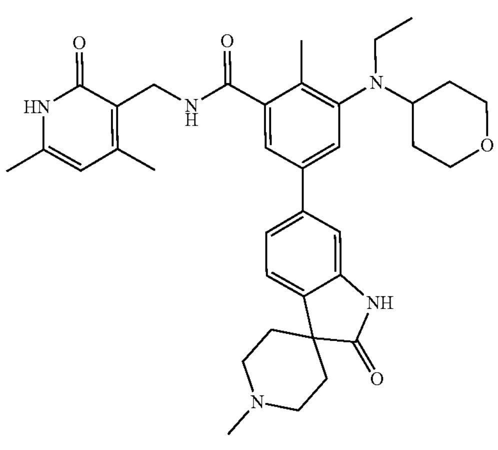

68

Step I Benzyl 6-bromo-2-oxospiro[dihydroindole-3,4'-piperidine]-1'-carboxylate 68b The compound 66b (6-bromo-1,3-dihydro-2H-indol-2-one) (2.9 g, 1.38 mmol) was dissolved in tetrahydrofuran (100 mL), and lithium bis(trimethylsilyl)amide (28 mL, 5.51 mmol) was slowly added dropwise at −78° C. The mixture was stirred at this temperature for 30 minutes, followed by adding benzyl bis(2-bromoethyl)carbamate (5.0 g, 1.38 mmol), slowly heating to 80° C. and stirring for 1 hour. After the reaction was completed, it was quenched with water under ice water bath, and the reaction solution was extracted by water and ethyl acetate. The organic phase was washed with saturated NaCl solution, dried with anhydrous sodium sulfate, filtered, concentrated, and purified by column chromatography to obtain the title compound 68b (700 mg, 1.69 mmol) with a yield of 12.3%.

Step II Benzyl 6-(3-(ethyl(tetrahydro-2H-pyran-4-yl)amino)-5-(methoxycarbonyl)-4-methylphenyl)-2-oxospiro[dihydroindole-3,4'-piperidine]-1'-carboxylate 68c The compound 68b (700 mg, 1.69 mmol) and compound 66a (methyl 3-(ethyl(tetrahydro-2H-pyran-4-yl)amino-2-methyl-5-(4,4,5,5-tetramethyl-1,3,2-dioxaborolan-2-yl)benzoate) (681 mg, 1.69 mmol) were dissolved in 1,4-dioxane (10.0 mL), [1,1'-bis(diphenylphosphino)ferrocene]dichloropalladium (247 mg, 0.338 mmol) and potassium carbonate (466 mg, 3.38 mmol) were added, the mixture was heated to 110° C. under the protection of nitrogen and stirred for 2 hours. The reaction solution was cooled down, spin-dried, extracted with dichloromethane for three times, washed with saturated NaCl solution, dried with anhydrous sodium sulfate, filtered, concentrated, and purified by plate chromatography to obtain the title compound 68c (210 mg, 0.344 mmol) with a yield of 20%.

Step III Methyl 3-(ethyl(tetrahydro-2H-pyran-4-yl)amino)-2-methyl-5-(2-oxospiro[dihydroindole-3,4'-piperidine]-6-yl)benzoate 68d The compound 68c (210 mg, 0.344 mmol) was dissolved in tetrahydrofuran (10.0 mL), and Pd/C (200 mg) was added. The reaction system was replaced with $H_2$ and stirred at room temperature for 2 hours until the reaction was completed. The reaction solution was filtered, concentrated to obtain the title compound 68d (150 mg, 0.314 mmol) with a yield of 91.5%.

Step IV Methyl 3-(ethyl(tetrahydro-2H-pyran-4-yl)amino)-2-methyl-5-(1'-methyl-2-oxospiro[dihydroindole-3,4'-piperidine]-6-yl)benzoate 68e The compound 68d (50 mg, 0.105 mmol) was dissolved in 1,2-dichloroethane (5.0 mL), and acetic acid (40 mg, 0.63 mmol) and paraformaldehyde (100 mg) were added. The mixture was stirred at room temperature for 30 minutes, and was added with sodium borohydride acetate (67 mg, 0.315 mmol) followed by stirring at room temperature for 4 hours until the reaction was completed. The reaction solution was quenched with water, extracted with dichloromethane for three times, washed with saturated NaCl solution, dried with anhydrous sodium sulfate, filtered, concentrated, and purified by plate chromatography to obtain the title compound 68e (50 g, 0.102 mmol) with a yield of 97%.

Step V 3-(ethyl(tetrahydro-2H-pyran-4-yl)amino)-2-methyl-5-(1'-methyl-2-oxospiro[dihydroindole-3,4'-piperidine]-6-yl)benzoic acid 68f The compound 68e (50 mg, 0.102 mmol) was dissolved in methanol (5.0 mL), sodium hydroxide (41 mg, 1.05 mmol) and water (1.0 mL) were added. The mixture stirred at room temperature for 4 hours until the reaction was completed. The reaction solution was neutralized to pH=6-7 with hydrochloric acid, extracted with dichloromethane for three times, washed with saturated NaCl solution, dried with anhydrous sodium sulfate, filtered, concentrated, and purified by plate chromatography to obtain the title compound 68f (40 mg, 0.084 mmol) with a yield of 82.3%.

Step VI N-((4,6-dimethyl-2-oxo-1,2-dihydropyridin-3-yl)methyl)-3-(ethyl(tetrahydro-2H-pyran-4-yl)amino)-2-methyl-5-(1'-methyl-2-oxospiro[dihydroindole-3,4'-piperidine]-6-yl)benzamide 68

The compound 68f (40 mg, 0.084 mmol) and 3-(aminomethyl)-4,6-dimethyl-1H-pyridin-2-one hydrochloride (19 mg, 0.10 mmol) was dissolved in N,N-dimethylformamide (2.0 mL), 1-(3-dimethylaminopropyl)-3-ethylcarbodiimide hydrochloride (32 mg, 0.168 mmol), 1-hydroxybenzotriazole (11 mg, 0.084 mmol) and triethylamine (42 mg, 0.42 mmol) were added. The mixture was heated to 50° C. and stirred for 2 hours until the reaction was completed. The reaction solution was washed with water, extracted with dichloromethane for three times, washed with saturated NaCl solution, dried with anhydrous sodium sulfate, filtered, concentrated, and purified by plate chromatography to obtain the title compound 68 (3.0 mg, 0.027 mmol) with a yield of 6%.

$^1$H NMR (400 MHz, DMSO-d6) δ 11.44 (s, 1H), 10.46 (s, 1H), 8.19 (t, J=5.0 Hz, 1H), 7.49 (d, J=7.7 Hz, 11-H), 7.34 (d, J=1.8 Hz, 1H), 7.20 (dd, J=7.8, 1.7 Hz, 1H), 7.16 (d, J=1.7 I-z, 1H), 7.04 (d, J=1.6 Hz, 1H), 5.86 (s, 1H), 4.29 (d, J=4.9 Hz, 2H), 3.83 (d, J=11.5 Hz, 2H), 3.06 (dq, J=16.8, 5.5, 4.3 Hz, 6H), 2.81 (s, 2H), 2.22 (d, J=17.1 Hz, 614), 2.11 (s, 3H), 1.89 (d, J=15.2 Hz, 4H), 1.66 (d, J=11.6 Hz, 2H), 154 (dt, J=12.1, 5.8 Hz, 3H), 1.24 (d, J=2.3 Hz, 3H), 0.83 (t, J=7.0 Hz, 3H),

MS m/z (ESI): 612.3 [M+H]$^+$.

Example 69 5-(1'-(cyclopropylmethyl)-2-oxospiro[dihydroindole-3,4'-piperidine]-6-yl)-N-((4,6-dimethyl-2-oxo-1,2-dihydropyridin-3-yl)methyl)-3-(ethyl(tetrahydro-2H-pyran-4-yl)amino)-2-methylbenzamide

69

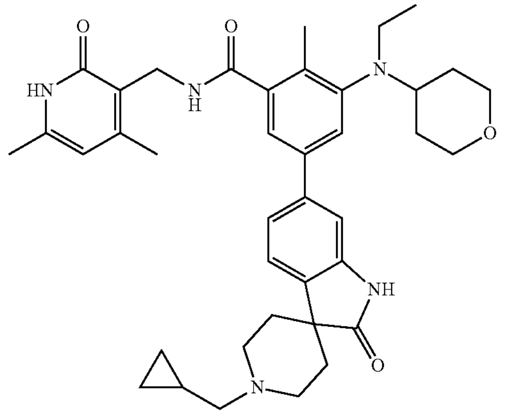

A similar method of Example 68 was used to obtain the title compound 69 with a yield of 13%, wherein the paraformaldehyde was replaced with cyclopropylcarboxaldehyde.

$^1$H NMR (400 MHz, DMSO-d6) δ 11.44 (s, 1H), 10.51 (s, 1H), 8.20 (t, J=5.0 Hz, 1H), 7.48 (s, 1H), 7.34 (d, J=1.9 Hz, 1LH), 7.22 (dd, J=7.7, 1.7 Hz, 1H), 7.16 (d, 1=1.7 Hz, 1H), 7.05 (d, J=1.6 Hz, 1H), 5.86 (d, J=1.1 Hz, 1H), 4.29 (d, J=4.9 Hz, 2H), 3.87-3.78 (m, 2H), 3.26-3.23 (m, 4H), 3.16-2.94 (m, 6H), 2.82 (s, 2H), 2.23 (d, J=17.4 Hz, 6H), 2.11 (s, 3H), 1.93 (d, J=21.2 Hz, 411), 1.72-1.46 (m, 5H), 1.06 (s, 1H), 0.84 (t, J=6.9 Hz, 3H), 0.60 (d, J=7.4 Hz, 2H), 0.31 (s, 2H),

MS m/z (ESI): 652.5 [M+H]$^+$.

Example 70 N-((4,6-dimethyl-2-oxo-1,2-dihydropyridin-3-yl)methyl)-3-(ethyl(tetrahydro-2H-pyran-4-yl)amino)-2-methyl-5-(2'-oxospiro[cyclohexane-1,3'-dihydroindole]-6'-yl)benzamide

70

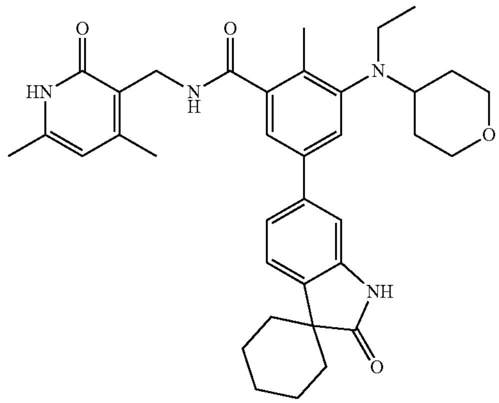

A similar method of Example 66 was used to obtain the title compound 70 with a yield of 18%, wherein the 2,2'-dibromodiethyl ether was replaced with 1,5-dibromopentane.

MS m/z (ESI): 597.3 [M+H]$^+$.

Example 71 N-((4,6-dimethyl-2-oxo-1,2-dihydropyridin-3-yl)methyl)-3-(ethyl(tetrahydro-2H-pyran-4-yl)amino)-2-methyl-5-(spiro[cyclohexane-1,3'-dihydroindole]-6'-yl)benzamide

71

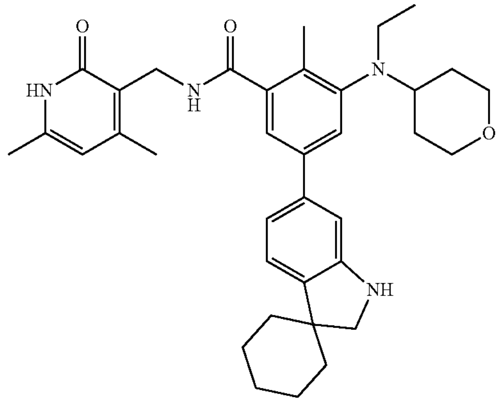

A similar method of Example 67 was used to obtain the title compound 71 with a yield of 24%, wherein the 2,2'-dibromodiethyl ether was replaced with 1,5-dibromopentane.

MS m/z (ESI): 583.3 [M+H]$^+$.

Example 72 N-((4,6-dimethyl-2-oxo-1,2-dihydropyridin-3-yl)methyl)-3-(ethyl(tetrahydro-2H-pyran-4-yl)amino)-2-methyl-5-(1-methyl-2',3',5',6'-tetrahydrospiro[dihydroindole-3,4'-pyran]-6-yl)benzamide

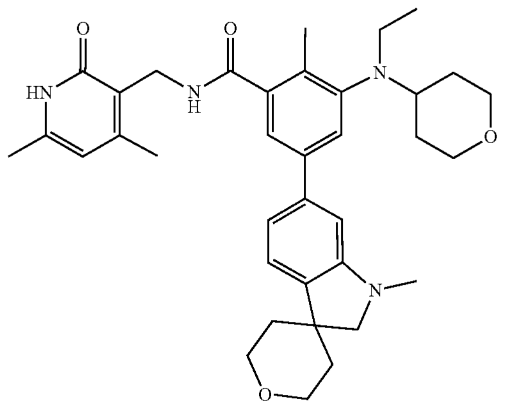

72

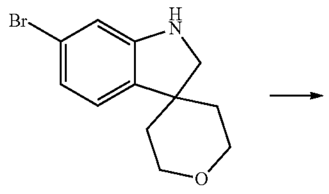

67a

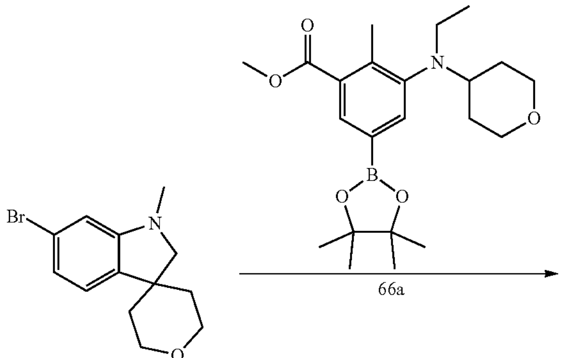

66a

72a

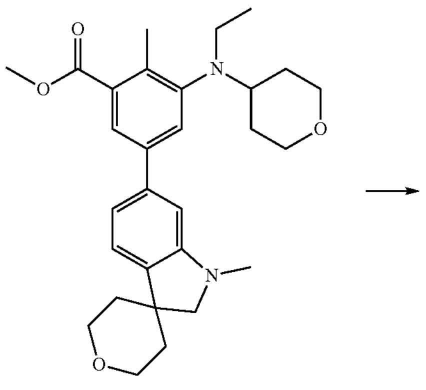

72b

-continued

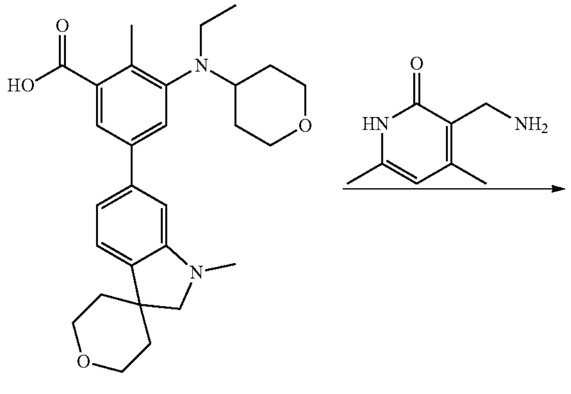

72c

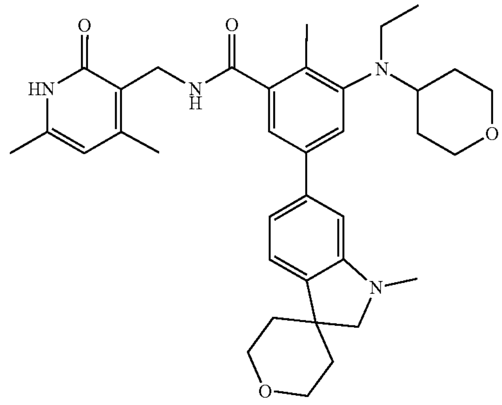

72

Step I 6-bromo-1-methyl-2',3',5',6'-tetrahydrospiro[dihydroindole-3,4'-pyran]72a The compound 67a (6-bromo-2',3',5',6'-tetrahydrospiro[dihydroindole-3,4'-pyran]) (150 mg, 0.56 mmol) was dissolved DMF (2 mL). Then iodomethane (158.9 mL, 1.12 mmol) and sodium hydride (67.2 mg, 1.68 mmol) were added slowly dropwise under ice bath, and the mixture was stirred under ice bath for 3 hours. The reaction was quenched with water under ice bath, and the reaction solution was extracted with ethyl acetate. The organic phase was washed with saturated NaCl solution, dried with anhydrous sodium sulfate, filtered, concentrated, and purified by column chromatography to obtain the title compound 72a (100 mg, 0.355 mmol) with a yield of 63.5%.

Step II Methyl 3-(ethyl(tetrahydro-2H-pyran-4-yl)amino)-2-methyl-5-(1-methyl-2',3',5',6'-tetrahydrospiro[dihydroindole-3,4'-pyran]-6-yl)benzoate 72b The compound 72a (100 mg, 0.35 mmol) and compound 66a (158 mg, 0.39 mmol) were dissolved in 1,4-dioxane (2.0 mL), [1,1'-bis(diphenylphosphino)ferrocene]dichloropalladium (26 mg, 0.0355 mmol) and potassium acetate (122 mg, 0.887 mmol) were added. The mixture was heated to 100° C. under the protection of nitrogen and stirred for 2 hours until the reaction was completed. The reaction solution was cooled down, spin-dried, extracted with dichloromethane for three times, washed with saturated NaCl solution, dried with anhydrous sodium sulfate, filtered, concentrated, and purified by plate chromatography to obtain the title compound 72b (120 mg, 0.25 mmol) with a yield of 70.6%.

Step III 3-(ethyl(tetrahydro-2H-pyran-4-yl)amino)-2-methyl-5-(1-methyl-2',3',5',6'-tetrahydrospiro[dihydroindole-3,4'-pyran]-6-yl)benzoic acid 72c The compound 72b (120 mg, 0.25 mmol) was dissolved in methanol (2.0 mL), sodium hydroxide (61 mg, 1.5 mmol) and water (1.0 mL) were added. The mixture stirred at room temperature for 4 hours until the reaction was completed. The reaction solution was neutralized to pH=6-7 with hydrochloric acid, extracted with dichloromethane for three times, washed with saturated NaCl solution, dried with anhydrous sodium sulfate, filtered, concentrated, and purified by plate chromatography to obtain the title compound 72c (110 mg, 0.24 mmol) with a yield of 94.8%.

Step IV N-((4,6-dimethyl-2-oxo-1,2-dihydropyridin-3-yl)methyl)-3-(ethyl(tetrahydro-2H-pyran-4-yl)amino)-2-methyl-5-(1-methyl-2',3',5',6'-tetrahydrospiro[dihydroindole-3,4'-pyran]-6-yl)benzamide The compound 72c (110 mg, 0.24 mmol) and 3-(aminomethyl)-4,6-dimethyl-1H-pyridin-2-one hydrochloride (67 mg, 0.355 mmol) were dissolved in N,N-dimethylformamide (2.0 mL), and 1-(3-dimethylaminopropyl)-3-ethylcarbodiimide hydrochloride (92 mg, 0.48 mmol), 1-hydroxybenzotriazole (32 mg, 0.24 mmol) and triethylamine (73 mg, 0.72 mmol) were added. The mixture was stirred at room temperature overnight until the reaction was completed. The reaction solution was washed with water, extracted with dichloromethane for three times, washed with saturated NaCl solution, dried with anhydrous sodium sulfate, filtered, concentrated, and purified by plate chromatography to obtain the title compound 72 (90.0 mg, 0.15 mmol) with a yield of 62.7%.

$^1$H NMR (400 MHz, DMSO-d6) δ 11 43 (s, 1H), 8.12 (s, 1H), 7.29 (s, 1H), 7.13 (d, J=1.8 Hz, 1H), 7.08 (d, J=7.6 Hz, 1H), 6.83-6.73 (m, 1H), 6.63 (d, J=1.6 Hz, 11), 5.82 (s, 1H), 4.25 (d, J=4.9 Hz, 2H), 3.83-3.71 (m, 4H), 3.46 (t, J=11.7 Hz, 2H), 3.29 (s, 2H), 3.26-3.13 (m, 2H), 3.09-2.91 (m, 3H), 2.75 (s, 3H), 2.18 (d, J=9.2 Hz, 6H), 2.07 (s, 3H), 1.80 (d, J=4.2 Hz, 2H), 1.62 (d, J=12.5 Hz, 2H), 1.50 (d, J=12.8 Hz, 4H), 0.79 (t, J=6.9 Hz, 3H).

MS m/z (ESI): 599.4 [[M+H]$^4$.

Example 73 N-((4,6-dimethyl-2-oxo-1,2-dihydropyridin-3-yl)methyl)-3-(ethyl(tetrahydro-2H-pyran-4-yl)amino)-2-methyl-5-(1-methyl-2-oxo-2',3',5',6'-tetrahydrospiro[dihydroindole-3,4'-pyran]-6-yl)benzamide

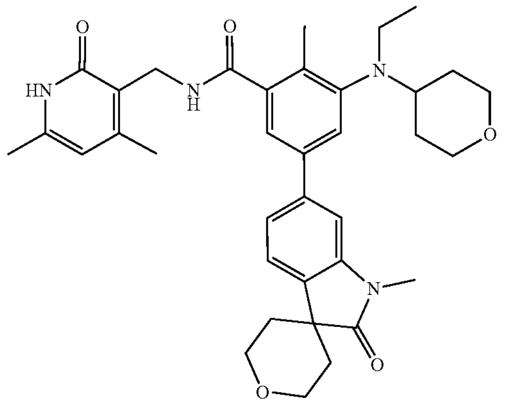

73

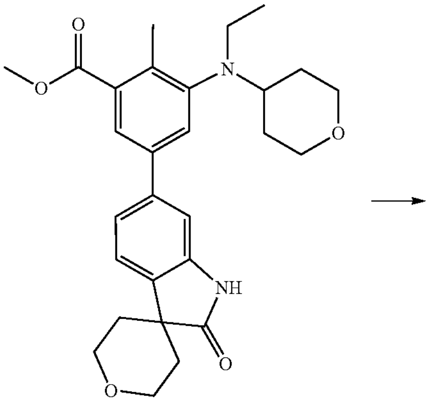

66d

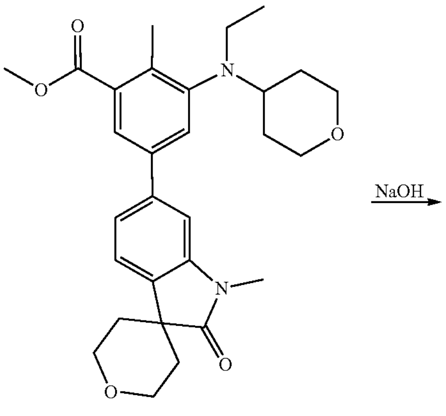

73a

-continued

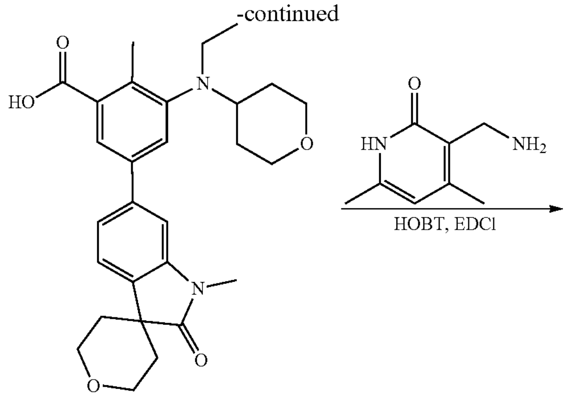

73b

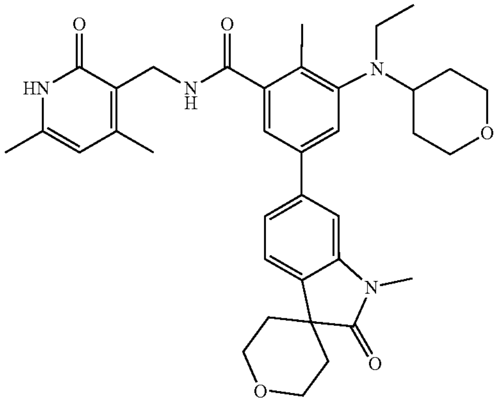

73

Step I Methyl 3-(ethyl(tetrahydro-2H-pyran-4-yl)amino)-2-methyl-5-(1-methyl-2-oxo-2',3',5',6'-tetrahydrospiro[indoline-3-yl]-3,4'-pyran]-6-yl)benzoate 73a The compound 66d (methyl 3-(ethyl(tetrahydro-2H-pyran-4-yl)amino)-2-methyl-5-(2-oxo-2',3',5',6'-tetrahydrospiro[dihydroindole-3,4'-pyran]-6-yl)benzoate) (150 mg, 0.313 mmol) was dissolved in DMF (2 mL), followed by adding NaH (25 mg, 0.626 mmol) dropwise under ice bath and stirring for 30 minutes. Then iodomethane (44 mg, 0.313 mmol) was added to the mixture and stirred for 6 hours under ice bath. The reaction was quenched with water under ice bath after being determined to be completed by TLC. The reaction solution was extracted with ethyl acetate, and the organic phase was washed with saturated NaCl solution, dried with anhydrous sodium sulfate, filtered, concentrated, and purified by column chromatography to obtain the title compound 73a (100 mg, 0.203 mmol) with a yield of 64.7%.

Step II 3-(ethyl(tetrahydro-2H-pyran-4-yl)amino)-2-methyl-5-(1-methyl-2-oxo-2',3',5',6'-tetrahydrospiro[indoline-3-yl]-3,4'-pyran]-6-yl)benzoic acid 73b The compound 73a (100 mg, 0.203 mmol) was dissolved in tetrahydrofuran (4.0 mL), sodium hydroxide (24 mg, 0.609 mmol) and water (1.0 mL) were added. The mixture was heated to 50° C. and stirred for 2 hours until the reaction was completed. The reaction solution was neutralized to pH=6-7 with hydrochloric acid, extracted with dichloromethane for three times, washed with saturated NaCl solution, dried with anhydrous sodium sulfate, filtered, concentrated, and purified by plate chromatography to obtain the title compound 73b (60 mg, 0.126 mmol) with a yield of 61.7%.

Step III N-((4,6-dimethyl-2-oxo-1,2-dihydropyridin-3-yl)methyl)-3-(ethyl(tetrahydro-2H-pyran-4-yl)amino)-2-methyl-5-(1-methyl-2-oxo-2',3',5',6'-tetrahydrospiro[dihydroindole-3,4'-pyran]-6-yl)benzamide 73

The compound 73b (60 mg, 0.126 mmol) and 3-(aminomethyl)-4,6-dimethyl-1H-pyridin-2-one hydrochloride (24 mg, 0.13 mmol) were dissolved in N,N-dimethylformamide (2.0 mL), and 1-(3-dimethylaminopropyl)-3-ethylcarbodiimide hydrochloride (43 mg, 0.26 mmol), 1-hydroxybenzotriazole (15 mg, 0.13 mmol) and triethylamine (32 mg, 0.3 mmol) were added. The mixture was heated to 50° C. and stirred for 4 hours until the reaction was completed. The reaction solution was washed with water, extracted with dichloromethane for three times, washed with saturated NaCl solution, dried with anhydrous sodium sulfate, filtered, concentrated, and purified by plate chromatography to obtain the title compound 73 (12.0 mg, 0.019 mmol) with a yield of 15.6%.

$^1$H NMR (400 MHz, DMSO-d) δ 11.45 (s, 1H), 0.17 (s, 1H), 7.58 (d, J=7.7 Hz, 1H), 7.38 (s, 1H), 7.23 (d, J=7.4 Hz, 2H), 7, 19 (s, 1H), 5.83 (s, 1H), 4.26 (d, J=4.9 Hz, 2H), 4.07-3.99 (m, 2H), 3.84-3.75 (m, 4H), 3.23 (d, J=11.5 Hz, H), 3.17 (s, 3H), 3.06 (d, J=7.3 Hz, 2H) 0.19 (d, J=12.5 Hz, 6H), 2.07 (s, 3H), 1.71 (s, 4H), 1.63 (d, J=12.4 Hz, 2H), 1.49 (d, J=8.4 Hz, 2H), 0.80 (t, J=6.9 Hz, 3H),

MS n/z (ES1): 613.3 $[M+H]^+$.

Example 74 5-(1-acetyl-2',3',5',6'-tetrahydrospiro[dihydroindole-3,4'-pyran]-6-yl)-N-((4,6-dimethyl-2-oxo-1,2-dihydropyridin-3-yl)methyl)-3-(ethyl(tetrahydro-2H-pyran-4-yl)amino)-2-methylbenzamide

74

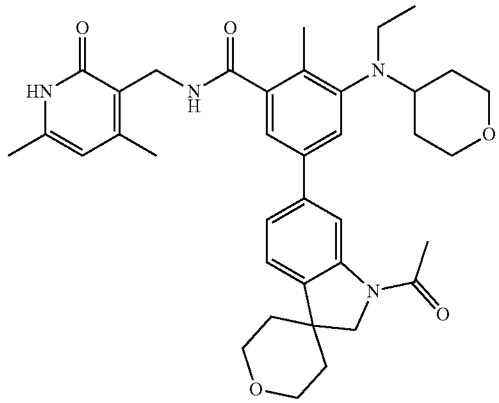

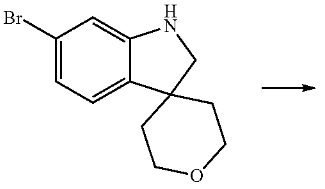

67a

-continued

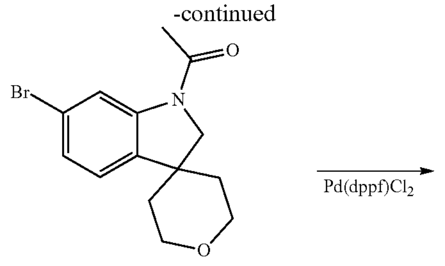

74a

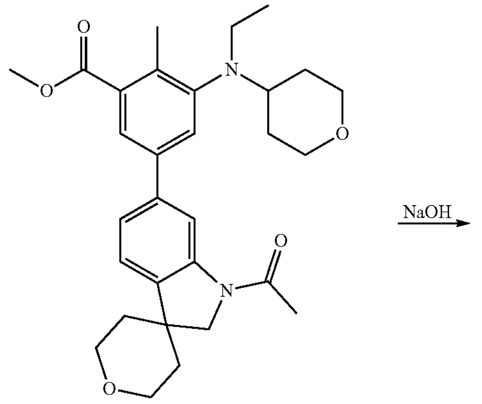

74b

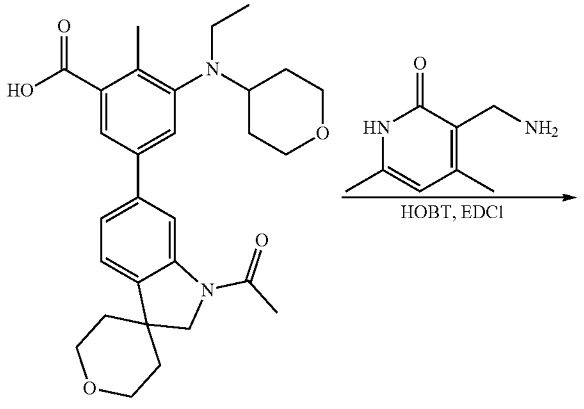

74c

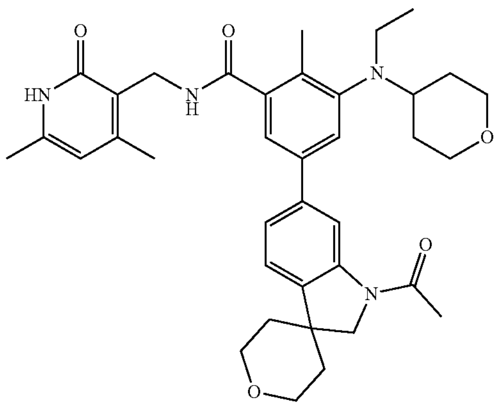

74

Step I 1-(6-bromo-2',3',5',6'-tetrahydrospiro[dihydroindole-3,4'-pyran]-1-yl)ethyl-1-one 74a The compound 67a (200 mg, 0.75 mmol) was dissolved in acetic anhydride (2 mL), and an aqueous solution (1 mL) of sodium hydroxide (33 mg, 0.825 mmol) was slowly added dropwise at room temperature, and the mixture was stirred at room temperature for 3 hours. The reaction was quenched with water, and the reaction solution was extracted with ethyl acetate, washed with saturated NaCl solution, dried with anhydrous sodium sulfate, filtered, concentrated, and purified by column chromatography to obtain the title compound 74a (90 mg, 0.291 mmol) with a yield of 38.8%.

Step II Methyl 5-(1-acetyl-2',3',5',6'-tetrahydrospiro[dihydroindole-3,4'-pyran]-6-yl)-3-(ethyl(tetrahydro-2H-pyran-4-yl)amino)-2-methylbenzoate 74b The compound 74a (90 mg, 0.29 mmol) and methyl 3-(ethyl(tetrahydro-2H-pyran-4-yl)amino-2-methyl-5-(4,4,5,5-tetramethyl-1,3,2-dioxaborolan-2-yl)benzoate (105 mg, 0.26 mmol) were dissolved in 1,4-dioxane (2.0 mL), [1,1'-bis(diphenylphosphino)ferrocene]dichloropalladium (26 mg, 0.0355 mmol) and potassium carbonate (122 mg, 0.887 mmol) were added, and the mixture was heated to 100° C. under the protection of nitrogen and stirred for 2 hours. The reaction solution was cooled down, spin-dried, extracted with dichloromethane for three times, washed with saturated NaCl solution, dried with anhydrous sodium sulfate, filtered, concentrated, and purified by plate chromatography to obtain the title compound 74b (100 mg, 0.19 mmol) with a yield of 65.5%.

Step III 5-(1-acetyl-2',3',5',6'-tetrahydrospiro[dihydroindole-3,4'-pyran]-6-yl)-3-(ethyl(tetrahydro-2H-pyran-4-yl)amino)-2-methyl benzoic acid 74c The compound 74b (100 mg, 0.19 mmol) was dissolved in methanol (2.0 mL), and sodium hydroxide (61 mg, 1.5 mmol) and water (1.0 mL) were added. The mixture was stirred at room temperature for 4 hours until the reaction was completed. The reaction solution was neutralized to pH=6-7 with hydrochloric acid, extracted with dichloromethane for three times, washed with saturated NaCl solution, dried with anhydrous sodium sulfate, filtered, concentrated, and purified by plate chromatography to obtain the title compound 74c (70 mg, 0.14 mmol) with a yield of 73.6%.

Step IV 5-(1-acetyl-2',3',5',6'-tetrahydrospiro[dihydroindole-3,4'-pyran]-6-yl)-N-((4,6-dimethyl-2-carbonyl-1,2-dihydropyridin-3-yl)methyl)-3-(ethyl(tetrahydro-2H-pyran-4-yl)amino)-2-methylbenzamide 74

The compound 74c (70 mg, 0.14 mmol) and 3-(aminomethyl)-4,6-dimethyl-1H-pyridin-2-one hydrochloride (67 mg, 0.355 mmol) was dissolved in N,N-dimethylformamide (2.0 mL), and 1-(3-dimethylaminopropyl)-3-ethylcarbodiimide hydrochloride (92 mg, 0.48 mmol), 1-hydroxybenzotriazole (32 mg, 0.24 mmol) and triethylamine (73 mg, 0.72 mmol) were added. The mixture was stirred at room temperature overnight until the reaction was completed. The reaction solution was washed with water, extracted with dichloromethane for three times, washed with saturated NaCl solution, dried with anhydrous sodium sulfate, filtered, concentrated, and purified by plate chromatography to obtain the title compound 74 (32.0 mg, 0.05 mmol) with a yield of 35.7%.

$^1$H NMR (400 MHz, DMSO-$d_6$) δ 11.43 (s, 1H), 8.12 (s, 1H), 7.29 (s, 1H), 7.13 (d, J=1.8 Hz, 1H), 7.08 (d, J=7.6 Hz, 1H), 6.83-6.73 (m, 1H, 6.63 (d, J=1.6 Hz, 1H), 5.82 (s, 1H), 4.25 (d, J=4.9 Hz, 2H), 3.83-3.71 (m, 4H), 3.46 (t, J=11.7

Hz, 2H), 3.29 (s, 2H), 3.26-3.13 (m, 2H), 3.09-2.91 (m, 3H), 2.75 (s, 3H), 2.18 (d, J=9.2 Hz, 6H), 2.07 (s, 3H), 1.80 (d, J=4.2 Hz, 2H), 1.62 (d, J=12.5 Hz, 2H), 1.50 (c, J=12.8 Hz, 4H), 0.79 (t, J=6.9 Hz, 3H),

MS m/z (ESI): 627.3 $[M+1H]^+$.

Example 75 5-(1-trifluoroacetyl-2',3',5',6'-tetrahydrospiro[dihydroindole-3,4'-pyran]-6-yl)-N-((4,6-dimethyl-2-carbonyl-1,2-dihydropyridin-3-yl)methyl)-3-(ethyl(tetrahydro-2H-pyran-4-yl)amino)-2-methylbenzamide

75

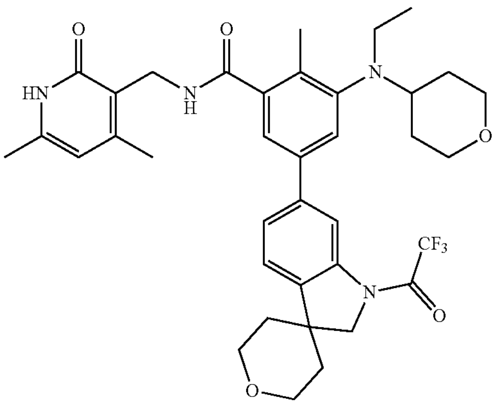

A similar method of Example 74 was used to obtain the title compound 75 with a yield of 19%, wherein the acetic anhydride was replaced with trifluoroacetic anhydride.

$^1$H NMR (400 MHz, DMSO-de) δ 11.42 (s, 1H), 8.24 (s, 1H), 8.19 (s, 1H), 7.50 (d, J=7.9 Hz, 1H), 7.46 (s, 1H), 7.30 (s, 1H), 7.13 (s, 1H), 5.82 (s, 1H), 4.31-4.14 (m, 4H), 3.83 (dd, J=23.8, 11.3 Hz, 4H), 3.48 (t, J=12, 1 Hz, 2H), 3.22 (t, J=11.4 Hz, 2H), 3.11-2.96 (m, 3H), 2.21 (s, 3H), 2.17 (s, 3H), 2.08 (d, J=8.1 Hz, 3H), 192 (t, J=12.1 Hz, 2H), 0.61 (d, J=11.7 Hz, 4H), 150 (d, J=12.4 Hz, 2H), 0.81 (t, J=6.9 Hz, 3H),

MS m/z (ESI): 681.3 $[M+H]^+$.

Example 76 N-((4,6-dimethyl-2-oxo-1,2-dihydropyridin-3-yl)methyl)-3-(ethyl(piperidin-4-yl)amino)-2-methyl-5-(2-oxo-2',3',5',6'-tetrahydrospiro[dihydroindole-3,4'-pyran]-6-yl)benzamide

76

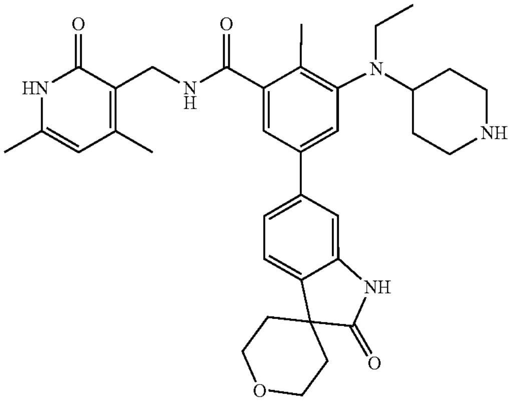

-continued

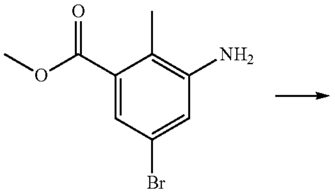

76a-1

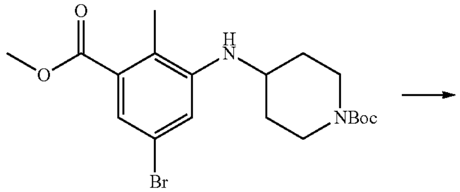

76a

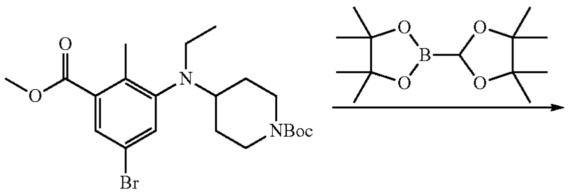

76b

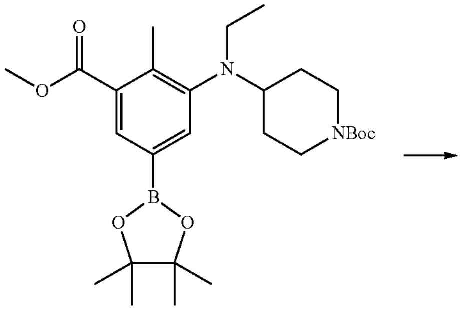

76c

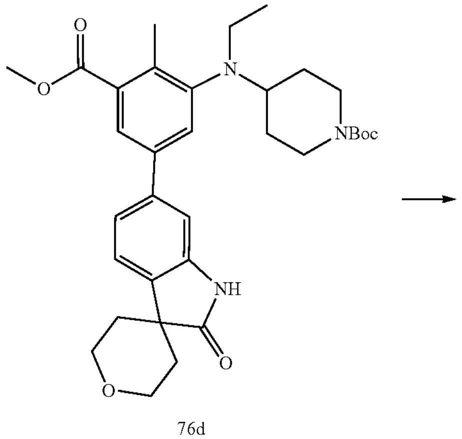

76d

-continued

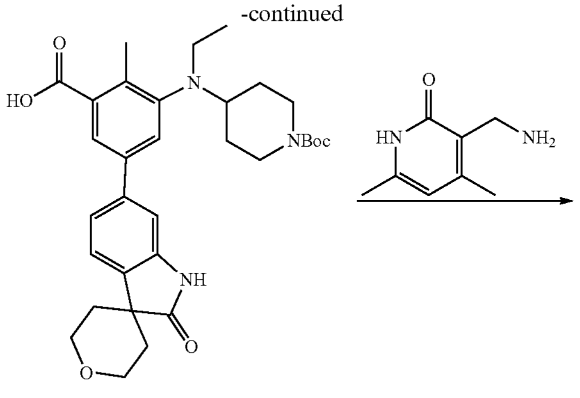

76e

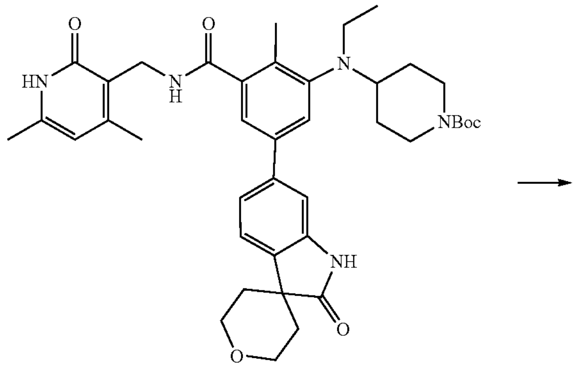

76f

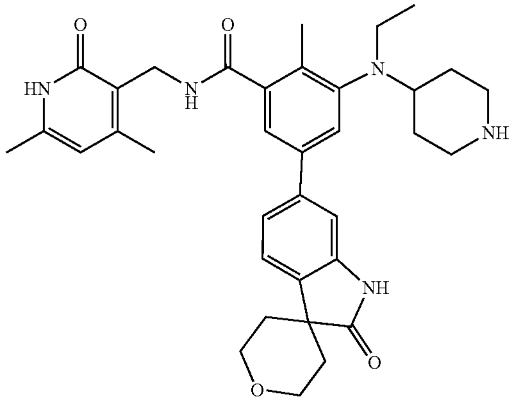

76

Step I Tert-butyl 4-((5-bromo-3-(methoxycarbonyl)-2-methylphenyl)amino)piperidin-1-carboxylate 76a The compound 76a-1 (2 g, 8.196 mmol) was dissolved in dichloromethane (50 mL), and acetic acid (1.5 g, 24.59 mmol) and tert-butyl 4-oxopiperidin-1-carboxylate (4.9 g, 24.59 mmol) were added. The mixture was stirred at room temperature for 30 minutes, added with sodium borohydride acetate (5.2 g, 24.59 mmol) followed by stirring at room temperature for 3.5 hours until the reaction was completed. The reaction solution was quenched with water, extracted with dichloromethane for three times, washed with saturated NaCl solution, dried with anhydrous sodium sulfate, filtered, concentrated, and purified by plate chromatography to obtain the title compound 76a (3.4 g, 7.98 mmol) with a yield of 95%.

Step II Tert-butyl 4-((5-bromo-3-(methoxycarbonyl)-2-methylphenyl)(ethyl)amino)piperidin-1-carboxylate 76b The compound 76a (3.4 g, 7.98 mmol) was dissolved in dichloromethane (50 mL), and acetic acid (1.436 g, 23.94 mmol) and acetaldehyde (1.755 g, 39.9 mmol) were added. The mixture was stirred at room temperature for 30 minutes, added with sodium borohydride acetate (5.075 g, 23.94 mmol) followed by stirring at room temperature for 3 hours until the reaction was completed. The reaction solution was quenched with water, extracted with dichloromethane for three times, washed with saturated NaCl solution, dried with anhydrous sodium sulfate, filtered, concentrated, and purified by plate chromatography to obtain the title compound 76b (3.2 g, 7 mmol) with a yield of 88%.

Step III Tert-butyl 4-(ethyl(3-(methoxycarbonyl)-2-methyl-5-(4,4,5,5-tetramethyl-1,3,2-dioxaborolan-2-yl)phenyl)amino)piperidin-1-formate 76c The compound 76b (1.2 g, 2.64 mmol) and bis(pinacolato)diboron (1.34 g, 5.28 mmol) were dissolved in 1,4-dioxane (20 mL), [1,1'-bis(diphenylphosphino)ferrocene]dichloropalladium (0.192 g, 0.264 mmol) and potassium acetate (0.776 g, 7.92 mmol) were added. The mixture was heated to 100° C. under the protection of nitrogen and stirred for 2 hours until the reaction was completed. The reaction solution was extracted with water and ethyl acetate, the organic phase was washed with saturated NaCl solution, dried with anhydrous sodium sulfate, filtered, concentrated, and purified by column chromatography to obtain the title compound 76c (1 g, 1.992 mmol) with a yield of 75%.

Step IV Tert-butyl 4-(ethyl(3-(methoxycarbonyl)-2-methyl-5-(2-oxo-2',3',5',6'-tetrahydrospiro[dihydroindole-3,4'-pyran]-6-yl)phenyl)amino)piperidin-1-formate 76d The compound 76c (600 mg, 1.195 mmol) and 6-bromo-2',3',5',6'-tetrahydrospiro[dihydroindole-3,4'-pyran]-2-one (336 mg, 1.195 mmol) were dissolved in 1,4-dioxane (2.0 mL), and tetrakis(triphenylphosphine)palladium (109 mg, 0.1195 mmol) and potassium carbonate (253 mg, 2.36 mmol) were added. The mixture was heated to 100° C. under the protection of nitrogen and stirred for 2 hours. The reaction solution was cooled down, spin-dried, extracted with dichloromethane for three times, washed with saturated NaCl solution, dried with anhydrous sodium sulfate, filtered, concentrated, and purified by plate chromatography to obtain the title compound 76d (250 mg, 0.433 mmol) with a yield of 36%.

Step V 3-((1-(tert-butoxycarbonyl)piperidin-4-yl)(ethyl)amino)-2-methyl-5-(2-oxo-2',3',5',6'-tetrahydrospiro[dihydroindole-3,4'-pyran]-6-yl)benzoic acid 76e The compound 76d (250 mg, 0.433 mmol) was dissolved in methanol (4.0 mL), and sodium hydroxide (87 mg, 2.165 mmol) and water (1.0 mL) were added. The mixture was stirred at room temperature for 4 hours until the reaction was completed. The reaction solution was neutralized to pH=6-7 with hydrochloric acid, extracted with dichloromethane for three times, washed with saturated NaCl solution, dried with anhydrous sodium sulfate, filtered, concentrated, and purified by plate chromatography to obtain the title compound 76e (200 mg, 0.355 mmol) with a yield of 82%.

MS m/z (ESI): 564 $[M+H]^+$.

Step VI Tert-butyl 4-((3-(((4,6-dimethyl-2-oxo-1,2-dihydropyridin-3-yl)methyl)carbamoyl)-2-methyl-5-(2-oxo-2',3',5',6'-tetrahydrospiro[dihydroindole-3,4'-pyran]-6-yl)phenyl)(ethyl)amino)piperidin-1-formate 76f The compound 76e (200 mg, 0.355 mmol) and 3-(aminomethyl)-4,6-dimethyl-1H-pyridin-2-one hydrochloride (29 mg, 0.16 mmol) was dissolved in N,N-dimethylformamide (5.0 mL), and 1-(3-dimethylaminopropyl)-3-ethylcarbodiimide hydrochloride (136 mg, 0.71 mmol), 1-hydroxybenzotriazole (48 mg, 0.355 mmol) and triethylamine (179 mg, 1.775 mmol) were added. The mixture was heated to 60° C. and stirred for 4 hours until the reaction was completed. The reaction solution was washed with water, extracted with dichloromethane for three times, washed with saturated NaCl solution, dried with anhydrous sodium sulfate, filtered, concentrated, and purified by plate chromatography to obtain the title compound 76f (150 mg, 0.215 mmol) with a yield of 60%.

Step VII N-((4,6-dimethyl-2-oxo-1,2-dihydropyridin-3-yl)methyl)-2-methyl-3-(ethyl(piperidin-4-yl)amino)-5-(2-oxo-2',3',5',6'-tetrahydrospiro[dihydroindole-3,4'-pyran]-6-yl)benzamide 76

The compound 76f (150 mg, 0.215 mmol) was dissolved in ethyl acetate (5.0 mL), added with hydrochloric acid in ethyl acetate (0.3 mL, 0.9 mmol), and the reaction was completed after stirring at room temperature for 2 hours. The reaction solution was spin-dried, added with methanol, neutralized with saturated potassium carbonate solution, filtered, concentrated, and purified by plate chromatography to obtain the title compound 76 (100 mg, 0.167 mmol) with a yield of 77%.

$^1H$ NMR (400 MHz. Methanol-$d_4$) δ 7.52 (d, J=7.8 Hz, 1H), 7.45 (d, J=1.9 Hz, 1H), 7.32 (d, J=1.8 Hz, 1H), 7.25 (dd, J=7.7, 1.7 Hz, 1H), 7.10 (d, J=1.7 Hz, 1H), 6.10 (s, 1H), 4.47 (s, 2H), 4.23-4.12 (m, 2H), 3.92 (dd, J=8.9, 4.4 Hz, 2H), 3.35 (d, J=12.8 Hz, 2H), 3.26 (s, 1H), 314 (d, J=7.1 Hz, 2H), 2.96 (s, 2H), 2.38 (s, 3H), 2.33 (s, 3H), 2.22 (s, 3H), 2.01 (s, 2H), 1.93-1.72 (m, 6H), 0.91 (t, J=7.0 Hz, 3H), MS m/z (ESI): 598 $[M+H]^+$.

Example 77 N-((4,6-dimethyl-2-oxo-1,2-dihydropyridin-3-yl)methyl)-3-(ethyl(tetrahydro-2H-pyran-4-yl)amino)-2-methyl-5-(2-oxo-2',3',5',6'-tetrahydrospiro[dihydroindole-3,4'-pyran]-5-yl)benzamide

77

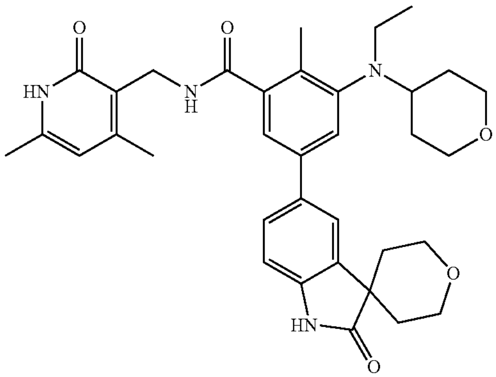

A similar method of Example 66 was used to obtain the title compound 77 with a yield of 10%, wherein the 6-bromo-1,3-dihydro-2H-indol-2-one was replaced with 5-bromo-1,3-dihydro-2H-indol-2-one.

$^1H$ NMR (400 MHz, DMSO-$d_6$) δ 11.36 (s, 1H), 1H), (s, 1H), 8.13 (t, J=5.0 Hz, 1H), 7.64 (d, J=1.8 Hz, J H), 7.40 (dd, J=8.1, 1.8 Hz, 1H), 7.33 (d, J=1.9 Hz, 1H), 7.18 (d, J=1.8 Hz, 1H), 6.88 (d, J=8.0 Hz, 1H) 5.82 (s, 1H), 4.26 (d, J=4.8 Hz, 2H), 4.11-4.01 (m, 2H), 3.86-3.72 (m, 4H), 3.22 (t, J=11.5 Hz, 2H), 3.06 (q, J=6.9 Hz, 2H), 2.98 (s, 1H), 2.20 (s, 3H), 2.18 (s, 3H), 2.07 (s, 3H), 1-87 (ddd, J=13.3, 8.7, 4.0 Hz, 2H), 1.71-1.59 (m, 4H), 1.49 (d, J=10.8 Hz, 2H), 0.81 (t, J=6.9 Hz, 3H), MS m/z (ESI): 599.3 $[M+H]^+$.

Example 78 N-((4,6-dimethyl-2-oxo-1,2-dihydropyridin-3-yl)methyl)-3-(ethyl(tetrahydro-2H-pyran-4-yl)amino)-2-methyl-5-(1-oxo-1,2',3,3',5',6'-hexahydrospiro[indene-2,4'-pyran]-6-yl)benzamide

78

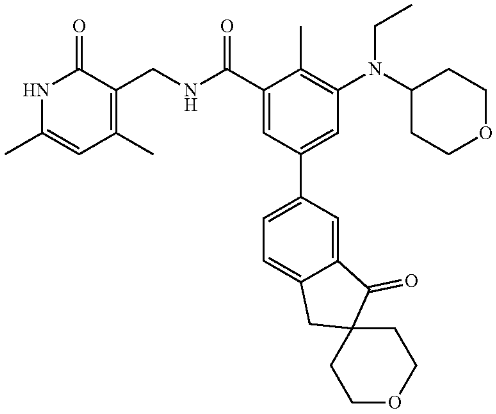

-continued

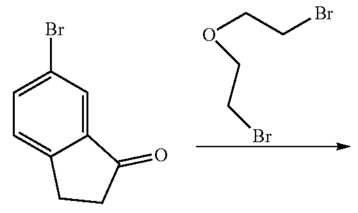

78a

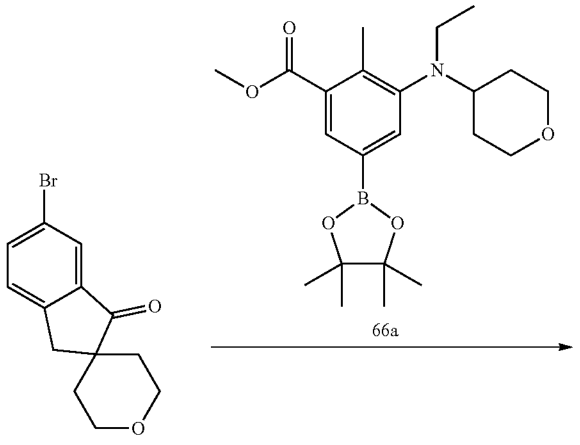

66a

78b

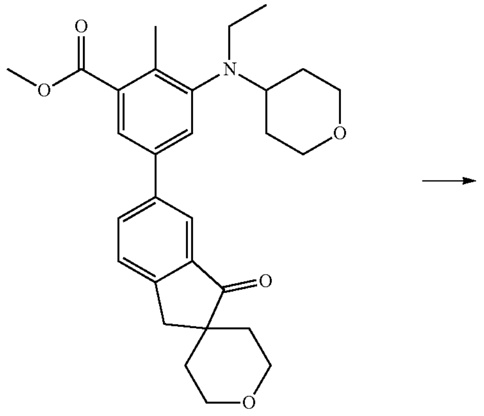

78c

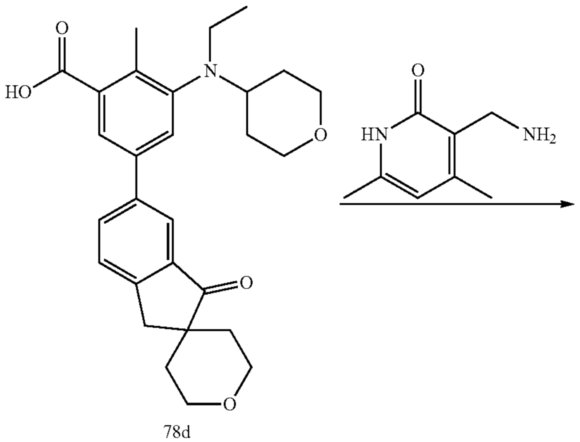

78d

-continued

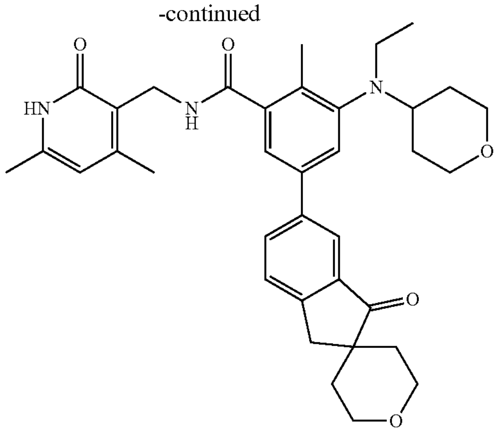

78

Step I 6-bromo-2',3',5',6'-tetrahydrospiro[indene-2, 4'-pyran]-1-(3H)-one 78b

The compound t-BuOK (3.99 g, 35.54 mmol) was added to toluene (40 mL) in a reaction flask and cooled to 0° C. Then the compound 78a (5 g, 3.69 mmol) and 2,2'-dibromodiethyl ether (6.04 g, 6.06 mmol) were added to toluene to obtain a mixed solution, which was added to the reaction flask dropwise. The mixture was heated to 110° C. and refluxed for 2.5 hours under stirring. A little residue of raw materials was determined by TLC monitoring. The reaction solution was poured to ice water, extracted with EA, dried with anhydrous sodium sulfate, spin-dried, and purified by flash column chromatography (petroleum ether: ethyl acetate=10:1) to obtain 500 mg of a relatively pure orange-yellow solid of compound 78b (500 mg, 1.78 mmol) with a yield of 7.2%.

MS m/z (ESI): 281 $[M+H]^+$.

Step II Methyl 3-(ethyl(tetrahydro-2H-pyran-4-yl) amino)-2-methyl-5-(1-oxo-1,2',3,3',5',6'-hexahydrospiro[indene-5-yl]-2,4'-pyran]-6-yl)benzoate 78c The compound 78b (500 mg, 1.78 mmol), compound 66a (840 mg, 2.08 mmol), $Pd(dppf)Cl_2$ (160 mg, 0.218 mmol), $K_2CO_3$ (737 mg, 5.34 mmol), 1,4-dioxane (8 mL) and $H_2O$ (2 mL) were added in a 100 mL single-necked flask. The mixture was heated to 110° C. under the protection of $N_2$ and stirred for 2 hours.

LCMS monitoring was used and determined that there was MS value of the product in the main peak; TLC monitoring was used and determined that there was trace amount of raw material remained. The reaction solution was added with EA, extracted with water, dried with anhydrous sodium sulfate, spin-dried, and purified by flash column chromatography (PE:EA=5:1) to obtain a light-yellow solid of compound 78c (700 mg, 1.47 mmol) with a yield of 82%.

MS m/z (ESI): 478.2 $[M+H]^+$.

Step III 3-(ethyl(tetrahydro-2H-pyran-4-yl)amino)-2-methyl-5-(1-oxo-1,2',3,3',5',6'-hexahydrospiro[indene-5-yl]-2,4'-pyran]-6-yl)benzoic acid 78d The compound 78c (160 mg, 0.335 mmol), MeOH (6 mL) and THF (2 mL) were added to a 25 mL single-necked flask to form a clear solution, which was added with saturated aqueous NaOH solution (2 mL) to form a turbid solution.

The solution was stirred at room temperature overnight. TLC monitoring was used and determined that the raw materials were completely reacted and there was a new spot formed. The reaction solution was neutralized, spin-dried, dissolved with DCM and filtered. The filtrate was spin-dried to obtain a light-yellow solid of target compound (140 mg, 0.302 mol) with a yield of 90%.

Step IV N-((4,6-dimethyl-2-oxo-1,2-dihydropyridin-3-yl)methyl)-3-(ethyl(tetrahydro-2H-pyran-4-yl) amino)-2-methyl-5-(1-oxo-1,2',3,3',5',6'-hexahydrospiro[indene-2,4'-pyran]-6-yl)benzamide 78

The compound 78d (140 mg, 0.302 mmol) was dissolved in DCM (2 mL), the compound 3-(aminomethyl)-4,6-dimethyl-1H-pyridin-2-one hydrochloride (121 mg, 0.453 mmol), EDCI (174 mg, 0.906 mmol) and HOBt (41 mg, 0.302 mmol) were added to the solution to form a turbid solution, which was added with DIPEA (195 mg, 1.51 mmol) and remained turbid. Then DMF (2 mL) was added to the obtained solution and reacted at 26° C. for 2 hours. TLC monitoring was used and determined that the raw materials were completely reacted and there were new spots formed. The reaction solution was added with water, extracted with EA, dried with anhydrous sodium sulfate and concentrated, and the obtained crude product was purified by plate chromatography (PE:EA=0:1) to obtain the title compound 78 (55 mg, 0.092 mmol) with a yield of 30.5%.

$^1$H NMR (400 MHz, $CDCl_3$) δ 10.68 (s, 1H), 7.87 (s, 1H), 7.78 (d, J=8 Hz, 1H), 7.48 (d, J=8 Hz, H), 7.31 (d, J=16 Hz, 1H), 7.20 (s, 1H), 5.92 (s, 1H), 4.55 (d, J=8 Hz, 2H), 4.06 (d, J=12 Hz, 2H), 3.94 (d, J=12 Hz, 2H), 3.62 (t, J=12 Hz, 2H), 3.33 (d, J=12 Hz, 2H), 3.16-3.06 (m, 3H), 3.00 (s, 1H), 2.40 (s, 3H), 2.34 (s, 3H), 2.19 (s, 3H), 2.2-2.04 (n, 2H), 1.69 (s, 2H), 0.32 (d, J=12 Hz, 2H) 088 (t, J=4 Hz, 2H) MS m/z (ESI): 598.3 $[M+H]^+$.

Example 79 Tert-butyl 6-(3-(((4,6-dimethyl-2-oxo-1,2-dihydropyridin-3-yl)methyl)carbamoyl)-5-(ethyl (tetrahydro-2H-pyran-4-yl)amino)-4-methylphenyl)-2-oxospiro[dihydroindole-3,4'-piperidine]-1'-carboxylate

79

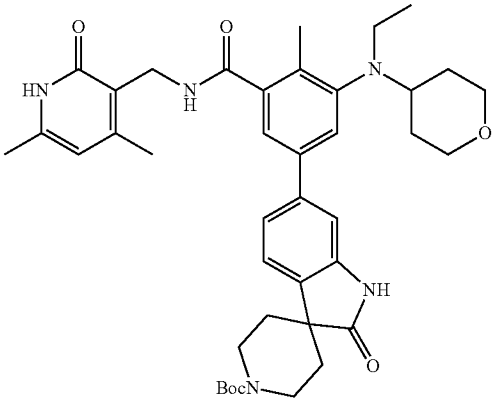

A similar method of Example 66 was used to obtain the title compound 79 with a yield of 8%, wherein the 6-bromo-2',3',5',6'-tetrahydrospiro[dihydroindole-3,4'-pyran]-2-one was replaced with tert-butyl 6-bromo-2-oxospiro[dihydroindole-3,4'-piperidine]-1'-formate.

MS m/z (ESI): 698.3 $[M+H]^+$.

Example 80 N-((4,6-dimethyl-2-oxo-1,2-dihydropyridin-3-yl)methyl)-3-(ethyl(tetrahydro-2H-pyran-4-yl)amino)-2-methyl-5-(2-oxospiro[dihydroindole-3,4'-piperidine]-6-yl)benzamide

80

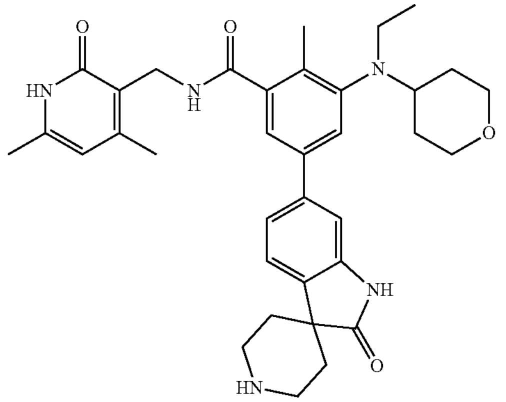

The compound 79 (50 mg, 0.072 mmol) was dissolved in ethyl acetate (5.0 mL), added with hydrochloric acid in ethyl acetate (5 mL). The mixture was stirred at room temperature for 2 hours until the reaction was completed. The reaction solution was spin-dried, added with methanol, neutralized with saturated potassium carbonate solution, filtered, concentrated, and purified by plate chromatography to obtain the title compound 80 (10 mg, 0.0167 mmol).

MS m/z (ESI): 598.3 $[M+H]^+$.

Example 81 N-((4,6-dimethyl-2-oxo-1,2-dihydropyridin-3-yl)methyl)-3-(ethyl(1-methylpiperidin-4-yl)amino)-2-methyl-5-(2-oxo-2',3',5',6'-tetrahydrospiro[dihydroindole-3,4'-pyran]-6-yl)benzamide

81

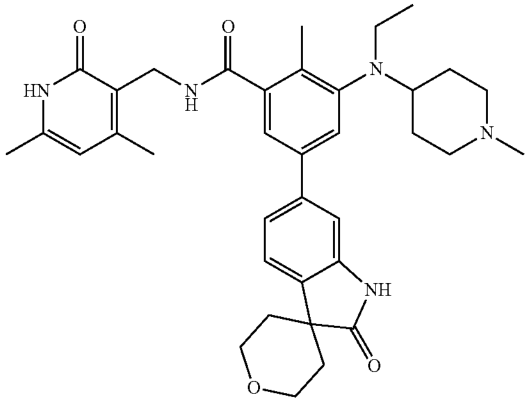

-continued

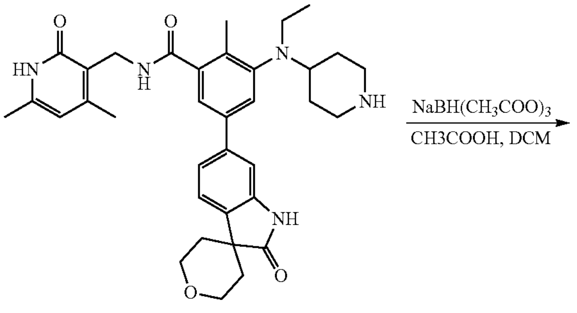

76

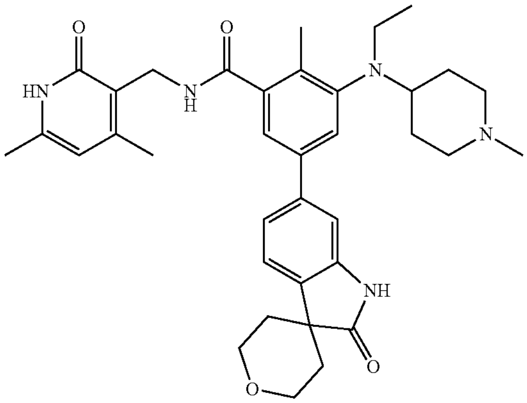

81

Step I N-((4,6-dimethyl-2-oxo-1,2-dihydropyridin-3-yl)methyl)-2-methyl-3-(ethyl(1-methylpiperidin-4-yl)amino)-5-(2-oxo-2',3',5',6'-tetrahydrospiro[dihydroindole-3,4'-pyran]-6-yl)benzamide 81

The compound 76 (30 mg, 0.05 mmol) was dissolved in 1,2-dichloroethane (5 mL), acetic acid (9 mg, 0.15 mmol) and paraformaldehyde (18 mg, 0.6 mmol) were added. The mixture was stirred at room temperature for 30 minutes, added with sodium borohydride acetate (32 mg, 0.15 mmol) followed by stirring at room temperature for 3 hours until the reaction was completed. The reaction solution was quenched with water, extracted with dichloromethane for three times, washed with saturated NaCl solution, dried with anhydrous sodium sulfate, filtered, concentrated, and purified by plate chromatography to obtain the title compound 81 (3 mg, 0.005 mmol) with a yield of 10%.

$^1$H NMR (400 MHz, Methanol-$d_4$) δ 752 (d, J=7.7 Hz, 1H), 7.40 (s, 1H), 7.29-7.18 (m, 2H), 7.09 (s, 1H), 6.09 (s, 1H), 4.47 (s, 2H), 4.17 (s, 2H), 3.94 (d, J=5.8 Hz, 2H), 3.13 (d, J=8.0 Hz, 3H), 2.85 (d, J=11.9 Hz, 3H), 2.51-2, 12 (m, 12H), 2.05 (s, 2H), 1.84 (d, J=30.8 Hz, 6H), 0.88 (s, 3H), MS m/z (ESI): 612 $[M+H]^+$.

Example 82 N-((4,6-dimethyl-2-oxo-1,2-dihydropyridin-3-yl)methyl)-2-methyl-3-(ethyl(1-(oxetan-3-yl)piperidin-4-yl)amino)-5-(2-oxo-2',3',5',6'-tetrahydrospiro[dihydroindole-3,4'-pyran]-6-yl)benzamide

82

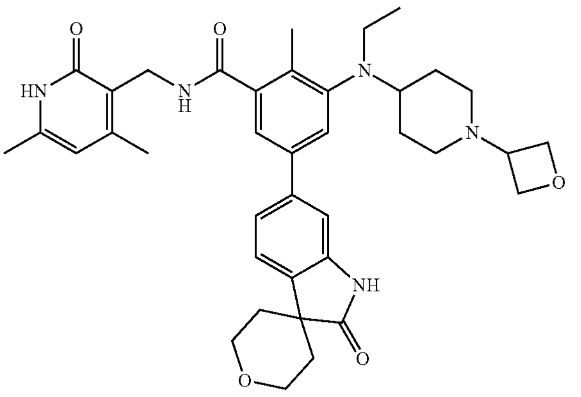

A similar method of Example 81 was used to obtain the title compound 82 with a yield of 7%, wherein the paraformaldehyde was replaced with 3-oxetanone.

$^1$H NMR (400 MHz, Methanol-$d_4$) δ 7.52 (d, J=7.8 Hz, 1H), 7.40 (s, 1H), 7.31-7.2 (r, 2H), 7.12-7.07 (m, 1H), 6.09 (s, 1H), 4.63 (t, J=6.6 Hz, 2H), 4.54 (t, J=6.3 Hz, 2H), 4.47 (s, 2H), 4.16 (d, J=7.8 Hz, 2H), 3.94 (d, J=7.6 Hz, 2H), 3.51-3.36 (m, 2H), 3.19-3.08 (m, 2H), 2.89 (s, 2H), 2.74 (d, J=10.7 Hz, 2M) 2.37 (d, J=1.5 Hz, 3H), 2.29 (s, 3H) 2.22 (s, 3H), 1.89-1.68 (m, 8H), 0.89 (t, J=6.9 Hz, 3H), MS m/z (ESF): 654 $[M+H]^+$.

Example 83 N-((4,6-dimethyl-2-oxo-1,2-dihydropyridin-3-yl)methyl)-3-(ethyl(tetrahydro-2H-pyran-4-yl)amino)-2-methyl-5-(1-methyl-2-oxo-2',3',5',6'-tetrahydrospiro[dihydroindole-3,4'-pyran]-5-yl) benzamide

83

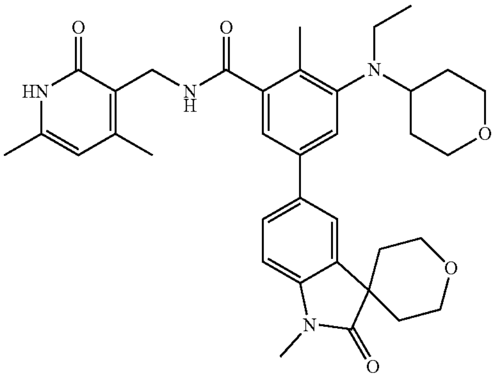

A similar method of Example 73 was used to obtain the title compound 83 with a yield of 33%, wherein the 6-bromo-1,3-dihydro-2H-indol-2-one was replaced with 5-bromo-1,3-dihydro-2H-indol-2-one.

MS m/z (ESI): 613 $[M+H]^+$.

Example 84 N-((4,6-dimethyl-2-oxo-1,2-dihydro-pyridin-3-yl)methyl)-3-(ethyl(tetrahydro-2H-pyran-4-yl)amino)-2-methyl-5-(1'-(oxetan-3-yl)-2-oxospiro[dihydroindole-3,4'-piperidine]-6-yl)benzamide

84

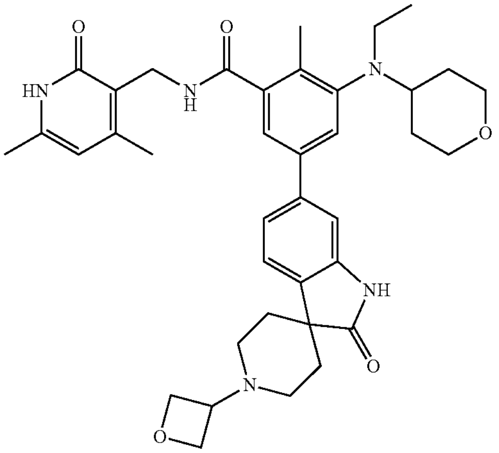

A similar method of Example 68 was used to obtain the title compound 84 with a yield of 13%, wherein the paraformaldehyde was replaced with 3-oxetanone.

MS m/z (ESI): 654.3 $[M+H]^+$.

Example 85 N-((4,6-dimethyl-2-oxo-1,2-dihydro-pyridin-3-yl)methyl)-3-(ethyl(tetrahydro-2H-pyran-4-yl)amino)-2-methyl-5-(1'-ethyl-2-oxospiro[dihydroindole-3,4'-piperidine]-6-yl)benzamide

85

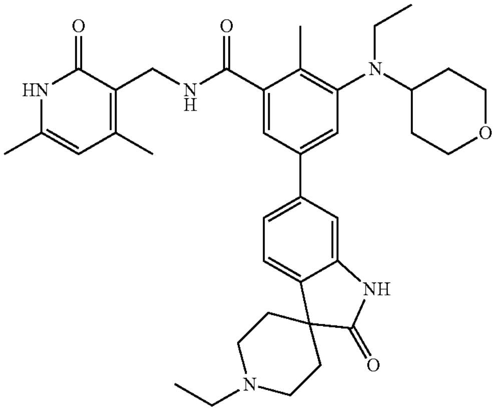

A similar method of Example 68 was used to obtain the title compound 85 with a yield of 21%, wherein the paraformaldehyde was replaced with acetaldehyde.

MS m/z (ESI): 626.3 $[M+H]^+$.

Example 86 N-((4,6-dimethyl-2-oxo-1,2-dihydro-pyridin-3-yl)methyl)-3-(ethyl(tetrahydro-2H-pyran-4-yl)amino)-2-methyl-5-(2'-oxospiro[cyclohexane-1,3'-dihydroindole]-6'-yl)benzamide

86

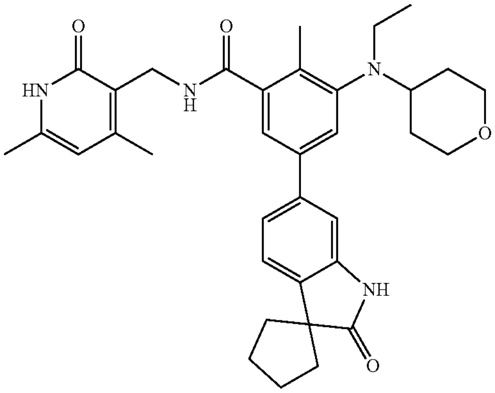

A similar method of Example 66 was used to obtain the title compound 86 with a yield of 18%, wherein the 2,2'-dibromodiethyl ether was replaced with 1,4-diiodobutane.

MS m/z (ESI): 582.3 $[M+H]^+$.

Example 87 N-((4,6-dimethyl-2-oxo-1,2-dihydro-pyridin-3-yl)methyl)-3-(ethyl(tetrahydro-2H-pyran-4-yl)amino)-2-methyl-5-(1'-methylsulfonyl-2-oxospiro[dihydroindole-3,4'-piperidine]-6-yl)benzamide

87

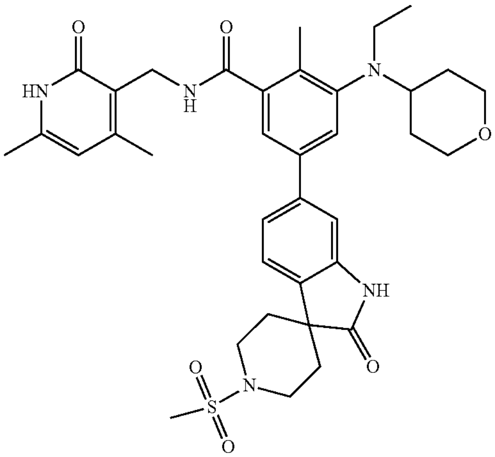

A similar method of Example 68 was used to obtain the title compound 87 with a yield of 10%, wherein the benzyl bis(2-bromoethyl)carbamate was replaced with N,N-bis(2-bromoethyl)methanesulfonamide.

MS m/z (ESI): 676.3 $[M+H]^+$.

Example 88 5-(1'-acetyl-2-oxospiro[dihydroindole-3,4'-piperidine]-6-yl)-N-((4,6-dimethyl-2-oxo-1,2-dihydropyridin-3-yl)methyl)-3-(ethyl(tetrahydro-2H-pyran-4-yl)amino)-2-methyl-5-(1'-acetyl-2-oxospiro[dihydroindole-3,4'-piperidine]-6-yl)benzamide

88

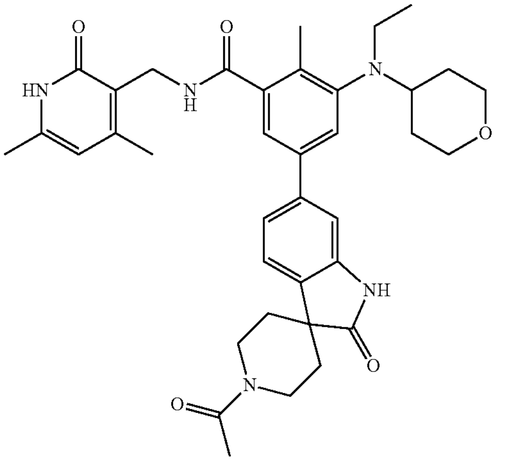

A similar method of Example 68 was used to obtain the title compound 88 with a yield of 33%, wherein the benzyl bis(2-bromoethyl)carbamate was replaced with N,N-bis(2-bromoethyl)acetamide.

MS m/z (ESI): 640.3 $[M+H]^+$.

Example 89 N-((4,6-dimethyl-2-oxo-1,2-dihydropyridin-3-yl)methyl)-3-(ethyl(tetrahydro-2H-pyran-4-yl)amino)-2-methyl-5-(2-oxo-2',3',5',6'-tetrahydrospiro[dihydroindole-3,4'-thiapyran]-6-yl)benzamide

89

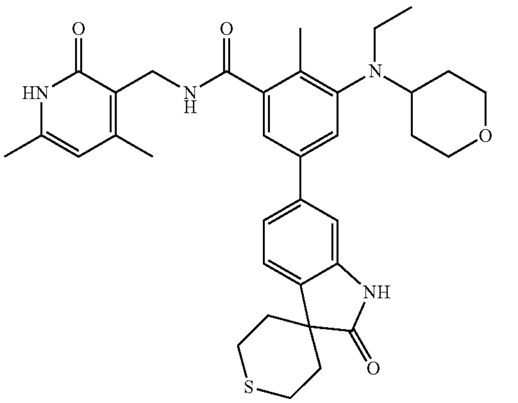

A similar method of Example 66 was used to obtain the title compound 89 with a yield of 12%, wherein the 6-bromo-2',3',5',6'-tetrahydrospiro[dihydroindole-3,4'-pyran]-2-one was replaced with 6-bromo-2',3',5',6'-tetrahydrospiro[dihydroindole-3,4'-thiapyran]-2-one (obtained according to the method disclosed in WO2009124692A1).

MS m/z (ESI): 615 $[M+H]^+$.

Example 90 N-((4,6-dimethyl-2-oxo-1,2-dihydropyridin-3-yl)methyl)-5-(1',1'-dioxo-2-oxo-2',3',5',6'-tetrahydrospiro[dihydroindole-3,4'-thiapyran]-6-yl)-3-(ethyl(tetrahydro-2H-pyran-4-yl)amino)-2-methylbenzamide

90

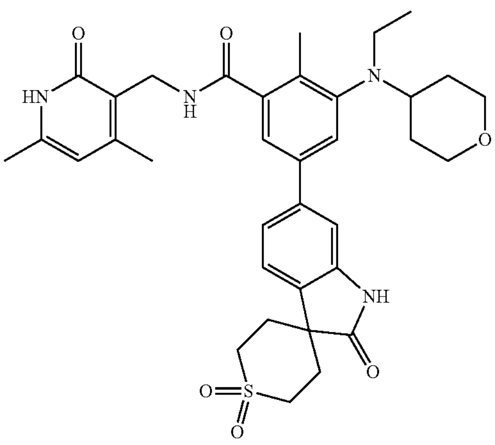

A similar method of Example 66 was used to obtain the title compound 90 with a yield of 20%, wherein the 6-bromo-2',3',5',6'-tetrahydrospiro[dihydroindole-3,4'-pyran]-2-one was replaced with 6-bromo-2',3',5',6'-tetrahydrospiro[dihydroindole-3,4'-thiapyran]-2-one-1',1'-dioxide (obtained according to the method disclosed in Bioorganic & Medicinal Chemistry Letters 21 (2011) 5270-5273).

MS m/z (ESI): 647 $[M+H]^+$.

Example 91 5-(4,4-difluoro-2'-oxospiro[cyclohexane-1,3'-dihydroindole]-6'-yl)-N-((4,6-dimethyl-2-oxo-1,2-dihydropyridin-3-yl)methyl)-3-(ethyl(tetrahydro-2H-pyran-4-yl)amino)-2-methylbenzamide

91

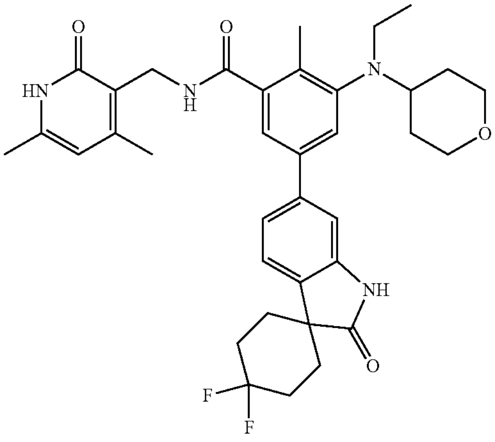

A similar method of Example 66 was used to obtain the title compound 91 with a yield of 13%, wherein the 6-bromo-2',3',5',6'-tetrahydrospiro[dihydroindole-3,4'-pyran]-2-one was replaced with 6'-bromo-4,4-difluorospiro[cyclohexane-1,3'-dihydroindole]-2'-one (obtained according to the method disclosed in WO2009124692A1).

MS m/z (ESI): 633 $[M+H]^+$.

Example 92 N-((4,6-Dimethyl-2-oxo-1,2-dihydropyridin-3-yl)methyl)-5-(2',4-dioxospiro[cyclohexane-1,3'-dihydroindole]-6'-yl)-3-(ethyl(tetrahydro-2H-pyran-4-yl)amino)-2-methylbenzamide

92

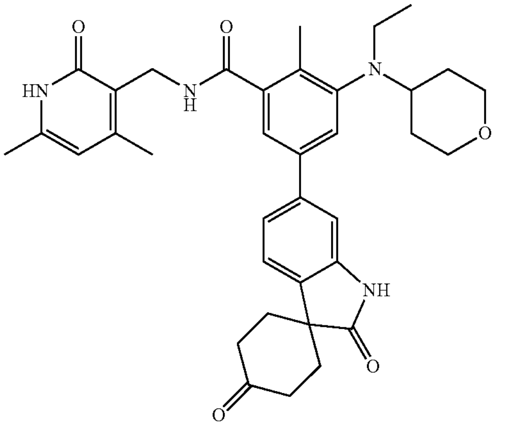

A similar method of Example 66 was used to obtain the title compound 92 with a yield of 8%, wherein the 6-bromo-2',3',5',6'-tetrahydrospiro[dihydroindole-3,4'-pyran]-2-one was replaced with 6'-bromospiro[cyclohexane-1,3'-dihydroindole]-2',4-dione (obtained according to the method disclosed in WO2009124692A1).

MS m/z (ESI): 611 $[M+H]^+$.

Example 93 N-((4,6-dimethyl-2-oxo-1,2-dihydropyridin-3-yl)methyl)-3-(ethyl(tetrahydro-2H-pyran-4-yl)amino)-5-(4-hydroxy-4-methyl-2'-oxospiro[cyclohexane-1,3'-dihydroindole]-6'-yl)-2-methylbenzamide

93

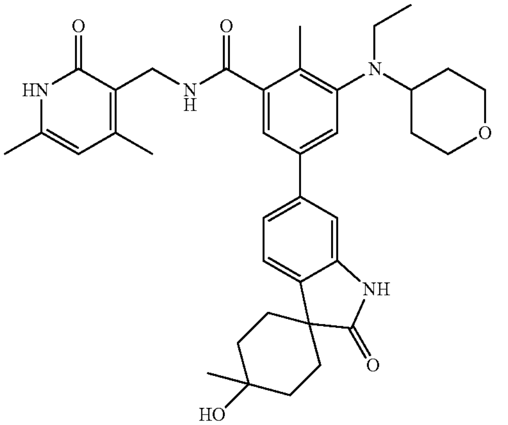

A similar method of Example 66 was used to obtain the title compound 93 with a yield of 18%, wherein the 6-bromo-2',3',5',6'-tetrahydrospiro[dihydroindole-3,4'-pyran]-2-one was replaced with 6'-bromo-4-hydroxy-4-methylspiro[cyclohexane-1,3'-dihydroindole]-2'-one (obtained according to the method disclosed in WO2009124692A1).

MS m/z (ESI): 627 $[M+H]^+$.

Example 94 N-((4,6-dimethyl-2-oxo-1,2-dihydropyridin-3-yl)methyl)-3-(ethyl(tetrahydro-2H-pyran-4-yl)amino)-5-(4-hydroxy-2'-oxospiro[cyclohexane-1,3'-dihydroindole]-6'-yl)-2-methylbenzamide

94

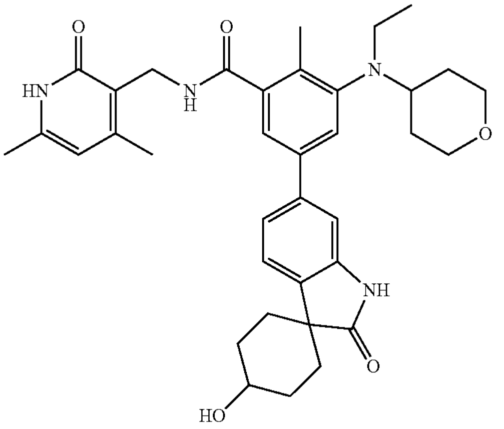

A similar method of Example 66 was used to obtain the title compound 94 with a yield of 20%, wherein the 6-bromo-2',3',5',6'-tetrahydrospiro[dihydroindole-3,4'-pyran]-2-one was replaced with 6'-bromo-4-hydroxyspiro[cyclohexane-1,3'-dihydroindole]-2'-one (obtained according to the method disclosed in WO2009124692A1).

MS m/z (ESI): 613 $[M+H]^+$.

Example 95 N-((4,6-Dimethyl-2-oxo-1,2-dihydropyridin-3-yl)methyl)-3-(ethyl(tetrahydro-2H-thiapyran-4-yl)amino)-2-methyl-5-(2-oxo-2',3',5',6'-tetrahydrospiro[dihydroindole-3,4'-pyran]-6-yl)benzamide

95

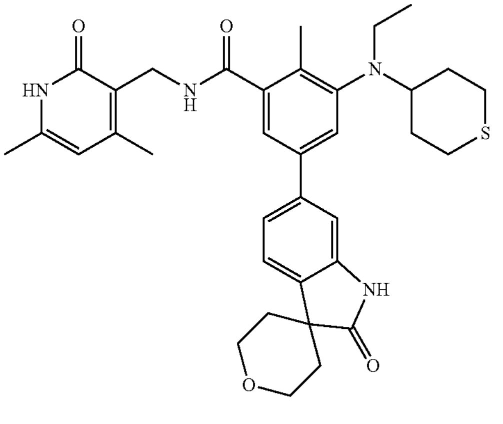

A similar method of Example 66 was used to obtain the title compound 95 with a yield of 33%, wherein the tetrahydro-4H-pyran-4-one was replaced with tetrahydrothiopyran-4-one.

MS m/z (ESI): 615 $[M+H]^+$.

Example 96 N-((4,6-Dimethyl-2-oxo-1,2-dihydropyridin-3-yl)methyl)-3-((ethyl)(1,1-dioxotetrahydro-2H-thiapyran-4-yl)amino)-2-methyl-5-(2-oxo-2',3',5',6'-tetrahydrospiro[dihydroindole-3,4'-pyran]-6-yl) benzamide

96

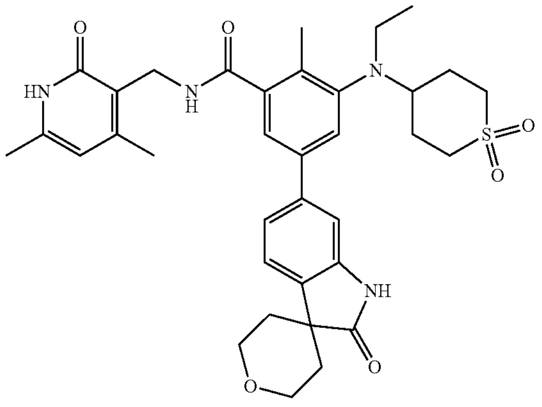

A similar method of Example 66 was used to obtain the title compound 96 with a yield of 33%, wherein the tetrahydro-4H-pyran-4-one was replaced with tetrahydrothiopyran-4-one-1,1-dioxide.

MS m/z (ESI): 647 [M+H]+.

Example 97 N-((4,6-Dimethyl-2-oxo-1,2-dihydropyridin-3-yl)methyl)-3-(ethyl(tetrahydro-2H-thiapyran-4-yl)amino)-2-methyl-5-(2-oxospiro[dihydroindole-3,4'-piperidine]-6-yl)benzamide

97

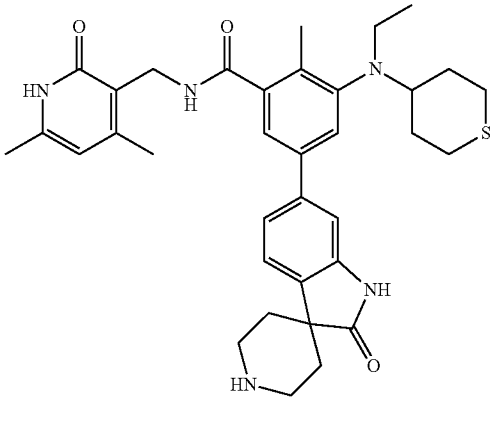

A similar method of Example 68 was used to obtain the title compound 97 with a yield of 17%, wherein the tetrahydro-4H-pyran-4-one was replaced with tetrahydrothiopyran-4-one.

MS m/z (ESI): 614 [M+H]+.

Example 98 N-((4,6-Dimethyl-2-oxo-1,2-dihydropyridin-3-yl)methyl)-3-((ethyl)(4-dimethylaminocyclohexyl)amino)-2-methyl-5-(2-oxo-2',3',5',6'-tetrahydrospiro[dihydroindole-3,4'-pyran]-6-yl) benzamide

98

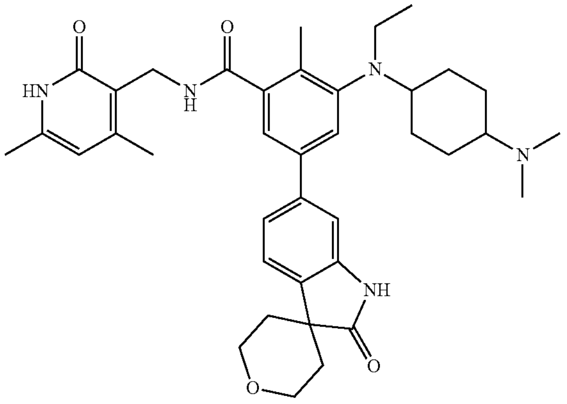

A similar method of Example 66 was used to obtain the title compound 98 with a yield of 15%, wherein the tetrahydro-4H-pyran-4-one was replaced with 4-dimethylaminocyclohexanone.

MS m/z (ESI): 640 [M+H]+.

Example 99 N-((4,6-Dimethyl-2-oxo-1,2-dihydropyridin-3-yl)methyl)-3-(ethyl(4-((2-methoxyethyl)(methyl)amino)cyclohexyl)amino)-2-methyl-5-(2-oxo-2',3',5',6'-tetrahydrospiro[dihydroindole-3,4'-pyran]-6-yl)benzamide

99

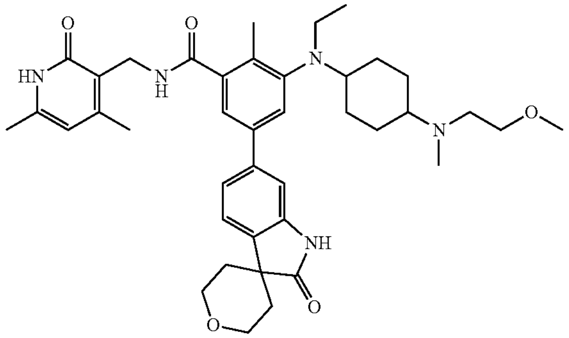

A similar method of Example 66 was used to obtain the title compound 99 with a yield of 10%, wherein the tetrahydro-4H-pyran-4-one was replaced with 4-((2-methoxyethyl)(methyl)amino)cyclohexyl-1-one.

MS m/z (ESI): 684 [M+H]+.

Example 100 N-((Ethyl)(4-dimethylamino-cyclohexyl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide

100

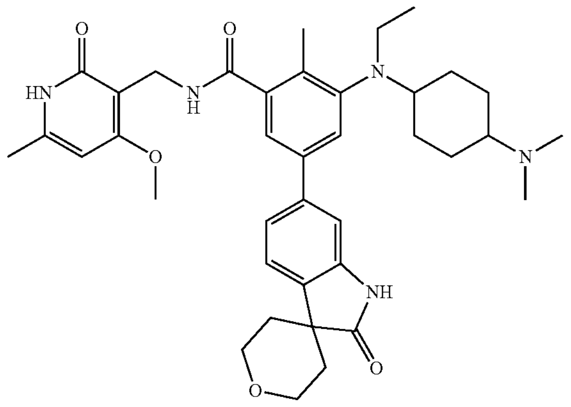

A similar method of Example 66 was used to obtain the title compound 100 with a yield of 18%, wherein the tetrahydro-4H-pyran-4-one was replaced with 4-dimethylaminocyclohexanone, and the 3-(aminomethyl)-4,6-dimethyl-1H-pyridin-2-one hydrochloride was replaced with 3-(aminomethyl)-4-methoxy-6-methyl-1H-pyridin-2-one trifluoroacetate.

MS m/z (ESI): 656 [M+H]+.

Example 101 N-((4,6-Dimethyl-2-oxo-1,2-dihydropyridin-3-yl)methyl)-3-(ethyl(tetrahydro-2H-pyran-4-yl)amino)-2-methyl-5-(2'-oxo-1',2,2',3,5,6-hexahydrospiro[pyran-4,3'-pyrrolo[3,2-b]pyridine]-6'-yl)benzamide

101

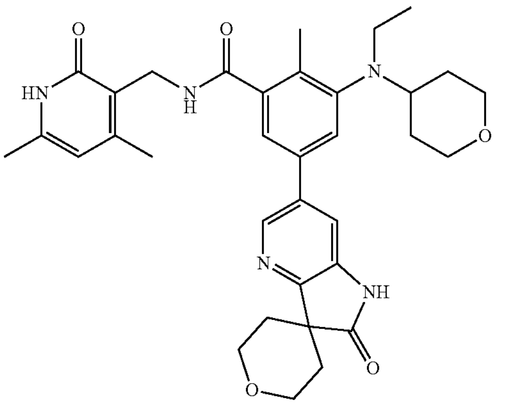

A similar method of Example 66 was used to obtain the title compound 101 with a yield of 20%, wherein the 6-bromo-2',3',5',6'-tetrahydrospiro[dihydroindole-3,4'-pyran]-2-one was replaced with 6'-bromo-2',3',5',6'-tetrahydrospiro[pyran-4,3'-pyrrolo[3,2-b]pyridine]-2'(1'H)-one (obtained according to the method disclosed in WO2009124692A1).

MS m/z (ESI): 600 [M+H]+.

Example 102 N-((4,6-Dimethyl-2-oxo-1,2-dihydropyridin-3-yl)methyl)-3-((ethyl)(3-methoxytetrahydro-2H-pyran-4-yl)amino)-2-methyl-5-(2-oxo-2',3',5',6'-tetrahydrospiro[dihydroindole-3,4'-pyran]-6-yl)benzamide

102

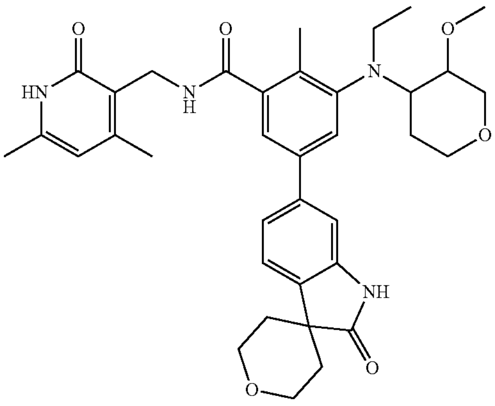

A similar method of Example 66 was used to obtain the title compound 102 with a yield of 12%, wherein the tetrahydro-4H-pyran-4-one was replaced with 3-methoxytetrahydro-4H-pyran-4-one.

MS m/z (ESI): 629.3 [M+H]+.

Example 103 N-((4,6-Dimethyl-2-oxo-1,2-dihydropyridin-3-yl)methyl)-3-(ethyl(3-fluoro-tetrahydro-2H-pyran-4-yl)amino)-2-methyl-5-(2-oxo-2',3',5',6'-tetrahydrospiro[dihydroindole-3,4'-pyran]-6-yl)benzamide

103

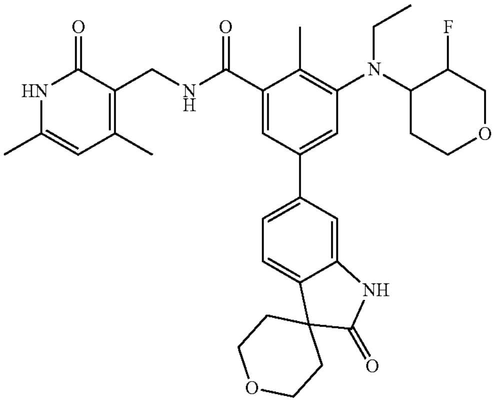

A similar method of Example 66 was used to obtain the title compound 103 with a yield of 15%, wherein the tetrahydro-4H-pyran-4-one was replaced with 3-fluorotetrahydro-4H-pyran-4-one.

MS m/z (ESI): 617 [M+H]+.

Example 104 N-((4,6-Dimethyl-2-oxo-1,2-dihydropyridin-3-yl)methyl)-3-(ethyl(2,6-dimethyltetrahydro-2H-pyran-4-yl)amino)-2-methyl-5-(2-oxo-2',3',5',6'-tetrahydrospiro[dihydroindole-3,4'-pyran]-6-yl)benzamide

104

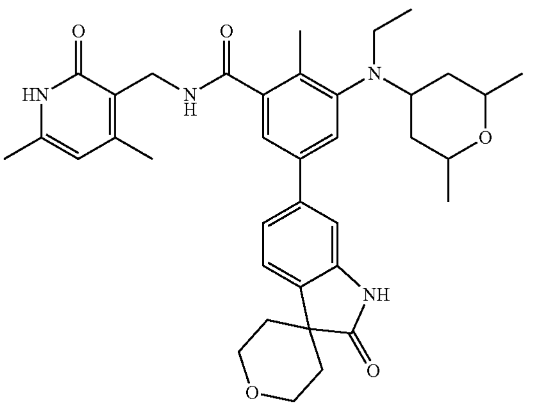

A similar method of Example 66 was used to obtain the title compound 104 with a yield of 18%, wherein the tetrahydro-4H-pyran-4-one was replaced with 2,6-dimethyltetrahydro-4H-pyran-4-one.

MS m/z (ESI): 627 $[M+H]^+$.

Example 105 N-((4,6-Dimethyl-2-oxo-1,2-dihydropyridin-3-yl)methyl)-3-(ethyl(tetrahydro-2H-pyran-4-yl)amino)-2-methyl-5-(2',3',5',6'-tetrahydro-2H-spiro[benzofuran-3,4'-pyran]-6-yl)benzamide

105

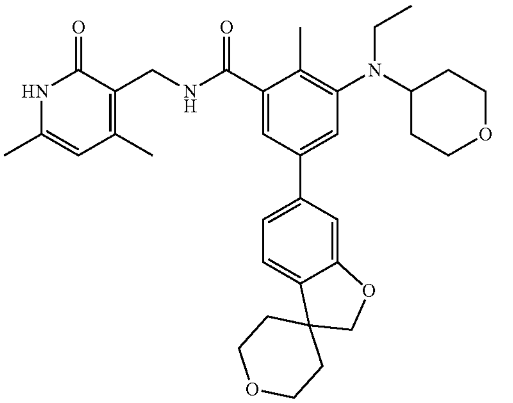

A similar method of Example 66 was used to obtain the title compound 105 with a yield of 5%, wherein the 6-bromo-2',3',5',6'-tetrahydrospiro[dihydroindole-3,4'-pyran]-2-one was replaced with 6'-bromo-2',3',5',6'-tetrahydro-2H-spiro[benzofuran-3,4'-pyran].

MS m/z (ESI): 586 $[M+H]^+$.

Example 106 N-((4,6-Dimethyl-2-oxo-1,2-dihydropyridin-3-yl)methyl)-3-(ethyl(tetrahydro-2H-pyran-4-yl)amino)-2-methyl-5-(1-oxo-2',3,3',4,5',6'-hexahydro-1H-spiro[naphthalene-2,4'-pyran]-6-yl)benzamide

106

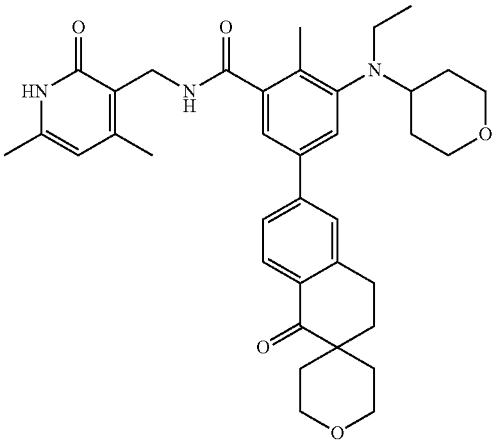

A similar method of Example 78 was used to obtain the title compound 106 with a yield of 28%, wherein the 6-bromo-1-indanone was replaced with 6-bromo-3,4-dihydronaphthalen-1(2H)-one.

MS m/z (ESI): 612 $[M+H]^+$.

Example 107 N-((4,6-Dimethyl-2-oxo-1,2-dihydropyridin-3-yl)methyl)-3-(ethyl(tetrahydro-2H-pyran-4-yl)amino)-2-methyl-5-(1'-methyl-1-oxo-1,3-dihydrospiro[indene-2,4'-piperidine]-6-yl)benzamide

107

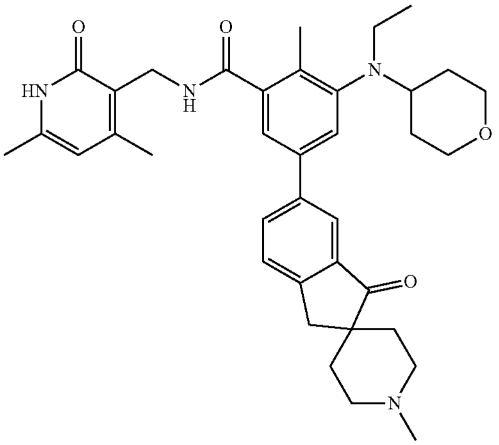

A similar method of Example 78 was used to obtain the title compound 107 with a yield of 18%, wherein the 2,2'-dibromodiethyl ether was replaced with N,N-bis(2-bromoethyl)methylamine.

MS m/z (ESI): 611 $[M+H]^+$.

Example 108 N-((4,6-Dimethyl-2-oxo-1,2-dihydropyridin-3-yl)methyl)-3-(ethyl(tetrahydro-2H-pyran-4-yl)amino)-5-(2,2',3,3',5',6'-hexahydrospiro[indene-1,4'-pyran]-5-yl)-2-methylbenzamide

108

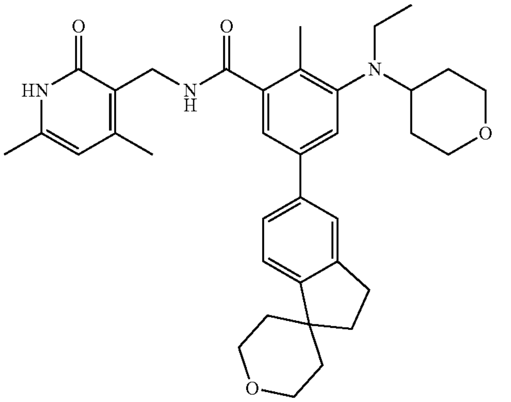

A similar method of Example 66 was used to obtain the title compound 108 with a yield of 13%, wherein the 6-bromo-2',3',5',6'-tetrahydrospiro[dihydroindole-3,4'-pyran]-2-one was replaced with 5-bromo-2,2',3,3',5',6'-hexahydrospiro[indene-1,4'-pyran].

MS m/z (ESI): 584.3 $[M+H]^+$.

Example 109 3-(Ethyl(1-(2,2,2-trifluoroethyl)piperidin-4-yl)amino)-N-((4-methoxy-6-methyl-2-oxo-1,2-dihydropyridin-3-yl)methyl)-2-methyl-5-(1-methyl-2-oxo-2',3',5',6'-tetrahydrospiro[dihydroindole-3,4'-pyran]-5-yl)benzamide

109

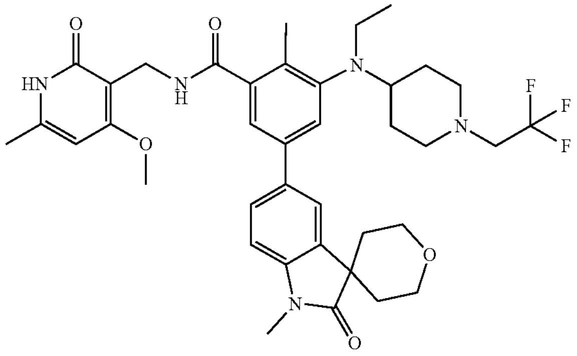

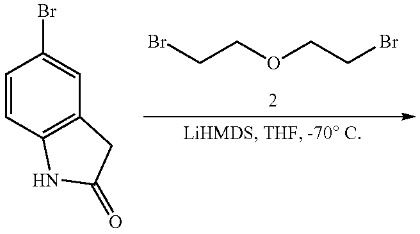

109a

-continued

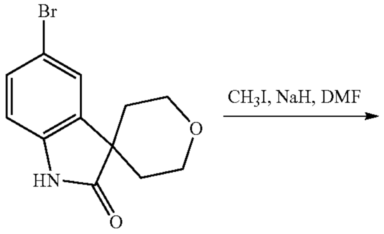

109b

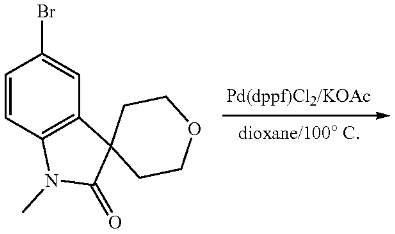

109c

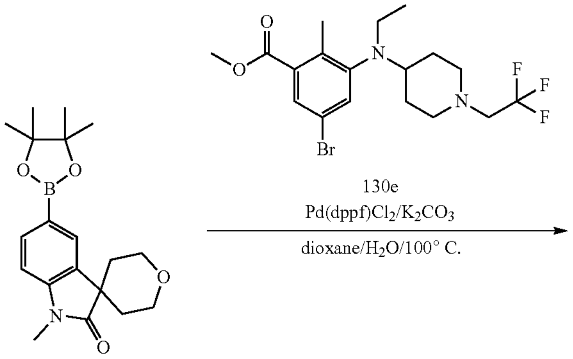

109d

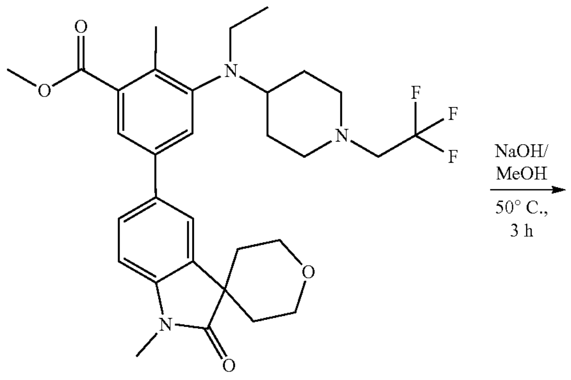

109f

-continued

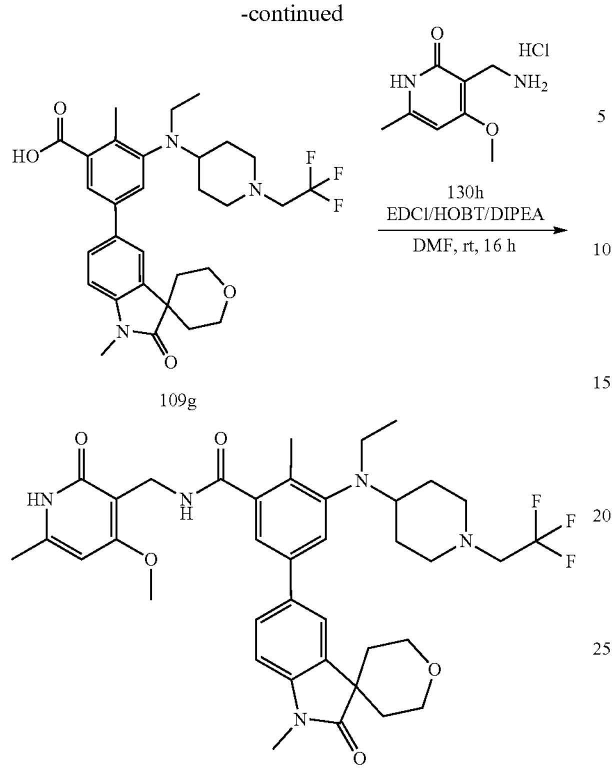

109g

109

Step I 5-Bromo-2',3',5',6'-tetrahydrospiro[dihydroindole-3,4'-pyran]-2-one 109b

The compound 109a (15 g, 70.75 mmol) and 1-bromo-2-(2-bromoethoxy)ethane (24.6 g, 106.13 mmol) were dissolved in THF (200 mL), and LiHMDS (283 mL, 283 mmol) was added dropwise slowly at −78° C. The mixture was naturally raised to room temperature and stirred overnight, which was then heated to 80° C. and stirred for 2 hours until the reaction was completed as determined by LCMS. The reaction solution was cooled to room temperature, added with saturated ammonium chloride aqueous solution to quench the reaction, extracted with EA, and the organic phase was dried with anhydrous sodium sulfate, concentrated, and slurried with methanol to obtain a light pink solid of compound 109b (11 g, 39.1 mmol) with a yield of 55.3%.

MS m/z (ESI): 282 $[M+1]^+$.

Step II 5-Bromo-1-methyl-2',3',5',6'-tetrahydrospiro[dihydroindole-3,4'-pyran]-2-one 109c The compound 109b (11 g, 39.15 mmol) was dissolved in DMF (100 mL), added with NaH (4.7 g, 117.45 mmol) in batches under stirring, stirred at room temperature for 30 minutes, added with iodomethane (11.1 g, 78.3 mmol), and stirred for another 1 hour until the reaction solution was completed as determined by LCMS. The reaction solution was added with water/EA (150 mL/100 mL), stirred for 2 minutes, and separated. The aqueous phase was extracted with EA (50 mL×3), and the organic phases were combined, washed with saturated NaCl solution for several times, dried with anhydrous sodium sulfate, and purified by column chromatography to obtain the title compound 109c (8.3 g, 28 mmol) with a yield of 71.5%.

MS m/z (ESI): 296.1 $[M+1]^+$.

Step III 1-Methyl-5-(4,4,5,5-tetramethyl-1,3,2-dioxaborolan-2-yl)-2',3',5',6'-tetrahydrospiro[dihydroindole-3,4'-pyran]-2-one 109d The compound 109c (5.3 g, 17.9 mmol) and bis(pinacolato)diboron (9.06 g, 35.8 mmol) were dissolved in 1,4-dioxane (200 mL), and [1,1'-bis(diphenylphosphino)ferrocene]dichloropalladium (1.308 g, 1.79 mmol) and potassium acetate (5.26 g, 53.7 mmol) were added. The mixture was heated to 100° C. under the protection of nitrogen and stirred for 2 hours until the reaction was completed. The reaction solution was added with water and extracted with ethyl acetate. The organic phase was washed with saturated NaCl solution for several times, dried with anhydrous sodium sulfate, filtered, concentrated, and purified by column chromatography to obtain the title compound 109d (6.0 g, 17.49 mmol) with a yield of 97.7%.

MS m/z (ESI): 344.3 $[M+1]^+$.

Step IV Methyl 3-(ethyl(1-(2,2,2-trifluoroethyl)piperidin-4-yl)amino)-2-methyl-5-(1-methyl-2-oxo-2',3',5',6'-tetrahydrospiro[dihydroindole-3,4'-pyran]-5-yl)benzoate 109f The compound 109d (1.1 g, 2.98 mmol), compound 109e (7.6 g, 17.49 mmol), Pd(dppf)$Cl_2$ (1.28 g, 1.749 mmol) and $K_2CO_3$ (7.24 g, 52.47 mmol) were dissolved in dioxane (200 mL) and $H_2O$ (50 mL). The mixture was heated to 90° C. under the protection of Ar and stirred for 3 hours. The reaction solution was cooled to room temperature, extracted with water and ethyl acetate, and the organic phase was washed with saturated NaCl solution, dried with anhydrous sodium sulfate, filtered, concentrated, and purified by column chromatography to obtain the title compound 109f (9.1 g, 15.9 mmol) with a yield of 90.8%.

MS m/z (ESI): 574.4 $[M+1]^+$.

Step V 3-(Ethyl(1-(2,2,2-trifluoroethyl)piperidin-4-yl)amino)-2-methyl-5-(1-methyl-2-oxo-2',3',5',6'-tetrahydrospiro[dihydroindole-3,4'-pyran]-5-yl)benzoic acid 109g The compound 109f (9.1 g, 15.88 mmol) was dissolved in a mixed solvent THF/MeOH/$H_2O$ (100 mL/100 mL/100 mL), and NaOH (6.3 g, 158.8 mmol) was added. The reaction solution was stirred at 50° C. for 3 hours, and TLC monitoring was used and determined that the raw materials were completely reacted. The reaction solution was neutralized with acetic acid, concentrated to remove MeOH, extracted with EA, dried with anhydrous sodium sulfate, filtered, and concentrated to obtain a target compound 109g (8.8 g, 15.74 mmol) with a yield of 99%.

MS m/z (ESI): 560.4 $[M+1]^+$.

Step VI 3-(Ethyl(1-(2,2,2-trifluoroethyl)piperidin-4-yl)amino)-N-((4-methoxy-6-methyl-2-oxo-1,2-dihydropyridin-3-yl)methyl)-2-methyl-5-(1-methyl-2-oxo-2',3',5',6'-tetrahydrospiro[dihydroindole-3,4'-pyran]-5-yl)benzamide 109

The compound 109g (4 g, 7.16 mmol) and compound 103h (1.46 g, 7.16 mmol) were dissolved in N, N-dimethylformamide (100 mL), and EDCI (2.74 g, 14.32 mmol), HOBT (996 mg, 7.16 mmol) and DIPEA (4.62 g, 35.8 mmol) were successively added. The mixture was heated to 60° C. for 2 hours until the reaction was completed. The reaction solution was cooled to room temperature, added with water dilution, and extracted with ethyl acetate. The organic phase was washed with saturated NaCl solution for several times, dried with anhydrous sodium sulfate, filtered, concentrated, and purified by column chromatography to obtain a crude product, which was then slurried with EA to obtain the compound 109 (1 g, 1.41 mmol) with a yield of 19.7%.

$^1$H NMR (400 MHz, DMSO-$d_6$) δ 11.38 (s, 1H), 7.93 (L J=4.6 Hz, 1H), 7.68 (d, J=1.8 Hz, 1H), 7.50 (dd, J=8.1, 1.8 Hz, 1H), 7.33 (d, J=1.9 Hz, 1H), 7.19 (d, J=1.8 Hz, 1H) 7.04 (d, J=8.2 Hz, 1H), 6.07-6.04 (s, 1H), 4.21 (d, J=4.6 Hz, 2H), 4.07 (ddd, J=121, 9.5, 3.01 Hz, 2H), 3.77 (m, 5H), 3.09 (m, 7H), 2.85 (d, J=11.3 Hz, 2H), 2.76 (m, 1H), 2.27 (t, J=11.2 Hz, 2H), 220 (s, 3H), 2.14 (s, 3H), 1.91 (m, 2H, 1.70-1.58 (m, 4H), 1.53 (q. J=11.7 Hz, 2H), 0.81 (t, J=69 Hz, 3H), MS m/z (ESI):710.6[M+1]$^+$.

Example 110 5-(1'-(Cyclopropylmethyl)-2-oxospiro[dihydroindole-3,4'-piperidine]-6-yl)-3-(ethyl(tetrahydro-2H-pyran-4-yl)amino)-N-((4-methyl-6-methyl-2-oxo-1,2-dihydropyridin-3-yl)methyl)-2-methylbenzamide 110

110

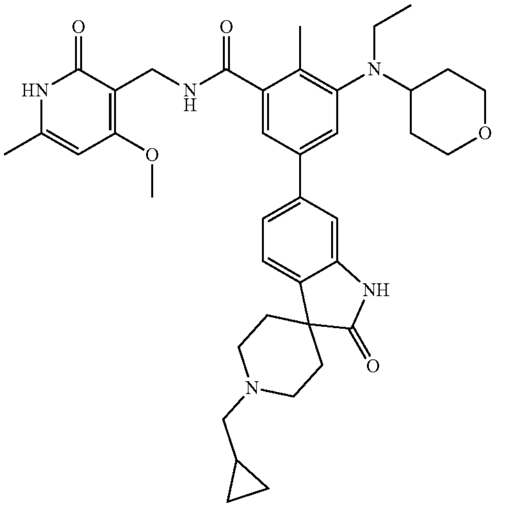 [SMILES: CCN(c1cc(-c2ccc3c(c2)N(C)CC32CCN(CC(F)(F)F)CC2)cc(C(=O)NCc2c(C)cc(C)[nH]c2=O)c1C)C1CCOCC1]

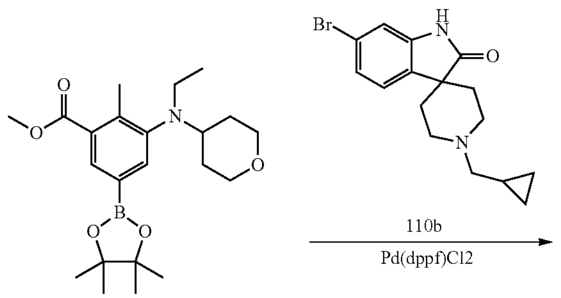

110a

-continued

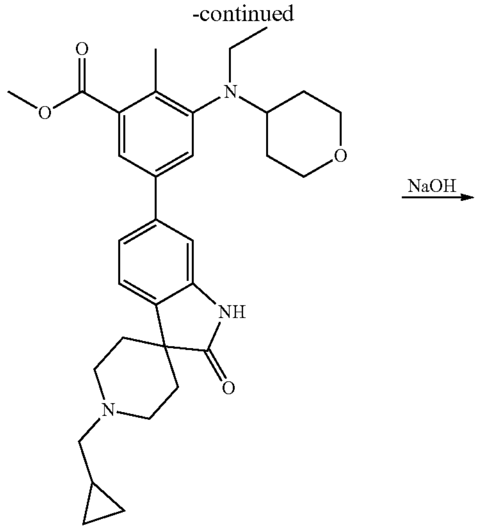

110c

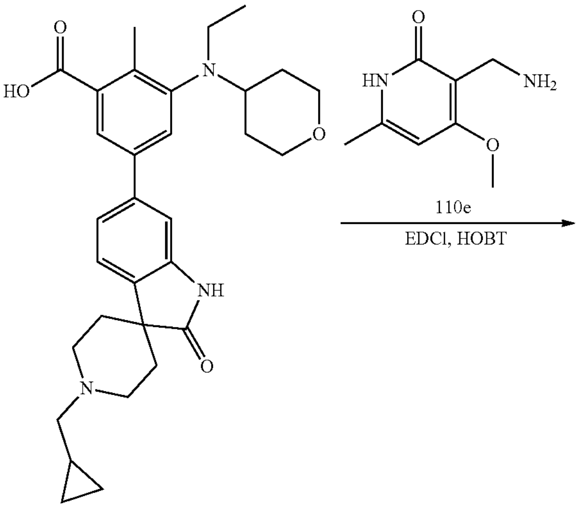

110d

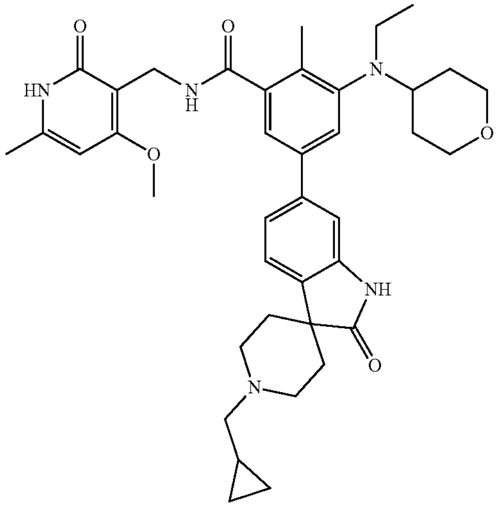

110

Step I Methyl 5-(1'-(cyclopropylmethyl)-2-oxospiro[methyl-3,4'-piperidine]-6-yl)-3-(ethyl(tetrahydro-2H-pyran-4-yl)amino)-2-methyl)benzoate 110c The compound 110a (500 mg, 1.24 mmol), compound 110b (415 mg, 1.24 mmol), potassium phosphate (788 mg, 3.27 mmol), dioxane (10 mL) and water (1 mL) were added to $Pd(dppf)Cl_2$ (88 mg, 0.12 mmol), and the mixture was refluxed at 110° C. for 2 hours. The reaction solution was cooled down, concentrated, and purified by flash column chromatography to obtain a compound 110c (0.51 g, 100 mmol) with a yield of 80%.

MS m/z (ESI): 532 $(M+1)^+$.

Step II 5-(1'-(Cyclopropylmethyl)-2-oxospiro[dihydroindole-3,4'-piperidine]-6-yl)-3-(ethyl(tetrahydro-2H-pyran-4-yl)amino)-2-benzoic acid 110d The compound 110c (0.51 g, 100 mmol) was dissolved in methanol (6 mL), added with 4 mL of NaOH (2 M), and reacted at 50° C. for 5 hours. The reaction solution was neutralized to pH=6-7 by adding 2 N HCl, and concentrated to obtain the title compound 110d (390 mg, 75 mmol) with a yield of 75%.

1H NMR (400 MHz. DMSO-d6) δ 7.48 (d, J=12.6 Hz, 2H), 7.20 (d, J=79 Hz, 1H), 7.02 (d, J=1.5 Hz, 1H), 3.80 (d, J=113 Hz, 2H), 3.21 (d, J=11.8 Hz, 3H), 3.07 (d, J=7.3 Hz, 3H), 3.01 (s, 2H), 2.80 (s, 1H), 2.42 (s, 4H), 10.96 (s, 1H), 1.83 (s, 2H), 1.64 (d, J=12.2 Hz, 2H), 1.48 (d, J=12.3 Hz, 2H), 1:20 (s, 3H), 0.93 (s, 1H), 0.80 (t, J=6.8 Hz, 4H), 0.50 (d, J=7.7 Hz, 2H), 0.16 (s, 2H),

MS m/z (ESI): 518 $(M+1)^+$.

Step III 5-(1'-(Cyclopropylmethyl)-2-oxospiro[dihydroindole-3,4'-piperidine]-6-yl)-3-(ethyl(tetrahydro-2H-pyran-4-yl)amino)-N-((4-methyl-6-methyl-2-oxo-1,2-dihydropyridin-3-yl)methyl)-2-methylbenzamide 110

The compound 110d (390 mg, 0.75 mmol), compound 110e (169 mg, 0.83 mmol), EDCI (286 mg, 1.5 mmol), HOBT (101 mg, 0.75 mmol) and TEA (227 mg, 2.25 mmol) were dissolved in DMF (10 mL), and the mixture was stirred at room temperature overnight. The reaction solution was concentrated, and purified by flash column chromatography to obtain a compound 110 (160 mg, 0.23 mmol) with a yield of 32%.

MS m/z (ESI): 668 $(M+1)^+$.

1H NMR (400 MHz, DMSO-d6) δ 11.45 (s, 1H), 10.46 (s, 1H), 8.20 (s, 1H), 7.55 (d, J=77 Hz, 1H), 7.31 (s, 1H), 7.19-7.13 (m, 1H), 7.12 (s, 1H), 7.01 (d, J=1.6 Hz, 1H), 5.83 (s, 1H), 4.25 (d, J=4.9 Hz, 2H), 4.05-3.96 (m, 2H), 3.79 (d, J=10.9 Hz, 3H), 3.21 (t, J=11.4 Hz, 2H), 3.09-2.93 (m, 3H), 2.21 (s, 2H), 2.16 (s, 2H), 2.07 (s, 3H), 1.66 (dd, J=31.1, 12.2 Hz, 6H), 1.51 (s, 2H), 0.80 (t, J=6.9 Hz, 3H),

Example 111 3-(Ethyl(tetrahydro-2H-pyran-4-yl)amino)-N-((4-methoxy-6-methyl-2-oxo-1,2-dihydropyridin-3-yl)methyl)-2-methyl-5-(2-oxospiro[dihydroindole-3,4'-piperidine]-6-yl)benzamide 111

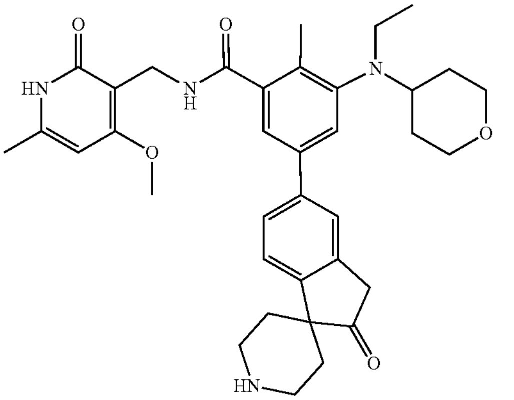

111

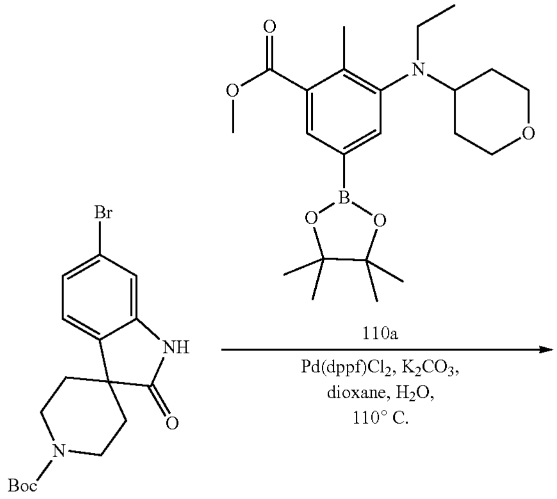

111a

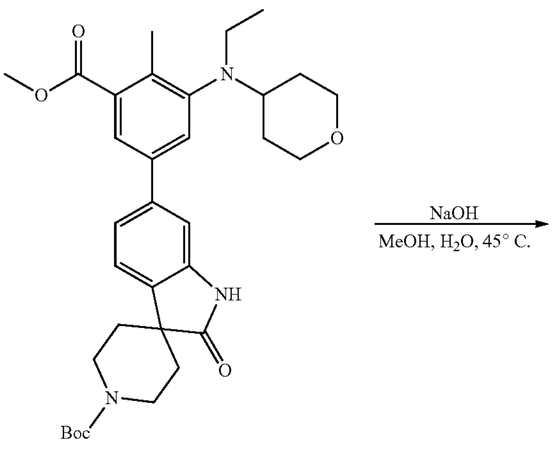

111b

-continued

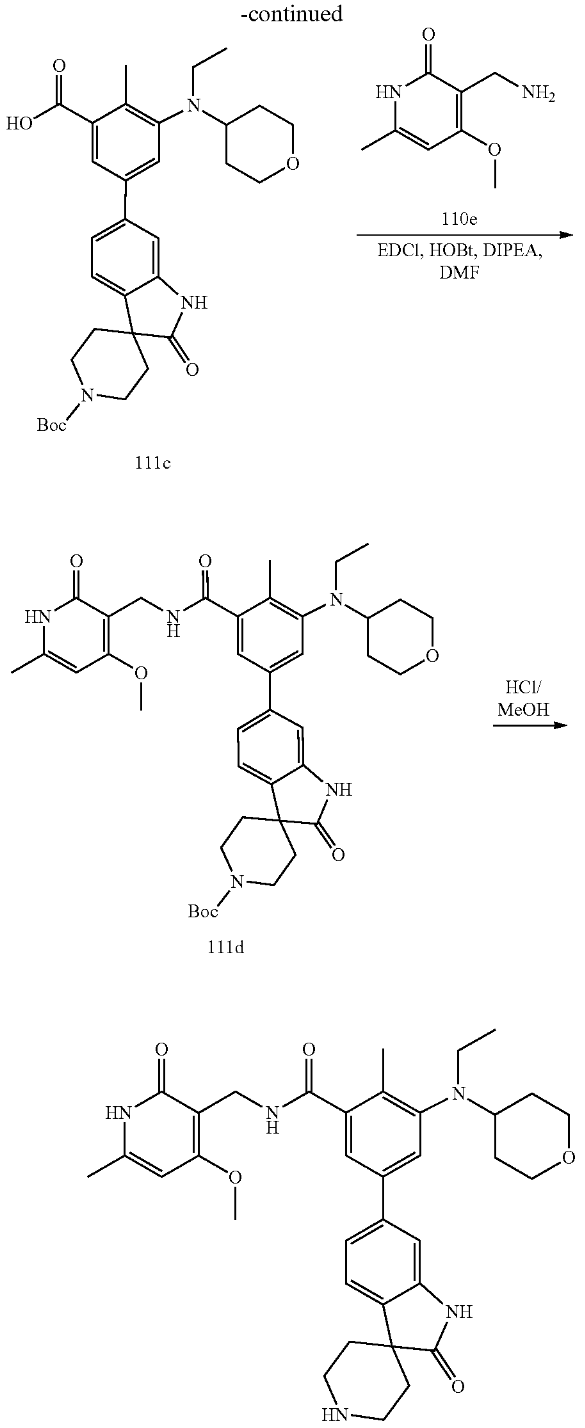

111c

111d

111

Step I tert-Butyl 6-(3-(ethyl(tetrahydro-2H-pyran-4-yl)amino)-5-(methoxycarbonyl)-4-methylphenyl)-2-oxospiro[dihydroindoline-3,4'-piperidine]-1'-formate 111b The compound 111a (450 mg, 1.18 mmol), compound 110a (520 mg, 1.30 mmol), $K_2CO_3$ (861 mg, 5.90 mmol), Pd(dppf)$Cl_2$ (100 mg, 0.118 mmol), dioxane (12 mL) and $H_2O$ (3 mL) were added in a 50 mL single-necked flask. The mixture was heated to 110° C. under the protection of $N_2$ and reacted for 2 hours. TLC monitoring was used and determined that the raw materials were completely reacted and there were new spots formed. The reaction solution was concentrated and purified by flash column chromatography to obtain a light-yellow oily product of the target compound 132b (660 mg, 1.14 mmol) with a yield of 97%.

Step II 5-(1'-(tert-Butoxycarbonyl)-2-oxospiro[dihydroindole-3,4'-piperidine]-6-yl)-3-(ethyl(tetrahydro-2H-pyran-4-yl)amino)-2-methylbenzoic acid 111c The compound 111b (660 mg, 1.14 mmol), MeOH (10 mL) were added in a 50 mL single-necked flask, and $H_2O$ (12 mL) and NaOH (480 mg, 12 mmol) were added. The mixture was heated to 45° C. and stirred for 2 hours. TLC monitoring was used and determined that the raw materials were completely reacted, and the reaction solution was neutralized with dilute hydrochloric acid, concentrated to remove MeOH, extracted with EA, dried with anhydrous sodium sulfate, filtered, and concentrated to obtain a light-yellow oily product of the target 111c (530 mg, 940 μmol) with a yield of 82%.

Step III tert-Butyl 6-(3-(ethyl(tetrahydro-2H-pyran-4-yl)amino)-5-(((4-methoxy-6-methyl-2-oxo-1,2-dihydropyridin-3-yl)methyl)carbamoyl)-4-methylphenyl)-2-oxospiro[dihydroindole-3,4'-piperidine]-1'-carboxylate 111d The compound 111c (530 mg, 940 μmol) was dissolved in DMF (6 mL), followed by adding EDCI (451 mg, 2.35 mmol), HOBt (127 mg, 940 μmol), DIPEA (972 mg, 7.52 mmol) and finally compound 110e (289 mg, 1.41 mmol), and the mixture was reacted 230° C. for 16 hours. TLC monitoring was used and determined that the raw materials were completely reacted and there were new spots formed. The reaction solution was concentrated, slurried with EA, filtered, slurried with MeOH, and filtered to obtain 400 mg of a white solid of the compound 111d (400 mg, 560 μmol) with a yield of 60%.

Step IV 3-(Ethyl(tetrahydro-2H-pyran-4-yl)amino)-N-((4-methoxy-6-methyl-2-oxo-1,2-dihydropyridin-3-yl)methyl)-2-methyl-5-(2-oxospiro[dihydroindole-3,4'-piperidine]-6-yl)benzamide 111

The compound 111d (400 mg, 560 μmol), HCl/MeOH (20 mL, 4 M) were added in a 50 mL single-necked flask and stirred at room temperature for 1.5 hours. TLC monitoring was used and determined that the raw materials were completely reacted and there were new spots formed. The reaction solution was concentrated, slurried with EA, filtered, and concentrated to obtain a red solid that was determined by 1H NMR, LCMS and HPLC to be compound 111 (220 mg, 358 μmol) with a yield of 64%.

1H NMR (400 MHz, Methanol-d4) δ 8 12 (s, 1H), 7.85 (s, 1H), 7.49 (s, 2H), 7.36 (s, 1H), 6.93 (s, 1H), 4.57 (s, 2H), 4.23 (s, 1H), 4.11 (s, 3H), 3.96 (d, J=6.6 Hz, 3H), 3.87-3.79 (m, 2H), 354-3.38 (m, 4H), 2.53 (d, J=10.4 Hz, 6H), 2.25 (d, J=11.4 Hz, 4H), 204 (d, J=14.8 Hz, 3H), 1.71 (s, 2H), 1.08 (t, J=7.0 Hz, 3H), MS n/z (ESI): 614.6 $[M+H]^+$.

Example 112 3-(Ethyl(3-methoxytetrahydro-2H-pyran-4-yl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 112

112

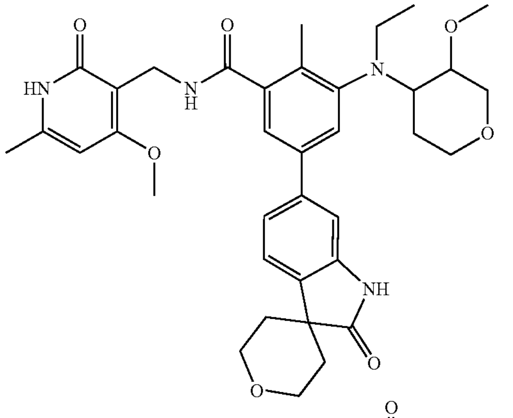

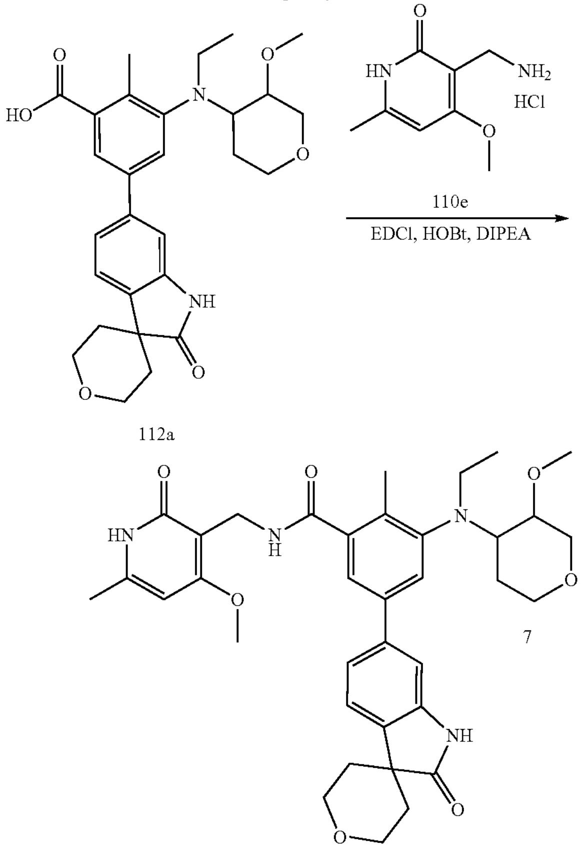

112a

7

112

Step I 3-(Ethyl(3-methoxytetrahydro-2H-pyran-4-yl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 112

The compound 112a (an intermediate of the compound 118) (95 mg, 192 mol), EDCI(110 mg, 576 μmol), HOBt (26 mg, 192 μmol), DMF(3 mL), DIPEA (0.27 mL, 1.54 mmol, 0.75 g/mL) were added in a 50 mL single-mouthed bottle, stirred for 3 minutes, and finally the compound 110e (77 mg, 288 μmol) was added. The mixture was reacted at 230° C. for 2 hours. TLC monitoring was used and determined that the raw materials were completely reacted and there were new spots formed. The reaction solution was added with water, extracted with EA, dried with anhydrous sodium sulfate, concentrated, and purified by flash column chromatography (PE:EA=0:1) to obtain a white solid product of the compound 112 (59.8 mg, 95 μmol) with a yield of 49%.

1H NMR (400 MHz, DMSO-d6) δ 11.42 (s, 1H), 10.44 (s, 1H), 7.98 (t, J=4.6 Hz, 1H), 7.58 (d, J=7.7 Hz, 1H), 7.41 (d, J=1.9 Hz, 1H), 7.23-7.17 (m, 2H), 7.04 (d, J=1.6 Hz, 1H), 6.09 (s, 1H), 4.24 (d, J=4.6 Hz, 2H), 4.09-4.02 (m, 2H), 3.95 (d, J=12.3 Hz, 1H), 3.81 (s, 6H), 3.27 (d, J=6.8 Hz, 2H), 324 (s, 3H), 3.17-3.11 (m, 2H), 3.10-3.05 (m, 1H), 2.27 (s, 3H), 2.17 (s, 3H), 1.92 (dd, J=12.2, 4.7 Hz, 1H), 1.73 (dt, J=21.0, 7.7 Hz, 4H), 0.42 (d, J=12.4 Hz, 1H), 0.81 (t, J=7.0 Hz, 3H),

MS n/z (ESI): 645.5 $[M+H]^+$.

Example 113 3-(Ethyl(tetrahydro-2H-pyran-4-yl)amino)-5-(2,2',3,3',5',6'-hexahydrospiro[indene-1,4'-pyran]-5-yl)-N-((4-methoxy-6-methyl-2-oxo-1,2-dihydropyridin-3-yl)methyl)-2-methylbenzamide 113

113

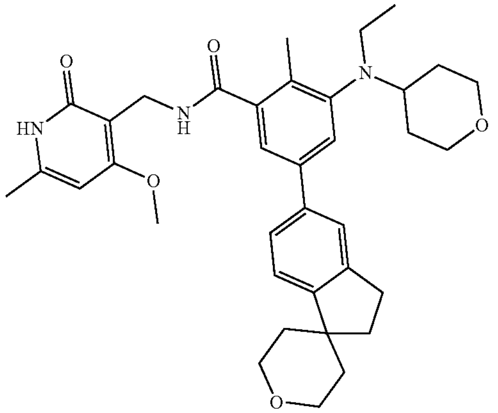

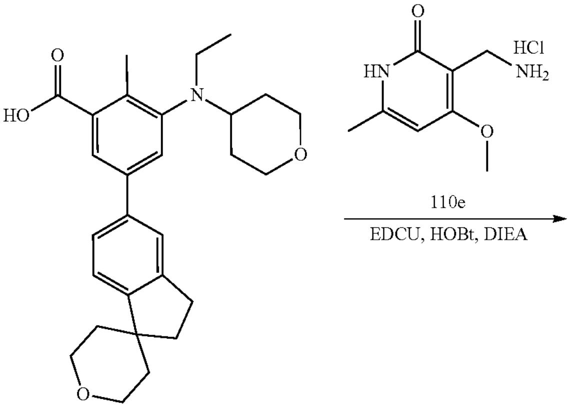

113a

-continued

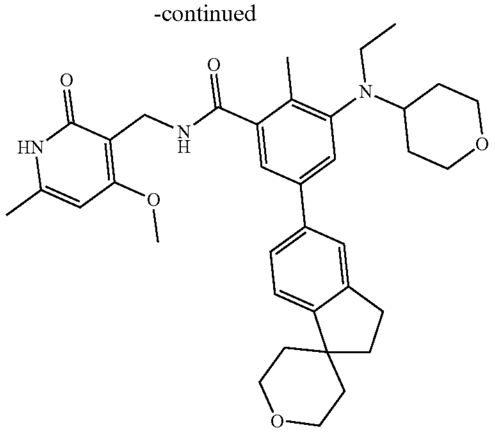

113

Step I 3-(Ethyl(tetrahydro-2H-pyran-4-yl)amino)-5-(2,2',3,3',5',6'-hexahydrospiro[indene-1,4'-pyran]-5-yl)-N-((4-methoxy-6-methyl-2-oxo-1,2-dihydropyridin-3-yl)methyl)-2-methylbenzamide 113

The compound 113a (an intermediate of the compound 126) (100 mg, 222 mol), EDCI (128 mg, 0.667 mmol), HOBt (30 mg, 0.222 mmol), DMF(3 mL), DIPEA (0.31 mL, 1.78 mmol, 0.75 g/mL) were added in a 50 mL single-mouthed bottle, stirred for 3 minutes at room temperature, and finally the compound 110e (68 mg, 0.333 mmol) was added. The mixture was reacted at 240° C. for 3 hours. TLC monitoring was used and determined that the raw materials were completely reacted and there were new spots formed. The reaction solution was added with water, extracted with EA, dried with anhydrous sodium sulfate, concentrated, and purified by flash column chromatography (PE:EA=0:1) to obtain a white solid of compound 134 (51.5 mg, 88 μmol) with a yield of 33%. 1H NMR (400 MHz, DMSO-d6) δ 11.41 (s, 1H), 7.97 (t, J=4.6 Hz. H), 7.41 (d, J=16.0 Hz, 2H), 7.36 (dd, J=5.6, 1.8 Hz, 1H), 7.28 (t, J=7.7 Hz, 1H), 721-7.17 (nm, 1H), 6.09 (s, 1H), 4.24 (t, J=4.4 Hz, 2H), 3.87-3.80 (m, 7H), 3.53 (d, J=12.1 Hz, 2H), 3.25 (t, J=11.5 Hz, 2H), 3.09 (dd, J=7.2, 5.6 Hz, 2H), 3.02 (s, 1H), 2.94-2.87 (n, 2H), 2.25 (s, 3H), 2.17 (d, J=0.7 Hz, 3H), 2.10 (dt, J=7.2, 3.7 Hz, 2H), 1.97-1.83 (m, 2H), 1.67 (d, J=12.7 Hz, 2H), 1.53 (d, J=12.4 Hz, 2H), 1.40 (d, J=13.1 Hz, 2H), 0.83 (dt, J=7.0, 3.4 Hz, 3H), MS m/z (ESI): 600.5 $[M+H]^+$.

Example 114 3-(Ethyl(tetrahydro-2H-pyran-4-yl)amino)-N-((4-methoxy-6-methyl-2-oxo-1,2-dihydropyridin-3-yl)methyl)-2-methyl-5-(1'-methyl-2-oxospiro[dihydroindole-3,4'-piperidine]-6-yl)benzamide

114

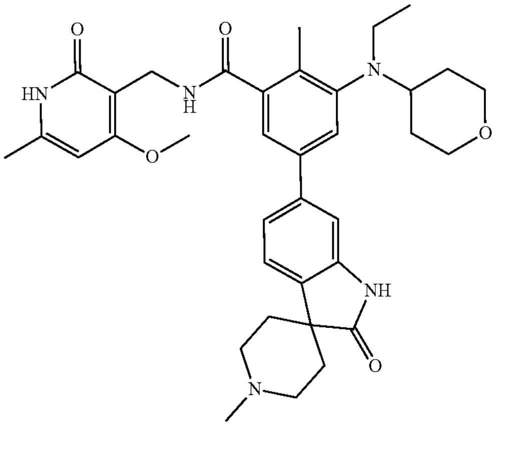

-continued

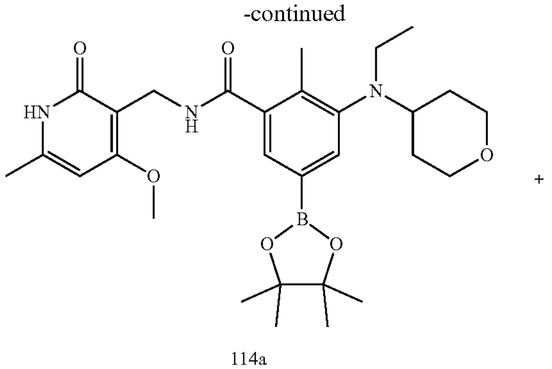

114a

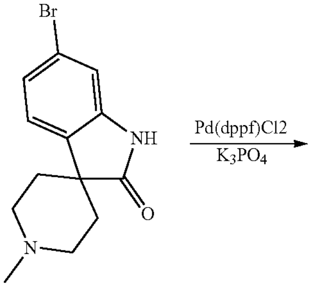

114b

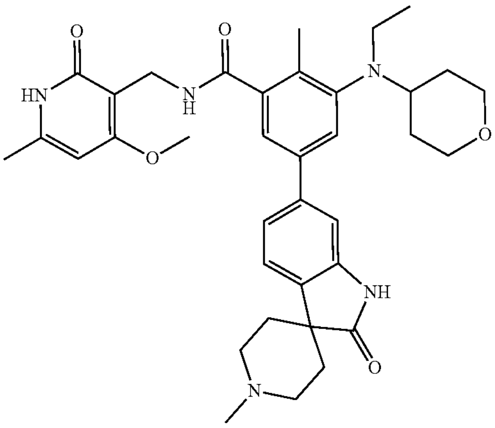

114

The compound 114a (400 mg, 0.74 mmol), compound 114b (219 mg, 0.74 mmol), Pd(dppf)$Cl_2$ (54 mg, 0.07 mmol) and potassium phosphate (313 mg, 1.48 mmol) were added to 1,4-dioxane (10 mL) and refluxed at 110° C. for 4 hours. The reaction solution was concentrated, and purified by flash column chromatography to obtain a compound 114 (190 mg, 0.30 mmol) with a yield of 40%.

1H NMR (400 MHz, DMSO-d6) δ 11.37 (s, 1H), 7.96 (t, J=4.5 Hz, 1H), 7.47 (s, 1H), 7.30 (s, 1H), 7.19-7.09 (m, 2H), 7.00 (s, 1H), 6.06 (s, 1H), 4.20 (d, J=4.5 Hz, 2H), 3.78 (s, 5H), 3.21 (t, J=11.4 Hz, 4H), 3.05 (d, J=7.2 Hz, 3H), 2.97 (s, 2H), 2.71 (s, 1H), 2.22 (s, 3H), 2, 4 (s, 3H), 1.91-1.69 (m, 5H), 1.62 (d, J=12.5 Hz, 2H), 1.49 (d, J=11.9 Hz, 2H), 0.80 (t, J=6.9 Hz, 3H),

MS m/z (ESI): $628(M+1)^+$.

Example 115 3-(Ethyl(tetrahydro-2H-pyran-4-yl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 115

115

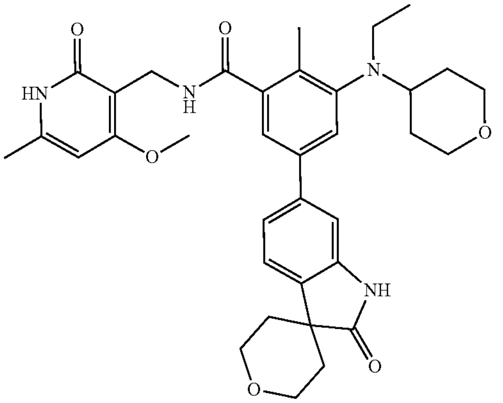

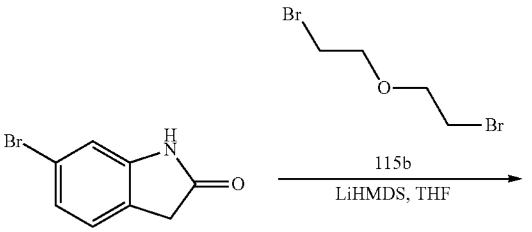

115a

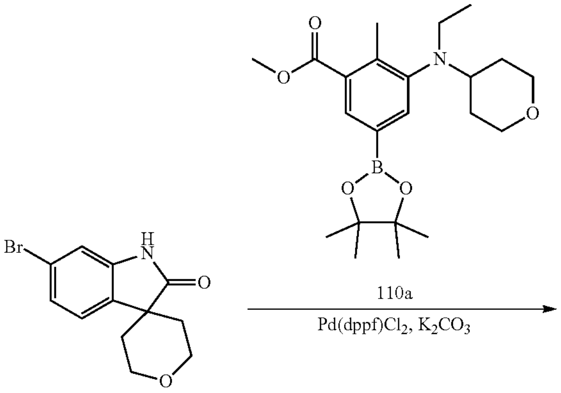

115c

-continued

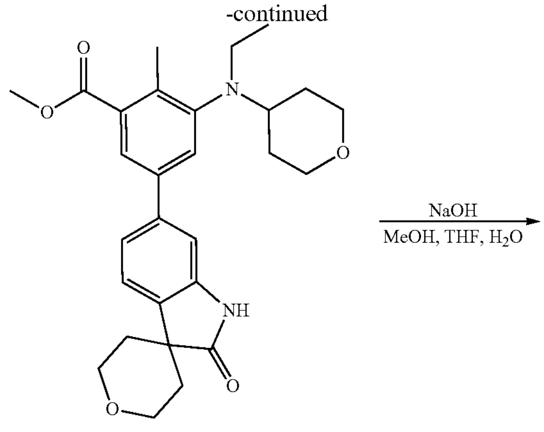

115d

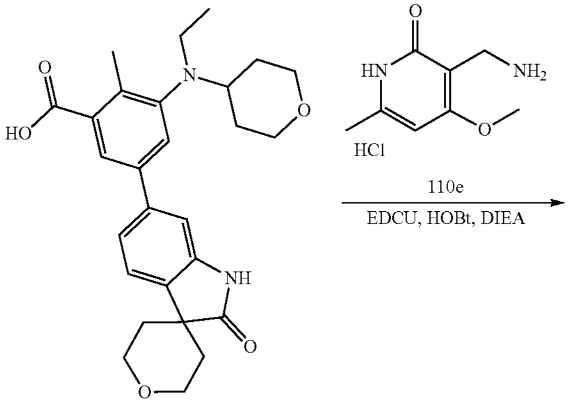

115e

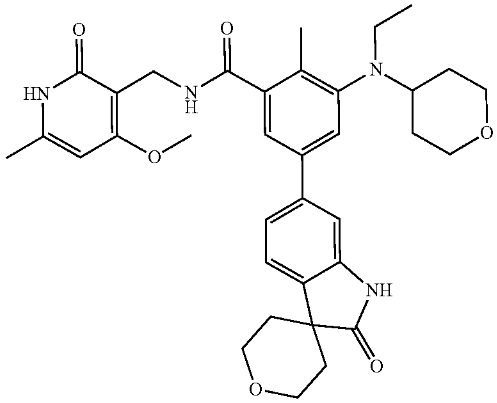

115

Step I 6-Bromo-2',3',5',6'-tetrahydrospiro[dihydroindole-3,4'-pyran]-2-one 115c

The compound 115a (10 g, 47.4 mmol) was dissolved in THF (100 mL), and the compound 115b (13.12 g, 56.88 mmol) was added. The mixture was cooled to −70° C. under the protection of $N_2$, and LiHMDS (189 mL, 189 mmol) was added to the flask dropwise slowly. The mixture was then heated to 70° C. slowly and stirred for 2 hours. TLC monitoring was used and determined that the raw materials were completely reacted and there were new spots formed. The reaction solution was added with saturated $NH_4Cl$ aqueous solution under ice bath to quench the reaction, which was then extracted with EA, concentrated, slurried with methanol, filtered, and washed with DCM to obtain 9 g of a light pink solid that was determined by $^1H$ NMR to be the target compound 115c (9 g, 31.9 mmol) with a yield of 67%.

1H NMR (400 MHz, DMSO-d6) δ 10.51 (s, 1H), 7.47 (d, J=8 Hz, 1H), 7.14 (d, J=8 Hz, 1H), 6.99 (s, 1H), 4.09-3.94 (m, 2H), 3.86-3.72 (m, 2H), 1.76-1.66 (m, 4H)

Step II Methyl 3-(ethyl(tetrahydro-2H-pyran-4-yl) amino)-2-methyl-5-(2-oxo-2',3',5',6'-tetrahydrospiro [dihydroindole-3,4'-pyran]-6-yl)benzoate 115d The compound 115c (250 mg, 886 μmol), compound 110a (429 mg, 1.06 mmol), Pd(dppf)$Cl_2$ (80 mg, 109 μmol), $K_2CO_3$ (367 mg, 2.66 mmol), dioxane (5 mL) and $H_2O$ (1.2 mL) were added in a 100 mL single-necked flask. The mixture was heated to 110° C. under the protection of $N_2$ and stirred for 2 hours.

TLC monitoring was used and determined that the raw materials were completely reacted. The reaction solution was spin-dried and purified by flash column chromatography (PE:EA=2:1) to obtain a light-yellow solid of the target compound 115d (230 mg, 450 μmol) with a yield of 54%.

MS m/z (ESI): 479 $(M+1)^+$.

Step III 3-(Ethyl(tetrahydro-2H-pyran-4-yl)amino)-2-methyl-5-(2-oxo-2',3',5',6'-tetrahydrospiro[dihydroindole-3,4'-pyran]-6-yl)benzoic acid 115e The compound 136b (230 mg, 480 μmol), MeOH (5 mL) were added in a 100 mL single-necked flask, and saturated NaOH aqueous solution (2.4 mL) was added. The mixture was heated to 45° C. and stirred for 1 hour. TLC monitoring was used and determined that the raw materials were completely reacted, and the reaction solution was neutralized with dilute hydrochloric acid, extracted with EA, dried with anhydrous sodium sulfate, filtered, and concentrated to obtain a light-yellow oily product of the target 115e (90 mg, 193 μmol) with a yield of 40%.

MS m/z (ESI): 465 $(M+1)^+$.

Step IV 3-(Ethyl(tetrahydro-2H-pyran-4-yl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 115

The compound 115e (90 mg, 194 μmol) was dissolved in DMF (3 mL), followed by adding EDCI (174 mg, 0.906 mmol), HOBt (41 mg, 0.302 mmol), DIPEA (195 mg, 1.51 mmol) and finally compound 115e (121 mg, 0.453 mmol), and the mixture was reacted 230° C. for 2 hours. TLC monitoring was used and determined that the raw materials were completely reacted and there were new spots formed. The reaction solution was added with water, extracted with EA, dried with anhydrous sodium sulfate, concentrated, and purified by flash column chromatography (PE:EA=0:1), concentrated, slurried with EA, and filtered to obtain a light red solid of the compound 115 (40 mg, 65 μmol) with a yield of 33.6%.

1H NMR (400 MHz, DMSO-d6) δ 11.41 (s, 1H), 10.42 (s, 1H), 8.00 (s, 1H), 7.58 (d, J=8 Hz, 1H), 7.34 (s, 11H), 7:20 (d, J=8 Hz, 1H), 7.16 (s, 1H), 7.03 (s, 1H), 6.09 (s, 1H), 423 (d, J=4 Hz, 2H), 4.08-4.01 (m, 2H), 3.88-3.77 (m, 7H), 325 (t, J=12 Hz, 2H), 3.11-2.09 (nm, 3H) 2.26 (s, 3H), 2.17 (s, 3H), 1.79-1.63 (m, 6H), 1.59-1.50 (m, 2H), 0.84 (t, J=8 Hz, 3H) MS m/z (ESI): 616.3 $[M+H]^+$.

Example 116 3-(Ethyl(piperidin-4-yl)amino)-N-((4-methoxy-6-methyl-2-oxo-1,2-dihydropyridin-3-yl) methyl)-2-methyl-5-(2-oxospiro[indole-3,4'-piperidine]-6-yl)benzamide

116

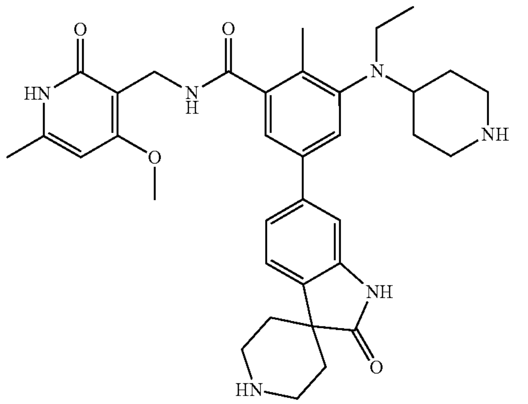

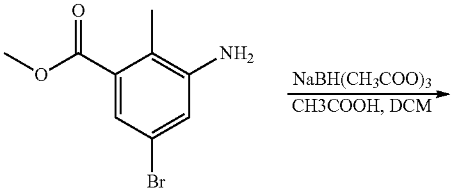

116a

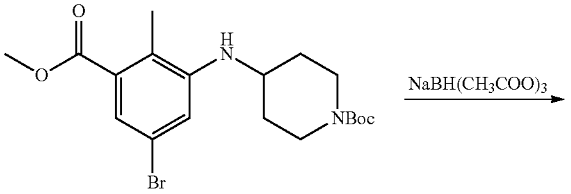

116b

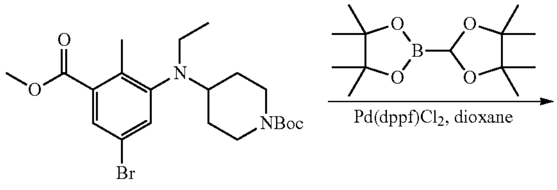

116c

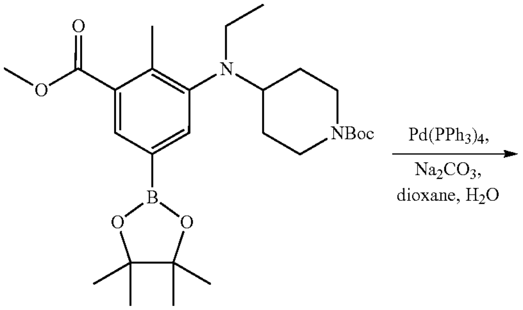

116d

-continued

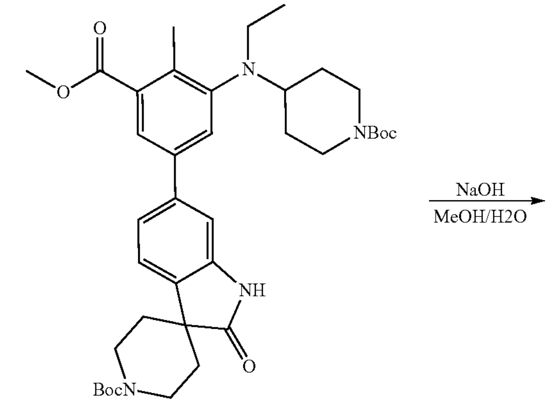

116e

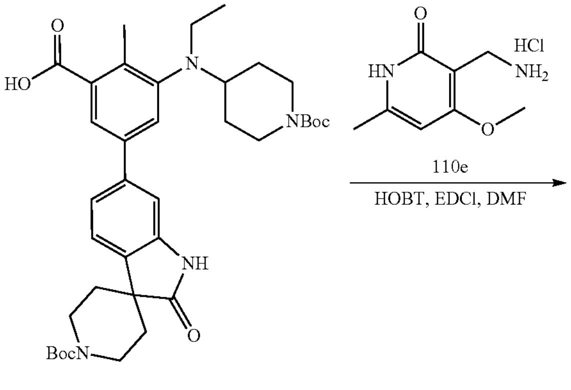

116f

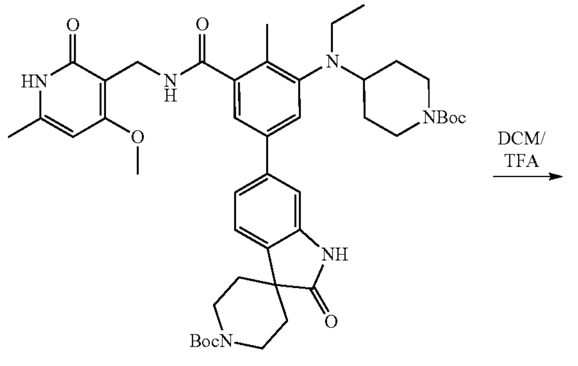

116g

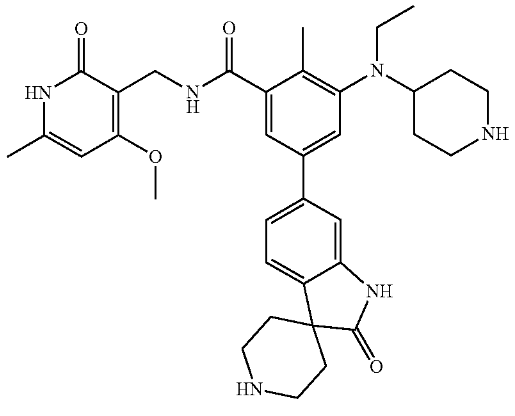

116

Step I tert-Butyl 4-((5-bromo-3-(methoxycarbonyl)-2-methylphenyl)amino)piperidin-1-carboxylate 116b The compound 116a (2 g, 8.196 mmol) was dissolved in dichloromethane (50 mL), and acetic acid (1.5 g, 24.59 mmol) and tert-butyl 4-oxopiperidin-1-carboxylate (4.9 g, 24.59 mmol) were added. The mixture was stirred at room temperature for 30 minutes, and was added with sodium borohydride acetate (5.2 g, 24.59 mmol) followed by stirring at room temperature for 3.5 hours until the reaction was completed. The reaction solution was added with water to quench the reaction, and was extracted with dichloromethane for three times, washed with saturated NaCl solution, dried with anhydrous sodium sulfate, filtered, concentrated, and purified by plate chromatography to obtain the title compound 116b (3.4 g, 7.98 mmol) with a yield of 95%.

MS m/z (ESI): 449 $[M+23]^+$.

Step II tert-Butyl 4-((5-bromo-3-(methoxycarbonyl)-2-methylphenyl)(ethyl)amino)piperidin-1-carboxylate 116c The compound 116a (3.4 g, 7.98 mmol) was dissolved in dichloromethane (50 mL), and acetic acid (1.436 g, 23.94 mmol) and acetaldehyde (1.755 g, 39.9 mmol) were added. The mixture was stirred at room temperature for 30 minutes, and was added with sodium borohydride acetate (5.075 g, 23.94 mmol) followed by stirring at room temperature for 3 hours until the reaction was completed. The reaction solution was added with water to quench the reaction, and was extracted with dichloromethane for three times, washed with saturated NaCl solution, dried with anhydrous sodium sulfate, filtered, concentrated, and purified by plate chromatography to obtain the title compound 116c (3.2 g, 7 mmol) with a yield of 88%.

MS m/z (ESI): 477 $[M+23]^+$.

Step III tert-Butyl 4-(ethyl(3-(methoxycarbonyl)-2-methyl-5-(4,4,5,5-tetramethyl-1,3,2-dioxaborolan-2-yl)phenyl)amino)piperidin-1-carboxylate 116d The compound 116c (1.2 g, 2.64 mmol) and bis(pinacolato)diboron (1.34 g, 5.28 mmol) were dissolved in 1,4-dioxane (20 mL), and [1,1'-bis(diphenylphosphino)ferrocene]dichloropalladium (0.192 g, 0.264 mmol) and potassium acetate (0.776 g, 7.92 mmol) were added. The mixture was heated to 100° C. under the protection of nitrogen and stirred for 2 hours until the reaction was completed. The reaction solution was extracted with water and ethyl acetate, and the organic phase was washed with saturated NaCl solution, dried with anhydrous sodium sulfate, filtered, concentrated, and purified by column chromatography to obtain the title compound 116d (1 g, 1.992 mmol) with a yield of 75%.

MS m/z (ESI): 503 $[M+1]^+$.

Step IV tert-Butyl 4-(ethyl(3-(methoxycarbonyl)-2-methyl-5-(2-oxo-2',3',5',6'-tetrahydrospiro[dihydroindole-3,4'-pyran]-6-yl)amino)piperidin-1-carboxylate 116e The compound 116d (1000 mg, 2 mmol) and tert-butyl 6-bromo-2-oxospiro[indoline-3,4'-piperidine]-1'-carboxylate (760 mg, 2 mmol) were dissolved in 1,4-dioxane (20 mL), and tetrakis(triphenylphosphine)palladium (231 mg, 0.1195 mmol) and potassium carbonate (424 mg, 4 mmol) were added. The mixture was heated to 100° C. under the protection of Ar and stirred for 4 hours. The reaction solution was cooled down, spin-dried, extracted with dichloromethane for three times, washed with saturated NaCl solution, dried with anhydrous sodium sulfate, filtered, concentrated, and purified by plate chromatography to obtain the title compound 116e (1100 mg, 1.62 mmol) with a yield of 81%.

MS m/z (ESI): 677 [M+1]$^+$.

Step V 5-(1'-(tert-butoxycarbonyl)-2-oxospiro[indoline-3,4'-piperidine]-6-yl)-3-((1-(tert-butoxycarbonyl)piperidin-4-yl)(ethyl)amino)-2-methylbenzoic acid 116f The compound 116e (1000 mg, 1.479 mmol) was dissolved in methanol (20 mL), and sodium hydroxide (296 mg, 7.396 mmol) and water (5 mL) were added. The mixture was stirred at room temperature for 24 hours until the reaction was completed. The reaction solution was neutralized with hydrochloric acid until pH=6-7, extracted with dichloromethane for three times, washed with saturated NaCl solution, dried with anhydrous sodium sulfate, filtered, concentrated, and purified by plate chromatography to obtain the title compound 116f (800 mg, 1.2 mmol) with a yield of 81%.

MS m/z (ESI): 663 [M+1]$^+$.

Step VI tert-Butyl 6-(3-((1-(tert-butoxycarbonyl)piperidin-4-yl)(ethyl)amino)-5-((4-methoxy-6-methyl-2-oxo-1,2-dihydropyridin3-yl)methyl)carboxylate 116g The compound 116f (300 mg, 0.453 mmol) and compound 110e (185 mg, 0.906 mmol) were dissolved in N,N-dimethylformamide (10 mL), and 1-(3-dimethylaminopropyl)-3-ethylcarbodiimide hydrochloride (173 mg, 0.906 mmol), 1-hydroxybenzotriazole (122 mg, 0.906 mmol) and triethylamine (366 mg, 3.624 mmol) were added. The reaction was completed following stirring at room temperature for 24 hours. The reaction solution was washed with water, extracted with dichloromethane for three times, washed with saturated NaCl solution, dried with anhydrous sodium sulfate, filtered, concentrated, and purified by plate chromatography to obtain the title compound 137g (286 mg, 0.359 mmol) with a yield of 77%.

MS m/z (ESI): 813 [M+H]$^+$.

Step VII 3-(Ethyl(piperidin-4-yl)amino)-N-((4-methoxy-6-methyl-2-oxo-1,2-dihydropyridin-3-yl)methyl)-2-methyl-5-(2-oxospiro[indole-3,4'-piperidine]-6-yl)benzamide 116

The compound 116g (250 mg, 0.3 mmol) was dissolved in DCM (5.0 mL), added with TFA (5 mL), and the reaction was completed following stirring at room temperature for 2 hours. The reaction solution was spin dried, added with methanol, neutralized with saturated potassium carbonate solution, filtered, concentrated, and purified by plate chromatography to obtain the title compound 116 (135 mg, 0.22 mmol) with a yield of 70%.

1H NMR (4(0 MHz, Methanol-d4) δ 7.44 (d, J=1.7 Hz, 1H), 7.39-7.30 (m, 2H), 7.27 (dd, J=7.8, 1.6 Hz, 1H), 7.13 (d, J=1.5 Hz, 1U), 6.24 (s, 14), 4.45 (s, 2H), 3.91 (s, 3H) 3.80 (td, J=12, 3, 3.5 Hz, 2H), 3.47-3.31 (m, 4H), 3.26 (s, 1H), 3.17-3.08 (m, 2H), 3.03-2.90 (m, 2H), 2.34 (s, 3H), 2:29 (d, J=0.8 Hz, 3H), 2.19 (td. J=11 3, 5.7 Hz, 2H), 2.01 (dd, J=10.4, 4.6 Hz, 4H), 1.81 (d, J=11.9 Hz, 2H), 0.90 (t, J=7.0 Hz, 3H), MS m/z (ES): 613 [M+H]$^+$.

Example 117 N-((4,6-dimethyl-2-oxo-1,2-dihydropyridin-3-yl)methyl)-3-(ethyl(piperidin-4-yl)amino)-2-methyl-5-(2-oxospiro[indole-3,4'-piperidine]-6-yl)benzamide

117

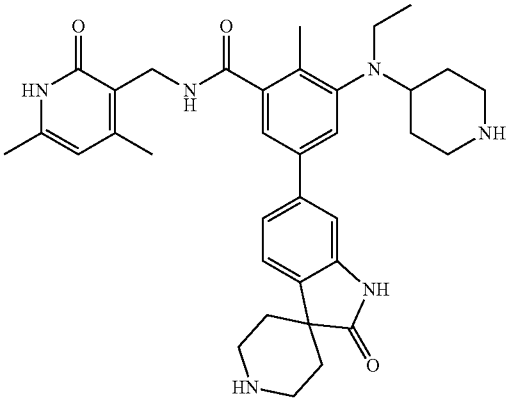

A similar method of Example 116 was used to obtain the title compound 117 with a yield of 52%, wherein the 3-(aminomethyl)-4-methoxy-6-methylpyridin-2(1H) hydrochloride was replaced with 3-(aminomethyl)-4,6-dimethylpyridin-2(1H) hydrochloride.

1H NMR (400 MHz, Methianol-d4) δ 7.44 (d, J=1.8 Hz, 1H), 7.36 (d, J=7.9 Hz, 1H), 7.32 (d, J=1.8 Hz, 1H), 7.28 (dd, J=7.8, 1.6 Hz, 1H), 7.12 (d, J=1.5 Hz, 1H), 6.10 (s, 1H), 4.47 (s, 2H), 3.86-3.76 (m, 2H), 3.44-3.32 (m, 4H), 3.27-3.21 (n, 1H), 3.18-3.09 (m, 2H), 2.96 (t, J=10.7 Hz, 2H), 238 (s, 3H), 2.32 (s, 3H), 222 (d, J=0.8 Hz, 3H), 2.21-2.12 (m, 2H), 2.02 (d, J=14.2 Hz, 4H), 1.80 (d, J=11.8 Hz, 2H), 0.91 (t, J=6.9 Hz, 3H), MS m/z (ESI): 597 [M+H]$^+$.

Example 118 N-((4,6-dimethyl-2-carbonyl-1,2-dihydropyridin-3-yl)methyl)-3-(ethyl(tetrahydro-2H-pyran-4-yl)amino)-5-(4-fluoro-2'-carbonylspiro[cyclohexano-1,3'-dihydroindole]-3-ene-5'-yl)-2-methylbenzamide 118

118

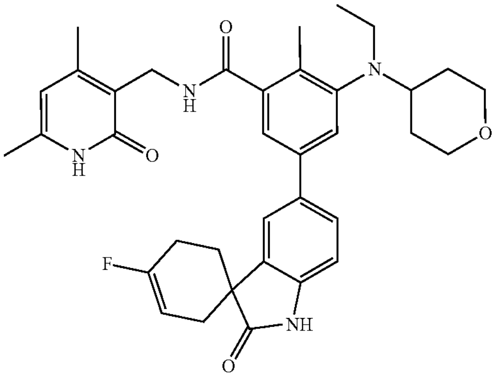

-continued

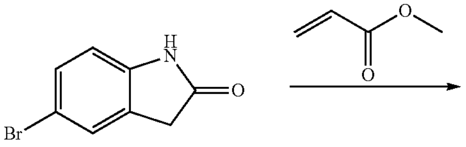

118a

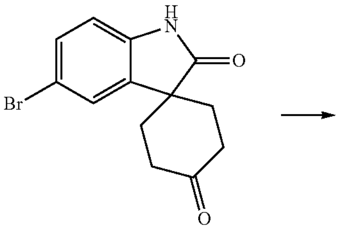

118b

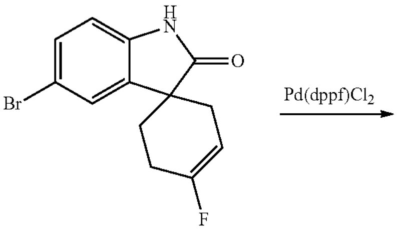

118c

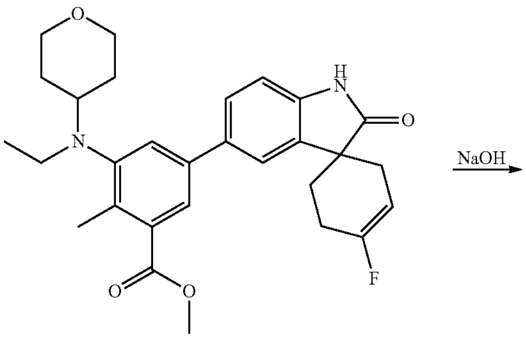

118d

-continued

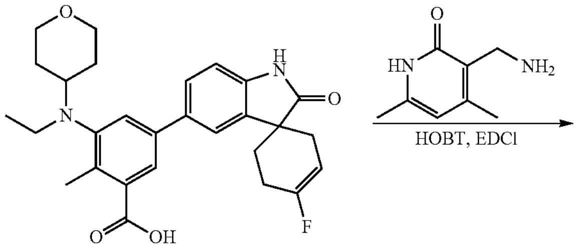

118e

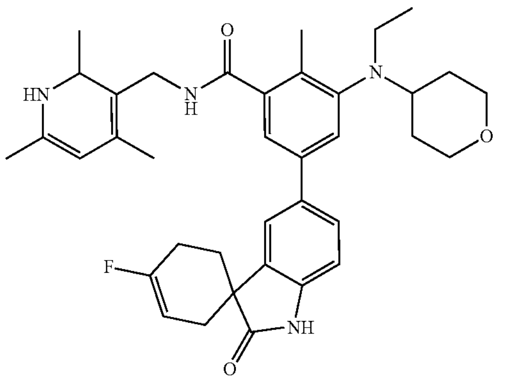

118

Step I 5'-Bromospiro[cyclohexano-1,3'-dihydroindole]-2',4-dione 118b

The compound 5-bromo-dihydroindol-2-one 118a (5.0 g, 23.7 mmol) was dissolved in tetrahydrofuran (50 mL), and methyl methacrylate (4.48 g, 52.14 mmol) was added. Potassium tert-butylate (7.99 g, 71.1 mmol) was then added slowly under ice bath and the protection of $N_2$. The solution was then stirred at room temperature for 1 hour, and TLC was used to determine that the raw materials disappeared. The reaction solution was refluxed at 100° C. for 1 hour, added with 50 mL of water, refluxed for another 2 hours, cooled to room temperature, and a large amount of solid was precipitated overnight, which was then suction-filtrated to obtain the compound 118b (1.6 g, 5.46 mmol) with a yield of 23.7%.

MS m/z (ESI): 294 $[M+H]^+$.

Step II 5'-Bromo-4-fluorospiro[cyclohexano-1,3'-dihydroindole]-3-ene-2'-one 118c The compound 118b (350 mg, 1.19 mmol) was dissolved in dichloromethane (4.0 mL), DAST (0.92 mL, 7.16 mmol) was added, and the mixture was stirred at room temperature for 2 hours. The reaction solution was cooled down, spin-dried, extracted with dichloromethane for three times, washed with saturated NaCl solution, dried with anhydrous sodium sulfate, filtered, concentrated, and purified by plate chromatography to obtain the title compound 118c (200 mg, 0.63 mmol) with a yield of 52.9%.

MS m/z (ESI): 296 $[M+H]^+$.

Step III Methyl 3-(ethyl(tetrahydro-2H-pyran-4-yl)amino)-5-(4-fluoro-2'-carbonylspiro[cyclohexano-1,3'-dihydroindole]-3-ene-5'-yl)-2-methylbenzoate 118d The compound 118c (150 mg, 0.51 mmol) and methyl 3-(ethyl(tetrahydro-2H-pyran-4-yl)amino-2-methyl-5-(4,4,5,5-tetramethyl-1,3,2-dioxaborolan-2-yl)benzoate (206 mg, 0.51 mmol) were dissolved in 1,4-dioxane (2.0 mL), and [1,1'-bis(diphenylphosphino)ferrocene]dichloropalladium (38 mg, 0.051 mmol) and potassium carbonate (176 mg, 1.27 mmol) were added, and the mixture was heated to 100° C. under the protection of nitrogen and stirred for 2 hours. The reaction solution was cooled down, spin-dried, extracted with dichloromethane for three times, washed with saturated NaCl solution, dried with anhydrous sodium sulfate, filtered, concentrated, and purified by plate chromatography to obtain the title compound 118d (200 mg, 0.41 mmol) with a yield of 80.3%.

MS m/z (ESI): 493 $[M+H]^+$.

Step III 3-(Ethyl(tetrahydro-2H-pyran-4-yl)amino)-5-(4-fluoro-2'-carbonylspiro[cyclohexano-1,3'-dihydroindole]-3-ene-5'-yl)-2-methylbenzoic acid 118e The compound 118d (200 mg, 0.41 mmol) was dissolved in methanol (2.0 mL), and sodium hydroxide (61 mg, 1.5 mmol) and water (1.0 mL) were added. The mixture was stirred at room temperature for 4 hours until the reaction was completed. The reaction solution was neutralized to pH=6-7 with hydrochloric acid, extracted with dichloromethane for three times, washed with saturated NaCl solution, dried with anhydrous sodium sulfate, filtered, concentrated, and purified by plate chromatography to obtain the title compound 118e (170 mg, 0.36 mmol) with a yield of 85.3%.

MS m/z (ESI): 479 $[M+H]^+$.

Step V N-((4,6-dimethyl-2-carbonyl-1,2-dihydropyridin-3-yl)methyl)-3-(ethyl(tetrahydro-2H-pyran-4-yl)amino)-5-(4-fluoro-2'-carbonylspiro[cyclohexano-1,3'-dihydroindole]-3-ene-5'-yl)-2-methylbenzamide 118

The compound 118e (170 mg, 0.35 mmol) and 3-(aminomethyl)-4,6-dimethyl-1H-pyridin-2-one trifluoroacetate (142 mg, 0.535 mmol) was dissolved in N,N-dimethylformamide (2.0 mL), and 1-(3-dimethylaminopropyl)-3-ethylcarbodiimide hydrochloride (134 mg, 0.7 mmol), 1-hydroxybenzotriazole (47 mg, 0.35 mmol) and triethylamine (106 mg, 1.05 mmol) were added. The mixture was stirred at room temperature overnight until the reaction was completed. The reaction solution was washed with water, extracted with dichloromethane for three times, washed with saturated NaCl solution, dried with anhydrous sodium sulfate, filtered, concentrated, and purified by plate chromatography to obtain the title compound 118 (17.0 mg, 0.027 mmol) with a yield of 7.9%.

1H NMR (400 MHz, Chloroform-d) δ 8.19 (s, 1H), 7.55 (d, J=1.6 Hz, 1H), 7.46 (d, J=7.6 Hz, 1H), 7.37 (d, J=1.8 Hz, 1H), 7.30 (dd, J=7.7, 1.7 Hz, 1H), 7.19 (d, J=1.8 Hz, 1H), 5.83 (s, 1H), 4:26 (d, J=4.9 Hz, 2H), 3.85-3.74 (m, 2H), 3.23 (t, J=11.4 Hz, 2H), 3.06 (q. J=7.1 Hz, 2H), 2.98 (d, J=10.8 Hz, 1H), 2.34 (t, J=12.7 Hz, 2H), 2.23 (s, 3H), 2.18 (s, 3H), 2.11-2.04 (m, 3H), 1.93 (d, J=7.8 Hz, 2H), 1.64 (d, J=12.4 Hz. 2H), 1.55-1.40 (m, 4H), 0.81 (t, J=6.9 Hz, 3H), MS m/z (ESI): 613.5 $[M+H]^+$.

Example 119 5-(4-Fluoro-2'-carbonylspiro[cyclohexano-1,3'-dihydroindole]-5'-yl)-N-((4,6-dimethyl-2-carbonyl-1,2-dihydropyridin-3-yl)methyl)-3-(ethyl(tetrahydro-2H-pyran-4-yl)amino)-2-methylbenzamide 119

119

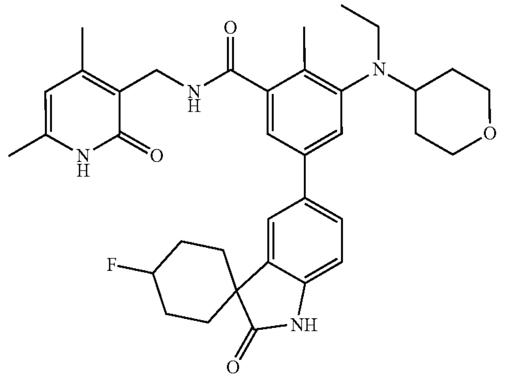

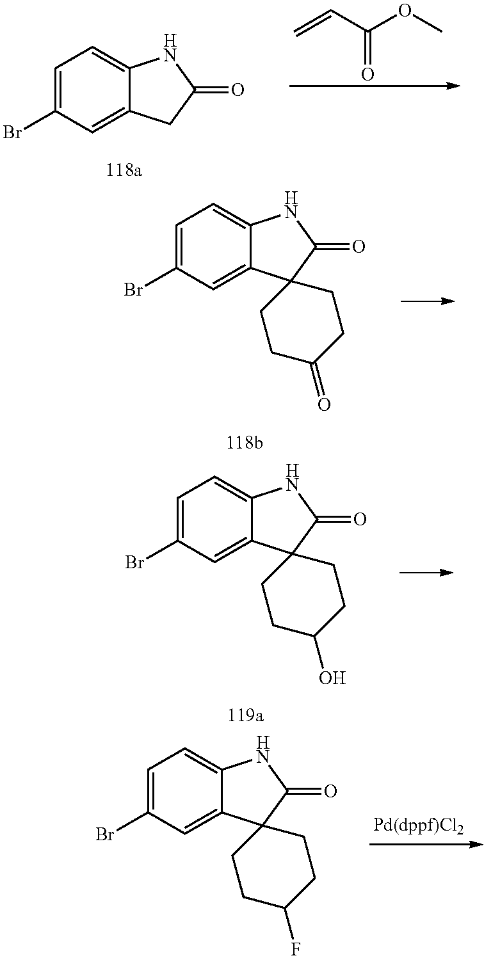

118a

118b

119a

119b

-continued

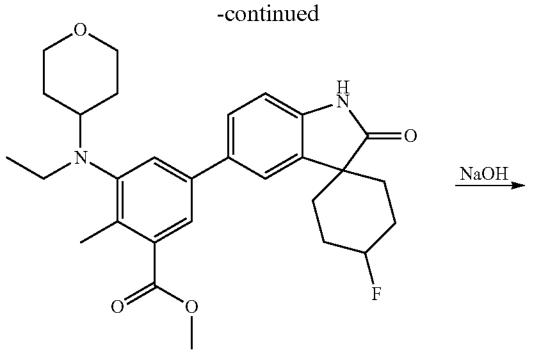

119c

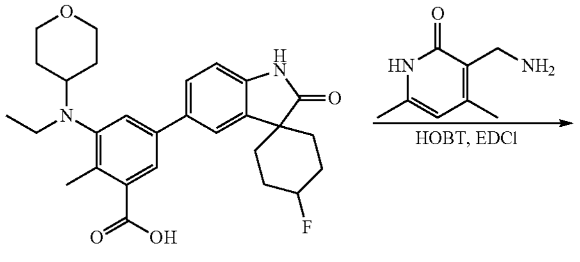

119d

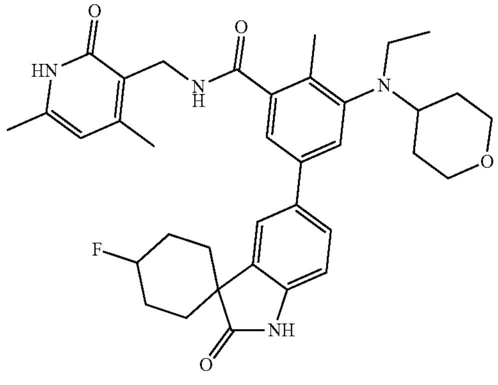

119

Step I 5-Bromospiro[dihydroindole-3,4'-piperidine]-2-one 118b

The compound 118b was obtained by the same reaction described in the step I of the Example 118.

Step II 5'-Bromo-4-hydroxyspiro[cyclohexano-1,3'-dihydroindole]-2'-one 119a

The compound 118b (300 mg, 1.02 mmol) was dissolved in methanol (3.0 mL), sodium borohydride (77 mg, 2.04 mmol) was added, and the mixture was stirred at room temperature for 2 hours. The reaction solution was concentrated and purified by column chromatography to obtain the title compound 119a (80 mg, 0.27 mmol) with a yield of 26.5%.

MS m/z (ESI): 296 [M+H]$^+$.

Step III 5'-Bromo-4-hydroxyspiro[cyclohexano-1,3'-dihydroindole]-2'-one 119b

The compound 119a (80 mg, 0.27 mmol) was dissolved in dichloromethane (10.0 mL), DAST (0.5 mL, 0.5 mmol) was added, and the mixture was stirred at room temperature for 2 hours. The reaction solution was cooled down, spin-dried, extracted with dichloromethane for three times, washed with saturated NaCl solution, dried with anhydrous sodium sulfate, filtered, concentrated, and purified by plate chromatography to obtain the title compound 119b (20 mg, 0.059 mmol) with a yield of 22.2%.

MS m/z (ESI): 298 [M+H]$^+$.

Step IV Methyl 5-(4-fluoro-2'-carbonylspiro[cyclohexano-1,3'-dihydroindole]-5'-yl)-3-(ethyl(tetrahydro-2H-pyran-4-yl)amino)-2-methylbenzoate 119c The compound 119b (20 mg, 0.06 mmol) and methyl 3-(ethyl(tetrahydro-2H-pyran-4-yl)amino-2-methyl-5-(4,4,5,5-tetramethyl-1,3,2-dioxaborolan-2-yl)benzoate (30 mg, 0.074 mmol) were dissolved in 1,4-dioxane (2.0 mL), and [1,1'-bis(diphenylphosphino)ferrocene]dichloropalladium (5 mg, 0.006 mmol) and potassium carbonate (21 mg, 0.15 mmol) were added, and the mixture was heated to 100° C. under the protection of nitrogen and stirred for 2 hours. The reaction solution was cooled down, spin-dried, extracted with dichloromethane for three times, washed with saturated NaCl solution, dried with anhydrous sodium sulfate, filtered, concentrated, and purified by plate chromatography to obtain the title compound 119c (30 mg, 0.06 mmol) with a yield of 100%.

MS m/z (ESI): 495 [M+H]$^+$.

Step V 5-(4-Fluoro-2'-carbonylspiro[cyclohexano-1,3'-dihydroindole]-5'-yl)-3-(ethyl(tetrahydro-2H-pyran-4-yl)amino)-2-methylbenzoic acid 119d The compound 119c (30 mg, 0.06 mmol) was dissolved in methanol (2.0 mL), and sodium hydroxide (61 mg, 1.5 mmol) and water (1.0 mL) were added. The mixture was stirred at room temperature for 4 hours until the reaction was completed. The reaction solution was neutralized to pH=6-7 with hydrochloric acid, extracted with dichloromethane for three times, washed with saturated NaCl solution, dried with anhydrous sodium sulfate, filtered, concentrated, and purified by plate chromatography to obtain the title compound 119d (18 mg, 0.037 mmol) with a yield of 62.5%.

MS m/z (ESI): 481 [M+H]$^+$.

Step VI 5-(4-Fluoro-2'-carbonylspiro[cyclohexano-1,3'-dihydroindole]-5'-yl)-N-((4,6-dimethyl-2-carbonyl-1,2-dihydropyridin-3-yl)methyl)-3-(ethyl(tetrahydro-2H-pyran-4-yl)amino)-2-methylbenzamide 119

The compound 119d (18 mg, 0.037 mmol) and 3-(aminomethyl)-4,6-dimethyl-1H-pyridin-2-one trifluoroacetate (15 mg, 0.056 mmol) was dissolved in N,N-dimethylformamide (2.0 mL), and 1-(3-dimethylaminopropyl)-3-ethylcarbodiimide hydrochloride (14 mg, 0.074 mmol), 1-hydroxybenzotriazole (5 mg, 0.037 mmol) and triethylamine (12 mg, 0.111 mmol) were added. The mixture was stirred at room temperature overnight until the reaction was completed. The reaction solution was washed with water, extracted with dichloromethane for three times, washed with saturated NaCl solution, dried with anhydrous sodium sulfate, filtered, concentrated, and purified by plate chromatography to obtain the title compound 140 (16.0 mg, 0.026 mmol) with a yield of 70.3%.

1H NMR (400 M Hz, D MSO-d6) δ 11.41 (s, 1H), 10.40 (s, 1H) 8.16 (t, J=4.5 Hz, 1H), 7.40 (d, J=7.8 Hz, 1H), 7.31 (dd, J=4.1, 1.9 Hz, 1H), 7.22 (d, J=7.7 Hz, 1H), 7.17 (dd, J=7.8, 1.7 Hz, 0H), 7.14-7.12 (m, 1H), 7.12 (q, J=1.4 Hz, 114), 7.02 (dd, J=7, 1, 1.7 Hz, 1H), 5.88 (s, 1H), 5.82 (s, 1H), 4.25 (d, J=4.9 Hz, 2H), 3.80 (d, J=11.2 Hz, 2H), 3.21 (t, J=11.4 Hz, 2H), 3.05 (q, J=7.0 Hz, 2H), 2.96 (d, J=11.5 Hz, 1H), 2.40 (d, J=17.9 Hz, 2H), 2.31-2.22 (m, 2H), 2.17 (s, 3H), 2.07 (s, 3H), 1.99-1.69 (m, 4H), J=0.62 (d, J=12.8 Hz, 2H), 1.49 (d, J=13.2 Hz, 3), 0.80 (t, J=6.9 Hz, 3H), MS nm/z (ESI): 615.5 $[M+H]^+$.
Example 120 3-(Ethyl(4-((2-methoxyethyl)(methyl)amino)cyclohexyl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 120
120
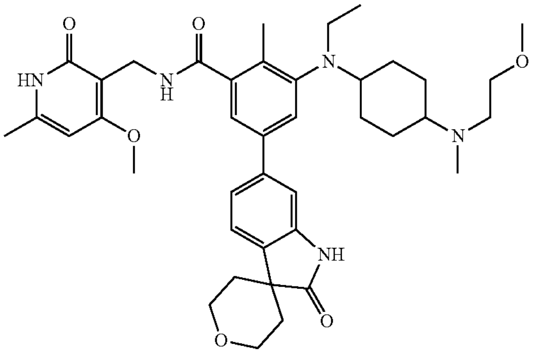
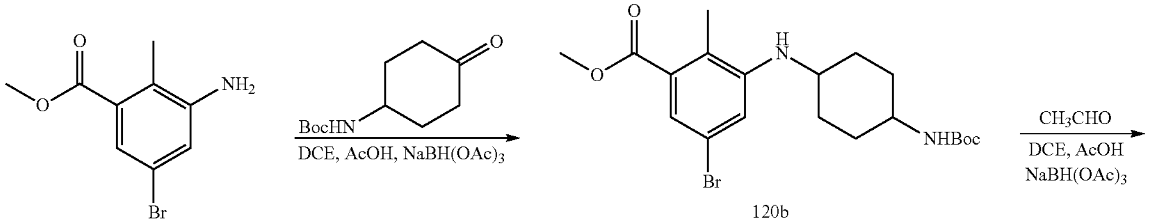
120a
120b
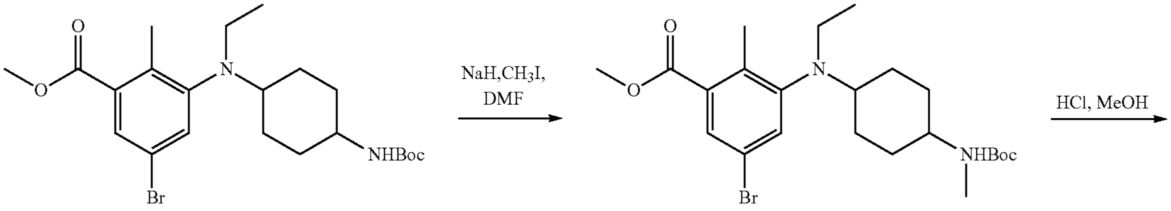
120c
120d
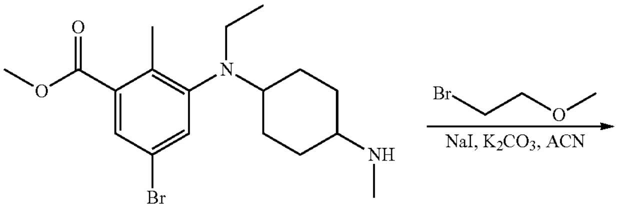
120e
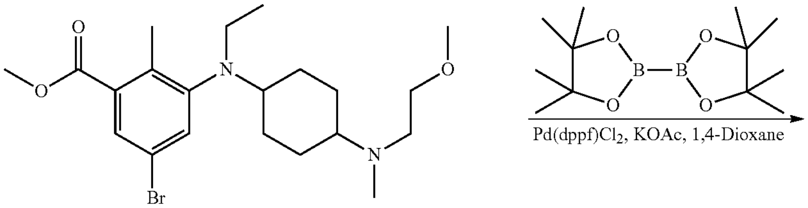
120f -continued
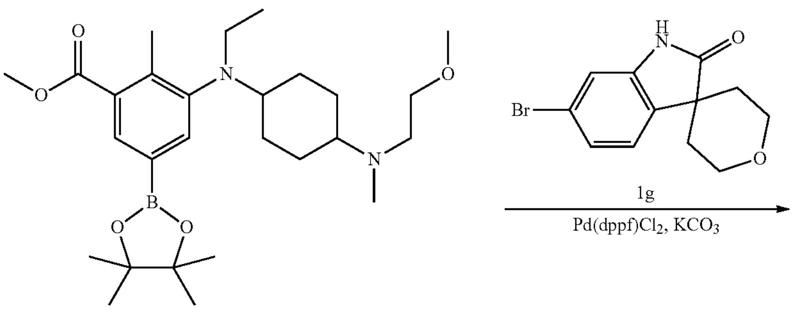
120g
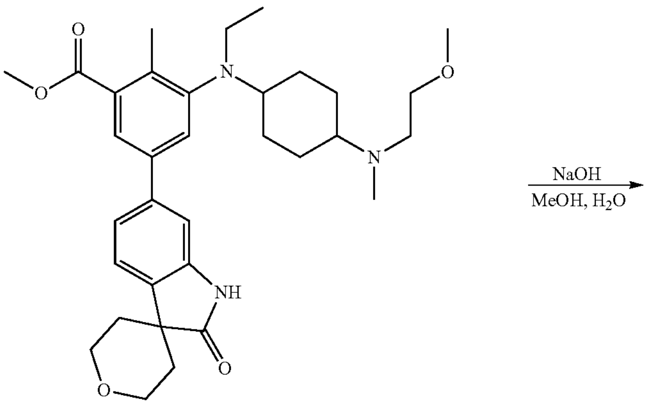
120I
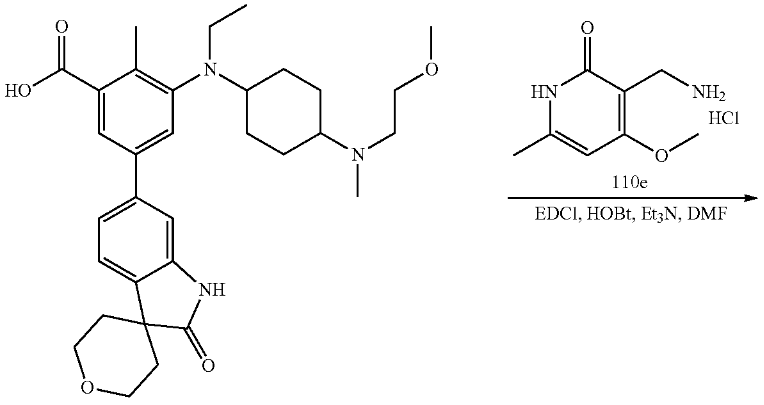
120j
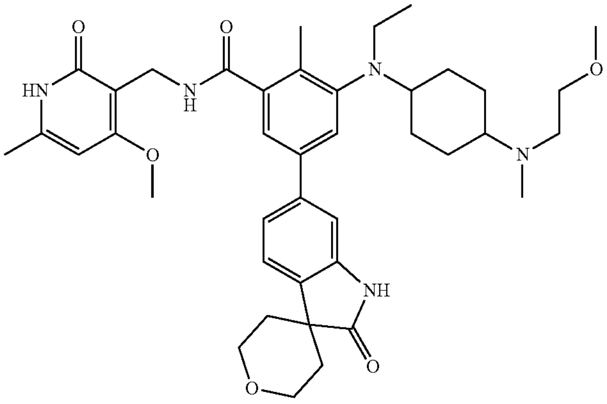
120

Step I tert-Butyl (2-((4-(4-(3-bromo-4-fluoro-phenyl)-5-oxo-4,5-dihydro-1,2,4-oxadiazol-3-yl)-1,2,5-oxadiazol-3-yl)(methyl)amino)ethyl)carbamate 120b The compound 120a (10 g, 40.9 mmol) and tert-butyl (4-oxocyclohexyl)carbamate (43.6 g, 205 mmol) were dissolved in DCE (250 mL), followed by adding acetic acid (12.2 g, 205 mmol) and stirring at room temperature for 0.5 hour. Then sodium triacetoxyborohydride (43.2 g, 205 mmol) was added to the mixture and stirred at room temperature overnight. The reaction solution was added with 9.8 g of sodium hydroxide and 500 mL of $H_2O$, stirred at room temperature for 0.5 hour, extracted with EA (150 mL×3), dried with anhydrous sodium sulfate, mixed, concentrated, and purified by column chromatography (petroleum ether: ethyl acetate=5:1) to obtain the title compound 120a (15 g, 34 mmol) with a yield of 83%.

MS m/z (ESI): 441 $[M+H]^+$.

Step II Methyl ((4-((tert-butoxycarbonyl)amino) cyclohexyl)(ethyl)amino)-2-methylbenzoate 120c The compound 120b (10 g, 22.6 mmol) was dissolved in 200 mL of DCE, and acetaldehyde (12.6 mL, 226 mmol) and acetic acid (8.13 g, 135.6 mmol) were added. The mixture was stirred at room temperature for 0.5 hour, followed by adding sodium triacetoxyborohydride (23.9 g, 113 mmol) under ice bath, naturally raising to room temperature and reacting overnight. A saturated sodium bicarbonate aqueous solution was then added to the mixture to adjust the pH to 7, and 200 mL of water was added for extraction. The aqueous phase was extracted with EA (100 mL×2). The organic phases were then combined, dried with anhydrous sodium sulfate, concentrated and mixed, and purified by column chromatography (petroleum ether: ethyl acetate=2: 1) to obtain the title compound 120c (8 g, 17.05 mmol) with a yield of 75%.

MS m/z (ESI): 469 $[M+H]^+$.

Step III Methyl ((4-((tert-butoxycarbonyl)(methyl) amino)cyclohexyl)(ethyl)amino)-2-methylbenzoate 120d The compound 120c (10 g, 21.3 mmol) was dissolved in 100 mL of DMF, followed by adding with iodomethane (13.3 ml, 213 mmol) and stirring for 20 minutes under ice water bath. The mixture was added with NaH (2.13 g, 53.2 mmol) slowly, naturally raised to room temperature, and reacted overnight. The reaction solution was added with 150 mL of ice water to quench the reaction, extracted with EA (70 mL×3), and the organic phases were combined, washed with saturated NaCl solution (50 mL×3), dried, mixed, and purified by column chromatography (petroleum ether: ethyl acetate=1:3) to obtain the title compound 120d (10 g, 20.7 mmol) with a yield of 97%.

MS m/z (ESI): 483 $[M+H]^+$.

Step IV Methyl 5-bromo-3-(ethyl(4-(methyl-amino) cyclohexyl)amino)-2-methylbenzoate 120e The compound 120d (9.5 g, 20.2 mmol) was dissolved in 100 mL of methanol solution, and 4 M hydrochloric acid in methanol (15 mL, 60 mmol) was added under ice water bath. The mixture was naturally raised to room temperature and reacted overnight. The reaction solution was evaporated to remove methanol, adjusted to pH=8 by saturated potassium carbonate solution, and extracted with a mixed solvent of methanol: dichloromethane=1:10 (50 mL×3). The organic phases were combined, dried, and evaporated to obtain a crude product of the title compound 120e (6.2 g, 16.1 mmol) with a yield of 82.4%.

MS m/z (ESI): 383 $[M+H]^+$.

Step V Methyl 5-bromo-3-(ethyl(4-((2-methoxy-ethyl)(methyl)amino)cyclohexyl)amino)-2-methyl-benzoate 120f The compound 120e (2.54 g, 6.52 mmol) was dissolved in 100 mL of acetonitrile, and 1-bromo-2-methoxyethane (2.7 g, 19.5 mmol), potassium carbonate (1.79 g, 13 mmol), and sodium iodide (586 mg, 3.91 mmol) were added. The mixture was heated to 65° C. and refluxed for 18 hours. The reaction solution was cooled down, diluted with 100 mL of water, and extracted with DCM (100 mL×3). The organic phases were combined, washed with saturated NaCl solution, mixed, concentrated, and purified by column chromatography (methanol: dichloromethane=1:6) to obtain the title compound 120f (2.7 g, 6.12 mmol) with a yield of 93.8%.

MS m/z (ESI): 441 $[M+H]^+$.

Step VI 3-(Ethyl(4-((2-methoxyethyl)(methyl) amino)cyclohexyl)amino)-2-methyl-5-(4,4,5,5-tetramethyl-1,3,2-dioxaborolan-2-yl)benzoic acid 120g The compound 120f (1 g, 2.26 mmol) was dissolved in 20 mL of 1,4-dioxane, and bis(pinacolato)diboron (861 mg, 3.39 mmol), $Pd(dppf)Cl_2$ (330 mg, 0.45 mmol) and KOAc (606 mg, 6.80 mmol) were added and well mixed, and the mixture was heated to 100° C. and refluxed for 3 hours. The reaction solution was diluted with 30 mL of water and extracted with EA (30 mL×3). The organic phases were combined, washed with 100 mL of saturated NaCl solution, dried, mixed, and purified by column chromatography (methanol: dichloromethane=1:2) to obtain the title compound 120g (1 g, 2.05 mmol) with a yield of 90.7%.

MS m/z (ESI): 489 $[M+H]^+$.

Step VII Methyl (4-(((2-methoxyethyl)(methyl) amino)cyclohexyl)amino)-2-methyl-5-(2-oxo-2',3',5',6'-tetrahydrospiro[dihydroindole-3,4'-pyran]-6-yl) benzoate 120i The compound 120g (1 g, 2.05 mmol) was dissolved in 8 mL of 1,4-dioxane and transferred to a microwave tube. The compound 1g (575 mg, 2.05 mmol), $Pd(dppf)_2Cl_2$ (150 mg, 0.205 mmol), potassium carbonate (707 mg, 5.125 mmol) and 1 mL of water were added to the microwave tube, which was then replaced with nitrogen, heated to 100° C. and reacted for 3 hours. The reaction solution was diluted with 20 mL of water and extracted with EA (20 mL×3). The organic phases were combined, washed with 100 mL of saturated NaCl solution, dried, mixed, and purified by column chromatography (methanol: dichloromethane=1:4) to obtain the title compound 120i (500 mg, 0.88 mmol) with a yield of 43.2%.

MS m/z (ESI): 564 $[M+H]^+$.

Step VIII 3-Ethyl(4-((2-methoxyethyl)(methyl) amino)cyclohexyl)amino)-2-methyl-5-(2-oxo-2',3',5',6'-tetrahydrospiro[dihydroindole-3,4'-pyran]-6-yl) benzoic acid 120j The compound 120i (500 mg, 0.887 mmol) was dissolved in a mixed solvent of 5 mL of methanol and 5 mL of water, and sodium hydroxide (350 mg, 8.87 mmol) was added and well mixed, and the mixture was heated to 60° C. and stirred for 5 hours. After cooling to room temperature, a 3 M hydrochloric acid solution was added dropwise to adjust pH=6. The solvent was evaporated, after which 3 mL of methanol was added. A white insoluble substance was filtered out and the residue was re-evaporated to obtain 500 mg of a crude product of the title compound 120j, which was used directly in the next step.

MS m/z (ESI): 550 $[M+H]^+$.

Example 120 3-(Ethyl(4-((2-methoxyethyl)(methyl) amino)cyclohexyl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 120

The compound 120j (250 mg, 0.454 mmol) was dissolved in 20 mL of DMF, and the compound 131e (140 mg, 0.682 mmol), EDCI (174 mg, 0.909 mmol), HOBt (61.4 mg, 0.454 mmol) and triethylamine (138 mg, 1.364 mmol) were added. The mixture was well mixed and stirred at room temperature overnight. The reaction solution was added with 30 mL of water and extracted with EA (30 mL×3). The organic phases were combined, washed with saturated NaCl solution (30 mL), dried, mixed, and purified by column chromatography (methanol: dichloromethane=1:6) to obtain the title compound 120 (97 mg, 0.138 mmol) with a yield of 30.5%.

1H NMR (400 MHz, Chloroform-d) δ 12.10 (s, 1H), 9.44 (s, 1H), 7.33 (d, J=7.9 Hz, 2H), 726 (dd, J=8.6, 1.7 Hz, 1H), 7.14 (ddd, J=7.7, 4.7, 1.6 Hz, 1H), 7.10 (d, J=1.5 Hz, 1H), 5.93 (d, J=2.8 Hz, 1H), 4.59 (d, J=5.6 Hz, 2H), 3.94-3.77 (m, 5H), 3.32 (d, J=4.3 Hz, 3H), 3.04 (q, J=7.2 Hz, 2H), 2.94 (s, 1H), 2.86 (d, J=0.6 Hz, 1H), 2.40 (s, 3H), 2.32 (s, 2H), 225 (d, J=4.3 Hz, 3H), 1.97-1.74 (n, 9H), 144-1.20 (m, 8H), 0.83 (td, J=6.9, 2.3 Hz, 3H), MS m/z (ESI):700 $[M+H]^+$.

Example 121 N-((4,6-dimethyl-2-oxo-1,2-dihydro-pyridin-3-yl)methyl)-3-(ethyl(4-(methyl(oxetan-3-yl) amino)cyclohexyl)amino)-2-methyl-5-(2-oxo-2',3',5', 6'-tetrahydrospiro[dihydroindole-3,4'-pyran]-6-yl) benzamide 121

121

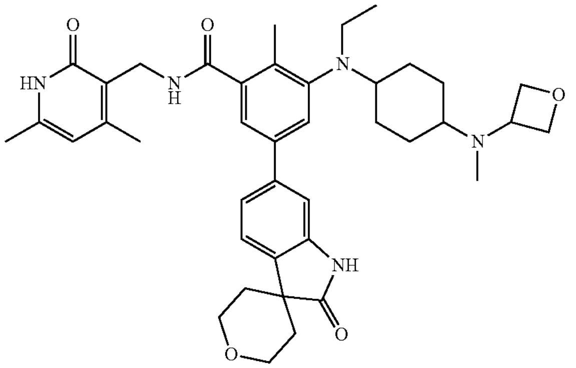

A similar method of Example 120 was used to obtain the title compound 121 with a yield of 24%, wherein the 1-bromo-2-methoxyethane was replaced with 3-oxetanone, and the 3-(aminomethyl)-4-methoxy-6-methylpyridin-2 (1H)-hydrochloride was replaced with 3-(aminomethyl)-4, 6-dimethylpyridin-2(1H)-hydrochloride.

1H NMR (400 MHz, Chloroform-d) δ 11.80 (s, 1H), 9.44 (s, 2H), 7.41 (s, 1H), 7.34 (d, J=7.7 Hz, 1H), 7.26 (d, J=2.9 Hz, 1H), 7.14 (d, J=7.1 Hz, 1H), 7.0 (s, 1H), 5.96 (s, 1H), 4.6-4.47 (n, 4H), 4.16 (s, 2H), 3.88 (dd, J=11.6, 5.5 Hz, 2H), 3.47 (s, 1H), 3.13-2.80 (m, 3H), 2.43 (s, 3H), 237 (s, 2H), 2.30 (d, J=7.1 Hz, 2H), 2.25-2.12 (m, 4H), 1.98-1.53 (m, 10H), 1.43-1.11 (m, 6H), 0.89-0.75 (n, 3H), MS m/z (ESI): 682 $[M+H]^+$.

Example 122 3-(Ethyl(4-(methyl(oxetan-3-yl) amino)cyclohexyl)amino)-N-((4-methoxy-6-methyl-2-oxo-1,2-dihydropyridin-3-yl)methyl)-2-methyl-5-(2-oxo-2',3',5',6'-tetrahydrospiro[dihydroindole-3,4'-pyran]-6-yl)benzamide 122

122

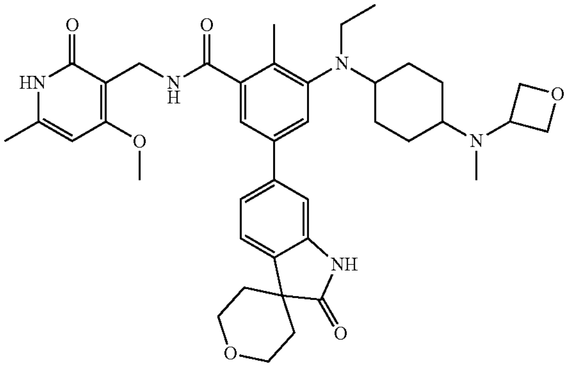

A similar method of Example 122 was used to obtain the title compound 122 with a yield of 17%, wherein the 1-bromo-2-methoxyethane was replaced with 3-oxetanone.

1H NMR (400 MHz, Chloroform-d) δ 12.02 (s, 1H), 9.40 (s, 2H), 7.45 (s, 1H), 7.38-7.28 (m, 2H), 7.15 (t, J=6.6 Hz, 1H), 7.09 (m, 1H), 5.93 (s, 1H), 4.59 (q, J=7.5, 7.0 Hz, 4H), 4.15 (d, J=8.6 Hz, 2H), 3.87 (d, J=11.5 Hz, 5H), 3.47 (s, 1H), 240 (s, 2H), 2.29 (d, J=23.3 Hz, 6H), 2.19 (s, 1H), 1.84 (s, 1H), 1.23 (s, 2H), 0.82 (q, J=6.6 Hz, 3H), MS m/z (ESI): 698$[M+H]^+$.

Example 123 3-(Ethyl(1-(2,2,2-trifluoroethyl)piperi-din-4-yl)amino)-N-((4-methoxy-6-methyl-2-oxo-1,2-dihydropyridin-3-yl)methyl)-2-methyl-5-(1-methyl-2-oxo-2',3',5',6'-tetrahydrospiro[dihydroindole-3,4'-pyran]-5-yl)benzamide

123

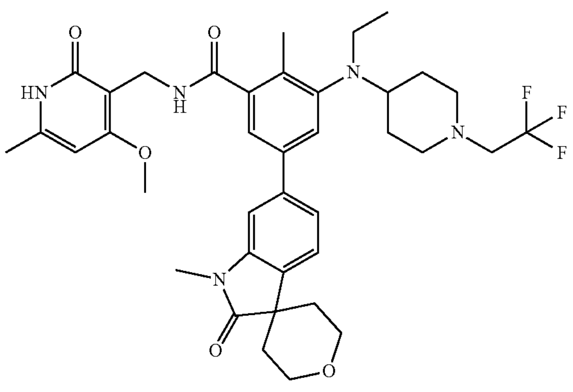

A similar method of Example 109 was used to obtain the title compound 123 with a yield of 26%, wherein the 5-bromooxindole was replaced with 6-bromooxindole.

1H NMR (400 MHz, DMSO-d6) δ 11.40 (s, 1H), 7.94 (t, J=4.6 Hz, 1H), 7.69 (d, J=1.8 Hz, 1H), 7.46 (dd, J=8.1, 1.7 Hz, 1H), 7.31 (d, J=2.0 Hz, 1H), 7.20 (d, J=1.9 Hz, 1H), 7.05 (d, J=8.1 Hz, 1H), 6.06 (s, 1H), 4.22 (d, J=4.5 Hz, 2H), 4.11-4.05 (m, 2H), 3.82-3.77 (m, 5H), 3.13-3.03 (n. 7H), 2.88-2.74 (m, 3H), 2.30-2.14 (m, 81), 1.93 (ddd, J=13.8, 9.1, 3.7 Hz, 2H), 1.65-1.49 (m, 6H), 0.82 (t J=6.9 Hz, 3H), MS m/z (ESI): 698[M+H]$^+$.

For the sake of clarity of the purpose, technical solutions and advantages of the present invention, the invention is further described in detail in combination with specific figures and examples. Obviously, the described examples are only a part of the examples of the present invention, rather than all the examples.

Based on the examples in this invention, all other examples obtained by those of ordinary skill in the art without creative work shall fall within the protection scope of this invention.

Bioactivity Experiment

Experiment I. Determination of the Activity of the Inventive Compounds to the Enhancer of Zeste Homolog 2 (EZH2) of Wild Type Polycomb Repressive Complex 2 (PRC2)

1. Experimental Purpose and Method

In this experiment, radiometric assay was used to determine the bonding strength of the inventive compounds to the enhancer of Zeste homolog 2 (EZH2) of wild-type Polycomb Repressive Complex 2 (PRC2), and a median inhibitory concentration (IC50) was used to test the in vitro activity of the compounds.

2. Experimental Scheme 2.1 Preparation of the Compounds for Experimental Purpose The compounds in Examples used in this experiment, 1-123, EPZ-6438 and GSK126, were dissolved in dimethyl sulfoxide (DMSO) to form a mother liquid of 10 mmol/L (mM). The maximum concentration when measuring was 1 mol/L (M), with a 5-fold dilution, a total of 7 concentration gradients, and duplicated wells were established.

2.2 Experimental Process

The compound to be tested and 10 microliters (μL) of wild-type EZH2 were added to each well and incubated at room temperature for 15 minutes (min), followed by adding polypeptide and [3H]-labeled methyl donor S-adenosylmethionine (SAM) and reacting at room temperature for 1 hour, and finally cold SAM was added to terminate the reaction. 25 μL of reaction solution was transferred to a scintillation plate, which was incubated at room temperature for 1 hour (h) and washed with deionized water and 0.1% Tween 20 for three times. A PerkinElmer liquid scintillation/luminescence counter was used to read the value, and GraphPad Prism 5 was used to calculate the median inhibitory concentration (IC50) of the compounds.

2.3 Experimental Results and Conclusions

The results showed that the median inhibitory concentration (IC50) of EPZ-6438 on wild-type EZH2 is 1.60 nanomole per liter (nM), and the median inhibitory concentration (IC50) of GSK126 on wild type EZH2 is 1.34 nanomole per liter (nM). All the compounds in Examples showed strong inhibitory effects on wild-type EZH2, and the results are shown in Table 1.

Experiment II. Determination of the Activity of the Inventive Compounds to Mutant Type PRC2 Complex (Mutant EZH2)

1. Test Method: AlphaLISA.

2. Experimental Process

According to the specification, test buffer was used to dilute the enzyme complex, methyl donor S-adenosylmethionine (SAM) (Sigma, Art. No. A7007), protease inhibitor (sinefungin) (Sigma, Art. No. S8559), biotinylated peptide substrate (AnaSpec, Art. No. 64440), 2.5 microliter of 4-fold enzyme complex (BPS, Art. No. 51004), 2.5 microliter of 4-fold test inhibitor buffer, 5 microliter of biotinylated histone (H3) and 2-fold methyl donor S-adenosylmethionine were added to a 384-well plate and incubated at room temperature. Finally, 15 microliter of detection solution mixture was added under weak light and incubated at room temperature for 60 minutes, and the value was recorded.

3 Experimental Results and Conclusions

The results showed that the IC50 of the positive drug EPZ-6438 on the Y641F-mutation of enhancer of Zeste homolog 2 (EZH2) is 1.70 nanomole per liter (nM), the IC50 on the A677-mutation of enhancer of Zeste homolog 2 (EZH2) is 1.91 nanomole per liter (nM), and the IC50 on the Y641-mutation of enhancer of Zeste homolog 2 (EZH2) is 1.24 nanomole per liter (nM). The median inhibitory concentration (IC50) of GSK126 on Y641F-mutation of EZH2 is 1.75 nanomole per liter (nM), the IC50 on A677G-mutation of EZH2 is 1.73 nanomole per liter (nM), and the IC50 on Y641N-mutation of EZH2 is 1.27 nanomole per liter (nM). All the compounds in Examples showed strong inhibitory effects on mutant EZH2, and the results are shown in Table 1.

TABLE 1

Inhibitory activity of the compound to PRC2 complex

| Compound ID | Wild-type EZH2 IC50 Nanomoles per Liter (nM) | Mutant type EZH2(Y641F) IC50 Nanomoles per Liter (nM) | Mutant type EZH2(A677G) IC59 Nanomoles per Liter (nM) | Mutant type EZH2(Y641N) IC50 Nanomoles per Liter (nM) |
|---|---|---|---|---|
| 1 | 1.00 | 0.90 | 0.54 | 0.43 |
| 2 | 0.80 | 0.72 | 0.50 | 0.30 |
| 3 | 0.45 | 0.21 | 0.14 | 0.08 |
| 4 | 1.55 | 1.40 | 0.98 | 0.59 |
| 5 | 0.60 | 0.46 | 0.33 | 0.16 |
| 6 | 0.75 | 0.20 | 0.20 | 0.07 |
| 7 | 0.60 | 0.36 | 0.22 | 0.15 |
| 8 | 0.35 | 0.48 | 0.29 | 0.23 |
| 9 | 0.70 | 0.52 | 0.37 | 0.28 |
| 10 | 0.56 | 0.39 | 0.21 | 0.18 |
| 11 | 0.85 | 0.68 | 0.42 | 0.17 |
| 12 | 0.70 | 0.43 | 0.34 | 0.11 |

TABLE 1-continued

Inhibitory activity of the compound to PRC2 complex

| Compound ID | Wild-type EZH2 IC50 Nanomoles per Liter (nM) | Mutant type EZH2(Y641F) IC50 Nanomoles per Liter (nM) | Mutant type EZH2(A677G) IC59 Nanomoles per Liter (nM) | Mutant type EZH2(Y641N) IC50 Nanomoles per Liter (nM) |
|---|---|---|---|---|
| 13 | 0.79 | 0.56 | 0.47 | 0.21 |
| 14 | 0.65 | 0.36 | 0.29 | 0.15 |
| 15 | 1.01 | 0.69 | 0.67 | 0.57 |
| 16 | 0.65 | 0.46 | 0.35 | 0.17 |
| 17 | 1.10 | 0.75 | 0.46 | 0.30 |
| 18 | 0.66 | 0.47 | 0.29 | 0.23 |
| 19 | 0.40 | 0.24 | 0.17 | 0.12 |
| 20 | 0.85 | 0.78 | 0.64 | 0.33 |
| 21 | 0.90 | 0.73 | 0.62 | 0.37 |
| 22 | 0.97 | 0.88 | 0.64 | 0.47 |
| 23 | 0.83 | 0.75 | 0.63 | 0.36 |
| 24 | 0.75 | 0.56 | 0.41 | 0.23 |
| 25 | 0.33 | 0.29 | 0.14 | 0.09 |
| 26 | 0.98 | 0.85 | 0.71 | 0.50 |
| 27 | 0.90 | 0.79 | 0.62 | 0.23 |
| 28 | 0.95 | 0.89 | 0.59 | 0.37 |
| 29 | 0.87 | 0.75 | 0.61 | 0.46 |
| 30 | 0.76 | 0.61 | 0.56 | 0.44 |
| 31 | 0.52 | 0.33 | 0.21 | 0.14 |
| 32 | 0.79 | 0.65 | 0.36 | 0.10 |
| 33 | 0.86 | 0.69 | 0.35 | 0.29 |
| 34 | 0.66 | 0.41 | 0.26 | 0.19 |
| 35 | 0.90 | 0.78 | 0.24 | 0.10 |
| 36 | 0.95 | 0.81 | 0.46 | 0.34 |
| 37 | 0.60 | 0.54 | 0.34 | 0.23 |
| 38 | 0.90 | 0.72 | 0.42 | 0.28 |
| 39 | 0.74 | 0.43 | 0.34 | 0.21 |
| 40 | 0.89 | 0.84 | 0.66 | 0.50 |
| 41 | 0.90 | 0.48 | 0.37 | 0.26 |
| 42 | 0.97 | 0.58 | 0.49 | 0.37 |
| 43 | 0.61 | 0.39 | 0.23 | 0.08 |
| 44 | 0.91 | 0.75 | 0.50 | 0.30 |
| 45 | 0.71 | 0.44 | 0.37 | 0.23 |
| 46 | 0.88 | 0.65 | 0.43 | 0.26 |
| 47 | 0.99 | 0.83 | 0.54 | 0.43 |
| 48 | 0.95 | 0.83 | 0.66 | 0.37 |
| 49 | 0.61 | 0.39 | 0.28 | 0.12 |
| 50 | 0.76 | 0.68 | 0.50 | 0.32 |
| 51 | 0.61 | 0.51 | 0.33 | 0.11 |
| 52 | 0.97 | 0.64 | 0.44 | 0.23 |
| 53 | 0.68 | 0.47 | 0.36 | 0.21 |
| 54 | 0.95 | 0.82 | 0.74 | 0.61 |
| 55 | 0.63 | 0.58 | 0.42 | 0.30 |
| 56 | 0.80 | 0.71 | 0.64 | 0.50 |
| 57 | 0.53 | 0.44 | 0.31 | 0.18 |
| 58 | 0.62 | 0.47 | 0.35 | 0.19 |
| 59 | 0.81 | 0.72 | 0.54 | 0.38 |
| 60 | 0.81 | 0.63 | 0.44 | 0.26 |
| 61 | 0.79 | 0.72 | 0.57 | 0.22 |
| 62 | 0.72 | 0.61 | 0.31 | 0.19 |
| 63 | 0.80 | 0.42 | 0.36 | 0.18 |
| 64 | 0.68 | 0.53 | 0.46 | 0.26 |
| 65 | 0.97 | 0.84 | 0.78 | 0.42 |
| 66 | 0.63 | 0.52 | 0.44 | 0.23 |
| 67 | 0.88 | 0.69 | 0.43 | 0.32 |
| 68 | 0.83 | 0.78 | 0.69 | 0.50 |
| 69 | 0.58 | 0.38 | 0.21 | 0.13 |
| 70 | 1.02 | 0.96 | 0.71 | 0.62 |
| 71 | 0.84 | 0.72 | 0.50 | 0.18 |
| 72 | 0.62 | 0.40 | 0.35 | 0.18 |
| 73 | 0.70 | 0.51 | 0.46 | 0.22 |
| 74 | 0.83 | 0.63 | 0.26 | 0.14 |
| 75 | 0.65 | 0.45 | 0.33 | 0.12 |
| 76 | 0.75 | 0.63 | 0.43 | 0.19 |
| 77 | 0.91 | 0.75 | 0.67 | 0.34 |
| 78 | 0.81 | 0.65 | 0.54 | 0.23 |
| 79 | 1.09 | 0.83 | 0.75 | 0.42 |
| 80 | 1.21 | 0.96 | 0.52 | 0.46 |
| 81 | 1.37 | 0.89 | 0.63 | 0.48 |
| 82 | 0.83 | 0.52 | 0.18 | 0.16 |
| 83 | 1.83 | 1.48 | 0.91 | 0.38 |
| 84 | 2.13 | 0.63 | 0.47 | 0.25 |

TABLE 1-continued

| Inhibitory activity of the compound to PRC2 complex | | | | |
|---|---|---|---|---|
| Compound ID | Wild-type EZH2 IC50 Nanomoles per Liter (nM) | Mutant type EZH2(Y641F) IC50 Nanomoles per Liter (nM) | Mutant type EZH2(A677G) IC59 Nanomoles per Liter (nM) | Mutant type EZH2(Y641N) IC50 Nanomoles per Liter (nM) |
| 85 | 0.81 | 0.82 | 0.38 | 0.42 |
| 86 | 0.72 | 0.52 | 0.31 | 0.32 |
| 87 | 0.46 | 0.53 | 0.42 | 0.31 |
| 88 | 0.96 | 0.61 | 0.51 | 0.42 |
| 89 | 1.32 | 0.43 | 0.46 | 0.33 |
| 90 | 1.42 | 0.73 | 0.58 | 0.29 |
| 91 | 0.95 | 0.49 | 0.71 | 0.24 |
| 92 | 0.87 | 0.68 | 0.57 | 0.37 |
| 93 | 1.12 | 0.57 | 0.42 | 0.40 |
| 94 | 1.31 | 0.73 | 0.77 | 0.62 |
| 95 | 0.78 | 0.53 | 0.48 | 0.28 |
| 96 | 1.24 | 0.88 | 0.57 | 0.49 |
| 97 | 0.85 | 0.59 | 0.38 | 0.37 |
| 98 | 0.67 | 0.36 | 0.28 | 0.21 |
| 99 | 0.96 | 0.84 | 0.78 | 0.46 |
| 100 | 1.05 | 0.79 | 0.78 | 0.42 |
| 101 | 1.16 | 0.95 | 0.82 | 0.57 |
| 102 | 0.96 | 0.89 | 0.73 | 0.45 |
| 103 | 0.92 | 0.63 | 0.52 | 0.36 |
| 104 | 0.46 | 0.31 | 0.27 | 0.19 |
| 105 | 1.13 | 0.93 | 0.83 | 0.62 |
| 106 | 0.98 | 0.82 | 0.71 | 0.32 |
| 107 | 1.03 | 0.86 | 0.67 | 0.43 |
| 108 | 0.94 | 0.79 | 0.68 | 0.49 |
| 109 | 0.81 | 0.72 | 0.63 | 0.54 |
| 110 | 0.69 | 0.47 | 0.34 | 0.28 |
| 111 | 0.75 | 0.66 | 0.33 | 0.19 |
| 112 | 1.02 | 0.82 | 0.51 | 0.48 |
| 113 | 0.75 | 0.54 | 0.38 | 0.27 |
| 114 | 1.12 | 0.93 | 0.45 | 0.32 |
| 115 | 0.97 | 0.84 | 0.41 | 0.38 |
| 116 | 0.89 | 0.72 | 0.59 | 0.41 |
| 117 | 1.08 | 0.94 | 0.61 | 0.43 |
| 118 | 0.91 | 0.58 | 0.45 | 0.32 |
| 119 | 0.98 | 0.95 | 0.76 | 0.63 |
| 120 | 1.26 | 0.68 | 0.53 | 0.48 |
| 121 | 1.04 | 0.74 | 0.68 | 0.53 |
| 122 | 0.87 | 0.58 | 0.43 | 0.21 |
| 123 | 1.15 | 0.92 | 0.72 | 0.52 |
| EPZ-6438 | 1.60 | 1.70 | 1.91 | 1.24 |
| GSK126 | 1.34 | 1.75 | 1.73 | 1.27 |

Experiment III. Analysis of the Effect of the Inventive Compounds on the Proliferation of Human Diffuse Large B-Cell Lymphoma Cells (WSU-DLCL2 Cell)

1. Experimental Purpose and Method

In this experiment, a Calcein AM staining method was used to determine the in vitro antiproliferative effect of the inventive compounds on human diffuse large B-cell lymphoma cells (WSU-DLCL2 cell).

2. Experimental Scheme 2.1 Cell Culture

The human diffuse large B-cell lymphoma cells (WSU-DLCL2 cell) were ordered from Cobioer, Nanjing, and were cultured with RPMI1640 (Kangning, 35417005), 10% fetal calf serum (Ausbina, 0986180) and 1% penicillin/streptomycin double-antibody (Kangning, 30002297). The cells were confirmed to be in good condition by microscopic observation, transferred to a 15 milliliter (mL) centrifuge tube, and centrifuged at 1000 rpm for 5 minutes. The supernatant was discarded, and the residue was added to a complete medium and pipetted to form a single cell suspension, which was then cultured in an incubator (Thermo, 3H) at 37° C. with 5% $CO_2$.

2.2 Preparation of the Compounds and Compound Plates

The compounds 1-123, EPZ-6438 and GSK126 used in this experiment were dissolved in dimethyl sulfoxide (DMSO) to form a mother liquid of 10 mmol/L (mM), and the compounds were gradient diluted with dimethyl sulfoxide (DMSO) to prepare a compound plate with 500 times the final concentration. 1.2 microliter (μL) of 500× compound was pipetted into a 200 microliter (μL) medium and pipetted uniformly to obtain a 3× compound intermediate plate. 50 microliters (μL) of 3× compound was pipetted into a cell culture plate in accordance with the set arrangement.

2.3 Experimental Process

The diffuse large B-cell lymphoma cells (WSU-DLCL2 cell) were collected and counted when growing well. The cell concentration was adjusted to 100000 cells/milliliter (cells/mL). The above cells were inoculated into a 96-well plate at 100 μL/well (10000 cells per well). The cells were placed in a carbon dioxide incubator and cultured for 4 days. The cell culture plate was taken out and mixed well, and a certain volume of cell suspension was pipetted, stained with Calcein AM, and counted with Acumen to obtain the number of cells per well. 10000 cells were reinoculated into a 96-well plate according to the number of cells detected. The compounds were added with the same method. The cells were placed in the carbon dioxide incubator and cultured for 3 days (7th day). The cell culture plate was taken out again and mixed well, and a certain volume of cell suspension was pipetted, stained with Calcein AM, and counted with Acumen to obtain the number of cells per well. The cells were cultured for another 4 days (11th day), and cell culture plate was taken out a third time and mixed well, and a certain volume of cell suspension was pipetted, stained with Calcein AM, and counted with Acumen to obtain the number of cells per well. 10000 cells were reinoculated into a 96-well plate according to the number of cells detected. The compounds were added with the same method. The cells were placed in the carbon dioxide incubator and cultured for 3 days (7th day). The cells were cultured for another 7 days (14th day), stained by Calcein AM, and a final count was obtained. The data of 14th day was processed to obtain the corresponding median inhibitory concentration (IC50).

2.4 Data Processing and Statistics

The cell survival rate was calculated by the formula: $V_{sample}/V_{vehicle\ control}\times 100\%$, wherein the $V_{sample}$ is the reading of the drug treatment group, and the $V_{vehicle\ control}$ is the mean value of solvent control group. The software of GraphPad Prism 5 was used to plot the S-type dose—survival rate curve using nonlinear regression model and to calculate the value of median inhibitory concentration (IC50).

2.5 Experimental Results and Conclusions

The results showed that the median inhibitory concentration (IC50) of EPZ-6438 on the proliferation inhibition of human diffuse large B-cell lymphoma cells (WSU-DLCL2 cell) is 37.23 nanomole per liter (nM), the median inhibitory concentration (IC50) of GSK126 on the proliferation inhibition of human diffuse large B-cell lymphoma cells (WSU-DLCL2 cell) is 83.54 nanomole per liter (nM). All the compounds in Examples showed strong inhibitory effects on human diffuse large B-cell lymphoma cells (WSU-DLCL2 cell), the inhibition activities of which were better than those of EPZ-6438 and GSK126.

The results are shown in Table 2.

Experiment IV. Analysis of the Effect of the Inventive Compounds on the Proliferation of Human Diffuse Large Cell Lymphoma B Lymphocytes (Pfeiffer Cell)

1. Experimental Purpose and Method

In this experiment, a Calcein AM staining method was used to determine the in vitro antiproliferative effect of the inventive compounds on human diffuse large cell lymphoma B lymphocytes (Pfeiffer cell).

2. Experimental Scheme 2.1 Cell Culture

The human diffuse large cell lymphoma B lymphocytes (Pfeiffer cell) were ordered from Cobioer, Nanjing, and were cultured with RPMI1640 (Kangning, 35417005), 20% fetal calf serum (Ausbina, 0986180) and 1% penicillin/streptomycin double-antibody (Kangning, 30002297). The cells were confirmed to be in good condition by microscopic observation, transferred to a 15 milliliter (mL) centrifuge tube, and centrifuged at 1000 rpm for 5 minutes. The supernatant was discarded, and the residue was added to a complete medium and pipetted to form a single cell suspension, which was then cultured in an incubator (Thermo, 3H) at 37° C. with 5% $CO_2$.

2.2 Preparation of the Compounds and Compound Plates

The compounds 1-123, EPZ-6438 and GSK126 used in this experiment were dissolved in dimethyl sulfoxide (DMSO) to form a mother liquid of 10 mmol/L (mM). The maximum concentration when measuring was 10 μmol/L (μM), and the compounds were gradient diluted with dimethyl sulfoxide (DMSO) to prepare a compound plate with 500 times the final concentration. 1.2 microliter (μL) of 500× compound was pipetted into a 200 microliter (μL) medium and pipetted uniformly to obtain a 3× compound intermediate plate. 50 microliters (μL) of 3× compound was pipetted into a cell culture plate in accordance with the set arrangement.

2.3 Experimental Process

The diffuse large cell lymphoma B lymphocytes (Pfeiffer cells) were collected and counted when growing well. The cell concentration was adjusted to 100000 cells/milliliter. The above cells were inoculated into a 96-well plate at 100 μL/well (10000 cells per well). The cells were placed in a carbon dioxide incubator and cultured for 4 days. The cell culture plate was taken out and mixed well, and a certain volume of cell suspension was pipetted, stained with Calcein AM, and counted with Acumen to obtain the number of cells per well. 10000 cells were reinoculated into a 96-well plate according to the number of cells detected. The compounds were added with the same method. The cells were placed in the carbon dioxide incubator and cultured for 3 days (7th day). The cell culture plate was taken out again and mixed well, and a certain volume of cell suspension was pipetted, stained with Calcein AM, and counted with Acumen to obtain the number of cells per well. The cells were cultured for another 4 days (11th day), and cell culture plate was taken out a third time and mixed well, and a certain volume of cell suspension was pipetted, stained with Calcein AM, and counted with Acumen to obtain the number of cells per well. 10000 cells were reinoculated into a 96-well plate according to the number of cells detected. The compounds were added with the same method. The cells were placed in the carbon dioxide incubator and cultured for 3 days (7th day). The cells were cultured for another 7 days (14th day), stained by Calcein AM, and a final count was obtained. The data of 14th day was processed to obtain the corresponding median inhibitory concentration (IC50).

2.4 Data Processing and Statistics

The cell survival rate was calculated by the formula: $V_{sample}/V_{vehiclecontrol}\times 100\%$, wherein the $V_{sample}$ is the reading of the drug treatment group, and the $V_{vehicle\ control}$ is the mean value of solvent control group. The software of GraphPad Prism 5 was used to plot the S-type dose—survival rate curve using nonlinear regression model and to calculate the value of median inhibitory concentration (IC50).

2.5 Experimental Results and Conclusions

The results showed that the median inhibitory concentration (IC50) of EPZ-6438 on the proliferation inhibition of human diffuse large cell lymphoma B lymphocytes (Pfeiffer cell) is 7.14 nanomole per liter (nM), the median inhibitory concentration (IC50) of GSK126 on the proliferation inhibition of human diffuse large cell lymphoma B lymphocytes (Pfeiffer cell) is 38.82 nanomole per liter (nM). All the compounds in Examples showed strong inhibitory effects on human diffuse large cell lymphoma B lymphocytes (Pfeiffer cell), the inhibition activities of which were better than that of EPZ-6438 and GSK126. The results are shown in Table 2.

Experiment V. Analysis of the Effect of the Inventive Compounds on the Proliferation of Human Diffuse Large B-Cell Lymphoma Cells (Karpas 422 Cell)

1. Experimental Purpose and Method

In this experiment, a Calcein AM staining method was used to determine the in vitro antiproliferative effect of the inventive compounds on human diffuse large B-cell lymphoma cells (Karpas 422 cell).

2. Experimental Scheme 2.1 Cell Culture

The human diffuse large B-cell lymphoma cells (Karpas 422 cell) were ordered from Cobioer, Nanjing, and were cultured with RPMI1640 (Kangning, 35417005), 20% fetal calf serum (Ausbina, 0986180) and 1% penicillin/streptomycin double-antibody (Kangning, 30002297). The cells were confirmed to be in good condition by microscopic observation, transferred to a 15 milliliter (mL) centrifuge tube, and centrifuged at 1000 rpm for 5 minutes. The supernatant was discarded, and the residue was added to a complete medium and pipetted to form a single cell suspension, which was then cultured in an incubator (Thermo, 3H) at 37° C. with 5% $CO_2$.

2.2 Preparation of the Compounds and Compound Plates

The compounds 1-123, EPZ-6438 and GSK126 used in this experiment were dissolved in dimethyl sulfoxide (DMSO) to form a mother liquid of 10 mmol/L (mM). The maximum concentration when measuring was 10 μmol/L (μM), and the compounds were gradient diluted with dimethyl sulfoxide (DMSO) to prepare a compound plate with 500 times the final concentration. 1.2 microliter (μL) of 500× compound was pipetted into a 200 microliter (μL) medium and pipetted uniformly to obtain a 3× compound intermediate plate. 50 microliters (μL) of 3× compound was pipetted into a cell culture plate in accordance with the set arrangement.

2.3 Experimental Process

The diffuse large B-cell lymphoma cells (Karpas 422 cell) were collected and counted when growing well. The cell concentration was adjusted to 100000 cells/milliliter. The above cells were inoculated into a 96-well plate at 100 μL/well (10000 cells per well). The cells were placed in a carbon dioxide incubator and cultured for 4 days. The cell culture plate was taken out and mixed well, and a certain volume of cell suspension was pipetted, stained with Calcein AM, and counted with Acumen to obtain the number of cells per well. 10000 cells were reinoculated into a 96-well plate according to the number of cells detected. The compounds were added with the same method. The cells were placed in the carbon dioxide incubator and cultured for 3 days (7th day). The cell culture plate was taken out again and mixed well, and a certain volume of cell suspension was pipetted, stained with Calcein AM, and counted with Acumen to obtain the number of cells per well. The cells were cultured for another 4 days (11th day), and cell culture plate was taken out a third time and mixed well, and a certain volume of cell suspension was pipetted, stained with Calcein AM, and counted with Acumen to obtain the number of cells per well. 10000 cells were reinoculated into a 96-well plate according to the number of cells detected. The compounds were added with the same method. The cells were placed in the carbon dioxide incubator and cultured for 3 days (7th day). The cells were cultured for another 7 days (14th day), stained by Calcein AM and a final count was obtained. The data of 14th day was processed to obtain the corresponding median inhibitory concentration (IC50).

2.4 Data Processing and Statistics

The cell survival rate was calculated by the formula: $V_{sample}/V_{vehicle\ control}\times 100\%$, wherein the $V_{sample}$ is the reading of the drug treatment group, and the $V_{vehicle\ control}$ is the mean value of solvent control group. The software of GraphPad Prism 5 was used to plot the S-type dose—survival rate curve using nonlinear regression model and to calculate the value of median inhibitory concentration (IC50).

2.5 Experimental Results and Conclusions

The results showed that the median inhibitory concentration (IC50) of EPZ-6438 on the proliferation inhibition of human diffuse large B-cell lymphoma cells (Karpas 422 cell) is 13.26 nanomole per liter (nM), the median inhibitory concentration (IC50) of GSK126 on the proliferation inhibition of human diffuse large B-cell lymphoma cells (Karpas 422 cell) is 51.37 nanomole per liter (nM). All the compounds in Examples showed strong inhibitory effects on human diffuse large B-cell lymphoma cells (Karpas 422 cell), the inhibition activities of which were better than those of EPZ-6438 and GSK126. The results are shown in Table 2.

TABLE 2

Inhibitory effect of compounds on the proliferation of EZH2 sensitive cells

| Compound ID | WSU-DLCL2 Proliferation IC50 Nanomoles per Liter (nM) | Pfeiffer Proliferation IC50 Nanomoles per Liter (nM) | Karpas422 Proliferation IC50 Nanomoles per Liter (nM) |
|---|---|---|---|
| 1 | 8.50 | 2.95 | 4.26 |
| 2 | 7.40 | 3.60 | 2.78 |
| 3 | 6.95 | 1.96 | 2.74 |
| 4 | 7.32 | 3.12 | 2.87 |
| 5 | 1.26 | 0.63 | 0.91 |
| 6 | 2.45 | 1.14 | 1.94 |
| 7 | 3.28 | 1.89 | 1.44 |
| 8 | 1.98 | 0.96 | 1.12 |
| 9 | 2.33 | 0.42 | 1.80 |
| 10 | 1.31 | 0.23 | 1.28 |
| 11 | 4.81 | 1.26 | 1.67 |
| 12 | 1.80 | 0.19 | 0.96 |
| 13 | 2.13 | 0.94 | 1.94 |
| 14 | 2.10 | 0.68 | 1.73 |
| 15 | 3.89 | 2.30 | 3.06 |
| 16 | 1.57 | 0.37 | 0.98 |
| 17 | 4.05 | 2.78 | 3.09 |
| 18 | 2.38 | 0.49 | 1.79 |
| 19 | 1.36 | 0.15 | 1.12 |
| 20 | 3.55 | 2.32 | 3.03 |
| 21 | 5.33 | 1.66 | 1.93 |
| 22 | 3.36 | 1.64 | 2.54 |
| 23 | 3.28 | 2.39 | 2.98 |
| 24 | 1.00 | 0.10 | 0.41 |
| 25 | 1.25 | 0.81 | 0.90 |
| 26 | 3.00 | 1.85 | 2.53 |
| 27 | 3.12 | 2.26 | 2.74 |
| 28 | 6.21 | 3.28 | 4.64 |
| 29 | 4.71 | 2.13 | 3.01 |
| 30 | 1.78 | 0.59 | 1.20 |
| 31 | 1.17 | 0.38 | 0.58 |
| 32 | 1.67 | 1.21 | 1.73 |
| 33 | 5.72 | 3.10 | 4.92 |
| 34 | 1.82 | 0.59 | 1.65 |
| 35 | 6.18 | 2.21 | 3.50 |
| 36 | 5.52 | 1.54 | 4.39 |
| 37 | 1.28 | 0.87 | 0.95 |
| 38 | 8.15 | 1.15 | 2.42 |
| 39 | 1.15 | 0.30 | 0.82 |
| 40 | 5.68 | 2.49 | 3.09 |
| 41 | 4.16 | 1.87 | 3.50 |
| 42 | 3.71 | 1.27 | 2.60 |
| 43 | 2.15 | 1.19 | 1.36 |
| 44 | 4.78 | 1.75 | 2.14 |
| 45 | 1.21 | 0.12 | 0.43 |
| 46 | 8.15 | 4.79 | 5.32 |
| 47 | 5.13 | 3.20 | 4.15 |
| 48 | 2.18 | 1.42 | 1.99 |
| 49 | 1.71 | 0.15 | 0.93 |
| 50 | 1.58 | 0.75 | 1.08 |
| 51 | 1.12 | 0.62 | 0.80 |

TABLE 2-continued

Inhibitory effect of compounds on the proliferation of EZH2 sensitive cells

| Compound ID | WSU-DLCL2 Proliferation IC50 Nanomoles per Liter (nM) | Pfeiffer Proliferation IC50 Nanomoles per Liter (nM) | Karpas422 Proliferation IC50 Nanomoles per Liter (nM) |
|---|---|---|---|
| 52 | 3.56 | 1.38 | 2.10 |
| 53 | 2.78 | 1.56 | 1.72 |
| 54 | 6.38 | 1.87 | 3.67 |
| 55 | 1.12 | 0.65 | 0.97 |
| 56 | 7.52 | 2.54 | 3.16 |
| 57 | 2.76 | 1.47 | 2.43 |
| 58 | 1.12 | 0.58 | 0.74 |
| 59 | 8.32 | 1.97 | 3.35 |
| 60 | 8.91 | 2.10 | 4.35 |
| 61 | 1.21 | 0.62 | 0.76 |
| 62 | 1.32 | 0.27 | 0.58 |
| 63 | 4.15 | 2.89 | 3.76 |
| 64 | 0.72 | 0.75 | 0.81 |
| 65 | 5.12 | 1.87 | 3.34 |
| 66 | 1.34 | 0.56 | 0.98 |
| 67 | 7.75 | 2.34 | 3.21 |
| 68 | 3.58 | 1.98 | 2.19 |
| 69 | 1.53 | 1.35 | 1.36 |
| 70 | 6.72 | 3.70 | 4.20 |
| 71 | 4.38 | 2.83 | 3.35 |
| 72 | 1.72 | 1.01 | 1.90 |
| 73 | 1.10 | 0.54 | 1.20 |
| 74 | 8.52 | 2.78 | 3.10 |
| 75 | 1.36 | 0.87 | 0.93 |
| 76 | 0.72 | 0.10 | 0.15 |
| 77 | 9.38 | 7.16 | 8.15 |
| 78 | 4.72 | 1.89 | 2.21 |
| 79 | 5.31 | 1.65 | 2.65 |
| 80 | 9.42 | 3.91 | 5.37 |
| 81 | 8.31 | 4.73 | 3.67 |
| 82 | 7.84 | 2.85 | 3.62 |
| 83 | 8.43 | 4.24 | 4.76 |
| 84 | 2.32 | 1.74 | 1.86 |
| 85 | 3.54 | 2.42 | 2.85 |
| 86 | 5.37 | 2.69 | 2.51 |
| 87 | 2.89 | 1.86 | 2.34 |
| 88 | 4.53 | 1.56 | 2.76 |
| 89 | 2.26 | 1.03 | 2.38 |
| 90 | 5.93 | 2.52 | 2.83 |
| 91 | 2.92 | 1.08 | 1.87 |
| 92 | 3.41 | 1.83 | 2.83 |
| 93 | 3.62 | 1.39 | 2.64 |
| 94 | 4.78 | 3.83 | 4.74 |
| 95 | 3.83 | 2.35 | 2.79 |
| 96 | 5.13 | 3.63 | 4.57 |
| 97 | 3.47 | 1.53 | 2.70 |
| 98 | 2.45 | 1.06 | 2.23 |
| 99 | 4.68 | 3.47 | 4.15 |
| 100 | 6.46 | 2.73 | 2.85 |
| 101 | 4.48 | 2.74 | 3.68 |
| 102 | 4.32 | 3.45 | 3.87 |
| 103 | 2.05 | 0.36 | 0.53 |
| 104 | 2.36 | 1.73 | 1.82 |
| 105 | 4.24 | 2.98 | 3.68 |
| 106 | 4.64 | 3.41 | 3.89 |
| 107 | 7.35 | 4.38 | 5.76 |
| 108 | 5.84 | 3.31 | 4.23 |
| 109 | 2.87 | 1.34 | 2.15 |
| 110 | 2.24 | 1.21 | 1.38 |
| 111 | 2.86 | 2.43 | 2.64 |
| 112 | 6.63 | 4.17 | 5.78 |
| 113 | 2.68 | 1.67 | 2.50 |
| 114 | 7.32 | 3.34 | 4.61 |
| 115 | 6.64 | 2.45 | 5.77 |
| 116 | 2.36 | 1.69 | 1.84 |
| 117 | 9.04 | 2.31 | 3.57 |
| 118 | 2.34 | 1.05 | 1.68 |
| 119 | 6.78 | 3.52 | 4.15 |
| 120 | 5.28 | 2.96 | 4.47 |
| 121 | 4.69 | 2.36 | 3.54 |
| 122 | 3.63 | 2.91 | 2.48 |
| 123 | 5.85 | 2.84 | 3.23 |

TABLE 2-continued

Inhibitory effect of compounds on the proliferation of EZH2 sensitive cells

| Compound ID | WSU-DLCL2 Proliferation IC50 Nanomoles per Liter (nM) | Pfeiffer Proliferation IC50 Nanomoles per Liter (nM) | Karpas422 Proliferation IC50 Nanomoles per Liter (nM) |
|---|---|---|---|
| EPZ-6438 | 37.23 | 7.14 | 13.26 |
| GSK126 | 83.54 | 38.82 | 51.37 |

Experiment VI. Pharmacokinetic Experiment of the Inventive Compounds in Rats

1. Abstract

Taking 8-week-old male SD rats weighing 200-300 g as experimental animals, the drug concentration in plasma at different times was measured by LC/MS/MS method after intravenous and intragastric administration of compound of Example 3, compound of Example 5, compound of Example 6, compound of Example 7, compound of Example 8, compound of Example 9, compound of Example 10, compound of Example 12, compound of Example 13, compound of Example 14, compound of Example 16, compound of Example 18, compound of Example 19, compound of Example 24, compound of Example 25, compound of Example 30, compound of Example 31, compound of Example 32, compound of Example 34, compound of Example 37, compound of Example 39, compound of Example 43, compound of Example 45, compound of Example 49, compound of Example 50, compound of Example 51, compound of Example 53, compound of Example 55, compound of Example 57, compound of Example 58, compound of Example 61, compound of Example 72, compound of Example 84, compound of Example 96, compound of Example 109, compound of Example 111, compound of Example 115, compound of Example 116 and compound of Example 122 to study the pharmacokinetic behavior of the compound of the present invention in rats and evaluate its pharmacokinetic characteristics.

2. Experimental Scheme 2.1 the Compounds for Experimental Purpose

The compound of Example 3, compound of Example 5, compound of Example 6, compound of Example 7, compound of Example 8, compound of Example 9, compound of Example 10, compound of Example 12, compound of Example 13, compound of Example 14, compound of Example 16, compound of Example 18, compound of Example 19, compound of Example 24, compound of Example 25, compound of Example 30, compound of Example 31, compound of Example 32, compound of Example 34, compound of Example 37, compound of Example 39, compound of Example 43, compound of Example 45, compound of Example 49, compound of Example 50, compound of Example 51, compound of Example 53, compound of Example 55, compound of Example 57, compound of Example 58, compound of Example 61, compound of Example 72, compound of Example 84, compound of Example 96, compound of Example 109, compound of Example 111, compound of Example 115, compound of Example 116 and compound of Example 122.

2.2 Preparation of the Compounds

A certain amount of compound was weighted and dissolved in 0.1% Tween under vortex and ultrasound, and 0.5% carboxymethyl cellulose sodium (CMC-NA) solution was added to form a uniform solution.

2.3 Plasma Collection and Processing

The above compounds were administered intravenously and orally to rats at a dose of 4 milligrams per kilogram (mg/kg) and 20 milligram per kilogram (mg/kg), 0.2 milliliter (mL) of blood was collected from the orbit at 0.083, 0.25, 0.5, 1.0, 2.0, 4.0, 6.0, 8.0, 12.0 and 24.0 hours after administration, transferred to anticoagulant tubes, and centrifuged at 4° C. at 600 rpm/minute for 10 minutes to separate plasma, which was then preserved at −80° C.

2.4 Experimental Results and Conclusions

The pharmacokinetic parameters of the inventive compounds after administration are shown in Table 3 below. As shown in Table 3, the inventive compounds have better metabolic characteristics and better bioavailability.

TABLE 3

The pharmacokinetic parameters of the inventive compounds after administration

| | Intravenous-Dose 4 miligrams per kilogram (mg/kg) | | Oral-Dose 20 milligrams per kilogram (mg/kg) | | |
|---|---|---|---|---|---|
| Compound | Area Curve (AUC, ng/mL · h) | Half life ($T_{1/2}$, h) | Blood Drug level (Cmax, ng/mL) | Area Curve (AUC, ng/mL · h) | Bioavailability (P %) |
| 3 | 947.98 | 1.15 | 415.00 | 1570.33 | 33.13 |
| 5 | 911.97 | 1.05 | 453.20 | 1565.85 | 34.34 |
| 6 | 936.02 | 1.26 | 493.67 | 1192.02 | 25.47 |
| 7 | 937.25 | 1.64 | 405.10 | 1435.87 | 30.64 |
| 8 | 997.34 | 1.07 | 454.90 | 1556.85 | 31.22 |
| 9 | 926.01 | 1.54 | 437.25 | 1522.36 | 32.88 |
| 10 | 897.98 | 1.31 | 515.00 | 1560.69 | 34.76 |
| 12 | 895.51 | 1.37 | 412.00 | 1509.38 | 33.71 |
| 13 | 975.12 | 1.87 | 433.33 | 1188.18 | 24.37 |
| 14 | 965.75 | 1.69 | 530.00 | 1291.69 | 26.75 |
| 16 | 956.23 | 1.42 | 480.00 | 1308.60 | 27.37 |
| 18 | 932.17 | 1.35 | 472.33 | 1188.05 | 25.49 |
| 19 | 995.34 | 1.72 | 430.00 | 1777.68 | 35.72 |
| 24 | 943.21 | 1.08 | 478.60 | 1353.98 | 28.71 |
| 25 | 1024.75 | 1.81 | 589.81 | 1725.68 | 33.68 |
| 30 | 878.95 | 1.24 | 442.53 | 1257.34 | 28.61 |
| 32 | 943.24 | 1.64 | 431.02 | 1356.38 | 28.76 |
| 34 | 965.72 | 1.32 | 594.23 | 1754.23 | 36.33 |
| 37 | 903.14 | 1.25 | 443.83 | 1540.76 | 34.12 |
| 39 | 897.32 | 1.62 | 477.83 | 1092.49 | 24.35 |
| 43 | 1032.12 | 1.64 | 489.81 | 1616.82 | 31.33 |
| 45 | 943.65 | 1.71 | 505.01 | 1305.07 | 27.66 |
| 49 | 996.53 | 1.31 | 597.83 | 1303.96 | 26.17 |
| 50 | 954.37 | 1.34 | 448.28 | 1346.62 | 28.22 |
| 55 | 932.75 | 1.53 | 437.62 | 1266.21 | 27.15 |
| 57 | 978.94 | 1.15 | 455.50 | 1288.29 | 26.32 |
| 58 | 893.24 | 1.42 | 499.88 | 1541.29 | 34.51 |
| 61 | 932.41 | 1.72 | 426.30 | 1248.96 | 26.79 |
| 72 | 889.75 | 1.31 | 566.59 | 1082.38 | 24.33 |
| 84 | 933.12 | 1.38 | 501.41 | 1186.93 | 25.44 |
| 96 | 989.75 | 1.64 | 435.53 | 1537.58 | 31.07 |
| 109 | 966.24 | 1.12 | 455.50 | 1607.34 | 53.27 |
| 111 | 977.13 | 1.34 | 402.80 | 1687.50 | 34.54 |
| 115 | 947.98 | 1.15 | 415.00 | 1570.33 | 33.13 |
| 116 | 911.97 | 1.05 | 453.20 | 1565.55 | 34.34 |
| 112 | 936.02 | 1.26 | 493.67 | 1192.02 | 25.47 |

Experiment VII. Acute Toxicity Experiment of the Inventive Compounds in Examples 1. Experimental Purpose and Method The purpose of this experiment is to test the acute toxicity of the compounds in mice.

Mice was given a single dose of different dosages of compound of Example 3, compound of Example 5, compound of Example 6, compound of Example 7, compound of Example 8, compound of Example 9, compound of Example 10, compound of Example 12, compound of Example 13, compound of Example 14, compound of Example 15, compound of Example 17, compound of Example 18, compound of Example 23, compound of Example 24, compound of Example 25, compound of Example 26, compound of Example 27, compound of Example 29, compound of Example 32, compound of Example 34, compound of Example 38, compound of Example 42, compound of Example 43, compound of Example 45, compound of Example 47, compound of Example 48, compound of Example 51, compound of Example 52, compound of Example 65, compound of Example 78, compound of Example 81, compound of Example 92, compound of Example 103 and compound of Example 112. The animals were observed for 14 days, and the death, poisoning reaction, weight change, diet, appearance and behavior were recorded. At the end of the experiment, the animals were dissected, and the organs were taken for histopathological examination.

2.4 Experimental Results and Conclusions

The median lethal dose (LD50) of the inventive compounds are >1000 milligram per kilogram (mg/kg), indicating a good safety. Compared with the control group, the administrated mice had no abnormal body weight and behavior within 14 days from the date of administration, indicating that the inventive compounds did not show obvious toxicity.

Experiment VIII. Pharmacodynamic Experiment of the Inventive Compounds of Examples 3, 8, 19, 25, 31, 51, 58, 66 and 72 in the Transplanted Tumor Model in Mice of Human Diffuse Large B-Cell Lymphoma Cells (WSU-DLCL2 Cell)

1. Abstract

Taking 8-week-old female SD mice (CB17/SCID) with weighing 18-20 g with severe combined immunodeficiency disease as experimental animals, the pharmacodynamic effects of the compound of Example 3, the compound of Example 8, the compound of Example 19, the compound of Example 25, the compound of Example 31, the compound of Example 51, the compound of Example 58, the compound of Example 66 and the compound of Example 72 on SCID transplanted tumor mice after intragastric administration were measured. The effect of the inventive compounds on tumor growth was discussed.

2. Experimental Scheme 2.1 the Compounds for Experimental Purpose

The compound of Example 3, the compound of Example 8, the compound of Example 19, the compound of Example 25, the compound of Example 31, the compound of Example 51, the compound of Example 58, the compound of Example 66 and the compound of Example 72.

2.2 Preparation of the Compounds

A certain amount of compound was weighted and dissolved in 0.1% Tween under vortex and ultrasound, and 0.5% carboxymethyl cellulose sodium (CMC-NA) solution was added to form a uniform solution.

2.3 Cell Culture

The human diffuse large B-cell lymphoma cells (WSU-DLCL2 cell) were ordered from Cobioer, Nanjing, and were cultured with RPMI1640 (Kangning, 35417005), 10% fetal calf serum (Ausbina, 0986180) and 1% penicillin/streptomycin double-antibody (Kangning, 30002297). The cells were confirmed to be in good condition by microscopic observation, transferred to a 15 milliliter (mL) centrifuge tube, and centrifuged at 1000 rpm for 5 minutes. The supernatant was discarded, and the residue was added to a complete medium and pipetted to form a single cell suspension, which was then cultured in an incubator (Thermo, 3H) at 37° C. with 5% $CO_2$.

2.4 Experimental Process Under sterile conditions, diffuse large B-cell lymphoma cells (WSU-DLCL2 cell) in logarithmic growth stage were digested and mixed with Matrigel and transplanted subcutaneously on the right back of mice (CB17/SCID) with severe combined immunodeficiency disease. Each mouse was inoculated with $1*10^7$ cells with a volume of 100 μL. After inoculation, the mice were randomly divided into 12 groups according to the tumor size balance evenly for in vivo pharmacodynamic experiments, with 6 mice in each group. The positive control group was given EPZ-6438 and GSK126, and the negative control group was given the same amount of menstruum. See Table 4 for specific design.

TABLE 4

Pharmacodynamic experiment of compounds in vivo

| Group | Number of Animals | Drugs under Test | Dosage (milligrams per kilogram, mg/kg) | Dose Volume (millilters per kilogram, ml/kg) | Administration Route | Administration Schedule |
|---|---|---|---|---|---|---|
| 1 | 6 | Solvent | NA | 10 | Intragastrically | Twice a day for 21 days |
| 2 | 6 | EPZ-6438 | 150 | 10 | Intragastrically | Twice a day for 21 days |
| 3 | 6 | G5K126 | 50 | 10 | Intraperitoneally | Once a day for 21 days |
| 4 | 6 | Example 3 | 150 | 10 | Intragastrically | Twice a day for 21 days |
| 5 | 6 | Example 8 | 150 | 10 | Intragastrically | Twice a day for 21 days |
| 6 | 6 | Example 19 | 150 | 10 | Intragastrically | Twice a day for 21 days |
| 7 | 6 | Example 25 | 150 | 10 | Intragastrically | Twice a day for 21 days |
| 8 | 6 | Example 31 | 150 | 10 | Intragastrically | Twice a day for 21 days |
| 9 | 6 | Example 51 | 150 | 10 | Intragastrically | Twice a day for 21 days |
| 10 | 6 | Example 58 | 150 | 10 | Intragastrically | Twice a day for 21 days |
| 11 | 6 | Example 66 | 150 | 10 | Intragastrically | Twice a day for 21 days |
| 12 | 6 | Example 72 | 150 | 10 | Intragastrically | Twice a day for 21 days |

2.5 Experimental Results and Conclusions

EPZ-6438 inhibited tumor growth by 59% at a dose concentration of 150 milligram per kilogram (mg/kg), GSK126 only inhibited tumor growth by 61% at a dose concentration of 50 milligram per kilogram (mg/kg), and the compound of Example 3, the compound of Example 8, the compound of Example 19, the compound of Example 25, the compound of Example 31, the compound of Example 51, the compound of Example 58, the compound of Example 66 and the compound of Example 72 inhibited tumor growth by 83%, 84%, 89%, 87%, 84%, 88%, 89%, 81% and 85% at a dose concentration of 150 milligram per kilogram (mg/kg), respectively. The results showed that the inventive compounds of Examples 3, 8, 19, 25, 31, 51, 58, 66 and 72 had stronger tumor growth inhibition than EPZ-6438 and GSK126 in the xenograft model of diffuse large B-cell lymphoma cells (WSU-DLCL2 cell-line).

Experiment IX. Pharmacodynamic Experiment of the Inventive Compounds of Examples 10, 57 and 72 in Combination with Other Drugs in the Transplanted Tumor Model in Mice of Human Diffuse Large B-Cell Lymphoma Cells (WSU-DLCL2 Cell)

1. Abstract

Taking 8-week-old female SD mice (CB17/SCID) with weighing 18-20 g with severe combined immunodeficiency disease as experimental animals, the pharmacodynamic effects of the compound of Example 10, the compound of Example 57 and the compound of Example 72 on SCID transplanted tumor mice after intragastric administration and in combination with other drugs were measured. The effect of the inventive compounds on tumor growth was discussed.

2. Experimental Scheme 2.1 the Compounds for Experimental Purpose

The compound of Example 10, the compound of Example 57 and the compound of Example 72

2.2 Preparation of the Compounds

A certain amount of compound was weighted and dissolved in 0.1% Tween under vortex and ultrasound, and 0.5% carboxymethyl cellulose sodium (CMC-NA) solution was added to form a uniform solution.

2.3 Cell Culture

The human diffuse large B-cell lymphoma cells (WSU-DLCL2 cell) were ordered from Cobioer, Nanjing, and were cultured with RPMI1640 (Kangning, 35417005), 10% fetal calf serum (Ausbina, 0986180) and 1% penicillin/streptomycin double-antibody (Kangning, 30002297). The cells were confirmed to be in good condition by microscopic observation, transferred to a 15 milliliter (mL) centrifuge tube, and centrifuged at 1000 rpm for 5 minutes. The supernatant was discarded, and the residue was added to a complete medium and pipetted to form a single cell suspension, which was then cultured in an incubator (Thermo, 311) at 37° C. with 5% $CO_2$.

2.4 Experimental Process

Under sterile conditions, diffuse large B-cell lymphoma cells (WSU-DLCL2 cell) in logarithmic growth stage were digested and mixed with Matrigel and transplanted subcutaneously on the right back of mice (CB17/SCID) with severe combined immunodeficiency disease. Each mouse was inoculated with $1*10^7$ cells with a volume of 100 μL. After inoculation, the mice were randomly divided into 10 groups according to the tumor size balance evenly for in vivo pharmacodynamic experiments, with 6 mice in each group. The positive control group was given EPZ-6438 and GSK126, and the negative control group was given the same amount of menstruum. See Table 5 for specific design.

TABLE 5

| Pharmacodynamic experiment of compounds in vivo | | | | | | |
|---|---|---|---|---|---|---|
| Group | Number of Animals | Drugs under Test | Dosage (milligrams per kilogram) | Dose Volume (milliliters per kilogram) | Administration Route | Administration Schedule |
| 1 | 6 | Solvent | NA | 10 | Intragastrically | Twice a day for 21 days |
| 2 | 6 | EPZ-6438 | 125 | 10 | Intragastrically | Twice a day for 21 days |
| 3 | 6 | GSK126 | 50 | 10 | Intraperitoneally | Once a day for 21 days |
| 4 | 6 | Example 10 | 125 | 10 | Intragastrically | Twice a day for 21 days |
| 5 | 6 | Example 57 | 125 | 10 | Intragastrically | Twice a day for 21 days |
| 6 | 6 | Example 72 | 125 | 10 | Intragastrically | Twice a day for 21 days |
| | | Example 10 | 125 | 10 | Intragastrically | Twice a day for 21 days |
| | | Cyclophosphamide | 30 | 10 | Intraperitoneally | |
| 7 | 6 | Hydroxyldaunorubicin | 2.475 | 10 | Intravenously | Once a day for 21 days |
| | | Oncovin | 0.375 | 10 | Intravenously | |
| | | Prednisone | 0.15 | 10 | Intragastrically | * |
| | | Example 57 | 125 | 10 | Intragastrically | Twice a day for 21 days |
| | | Cyclophosphamide | 30 | 10 | Intraperitoneally | |
| 8 | 6 | Hydroxyldaunorubicin | 2.475 | 10 | Intravenously | Once a day for 21 days |
| | | Oncovin | 0.375 | 10 | Intravenously | |
| | | Prednisone | 0.15 | 10 | Intragastrically | * |
| | | Example 72 | 125 | 10 | Intragastrically | Twice a day for 21 days |
| | | Cyclophosphamide | 30 | 10 | Intraperitoneally | |
| 9 | 6 | Hydroxyldaunorubicin | 2.475 | 10 | Intravenously | Once a day for 21 days |
| | | Oncovin | 0.375 | 10 | Intravenously | |
| | | Prednisone | 0.15 | 10 | Intragastrically | * |
| | | Cyclophosphamide | 30 | 10 | Intraperitoneally | |
| 10 | 6 | Hydroxyldaunorubicin | 2.475 | 10 | Intravenously | Once a day for 21 days |
| | | Oncovin | 0.375 | 10 | Intravenously | |
| | | Prednisone | 0.15 | 10 | Intragastrically | * |

#CHOP: Cyclophosphamide, Hydroxyldaunorubicin, Oncovin and Prednisone.

* Day 1 to 5, once a day

#CHOP: Cyclophosphamide, Hydroxyldaunorubicin, Oncovin and Prednisone. * Day 1 to 5, once a day 2.5 Experimental Results and Conclusions EPZ-6438 inhibited tumor growth by 65% at a dose concentration of 125 milligram per kilogram (mg/kg), GSK126 inhibited tumor growth by 58% at a dose concentration of 50 milligram per kilogram (mg/kg); the compound of Example 10 inhibited tumor growth by 83% at a dose concentration of 125 milligram per kilogram (mg/kg), the compound of Example 57 inhibited tumor growth by 81% at a dose concentration of 125 milligram per kilogram (mg/kg), and the compound of Example 72 inhibited tumor growth by 83% at a dose concentration of 125 milligram per kilogram (mg/kg); the inhibitory effect of the combined administration of four positive control drugs on tumor growth was 72%, while the inhibitory effect of four positive control drugs combined with the compound of Example 10 exceeded 98% with tumors in several mouse disappeared, the inhibitory effect of four positive control drugs combined with the compound of Example 57 exceeded 99% with tumors in several mouse disappeared, and the inhibitory effect of four positive control drugs combined with the compound of Example 72 exceeded 98% with tumors in several mouse disappeared. It shows that the compound of Example 10, the compound of Example 57 and the compound of Example 72 of the invention have good curative effect in the xenograft model of human diffuse large B-cell lymphoma cells (WSU-DLCL2 cell); in combination with #CHOP, they had stronger inhibitory effects on tumor growth in the xenograft model of human diffuse large B-cell lymphoma cells (WSU-DLCL2 cell), which may provide a more effective drug regimen and choice in clinic in the future.

Experiment X. Pharmacodynamic Experiment of the Inventive Compounds of Examples 5, 7, 9, 12, 34, 77, 83, 93 and 109 in the Transplanted Tumor Model in Mice of Human Diffuse Large Cell Lymphoma B Lymphocytes (Pfeiffer Cell)

1. Abstract

Taking 8-week-old female SD mice (CB17/SCID) with weighing 18-20 g with severe combined immunodeficiency disease as experimental animals, the pharmacodynamic effects of the compound of Example 5, the compound of Example 7, the compound of Example 9, the compound of Example 12, the compound of Example 34, the compound of Example 77, the compound of Example 83, the compound of Example 93 and the compound of Example 109 on SCID transplanted tumor mice after intragastric administration were measured. The effect of the inventive compounds on tumor growth was discussed.

2. Experimental Scheme 2.1 the Compounds for Experimental Purpose

The compound of Example 5, the compound of Example 7, the compound of Example 9, the compound of Example 12, the compound of Example 34, the compound of Example 77, the compound of Example 83, the compound of Example 93 and the compound of Example 109.

2.2 Preparation of the Compounds

A certain amount of compound was weighted and dissolved in 0.1% Tween under vortex and ultrasound, and 0.5% carboxymethyl cellulose sodium (CMC-NA) solution was added to form a uniform solution.

2.3 Cell Culture

The human diffuse large cell lymphoma B lymphocytes (Pfeiffer cell) were ordered from Cobioer, Nanjing, and were cultured with RPMI1640 (Kangning, 35417005), 20% fetal calf serum (Ausbina, 0986180) and 1% penicillin/streptomycin double-antibody (Kangning, 30002297). The cells were confirmed to be in good condition by microscopic observation, transferred to a 15 milliliter (mL) centrifuge tube, and centrifuged at 1000 rpm for 5 minutes. The supernatant was discarded, and the residue was added to a complete medium and pipetted to form a single cell suspension, which was then cultured in an incubator (Thermo, 3H) at 37° C. with 5% $CO_2$.

2.4 Experimental Process

Under sterile conditions, human diffuse large cell lymphoma B lymphocytes (Pfeiffer cell) in logarithmic growth stage were digested and mixed with Matrigel and transplanted subcutaneously on the right back of mice (beige SCID) with severe combined immunodeficiency disease. Each mouse was inoculated with $1*10^7$ cells with a volume of 100 μL. After inoculation, the mice were randomly divided into 12 groups according to the tumor size balance evenly for in vivo pharmacodynamic experiments, with 6 mice in each group. The positive control group was given EPZ-6438 and GSK126, and the negative control group was given the same amount of menstruum. See Table 6 for specific design.

TABLE 6

Pharmacodynamic experiment of compounds in vivo

| Group | Number of Animals | Drugs under Test | Dosage (milligrams per kilogram, mg/kg) | Dose Volume (milliliters per kilogram, ml/kg) | Administration Route | Administration Schedule |
|---|---|---|---|---|---|---|
| 1 | 6 | Solvent | NA | 10 | Intragastrically | Once a day for 21 days |
| 2 | 6 | EPZ-6438 | 100 | 10 | Intragastrically | Once a day for 21 days |
| 3 | 6 | GSK126 | 50 | 10 | Intraperitoneally | Once a day for 21 days |
| 4 | 6 | Example 5 | 100 | 10 | Intragastrically | Once a day for 21 days |
| 5 | 6 | Example 7 | 100 | 10 | Intragastrically | Once a day for 21 days |
| 6 | 6 | Example 9 | 100 | 10 | Intragastrically | Once a day for 21 days |
| 7 | 6 | Example 12 | 100 | 10 | Intragastrically | Once a day for 21 days |
| 8 | 6 | Example 34 | 100 | 10 | Intragastrically | Once a day for 21 days |
| 9 | 6 | Example 77 | 100 | 10 | Intragastrically | Once a day for 21 days |
| 10 | 6 | Example 83 | 100 | 10 | Intragastrically | Once a day for 21 days |
| 11 | 6 | Example 93 | 100 | 10 | Intragastrically | Once a day for 21 days |
| 12 | 6 | Example 109 | 100 | 10 | Intragastrically | Once a day for 21 days |

2.5 Experimental Results and Conclusions

EPZ-6438 inhibited tumor growth by 77% at a dose concentration of 100 milligram per kilogram (mg/kg), GSK126 inhibited tumor growth by 68% at a dose concentration of 50 milligram per kilogram (mg/kg), and the compound of Example 5, the compound of Example 7, the compound of Example 9, the compound of Example 12, the compound of Example 34, the compound of Example 77, the compound of Example 83, the compound of Example 93 and the compound of Example 109 inhibited tumor growth by 98%, 95%, 97%, 99%, 96%, 100%, 98%, 94% and 101% at a dose concentration of 100 milligram per kilogram (mg/kg), respectively. The results showed that the inventive compounds of Examples 5, 7, 9, 12, 34, 37, 43, 53 and 69 had stronger tumor growth inhibition than EPZ-6438 and GSK126 in the xenograft model of human diffuse large cell lymphoma B lymphocytes (Pfeiffer cell).

The above are only the preferred examples of the present invention and are not intended to limit this invention. Any modification, equivalent replacement, improvement, etc. made within the spirit and principle of this application shall be included within the scope of protection of this invention.

The invention claimed is:

1. A compound or a tautomer, a mesomer, a racemate, an enantiomer, a diastereoisomer or a mixture thereof, a pharmaceutically acceptable salt, a polymorph, a solvate or an isotope derivative thereof, wherein the compound 1s selected from the group consisting of:

1

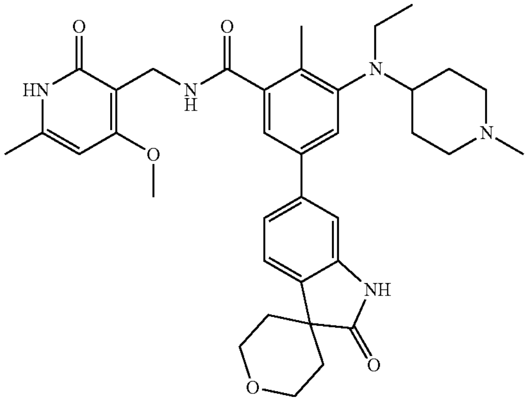

,

-continued

2

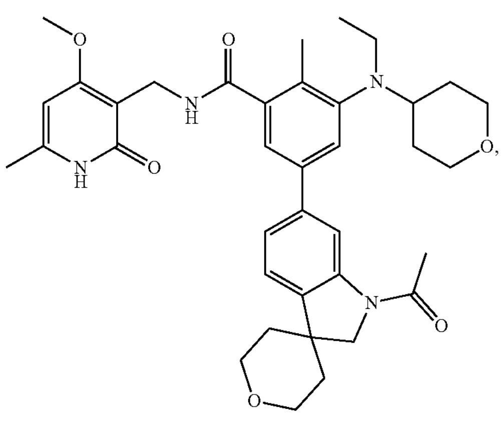

,

-continued
3
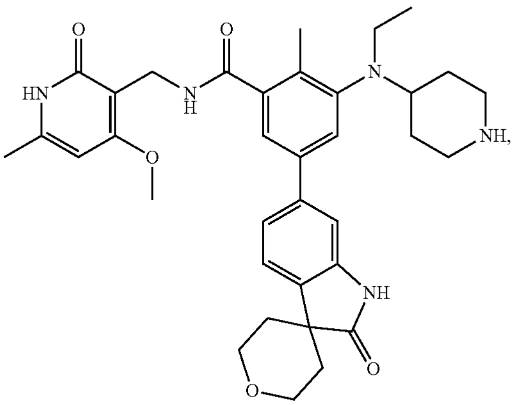
4
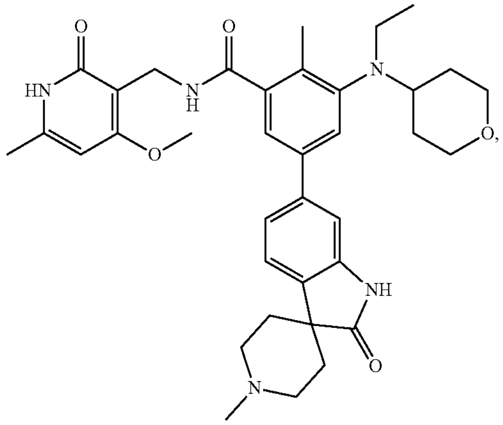
5
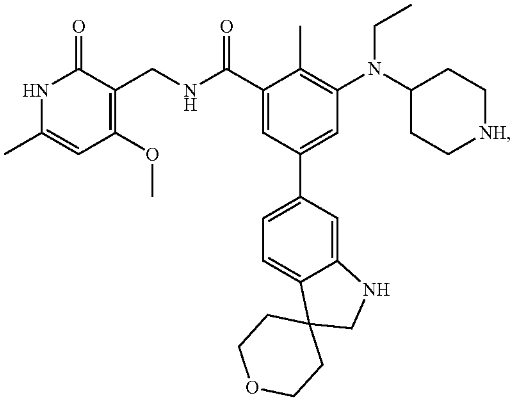
6
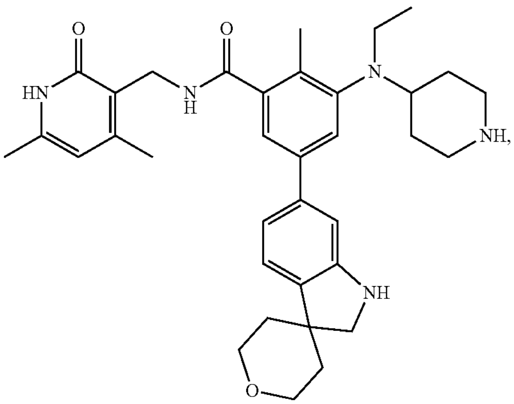
-continued
7
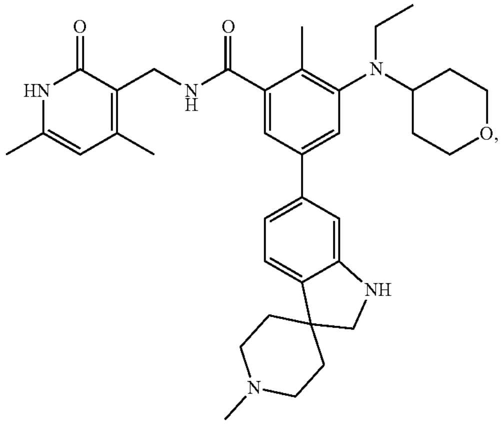
8-1
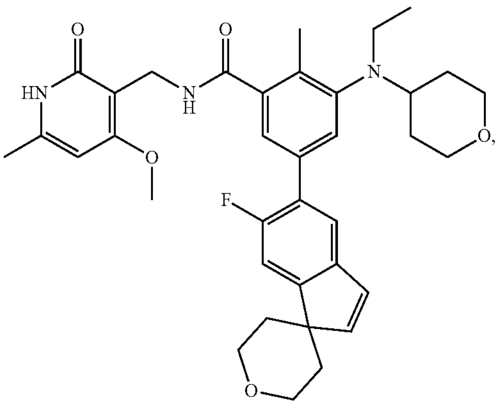
8-2
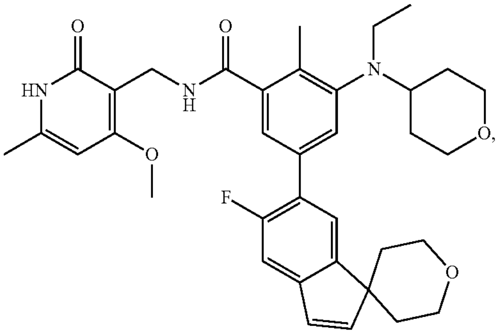
9-1
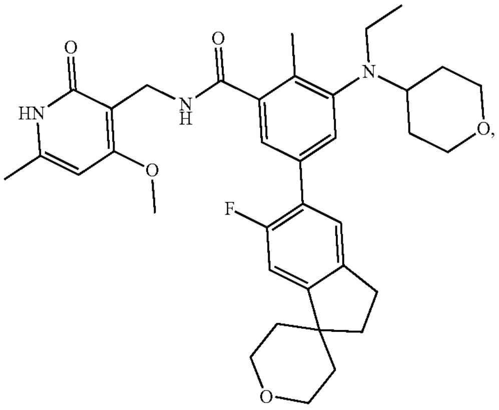

-continued
9-2
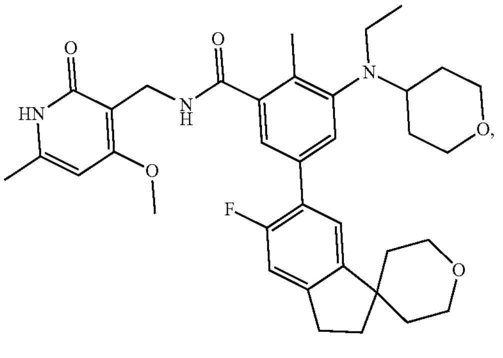
10
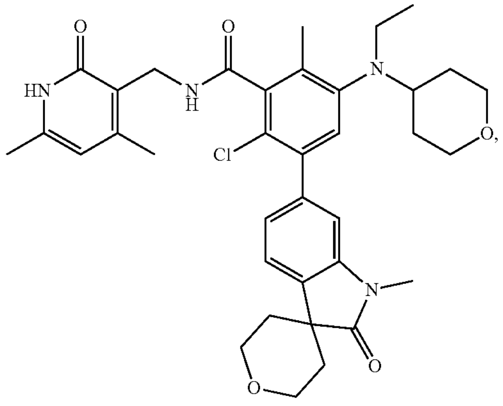
11
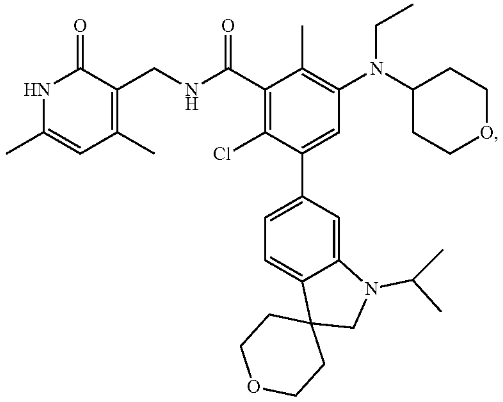
12
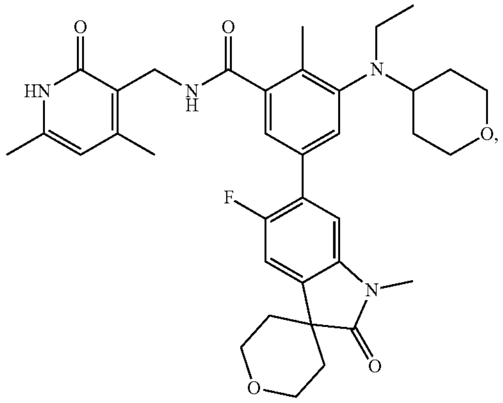
-continued
13
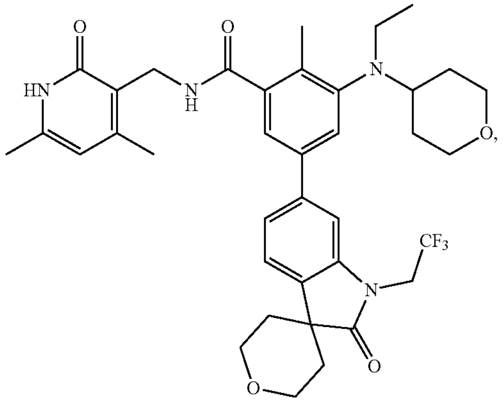
14
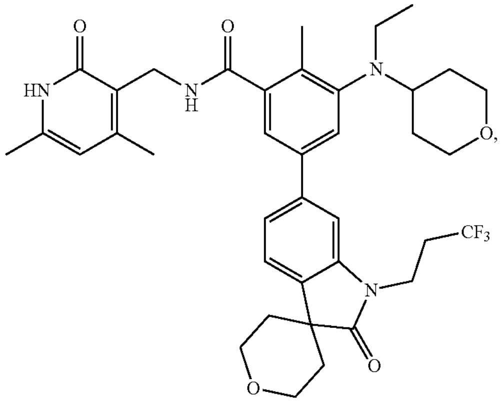
15
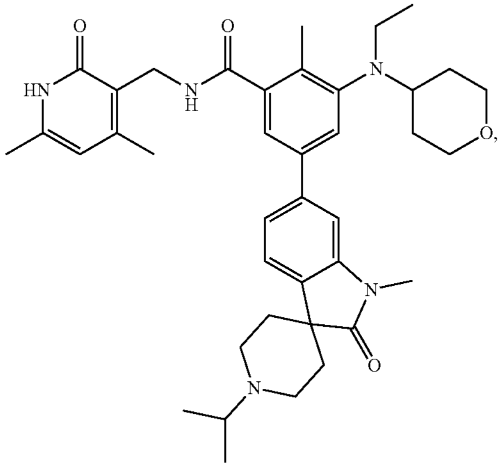
16
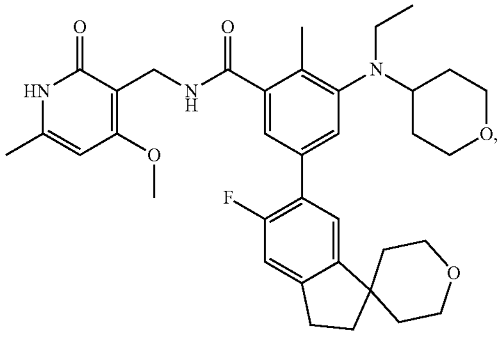

-continued
17
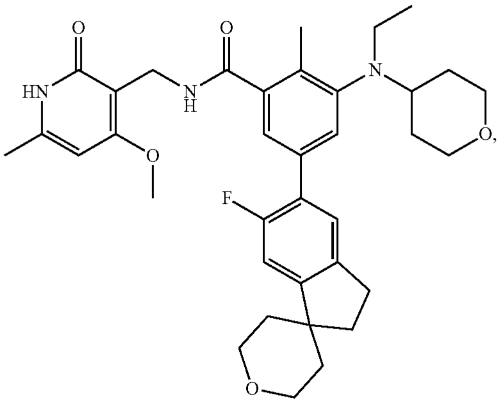
18
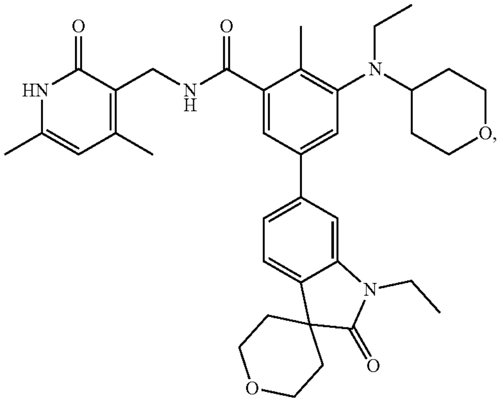
19
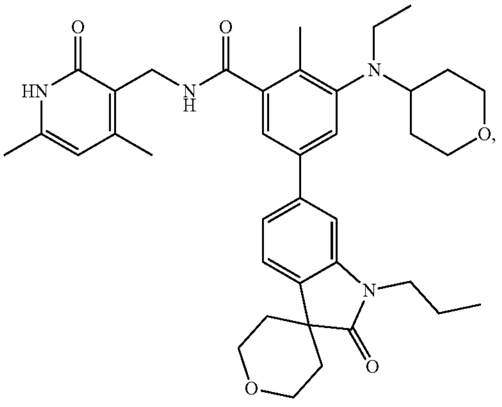
20
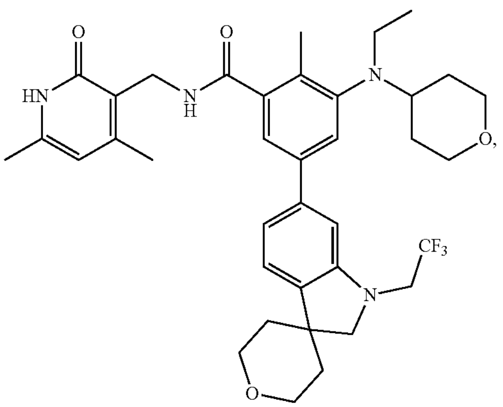
-continued
21
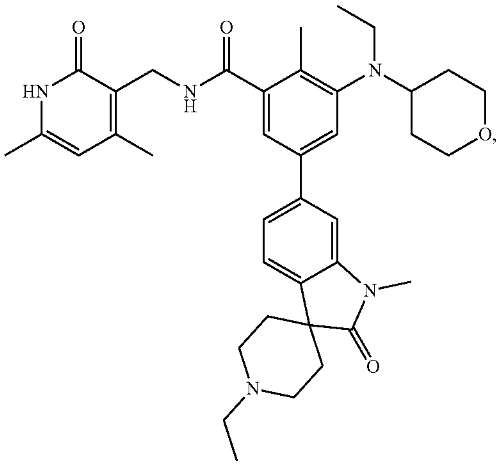
22
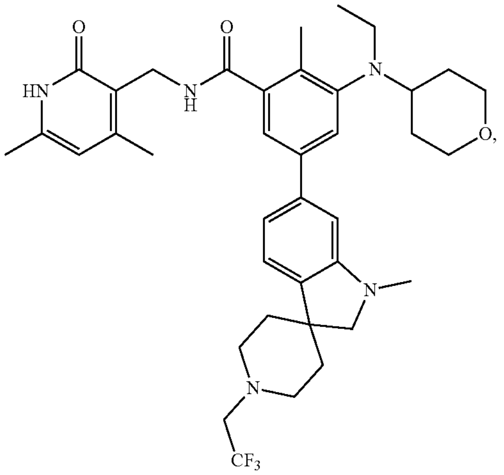
23
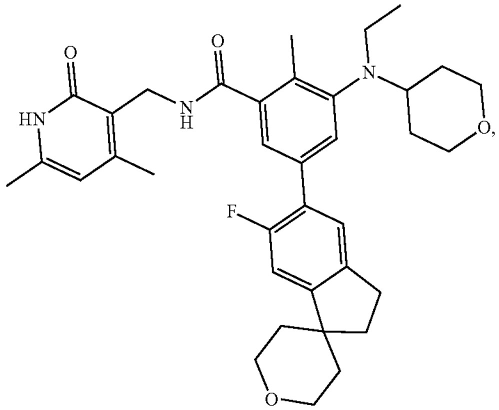

-continued
24
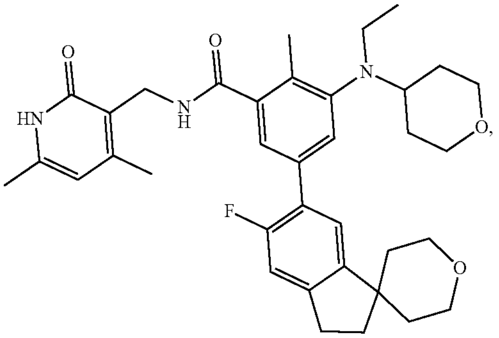
25
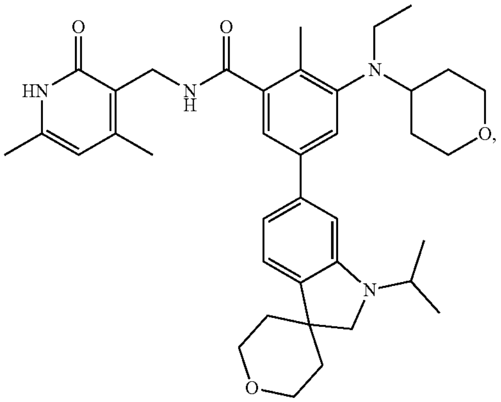
26
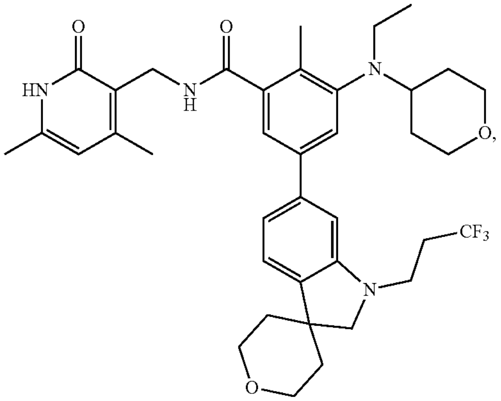
27
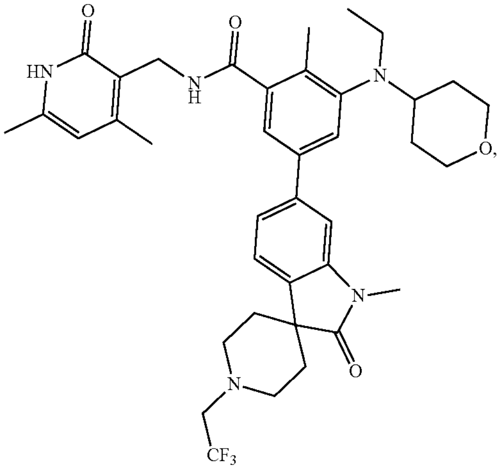
-continued
28
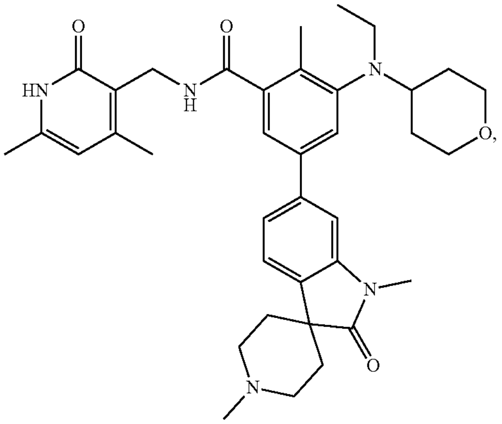
29
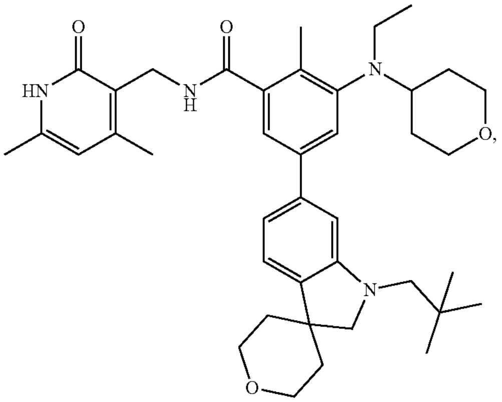
30
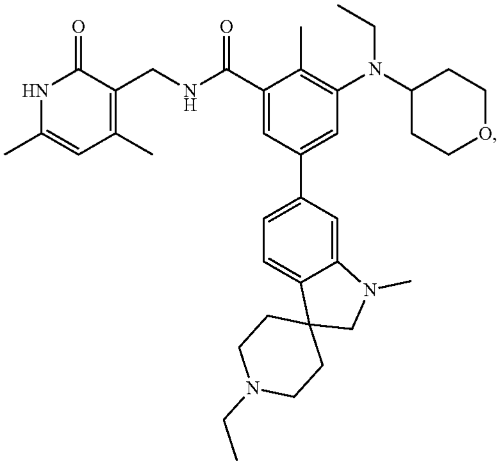

-continued
31
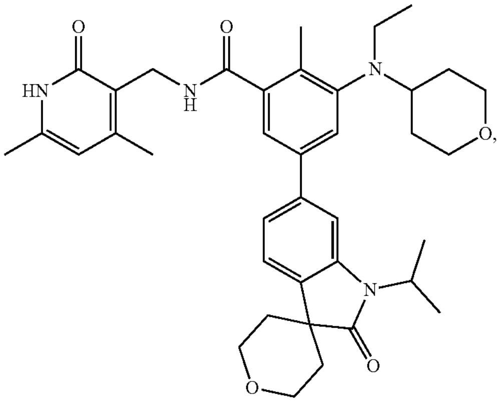
32
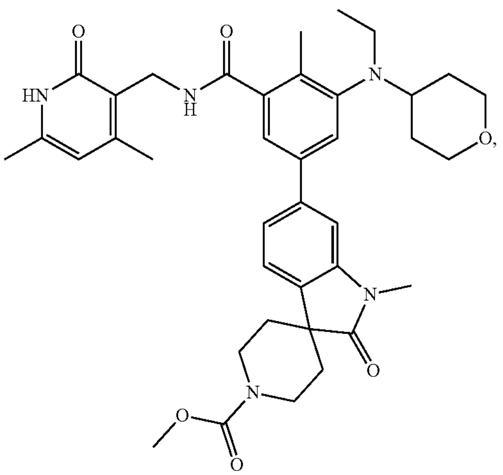
33
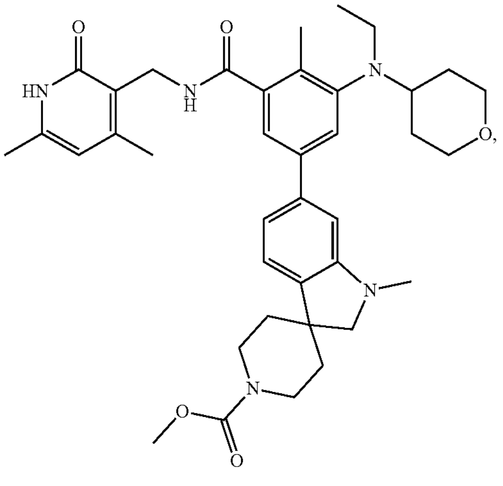
-continued
34
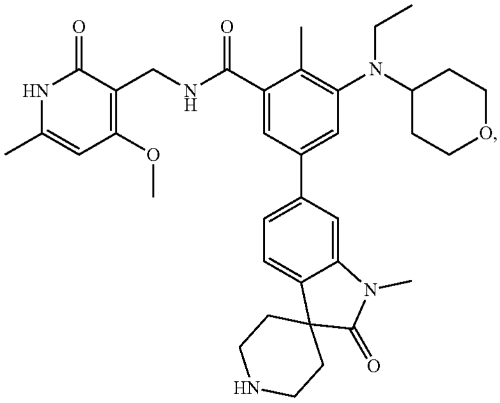
35-1
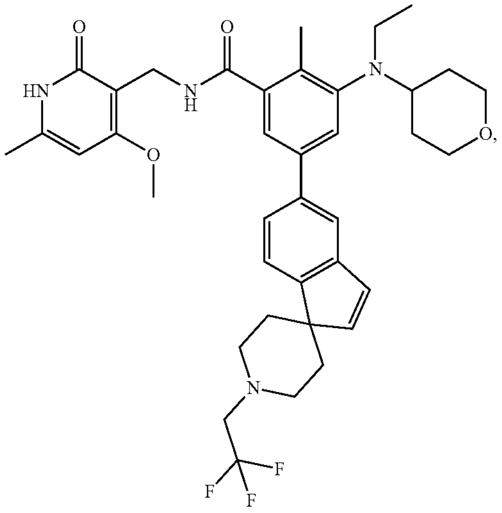
35-2
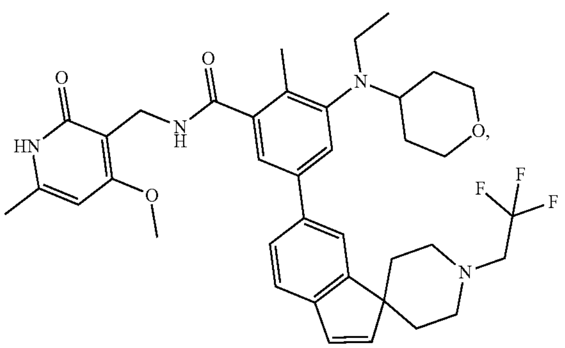

-continued
36-1
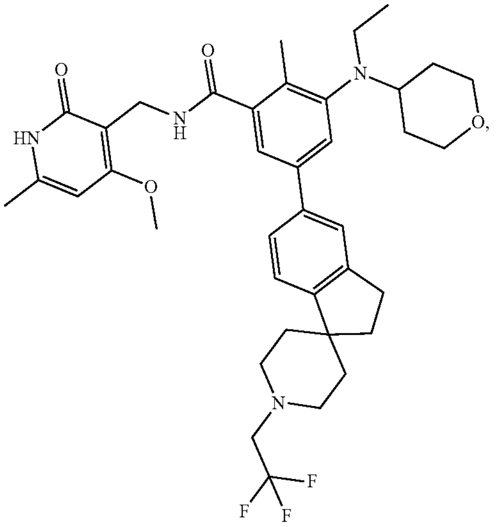
36-2
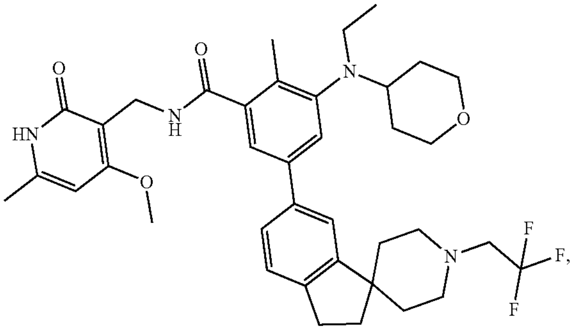
37
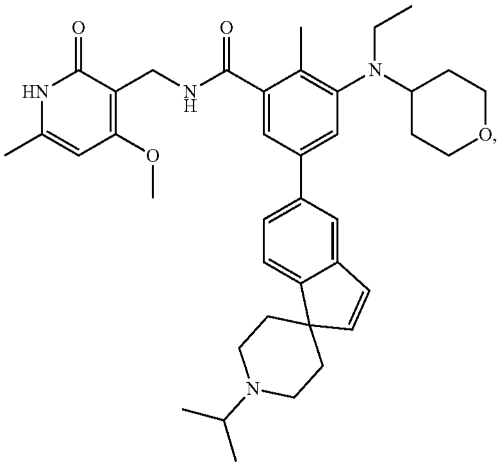
-continued
38
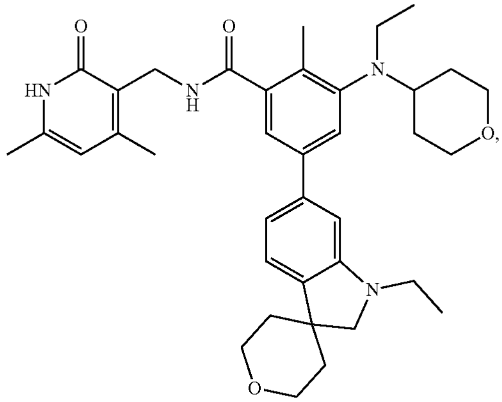
39
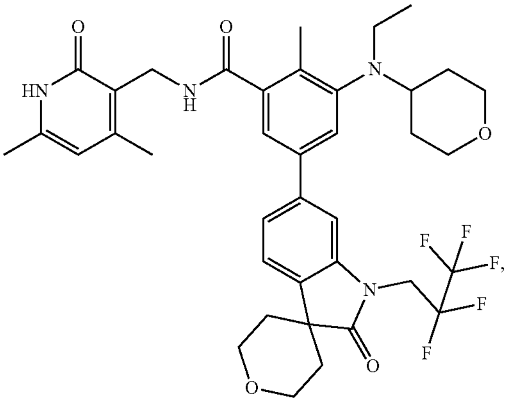
40
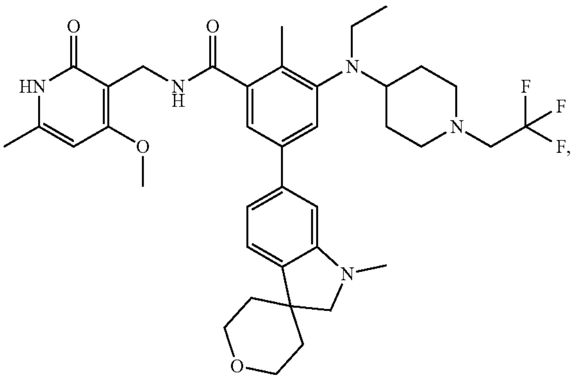
41
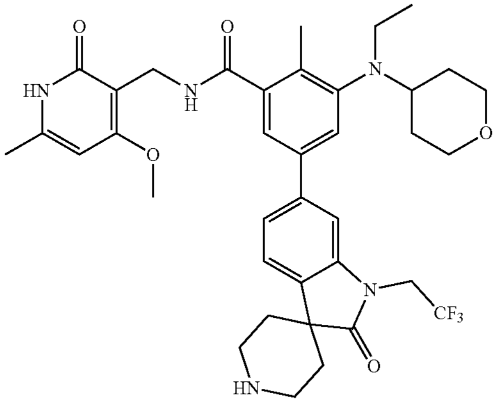

-continued
42-1
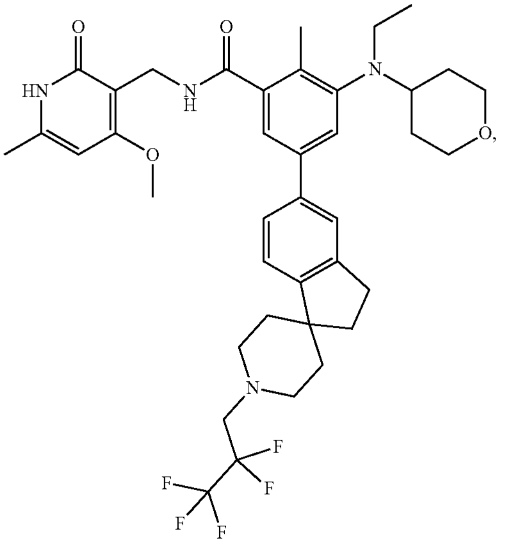
42-2
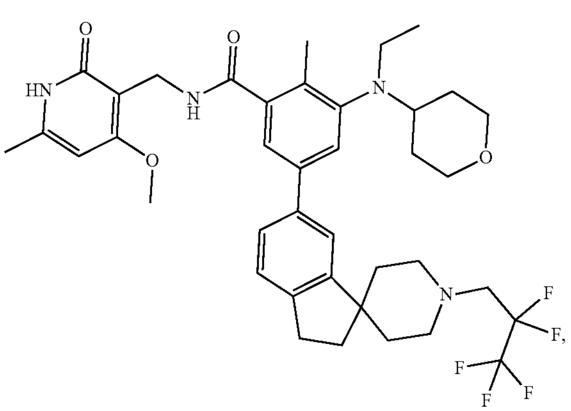
43
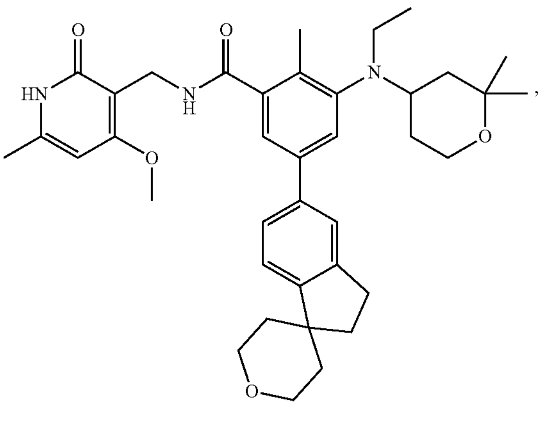
-continued
44
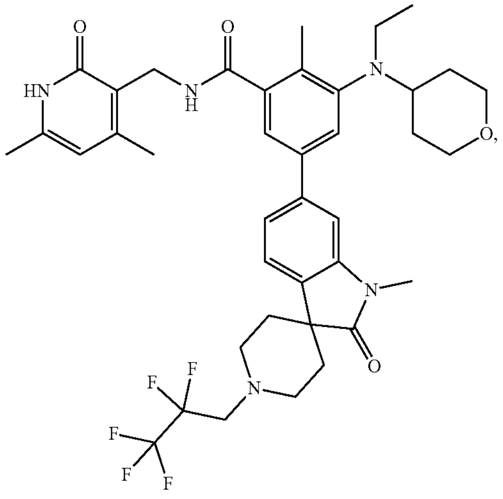
45
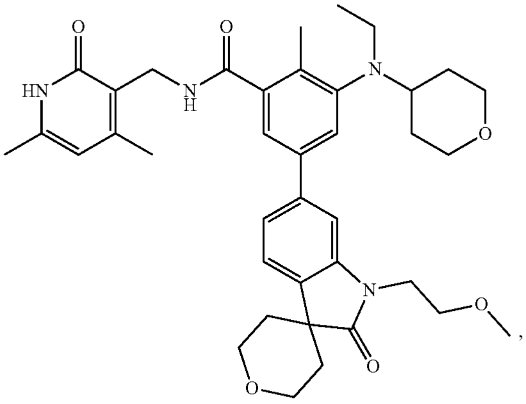
46
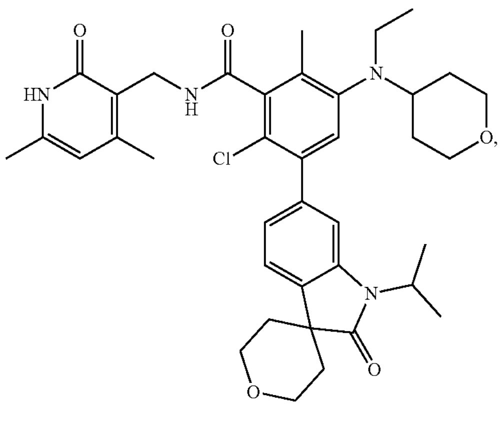

-continued
47
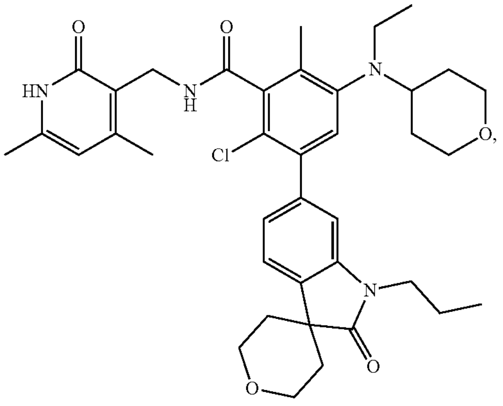
48
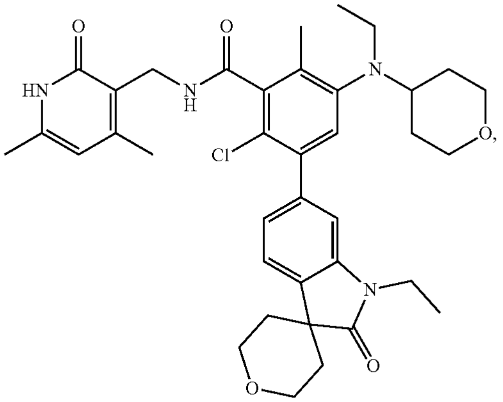
49
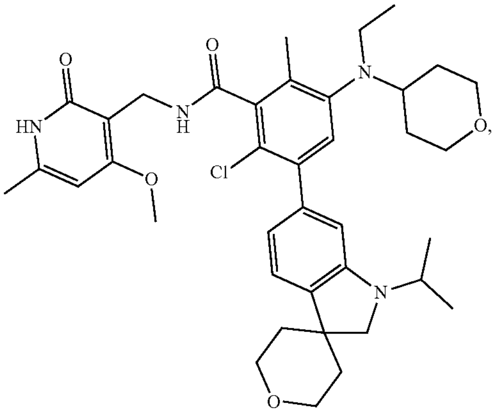
50
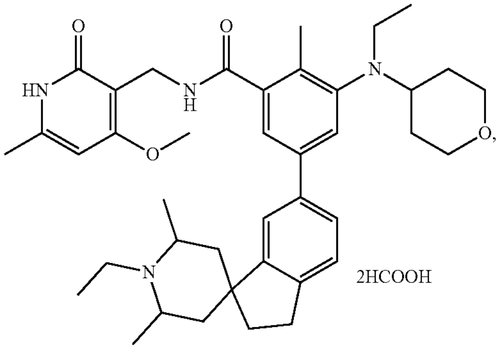
2HCOOH
-continued
51
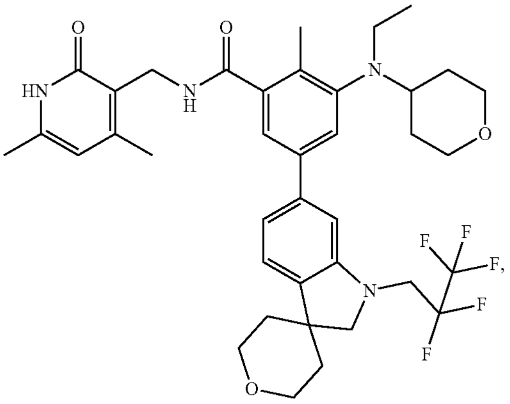
52
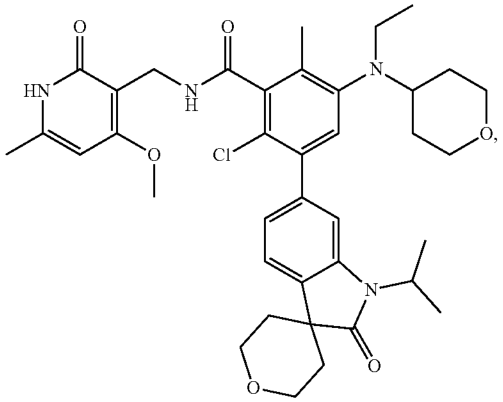
53
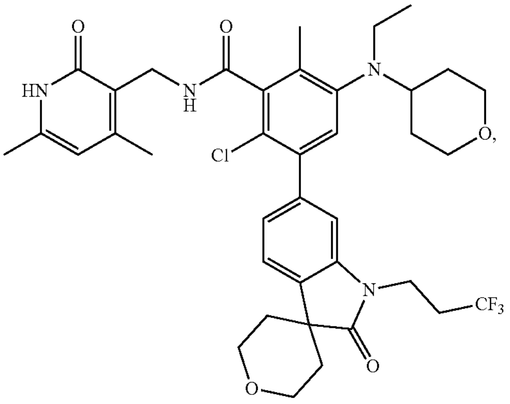
54
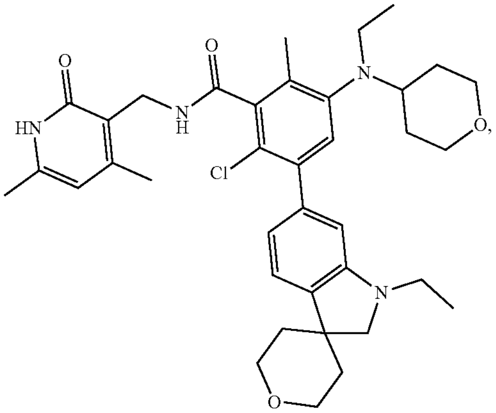

-continued
55
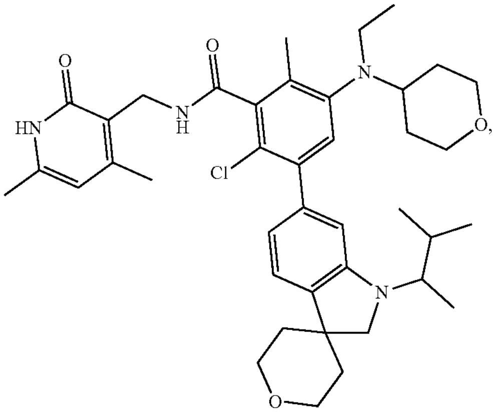
56
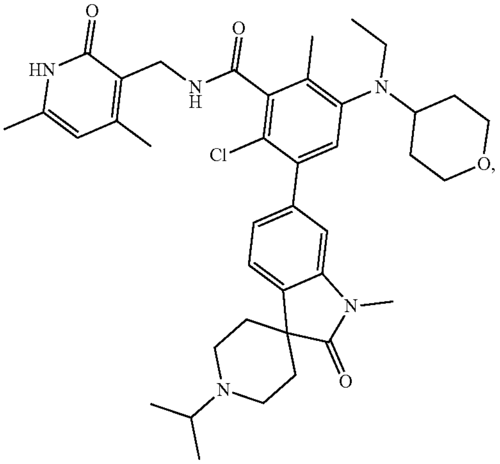
57
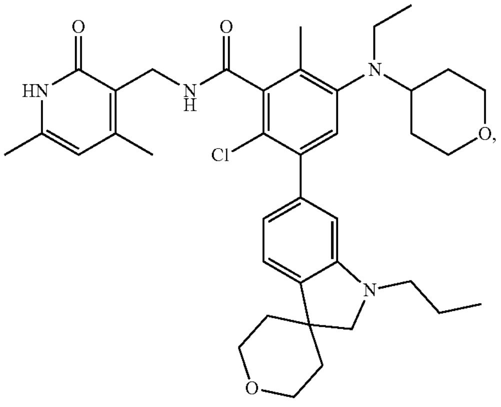
-continued
58
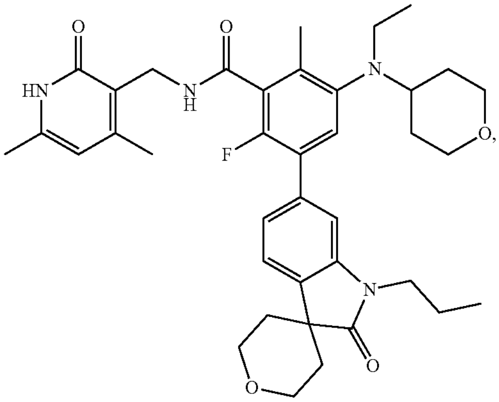
59
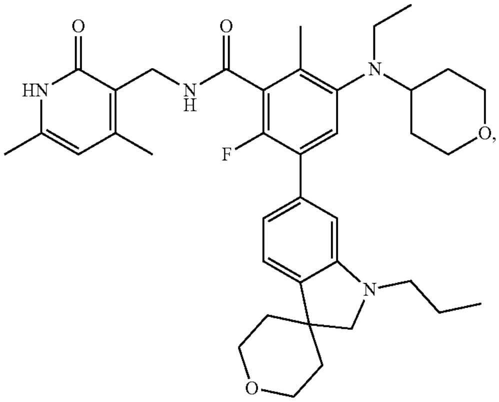
60
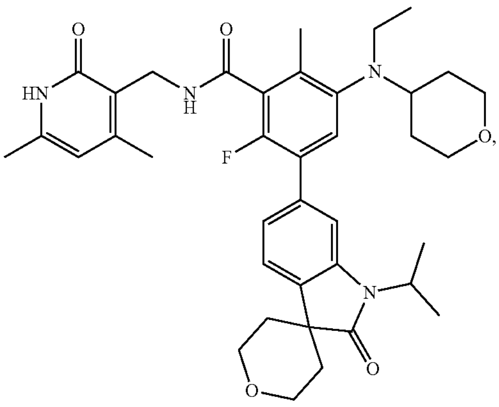

61
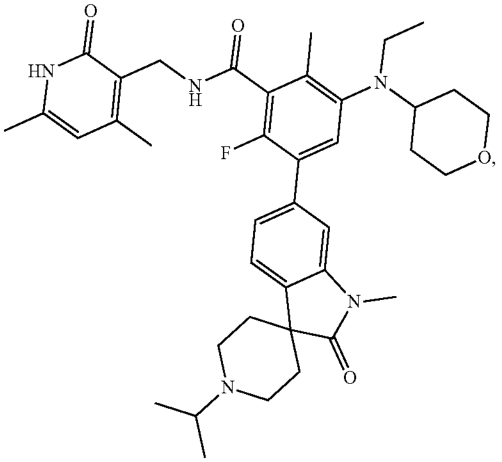
62
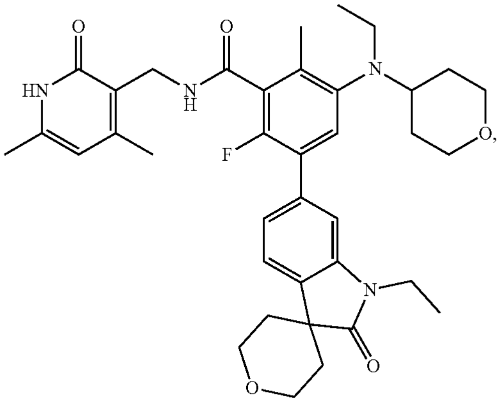
63
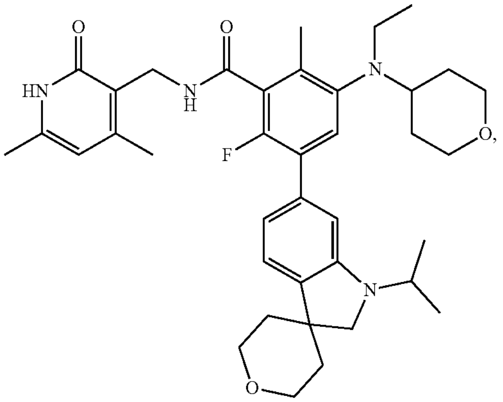
64
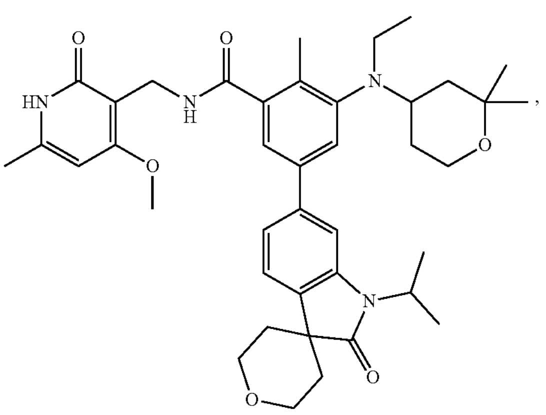
65
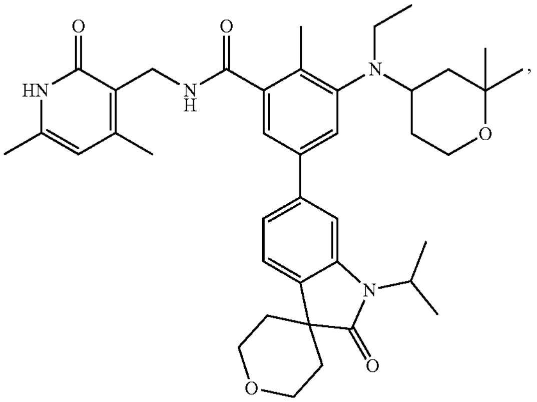
66
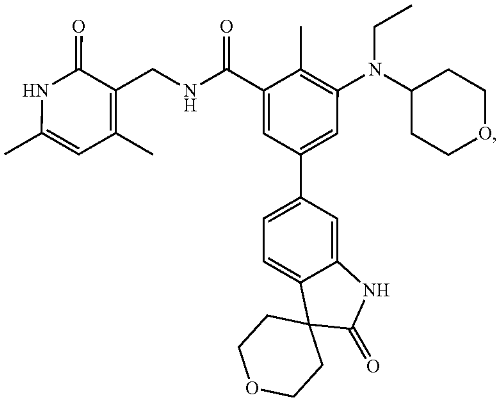

67
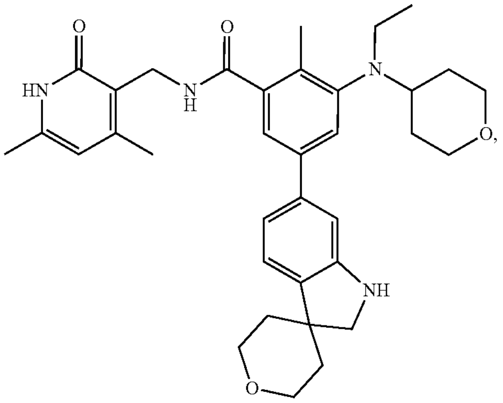
68
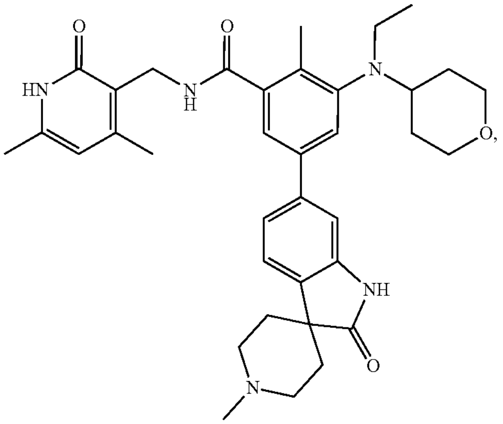
69
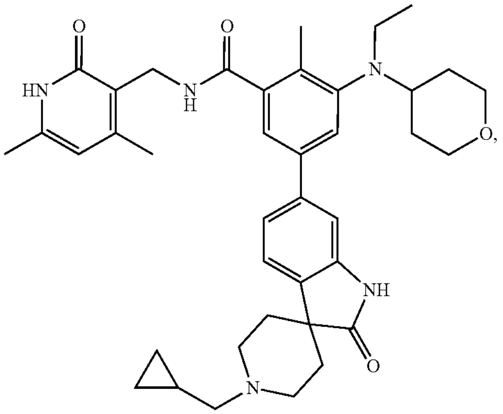
70
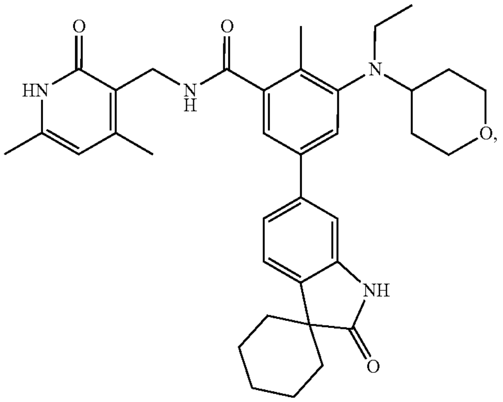
71
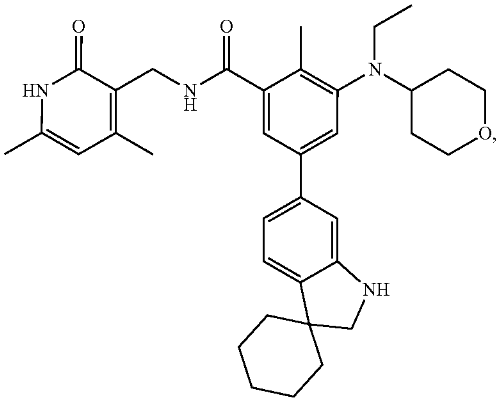
72
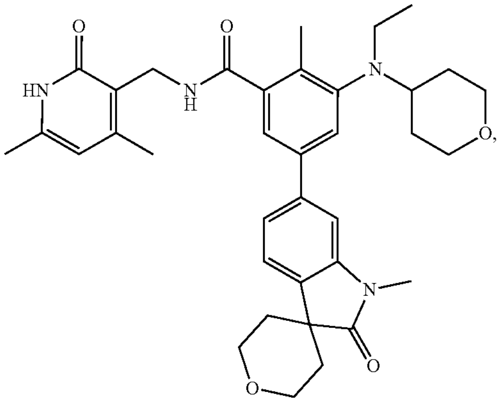
73
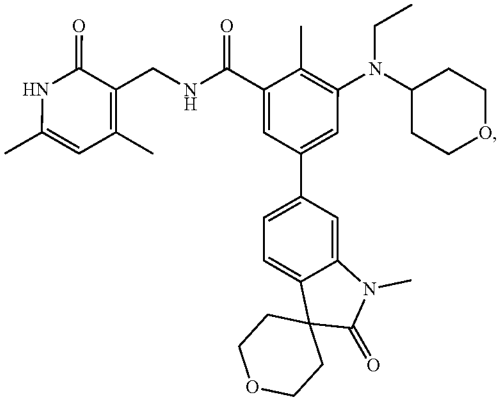
74
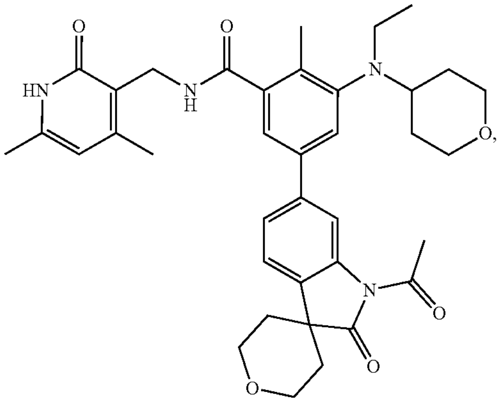

-continued
75
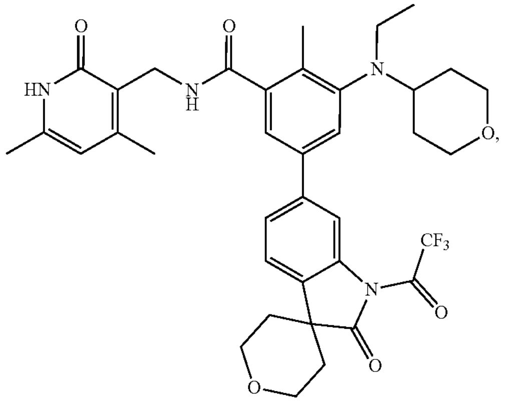
76
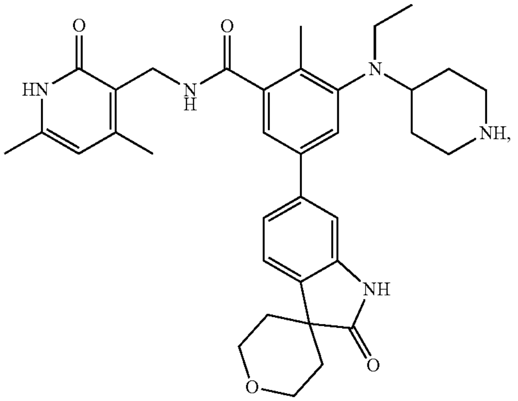
77
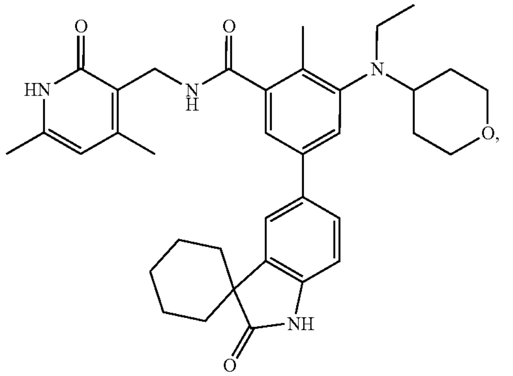
78
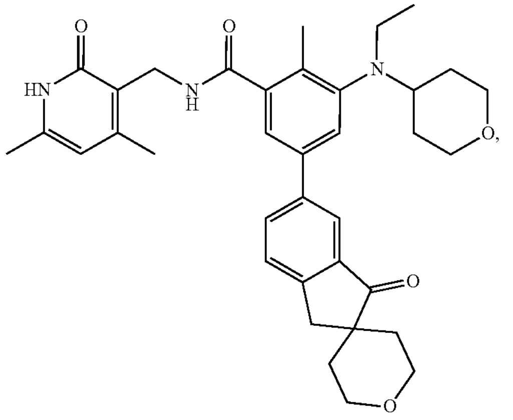
-continued
79
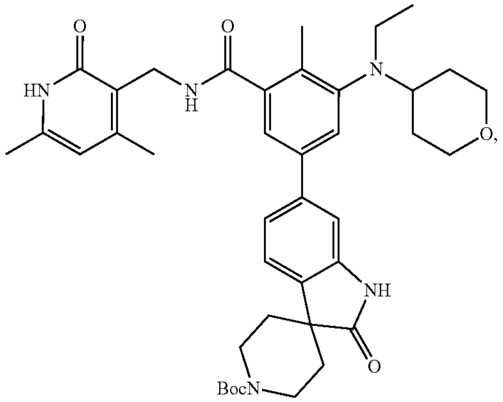
80
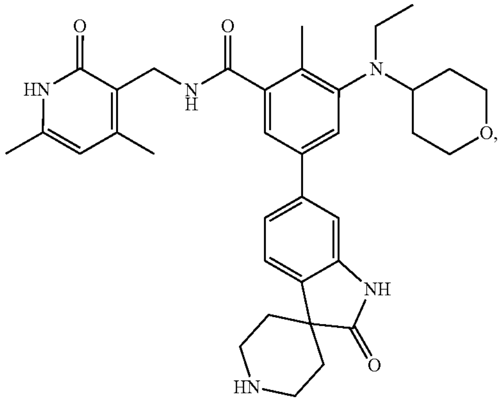
81
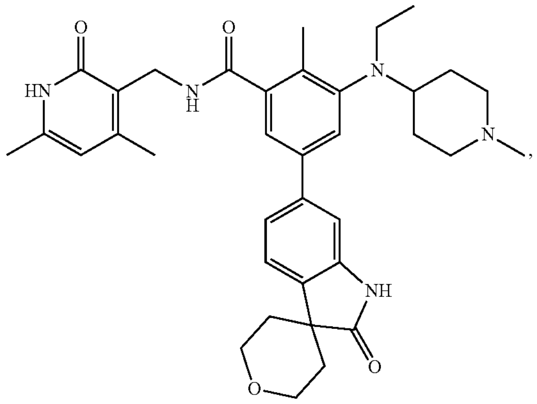
82
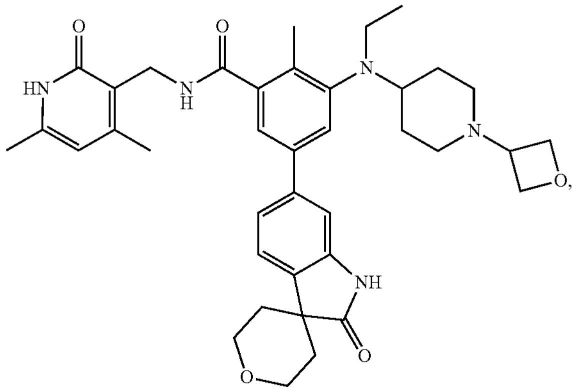

-continued
83
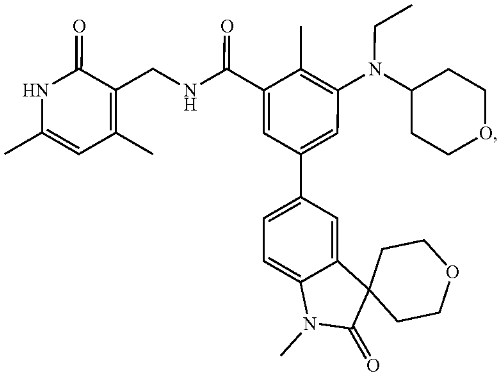
84
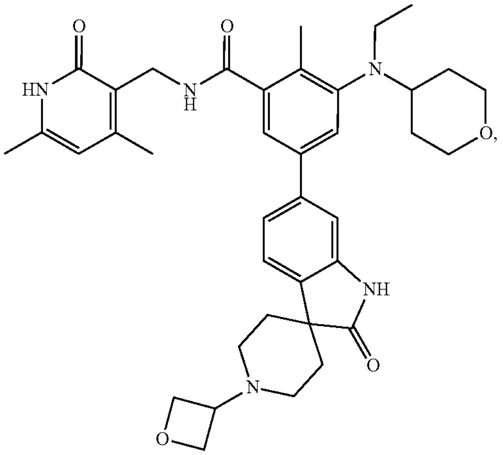
85
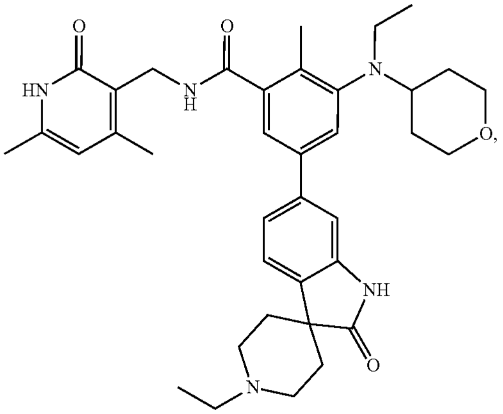
86
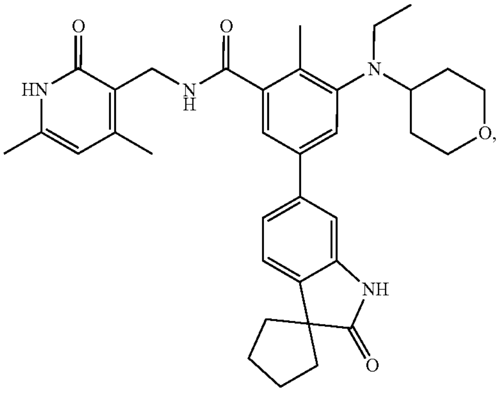
-continued
87
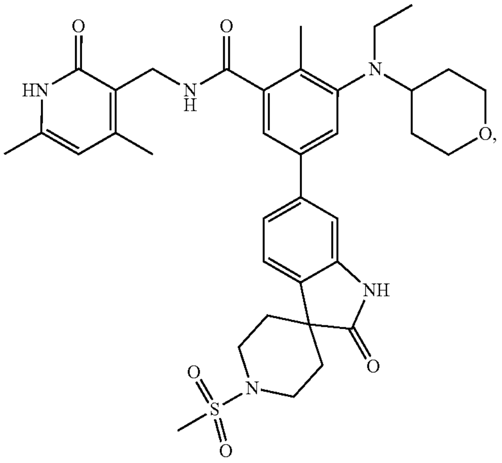
88
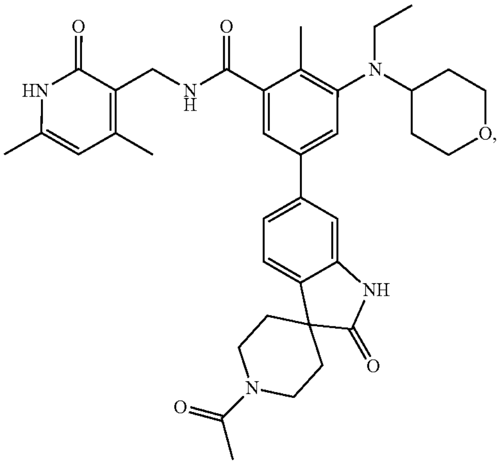
89
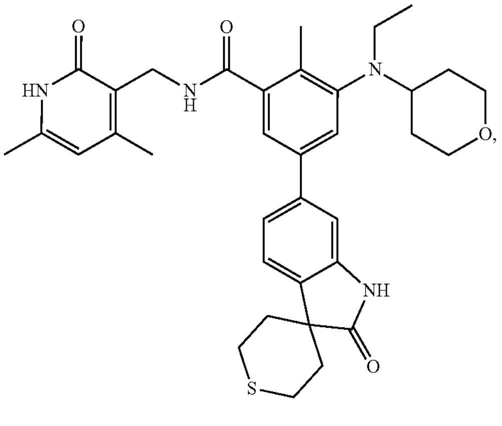

-continued
90
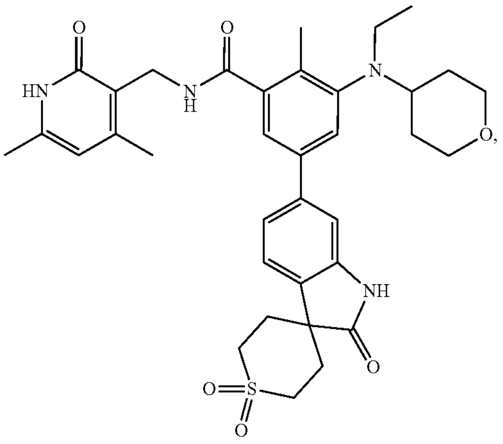
91
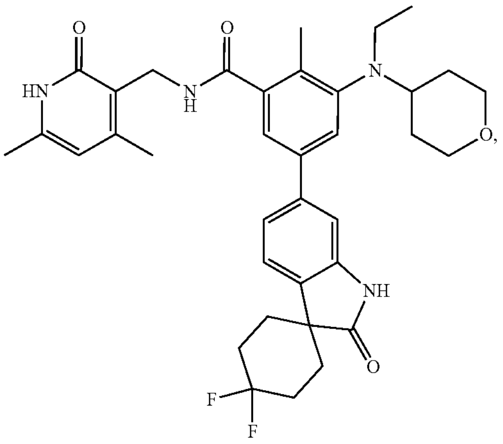
92
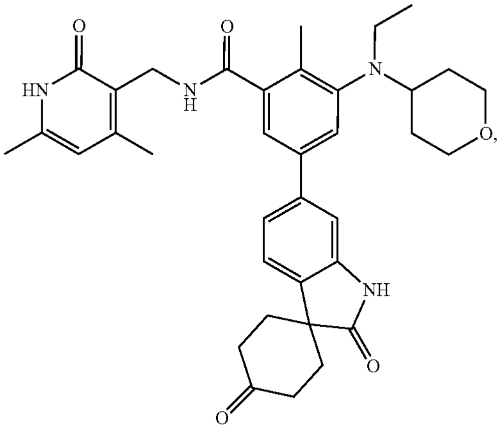
-continued
93
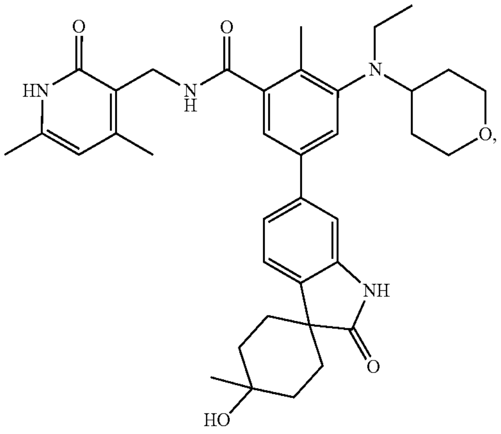
94
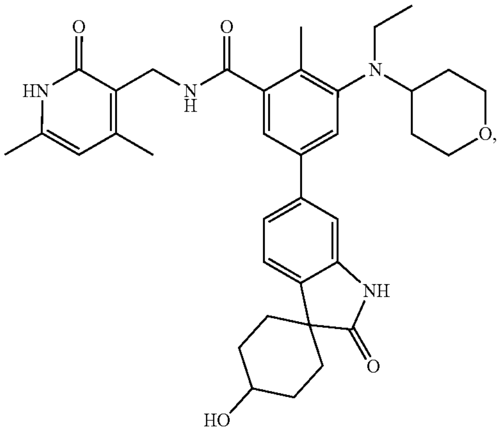
95
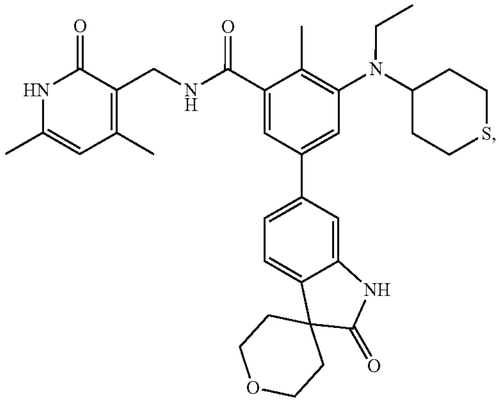

-continued
96
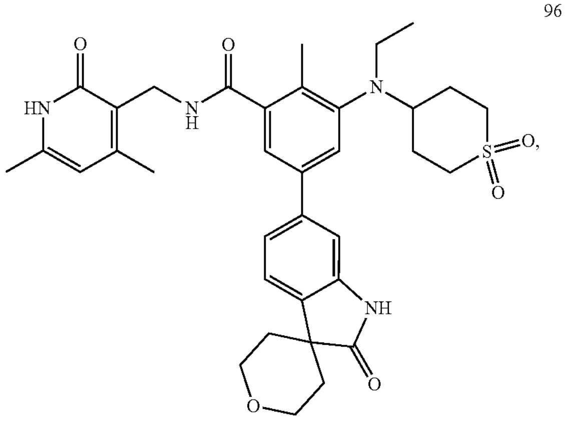
97
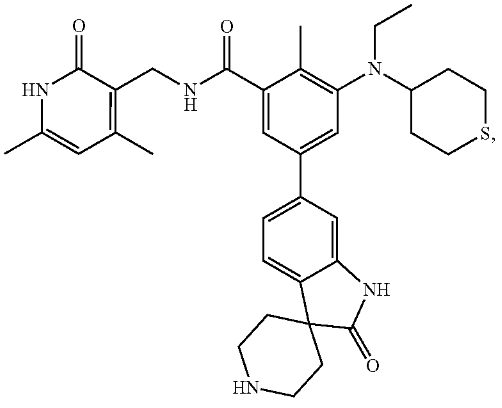
98
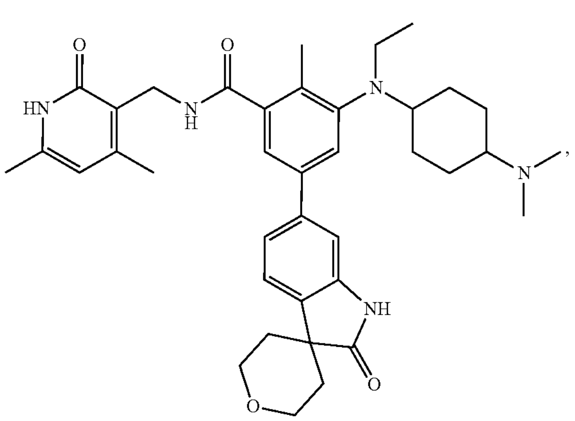
99
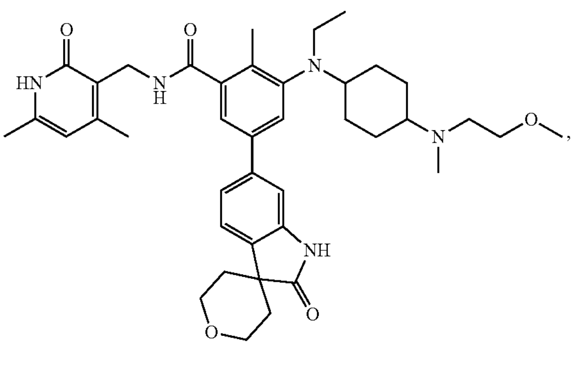
-continued
100
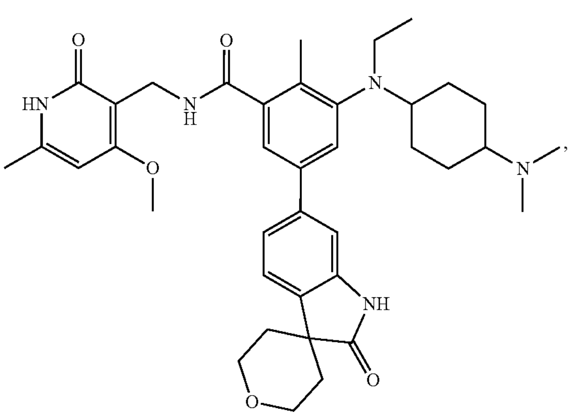
101
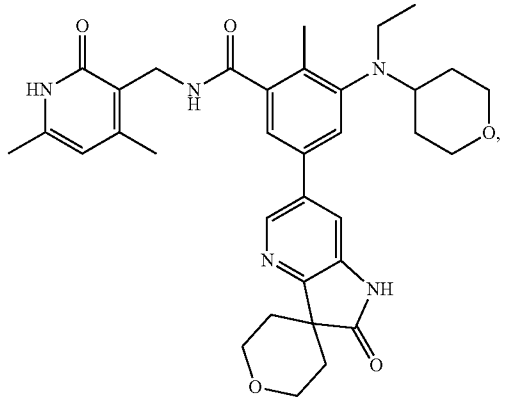
102
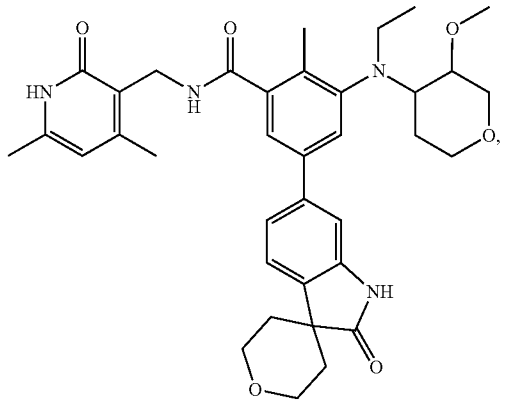
103
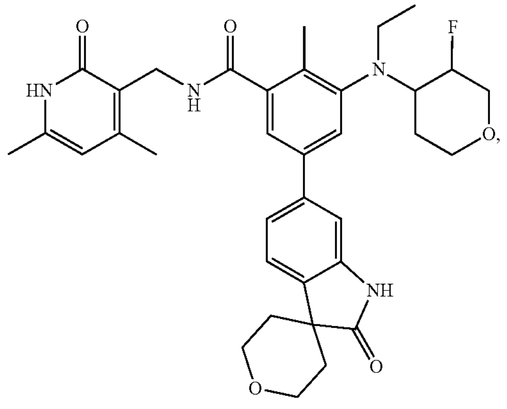

-continued
104
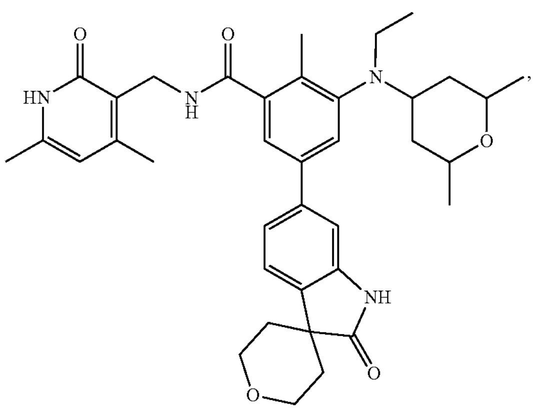
105
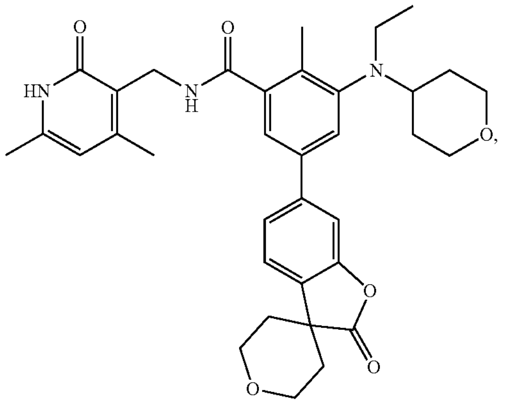
106
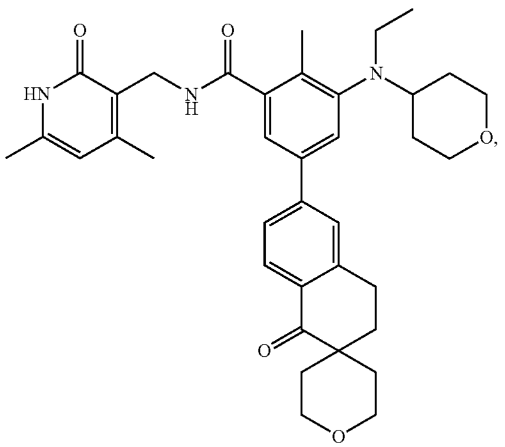
-continued
107
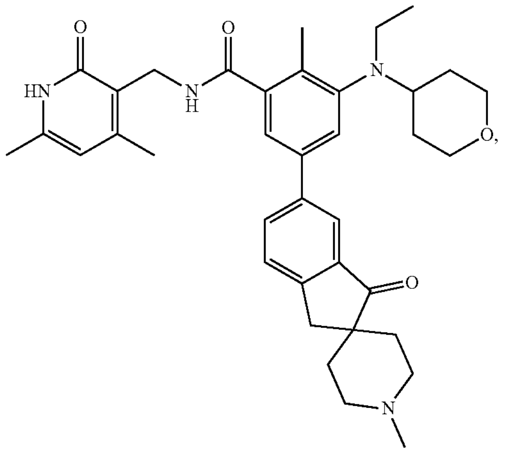
108
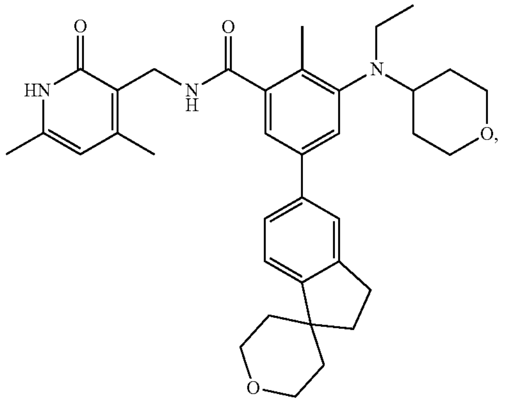
109
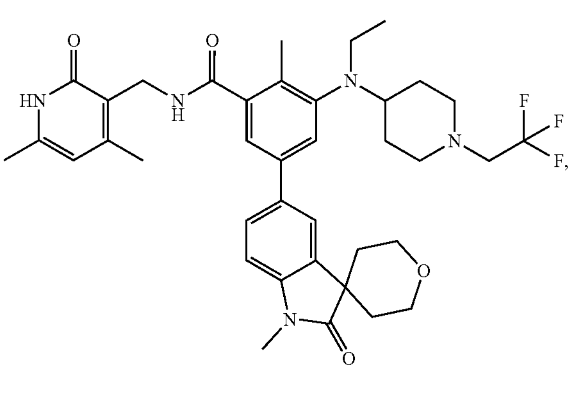

-continued
110
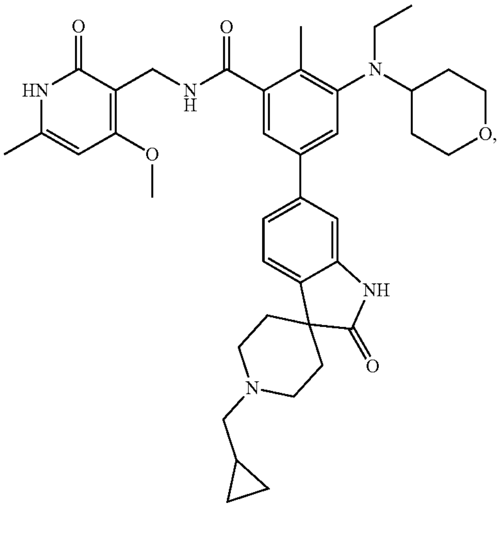
111
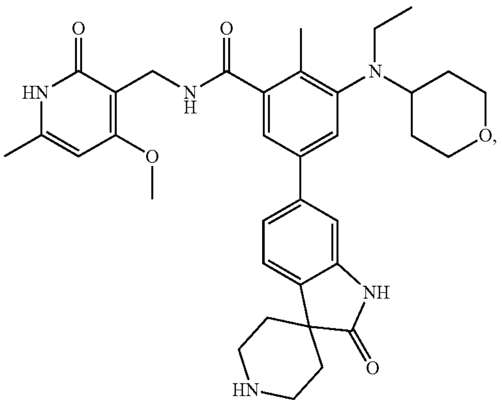
112
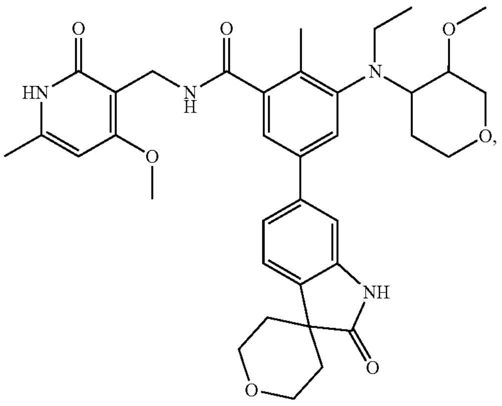
-continued
113
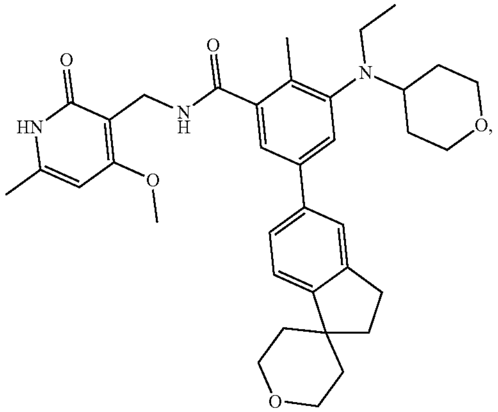
114
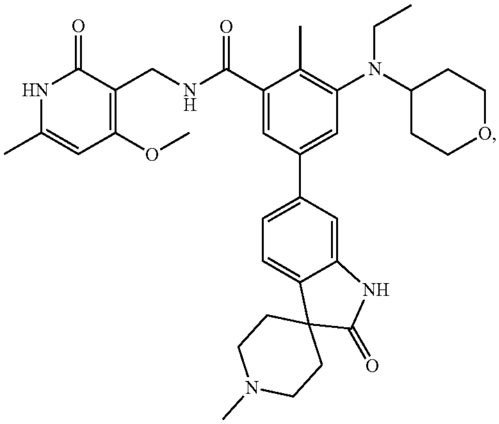
115
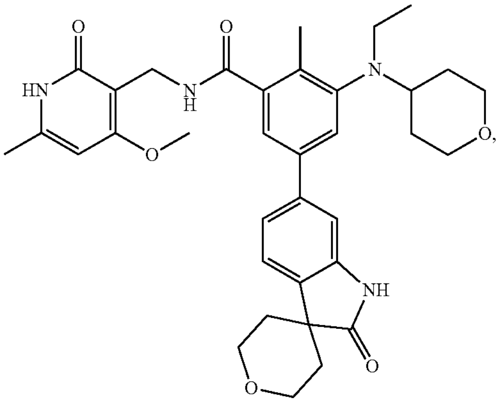

-continued
116
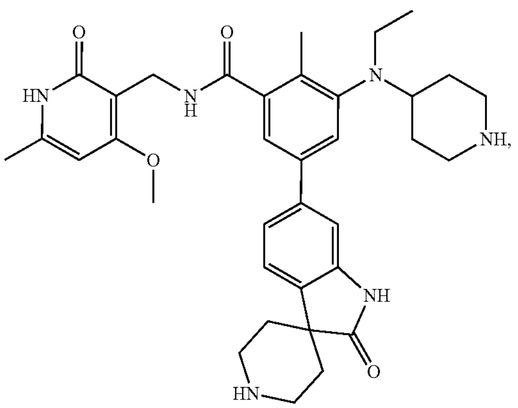
117
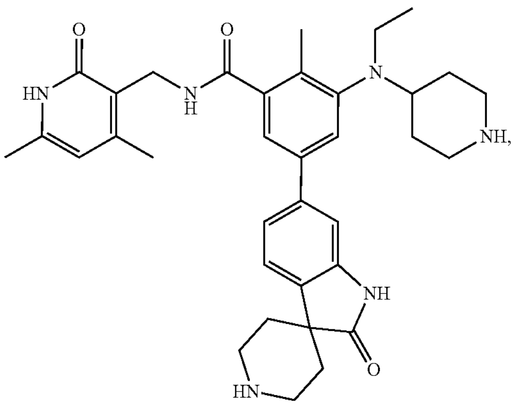
118
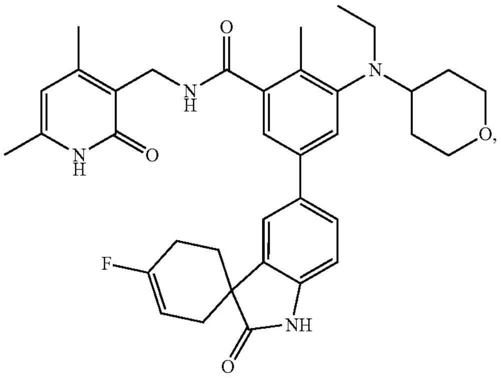
119
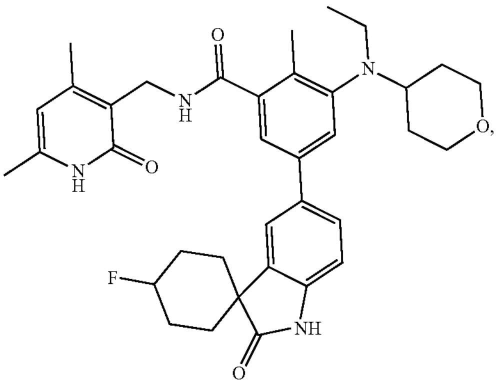
-continued
120
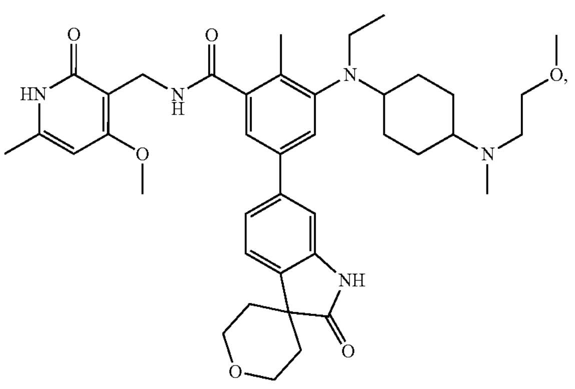
121
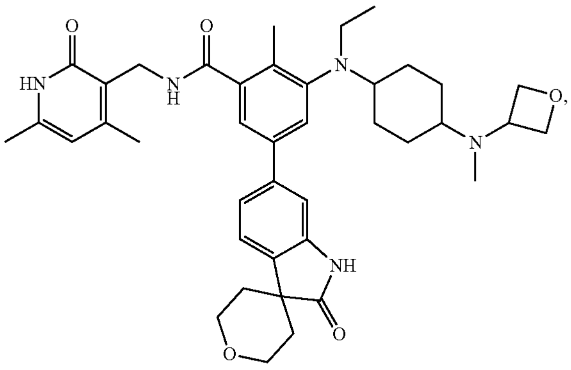
122
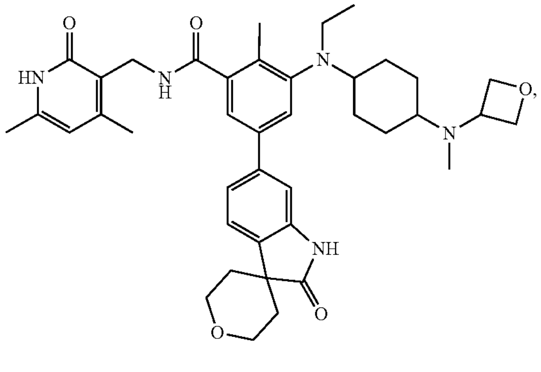
and
123
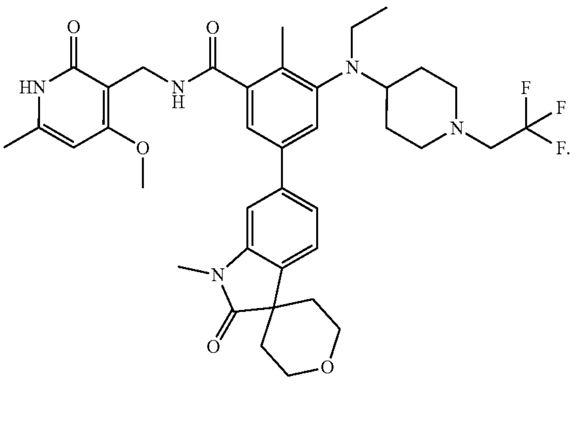
2. A pharmaceutical composition, comprising a therapeutically effective amount of the compound, or the tautomer, mesomer, racemate, enantiomer, diastereoisomer or mixture thereof, pharmaceutically acceptable salt, polymorph, solvate or isotope derivative thereof according to claim 1, and optionally one or more pharmaceutically acceptable carriers and/or diluents.

3. A method for treating an EZH2-mediated tumor, an EZH2-mediated inflammatory enteritis, or an EZH2-mediated autoimmune encephalomyelitis, wherein the method comprises administering a therapeutically effective amount of the compound, or the tautomer, mesomer, racemate, enantiomer, diastereoisomer or mixture thereof, pharmaceutically acceptable salt, polymorph, solvate or isotope derivative thereof according to claim 1 to a subject in need.

4. A method for treating an EZH2-mediated tumor, an EZH2-mediated inflammatory enteritis, or an EZH2-mediated autoimmune encephalomyelitis, wherein the method comprises administering a pharmaceutical composition comprising a therapeutically effective amount of the compound, or the tautomer, mesomer, racemate, enantiomer, diastereoisomer or mixture thereof, pharmaceutically acceptable salt, polymorph, solvate or isotope derivative thereof according to claim 1, and one or more pharmaceutically acceptable carriers and/or diluents, to a subject in need.

* * * * *